United States Patent
Ikegami et al.

(10) Patent No.: US 6,448,444 B2
(45) Date of Patent: Sep. 10, 2002

(54) OXIME COMPOUNDS, THEIR USE, AND INTERMEDIATES FOR THEIR PRODUCTION

(75) Inventors: Hiroshi Ikegami, Toyonaka; Keiichi Izumi, Narashino; Masaya Suzuki, Takarazuka; Noriyasu Sakamoto; Shigeru Saito, both of Toyonaka, all of (JP)

(73) Assignee: Sumitomo Chemical Company, Limited, Osaka-fu (JP)

( * ) Notice: Subject to any disclaimer, the term of this patent is extended or adjusted under 35 U.S.C. 154(b) by 0 days.

(21) Appl. No.: 09/839,201

(22) Filed: Apr. 23, 2001

Related U.S. Application Data

(62) Division of application No. 09/402,199, filed as application No. PCT/JP98/01342 on Mar. 26, 1998.

(30) Foreign Application Priority Data

| Apr. 8, 1997 | (JP) | 9-89831 |
| Aug. 6, 1997 | (JP) | 9-245892 |
| Aug. 7, 1997 | (JP) | 9-247400 |

(51) Int. Cl.[7] ............. C07C 251/32; A01N 33/24; A01N 43/40
(52) U.S. Cl. ......... 564/265; 514/277; 514/640; 546/264; 546/329; 564/253; 564/254
(58) Field of Search .......... 514/640, 253, 514/277; 564/253, 254, 256, 265; 546/264, 329; 504/250, 244

(56) References Cited

U.S. PATENT DOCUMENTS

| 4,514,406 A | * | 4/1985 | Ohsumi et al. | 514/352 |
| 4,647,698 A | * | 3/1987 | Henrick et al. | 564/256 |
| 4,753,960 A | * | 6/1988 | Holan et al. | 514/464 |
| 5,728,696 A | * | 3/1998 | Kuhn et al. | 514/235.5 |
| 5,872,137 A | * | 2/1999 | Sakamoto et al. | 514/345 |

FOREIGN PATENT DOCUMENTS

| EP | 0184546 | 6/1986 |
| JP | A62252756 | 11/1987 |
| WO | 9604228 | 2/1996 |
| WO | 9611909 | 4/1996 |
| WO | 9633160 | 10/1996 |

* cited by examiner

*Primary Examiner*—Jean F. Vollano
(74) *Attorney, Agent, or Firm*—Birch, Stewart, Kolasch & Birch, LLP

(57) ABSTRACT

Oxime compounds of formula (1)

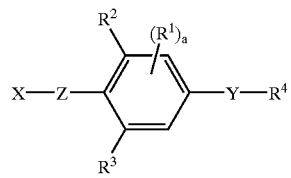

wherein $R^1$, $R^2$, and $R^3$ are independently halogen, $C_1$–$C_3$ alkyl, $C_1$–$C_3$ halolalkyl, $C_1$–$C_3$ alkoxy, $C_1$–$C_3$ haloalkoxy, nitro, or cyano; $R^4$ is 3,3-dihalogeno-2-propenyl; a is an integer of 0 to 2; Y is oxygen, sulfur, or NH; Z is oxygen, sulfur, or $NR^5$ wherein $R^5$ is hydrogen, acetyl, or $C_1$–$C_3$ alkyl; and X is of formula (2)

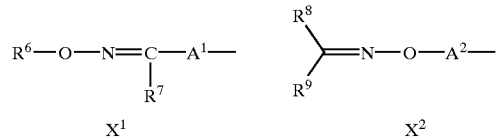

insecticidal/acaricidal agents containing them as active ingredients; and intermediates for their production.

42 Claims, No Drawings

OXIME COMPOUNDS, THEIR USE, AND INTERMEDIATES FOR THEIR PRODUCTION

This application is a divisional of co-pending application Ser. No. 09/402,199 filed on Oct. 1, 1999, and for which priority is claimed under 35 U.S.C. §120, application Ser. No. 09/402,199 is the national phase of PCT International Application No. PCT/JP98/01342 filed on Mar. 26, 1998 under 35 U.S.C. §371. The entire contents of each of the above-identified applications are hereby incorporated by reference. This application also claims priority of application Nos. 089831/1997; 245892/1997; and 247400/1997 filed in Japan on Apr. 8, 1997; Aug. 6, 1997; and Aug. 7, 1997, respectively under 35 U.S.C. §119.

TECHNICAL FIELD

The present invention relates to oxime compounds, their use, and intermediates for their production.

BACKGROUND ART

As disclosed, for example, in JP-A 61-72733 and JP-A 61-260054, it is well known that certain types of oxime compounds can be used as the active ingredients of insecticides. These compounds are, however, not necessarily satisfactory for the active ingredients of insecticidal/acaricidal agents in view of their insecticidal activity.

DISCLOSURE OF THE INVENTION

Under these circumstances, the present inventors have extensively studied to find out compounds with excellent insecticidal/acaricidal activity. As a result, they have found that oxime compounds of formula (1) as depicted below have excellent insecticidal/acaricidal activity, thereby completing the present invention.

Thus, the present invention provides oxime compounds of formula (1)

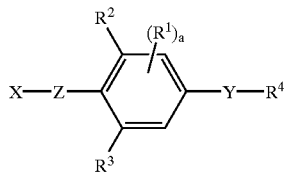

(hereinafter referred to as the present compound(s)) wherein:
$R^1$, $R^2$, and $R^3$ are independently halogen, $C_1$–$C_3$ alkyl, $C_1$–$C_3$ haloalkyl, $C_1$–$C_3$ alkoxy, $C_1$–$C_3$ haloalkoxy, nitro, or cyano;
$R^4$ is 3,3-dihalogeno-2-propenyl;
a is an integer of 0 to 2;
Y is oxygen, sulfur, or NH;
Z is oxygen, sulfur, or $NR^5$ wherein $R^5$ is hydrogen, acetyl, or $C_1$–$C_3$ alkyl;
X is $X^1$ or $X^2$ of formula (2)

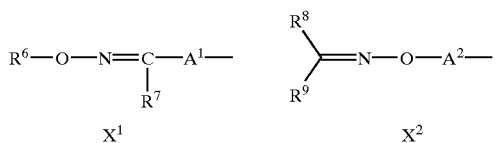

wherein:
$R^6$ is hydrogen, $C_1$–$C_8$ alkyl, $C_2$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, or triphenylmethyl,
or $C_3$–$C_7$ cycloalkyl optionally substituted with $C_1$–$C_4$ alkyl,
or $C_4$–$C_{10}$ cycloalkylalkyl optionally substituted with $C_1$–$C_4$ alkyl on the ring thereof,
or $C_5$–$C_6$ cycloalkenyl optionally substituted with $C_1$–$C_4$ alkyl,
or $C_6$–$C_8$ cycloalkenylalkyl optionally substituted with $C_1$–$C_4$ alkyl on the ring thereof,
or $C_1$–$C_6$ alkyl substituted with cyano, nitro, ($C_1$–$C_4$ alkoxy)carbonyl, $C_1$–$C_4$ alkylthio, or $C_1$–$C_4$ alkoxy,
or $T^1$-1, $T^1$-2, $T^1$-3, $T^1$-4, $T^1$-5, $T^1$-6, or $T^1$-7 of formula (3)

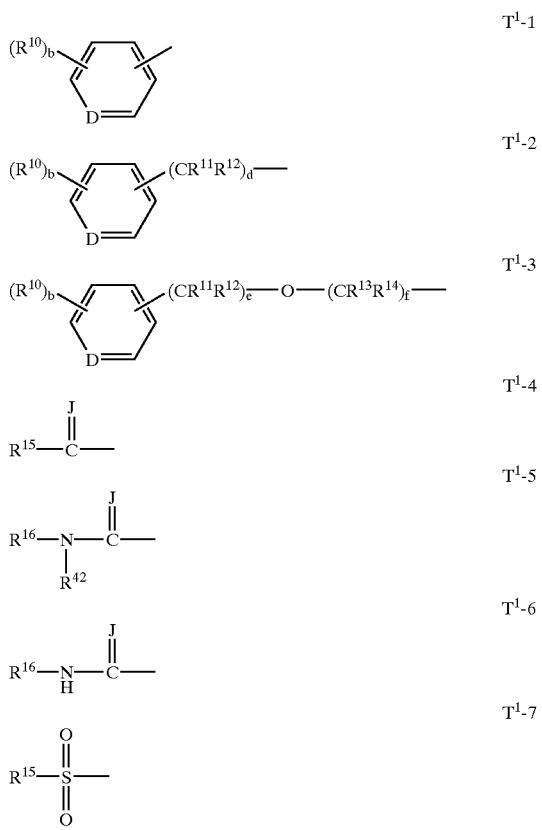

wherein:
$(R^{10})_b$'s are zero to five identical or different substituents selected from halogen, $C_1$–$C_6$ alkyl, $C_1$–$C_3$ haloalkyl, $C_2$–$C_6$ alkenyl, $C_2$–$C_6$ haloalkenyl, $C_2$–$C_6$ alkynyl, $C_2$–$C_6$ haloalkynyl, $C_1$–$C_6$ alkoxy, $C_1$–$C_3$ haloalkoxy, $C_3$–$C_6$ alkenyloxy, $C_3$–$C_6$ haloalkenyloxy, $C_3$–$C_6$ alkynyloxy; $C_3$–$C_6$ haloalkynyloxy, ($C_1$–$C_5$ alkoxy)carbonyl, cyano, or nitro;

$R^{11}$, $R^{12}$, $R^{13}$, and $R^{14}$ are independently hydrogen, $C_1$–$C_3$ alkyl, or trifluoromethyl;

D is —CH= or nitrogen;

J is oxygen or sulfur;

b is an integer of 0 to 5;

d is an integer of 1 to 3;

e is an integer of 0 to 3;

f is an integer of 2 to 4;

$R^{15}$ is $C_1$–$C_6$ alkyl, $C_1$–$C_3$ haloalkyl, $C_2$–$C_6$ alkenyl, or $C_3$–$C_6$ cycloalkyl, or phenyl optionally substituted with halogen, $C_1$–$C_4$ alkyl, $C_1$–$C_3$ haloalkyl, $C_1$–$C_4$ alkoxy, or $C_1$–$C_3$ haloalkoxy; and $R^{16}$ and $R^{42}$ are independently $C_1$–$C_6$ alkyl, $C_2$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, or $C_3$–$C_6$ cycloalkyl, or phenyl optionally substituted with halogen, $C_1$–$C_4$ alkyl, $C_1$–$C_3$ haloalkyl, $C_1$–$C_4$ alkoxy, or $C_1$–$C_3$ haloalkoxy, or benzyl optionally substituted with halogen, $C_1$–$C_4$ alkyl, $C_1$–$C_3$ haloalkyl, $C_1$–$C_4$ alkoxy, or $C_1$–$C_3$ haloalkoxy on the ring thereof;

$R^7$ is hydrogen, $C_1$–$C_6$ alkyl, $C_1$–$C_3$ haloalkyl, $C_3$–$C_6$ cycloalkyl, cyano, cyano $C_1$–$C_3$ alkyl, ($C_1$–$C_4$ alkoxy)carbonyl, or ($C_1$–$C_4$ alkoxy)carbonyl ($C_1$–$C_3$)alkyl, or phenyl optionally substituted with halogen, $C_1$–$C_4$ alkyl, $C_1$–$C_3$ haloalkyl, $C_1$–$C_3$ alkoxy, or $C_1$–$C_3$ haloalkoxy, or benzyl optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof;

$R^8$ and $R^9$ are independently hydrogen, $C_1$–$C_{11}$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_{10}$ alkoxyalkyl, $C_2$–$C_{10}$ alkylthioalkyl, or naphthyl, or $C_3$–$C_7$ cycloalkyl optionally substituted with $C_1$–$C_4$ alkyl, or $C_4$–$C_{10}$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ on the ring thereof, or $T^2$-1 or $T^2$-2 of formula (4)

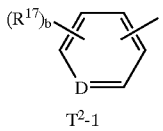 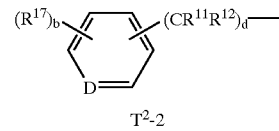

wherein:

($R^{17}$)$_b$'s are zero to five identical or different substituents selected from halogen, $C_1$–$C_6$ alkyl, $C_1$–$C_3$ haloalkyl, $C_2$–$C_6$ alkenyl, $C_2$–$C_6$ haloalkenyl, $C_2$–$C_6$ alkynyl, $C_2$–$C_6$ haloalkynyl, $C_1$–$C_6$ alkoxy, $C_1$–$C_3$ haloalkoxy, $C_3$–$C_6$ alkenyloxy, $C_3$–$C_6$ haloalkenyloxy, $C_3$–$C_6$ alkynyloxy, $C_3$–$C_6$ haloalkynyloxy, $C_1$–$C_3$ alkylthio, $C_1$–$C_3$ haloalkylthio, $C_1$–$C_2$ alkylsulfinyl, $C_1$–$C_2$ alkylsulfonyl, $C_1$–$C_2$ haloalkylsulfinyl, $C_1$–$C_2$ haloalkylsulfonyl, $C_1$–$C_3$ hydroxyalkyl, $C_2$–$C_4$ alkoxyalkyl, $C_2$–$C_4$ alkylthioalkyl, dimethylamino, acetamido, acetyl, formyl, carboxyl, ($C_1$–$C_2$ alkyl)aminocarbonyl, [di($C_1$–$C_2$ alkyl)amino]carbonyl, ($C_1$–$C_6$ alkoxy)carbonyl, $C_3$–$C_6$ cycloalkyl, $C_5$–$C_6$ cycloalkenyl, $C_3$–$C_6$ cycloalkyloxy, $C_5$–$C_6$ cycloalkenyloxy, pentafluorosulfanyl ($F_5S$), cyano, or nitro, or phenyl optionally substituted with halogen, $C_1$–$C_4$ alkyl, $C_1$–$C_3$ haloalkyl, $C_1$–$C_3$ alkoxy, or $C_1$–$C_3$ haloalkoxy, or phenoxy optionally substituted with halogen, $C_1$–$C_4$ alkyl, $C_1$–$C_3$ haloalkyl, $C_1$–$C_3$ alkoxy, or $C_1$–$C_3$ haloalkoxy, or benzyl optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof, or benzyloxy optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof, or when b is 2 to 5, two adjacent $R^{17}$'s are combined together at their ends to form trimethylene or tetramethylene, or when b is 2 to 5, two adjacent $R^{17}$'s are combined together at their ends to form methylenedioxy optionally substituted with halogen or $C_1$–$C_3$ alkyl, or when b is 2 to 5, two adjacent $R^{17}$'s are combined together at their ends to form ethylenedioxy optionally substituted with halogen or $C_1$–$C_3$ alkyl;

D is —CH= or nitrogen;

$R^{11}$ and $R^{12}$ are independently hydrogen, $C_1$–$C_3$ alkyl, or trifluoromethyl;

b is an integer of 0 to 5; and d is an integer of 1 to 3;

or a heterocyclic group, exclusive of pyridine ring, which heterocyclic group may be optionally substituted with one to three identical or different ($R^{18}$)$_g$'s, wherein:

$R^{18}$ is halogen, $C_1$–$C_6$ alkyl, $C_1$–$C_3$ haloalkyl, $C_2$–$C_6$ alkenyl, $C_2$–$C_6$ haloalkenyl, $C_2$–$C_6$ alkynyl, $C_2$–$C_6$ haloalkynyl, $C_1$–$C_6$ alkoxy, $C_1$–$C_3$ haloalkoxy, $C_3$–$C_6$ alkenyloxy, $C_3$–$C_6$ haloalkenyloxy, $C_3$–$C_6$ alkynyloxy, $C_3$–$C_6$ haloalkynyloxy, $C_1$–$C_3$ alkylthio, $C_1$–$C_3$ haloalkylthio, $C_1$–$C_2$ alkylsulfinyl, $C_1$–$C_2$ alkylsulfonyl, $C_1$–$C_2$ haloalkylsulfinyl, $C_1$–$C_2$ haloalkylsulfonyl, $C_1$–$C_3$ hydroxyalkyl, $C_2$–$C_4$ alkoxyalkyl, $C_2$–$C_4$ alkylthioalkyl, cyano, or nitro, or phenyl optionally substituted with halogen, $C_1$–$C_4$ alkyl, $C_1$–$C_3$ haloalkyl, $C_1$–$C_3$ alkoxy, or $C_1$–$C_3$ haloalkoxy; and g is an integer of 1 to 3;

or $R^8$ and $R^9$ are combined together at their ends to form a saturated or unsaturated 5- or 6-membered ring containing zero to two oxygen or sulfur atoms in the ring;

$A^1$ is $A^1$-1, $A^1$-2, $A^1$-3, $A^1$-4, $A^1$-5, $A^1$-6, $A^1$-7, $A^1$-8, $A^1$-9, $A^1$-10, $A^1$-11, or $A^1$-12 of formula (5)

$A^1$-1: —$(CR^{19}=CR^{20})_h$—$(CR^{21}R^{22})_i$—

$A^1$-2: —$(CR^{19}=CR^{20})_h$—$(CR^{21}R^{22})_j$—$Q^1$—$(CR^{23}R^{24})_k$—

$A^1$-3: —$(CR^{19}=CR^{20})_h$—$(CR^{21}R^{22})_j$—$Q^1$—$(CR^{23}R^{24})_m$—$CR^{25}=CR^{26}$—$(CR^{27}R^{28})_n$—

$A^1$-4: —$(CR^{19}=CR^{20})_h$—$(CR^{21}R^{22})_j$—$Q^1$—$(CR^{23}R^{24})_m$—C≡C—$(CR^{25}R^{26})_n$—

$A^1$-5: —$(CR^{19}=CR^{20})_h$—$(CR^{21}R^{22})_j$—$Q^1$—$(CR^{23}R^{24})_p$—E—$(CR^{25}R^{26})_q$—

$A^1$-6: —$(CR^{19}=CR^{20})_h$—$(CR^{21}R^{22})_j$—$Q^1$—$(CR^{23}R^{24})_r$—$Q^2$—$(CR^{25}R^{26})_s$—

A$^1$-7: —U$^1$—(CR$^{19}$R$^{20}$)$_t$—(CR$^{23}$=CR$^{24}$)$_h$—(CR$^{25}$R$^{26}$)$_u$—(CR$^{27}$=CR$^{28}$)$_p$—(CR$^{29}$R$^{30}$)$_j$—

A$^1$-8: —U$^2$—(CR$^{19}$R$^{20}$)$_j$—(CR$^{23}$=CR$^{24}$)$_h$—(CR$^{25}$R$^{26}$)$_u$—(CR$^{27}$=CR$^{28}$)$_p$—(CR$^{29}$R$^{30}$)$_v$—

A$^1$-9: —U$^1$—(CR$^{19}$R$^{20}$)$_t$—(CR$^{23}$=CR$^{24}$)$_h$—(CR$^{25}$R$^{26}$)$_j$—Q$^1$—(CR$^{27}$R$^{28}$)$_v$—(CR$^{29}$=CR$^{30}$)$_p$—(CR$^{31}$R$^{32}$)$_w$—

A$^1$-10: —U$^2$—(CR$^{19}$R$^{20}$)$_j$—(CR$^{23}$=CR$^{24}$)$_h$—(CR$^{25}$R$^{26}$)$_v$—Q$^1$—(CR$^{27}$R$^{28}$)$_w$—(CR$^{29}$=CR$^{30}$)$_p$—(CR$^{31}$R$^{32}$)$_x$—

A$^1$-11: —U$^1$—(CR$^{19}$R$^{20}$)$_t$—Q$^1$—(CR$^{23}$R$^{24}$)$_h$—E—(CR$^{25}$R$^{26}$)$_p$—

A$^1$-12: —U$^1$—(CR$^{19}$R$^{20}$)$_t$—Q$^1$—(CR$^{23}$R$^{24}$)$_j$—C≡C—(CR$^{25}$R$^{26}$)$_m$— wherein:

$R^{19}$, $R^{20}$, $R^{21}$, $R^{23}$, $R^{24}$, $R^{25}$, $R^{26}$, $R^{27}$, $R^{28}$, $R^{29}$, $R^{30}$, $R^{31}$, and $R^{32}$ are independently hydrogen, $C_1$–$C_3$ alkyl, or trifluoromethyl;

$R^{22}$ is hydrogen, $C_1$–$C_3$ alkyl, or trifluoromethyl, or when h is 0 and i is 1 in A$^1$-1, $R^{22}$ and $R^7$ may be combined together at their ends to form trimethylene, tetramethylene, or pentamethylene, each of which may be optionally substituted with $C_1$–$C_3$ alkyl, or when h is 0 and j is 1, in A$^1$-2, A$^1$-3, A$^1$-4, A$^1$-5, or A$^1$-6, $R^{22}$ and $R^7$ may be combined together at their ends to form trimethylene, tetramethylene, or pentamethylene, each of which may be optionally substituted with $C_1$–$C_3$ alkyl;

h is an integer of 0 or 1;
i is an integer of 1 to 6;
j is an integer of 1 to 3;
k is an integer of 2 to 8;
m is an integer of 1 to 3;
n is an integer of 1 to 3;
p is an integer of 0 or 1;
q is an integer of 0 or 1;
r is an integer of 2 to 4;
s is an integer of 2 to 4;
t is an integer of 0 to 3;
u is an integer of 0 to 3;
v is an integer of 1 to 4;
w is an integer of 1 to 4;
x is an integer of 2 to 4;

$Q^1$ is oxygen, $S(O)_y$, or $NR^{33}$ wherein $R^{33}$ is hydrogen or $C_1$–$C_3$ alkyl, and y is an integer of 0 to 2;

$Q^2$ is oxygen, $S(O)_z$, or $NR^{34}$ wherein $R^{34}$ is hydrogen or $C_1$–$C_3$ alkyl, and z is an integer of 0 to 2;

E is $C_5$–$C_6$ cycloalkylene;
$U^1$ is $U^1$ of formula (6)

—G$^1$—W— wherein:
W is an optionally substituted benzene ring or an optionally substituted heterocyclic ring;
$G^1$ is $G^1$-1 or $G^1$-2 of formula (7)

G$^1$-1: —(CR$^{35}$R$^{36}$)$_{a1}$—

G$^1$-2: —(CR$^{35}$R$^{36}$)$_{b1}$—Q$^2$—(CR$^{37}$R$^{38}$)$_{d1}$— wherein:
$Q^2$ is oxygen, $S(O)_z$, or $NR^{34}$ wherein $R^{34}$ is hydrogen or $C_1$–$C_3$ alkyl, and z is an integer of 0 to 2;

$R^{35}$, $R^{36}$, $R^{37}$, and $R^{38}$ are independently hydrogen, $C_1$–$C_3$ alkyl, or trifluoromethyl;
a1 is an integer of 0 to 4;
b1 is an integer of 1 to 3; and
d1 is an integer of 0 to 2;
$U^2$ is $U^2$ of formula (8)

—G$^1$—W—G$^2$— wherein:
W is an optionally substituted benzene ring or an optionally substituted heterocyclic ring;
$G^1$ is $G^1$-1 or $G^1$-2 of formula (7)

G$^1$-1: —(CR$^{35}$R$^{36}$)$_{a1}$—

G$^1$-2: —(CR$^{35}$R$^{36}$)$_{b1}$—Q$^2$—(CR$^{37}$R$^{38}$)$_{d1}$ wherein:
is oxygen, $S(O)_z$, or $NR^{34}$ wherein $R^{34}$ is hydrogen or $C_1$–$C_3$ alkyl, and z is an integer of 0 to 2;
$R^{35}$, $R^{36}$, $R^{37}$, and $R^{38}$ are independently hydrogen, $C_1$–$C_3$ alkyl, or trifluoromethyl;
a1 is an integer of 0 to 4;
b1 is an integer of 1 to 3; and
d1 is an integer of 0 to 2; and
$G^2$ is oxygen, $S(O)_{e1}$, or $NR^{39}$ wherein $R^{39}$ is hydrogen or $C_1$–$C_3$ alkyl, and e1 is an integer of 0 to 2;

A$^2$ is A$^2$-1, A$^2$-2, A$^2$-3, A$^2$-4, A$^2$-5, A$^2$-6, A$^2$-7, A$^2$-7, A$^2$-8, A$^2$-9, or A$^2$-10, of formula (9)

A$^2$-1: —(CR$^{19}$R$^{20}$)$_j$—(CR$^{23}$=CR$^{24}$)$_h$—(CR$^{25}$R$^{26}$)$_t$—(CR$^{27}$=CR$^{28}$)$_p$—(CR$^{29}$R$^{30}$)$_m$—

A$^2$-2: —(CR$^{19}$R$^{20}$)$_j$—(CR$^{23}$=CR$^{24}$)$_h$—(CR$^{25}$R$^{26}$)$_m$—Q$^1$—CR$^{27}$R$^{28}$)$_n$—(CR$^{29}$=CR$^{30}$)$_p$—(CR$^{31}$R$^{32}$)$_{f1}$—

A$^2$-3: —U$^3$—(CR$^{19}$R$^{20}$)$_t$—(CR$^{23}$=CR$^{24}$)$_h$—(CR$^{25}$R$^{26}$)$_u$—(CR$^{27}$=CR$^{28}$)$_p$—(CR$^{29}$R$^{30}$)$_j$—

A$^2$-4: —U$^4$—(CR$^{19}$R$^{20}$)$_j$—(CR$^{23}$=CR$^{24}$)$_h$—(CR$^{25}$R$^{26}$)$_t$—(CR$^{27}$=CR$^{28}$)$_p$—(CR$^{29}$R$^{30}$)$_m$—

A$^2$-5: —U$^3$—(CR$^{19}$R$^{20}$)$_t$—(CR$^{23}$=CR$^{24}$)$_h$—(CR$^{25}$R$^{26}$)$_j$—Q$^1$—(CR$^{27}$R$^{28}$)$_m$—(CR$^{29}$=CR$^{30}$)$_p$—(CR$^{31}$R$^{32}$)$_n$—

A$^2$-6: —U$^4$—(CR$^{19}$R$^{20}$)$_j$—(CR$^{23}$=CR$^{24}$)$_h$—(CR$^{25}$R$^{26}$)$_m$—Q$^1$—(CR$^{27}$R$^{28}$)$_n$—(CR$^{29}$=CR$^{30}$)$_p$—(CR$^{31}$R$^{32}$)$_{f1}$—

A$^2$-7: —U$^3$—(CR$^{19}$R$^{20}$)$_t$—Q$^1$—(CR$^{23}$R$^{24}$)$_h$—E—(CR$^{25}$R$^{26}$)$_p$—

A$^2$-8: —U$^3$—(CR$^{19}$R$^{20}$)$_t$—Q$^1$—(CR$^{23}$R$^{24}$)$_j$—C≡C—(CR$^{25}$R$^{26}$)$_m$—

A$^2$-9: —(CR$^{19}$R$^{20}$)$_h$—E—(CR$^{23}$R$^{24}$)$_p$—

A$^2$-10: —(CR$^{19}$R$^{20}$)$_j$—C≡—C—(CR$^{23}$R$^{24}$)$_m$— wherein:
$R^{19}$, $R^{20}$, $R^{23}$, $R^{24}$, $R^{25}$, $R^{26}$, $R^{27}$, $R^{28}$, $R^{29}$, $R^{30}$, $R^{31}$, and $R^{32}$ are independently hydrogen, $C_1$–$C_3$ alkyl, or trifluoromethyl;

h is an integer of 0 or 1;
j is an integer of 1 to 3;
m is an integer of 1 to 3;
n is an integer of 1 to 3;
p is an integer of 0 or 1;
t is an integer of 0 to 3;
u is an integer of 0 to 3;
f1 is an integer of 1 to 3;

$Q^1$ is oxygen, $S(O)_y$, or $NR^{33}$ wherein $R^{33}$ is hydrogen or $C_1$–$C_3$ alkyl, and y is an integer of 0 to 2;

E is $C_5$–$C_6$ cycloalkylene;

$U^3$ is $U^3$-1, $U^3$-2, or $U^3$-3 of formula (10)

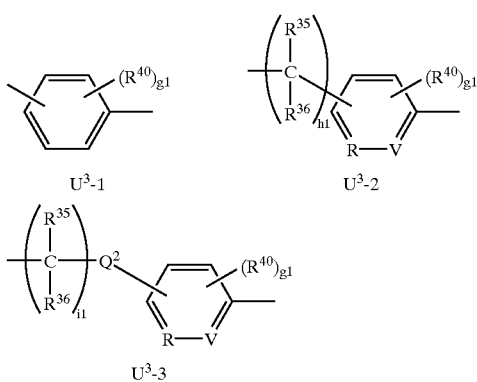

wherein:
$R^{35}$ and $R^{36}$ are independently hydrogen, $C_1$–$C_3$ alkyl, or trifluoromethyl;
$(R^{40})_{g1}$'s are zero to four identical or different substituents selected from halogen, $C_1$–$C_4$ alkyl, $C_1$–$C_3$ haloalkyl, $C_1$–$C_3$ alkoxy, or $C_1$–$C_3$ haloalkoxy;
R and V are independently —CH= or nitrogen;
g1 is an integer of 0 to 4;
h1 is an integer of 1 to 3;
i1 is an integer of 2 or 3; and
$Q^2$ is oxygen, $S(O)_z$, or $NR^{34}$ wherein $R^{34}$ is hydrogen or $C_1$–$C_3$ alkyl, and z is an integer of 0 to 2; $U^4$ is $U^4$-1, $U^4$-2, or $U^4$-3 of formula (11)

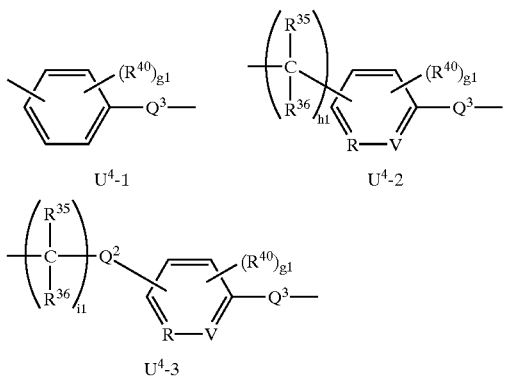

wherein:
$R^{35}$ and $R^{36}$ are independently hydrogen, $C_1$–$C_3$ alkyl, or trifluoromethyl;
$(R^{40})_{g1}$'s are zero to four identical or different substituents selected from halogen, $C_1$–$C_4$ alkyl, $C_1$–$C_3$ haloalkyl, $C_1$–$C_3$ alkoxy, or $C_1$–$C_3$ haloalkoxy;
R and V are independently —CH= or nitrogen;
g1 is an integer of 0 to 4;
h1 is an integer of 1 to 3;
i1 is an integer of 2 or 3;
$Q^2$ is oxygen, $S(O)_z$, or $NR^{34}$ wherein $R^{34}$ is hydrogen or $C_1$–$C_3$ alkyl, and z is an integer of 0 to 2; and
$Q^3$ is oxygen, $S(O)_{e1}$, or $NR^{39}$ wherein $R^{39}$ is hydrogen or $C_1$–$C_3$ alkyl, and e1 is an integer of 0 to 2; and insecticidal/acaricidal agents containing them as active ingredients.

In particular, the oxime compounds of formula (1) wherein X is $X^1$ and $R^6$ is hydrogen are useful both as the active ingredients of insecticidal/acaricidal agents and as the intermediates for the production of these active ingredient compounds.

The present invention further provides hydroxylamine compounds of formula (12)

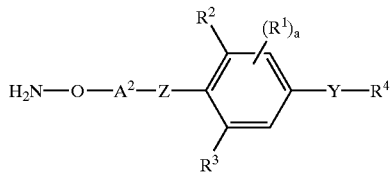

wherein $R^1$, $R^2$, $R^3$, $R^4$, a, Y, Z, and $A^2$ are as defined above, and salts thereof (e.g., inorganic acid salts such as hydrochlorides, sulfates, and nitrates).

The present invention further provides compounds of formula (13)

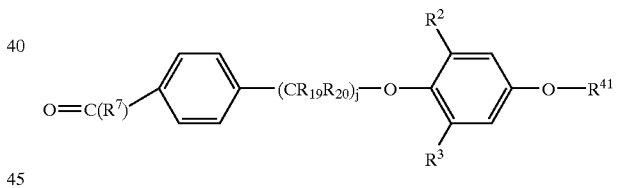

wherein $R^2$, $R^3$, $R^7$, $R^{19}$, $R_{20}$, and j are as defined above, and $R^{41}$ is 3,3-dichloro-2-propenyl, 3,3-dibromo-2-propenyl, or 3-bromo-3-chloro-2-propenyl, which are useful as the intermediates for the production of the present compounds.

The present invention further provides compounds of formula (14)

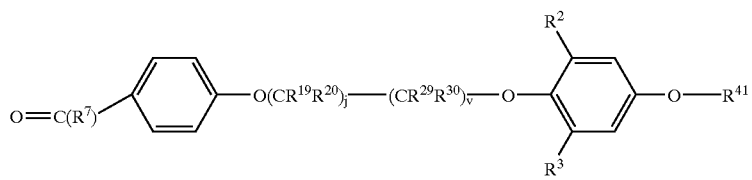

wherein $R^2$, $R^3$, $R^7$, $R^{19}$, $R^{20}$, $R^{29}$, $R^{30}$, $R^{41}$, j, and v are as defined above, which are useful as the intermediates for the production of the present compounds.

The present invention further provides phenol compounds of formula (50)

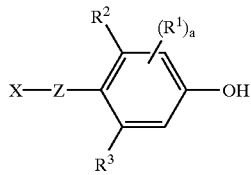

wherein $R^1$, $R^2$, $R^3$, a, X, and Z are as defined above, with the proviso that when X is $X^1$, $R^6$ is not hydrogen, which are useful as the intermediates for the production of the present compounds.

MODE FOR CARRYING OUT THE INVENTION

The halogen represented by $R^1$, $R^2$, $R^3$, $R^{10}$, $R^{17}$, $R^{18}$, or $R^{40}$ may include fluorine, chlorine, bromine, and iodine.

The $C_1$–$C_3$ alkyl represented by $R^1$, $R^2$, $R^3$, $R^5$, $R^{11}$, $R^{12}$, $R^{13}$, $R^{14}$, $R^{19}$, $R^{20}$, $R^{21}$, $R^{22}$, $R^{23}$, $R^{24}$, $R^{25}$, $R^{26}$, $R^{27}$, $R^{28}$, $R^{29}$, $R^{30}$, $R^{31}$, $R^{32}$, $R^{33}$, $R^{34}$, $R^{35}$, $R^{36}$, $R^{37}$, $R^{38}$, or $R^{39}$ may include methyl, ethyl, n-propyl, and isopropyl.

The $C_1$–$C_8$ alkyl represented by $R^6$ may include, for example, methyl, ethyl, n-propyl, isopropyl, n-butyl, isobutyl, sec-butyl, tert-butyl, n-pentyl, isopentyl, neopentyl, tert-pentyl, 1-ethylpropyl, n-hexyl, isohexyl, 2-ethylbutyl, 1-methylpentyl, 1-ethylbutyl, 3-methylpentyl, 1,3-dimethylbutyl, n-heptyl, 1-ethyl-1-methylbutyl, n-octyl, and 1-methylheptyl.

The $C_1$–$C_6$ alkyl represented by $R^7$, $R^{10}$, $R^{15}$, $R^{16}$, $R^{42}$, $R^{17}$, or $R^{18}$ may include, for example, methyl, ethyl, n-propyl, isopropyl, n-butyl, isobutyl, sec-butyl, tert-butyl, n-pentyl, isopentyl, neopentyl, tert-pentyl, 1-ethylpropyl, n-hexyl, isohexyl, 2-ethylbutyl, 1-methylpentyl, 1-ethylbutyl, 3-methylpentyl, and 1,3-dimethylbutyl.

The $C_1$–$C_{11}$ alkyl represented by $R^8$ or $R^9$ may include, for example, methyl, ethyl, n-propyl, isopropyl, n-butyl, isobutyl, sec-butyl, tert-butyl, n-pentyl, isopentyl, neopentyl, tert-pentyl, 1-ethylpropyl, n-hexyl, isohexyl, 2-ethylbutyl, 1-methylpentyl, 1-ethylbutyl, 3-methylpentyl, 1,3-dimethylbutyl, n-heptyl, 1-ethyl-1-methylbutyl, n-octyl, 1-methylheptyl, n-nonyl, n-decyl, and n-undecyl.

The $C_1$–$C_4$ alkyl represented by $R^{40}$ may include methyl, ethyl, n-propyl, isopropyl, n-butyl, isobutyl, sec-butyl, and tert-butyl.

The $C_1$–$C_3$ haloalkyl represented by $R^1$, $R^2$, $R^3$, $R^7$, $R^{10}$, $R^{15}$, $R^{17}$, $R^{18}$, or $R^{40}$ may include, for example, trifluoromethyl, difluoromethyl, bromodifluoromethyl, 1-fluoroethyl, 1-chloroethyl, 1-bromoethyl, perfluoroethyl, 2-bromo-1,1,2,2-tetrafluoroethyl, 1,1,2,2-tetrafluoroethyl, 2-chloro-1,1,2-trifluoroethyl, 2-bromo-1,1,2-trifluoroethyl, 2,2,2-trifluoroethyl, 2,2,2-trichloroethyl, 2,2,2-tribromoethyl, 2-fluoroethyl, 2-chloroethyl, 2-bromoethyl, 2-iodoethyl, 2,2-difluoroethyl, 2,2-dichloroethyl, 2,2-dibromoethyl, 3-fluoropropyl, 3-chloropropyl, 3-bromopropyl, 3-iodopropyl, 3,3,3-trifluoropropyl, 2,2,2,3,3,3-hexafluoropropyl, 1,1,1,3,3,3-hexafluoro-2-propyl, 2-fluoropropyl, 2-chloropropyl, 2-bromopropyl, 2-iodopropyl, and 2,3-dibromopropyl.

The $C_2$–$C_6$ haloalkyl represented by $R^6$, $R^{16}$, or $R^{42}$ may include, for example, 2,2,2-trifluoroethyl, 2,2,2-trichloroethyl, 2,2,2-tribromoethyl, 2-fluoroethyl, 2-chloroethyl, 2-bromoethyl, 2-iodoethyl, 2,2-difluoroethyl, 2,2-dichloroethyl, 2,2-dibromoethyl, 3-fluoropropyl, 3-chloropropyl, 3-bromopropyl, 3-iodopropyl, 3,3,3-trifluoropropyl, 2,2,2,3,3,3-hexafluoropropyl, 1,1,1,3,3,3-hexafluoro-2-propyl, 2-fluoropropyl, 2-chloropropyl, 2-bromopropyl, 2-iodopropyl, 2,3-dibromopropyl, 4-fluorobutyl, 4-chlorobutyl, 4-bromobutyl, 4-iodobutyl, 3-chloro-2,2-dimethylpropyl, 3-bromo-2,2-dimethylpropyl, 2,2,3,3,4,4,5,5-octafluoropentyl, 6-chlorohexyl, and 6-bromohexyl.

The $C_1$–$C_6$ haloalkyl represented by $R^8$ or $R^9$ may include, for example, trifluoromethyl, trichloromethyl, difluoromethyl, bromodifluoromethyl, 2,2,2-trifluoroethyl, 2,2,2-trichloroethyl, 2,2,2-tribromoethyl, 2-fluoroethyl, 2-chloroethyl, 2-bromoethyl, 2-iodoethyl, 2,2-difluoroethyl, 2,2-dichloroethyl, 2,2-dibromoethyl, 3-fluoropropyl, 3-chloropropyl, 3-bromopropyl, 3-iodopropyl, 3,3,3-trifluoropropyl, 2,2,2,3,3,3-hexafluoropropyl, 1,1,1,3,3,3-hexafluoro-2-propyl, 2-fluoropropyl, 2-chloropropyl, 2-bromopropyl, 2-iodopropyl, 2,3-dibromopropyl, 4-fluorobutyl, 4-chlorobutyl, 4-bromobutyl, 4-iodobutyl, 3-chloro-2,2-dimethylpropyl, 3-bromo-2,2-dimethylpropyl, 2,2,3,3,4,4,5,5-octafluoropentyl, 6-chlorohexyl, and 6-bromohexyl.

The $C_1$–$C_3$ alkoxy represented by $R^1$, $R^2$, $R^3$, or $R^{40}$ may include methoxy, ethoxy, n-propyloxy, and isopropyloxy.

The $C_1$–$C_6$ alkoxy represented by $R^{10}$, $R^{17}$, and $R^{18}$ may include, for example, methoxy, ethoxy, n-propyloxy, isopropyloxy, n-butyloxy, isobutyloxy, sec-butyloxy, tert-butyloxy, n-pentyloxy, isopentyloxy, neopentyloxy, tertpentyloxy, 1-ethylpropyloxy, n-hexyloxy, isohexyloxy, 2-ethylbutyloxy, 1-methylpentyloxy, 1-ethylbutyloxy, 3-methylpentyloxy, and 1,3-diemthylbutyloxy.

The $C_1$–$C_3$ haloalkoxy represented by $R^1$, $R^2$, $R^3$, $R^{10}$, $R^{17}$, $R^{18}$, or $R^{40}$ may include, for example, trifluoromethoxy, bromodifluoromethoxy, 1-fluoroethoxy, 1-chloroethoxy, 1-bromoethoxy, perfluoroethoxy, 2-bromo-1,1,2,2-tetrafluoroethoxy, 1,1,2,2-tetrafluoroethoxy, 2-chloro-1,1,2-trifluoroethoxy, 2-bromo-1,1,2-trifluoroethoxy, 2,2,2-trifluoroethoxy, 2,2,2-trichloroethoxyethoxy, 2,2,2-tribromoethoxy, 2-fluoroethoxy, 2-chloroethoxy, 2-bromoethoxy, 2-iodoethoxy, 2,2-difluoroethoxy, 2,2-dichloroethoxy, 2,2-dibromoethoxy, 3-fluoropropyloxy, 3-chloropropyloxy, 3-bromopropyloxy, 3-iodopropyloxy, 3,3,3-trifluoropropyloxy, 2,2,2,3,3,3-hexafluoropropyloxy, 1,1,1,3,3,3-hexafluoro-2-propyloxy, 2-fluoropropyloxy, 2-chloropropyloxy, 2-bromopropyloxy, 2-iodopropyloxy, and 2,3-dibromopropyloxy.

The $C_3$–$C_6$ alkenyl represented by $R^6$, $R^{16}$, or $R^{42}$ may include, for example, allyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1-ethyl-2-propenyl, 2-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, and 4-methyl-4-pentenyl.

The $C_3$–$C_6$ haloalkenyl represented by $R^6$, $R^{16}$, or $R^{42}$ may include, for example, 3-chloro-2-propenyl, 3-bromo-2-propenyl, 2-chloro-2-propenyl, 2-bromo-2-propenyl, 3,3-dichloro-2-propenyl, 3,3-dibromo-2-propenyl, 3,3-difluoro-2-propenyl, 2,3-dichloro-2-propenyl, 2,3-dibromo-2- propenyl, 2-chloromethyl-2-propenyl, 4-chloro-2-butenyl, 3-chloro-4,4,4-trifluoro-2-butenyl, 3-bromo-4,4,4-trifluoro-2-butenyl, 3,4-dichloro-4,4-difluoro-2-butenyl, 3,4,4,4-tetrafluoro-3-butenyl, 4,4-dichloro-3-butenyl, 4,4-dibromo-3-butenyl, 5,5-dichloro-4-pentenyl, 5,5,-dibromo-4-pentenyl, 6,6-dichloro-5-hexenyl, and 6,6-dibormo-5-hexenyl.

The $C_3–C_6$ alkynyl represented by $R^6$, $R^{16}$, or $R^{42}$ may include, for example, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1-ethyl-2-propynyl, 2-hexynyl, 3-hexynyl, 4-hexynyl, 5-hexynyl, 1-ethyl-2-butynyl, 1-ethyl-3-butynyl, and 2-ethyl-3-butynyl.

The $C_3–C_6$ haloalkynyl represented by $R^6$, $R^{16}$, or $R^{42}$ may include, for example, 3-chloro-2-propynyl, 3-bromo-2-propynyl, 4-chloro-2-butynyl, 4-chloro-3-butynyl, 4-bromo-2-butynyl, 4-bromo-3-butynyl, 5-chloro-4-pentynyl, 4-chloro-1-methyl-2-butynyl, 4-chloro-1-methyl-3-butynyl, 4-chloro-2-methyl-3-butynyl, 5-bromo-4-pentynyl, 4-bromo-1-methyl-2-butynyl, 4-bromo-1-methyl-3-butynyl, 4-bromo-2-methyl-3-butynyl, 6-chloro-5-hexynyl, and 6-bromo-5-hexynyl.

The $C_2–C_6$ alkenyl $R^8$, $R^9$, $R^{10}$, $R^{15}$, $R^{17}$, or $R^{18}$ may include, for example, vinyl, 1-propenyl, isopropenyl, 1-butenyl, allyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1-ethyl-2-propenyl, 2-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, and 4-methyl-4-pentenyl.

The $C_2–C_6$ haloalkenyl represented by $R^8$, $R^9$, $R^{10}$, $R^{17}$, or $R^{18}$ may include, for example, 2-chloroethenyl, 2-bromoethenyl, 2,2-dichloroethenyl, 2,2-dibromoethenyl, 3-chloro-2-propenyl, 3-bromo-2-propenyl, 2-chloro-2-propenyl, 2-bromo-2-propenyl, 3,3-dichloro-2-propenyl, 3,3-dibromo-2-propenyl, 3,3-difluoro-2-propenyl, 2,3-dichloro-2-propenyl, 2,3-dibromo-2-propenyl, 2-chloromethyl-2-propenyl, 4-chloro-2-butenyl, 3-chloro-4,4,4-trifluoro-2-butenyl, 3-bromo-4,4,4-trifluoro-2-butenyl, 3,4-dichloro-4,4-difluoro-2-butenyl, 3,4,4,4-tetrafluoro-2-butenyl, 4,4-dichloro-3-butenyl, 4,4-dibromo-3-butenyl, 5,5-dichloro-4-pentenyl, 5,5-dibromo-4-pentenyl, 6,6-dichloro-5-hexenyl, and 6,6-dibromo-5-hexenyl.

The $C_2–C_6$ alkynyl represented by $R^8$, $R^9$, $R^{10}$, $R^{17}$, or $R^{18}$ may include, for example, ethynyl, 1-propynyl, 1-butynyl, 2-propynyl, 2-butynyl, 3-butynyl, 1-methyl-2-propynyl, 2-pentynyl, 3-pentynyl, 4-pentynyl, 1-methyl-2-butynyl, 1-methyl-3-butynyl, 2-methyl-3-butynyl, 1-ethyl-2-propynyl, 2-hexynyl, 3-hexynyl, 4-hexynyl, 5-hexynyl, 1-ethyl-2-butynyl, 1-ethyl-3-butynyl, and 2-methyl-3-butynyl.

The $C_2–C_6$ haloalkynyl represented by $R^8$, $R^9$, $R^{10}$, $R^{17}$, or $R^{18}$ may include, for example, 2-chloroethynyl, 2-bromoethynyl, 3-chloro-2-propynyl, 3-bromo-2-propynyl, 4-chloro-2-butynyl, 4-chloro-3-butynyl, 4-bromo-2-butynyl, 4-bromo-3-butynyl, 5-chloro-4-pentynyl, 4-chloro-1-methyl-2-butynyl, 4-chloro-1-methyl-3-butynyl, 4-chloro-2-methyl-3-butynyl, 5-bromo-4-pentynyl, 4-bromo-1-methyl-2-butynyl, 4-bromo-1-methyl-3-butynyl, 4-bromo-2-methyl-3-butynyl, 6-chloro-5-hexynyl, and 6-bromo-5-hexynyl The $C_3–C_6$ cycloalkyl represented by $R^7$, $R^{15}$, $R^{16}$, $R^{17}$, or $R^{42}$ may include cyclopropyl, cyclobutyl, cyclopentyl, or cyclohexyl.

The $C_2–C_{10}$ alkoxyalkyl represented by $R^8$ or $R^9$ may include, for example, methoxymethyl, ethoxymethyl, n-propyloxymethyl, isopropyloxymethyl, 2-methoxyethyl, 1-methoxyethyl, 2-ethoxyethyl, 1-ethoxyethyl, 3-methoxypropyl, 2-methoxypropyl, 1-methoxypropyl, 2-methoxy-1-methylethyl, 2-propyloxyethyl, 2-isopropyloxyethyl, 2-ethoxypropyl, 2-ethoxy-1-methylethyl, 2-methoxybutyl, 1-ethyl-2-methoxyethyl, 3-ethoxypropyl, 3-methoxybutyl, 3-methoxy-2-methylpropyl, 3-methoxy-1-methylpropyl, 2-butoxyethyl, 3-methoxy-3-methylbutyl, and 2-butoxy-1-methylethyl.

The $C_2–C_{10}$ alkylthioalkyl represented by $R^8$ or $R^9$ may include, for example, methylthiomethyl, ethylthiomethyl, propylthiomethyl, isopropylthiomethyl, 2-methylthiomethyl, 1-methylthioethyl, 2-ethylthioethyl, 1-ethylthioethyl, 3-methylthiopropyl, 2-methylthiopropyl, 1-methylthiopropyl, 2-methylthio-1-methylethyl, 2-propylthioethyl, 2-isopropylthioethyl, 2-ethylthiopropyl, 2-ethylthio-1-methylethyl, 2-methylthiobutyl, 1-ethyl-2-methylthioethyl, 3-ethylthiopropyl, 3-methylthiobutyl, 2-methyl-3-methylthiopropyl, 1-methyl-3-methylthiopropyl, 4-methylthiobutyl, 1-methyl-2-methylthiopropyl, 2-isobutylthioethyl, 2-sec-butylthioethyl, 3-isobutylthiopropyl, and 3-sec-butylthiopropyl.

The $C_3–C_6$ alkenyloxy represented by $R^{10}$, $R^{17}$, or $R^{18}$ may include, for example, allyloxy, 2-butenyloxy, 3-butenyloxy, 1-methyl-2-propenyloxy, 2-methyl-2-propenyloxy, 2-pentenyloxy, 3-pentenyloxy, 4-pentenyloxy, 1-methyl-2-butenyloxy, 2-methyl-2-butenyloxy, 3-methyl-2-butenyloxy, 1-methyl-3-butenyloxy, 2-methyl-3-butenyloxy, 3-methyl-3-butenyloxy, 1-ethyl-2-propenyloxy, 2-ethyl-2-propenyloxy, 2-hexenyloxy, 3-hexenyloxy, 4-hexenyloxy, 5-hexenyloxy, 1-methyl-2-pentenyloxy, 2-methyl-2-pentenyloxy, 3-methyl-2-pentenyloxy, 4-methyl-2-pentenyloxy, 1-methyl-3-pentenyloxy, 2-methyl-3-pentenyloxy, 3-methyl-3-pentenyloxy, 4-methyl-3-pentenyloxy, 1-methyl-4-pentenyloxy, 2-methyl-4-pentenyloxy, 3-methyl-4-pentenyloxy, and 4-methyl-4-pentenyloxy.

The $C_3–C_6$ haloalkenyloxy represented by $R^{10}$, $R^{17}$, or $R^{18}$ may include, for example, 3-chloro-2-propenyloxy, 3-bromo-2-propenyloxy, 2-chloro-2-propenyloxy, 2-bromo-2-propenyloxy, 3,3-dichloro-2-propenyloxy, 3,3-dibromo-2-propenyloxy, 3,3-difluoro-2-propenyloxy, 2,3-dichloro-2-propenyloxy, 2,3-dibromo-2-propenyloxy, 2-chloromethyl-2-propenyloxy, 4-chloro-2-butenyloxy, 3-chloro-4,4,4-trifluoro-2-butenyloxy, 3-bromo-4,4,4-trifluoro-2-butenyloxy, 3,4-dichloro-4,4-difluoro-2-butenyloxy, 3,4,4,4-tetrafluoro-2-butenyloxy, 4,4-dichloro-3-butenyloxy, 4,4-dibromo-3-butenyloxy, 5,5-dichloro-4-pentenyloxy, 5,5-dibromo-4-pentenyloxy, 6,6-dichloro-5-hexenyloxy, and 6,6-dibrmo-5-hexenyloxy.

The $C_3–C_6$ alkynyloxy represented by $R^{10}$, $R^{17}$, or $R^{18}$ may include, for example, 2-propynyloxy, 2-butynyloxy, 3-butynyloxy, 1-methyl-2-propynyloxy, 2-pentynyloxy, 3-pentynyloxy, 4-pentynyloxy, 1-methyl-2-butynyloxy, 1-methyl-3-butynyloxy, 2-methyl-3-butynyloxy, 1-ethyl-2-propynyloxy, 2-hexynyloxy, 3-hexynyloxy, 4-hexynyloxy, 5-hexynyloxy, 1-ethyl-2-butynyloxy, 1-ethyl-3-butynyloxy, and 2-ethyl-3-butynyloxy.

The $C_3–C_6$ haloalkynyloxy represented by $R^{10}$, $R^{17}$, or $R^{18}$ may include, for example, 3-chloro-2-propynyloxy, 3-bromo-2-propynyloxy, 4-chloro-2-butynyloxy, 4-chloro- 3-butynyloxy, 4-bromo-2-butynyloxy, 4-bromo-3-butynyloxy, 5-chloro-4-pentynyloxy, 4-chloro-1-methyl-2-butynyloxy, 4-chloro-1-methyl-3-butynyloxy, 4-chloro-2-methyl-3-butynyloxy, 5-bromo-4-pentynyloxy, 4-bromo-1-methyl-2-butynyloxy, 4-bromo-1-methyl-3-butynyloxy, 4-bromo-2-methyl-3-butynyloxy, 6-chloro-5-hexynyloxy, and 6-bromo-5-hexynyloxy.

The ($C_1$–$C_5$ alkoxy)carbonyl represented by $R^{10}$ may include, for example, methoxycarbonyl, ethoxycarbonyl, n-propyloxycarbonyl, isopropyloxycarbonyl, n-butyloxycarbonyl, isobutyloxycarbonyl, sec-butyloxycarbonyl, tert-butyloxycarbonyl, n-pentyloxycarbonyl, isopentyloxycarbonyl, neopentyloxycarbonyl, tert-pentyloxycarbonyl, and 1-ethylpropyloxycarbonyl.

The $C_1$–$C_3$ alkylthio represented by $R^{17}$ or $R^{18}$ may include methylthio, ethylthio, propylthio, and isopropylthio.

The $C_1$–$C_3$ haloalkylthio represented by $R^{17}$ or $R^{18}$ may include, for example, trifluoromethylthio, difluoromethylthio, bromodifluoromethylthio, 2,2,2-trifluoroethylthio, 2-chloro-1,1,2-trifluoroethylthio, 2-bromo-1,1,2-trifluoroethylthio, 1,1,2,2-tetrafluoroethylthio, 2-chloroethylthio, 2-fluoroethylthio, 2-bromoethylthio, 1,1,2,2,2-pentafluoroethylthio, 3-fluoropropylthio, 3-chloropropylthio, 3-bromopropylthio, 2,2,3,3,3-pentafluoropropylthio, and 3,3,3-trifluoropropylthio.

The $C_1$–$C_2$ alkylsulfinyl represented by $R^{17}$ or $R^{18}$ may include methylsulfinyl or ethylsulfinyl.

The $C_1$–$C_2$ alkylsulfonyl represented by $R^{17}$ or $R^{18}$ may include methylsulfonyl and ethylsulfonyl.

The $C_1$–$C_2$ haloalkylsulfinyl represented by $R^{17}$ or $R^{18}$ may include, for example, trifluoromethylsulfinyl, 2,2,2-trifluoroethylsulfinyl, and perfluoroethylsulfinyl.

The $C_1$–$C_2$ haloalkylsulfonyl represented by $R^{17}$ or $R^{18}$ may include, for example, trifluoromethylsulfonyl, 2,2,2-trifluoroethylsulfonyl, and perfluoroethylsulfonyl.

The $C_1$–$C_3$ hydroxyalkyl represented by $R^{17}$ or $R^{18}$ may include hydroxymethyl, 2-hydroxyethyl, and 3-hydroxypropyl.

The $C_2$–$C_4$ alkoxyalkyl represented by $R^{17}$ or $R^{18}$ may include, for example, methoxymethyl, ethoxymethyl, propyloxymethyl, isopropyloxymethyl, 2-methoxyethyl, 1-methoxyethyl, 2-ethoxyethyl, 1-ethoxyethyl, 3-methoxypropyl, 2-methoxypropyl, 1-methoxypropyl, and 2-methoxy-1-methylethyl.

The $C_2$–$C_4$ alkylthioalkyl represented by $R^{17}$ or $R^{18}$ may include, for example, methylthiomethyl, ethylthiomethyl, propylthiomethyl, isopropylthiomethyl, 2-methylthioethyl, 1-methylthioethyl, 2-ethylthioethyl, 1-ethylthioethyl, 3-methylthiopropyl, 2-methylthiopropyl, 1-methylthiopropyl, and 2-methylthio-1-methylethyl.

The ($C_1$–$C_2$ alkyl)aminocarbonyl represented by $R^{17}$ may include methylaminocarbonyl or ethylaminocarbonyl.

The di($C_1$–$C_2$ alkyl)aminocarbonyl represented by $R^{17}$ may include dimethylaminocarbonyl, N-methyl-N-ethylaminocarbonyl, or diethylaminocarbonyl.

The ($C_1$–$C_6$ alkoxy)carbonyl represented by $R^{17}$ may include, for example, methoxycarbonyl, ethoxycarbonyl, n-propyloxycarbonyl, isopropyloxycarbonyl, n-butyloxycarbonyl, isobutyloxycarbonyl, sec-butyloxycarbonyl, tert-butyloxycarbonyl, n-pentyloxycarbonyl, isopentyloxycarbonyl, neopentyloxycarbonyl, tert-pentyloxycarbonyl, 1-ethylpropyloxycarbonyl, n-hexyloxycarbonyl, isohexyloxycarbonyl, 2-ethylbutyloxycarbonyl, 1-methylpentyloxycarbonyl, 1-ethylbutyloxycarbonyl, 3-methylpentyloxycarbonyl, and 1,3-dimethylbutylcarbonyl.

The $C_5$–$C_6$ cycloalkenyl represented by $R^{17}$ may include 1-cyclopentenyl, 2-cyclopentenyl, 3-cyclopentenyl, 1-cyclohexenyl, 2-cyclohexenyl, or 3-cyclohexenyl.

The $C_3$–$C_6$ cycloalkyloxy represented by $R^{17}$ may include cyclopropyloxy, cyclobutyloxy, cyclopentyloxy, or cyclohexyloxy.

The $C_5$–$C_6$ cycloalkenyloxy represented by $R^{17}$ may include 1-cyclopentenyloxy, 2-cyclopentenyloxy, 3-cyclopentenyloxy, 1-cyclohexenyloxy, 2-cyclohexenyloxy, or 3-cyclohexenyloxy.

The 3,3-dihalogeno-substituted-2-propenyl represented by $R^4$ may include, for example, 3,3-dichloro-2-propenyl, 3,3-dibromo-2-propenyl, 3-bromo-3-chloro-2-propenyl, 3-chloro-3-fluoro-2-propenyl, and 3-bromo-3-fluoro-2-propenyl.

The $C_3$–$C_7$ cycloalkyl optionally substituted with $C_1$–$C_4$ alkyl, which is represented by $R^6$, $R^8$, or $R^9$, may include, for example, cyclopropyl, cyclobutyl, cyclopentyl, cyclohexyl, 2-methylcyclopentyl, 3-methylcyclopentyl, 2-methylcyclohexyl, 3-methylcyclohexyl, 4-methylcyclohexyl, 4-ethylcyclohexyl, 4-n-propylcyclohexyl, 4-isopropylcyclohexyl, and 4-tert-butylcyclohexyl.

The $C_4$–$C_{10}$ cycloalkylalkyl optionally substituted with $C_1$–$C_4$ alkyl on the ring thereof, which is represented by $R^6$, $R^8$, or $R^9$, may include, for example, cyclopropylmethyl, cyclobutylmethyl, cyclopentylmethyl, cyclohexylmethyl, 1-cyclopropylethyl, (2-methylcyclopropyl)methyl, 2-(2-methylcyclopropyl)ethyl, 2-cyclopentylethyl, 3-cyclopentylpropyl, 2-cyclohexylethyl, and 3-cyclohexylpropyl.

The $C_5$–$C_6$ cycloalkenyl optionally substituted with $C_1$–$C_4$ alkyl, which is represented by $R^6$, $R^8$, or $R^9$, may include, for example, 2-cyclopentenyl, 3-cyclopentenyl, 2-cyclohexenyl, 3-cyclohexenyl, 3,5,5-trimethyl-2-cyclohexenyl, and 3-methyl-2-cyclohexenyl.

The $C_6$–$C_8$ cycloalkenylalkyl optionally substituted with $C_1$–$C_4$ alkyl on the ring thereof, which is represented by $R^6$, $R^8$, or $R^9$, may include, for example, (1-cyclopentenyl)methyl, (2-cyclopentenyl)methyl, (1-cyclohexenyl)methyl, (2-cyclohexenyl)methyl, (3-cyclophexenyl)methyl, and 2-(3-cyclohexenyl)ethyl.

The halogen in the phenyl optionally substituted with halogen, $C_1$–$C_4$ alkyl, $C_1$–$C_3$ haloalkyl, $C_1$–$C_3$ alkoxy, or $C_1$–$C_3$ haloalkoxy, which is represented by $R^7$, $R^{15}$, $R^{16}$, $R^{17}$, $R^{18}$, or $R^{42}$, may include fluorine, chlorine, bromine, or iodine.

The $C_1$–$C_4$ alkyl in the phenyl optionally substituted with halogen, $C_1$–$C_4$ alkyl, $C_1$–$C_3$ haloalkyl, $C_1$–$C_3$ alkoxy, or $C_1$–$C_3$ haloalkoxy, which is represented by $R^7$, $R^{15}$, $R^{16}$, $R^{17}$, $R^{18}$, or $R^{42}$, may include methyl, ethyl, n-propyl, isopropyl, n-butyl, sec-butyl, tert-butyl, and isobutyl.

The $C_1$–$C_3$ haloalkyl in the phenyl optionally substituted with halogen, $C_1$–$C_4$ alkyl, $C_1$–$C_3$ haloalkyl, $C_1$–$C_3$ alkoxy, or $C_1$–$C_3$ haloalkoxy, which is represented by $R^7$, $R^{15}$, $R^{16}$, $R^{17}$, $R^{18}$, or $R^{42}$, may include, for example, trifluoromethyl, difluoromethyl, bromodifluoromethyl, 1-fluoroethyl, 1-chloroethyl, 1-bromoethyl, perfluoroethyl, 2-bromo-1,1,2,2-tetrafluoroethyl, 1,1,2,2-tetrafluoroethyl, 2-chloro-1,1,2-trifluoroethyl, 2-bromo-1,1,2-trifluoroethyl, 2,2,2-trifluoroethyl, 2,2,2-trichloroethyl, 2,2,2-tribromoethyl, 2-fluoroethyl, 2-chloroethyl, 2-bromoethyl, 2-iodoethyl, 2,2-difluoroethyl, 2,2-dichloroethyl, 2,2-dibromoethyl, 3-fluoropropyl, 3-chloropropyl, 3-bromopropyl, 3-iodopropyl, 3,3,3-trifluoropropyl, 2,2,2,3,3,3-hexafluoropropyl, 1,1,1,3,3,3-hexafluoro-2-propyl, 2-fluoropropyl, 2-chloropropyl, 2-bromopropyl, 2-iodopropyl, and 2,3-dibromopropyl.

The $C_1$–$C_3$ alkoxy in the phenyl optionally substituted with halogen, $C_1$–$C_4$ alkyl, $C_1$–$C_3$ haloalkyl, $C_1$–$C_3$ alkoxy, or $C_1$–$C_3$ haloalkoxy, which is represented by $R^7$, $R^{15}$, $R^{16}$, $R^{17}$, $R^{18}$, or $R^{42}$, may include methoxy, ethoxy, n-propyloxy, or isopropyloxy.

The $C_1$–$C_3$ haloalkoxy in the phenyl optionally substituted with halogen, $C_1$–$C_4$ alkyl, $C_1$–$C_3$ haloalkyl, $C_1$–$C_3$ alkoxy, or $C_1$–$C_3$ haloalkoxy, which is represented by $R^7$, $R^{15}$, $R^{16}$, $R^{17}$, $R^{18}$, or $R^{42}$, may include, for example, trifluoromethoxy, bromodifluoromethoxy, 1-fluoroethoxy, 1-chloroethoxy, 1-bromoethoxy, perfluoroethoxy, 2-bromo-1,1,2,2-tetrafluoroethoxy, 1,1,2,2-tetrafluoroethoxy, 2-chloro-1,1,2-trifluoroethoxy, 2-bromo-1,1,2-trifluoroethoxy, 2,2,2-trifluoroethoxy, 2,2,2-trichloroethoxy, 2,2,2-tribromoethoxy, 2-fluoroethoxy, 2-chloroethoxy, 2-bromoethoxy, 2-iodoethoxy, 2,2-difluoroethoxy, 2,2-dichloroethoxy, 2,2-dibromoethoxy, 3-fluoropropyloxy, 3-chloropropyloxy, 3-bromopropyloxy, 3-iodopropyloxy, 3,3,3-trifluoropropyloxy, 2,2,2,3,3,3-hexafluoropropyloxy, 1,1,1,3,3,3-hexafluoro-2-propyloxy, 2-fluoropropyloxy, 2-chloropropyloxy, 2-bromopropyloxy, 2-iodopropyloxy, and 2,3-dibromopropyloxy.

The halogen in the benzyl optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof, which is represented by $R^7$, $R^{16}$, $R^{17}$, or $R^{42}$, may include fluorine, chlorine, bromine, or iodine.

The $C_1$–$C_4$ alkyl in the benzyl optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof, which is represented by $R^7$, $R^{16}$, $R^{17}$, or $R^{42}$, may include methyl, ethyl, n-propyl, isopropyl, n-butyl, sec-butyl, tert-butyl, and isobutyl.

The $C_1$–$C_3$ haloalkyl in the benzyl optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof, which is represented by $R^7$, $R^{16}$, $R^{17}$, or $R^{42}$, may include, for example, trifluoromethyl, difluoromethyl, bromodifluoromethyl, 1-fluoroethyl, 1-chloroethyl, 1-bromoethyl, perfluoroethyl, 2-bromo-1,1,2,2-tetrafluoroethyl, 1,1,2,2-tetrafluoroethyl, 2-chloro-1,1,2-trifluoroethyl, 2-bromo-1,1,2-trifluoroethyl, 2,2,2-trifluoroethyl, 2,2,2-trichloroethyl, 2,2,2-tribromoethyl, 2-fluoroethyl, 2-chloroethyl, 2-bromoethyl, 2-iodoethyl, 2,2-difluoroethyl, 2,2-dichloroethyl, 2,2-dibromoethyl, 3-fluoropropyl, 3-chloropropyl, 3-bromopropyl, 3-iodopropyl, 3,3,3-trifluoropropyl, 2,2,2,3,3,3-hexafluoropropyl, 1,1,1,3,3,3-hexafluoro-2-propyl, 2-fluoropropyl, 2-chloropropyl, 2-bromopropyl, 2-iodopropyl, and 2,3-dibromopropyl.

The $C_1$–$C_3$ alkoxy in the benzyl optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof, which is represented by $R^7$, $R^{16}$, $R^{17}$, or $R^{42}$, may include methoxy, ethoxy, n-propyloxy, or isopropyloxy.

The $C_1$–$C_3$ haloalkoxy in the benzyl optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof, which is represented by $R^7$, $R^{16}$, $R^{17}$, or $R^{42}$, may include, for example, trifluoromethoxy, bromodifluoromethoxy, 1-fluoroethoxy, 1-chloroethoxy, 1-bromoethoxy, perfluoroethoxy, 2-bromo-1,1,2,2-tetrafluoroethoxy, 1,1,2,2-tetrafluoroethoxy, 2-chloro-1,1,2-trifluoroethoxy, 2-bromo-1,1,2-trifluoroethoxy, 2,2,2-trifluoroethoxy, 2,2,2-trichloroethoxy, 2,2,2-tribromoethoxy, 2-fluoroethoxy, 2-chloroethoxy, 2-bromoethoxy, 2-iodoethoxy, 2,2-difluoroethoxy, 2,2-dichloroethoxy, 2,2-dibromoethoxy, 3-fluoropropyloxy, 3-chloropropyloxy, 3-bromopropyloxy, 3-iodopropyloxy, 3,3,3-trifluoropropyloxy, 2,2,2,3,3,3-hexafluoropropyloxy, 1,1,1,3,3,3-hexafluoro-2-propyloxy, 2-fluoropropyloxy, 2-chloropropyloxy, 2-bromopropyloxy, 2-iodopropyloxy, and 2,3-dibormopropyloxy.

The halogen in the phenoxy or benzyloxy optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof, which is represented by $R^{17}$, may include fluorine, chlorine, bromine, or iodine.

The $C_1$–$C_4$ alkyl in the phenoxy or benzyloxy optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof, which is represented by $R^{17}$, may include methyl, ethyl, n-propyl, isopropyl, n-butyl, sec-butyl, tert-butyl, and isobutyl.

The $C_1$–$C_3$ haloalkyl in the phenoxy or benzyloxy optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof, which is represented by $R^{17}$, may include, for example, trifluoromethyl, difluoromethyl, bromodifluoromethyl, 1-fluoroethyl, 1-chloroethyl, 1-bromoethyl, perfluoroethyl, 2-bromo-1,1,2,2-tetrafluoroethyl, 1,1,2,2-tetrafluoroethyl, 2-chloro-1,1,2-trifluoroethyl, 2-bromo-1,1,2-trifluoroethyl, 2,2,2-trifluoroethyl, 2,2,2-trichloroethyl, 2,2,2-tribromoethyl, 2-fluoroethyl, 2-chloroethyl, 2-bromoethyl, 2-iodoethyl, 2,2-difluoroethyl, 2,2-dichloroethyl, 2,2-dibromoethyl, 3-fluoropropyl, 3-chloropropyl, 3-bromopropyl, 3-iodopropyl, 3,3,3-trifluoropropyl, 2,2,2,3,3-hexafluoropropyl, 1,1,1,3,3,3-hexafluoro-2-propyl, 2-fluoropropyl, 2-chloropropyl, 2-bromopropyl, 2-iodopropyl, and 2,3-dibromopropyl.

The $C_1$–$C_3$ alkoxy in the phenoxy or benzyloxy optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof, which is represented by $R^{17}$, may include methoxy, ethoxy, n-propyloxy, or isopropyloxy.

The $C_1$–$C_3$ haloalkoxy in the phenoxy or benzyloxy optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof, which is represented by $R^{17}$, may include, for example, trifluoromethoxy, bromodifluoromethoxy, 1-fluoroethoxy, 1-chloroethoxy, 1-bromoethoxy, perfluoroethoxy, 2-bromo-1,1,2,2-tetrafluoroethoxy, 1,1,2,2-tetrafluoroethoxy, 2-chloro-1,1,2-trifluoroethoxy, 2-bromo-1,1,2-trifluoroethoxy, 2,2,2-trifluoroethoxy, 2,2,2-trichloroethoxy, 2,2,2-tribromoethoxy, 2-fluoroethoxy, 2-chloroethoxy, 2-bromoethoxy, 2-iodoethoxy, 2,2-difluoroethoxy, 2,2-dichloroethoxy, 2,2-dibromoethoxy, 3-fluoropropyloxy, 3-chloropropyloxy, 3-bromopropyloxy, 3-iodopropyloxy, 3,3,3-trifluoropropyloxy, 2,2,2,3,3,3-hexafluoropropyloxy, 1,1,1,3,3,3-hexafluoro-2-propyloxy, 2-fluoropropyloxy, 2-chloropropyloxy, 2-bromopropyloxy, 2-iodopropyloxy, and 2,3-dibormopropyloxy.

The halogen in the methylenedioxy optionally substituted with halogen or $C_1$–$C_3$ alkyl, which is represented by $R^{17}$ and which is formed from two adjacent $R^{17}$'s combined together at their ends when b is 2 to 5, may include fluorine, chlorine, bromine, or iodine.

The $C_1$–$C_3$ alkyl in the methylenedioxy optionally substituted with halogen or $C_1$–$C_3$ alkyl, which is represented by $R^{17}$ and which is formed from two adjacent $R^{17}$'s combined together at their ends when b is 2 to 5, may include methyl, ethyl, n-propyl, and isopropyl.

The halogen in the ethylenedioxy optionally substituted with halogen or $C_1$–$C_4$ alkyl, which is represented by $R^{17}$ and which is formed from two adjacent $R^{17}$'s combined together at their ends when b is 2 to 5, may include fluorine, chlorine, bromine, or iodine.

The $C_1$–$C_3$ alkyl in the ethylenedioxy optionally substituted with halogen or $C_1$–$C_3$ alkyl, which is represented by $R^{17}$ and which is formed from two adjacent $R^{17}$'s combined together at their ends when b is 2 to 5, may include methyl, ethyl, n-propyl, and isopropyl.

$R^8$ and $R^9$, when combined, together at their ends to form a saturated or unsaturated 5- or 6-membered ring containing zero to two oxygen or sulfur atoms in the ring thereof, represent tetramethylene optionally substituted with $C_1$–$C_4$ alkyl or halogen; pentamethylene optionally substituted with $C_1$–$C_4$ alkyl or halogen; butenylene optionally substituted with $C_1$–$C_4$ alkyl or halogen; pentenylene optionally substituted with $C_1$–$C_4$ alkyl or halogen; or pentadienylene optionally substituted with $C_1$–$C_4$ alkyl or halogen; examples of which are tetramethylene, 1-methyltetramethylene, 2-methyltetramethylene, 1,1-dimethyltetramethylene, 1,3-dimethyltetramethylene, pentamethylene, 1-methylpentamethylene, 2-methylpentamethylene, 3-methylpentamethylene, 3-ethylpentamethylene, 3-tert-butylpentamethylene, 1,1-dimethylpentamethylene, 1,5-dimethylpentamethylene, 1-chloropentamethylene, 1-methoxypentamethylene, 1-butenylene, 1-methyl-1-butenylene, 2-methyl-1-butenylene, 1-pentenylene, 2-methyl-1-pentenylene, 3,3-dimethyl-1-pentenylene, 2-oxa-1-methyltetramethylene, 3-oxapentamethylene, 3-oxa-1,4-pentadienylene, 2-thiatetramethylene, 3-thiapentamethylene, 3,3-dimethyl-2,4-dioxapentamethylene, and 2,4-dithiapentamethylene. In these groups, each methylene or methine linkage may be replaced with an oxygen or sulfur atom.

The $C_5$–$C_6$ cycloalkylene represented by E may include 1,2-cyclohexylene, 1,3-cyclohexylene, 1,4-cyclohexylene, 1,2-cyclopentylene, and 1,3-cyclopentylene.

The $C_1$–$C_6$ alkyl substituted with cyano, nitro, ($C_1$–$C_4$ alkoxy)carbonyl, $C_1$–$C_4$ alkylthio, or $C_1$–$C_4$ alkoxy, which is represented by $R^6$, may include, for example, cyanomethyl, 1-cyanoethyl, 2-cyanoethyl, 3-cyanopropyl, nitromethyl, 1-nitroethyl, 1-methyl-1-nitroethyl, methoxycarbonylmethyl, ethoxycarbonylmethyl, isopropoxycarbonylmethyl, 1-(methoxycarbonyl)ethyl, 2-(methoxycarbonyl)ethyl, methoxymethyl, ethoxymethyl, 1-methoxyethyl, 2-methoxyethyl, 2-ethoxyethyl, 2,2-dimethoxyethyl, 2,2-diethoxyethyl, 2,2-dimethoxypropyl, 2,2-diethoxypropyl, 3,3-dimethoxypropyl, 3,3-diethoxypropyl, 2,3-dimethoxypropyl, methylthiomethyl, 2-methylthioethyl, and 2,2-di(methylthio)ethyl.

In the case where h is 0 and i is 1 in $A^1$-1, $R^{22}$ and $R^7$, when combined together at their ends to form trimethylene, tetramethylene, or pentamethylene, which is optionally substituted with $C_1$–$C_3$ alkyl, may include, for example, trimethylene, 1-methyltrimethylene, 2-methyltrimethylene, tetramethylene, 1-methyltetramethylene, 2-methyltetramethylene, and pentamethylene.

In the case where h is 0 and j is 1 in $A^1$-2, $A^1$-3, $A^1$-4, $A^1$-5, or $A^1$-6, $R^{22}$ and $R^7$, when combined together at their ends to form trimethylene, tetramethylene, or pentamethylene, which is optionally substituted with $C_1$–$C_3$ alkyl, may include, for example, trimethylene, 1-methyltrimethylene, 2-methyltrimethylene, tetramethylene, 1-methyltetramethylene, 2-methyltetramethylene, and pentamethylene.

Preferred examples of the present compounds are as follows:

oxime compounds of formula (1) wherein X is $X^1$;

oxime compounds of formula (1) wherein X is $X^1$, and $A^1$ is $A^1$-1, $A^1$-2, $A^1$-3, $A^1$-4, $A^1$-5, or $A^1$-6;

oxime compounds of formula (1) wherein $A^1$ is $A^1$-1, $A^1$-2, $A^1$-3, $A^1$-4, $A^1$-5, or $A^1$-6, and Y and Z are both oxygen;

oxime compounds of formula (1) wherein $A^1$ is $A^1$-1, $A^1$-2, $A^1$-3, $A^1$-4, $A^1$-5, or $A^1$-6, and a is 0;

oxime compounds of formula (1) wherein $A^1$ is $A^1$-1, $A^1$-2, $A^1$-3, $A^1$-4, $A^1$-5, or $A^1$-6, and $R^1$, $R^2$, and $R^3$ are independently halogen or $C_1$–$C_3$ alkyl;

oxime compounds of formula (1) wherein X is $X^1$ and $A^1$ is $A^1$-1.

oxime compounds of formula (1) wherein X is $X^1$, and $A^1$ is $A^1$-2, $A^1$-3, $A^1$-4, $A^1$-5, or $A^1$-6;

oxime compounds of formula (1) wherein $A^1$ is $A^1$-2, $A^1$-3, $A^1$-4, $A^1$-5, or $A^1$-6, and $Q^1$ is oxygen.

oxime compounds of formula (1) wherein $A^1$ is $A^1$-1, $A^1$-2, $A^1$-3, $A^1$-4, $A^1$-5, or $A^1$-6, and $R^6$ is $C_1$–$C_8$ alkyl, $C_2$–$C_6$ haloalkyl, $C_3$–$C_6$ alkenyl, $C_3$–$C_6$ haloalkenyl, $C_3$–$C_6$ alkynyl, or $C_3$–$C_6$ haloalkynyl, or $C_3$–$C_7$ cycloalkyl optionally substituted with $C_1$–$C_4$ alkyl, or $C_4$–$C_{10}$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ alkyl on the ring thereof, or $C_1$–$C_6$ alkyl substituted with cyano, nitro, ($C_1$–$C_4$ alkoxy)carbonyl, $C_1$–$C_4$ alkylthio, or $C_1$–$C_4$ alkoxy;

oxime compounds of formula (1) wherein $A^1$ is $A^1$-1, $A^1$-2, $A^1$-3, $A^1$-4, $A^1$-5, or $A^1$-6, and $R^6$ is hydrogen.

oxime compounds of formula (1) wherein $A^1$ is $A^1$-1, $A^1$-2, $A^1$-3, $A^1$-4, $A^1$-5, or $A^1$-6, and $R^6$ is triphenylmethyl, or $T^1$-1, $T^1$-2, or $T^1$-3.

oxime compounds of formula (1) wherein $A^1$ is $A^1$-1, $A^1$-2, $A^1$-3, $A^1$-4, $A^1$-5, or $A^1$-6, and $R^6$ is $T^1$-4, $T^1$-5, $T^1$-6, or $T^1$-7;

oxime compounds of formula (1) wherein $A^1$ is $A^1$-1, $A^1$-2, $A^1$-3, $A^1$-4, $A^1$-5, or $A^1$-6, and $R^7$ is hydrogen, $C_1$–$C_6$ alkyl, $C_1$–$C_3$ haloalkyl, or $C_3$–$C_6$ cycloalkyl;

oxime compounds of formula (1) wherein $A^1$ is $A^1$-1, $A^1$-2, $A^1$-3, $A^1$-4, $A^1$-5, or $A^1$-6, and $R^7$ is phenyl optionally substituted with halogen, $C_1$–$C_4$ alkyl, $C_1$–$C_3$ haloalkyl, $C_1$–$C_3$ alkoxy, or $C_1$–$C_3$ haloalkoxy, or benzyl optionally substituted with halogen, $C_1$–$C_4$ alkyl, $C_1$–$C_3$ haloalkyl, $C_1$–$C_3$ alkoxy, or $C_1$–$C_3$ haloalkoxy on the ring thereof.

oxime compounds of formula (1) wherein X is $X^1$, $R^7$ is hydrogen, $C_1$–$C_6$ alkyl, or $C_1$–$C_3$ haloalkyl, $A^1$ is $A^1$-1, and $R^6$ is $C_1$–$C_8$ alkyl, $C_2$–$C_6$ haloalkyl, $C_3$–$C_6$ alkenyl, $C_3$–$C_6$ haloalkenyl, $C_3$–$C_6$ alkynyl, or $C_3$–$C_6$ haloalkynyl, or $C_3$–$C_7$ cycloalkyl optionally substituted with $C_1$–$C_4$ alkyl, or $C_4$–$C_{10}$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ alkyl on the ring thereof;

oxime compounds of formula (1) wherein X is $X^1$, $R^7$ is hydrogen, $C_1$–$C_6$ alkyl, or $C_1$–$C_3$ haloalkyl, $A^1$ is $A^1$-1, and $R^6$ is $T^1$-1 or $T^1$-2;

oxime compounds of formula (1) wherein X is $X^1$, $R^7$ is hydrogen, $C_1$–$C_6$ alkyl, or $C_1$–$C_3$ haloalkyl, $A^1$ is $A^1$-3, or $A^1$ is $A^1$-2 and k is an integer of 2 to 6, and $R^6$ is $C_1$–$C_8$ alkyl, $C_2$–$C_6$ haloalkyl, $C_3$–$C_6$ alkenyl, $C_3$–$C_6$ haloalkenyl, $C_3$–$C_6$ alkynyl, or $C_3$–$C_6$ haloalkynyl, or $C_3$–$C_7$ cycloalkyl optionally substituted with $C_1$–$C_4$ alkyl, or $C_4$–$C_{10}$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ alkyl on the ring thereof, oxime compounds of formula (1) wherein X is $X^1$, $R^7$ is hydrogen, $C_1$–$C_6$ alkyl, or $C_1$–$C_3$ haloalkyl, $A^1$ is $A^1$-3, or $A^1$ is $A^1$-2 and k is an integer of 2 to 6, and $R^6$ is $T^1$-1 or $T^1$-2;

oxime compounds of formula (1) wherein X is $X^1$, $R^7$ is hydrogen, $C_1$–$C_6$ alkyl, or $C_1$–$C_3$ haloalkyl, $A^1$ is $A^1$-3, or $A^1$ is $A^1$-2 and k is an integer of 2 to 6, $Q^1$ is oxygen, and $R^6$ is $C_1$–$C_8$ alkyl, $C_2$–$C_6$ haloalkyl, $C_3$–$C_6$ alkenyl, $C_3$–$C_6$ haloalkenyl, $C_3$–$C_6$ alkynyl, or $C_3$–$C_6$ haloalkynyl, or $C_3$–$C_7$ cycloalkyl optionally substituted with $C_1$–$C_4$ alkyl, or $C_4$–$C_{10}$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ alkyl on the ring thereof, or $T^1$-1 or $T^1$-2;

oxime compounds of formula (1) wherein $R^2$ and $R^3$ are independently chlorine or $C_1$–$C_3$ alkyl, a is 0, $R^4$ is 3,3-dichloro-2-propenyl or 3,3-dibromo-2-propenyl, Y and Z are both oxygen, X is $X^1$, $R^6$ is $C_1$–$C_5$ alkyl, $C_2$–$C_4$ haloalkyl, $C_3$–$C_6$ alkenyl, or $C_3$–$C_6$ haloalkenyl, $R^7$ is hydrogen, $C_1$–$C_4$ alkyl, or trifluoromethyl, $A^1$ is $A^1$-1, $R^{21}$ and $R^{22}$ are both hydrogen, h is 0, and i is an integer of 3 to 5;

oxime compounds of formula (1) wherein $R^2$ and $R^3$ are independently chlorine or $C_1$–$C_3$ alkyl, a is 0, $R^4$ is 3,3-dichloro-2-propenyl or 3,3-dibromo-2-propenyl, Y and Z are both oxygen, X is $X^1$, $R^6$ is $C_1$–$C_5$ alkyl, $C_2$–$C_4$ haloalkyl, $C_3$–$C_6$ alkenyl, or $C_3$–$C_6$ haloalkenyl, $R^7$ is hydrogen, $C_1$–$C_4$ alkyl, or trifluoromethyl, $A^1$ is $A^1$-2, $R^{21}$, $R^{22}$, $R^{23}$, and $R^{24}$ are all hydrogen, h is 0, $Q^1$ is oxygen, j is 1, and k is an integer of 3 to 6;

oxime compounds of formula (1) wherein X is $X^1$, $A^1$ is $A^1$-1, $R^{21}$ and $R^{22}$ are both hydrogen, h is 0, i is an integer of 3 to 5, Y and Z are both oxygen, $R^2$ and $R^3$ are both chlorine, a is 0, $R^4$ is 3,3-dichloro-2-propenyl, $R^6$ is isopropyl, isobutyl, sec-butyl, tert-butyl, 2,2,2-trifluoroethyl, 2,2,2-trichloroethyl, 2,2,2-tribromoethyl, 1,1,1,3,3,3-hexafluoro-2-propyl, or 3,3-dichloro-2-propenyl, and $R^7$ is hydrogen;

oxime compounds of formula (1) wherein X is $X^1$, $A^1$ is $A^1$-2, $R^{21}$, $R^{22}$, $R^{23}$, and $R^{24}$ are all hydrogen, h is 0, $Q^1$ is oxygen, j is 1, k is an integer of 3 to 6, Y and Z are both oxygen, $R^2$ and $R^3$ are both chlorine, a is 0, $R^4$ is 3,3-dichloro-2-propenyl, $R^6$ is isopropyl, isobutyl, sec-butyl, tert-butyl, 2,2,2-trifluoroethyl, 2,2,2-trichloroethyl, 2,2,2-tribromoethyl, 1,1,1,3,3,3-hexafluoro-2-propyl, or 3,3-dichloro-2-propenyl, and $R^7$ is hydrogen or methyl;

oxime compounds of formula (1) wherein X is $X^1$, and $A^1$ is $A^1$-7, $A^1$-8, $A^1$-9, $A^1$-10, $A^1$-11, or $A^1$-12;

oxime compounds of formula (1) wherein $A^1$ is $A^1$-7, $A^1$-8, $A^1$-9, $A^1$-10, $A^1$-11, or $A^1$-12, and Y and Z are both oxygen;

oxime compounds of formula (1) wherein $A^1$ is $A^1$-7, $A^1$-8, $A^1$-9, $A^1$-10, $A^1$-11, or $A^1$-12, and a is 0;

oxime compounds of formula (1) wherein $A^1$ is $A^1$-7, $A^1$-8, $A^1$-9, $A^1$-10, $A^1$-11, or $A^1$-12, and $R^1$, $R^2$, and $R^3$ are independently halogen or $C_1$–$C_3$ alkyl;

oxime compounds of formula (1) wherein $A^1$ is $A^1$-7;

oxime compounds of formula (1) wherein $A^1$ is $A^1$-8 and $G^2$ is oxygen;

oxime compounds of formula (1) wherein $A^1$ is $A^1$-9 and $Q^1$ is oxygen;

oxime compounds of formula (1) wherein $A^1$ is $A^1$-10, and $Q^1$ and $G^2$ are both oxygen;

oxime compounds of formula (1) wherein $A^1$ is $A^1$-11 and $Q^1$ is oxygen;

oxime compounds of formula (1) wherein $A^1$ is $A^1$-12 and $Q^1$ is oxygen;

oxime compounds of formula (1) wherein $A^1$ is $A^1$-7, $A^1$-8, $A^1$-9, $A^1$-10, $A^1$-11, or $A^1$-12, and $G^1$ is $G^1$-1;

oxime compounds of formula (1) wherein $A^1$ is $A^1$-7, $A^1$-8, $A^1$-9, $A^1$-10, $A^1$-11, or $A^1$-12, $G^1$ is $G^1$-2, and $Q^2$ is oxygen;

oxime compounds of formula (1) wherein $A^1$ is $A^1$-7, $A^1$-8, $A^1$-9, $A^1$-10, $A^1$-11, or $A^1$-12, $R^6$ is hydrogen, $C_1$–$C_8$ alkyl, $C_2$–$C_6$ haloalkyl, $C_3$–$C_6$ alkenyl, $C_3$–$C_6$ haloalkenyl, $C_3$–$C_6$ alkynyl, or $C_3$–$C_6$ haloalkynyl, or $C_3$–$C_7$ cycloalkyl optionally substituted with $C_1$–$C_4$ alkyl, or $C_3$–$C_7$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ alkyl on the ring thereof, or more preferably, $C_1$–$C_8$ alkyl, $C_2$–$C_6$ haloalkyl, $C_3$–$C_6$ alkenyl, or $C_3$–$C_6$ haloalkenyl;

oxime compounds of formula (1) wherein $A^1$ is $A^1$-7, $A^1$-8, $A^1$-9, $A^1$-10, $A^1$-11, or $A^1$-12, and W is a benzene ring, a heterocyclic 6-membered ring containing at least oxygen, sulfur, or nitrogen atom, a heterocyclic 5-membered ring containing at least one oxygen, sulfur, or nitrogen atom, or any one of these rings substituted with one to four identical or different $(R^{40})_{g2}$'s, wherein $R^{40}$ is halogen, $C_1$–$C_4$ alkyl, $C_1$–$C_3$ haloalkyl, $C_1$–$C_3$ alkoxy, or $C_1$–$C_3$ haloalkoxy, and g2 is an integer of 1 to 4;

oxime compounds of formula (1) wherein $A^1$ is $A^1$-7, $A^1$-8, $A^1$-9, $A^1$-10, $A^1$-11, or $A^1$-12, and W is a benzene ring, a pyridine ring, a pyridazine ring, a pyrimidine ring, a pyradine ring, a furan ring, a thiophene ring, a pyrrole ring, an oxazole ring, an isoxazole ring, a thiazole ring, an isothiazole ring, a pyrazole ring, an imidazole ring, or any one of these rings substituted with one to four identical or different $(R^{40})_{g2}$'s;

oxime compounds of formula (1) wherein $A^1$ is $A^1$-7, $A^1$-8, $A^1$-9, $A^1$-10, $A^1$-11, or $A^1$-12, and W is a benzene ring, a pyridine ring, a pyridazine ring, or any one of these rings substituted with one to four identical or different $(R^{40})_{g2}$'s;

oxime compounds of formula (1) wherein $A^1$ is $A^1$-7, $A^1$-8, $A^1$-9, $A^1$-10, $A^1$-11, or $A^1$-12, and W is a furan ring, a thiophene ring, a pyrrole ring, or any one of these rings substituted with one or four identical or different $(R^{40})_{g2}$'s;

oxime compounds of formula (1) wherein $A^1$ is $A^1$-7, $A^1$-8, $A^1$-9, $A^1$-10, $A^1$-11, or $A^1$-12, and W is a benzene ring, 2,3-pyridinediyl, 2,4-pyridinediyl, 2,5-pyridinediyl, 2,6-pyridinediyl, 3,5-pyridinediyl, 3,4-pyridinediyl, 3,4-pyridazinediyl, 3,5-pyridazinediyl, 3,6-pyridazinediyl, or any one of these rings substituted with one to four identical or different $(R^{40})_{g2}$'s;

oxime compounds of formula (1) wherein $R^2$ and $R^3$ are independently halogen or $C_1$–$C_3$ alkyl, $R^4$ is 3,3-dichloro-2-propenyl, a is 0, Y and Z are both oxygen, $R^6$ is $C_1$–$C_8$ alkyl, $C_2$–$C_6$ haloalkyl, $C_3$–$C_6$ alkenyl, or $C_3$–$C_6$ haloalkenyl, $A^1$ is $A^1$-7, $G^1$ is $G^1$-1, a1 is 0, W is 1,3-phenylene or 1,4-phenylene, h and p are both 0, and $R^{19}$, $R^{20}$, $R^{25}$, $R^{26}$, $R^{29}$, and $R^{30}$ are all hydrogen;

oxime compounds of formula (1) wherein $R^2$ and $R^3$ are independently halogen or $C_1$–$C_3$ alkyl, $R^4$ is 3,3-dichloro-2-propenyl, a is 0, Y and Z are both oxygen, $R^6$ is $C_1$–$C_8$ alkyl, $C_2$–$C_6$ haloalkyl, $C_3$–$C_6$ alkenyl, or $C_3$–$C_6$ haloalkenyl, $A^1$ is $A^1$-8, $G^1$ is $G^1$-1, a1 is 0, $G^2$ is oxygen, W is 1,3-phenylene or 1,4-phenylene, h and p are both 0, and $R^{19}$, $R^{20}$, $R^{25}$, $R^{26}$, $R^{29}$, and $R^{30}$ are all hydrogen;

oxime compounds of formula (1) wherein X is $X^2$;

oxime compounds of formula (1) wherein X is $X^2$, and Y and Z are both oxygen;

oxime compounds of formula (1) wherein X is $x^2$ and a is 0;

oxime compounds of formula (1) wherein X is $X^2$, and $R^1$, $R^2$, and $R^3$ are independently halogen or $C_1$–$C_3$ alkyl;

oxime compounds of formula (1) wherein $A^2$ is $A^2$-1;

oxime compounds of formula (1) wherein $A^2$ is $A^2$-2 and $Q^1$ is oxygen;

oxime compounds of formula (1) wherein $A^2$ is $A^2$-3 and $Q^2$ is oxygen;

oxime compounds of formula (1) wherein $A^2$ is $A^2$-4, and $Q^2$ and $Q^3$ are both oxygen;

oxime compounds of formula (1) wherein $A^2$ is $A^2$-5 and $Q^1$ is oxygen;

oxime compounds of formula (1) wherein $A^2$ is $A^2$-6 and $Q^1$ is oxygen;

oxime compounds of formula (1) wherein $A^2$ is $A^2$-7 or $A^2$-9, and $Q^1$ and $Q^2$ are both oxygen;

oxime compounds of formula (1) wherein $A^2$ is $A^2$-8 or $A^2$-10, and $Q^1$ and $Q^2$ are both oxygen;

oxime compounds of formula (1) wherein $A^2$ is $A^2$-5, and $Q^1$ and $Q^2$ are both oxygen;

oxime compounds of formula (1) wherein $A^2$ is $A^2$-6, and $Q^1$, $Q^2$, and $Q^3$ are all oxygen;

oxime compounds of formula (1) wherein $A^2$ is $A^2$-1, h and p are both 0, and $R^{19}$, $R^{20}$, $R^{25}$, $R^{26}$, $R^{29}$, and $R^{30}$ are all hydrogen;

oxime compounds of formula (1) wherein $A^2$ is $A^2$-2, h and p are both 0, $R^{19}$, $R^{20}$, $R^{25}$, $R^{26}$, $R^{27}$, $R^{28}$, $R^{31}$, and $R^{32}$ are all hydrogen, and $Q^1$ is oxygen;

oxime compounds of formula (1) wherein $A^2$ is $A^2$-3, h and p are both 0, $R^{19}$, $R^{20}$, $R^{25}$, $R^{26}$, $R^{29}$, $R^{30}$, $R^{35}$, and $R^{36}$ are all hydrogen, and $Q^1$ is oxygen;

oxime compounds of formula (1) wherein $A^2$ is $A^2$-4, h and p are both 0, $R^{19}$, $R^{20}$, $R^{25}$, $R^{26}$, $R^{29}$, $R^{30}$, $R^{35}$, and $R^{36}$ are all hydrogen, and $Q^2$ and $Q^3$ are both oxygen;

oxime compounds of formula (1) wherein $A^2$ is $A^2$-5, h and p are both 0, $R^{19}$, $R^{20}$, $R^{25}$, $R^{26}$, $R^{27}$, $R^{28}$, $R^{31}$, $R^{32}$, $R^{35}$, and $R^{36}$ are all hydrogen, and $Q^1$ and $Q^2$ are both oxygen;

oxime compounds of formula (1) wherein $A^2$ is $A^2$-6, h and p are both 0, $R^{19}$, $R^{20}$, $R^{25}$, $R^{26}$, $R^{27}$, $R^{28}$, $R^{31}$, $R^{32}$, $R^{35}$, and $R^{36}$ are all hydrogen and $Q^1$ and $Q^2$, and $Q^3$ are all oxygens;

oxime compounds of formula (1) wherein $A^2$ is $A^2$-7 or $A^2$-9, h and p are both 0, $R^{19}$, $R^{20}$, $R^{23}$, $R^{24}$, $R^{25}$, $R^{26}$, $R^{35}$, and $R^{36}$ are all hydrogen, and $Q^1$ and $Q^2$ are both oxygen;

oxime compounds of formula (1) wherein $A^2$ is $A^2$-8 or $A^2$-10, h and p are both 0, $R^{19}$, $R^{23}$, $R^{24}$, $R^{25}$, $R^{26}$, $R^{35}$, and $R^{36}$ are all hydrogen, and $Q^1$ and $Q^2$ are both oxygen;

oxime compounds of formula (1) wherein X is $X^2$, and $R^8$ and $R^9$ are independently hydrogen, $C_1$–$C_{11}$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_{10}$ alkoxyalkyl, $C_2$–$C_{10}$ alkylthioalkyl, or naphthyl, or $C_3$–$C_7$ cycloalkyl optionally substituted with $C_1$–$C_4$ alkyl, or $C_4$–$C_{10}$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ alkyl on the ring thereof, or $T^2$-1 or $T^2$-2 of formula (4)

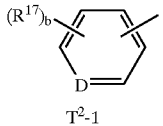 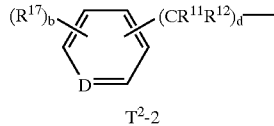

wherein $R^{17}$, D, $R^{11}$, $R^{12}$, b, and d are as defined above, or a heterocyclic 6-membered ring, exclusive of pyridine ring, containing at least one oxygen, sulfur, or nitrogen atom, which heterocyclic 6-membered ring may be optionally substituted with one to three identical or different $(R^{18})_g$'s, and $R^{18}$ and g are as defined above, or a heterocyclic 5-membered ring containing at least one oxygen, sulfur, or nitrogen atom, which heterocyclic 5-membered ring may be optionally substituted with one to three identical or different $(R^{18})_g$'s, and $R^{18}$ and g are as defined above, or $R^8$ and $R^9$ are combined together at their ends to form a saturated or unsaturated 5- or 6-membered ring containing zero to two oxygen or sulfur atoms in the ring thereof;

oxime compounds of formula (1) wherein X is $X^2$, and $R^8$ and $R^9$ are independently hydrogen, $C_1$–$C_{11}$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_{10}$ alkoxyalkyl, $C_2$–$C_{10}$ alkylthioalkyl, or naphthyl, or $C_3$–$C_7$ cycloalkyl optionally substituted with $C_1$–$C_4$ alkyl, or $C_4$–$C_{10}$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ alkyl on the ring thereof,

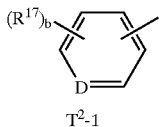 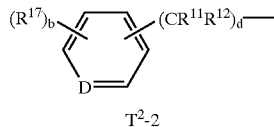

or $T^2$-1 or $T^2$-2 of formula (4)

wherein $R^{17}$, D, $R^{11}$, $R^{12}$, b, and d are as defined above, or 2-furyl, 3-furyl, 2-thienyl, 3-thienyl, 2-pyrrolyl, or 3-pyrrolyl, each of which heterocyclic groups may be optionally substituted with one to three identical or different $(R^{18})_g$ wherein $R^{18}$ and g are as defined above, or $R^8$ and $R^9$ are combined together at their ends to form a saturated or unsaturated 5- or 6-membered ring containing zero to two oxygen or sulfur atoms in the ring thereof;

oxime compounds of formula (1) wherein X is $X^2$, and $R^8$ and $R^9$ are independently hydrogen, $C_1$–$C_{11}$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_{10}$ alkoxyalkyl, or $C_2$–$C_{10}$ alkylthioalkyl, or $C_3$–$C_7$ cycloalkyl optionally substituted with $C_1$–$C_4$ alkyl, or $C_4$–$C_{10}$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ alkyl on the ring thereof, or $T^2$-1 or $T^2$-2 of formula (4)

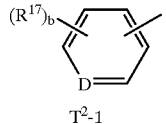 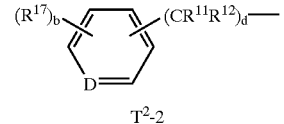

wherein $R^{17}$, D, $R^{11}$, $R^{12}$, b, and d are as defined above, or $R^8$ and $R^9$ are combined together at their ends to form a saturated or unsaturated 5- or 6-membered ring containing zero to two oxygen or sulfur atoms in the ring thereof, oxime compounds of formula (1) wherein X is $X^2$, and $R^8$ and $R^9$ are independently hydrogen, $C_1$–$C_{11}$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_{10}$ alkoxyalkyl, or $C_2$–$C_{10}$ alkylthioalkyl, or $C_3$–$C_7$ cycloalkyl optionally substituted with $C_1$–$C_4$ alkyl, or $C_4$–$C_{10}$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ alkyl on the ring thereof, or $R^8$ and $R^9$ are combined together at their ends to form a saturated or unsaturated 5- or 6-membered ring containing zero to two oxygen or sulfur atoms in the ring thereof; and oxime compounds of formula (1) wherein X is $X^2$, and $R^8$ and $R^9$ are independently hydrogen, $C_1$–$C_{11}$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_{10}$ alkoxyalkyl, or $C_2$–$C_{10}$ alkylthioalkyl, or $C_3$–$C_7$ cycloalkyl optionally substituted with $C_1$–$C_4$ alkyl, or $C_4$–$C_{10}$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ alkyl on the ring thereof.

Particularly preferred examples of the present compounds are as follows:

(187) 4-(2,6-dichloro-4-(3,3-dichloro-2-propenyloxy)phenoxy)butanal O-isopropyloxime (169) 5-(2,6-dichloro-4-(3,3-dichloro-2-propenyloxy)phenoxy)pentanal O-isopropyloxime (188) 6-(2,6-dichloro-4-(3,3-dichloro-2-propenyloxy)phenoxy)hexanal O-isopropyloxime

(26) 4-(2,6-dichloro-4-(3,3-dichloro-2-propenyloxy)phenoxy)butanal O-tert-butyloxime

(16) 5-(2,6-dichloro-4-(3,3-dichloro-2-propenyloxy)phenoxy)pentanal O-tert-butyloxime (134) 6-(2,6-dichloro-4-(3,3-dichloro-2-propenyloxy)phenoxy)hexanal O-tert-butyloxime (189) 4-(2,6-dichloro-4-(3,3-dichloro-2-propenyloxy)phenoxy)butanal O-(2,2,2-trichloroethyl)oxime (170) 5-(2,6-dichloro-4-(3,3-dichloro-2-propenyloxy)phenoxy)pentanal O-(2,2,2-trichloroethyl)oxime (190) 6-(2,6-dichloro-4-(3,3-dichloro-2-propenyloxy)phenoxy)hexanal O-(2,2,2-trichloroethyl)oxime

(24) 4-(2,6-dichloro-4-(3,3-dichloro-2-propenyloxy)phenoxy)butanal O-(3,3-dichloro-2-propenyl)oxime

(17) 5-(2,6-dichloro-4-(3,3-dichloro-2-propenyloxy)phenoxy)pentanal O-(3,3-dichloro-2-propenyl)oxime

(76) 6-(2,6-dichloro-4-(3,3-dichloro-2-propenyloxy)phenoxy)hexanal O-(3,3-dichloro-2-propenyl)oxime (165) 4-(2,6-dichloro-4-(3,3-dichloro-2-propenyloxy)phenoxy)butyloxyacetaldehyde O-isopropyloxime (152) 5-(2,6-dichloro-4-(3,3-dichloro-2-propenyloxy)phenoxy)pentyloxyacetaldehyde O-isopropyloxime (191) 4-(2,6-dichloro-4-(3,3-dichloro-2-propenyloxy)phenoxy)butyloxyacetone O-isopropyloxime (172) 5-(2,6-dichloro-4-(3,3-dichloro-2-propenyloxy)phenoxy)pentyloxyacetone O-isopropyloxime (6) 4-(2,6-dichloro-4-(3,3-dichloro-2-propenyloxy)phenoxy)butyloxyacetaldehyde O-tert-butyloxime

(14) 5-(2,6-dichloro-4-(3,3-dichloro-2-propenyloxy)phenoxy)pentyloxyacetaldehyde O-tert-butyloxime (103) 4-(2,6-dichloro-4-(3,3-dichloro-2-propenyloxy)phenoxy)butyloxyacetone O-tert-butyloxime (104) 5-(2,6-dichloro-4-(3,3-dichloro-2-propenyloxy)phenoxy)pentyloxyacetone O-tert-butyloxime (167) 4-(2,6-dichloro-4-(3,3-dichloro-2-propenyloxy)phenoxy)butyloxyacetaldehyde O-(2,2,2-trichloroethyl)oxime (160) 5-(2,6-dichloro-4-(3,3-dichloro-2-propenyloxy)phenoxy)pentyloxyacetaldehyde O-(2,2,2-trichloroethyl)oxime (192) 4-(2,6-dichloro-4-(3,3-dichloro-2-propenyloxy)phenoxy)butyloxyacetone O-(2,2,2-trichloroethyl)oxime (173) 5-(2,6-dichloro-4-(3,3-dichloro-2-propenyloxy)phenoxy)pentyloxyacetone O-(2,2,2-trichloroethyl)oxime (2) 4-(2,6-dichloro-4-(3,3-dichloro-2-propenyloxy)phenoxy)butyloxyacetaldehyde O-(3,3-dichloro-2-propenyl)oxime

(15) 5-(2,6-dichloro-4-(3,3-dichloro-2-propenyloxy)phenoxy)pentyloxyacetaldehyde O-(3,3-dichloro-2-propenyl)oxime

(46) 4-(2,6-dichloro-4-(3,3-dichloro-2-propenyloxy)phenoxy)butyloxyacetone O-(3,3-dichloro-2-propenyl)oxime

(47) 5-(2,6-dichloro-4-(3,3-dichloro-2-propenyloxy)phenoxy)pentyloxyacetone O-(3,3-dichloro-2-propenyl)oxime (329) 4-(2,6-dichloro-4-(3,3-dichloro-2-propenyloxy)phenoxy)methylbenzaldehyde O-sec-butyloxime (314) 4-(2,6-dichloro-4-(3,3-dichloro-2-propenyloxy)phenoxy)methylbenzaldehyde O-t-butyloxime (355) 4-(2-(2,6-dichloro-4-(3,3-dichloro-2-propenyloxy)phenoxy)ethyl)benzaldehyde O-sec-butyloxime (357) 4-(2-(2,6-dichloro-4-(3,3-dichloro-2-propenyloxy)phenoxy)ethyl)benzaldehyde O-allyloxime (358) 4-(2-(2,6-dichloro-4-(3,3-dichloro-2-propenyloxy)phenoxy)ethyl)benzaldehyde O-(3,3-dichloro-2-propenyl)oxime (338) 4-(3-(2,6-dichloro-4-(3,3-dichloro-2-propenyloxy)phenoxy)propyloxy)benzaldehyde O-n-propyloxime (339) 4-(3-(2,6-dichloro-4-(3,3-dichloro-2-propenyloxy)phenoxy)propyloxy)benzaldehyde O-isopropyloxime (340) 4-(3-(2,6-dichloro-4-(3,3-dichloro-2-propenyloxy)phenoxy)propyloxy)benzaldehyde O-sec-butyloxime (291) 4-(3-(2,6-dichloro-4-(3,3-dichloro-2-propenyloxy)phenoxy)propyloxy)benzaldehyde O-t-butyloxime (293) 4'-(3-(2,6-dichloro-4-(3,3-dichloro-2-propenyloxy)phenoxy)propyloxy)acetophenone O-ethyloxime (318) 4'-(3-(2,6-dichloro-4-(3,3-dichloro-2-propenyloxy)phenoxy)propyloxy)propiophenone O-ethyloxime (297) 4'-(4-(2,6-dichloro-4-(3,3-dichloro-2-propenyloxy)phenoxy)butyloxy)acetophenone O-ethyloxime (310) 4'-(4-(2,6-dichloro-4-(3,3-dichloro-2-propenyloxy)phenoxy)butyloxy)acetophenone O-n-propyloxime (315) 4-(4-(2,6-dichloro-4-(3,3-dichloro-2-propenyloxy)phenoxy)butyloxy)benzaldehyde O-isopropyloxime (391) 4'-(3-(2,6-dichloro-4-(3,3-dichloro-2-propenyloxy)phenoxy)propyloxy)-2,2,2-trifluoroacetophenone O-ethyloxime (529) 4-(trifluoromethyl)benzaldehyde O-(4-(2,6-dichloro-4-(3,3-dichloro-2-propenyloxy)phenoxy)butyl)oxime (531) 4'-(trifluoromethyl)acetophenone O-(4-(2,6-dichloro-4-(3,3-dichloro-2-propenyloxy)phenoxy)butyl)oxime (545) trimethylacetaldehyde O-(5-(2,6-dichloro-4-(3,3-dichloro-2-propenyloxy)phenoxy)pentyl)oxime (559) 3,3-dimethyl-2-butanone O-(5-(2,6-dichloro-4-(3,3-dichloro-2-propenyloxy)phenoxy)pentyl)oxime (562) 3,3-dimethyl-2-butanone O-(4-(2,6-dichloro-4-(3,3-dichloro-2-propenyloxy)phenoxy)butyl)oxime (563) 4-methyl-2-pentanone O-(4-(2,6-dichloro-4-(3,3-dichloro-2-propenyloxy)phenoxy)butyl)oxime (564) 4-methyl-2-pentanone O-(5-(2,6-dichloro-4-(3,3-dichloro-2-propenyloxy)phenoxy)pentyl)oxime (582) 3-methyl-2-butanone O-(5-(2,6-dichloro-4-(3,3-dichloro-2-propenyloxy)phenoxy)pentyl)oxime The above numbers preceding the compound names are also used below for designating the present compounds.

The present compounds can be produced, for example, by the following production processes A to M.

Production process A (the compounds of formula (1) wherein X is $X^1$ and $R^6$ is hydrogen are excluded)

This is the production process in which a compound of formula (15)

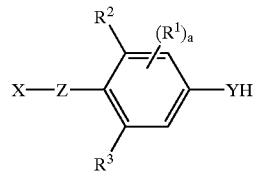

wherein $R^1$, $R^2$, $R^3$, a, X, Y, and Z are as defined above, with the proviso that when X is $X^1$, $R^6$ is not hydrogen, is reacted with a compound of formula (16)

wherein $R^4$ is as defined above and L is halogen (e.g., chlorine, bromine, iodine), mesyloxy, or tosyloxy.

The reaction is preferably effected in the presence of an appropriate base and in an inert solvent.

The solvent which can be used may include ketones such as acetone, methyl ethyl ketone, and cyclohexanone; ethers such as 1,2-dimethoxyethane, tetrahydrofuran, dioxane, and dialkyl (e.g., $C_1$–$C_4$) ether (e.g., diethyl ether, diisopropyl ether); polar solvents such as N,N-dimethylformamide, dimethylsulfoxide, hexamethylphosphoric triamide, sulforane, acetonitrile, and nitromethane; halogenated hydrocarbons such as dichloromethane, chloroform, 1,2-dichloroethane, and chlorobenzene; hydrocarbons such as toluene, benzene, and xylene; and water. If necessary, these solvents may also be used in admixture.

The base which can be used may include hydroxides of alkali metals or alkaline earth metals, such as lithium hydroxide, sodium hydroxide, potassium hydroxide, and calcium hydroxide; carbonates of alkali metals or alkaline earth metals, such as lithium carbonate, potassium carbonate, sodium carbonate, and calcium carbonate; hydrides of alkali metals or alkaline earth metals, such as lithium hydride, sodium hydride, potassium hydride, and calcium hydride; alkoxides (e.g., $C_1$–$C_4$) of alkali metals, such as sodium methoxide, sodium ethoxide, and potassium tert-butoxide; and organic bases such as triethylamine and pyridine. In necessary, catalysts such as ammonium salts (e.g., triethylbenzylammonium chloride) may be added to the reaction system in an amount of 0.01 to 1 mole relative to 1 mole of the compound of formula (15).

The reaction temperature, although it can be usually selected in the range of –20° C. to the boiling point of a solvent used in the reaction or 150° C., is more preferably in the range of –5° C. to the boiling point of the solvent used in the reaction or 100° C.

The molar ratio of the starting materials and base to be used in the reaction may be suitably selected; however, it is favorable that the reaction is effected at the equimolar ratio or a ratio close thereto.

After completion of the reaction, the reaction mixture is subjected to ordinary post-treatments such as extraction with an organic solvent and/or concentration. Thus, the desired present compounds can be isolated. If necessary, further purification may be carried out by an ordinary technique such as chromatography, distillation, or recrystallization.

Production process B (for the present compounds wherein Y is oxygen, with the proviso that when X is $X^1$, $R^6$ is not hydrogen)

This is the production process in which the compound of formula (15) wherein Y is oxygen is reacted with an alcohol compound of formula (17)

HO—$R^4$ wherein $R^4$ is as defined above.

The reaction is preferably effected in the presence of an appropriate dehydrating agent and, if necessary, in an inert solvent.

The dehydrating agent which can be used may include, for example, dicyclohexylcarbodiimide, dialkyl (e.g., $C_1$–$C_4$) azodicarboxylate (e.g., diethylazodicarboxylate, and diisopropylazodicarboxylate)—trialkyl (e.g., $C_1$–$C_{20}$) phosphine or triarylphosphine (e.g., triphenylphosphine, trioctylphosphine, tributylphosphine) systems.

The solvent which can be used may include, for example, hydrocarbons such as benzene, xylene, and toluene; ethers such as diethyl ether, diisopropyl ether, tetrahydrofuran, and dioxane; and halogenated hydrocarbons such as carbon tetrachloride, dichloromethane, chlorobenzene, and dichlorobenzene.

The reaction temperature can be usually selected in the range of –20° C. to 200° C. or the boiling point of a solvent used in the reaction.

The molar ratio of the starting materials and base to be used in the reaction may be suitably selected; however, it is favorable that the reaction is effected at the equimolar ratio or a ratio close thereto.

After completion of the reaction, the reaction mixture is subjected to ordinary post-treatments such as extraction with an organic solvent and/or concentration. Thus, the desired present compounds can be isolated. If necessary, further purification may be carried out by an ordinary technique such as chromatography, distillation, or recrystallization.

Production process C (for the present compounds wherein Y and Z are both oxygen, with the proviso that when X is $X^1$, $R^6$ is not hydrogen)

This is the production process in which a compound of formula (18)

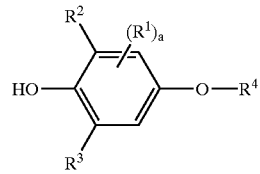

wherein $R^1$, $R^2$, $R^3$, $R^4$, and a are as defined above, is reacted with a compound of formula (19)

X—L wherein X and L are as defined above, with the proviso that when X is $X^1$, $R^6$ is hydrogen.

The reaction is preferably effected in the presence of an appropriate base and in an inert solvent.

The solvent which can be used may include ketones such as acetone, methyl ethyl ketone, and cyclohexanone; ethers such as 1,2-dimethoxyethane, tetrahydrofuran, dioxane, and dialkyl (e.g., $C_1$–$C_4$) ether (e.g., diethyl ether, diisopropyl ether); polar solvents such as N,N-dimethylformamide, dimethylsulfoxide, hexamethylphosphoric triamide, sulforane, acetonitrile, and nitromethane; halogenated hydrocarbons such as dichloromethane, chloroform, 1,2-dichloroethane, and chlorobenzene; hydrocarbons such as toluene, benzene, and xylene; and water. If necessary, these solvents may also be used in admixture.

The base which can be used may include hydroxides of alkali metals or alkaline earth metals, such as lithium hydroxide, sodium hydroxide, potassium hydroxide, and calcium hydroxide; carbonates of alkali metals or alkaline earth metals, such as lithium carbonate, potassium carbonate, sodium carbonate, and calcium carbonate; hydrides of alkali metals or alkaline earth metals, such as lithium hydride, sodium hydride, potassium hydride, and calcium hydride; alkoxides (e.g., $C_1$–$C_4$) of alkali metals, such as sodium methoxide, sodium ethoxide, and potassium tert-butoxide; and organic bases such as triethylamine and pyridine. In necessary, catalysts such as ammonium salts (e.g., triethylbenzylammonium chloride) may be added to the reaction system in an amount of 0.01 to 1 mole relative to 1 mole of the compound of formula (18).

The reaction temperature, although it can be usually selected in the range of −20° C. to the boiling point of a solvent used in the reaction or 150° C., is more preferably in the range of −5° C. to the boiling point of the solvent used in the reaction or 100° C.

The molar ratio of the starting materials and base to be used in the reaction may be suitably selected; however, it is favorable that the reaction is effected at the equimolar ratio or a ratio close thereto.

After completion of the reaction, the reaction mixture is subjected to ordinary post-treatments such as extraction with an organic solvent and/or concentration. Thus, the desired present compounds can be isolated. If necessary, further purification may be carried out by an ordinary technique such as chromatography, distillation, or recrystallization.

Production process D (for the present compounds wherein Y and Z are both oxygen, with the proviso that when X is $X^1$, $R^6$ is not hydrogen)

This is the production process in which a compound of formula (18) is reacted with a compound of formula (20)

X—OH wherein X is as defined above, with the proviso that when X is $X^1$, $R^6$ is not hydrogen.

The reaction is preferably effected in the presence of an appropriate dehydrating agent and, if necessary, in an inert solvent.

The dehydrating agent which can be used may include, for example, dicyclohexylcarbodiimide, dialkyl (e.g., $C_1$–$C_4$) azodicarboxylate (e.g., diethylazodicarboxylate, and diisopropylazodicarboxylate)—trialkyl (e.g., $C_1$–$C_{20}$) phosphine or triarylphosphine (e.g., triphenylphosphine, trioctylphosphine, tributylphosphine) systems.

The solvent which can be used may include, for example, hydrocarbons such as benzene, xylene, and toluene; ethers such as diethyl ether, diisopropyl ether, tetrahydrofuran, and dioxane; and halogenated hydrocarbons such as carbon tetrachloride, dichloromethane, chlorobenzene, and dichlorobenzene.

The reaction temperature can be usually selected in the range of −20° C. to 200° C. or the boiling point of a solvent used in the reaction.

The molar ratio of starting materials and dehydrating agent to be used in the reaction may be suitably selected; however, it is favorable that the reaction is effected at the equimolar ratio or a ratio close thereto.

After completion of the reaction, the reaction mixture is subjected to ordinary post-treatments such as extraction with an organic solvent and/or concentration. Thus, the desired present compounds can be isolated. If necessary, further purification may be carried out by an ordinary technique such as chromatography, distillation, or recrystallization.

Production process E (for the present compounds wherein X is $X^1$)

This is the production process in which a hydroxylamine compound of formula (21)

$R^6O$—$NH_2$ wherein $R^6$ is as defined above, or a salt thereof, is reacted with a carbonyl compound of formula (22)

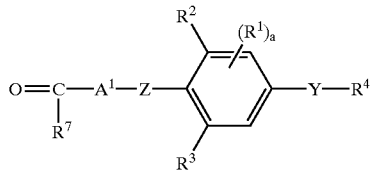

wherein $R^1$, $R^2$, $R^3$, $R^4$, $R^7$, $A^1$, Y, Z, and a are as defined above.

The reaction can be effected in an inert solvent and, if necessary, in the presence of a base or an acid.

The solvent which can be used may include, for example, alcohols such as methanol and ethanol; ethers such as diethyl ether, tetrahydrofuran, and dioxane; acetic acid; and water. If necessary, these solvents may also be used in admixture.

The base which can be used may include hydroxides of alkali metals or alkaline earth metals, such as lithium hydroxide, sodium hydroxide, potassium hydroxide, and calcium hydroxide; carbonates of alkali metals or alkaline earth metals, such as lithium carbonate, potassium carbonate, sodium carbonate, and calcium carbonate; hydrides of alkali metals or alkaline earth metals, such as lithium hydride, sodium hydride, potassium hydride, and calcium hydride; alkoxides (e.g., $C_1$–$C_4$) of alkali metals, such as sodium methoxide, sodium ethoxide, and potassium tert-butoxide; and organic bases such as triethylamine and pyridine. The amount of base to be used, if necessary, in the reaction is preferably 1 mole or more relative to 1 mole of the hydroxylamine compound of formula (21). The organic bases such as triethylamine and pyridine can serve both as the base and as the solvent, when the reaction is effected with them in large excess relative to the hydroxylamine compound of formula (21).

The acid which can be used may include, for example, hydrochloric acid, sulfuric acid, and p-toluenesulfonic acid. The acid can be used in the reaction at a catalytic amount ranging from 0.01 to 1 equivalent relative to the carbonyl compound of formula (22).

The hydroxylamine compound as the starting material, although it can be used as such in the reaction, is usually used in the form of an inorganic acid salt, such as hydrochloride or sulfate.

The reaction temperature, although it can be usually selected in the range of −20° C. to the boiling point of a solvent used in the reaction or 150° C., is more preferably in the range of 0° C. to the boiling point of the solvent used in the reaction or 60° C.

The molar ratio of the starting materials and reagents to be used in the reaction may be freely selected; however, it is favorable that the reaction of the carbonyl compound of formula (22) and the hydroxylamine compound of formula (21) or a salt thereof is effected at the equimolar ratio or a ratio close thereto.

After completion of the reaction, the reaction mixture is subjected to ordinary post-treatments such as extraction with an organic solvent and/or concentration. Thus, the desired present compounds can be isolated. If necessary, further purification may be carried out by an ordinary technique such as chromatography, distillation, or recrystallization.

Production process F (for the present compounds wherein X is $X^1$, with the proviso that $R^6$ is not hydrogen, $T^1$-4, $T^1$-5, $T^1$-6, or $T^1$-7)

This is the production process in which a compound of formula (23)

wherein $R^6$ and L are as defined above, with the proviso that $R^6$ is not hydrogen, $T^1$-4, $T^1$-5, $T^1$-6, or $T^1$-7, is reacted with a compound of formula (24)

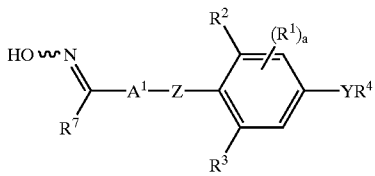

wherein $R^1$, $R^2$, $R^3$, $R^4$, $R^7$, $A^1$, Y, Z, and a are as defined above (i.e., the present compound wherein X is $X^1$ and $R^6$ is hydrogen).

The reaction is preferably effected in the presence of an appropriate base and in an inert solvent.

The solvent which can be used may include ketones such as acetone, methyl ethyl ketone, and cyclohexanone; ethers such as 1,2-dimethoxyethane, tetrahydrofuran, dioxane, and dialkyl (e.g., $C_1$–$C_4$) ether (e.g., diethyl ether, diisopropyl ether); polar solvents such as N,N-dimethylformamide, dimethylsulfoxide, hexamethylphosphoric triamide, sulforane, acetonitrile, and nitromethane; halogenated hydrocarbons such as dichloromethane, chloroform, 1,2-dichloroethane, and chlorobenzene; hydrocarbons such as toluene, benzene, and xylene; and water. If necessary, these solvents may also be used in admixture.

The base which can be used may include hydroxides of alkali metals or alkaline earth metals, such as lithium hydroxide, sodium hydroxide, potassium hydroxide, and calcium hydroxide; carbonates of alkali metals or alkaline earth metals, such as lithium carbonate, potassium carbonate, sodium carbonate, and calcium carbonate; hydrides of alkali metals or alkaline earth metals, such as lithium hydride, sodium hydride, potassium hydride, and calcium hydride; alkoxides (e.g., $C_1$–$C_4$) of alkali metals, such as sodium methoxide, sodium ethoxide, and potassium tert-butoxide; and organic bases such as triethylamine and pyridine. In necessary, catalysts such as ammonium salts (e.g., triethylbenzylammonium chloride) may be added to the reaction system in an amount of 0.01 to 1 mole relative to 1 mole of the compound of formula (24).

The reaction temperature, although it can be usually selected in the range of $-20°$ C. to the boiling point of a solvent used in the reaction or $150°$ C., is more preferably in the range of $-5°$ C. to the boiling point of the solvent used in the reaction or $100°$ C.

The molar ratio of the starting materials and base to be used in the reaction may be freely selected; however, it is favorable that the reaction is effected at the equimolar ratio or a ratio close thereto.

After completion of the reaction, the reaction mixture is subjected to ordinary post-treatments such as extraction with an organic solvent and/or concentration. Thus, the desired present compounds can be isolated. If necessary, further purification may be carried out by an ordinary technique such as chromatography, distillation, or recrystallization.

Production process G (for the present compounds wherein Y and Z are both oxygen, X is $X^1$, $A^1$ is $A^1$-8, and e1 is 0, with the proviso that $R^6$ is not hydrogen).

This is the production process in which a compound of formula (25)

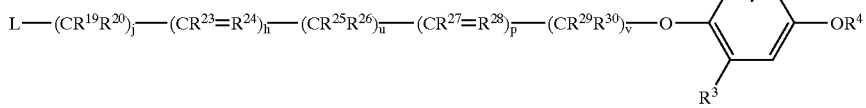

wherein $R^1$, $R^2$, $R^3$, $R^4$, $R^{19}$, $R^{20}$, $R^{23}$, $R^{24}$, $R^{25}$, $R^{26}$, $R^{27}$, $R^{28}$, $R^{29}$, $R^{30}$, a, h, j, p, u, v, and L are as defined above, is reacted with a compound of formula (26)

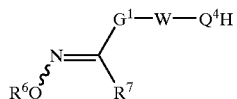

wherein $R^6$, $R^7$, $G^1$, and W are as defined above, $Q^4$ is oxygen, sulfur, or $NR^{39}$, and $R^{39}$ is as defined above.

The reaction is preferably effected in the presence of an appropriate base and in an inert solvent.

The solvent which can be used may include ketones such as acetone, methyl ethyl ketone, and cyclohexanone; ethers such as 1,2-dimethoxyethane, tetrahydrofuran, dioxane, and dialkyl (e.g., $C_1$–$C_4$) ether (e.g., diethyl ether, diisopropyl ether); polar solvents such as N,N-dimethylformamide, dimethylsulfoxide, hexamethylphosphoric triamide, sulforane, acetonitrile, and nitromethane; halogenated hydrocarbons such as dichloromethane, chloroform, 1,2-dichloroethane, and chlorobenzene; hydrocarbons such as toluene, benzene, and xylene; and water. If necessary, these solvents may also be used in admixture.

The base which can be used may include hydroxides of alkali metals or alkaline earth metals, such as lithium hydroxide, sodium hydroxide, potassium hydroxide, and calcium hydroxide; carbonates of alkali metals or alkaline earth metals, such as lithium carbonate, sodium carbonate, potassium carbonate, and calcium carbonate; hydrides of alkali metals or alkaline earth metals, such as lithium hydride, sodium hydride, potassium hydride, and calcium hydride; alkoxides (e.g., $C_1$–$C_4$) of alkali metals, such as sodium methoxide, sodium ethoxide, and potassium tert-butoxide; and organic bases such as triethylamine and pyridine. In necessary, catalysts such as ammonium salts (e.g., triethylbenzylammonium chloride) may be added to the reaction system in an amount of 0.01 to 1 mole relative to 1 mole of the compound of formula (25).

The reaction temperature can be usually selected in the range of −20° C. to the boiling point of a solvent used in the reaction or 150° C.

The molar ratio of the starting materials and base to be used in the reaction may be suitably selected; however, it is favorable that the reaction is effected at the equimolar ratio or a ratio close thereto.

After completion of the reaction, the reaction mixture is subjected to ordinary post-treatments such as extraction with an organic solvent and/or concentration. Thus, the desired present compounds can be isolated. If necessary, further purification may be carried out by an ordinary technique such as chromatography, distillation, or recrystallization.

Production process H (for the present compounds wherein Y and Z are both oxygen, X is $X^2$, $A^2$ is $A^2$-4, and e1 is 0)

This is the production process in which a compound of formula (27)

The solvent which can be used may include ketones such as acetone, methyl ethyl ketone, and cyclohexanone; ethers such as 1,2-dimethoxyethane, tetrahydrofuran, dioxane, and dialkyl (e.g., $C_1$–$C_4$) ether (e.g., diethyl ether, diisopropyl ether); polar solvents such as N,N-dimethylformamide, dimethylsulfoxide, hexamethylphosphoric triamide, sulforane, acetonitrile, and nitromethane; halogenated hydrocarbons such as dichloromethane, chloroform, 1,2-dichloroethane, and chlorobenzene; hydrocarbons such as toluene, benzene, and xylene; and water. If necessary, these solvents may also be used in admixture.

The base which can be used may include hydroxides of alkali metals or alkaline earth metals, such as lithium hydroxide, sodium hydroxide, potassium hydroxide, and calcium hydroxide; carbonates of alkali metals or alkaline earth metals, such as lithium carbonate, sodium carbonate, potassium carbonate, and calcium carbonate; hydrides of alkali metals or alkaline earth metals, such as lithium hydride, sodium hydride, potassium hydride, and calcium hydride; alkoxides (e.g., $C_1$–$C_4$) of alkali metals, such as sodium methoxide, sodium ethoxide, and potassium tert-butoxide; and organic bases such as triethylamine and pyridine. In necessary, catalysts such as ammonium salts (e.g., triethylbenzylammonium chloride) may be added to the reaction system in an amount of 0.01 to 1 mole relative to 1 mole of the compound of formula (27).

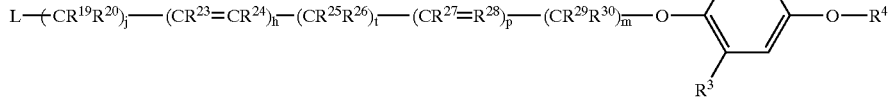

wherein $R^1$, $R^2$, $R^3$, $R^4$, $R^{19}$, $R^{20}$, $R^{23}$, $R^{24}$, $R^2$, $R^{26}$, $R^{27}$, $R^{28}$, $R^{29}$, $R^{30}$, j, h, p, m, a, and L are as defined above, is reacted with compound $U^5$-1, $U^5$-2, or $U^5$-3 of formula (28)

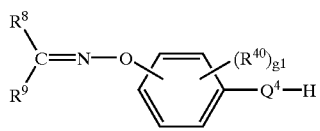

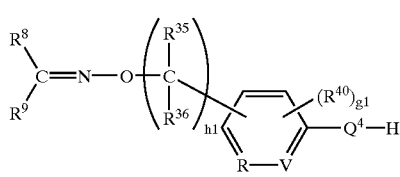

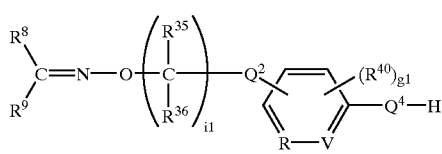

wherein $R^8$, $R^9$, $R^{35}$, $R^{36}$, $R^{40}$ g1, h1, i1, R, V, $Q^2$, and $Q^4$ are as defined above.

The reaction is preferably effected in the presence of an appropriate base and in an inert solvent.

The reaction temperature can be usually selected in the range of −20° C. to the boiling point of a solvent used in the reaction or 150° C.

The molar ratio of the starting materials and base to be used in the reaction may be freely selected; however, it is favorable that the reaction is effected at the equimolar ratio or a ratio close thereto.

After completion of the reaction, the reaction mixture is subjected to ordinary post-treatments such as extraction with an organic solvent and/or concentration. Thus, the desired present compounds can be isolated. If necessary, further purification may be carried out by an ordinary technique such as chromatography, distillation, or recrystallization.

Production process I (for the present compounds wherein X is $X^2$).

This is the production process in which an O-substituted hydroxylamine compound of formula (29)

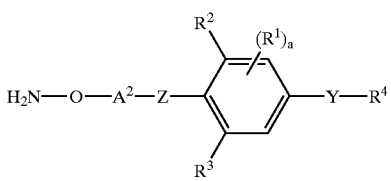

wherein $R^1$, $R^2$, $R^3$, $R^4$, $A^2$, Z, Y, and a are as defined above, or a salt thereof, is reacted with a carbonyl compound of formula (30)

wherein $R^8$ and $R^9$ are as defined above.

The reaction can be effected in an inert solvent and, if necessary, in the presence of a base.

The solvent which can be used may include, for example, alcohols such as methanol and ethanol; ethers such as diethyl ether, tetrahydrofuran, and dioxane; pyridine; and water. The carbonyl compound of formula (30) may also be used as the solvent. If necessary, these solvents may also be used in admixture.

The base which can be used may include, for example, triethylamine, pyridine, and sodium acetate.

The O-substituted hydroxylamine compound as the starting material is usually used in the form of an inorganic acid salt such as hydrochloride.

The reaction temperature is usually in the range of 0° C. to 150° C.

The molar ratio of the starting materials and reagents to be used in the reaction may be suitably selected; however, it is preferred that the reaction of the carbonyl compound of formula (30) and the O-substituted hydroxylamine compound of formula (29) or a salt thereof is effected at the equimolar ratio or a ratio close thereto. The amount of base to be used, if necessary, in the reaction is preferably 1 mole or more relative to 1 mole of the compound of formula (29).

After completion of the reaction, the reaction mixture is subjected to ordinary post-treatments such as extraction with an organic solvent and/or concentration. Thus, the desired present compounds can be isolated. If necessary, further purification may be carried out by an ordinary technique such as chromatography, distillation, or recrystallization.

Production process J (for the present compounds wherein X is $X^2$).

This is the production process in which a compound of formula (31)

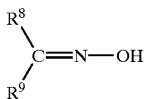

wherein $R^8$ and $R^9$ are as defined above, is reacted with a compound of formula (32)

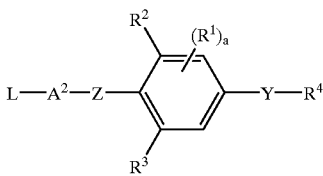

wherein $R^1$, $R^2$, $R^3$, $R^4$, $A^2$, Z, Y, a, and L are as defined above.

The reaction is preferably effected in the presence of an appropriate base and in an inert solvent.

The solvent which can be used may include ketones such as acetone, methyl ethyl ketone, and cyclohexanone; ethers such as 1,2-dimethoxyethane, tetrahydrofuran, dioxane, and dialkyl (e.g., $C_1$–$C_4$) ether (e.g., diethyl ether, diisopropyl ether); polar solvents such as N,N-dimethylformamide, dimethylsulfoxide, hexamethylphosphoric triamide, sulforane, acetonitrile, and nitromethane; halogenated hydrocarbons such as dichloromethane, chloroform, 1,2-dichloroethane, and chlorobenzene; hydrocarbons such as toluene, benzene, and xylene; and water. If necessary, these solvents may also be used in admixture.

The base which can be used may include hydroxides of alkali metals or alkaline earth metals, such as lithium hydroxide, sodium hydroxide, potassium hydroxide, and calcium hydroxide; carbonates of alkali metals or alkaline earth metals, such as lithium carbonate, sodium carbonate, potassium carbonate, and calcium carbonate; hydrides of alkali metals or alkaline earth metals, such as lithium hydride, sodium hydride, potassium hydride, and calcium hydride; alkoxides (e.g., $C_1$–$C_4$) of alkali metals, such as sodium methoxide, sodium ethoxide, and potassium tert-butoxide; and organic bases such as triethylamine and pyridine. In necessary, catalysts such as ammonium salts (e.g., triethylbenzylammonium chloride) may be added to the reaction system in an amount of 0.01 to 1 mole relative to 1 mole of the compound of formula (31).

The reaction temperature can be usually selected in the range of –20° C. to the boiling point of a solvent used in the reaction or 150° C.

The molar ratio of the starting materials and base to be used in the reaction may be freely selected; however, it is favorable that the reaction is effected at the equimolar ratio or a ratio close thereto.

After completion of the reaction, the reaction mixture is subjected to ordinary post-treatments such as extraction with an organic solvent and/or concentration. Thus, the desired present compounds can be isolated. If necessary, further purification may be carried out by an ordinary technique such as chromatography, distillation, or recrystallization.

Production process K (for the compounds wherein X is $X^1$ and $R^6$ is $T^1$-4, $T^1$-5, or $T^1$-7).

This is the production process in which a compound of formula (33)

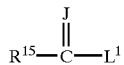

wherein J and $R^{15}$ are as defined above, and $L^1$ is chlorine or bromine (when $R^6$ is $T^1$-4), or a compound of formula (34)

wherein $R^{15}$ is as defined above (when $R^6$ is $T^1$-4), or a compound of formula (35)

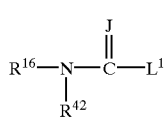

wherein J, $R^{16}$, $R^{42}$, and $L^1$ are as defined above (when $R^6$ is $T^1$-5), or a sulfonyl halide compound of formula (36)

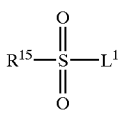

wherein $R^{15}$ and $L^1$ are as defined above (when $R^6$ is $T^1$-7), is reacted with a compound of formula (24).

The reaction is preferably effected in the presence of an appropriate base and in an inert solvent.

The solvent which can be used may include ketones such as acetone, methyl ethyl ketone, and cyclohexanone; ethers such as 1,2-dimethoxyethane, tetrahydrofuran, dioxane, and dialkyl (e.g., $C_1$–$C_4$) ether (e.g., diethyl ether, diisopropyl ether); polar solvents such as N,N-dimethylformamide, dimethylsulfoxide, hexamethylphosphoric triamide, sulforane, acetonitrile, and nitromethane; halogenated hydrocarbons such as dichloromethane, chloroform, 1,2-dichloroethane, and chlorobenzene; hydrocarbons such as toluene, benzene, and xylene; and water. If necessary, these solvents may also be used in admixture.

The base which can be used may include hydroxides of alkali metals or alkaline earth metals, such as lithium hydroxide, sodium hydroxide, potassium hydroxide, and calcium hydroxide; carbonates of alkali metals or alkaline earth metals, such as lithium carbonate, potassium carbonate, sodium carbonate, and calcium carbonate; hydrides of alkali metals or alkaline earth metals, such as lithium hydride, sodium hydride, potassium hydride, and calcium hydride; alkoxides (e.g., $C_1$–$C_4$) of alkali metals, such as sodium methoxide, sodium ethoxide, and potassium tert-butoxide; and organic bases such as triethylamine and pyridine. In particular, organic bases such as triethylamine or pyridine are preferably used.

The reaction temperature, although it can be usually selected in the range of –20° C. to the boiling point of a solvent used in the reaction or 150° C., is more preferably in the range of –5° C. to the boiling point of the solvent used in the reaction or 50° C.

The molar ratio of the starting materials and base to be used in the reaction may be freely selected; however, it is favorable that the reaction is effected with the compound of formula (33), (34), (35), or (36) and the base in an amount of 1 to 5 moles, respectively, relative to 1 mole of the compound of formula (24).

After completion of the reaction, the reaction mixture is subjected to ordinary post-treatments such as extraction with an organic solvent and/or concentration. Thus, the desired present compounds can be isolated. If necessary, further purification may be carried out by an ordinary technique such as chromatography, distillation, or recrystallization.

Production process L (for the present compounds wherein X is $X^1$ and $R^6$ is $T^1$-6).

This is the production process in which an isocyanate compound or an isothiocyanate compound of formula (37)

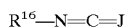

wherein J and $R^{16}$ are as defined above, is reacted with a compound of formula (24).

The reaction is effected, if necessary, in the presence of an appropriate catalyst and in an inert solvent.

The solvent which can be used may include ketones such as acetone, methyl ethyl ketone, and cyclohexanone; ethers such as 1,2-dimethoxyethane, tetrahydrofuran, dioxane, and dialkyl (e.g., $C_1$–$C_4$) ether (e.g., diethyl ether, diisopropyl ether); polar solvents such as N,N-dimethylformamide, dimethylsulfoxide, hexamethylphosphoric triamide, sulforane, acetonitrile, and nitromethane; halogenated hydrocarbons such as dichloromethane, chloroform, 1,2-dichloroethane, and chlorobenzene; and hydrocarbons such as toluene, benzene, and xylene. If necessary, these solvents may also be used in admixture.

As the catalyst, for example, bases such as triethylamine, pyridine, and sodium acetate, or acids such as aluminum chloride, hydrogen chloride, and boron trifluoride ether complex ($BF_3 \cdot (C_2H_5)_2O$), can be used.

The reaction temperature, although it can be usually selected in the range of –20° C. to the boiling point of a solvent used in the reaction, is more preferably in the range of –5° C. to the boiling point of the solvent used in the reaction.

The molar ratio of the starting materials be used in the reaction may be freely selected; however, it is favorable that the reaction is effected at the equimolar ratio or a ratio close thereto.

After completion of the reaction, the reaction mixture is subjected to ordinary post-treatments such as extraction with an organic solvent and/or concentration. Thus, the desired present compounds can be isolated. If necessary, further purification may be carried out by an ordinary technique such as chromatography, distillation, or recrystallization.

Production process M (for the present compounds wherein X is $X^1$ and $R^6$ is tert-butyl).

This is the production process in which isobutene ($CH_2$=$C(CH_3)_2$) is reacted with a compound of formula (24).

The reaction is effected in the presence of an appropriate acid catalyst and in an inert solvent.

The solvent which can be used may include, for example, hydrocarbons such as toluene, benzene, and xylene; halogenated hydrocarbons such as dichloromethane, chloroform, 1,2-dichloroethane, and chlorobenzene; ethers such as 1,2-dimethoxyethane, tetrahydrofuran, and dioxane, dialkyl (e.g., $C_1$–$C_4$) ethers (e.g., diethyl ether, diisopropyl ether); and esters such as ethyl acetate. If necessary, these solvents may also be used in admixture.

The acid catalyst which can be used may include, for example, inorganic acids such as hydrochloric acid, hydrobromic acid, perchloric acid, sulfuric acid, nitric acid, and phosphoric acid; and organic acids such as trifluoroacetic acid, trichloroacetic acid, methanesulfonic acid, benzenesulfonic acid, p-toluenesulfonic acid, and camphorsulfonic acid. In particular, sulfuric acid is preferably used.

The reaction temperature, although it can be usually selected in the range of –50° C. to 50° C. or the boiling point of a solvent used in the reaction, is usually in the range of 0° C. to 30° C.

The molar ratio of the starting materials to be used in the reaction may be suitably selected; however, the reaction is preferably effected with the use of isobutene in an amount of 1 mole or more relative to 1 mole of the compound of formula (24).

After completion of the reaction, the reaction mixture is subjected to ordinary post-treatments such as extraction with an organic solvent and/or concentration. Thus, the desired present compounds can be isolated. If necessary, further purification may be carried out by an ordinary technique such as chromatography, distillation, or recrystallization.

For the present compounds, there may exist optical isomers based on the presence of at least one asymmetric carbon atom, and the optical isomers having biological activity, whether they are either in (+)-form or in (–)-form, and their mixtures at any ratio are, of course, included within the scope of the present invention. Furthermore, there may exist geometrical isomers based on the presence of at least one double bond, and the geometrical isomers having bio logical activity, whether they are either in cis-form or in trans-form, and their mixtures at any ratio are, of course, included within the scope of the present invention.

The compounds of formula (12), which are useful as the intermediates for the production of the present compounds, also have insecticidal/acaricidal activity and can therefore be formulated or used as the active ingredients of insecticidal/acaricidal agents, in the same manner as the case of the present compounds.

The specific examples of the present compounds are shown below; however, the present compounds are not limited to these examples.

Formula 1

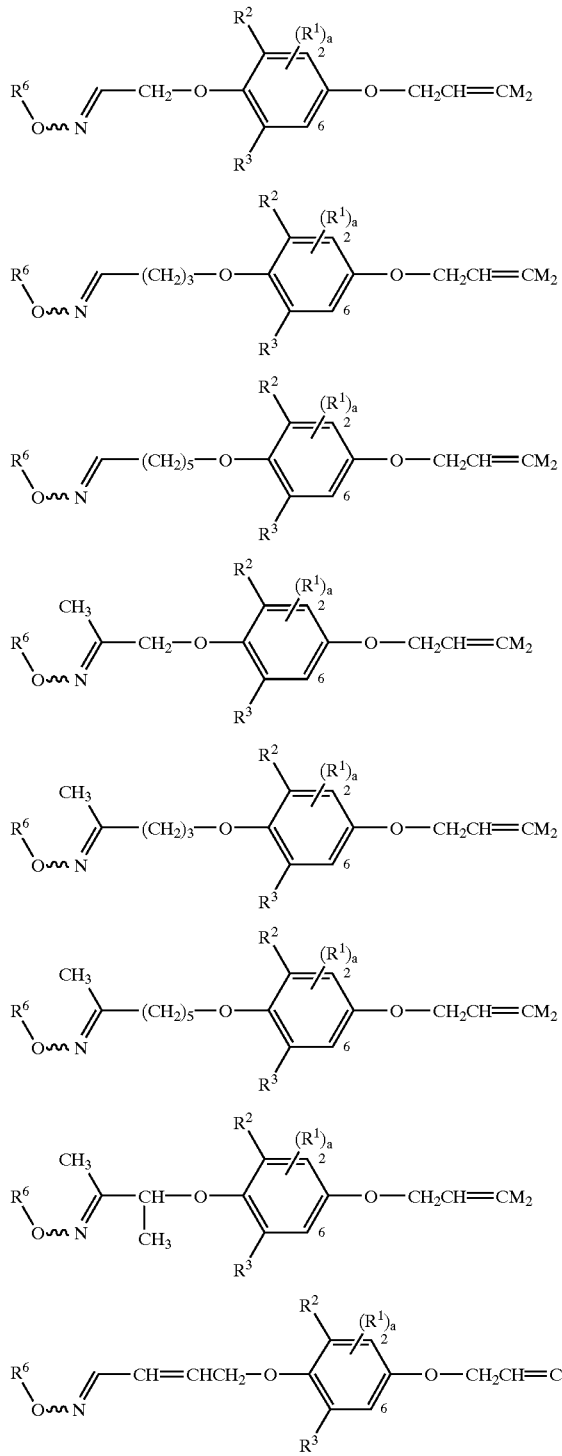
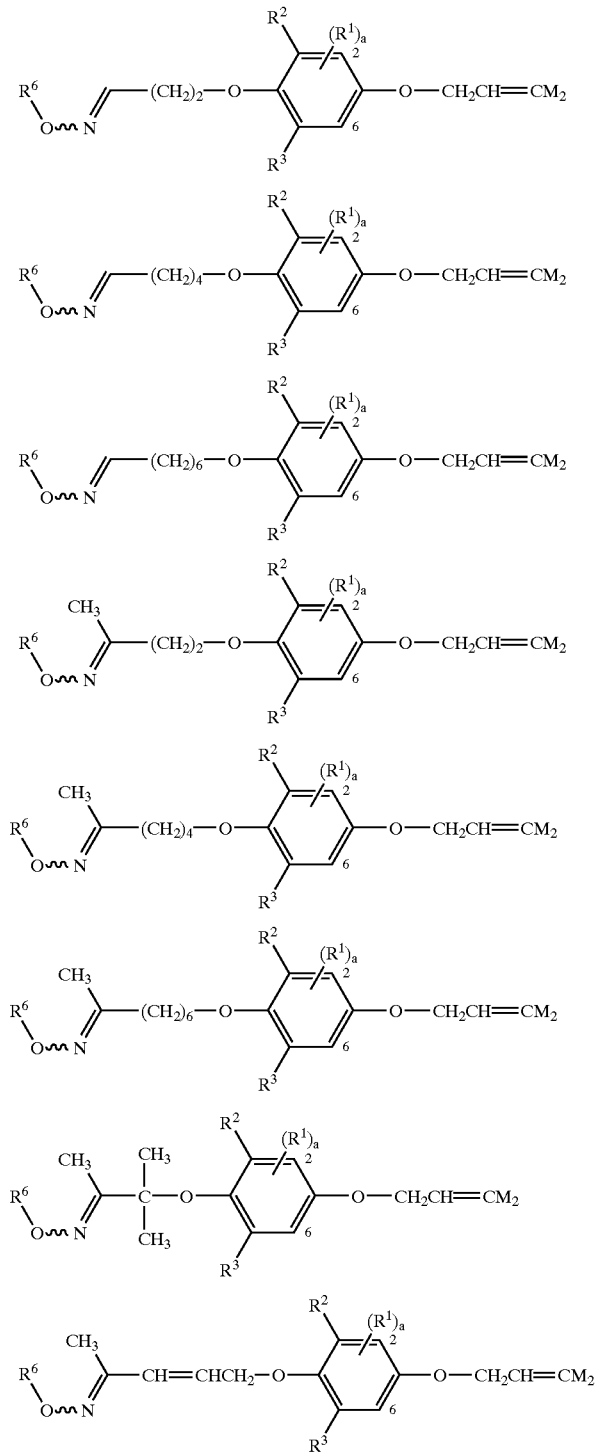

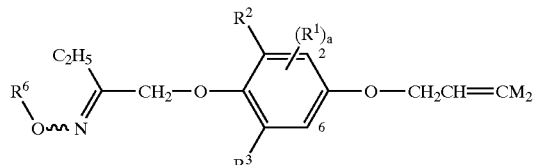
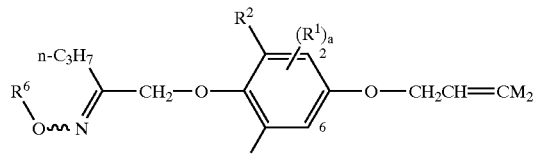
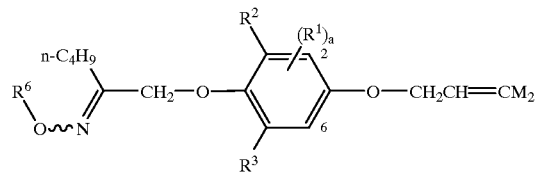
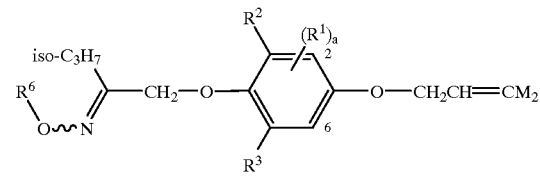
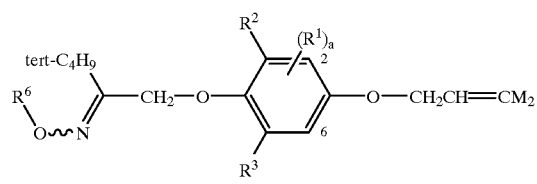
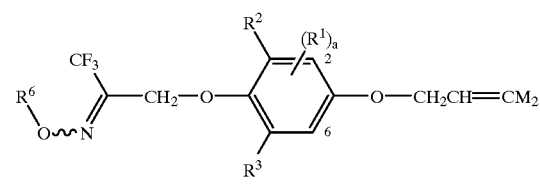
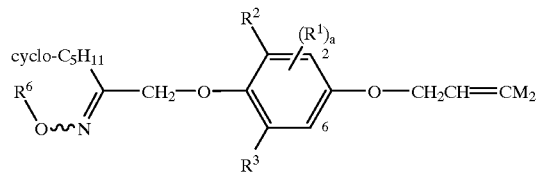
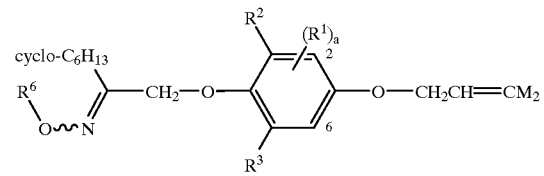
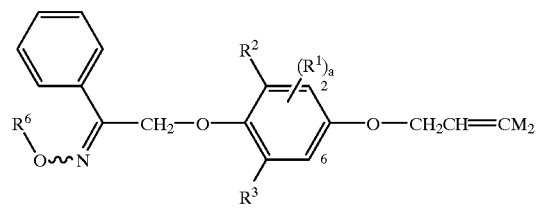
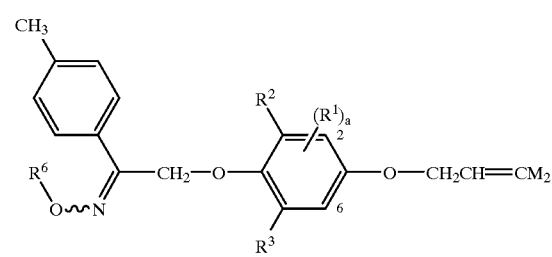
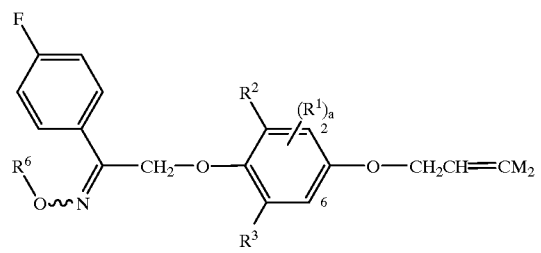
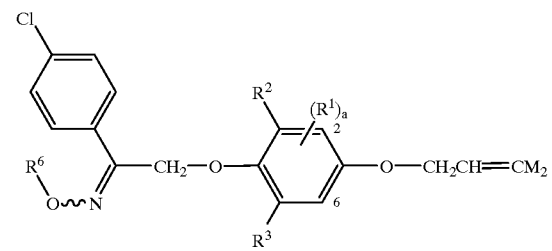

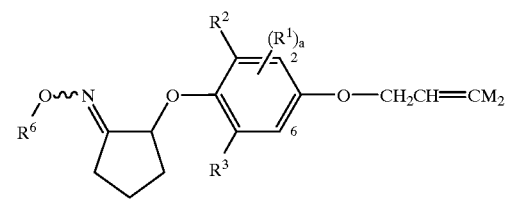
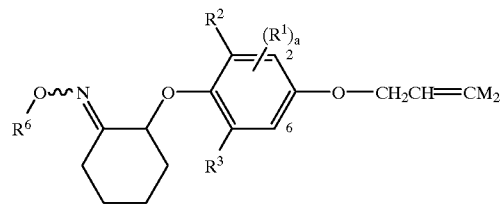
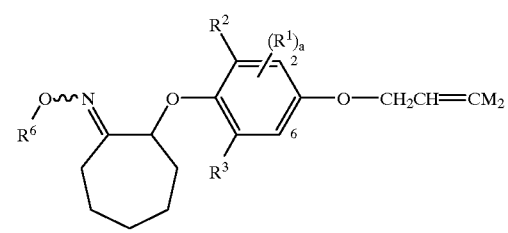

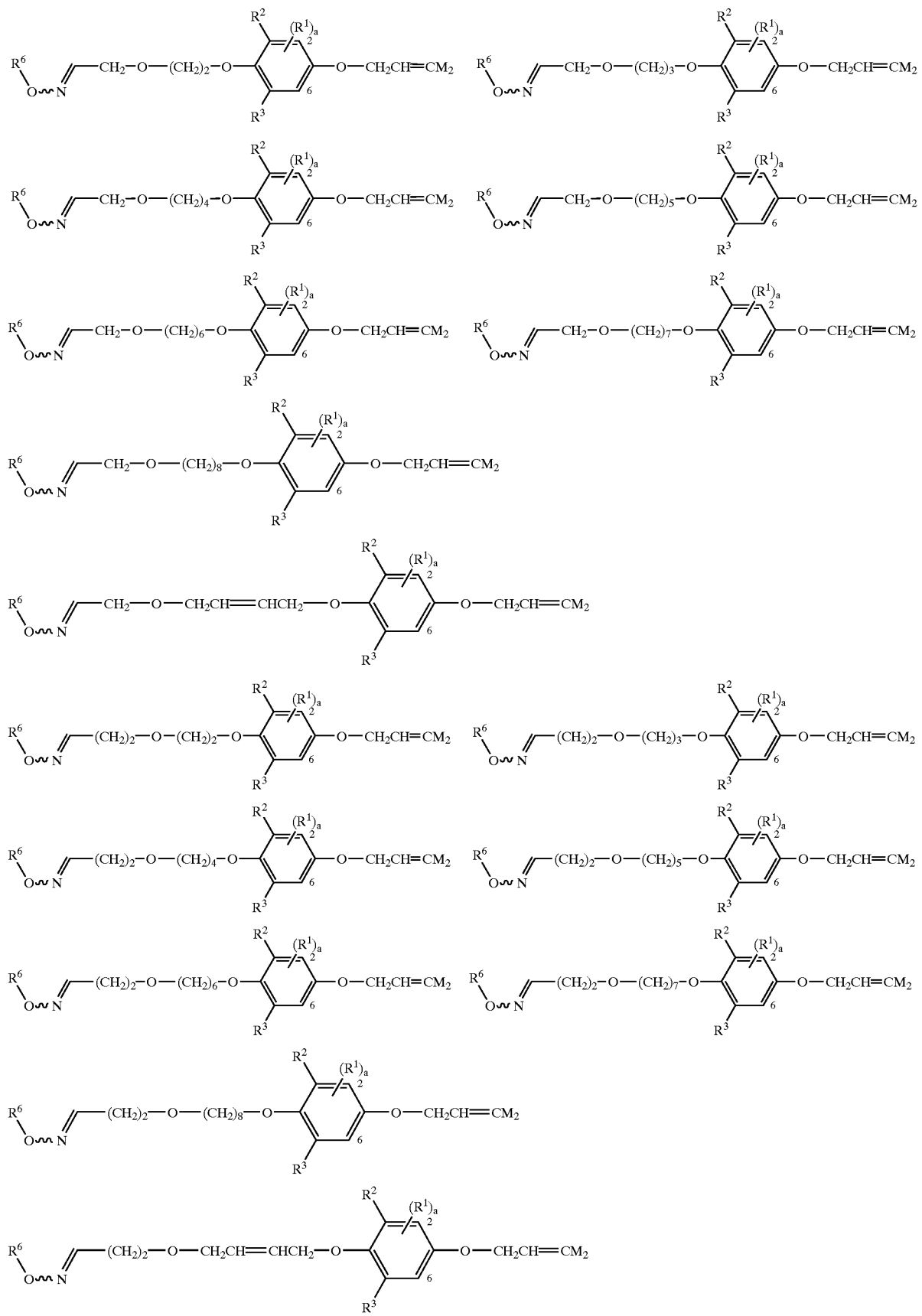

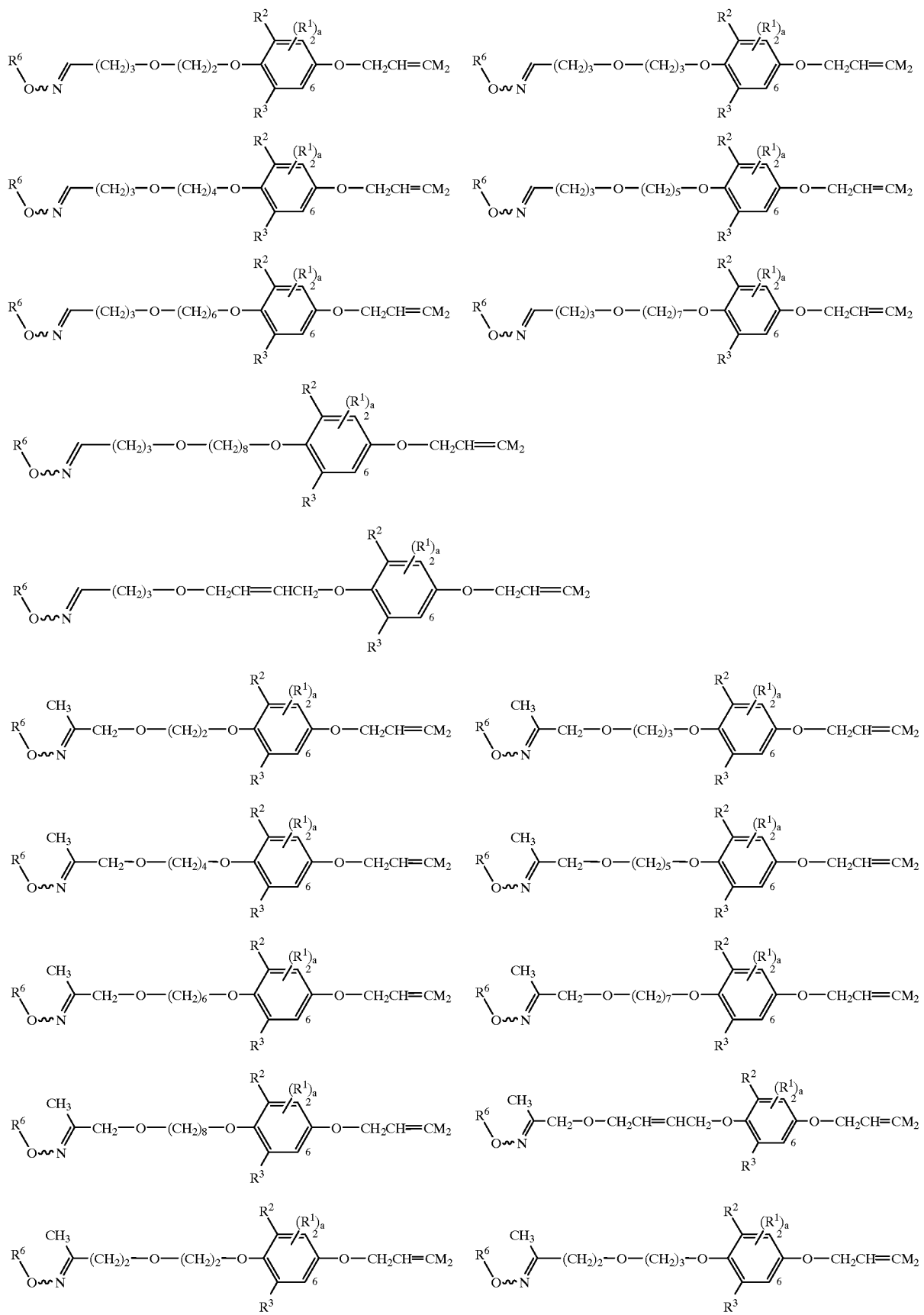

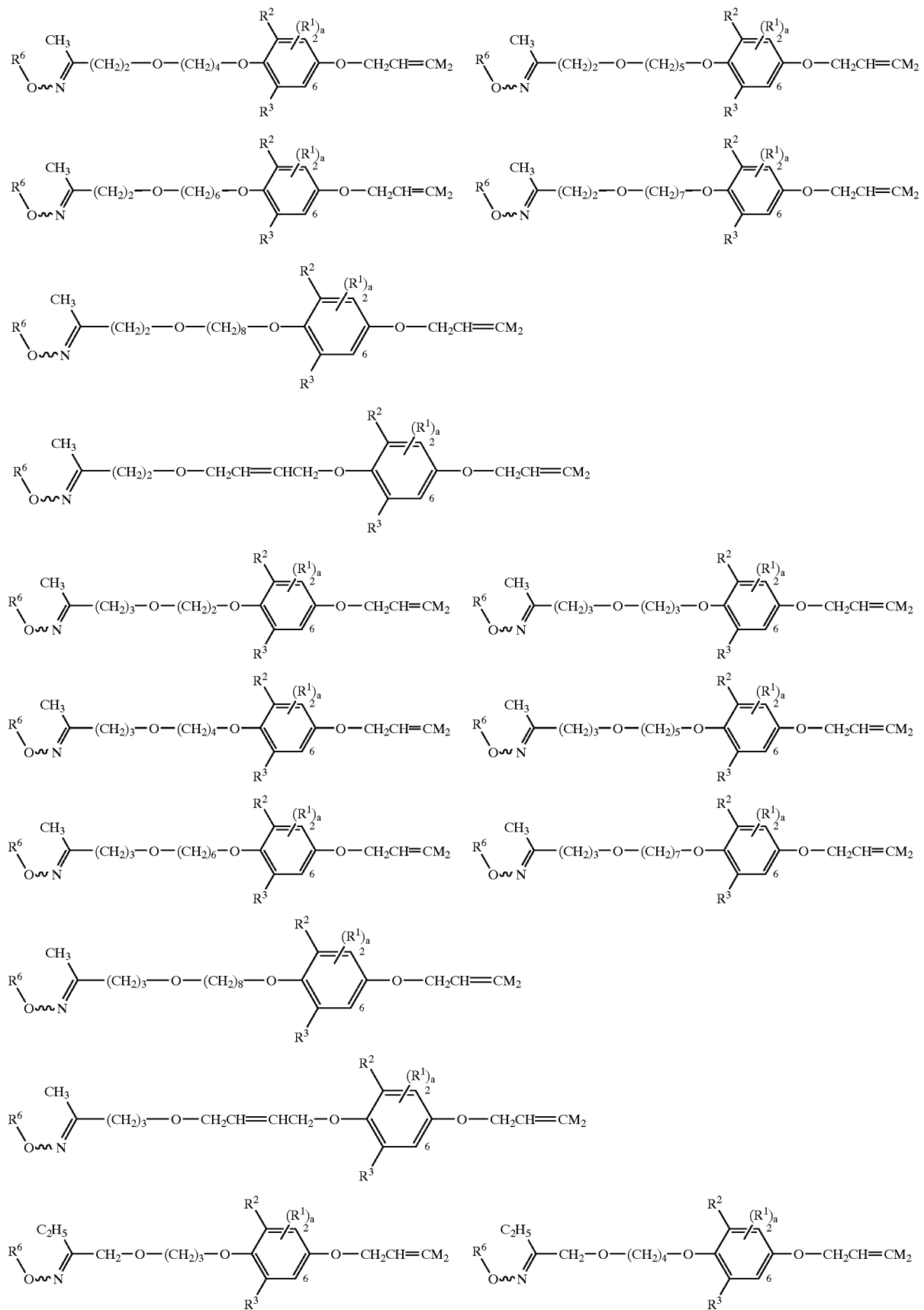

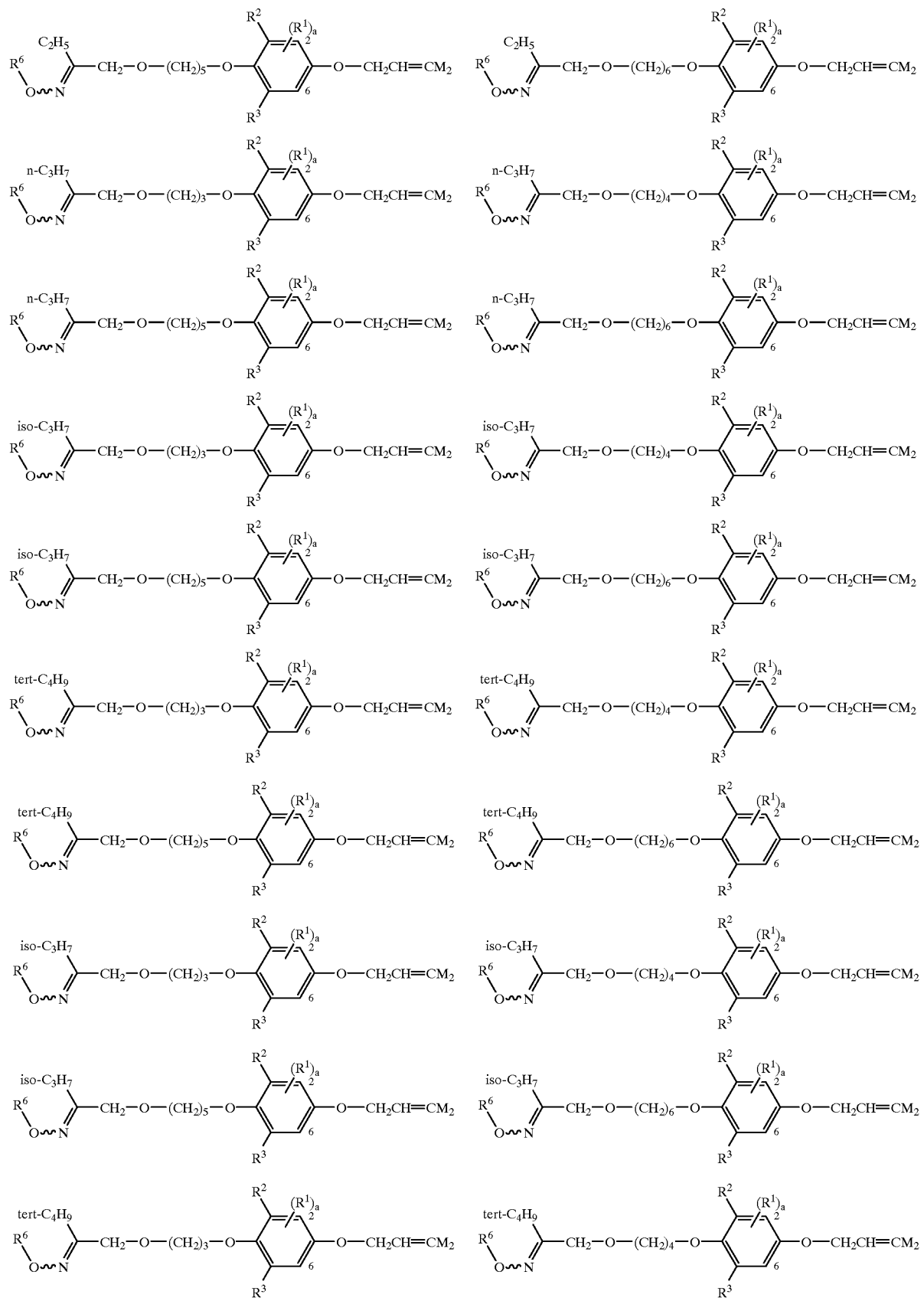

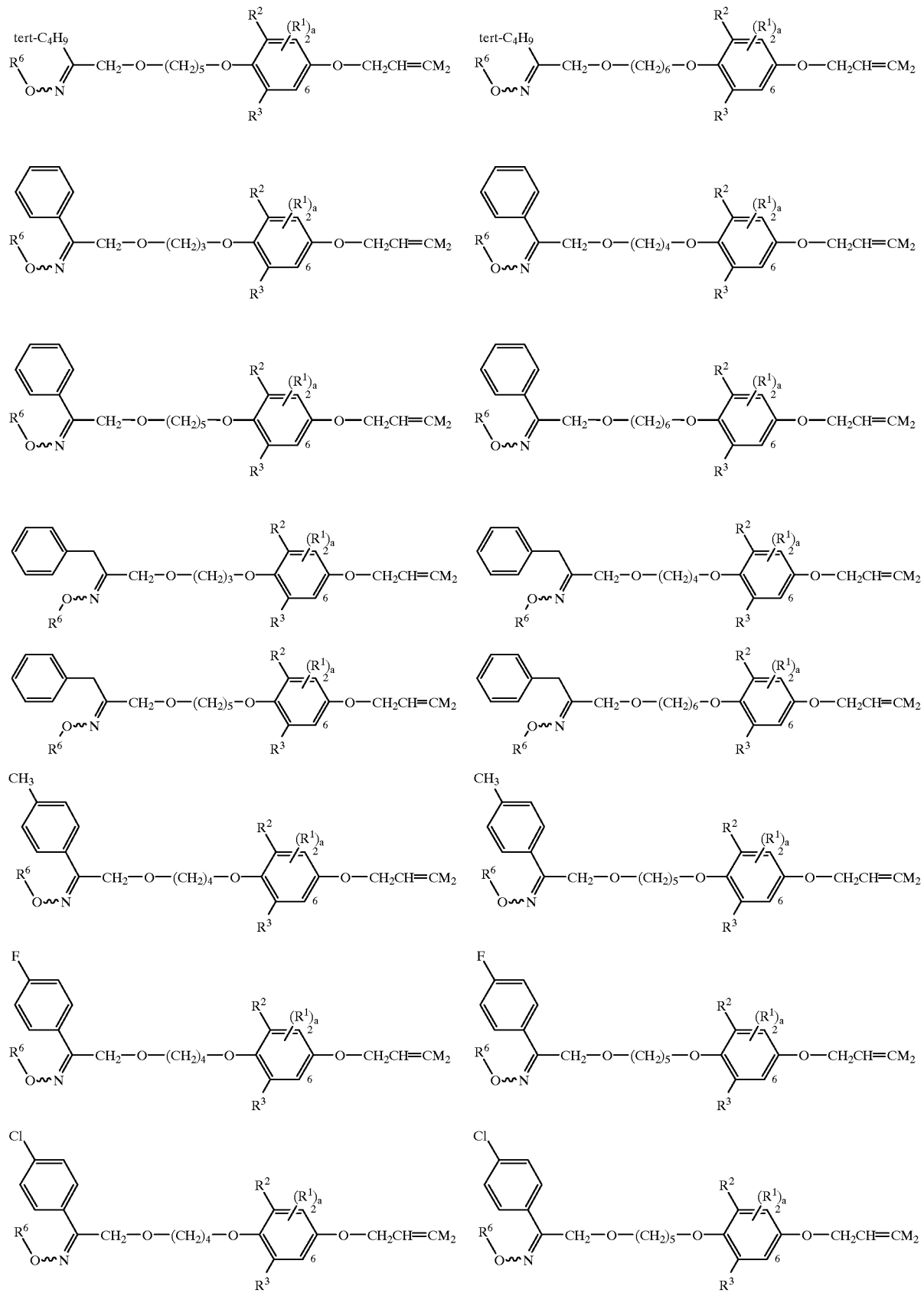

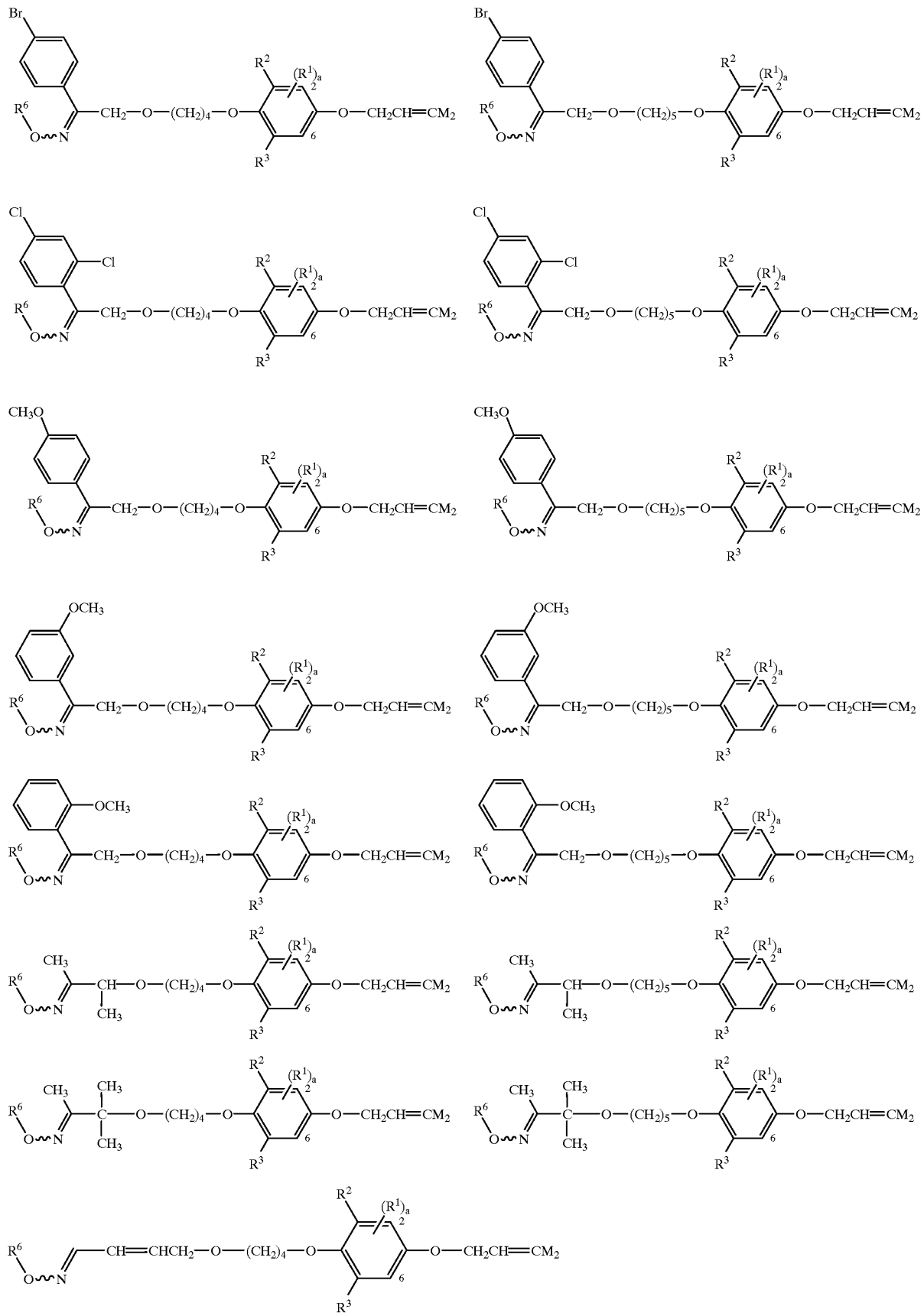

-continued
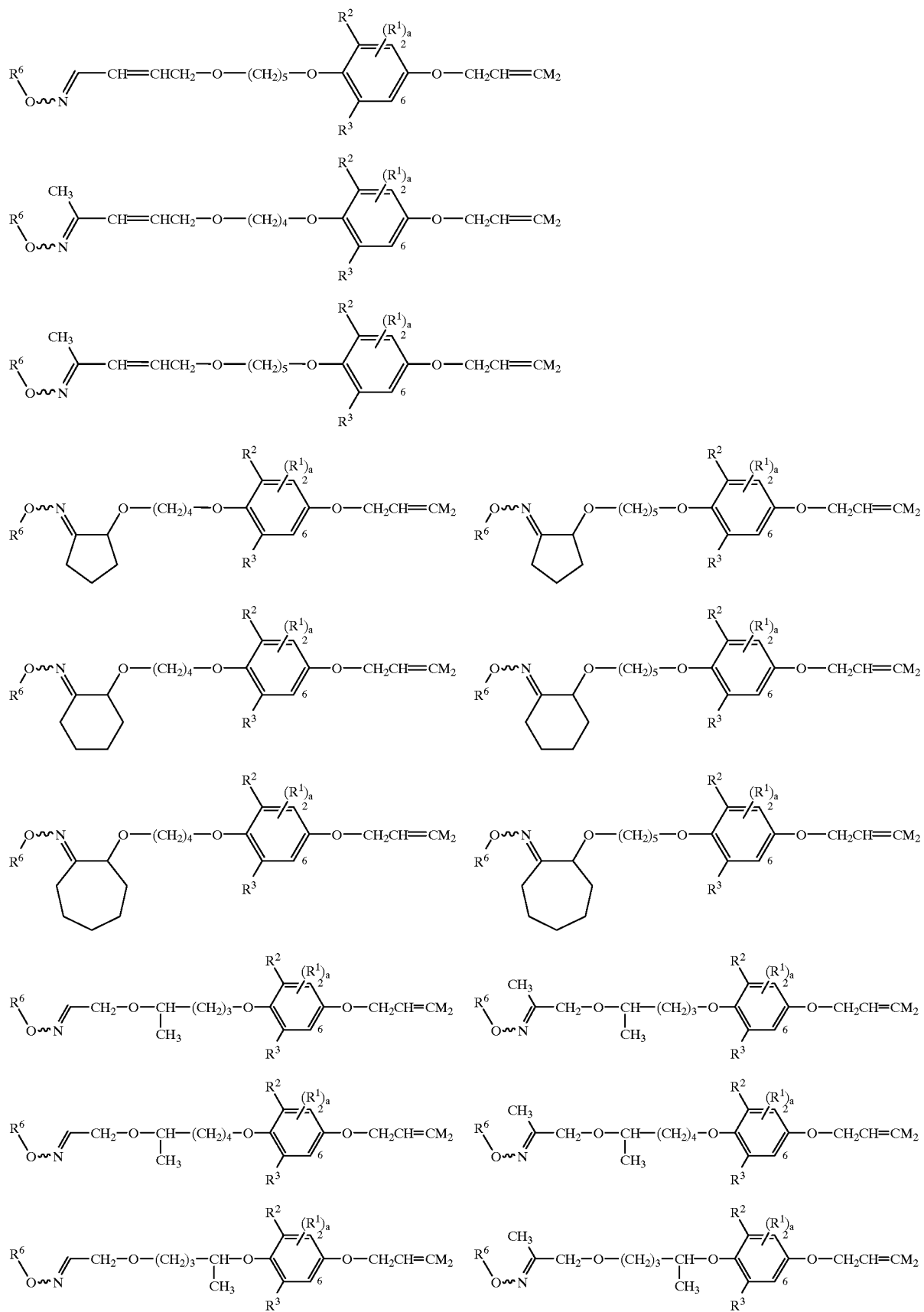

-continued
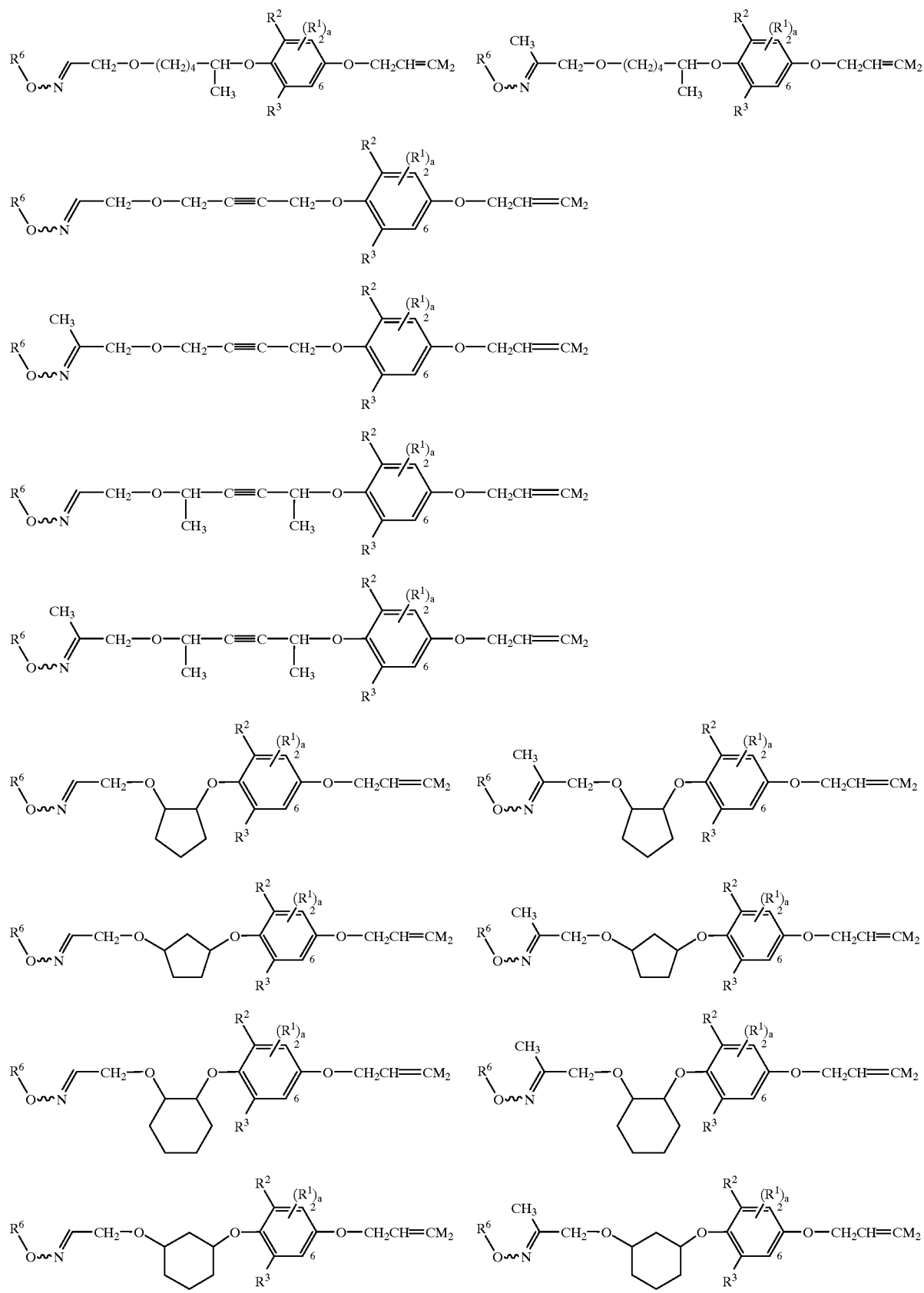

-continued
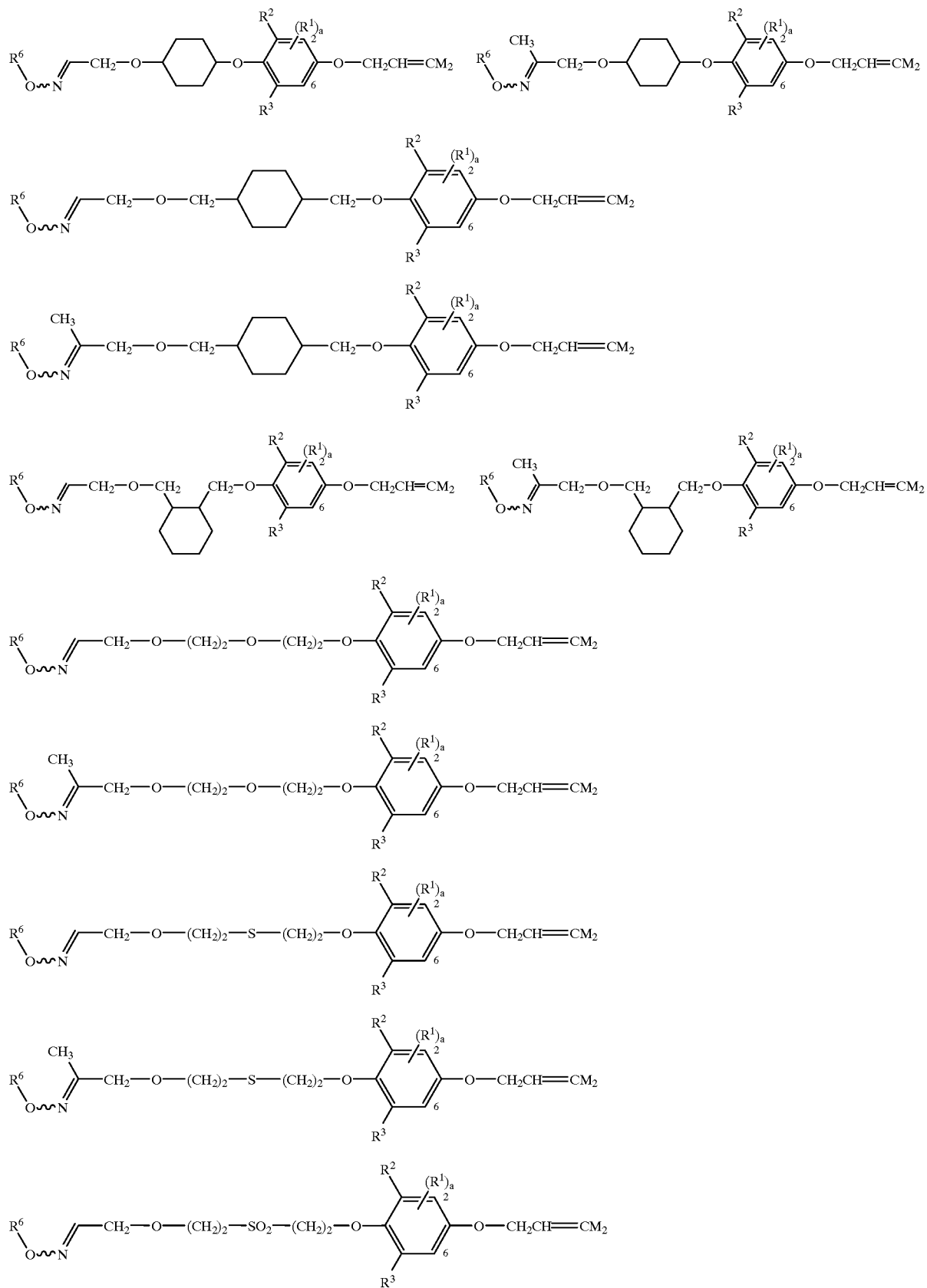

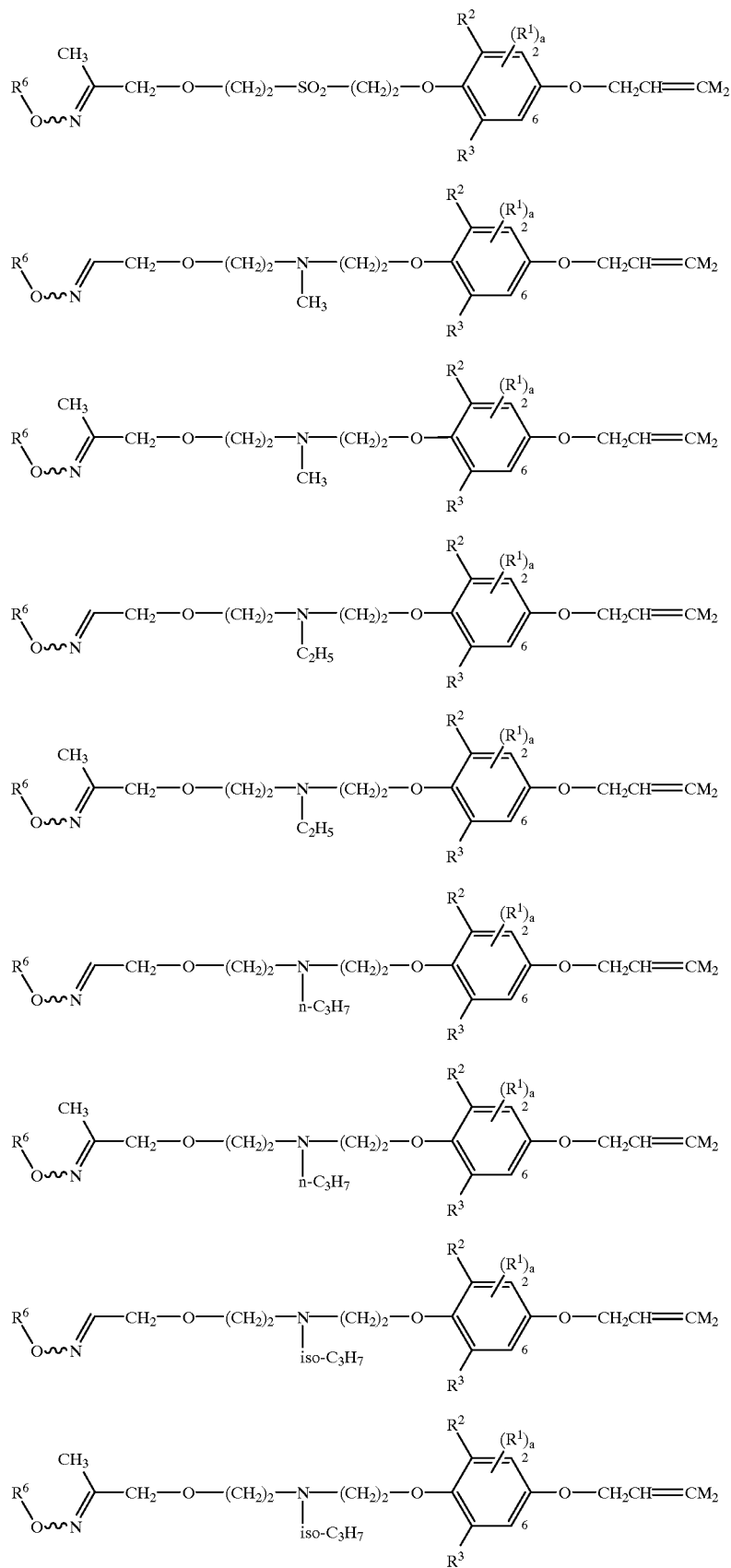

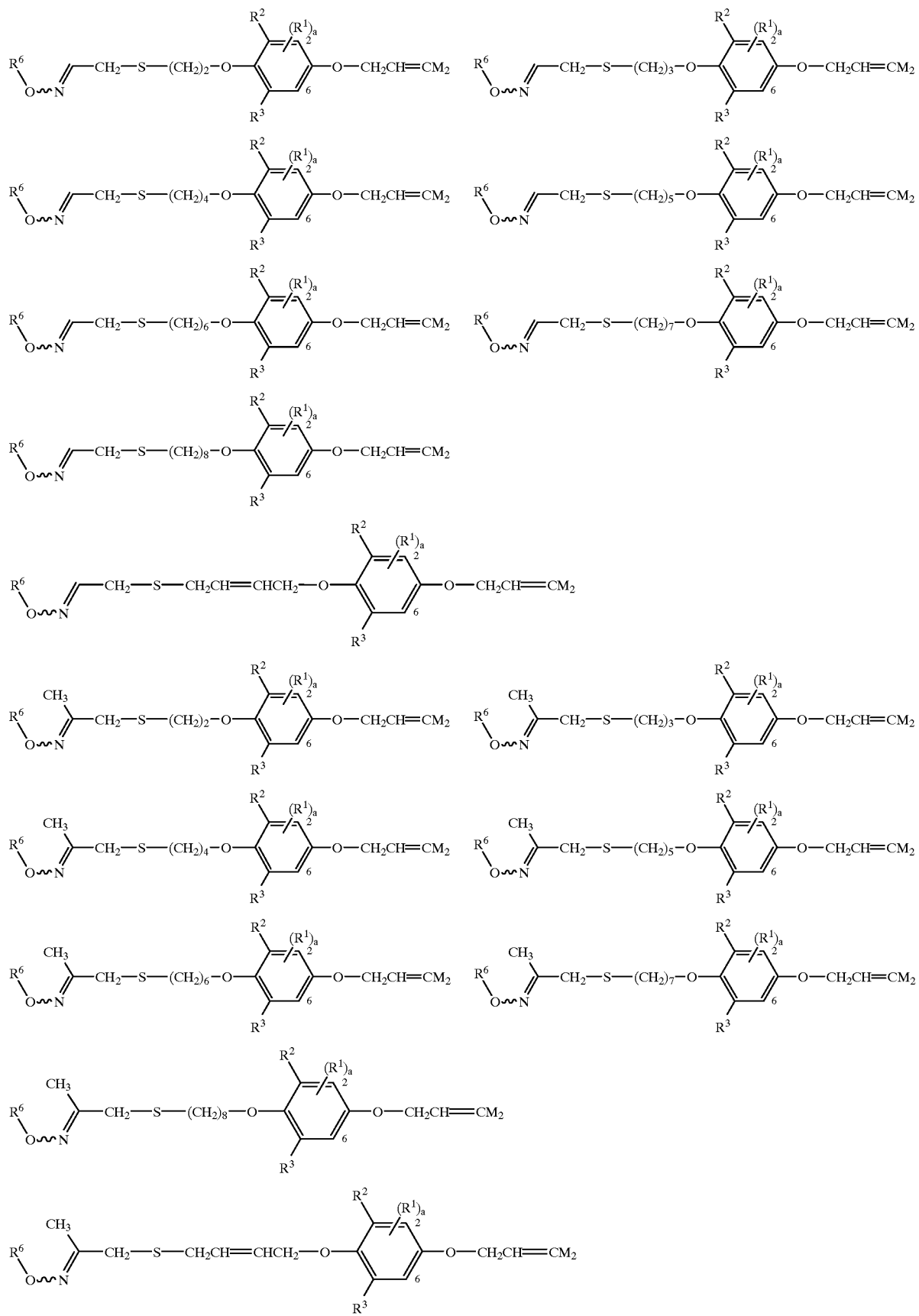

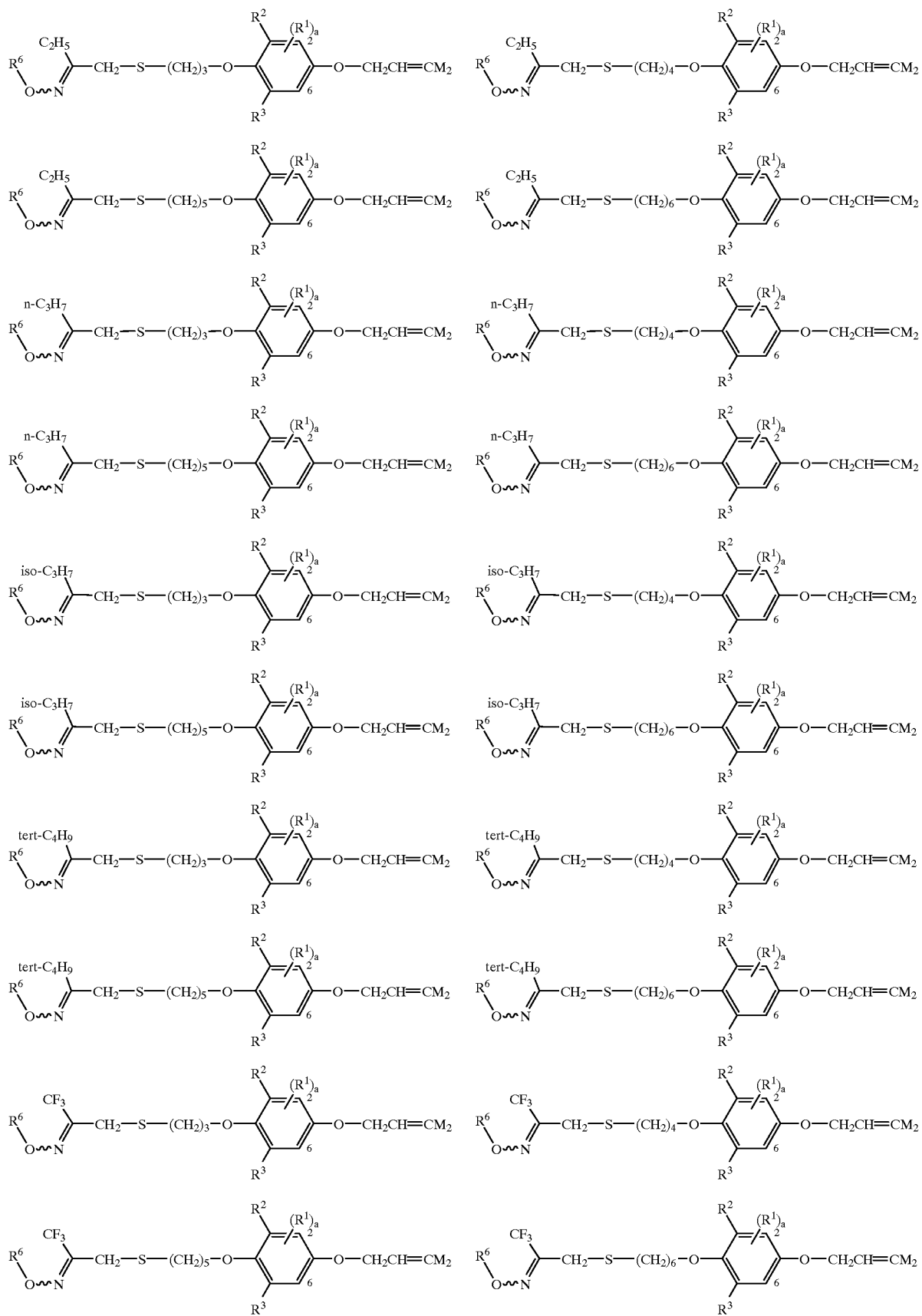

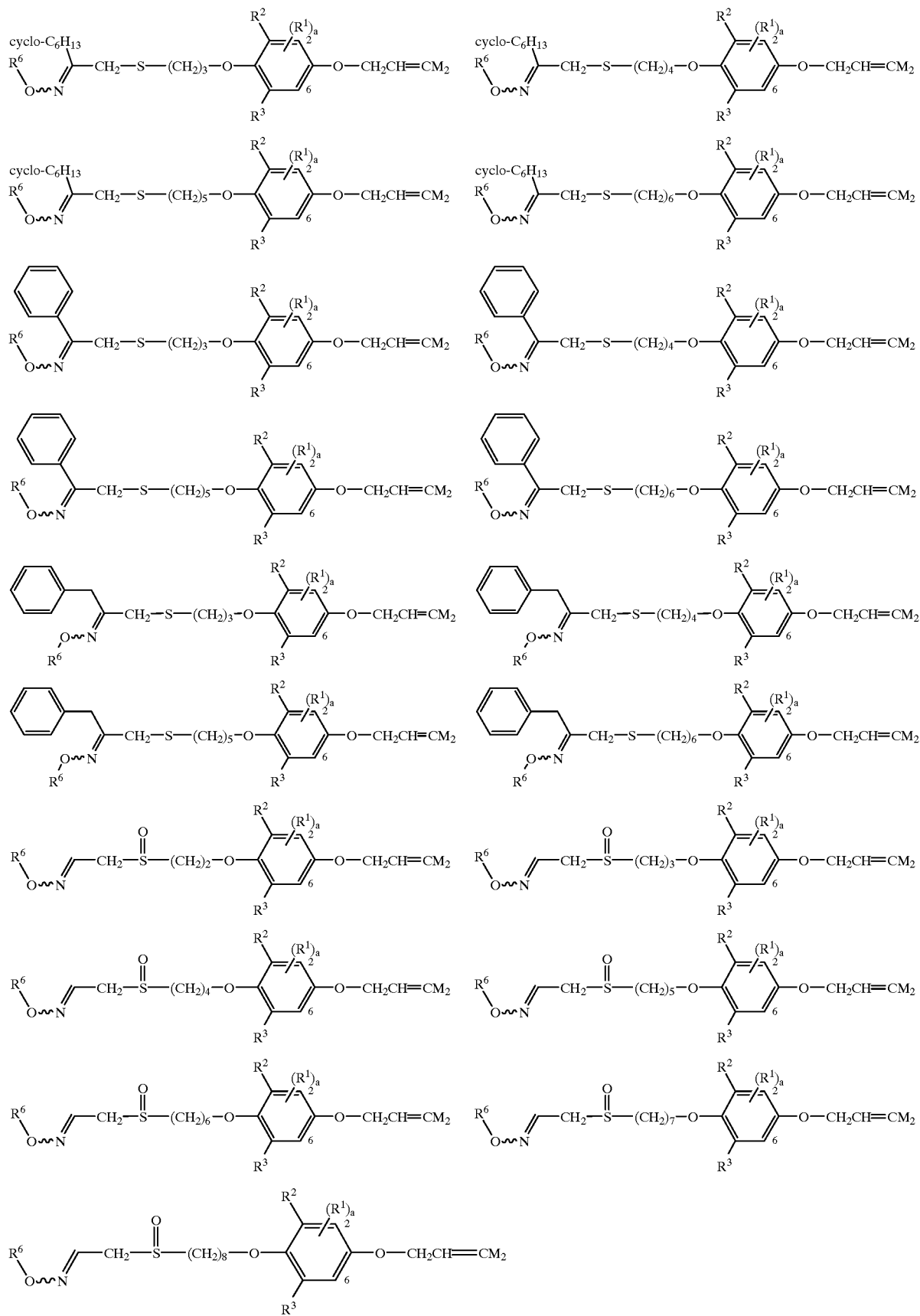

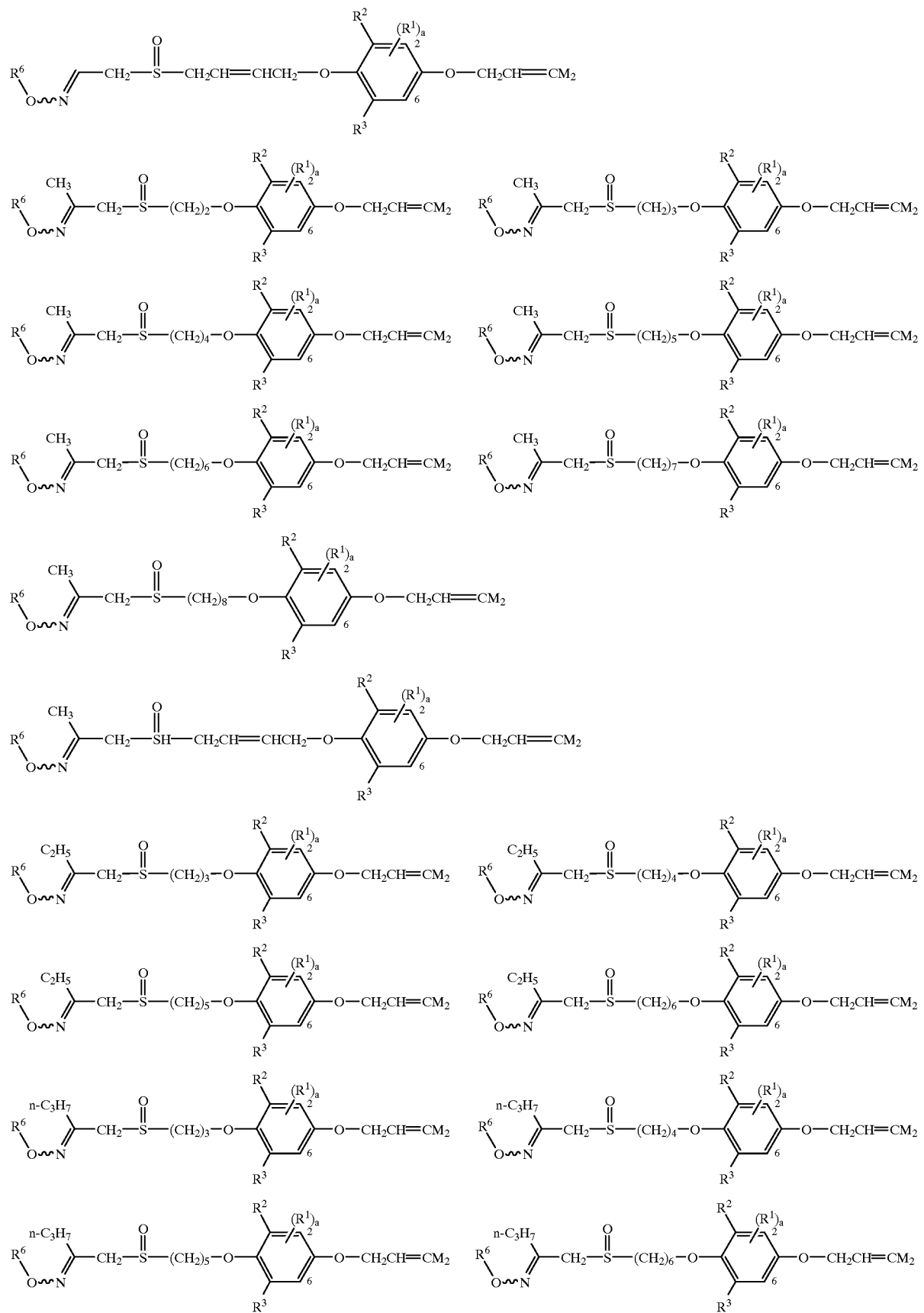

-continued
71
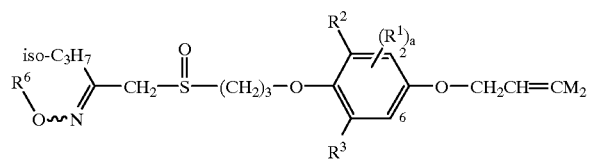
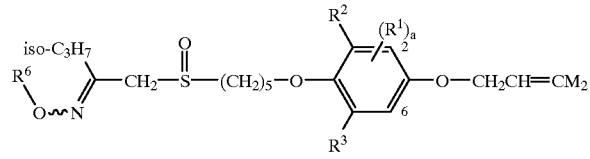
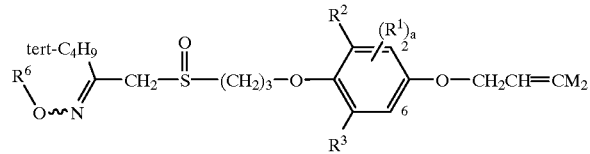
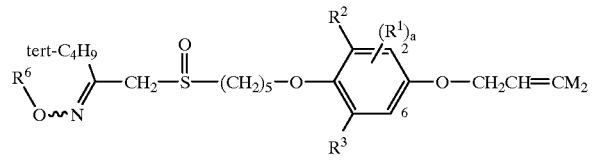
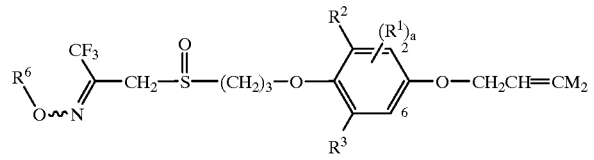
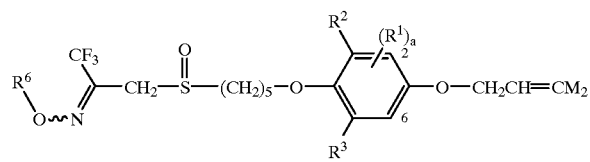
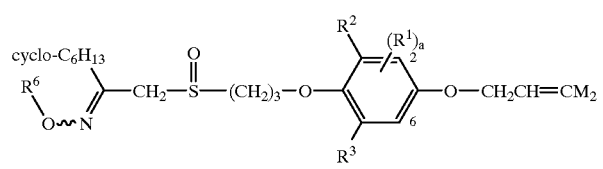
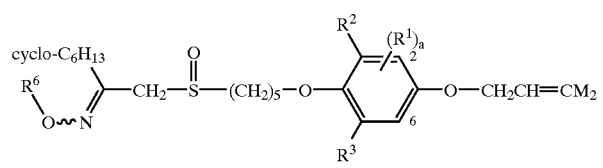
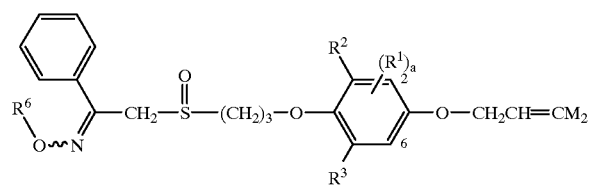
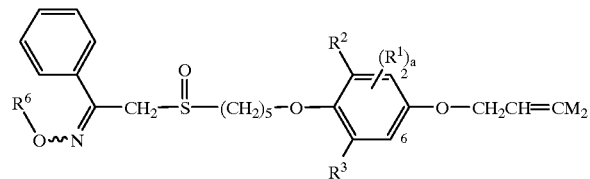
72
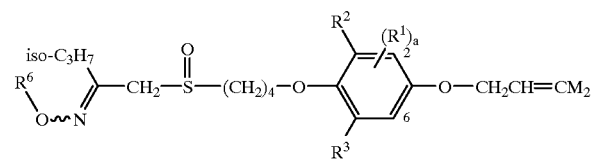
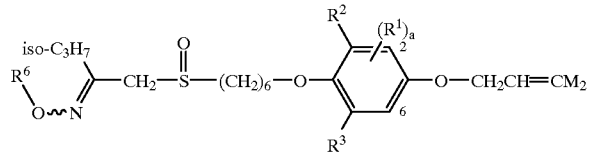
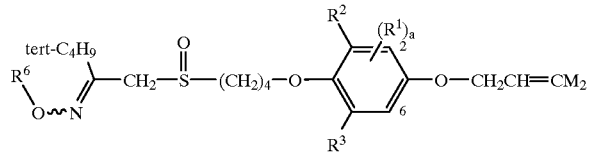
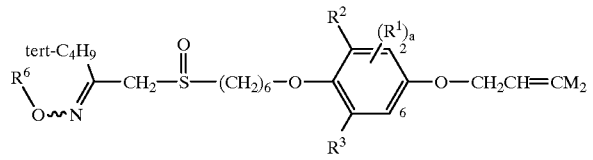
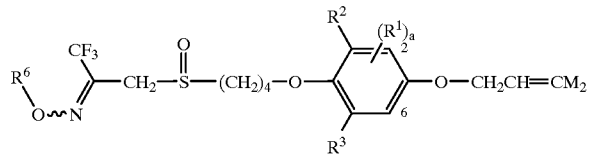
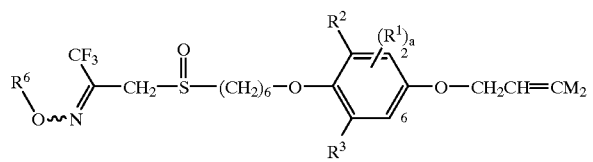
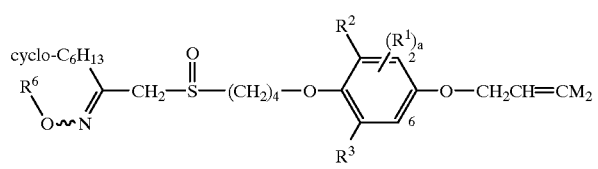
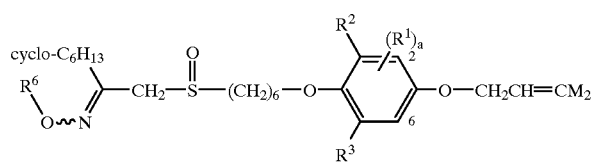
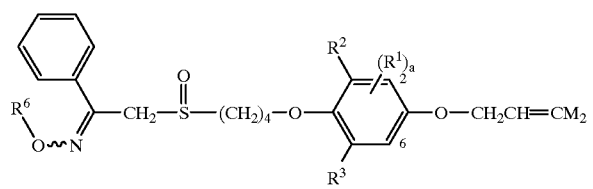
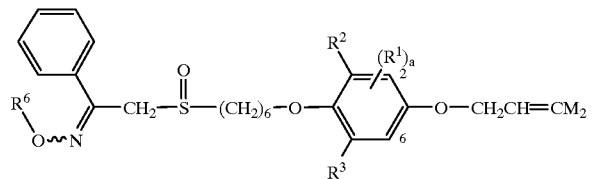

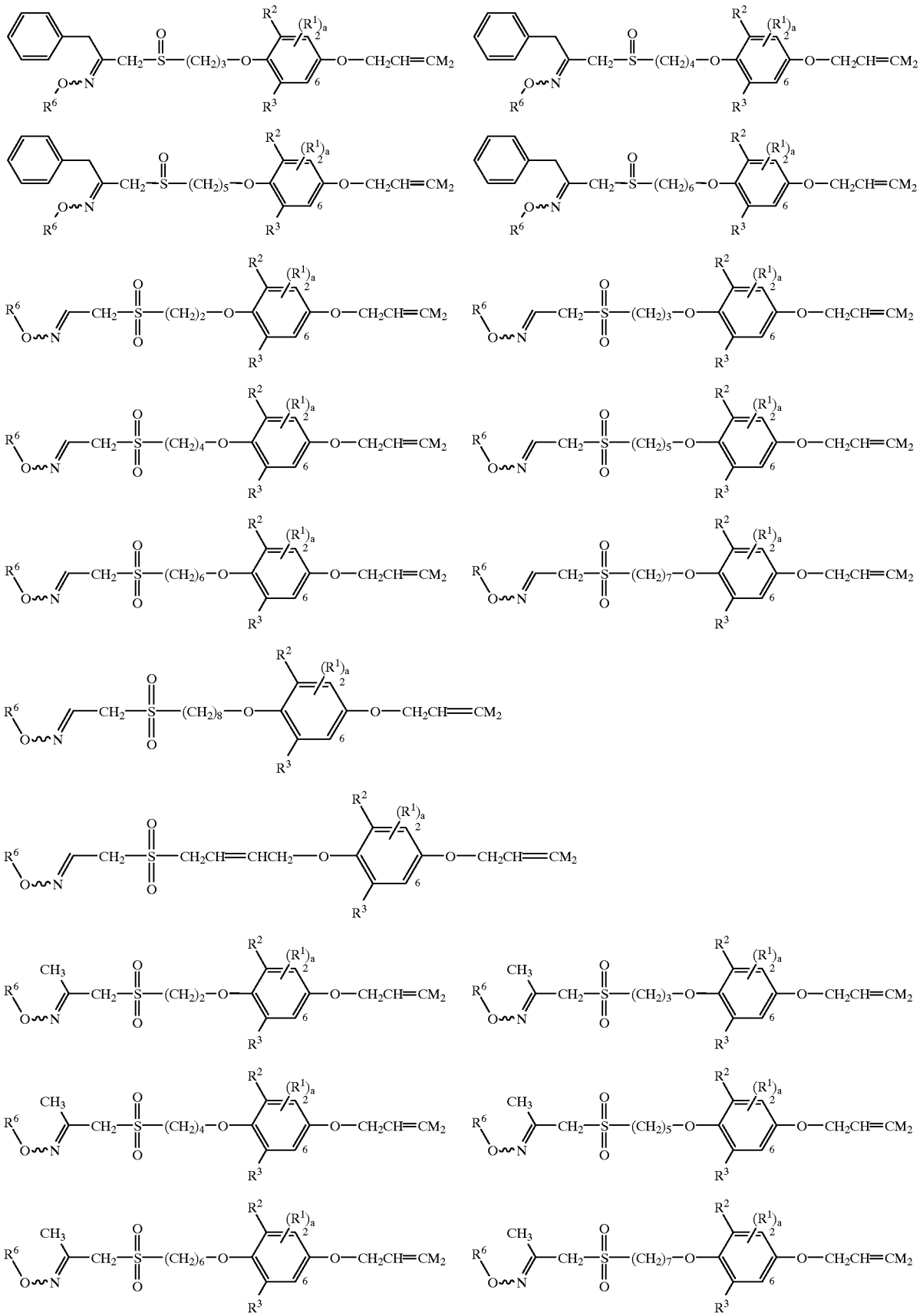

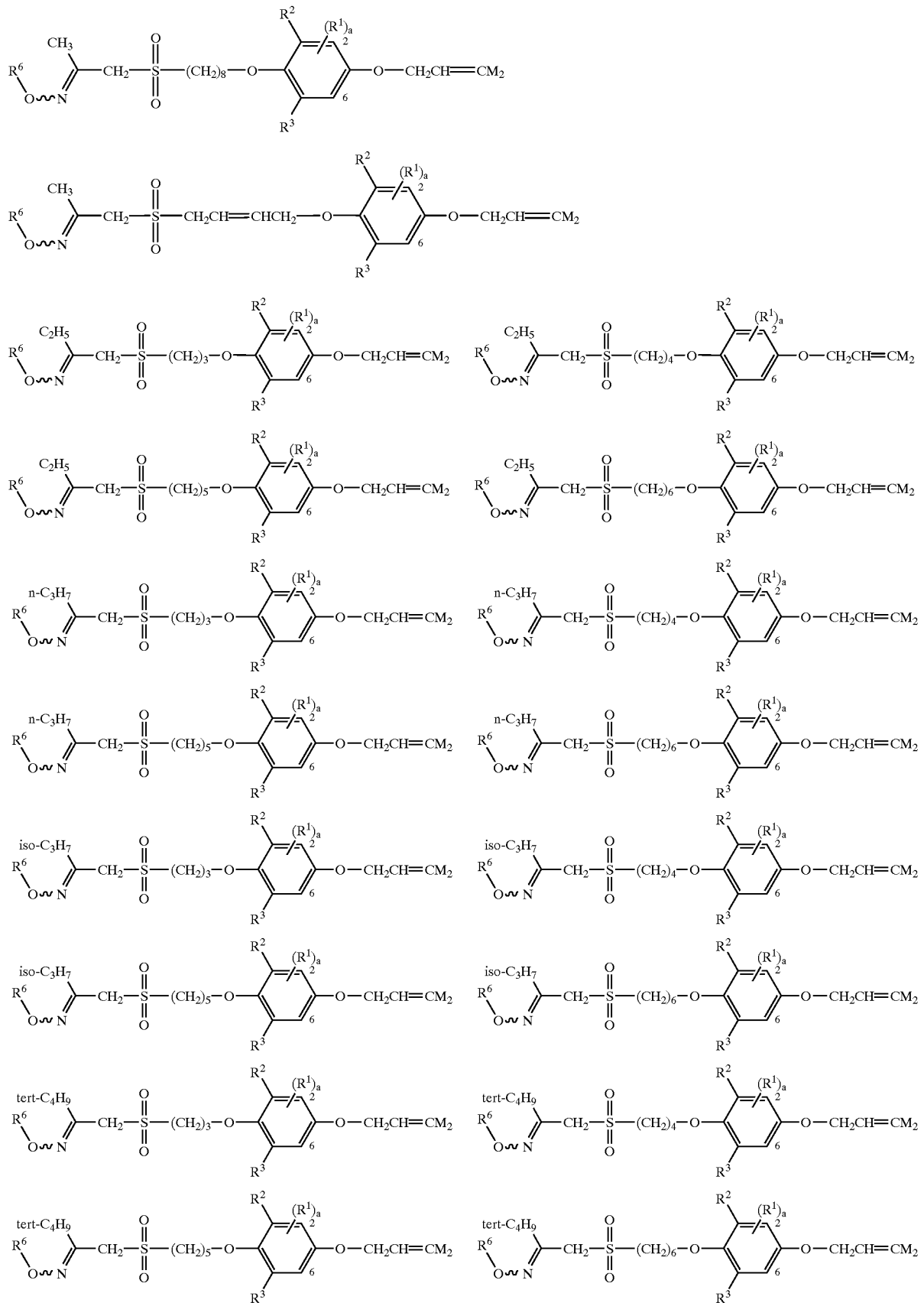

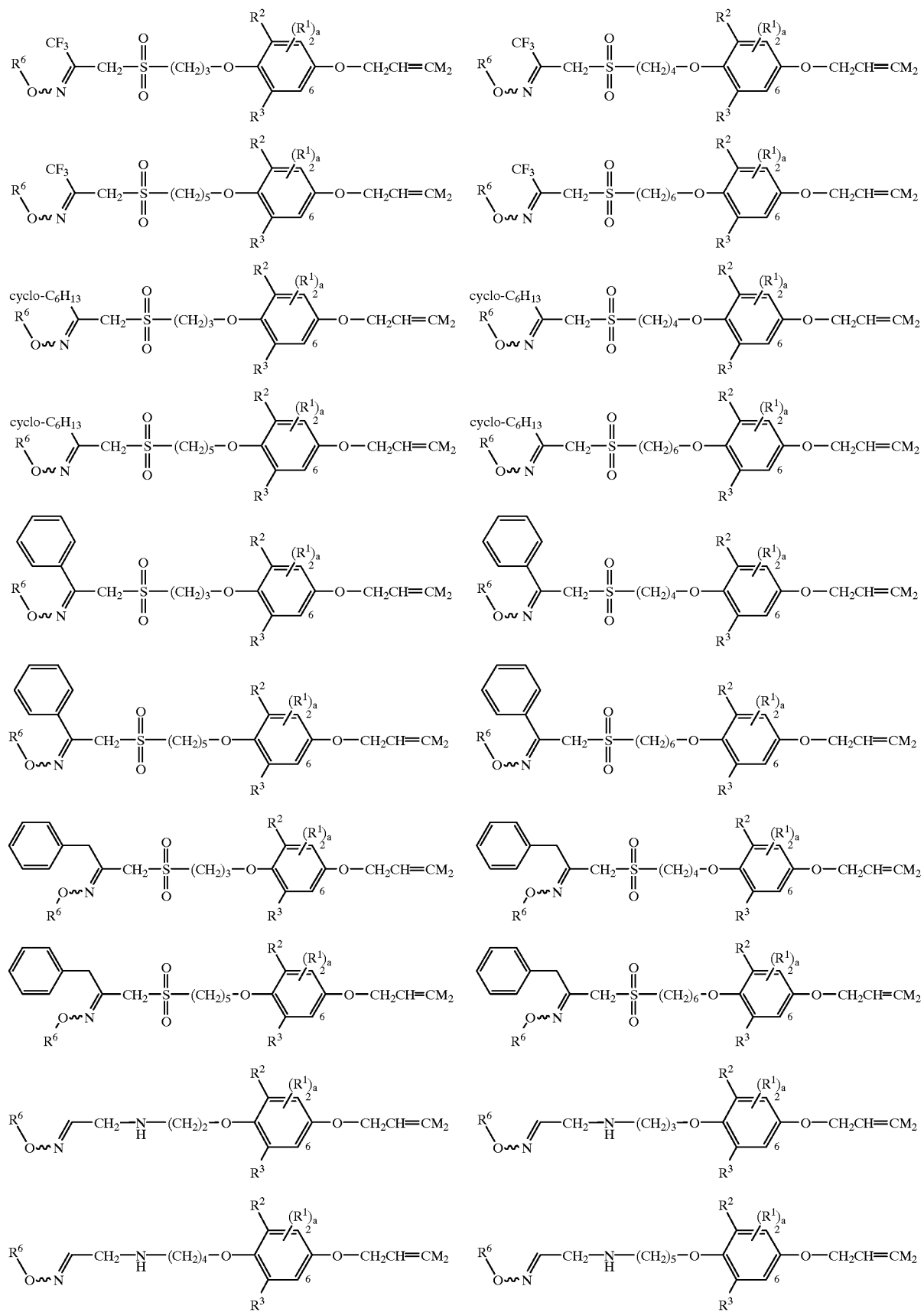

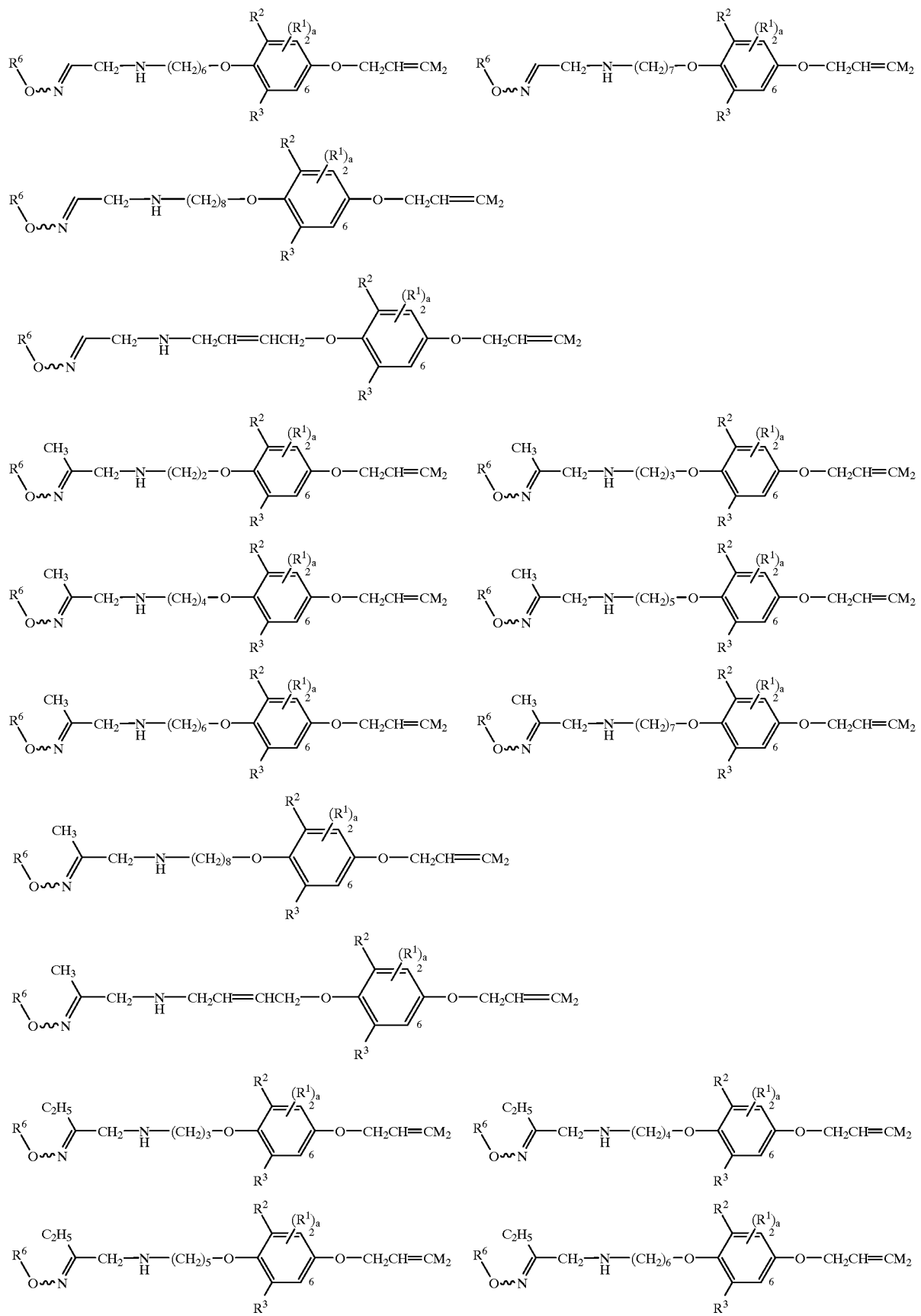

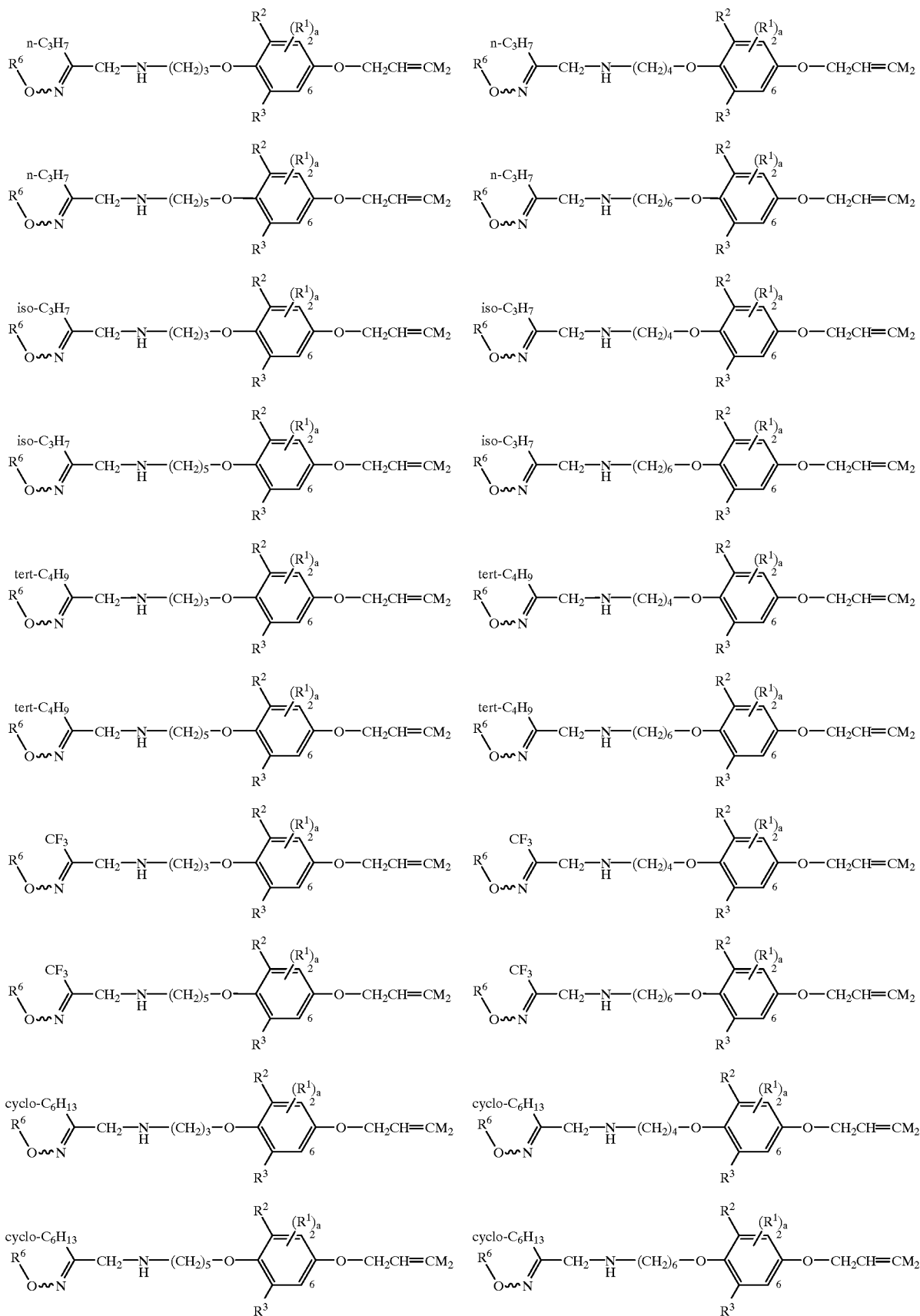

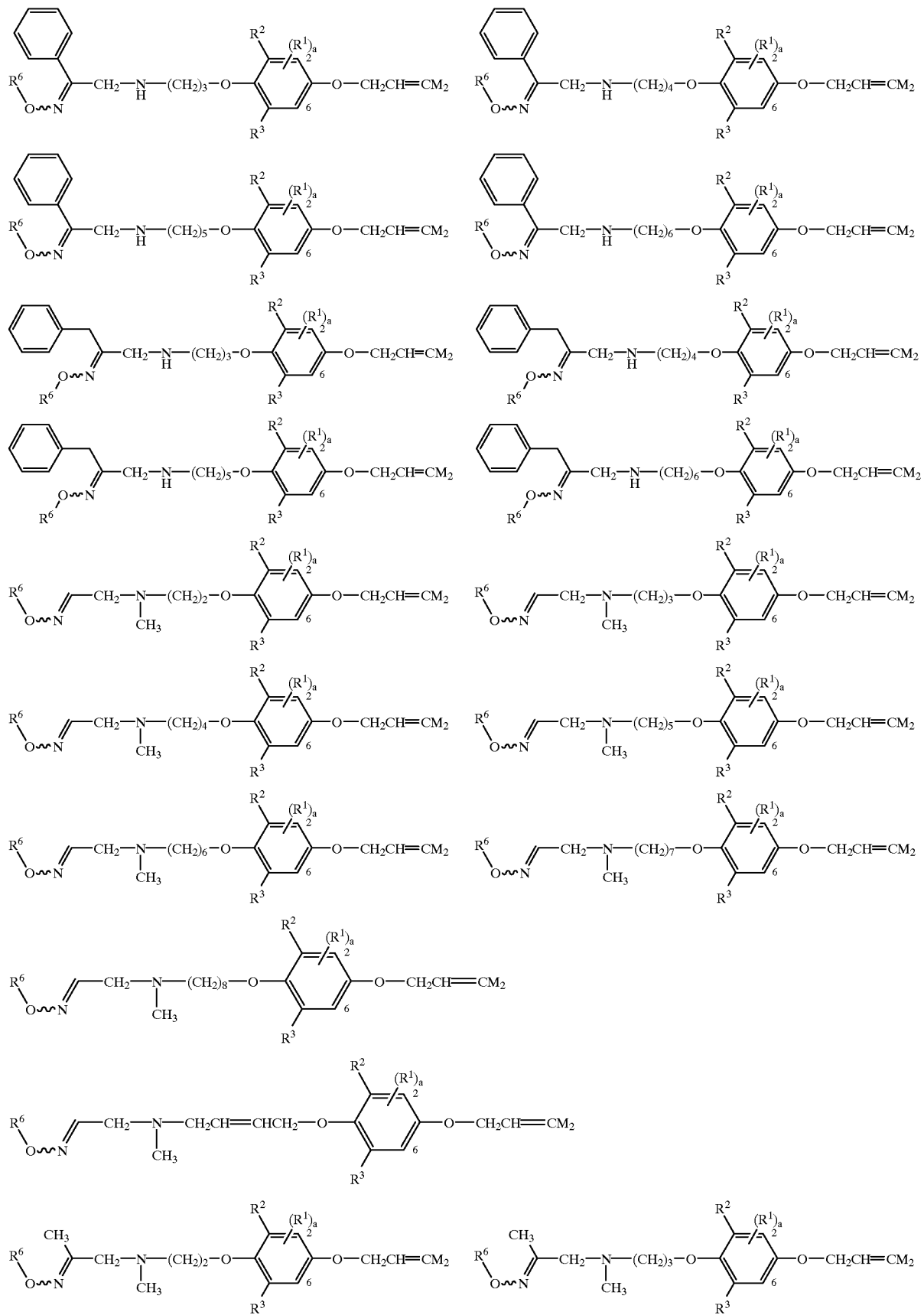

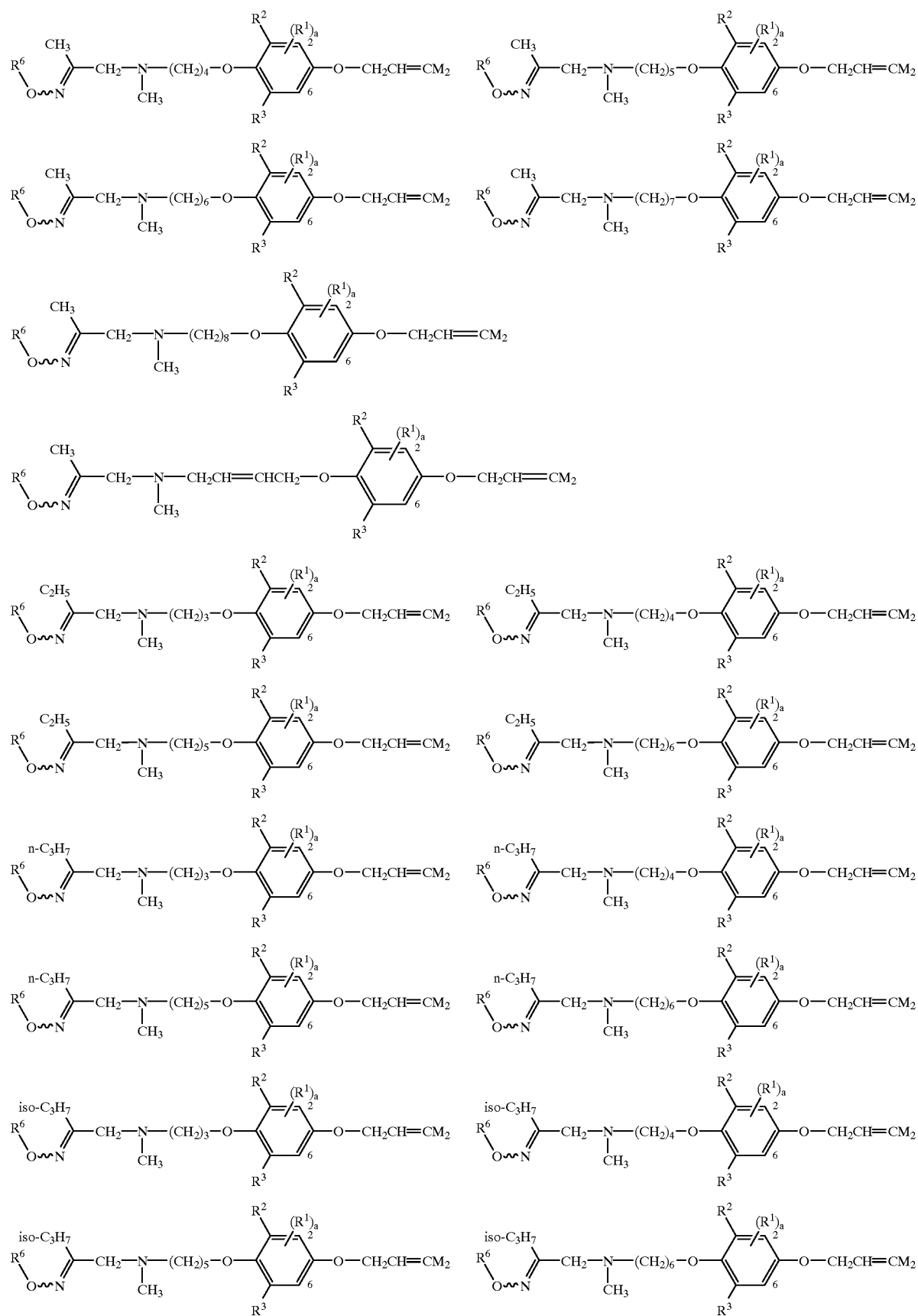

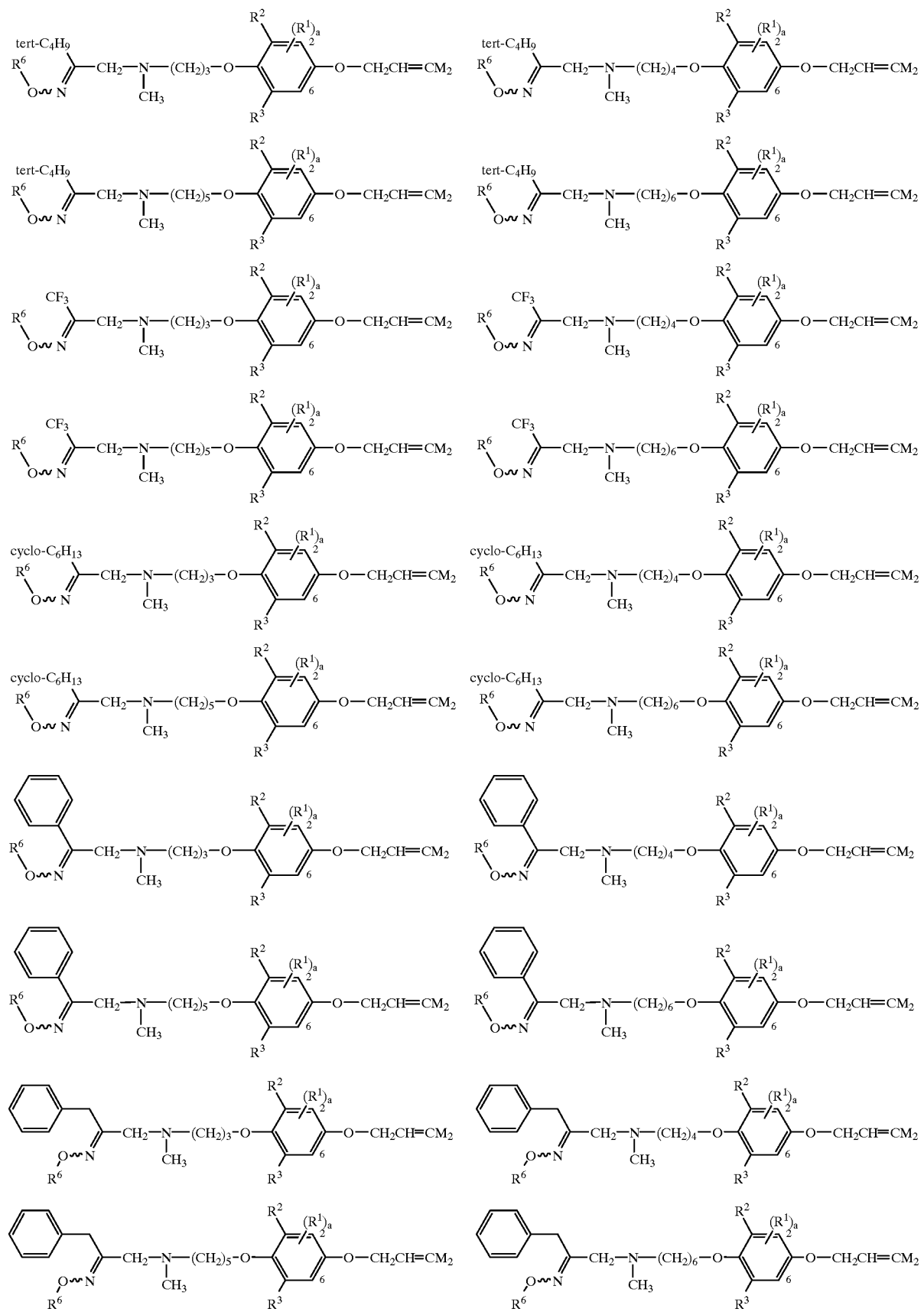

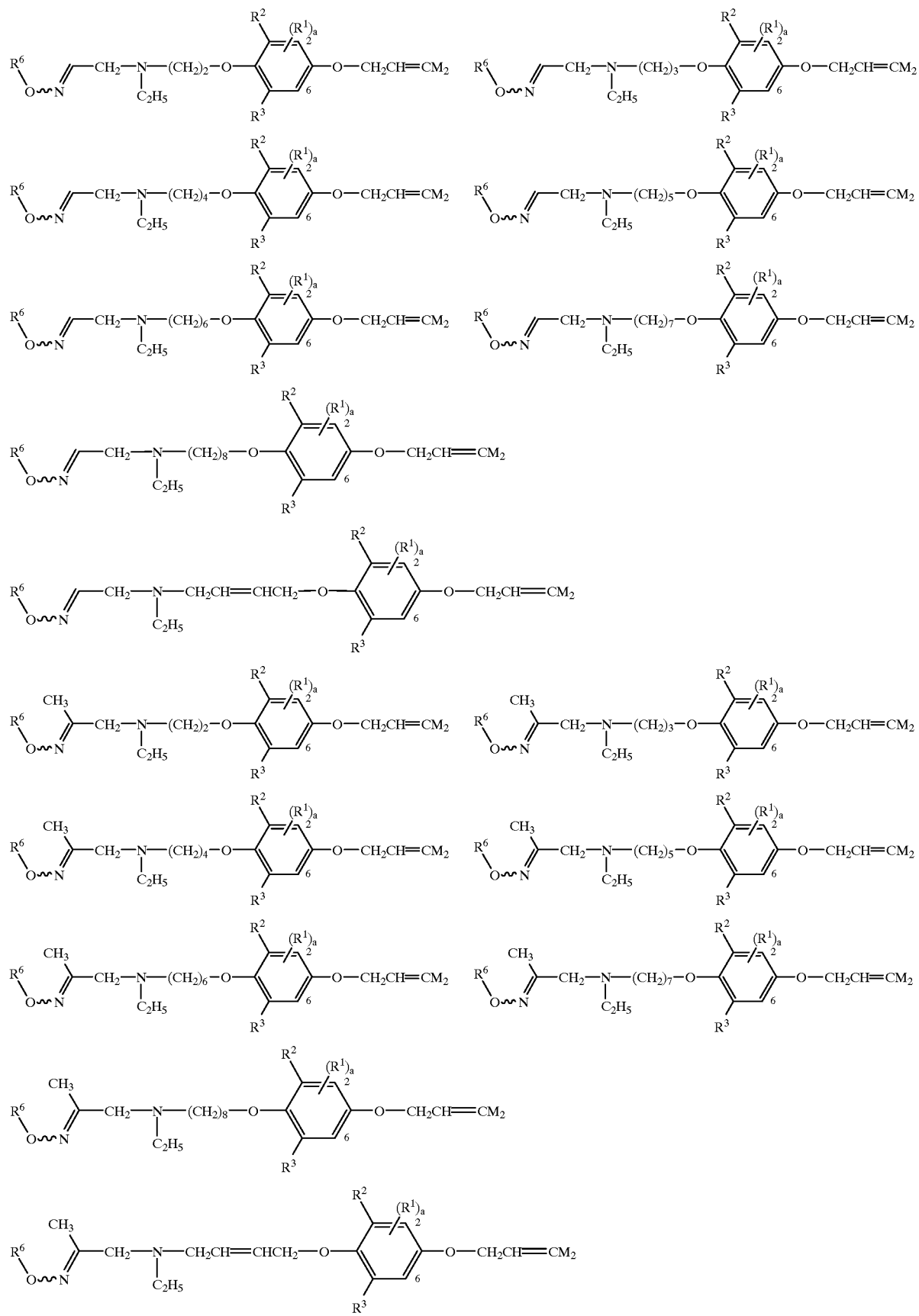

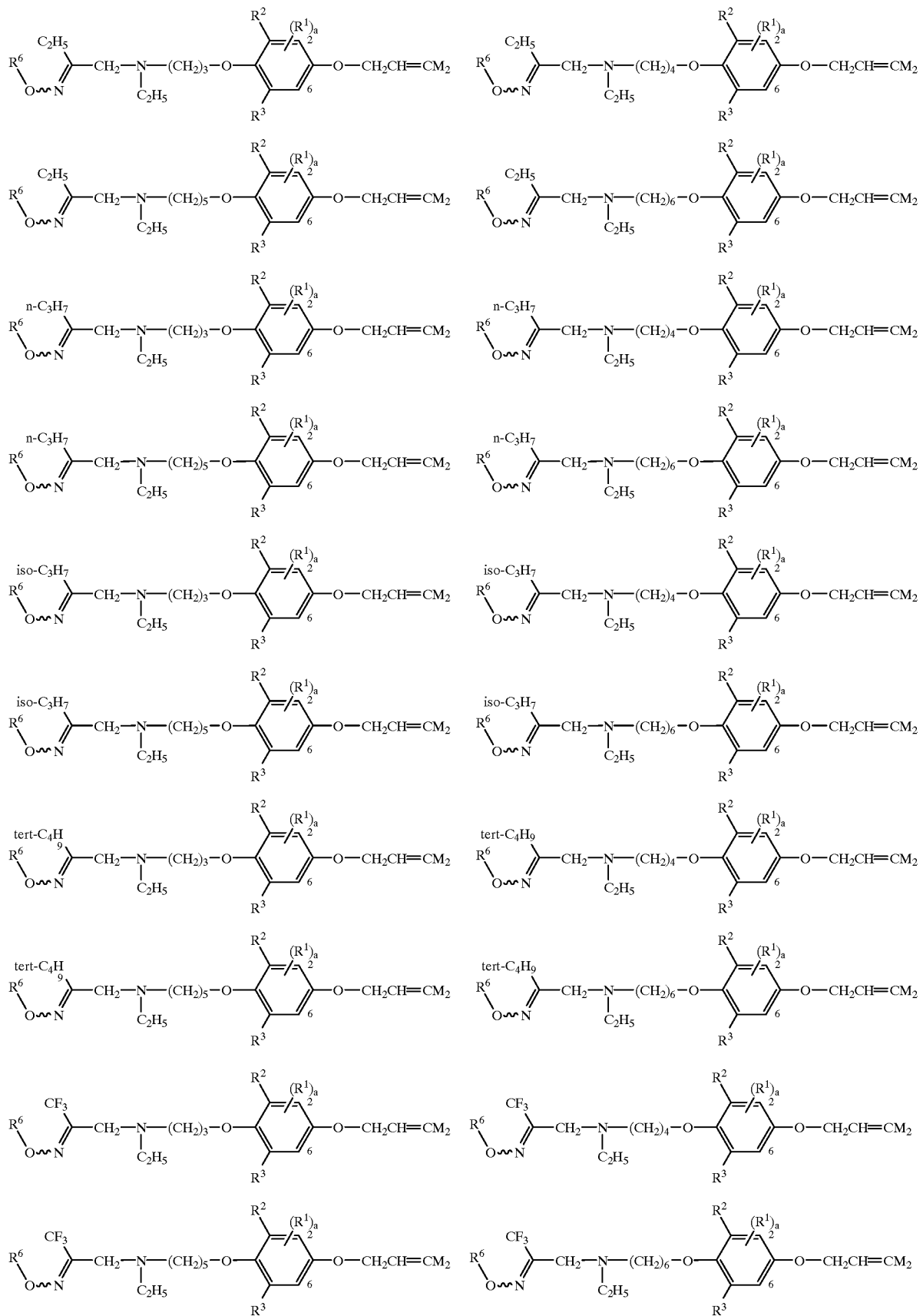

-continued
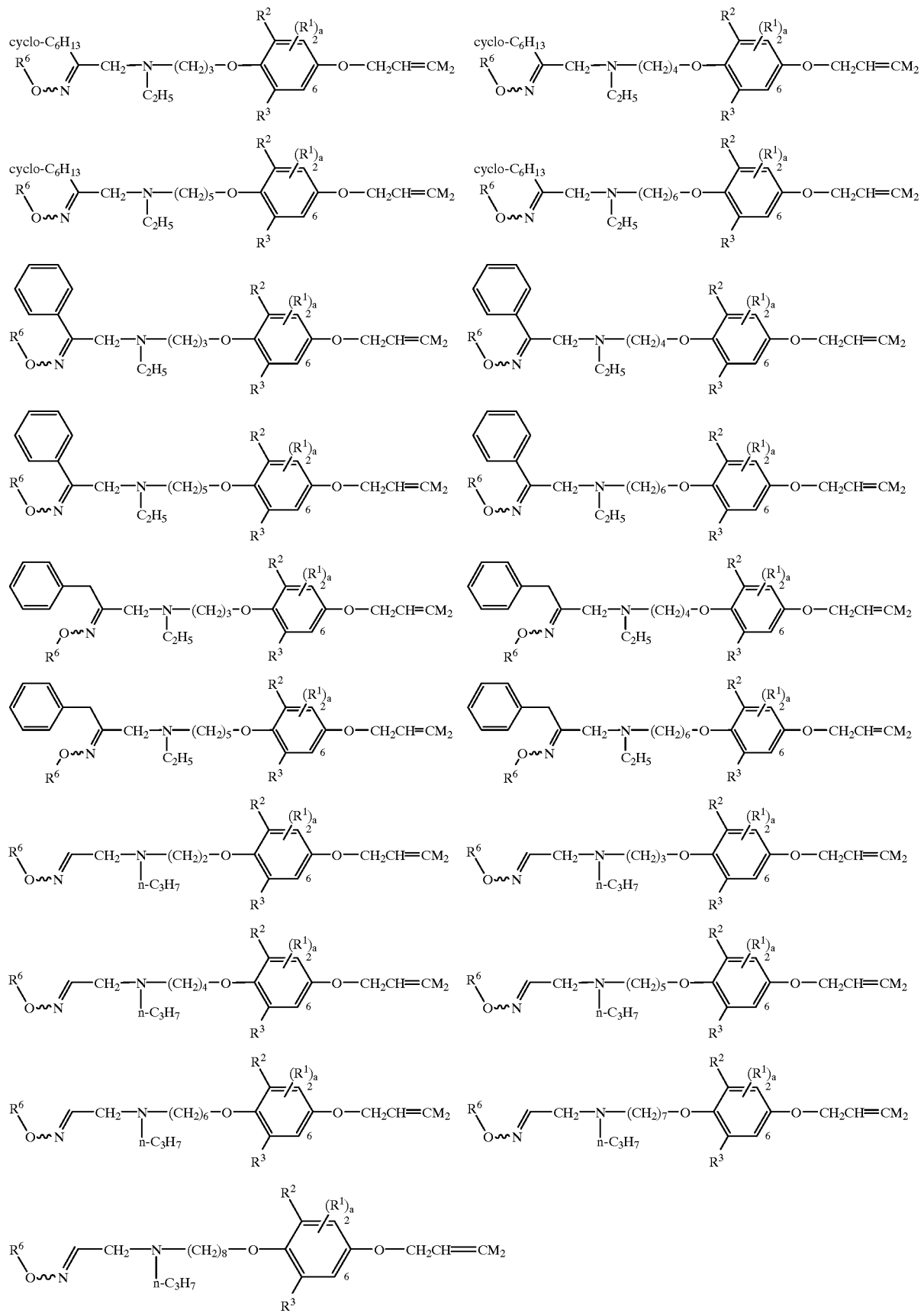

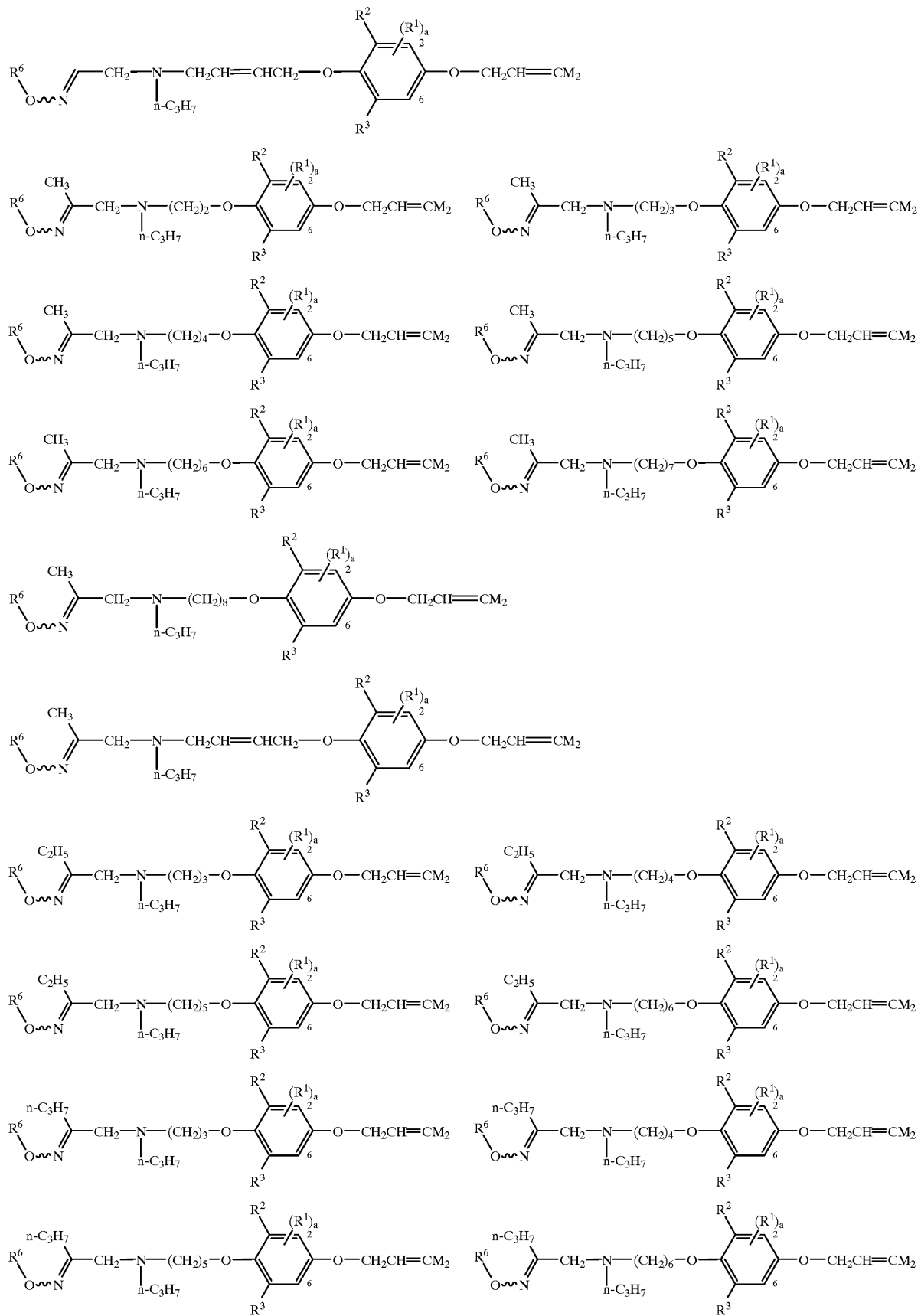

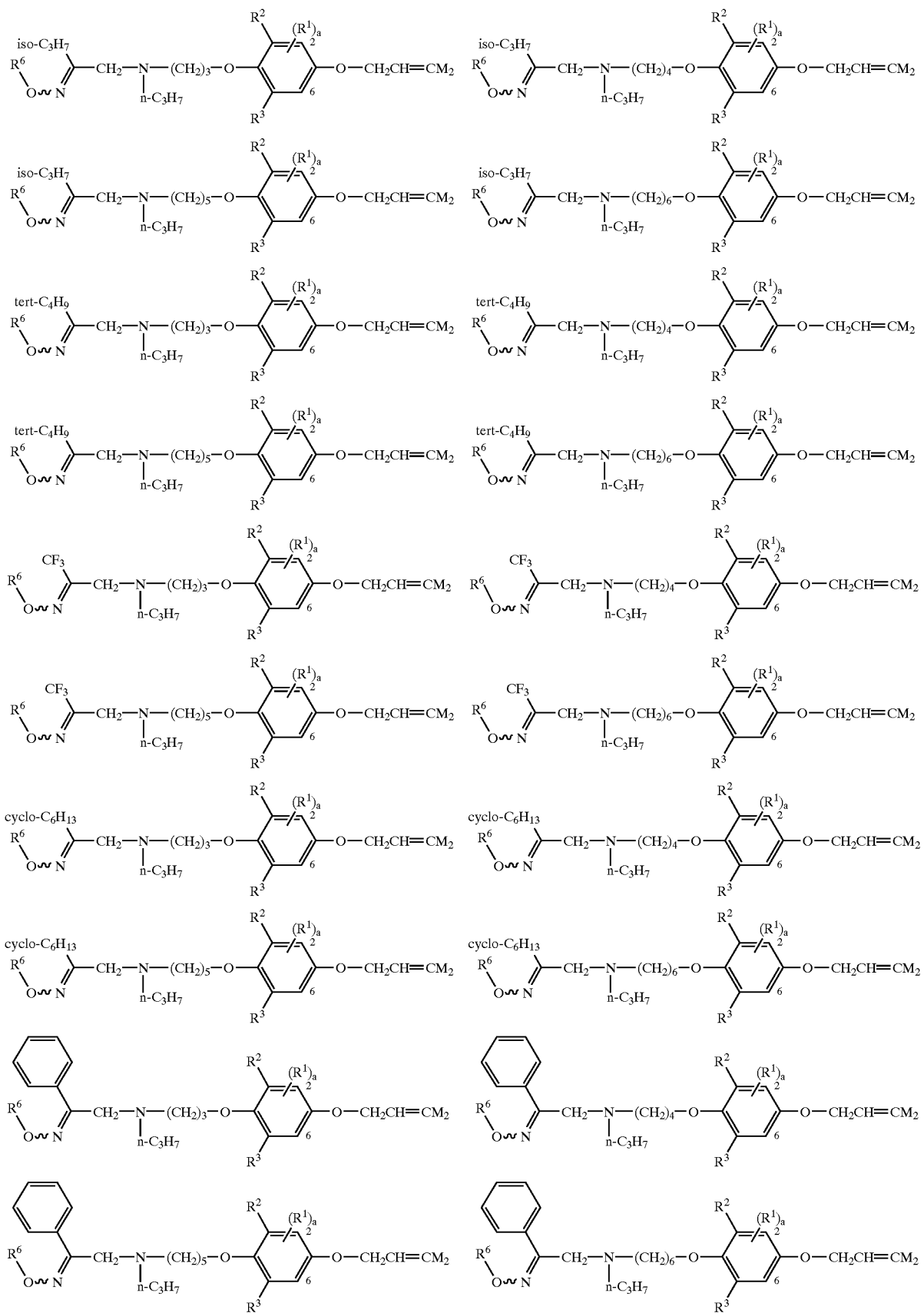

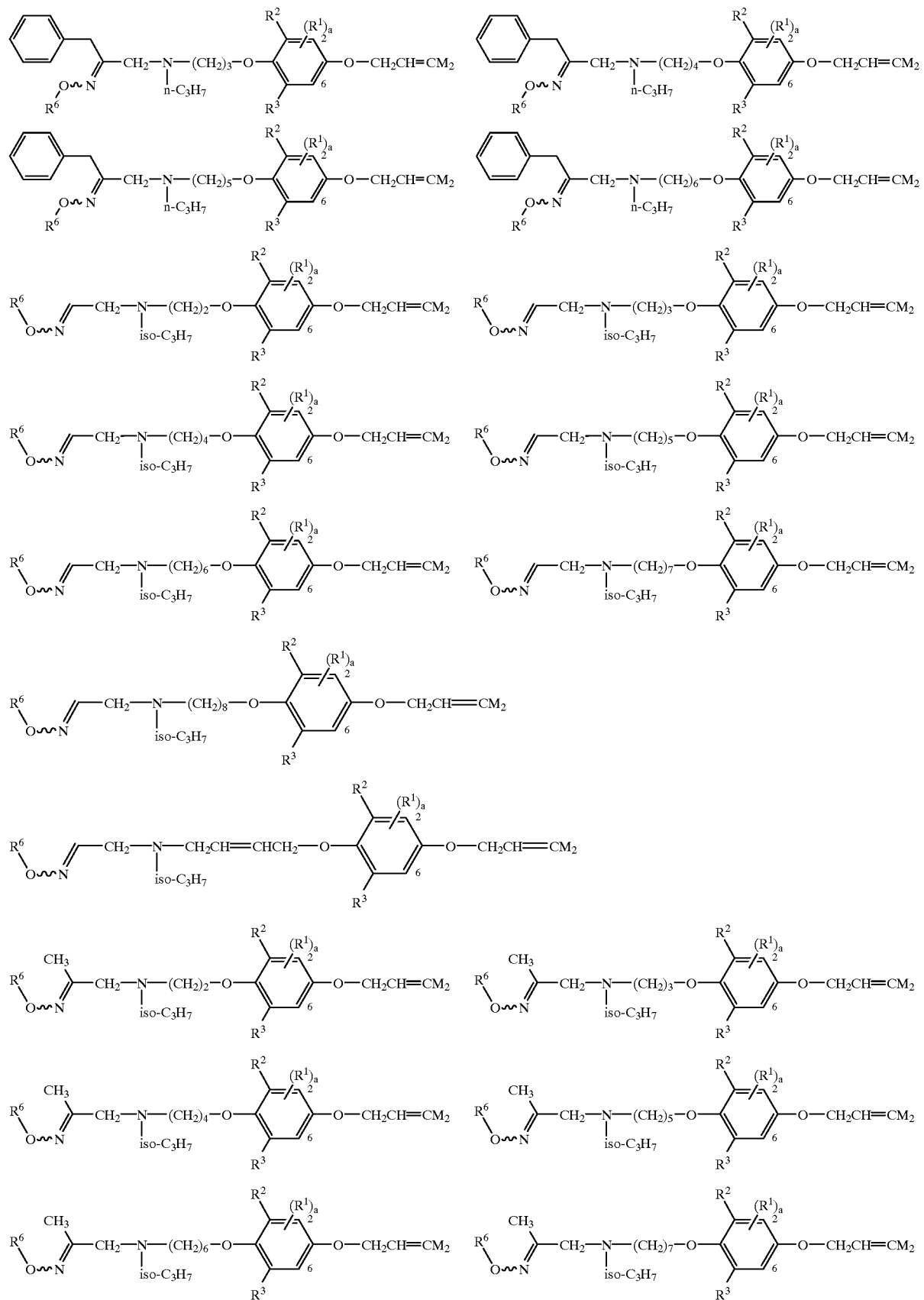

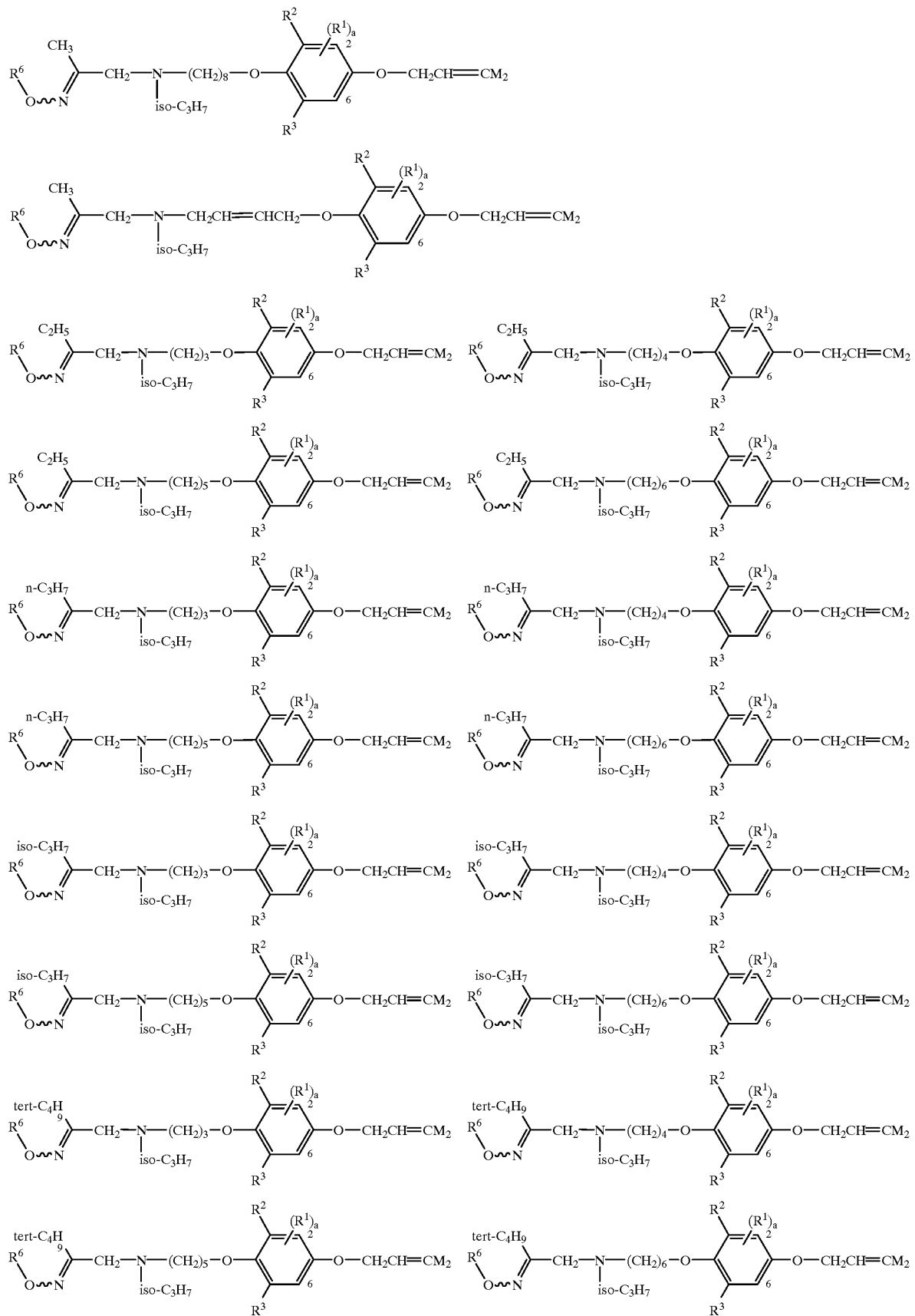

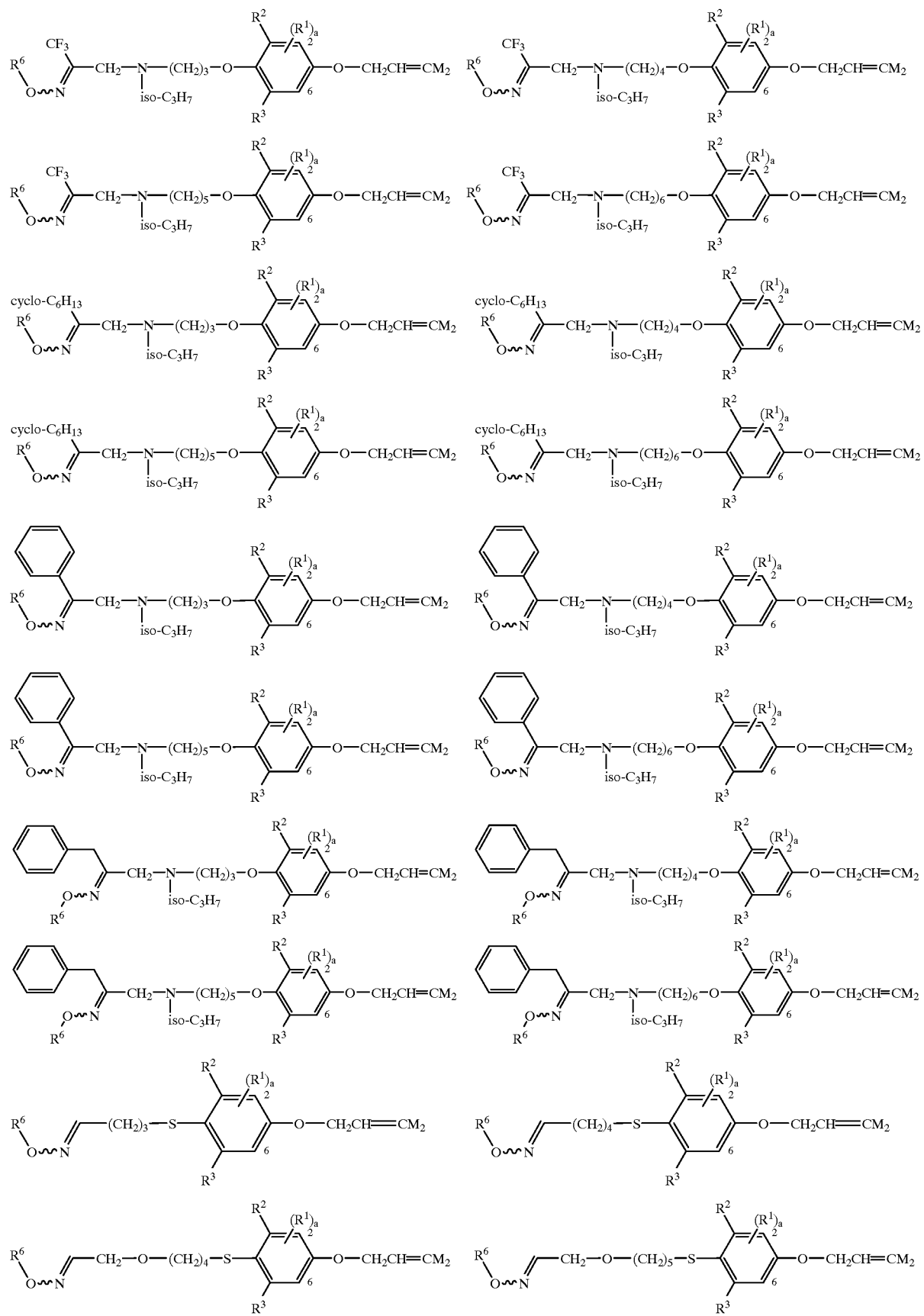

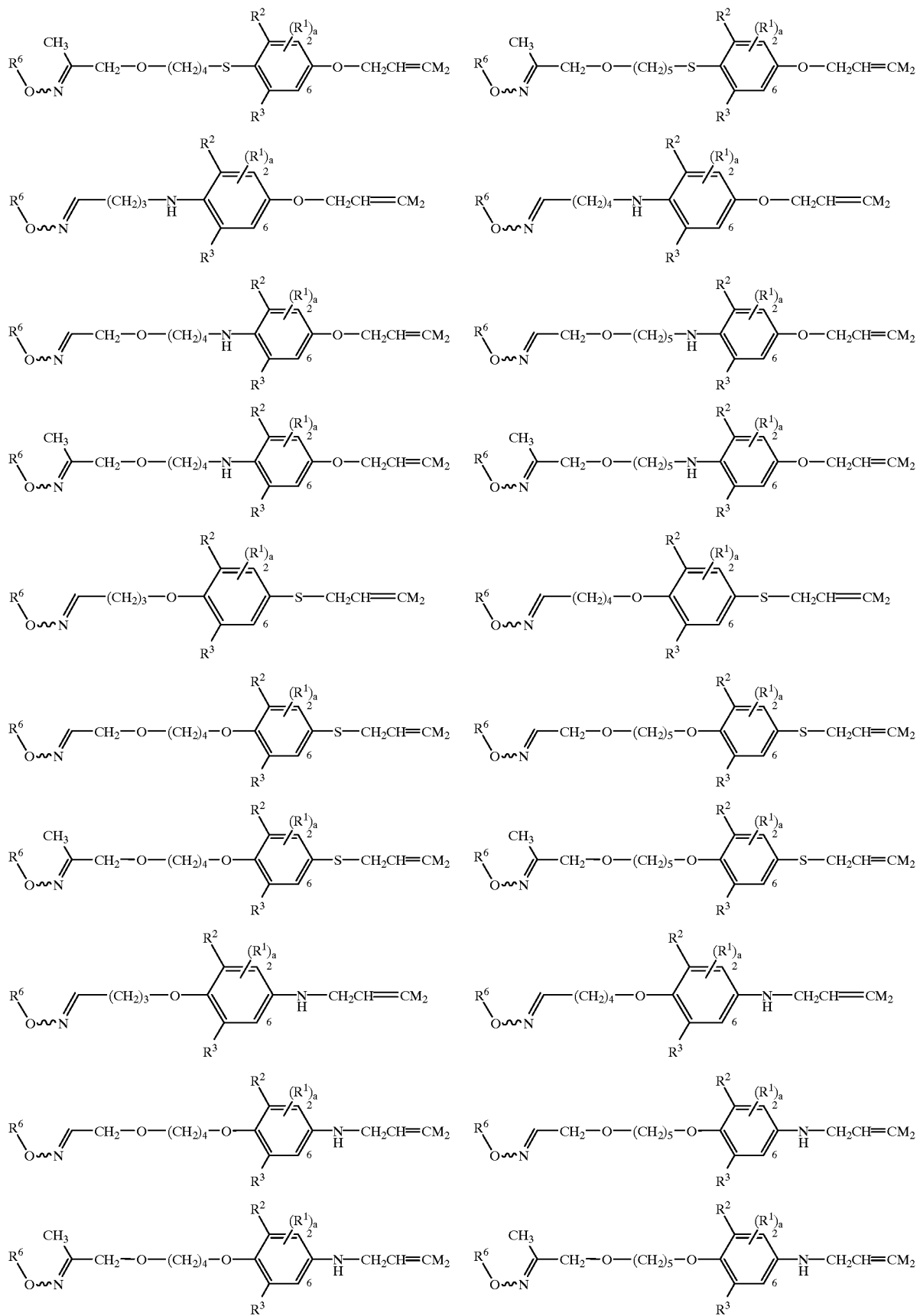

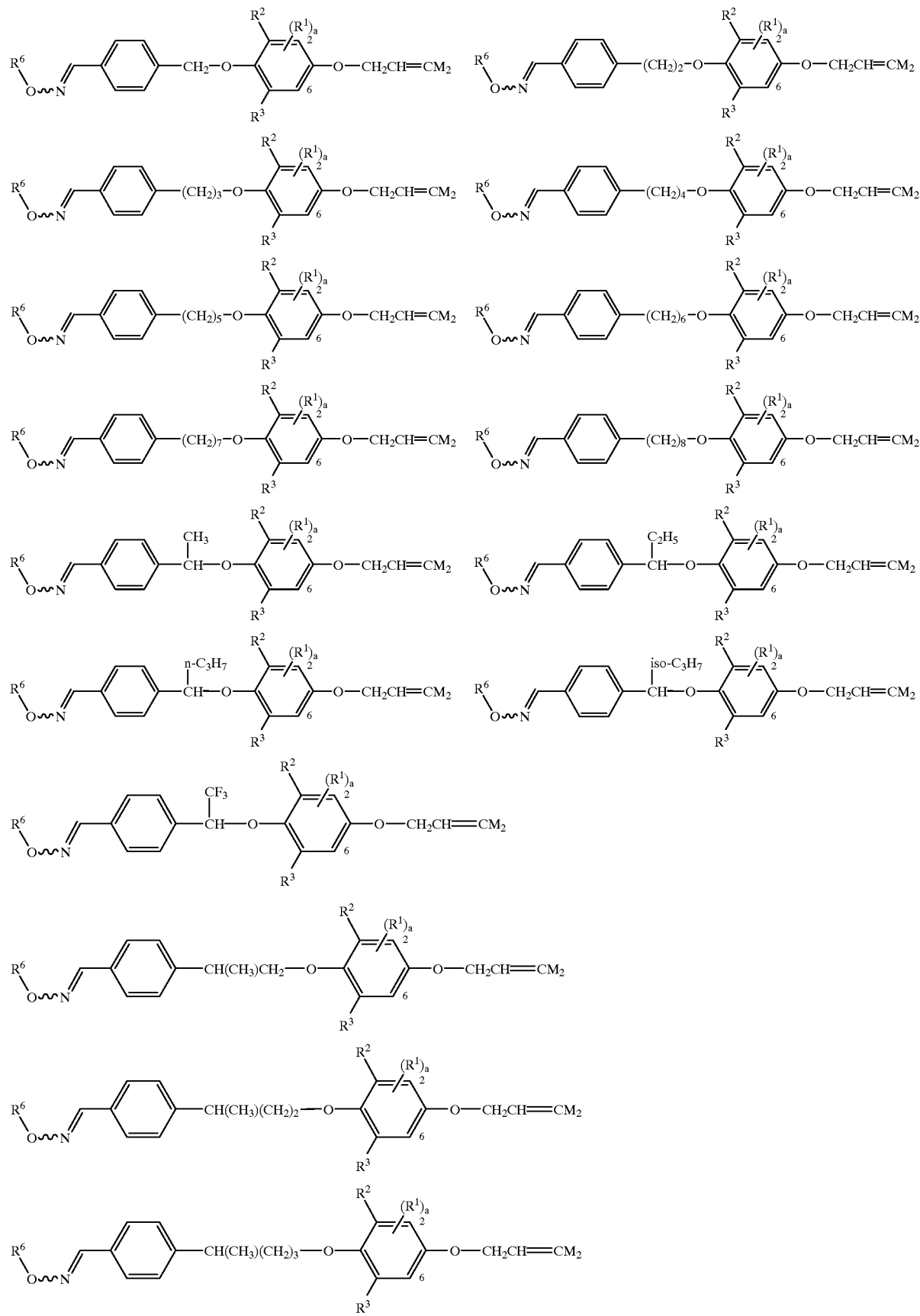

-continued
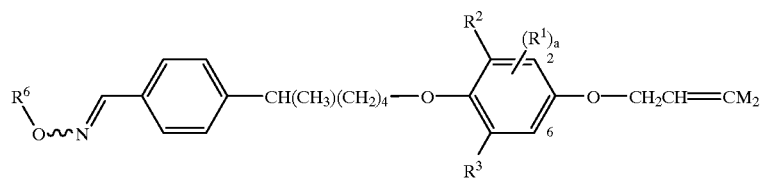
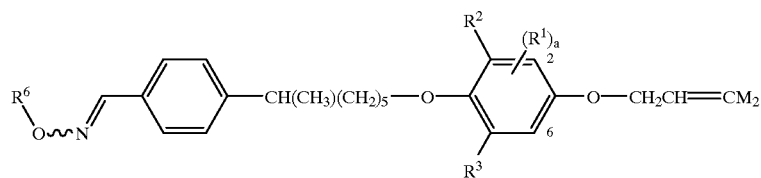
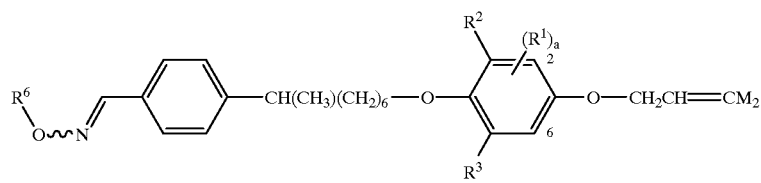
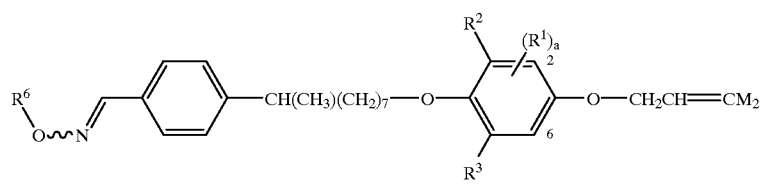
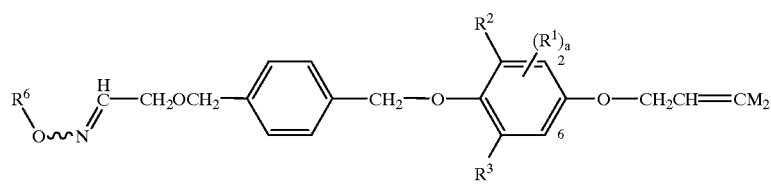
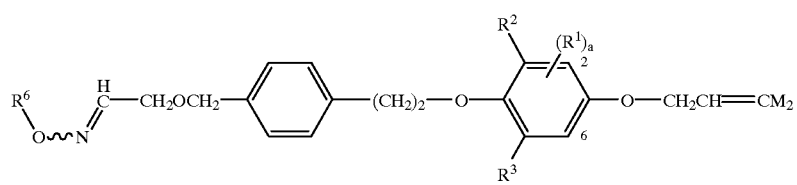
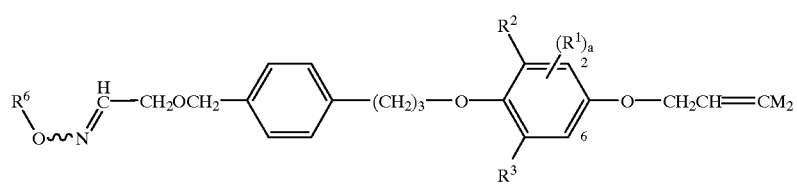
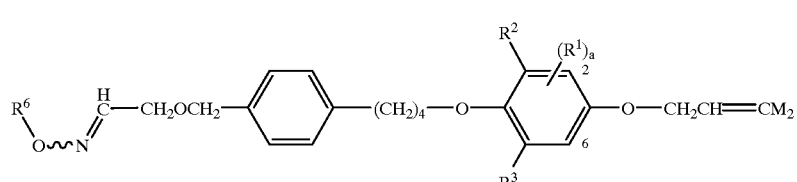
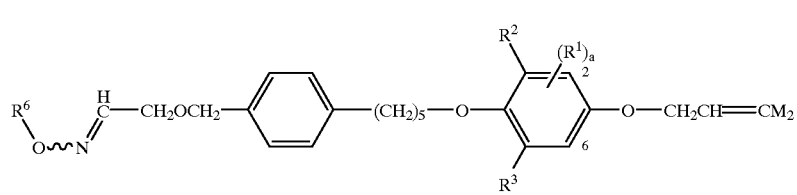

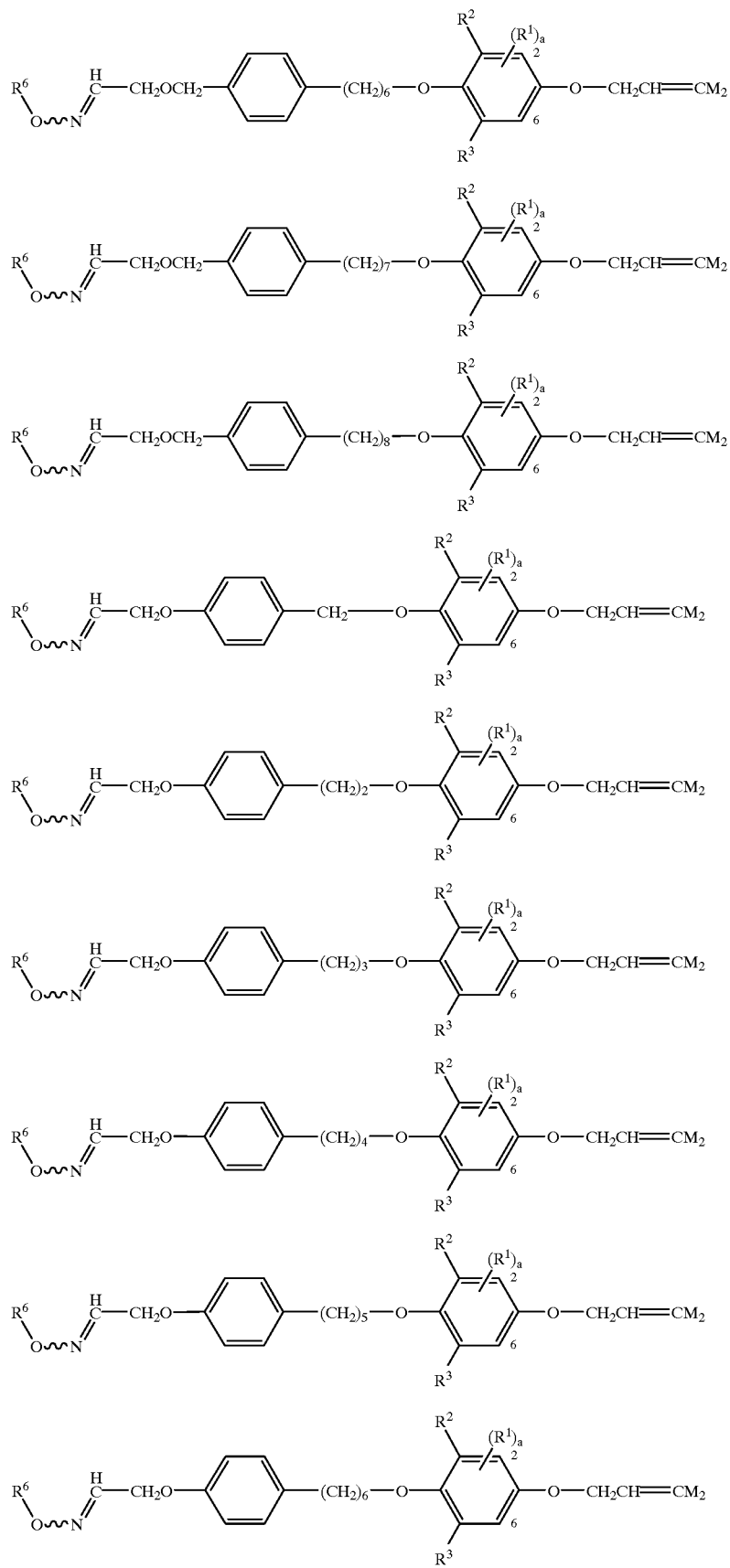

-continued
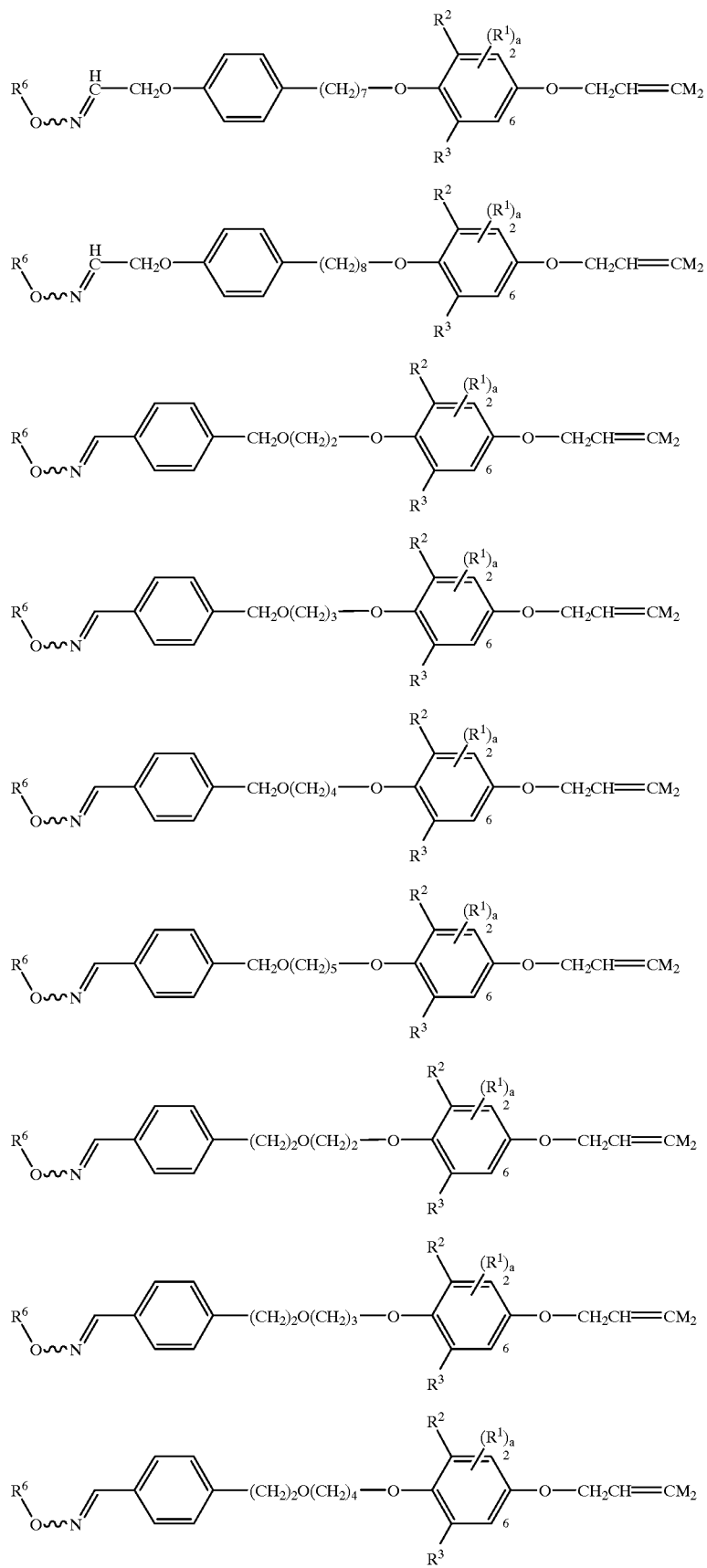

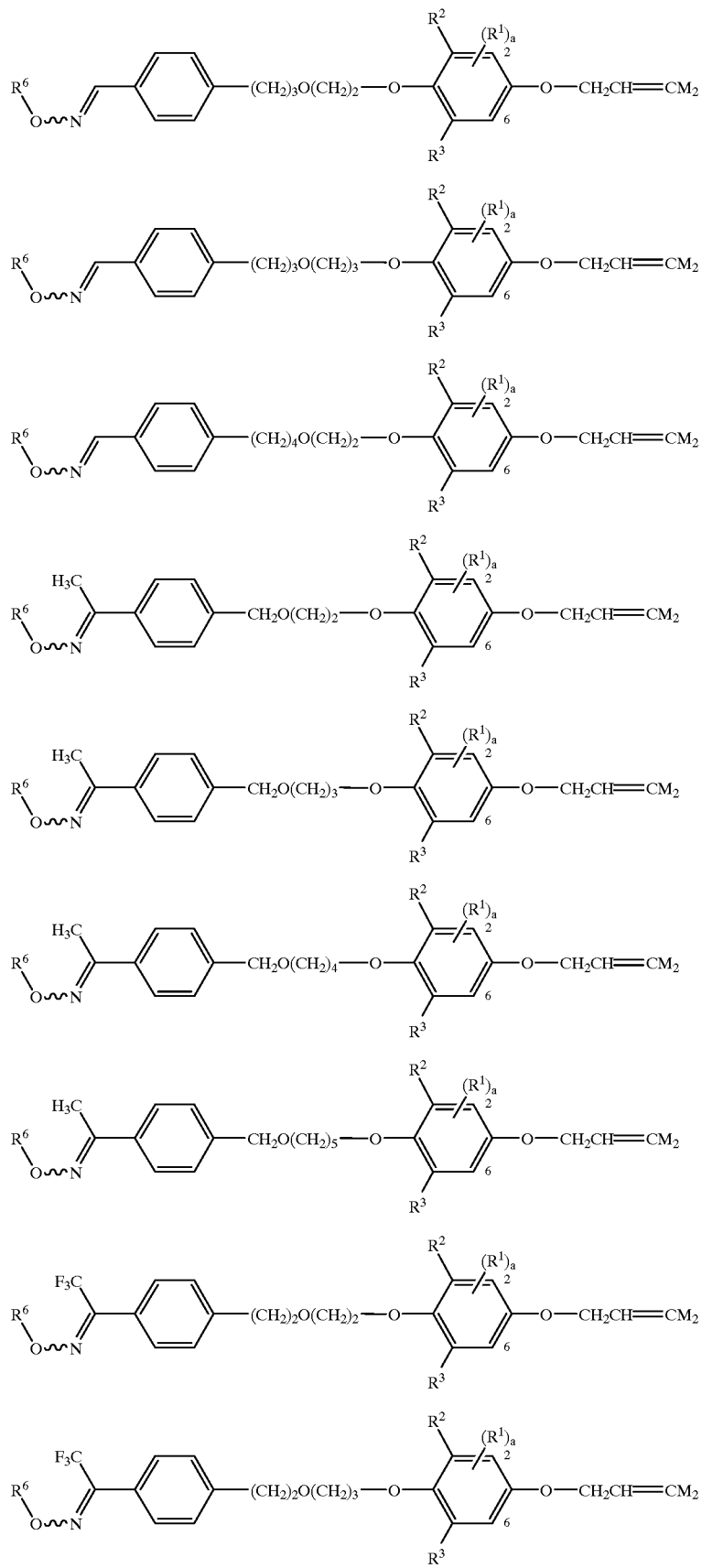

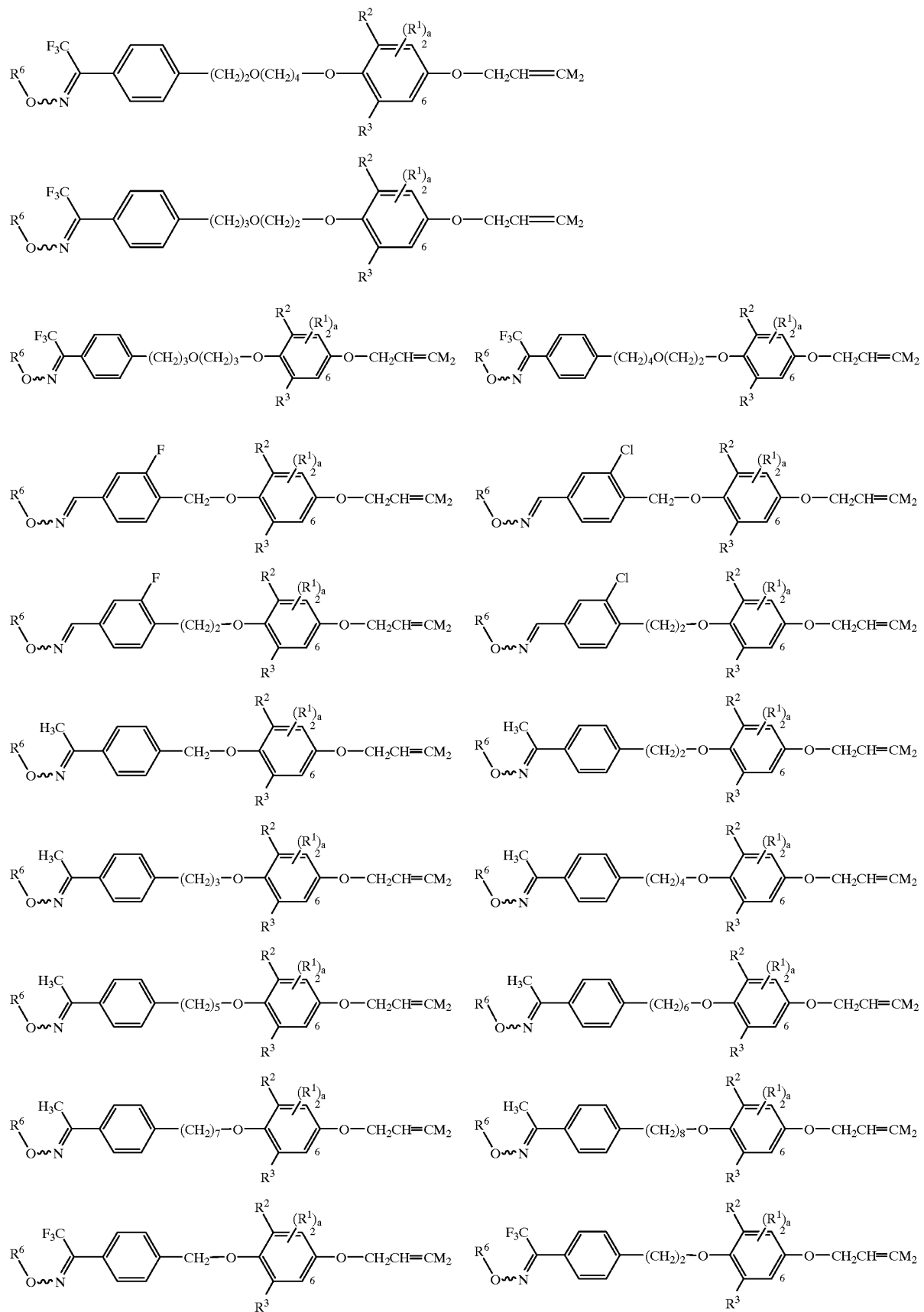

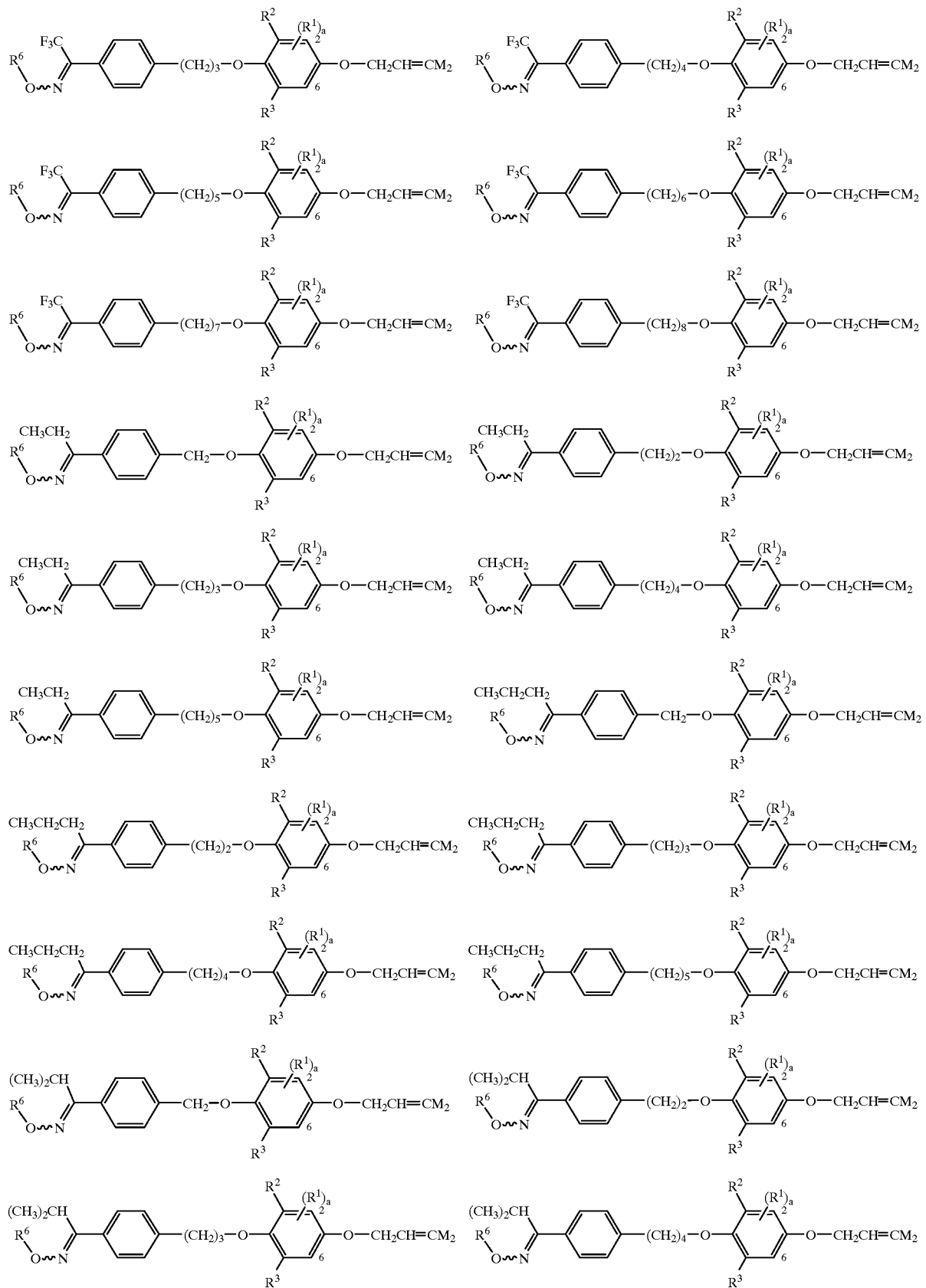

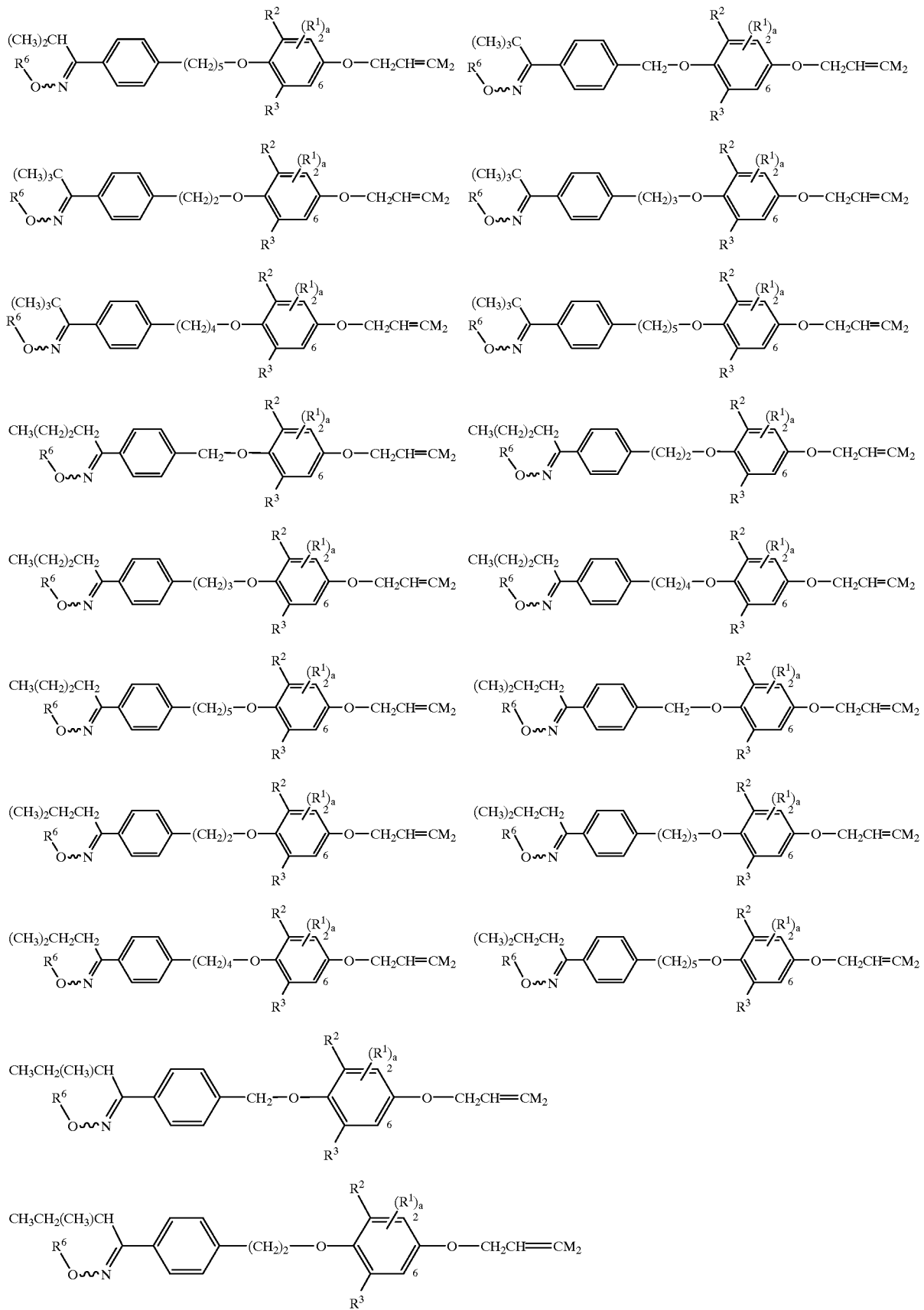

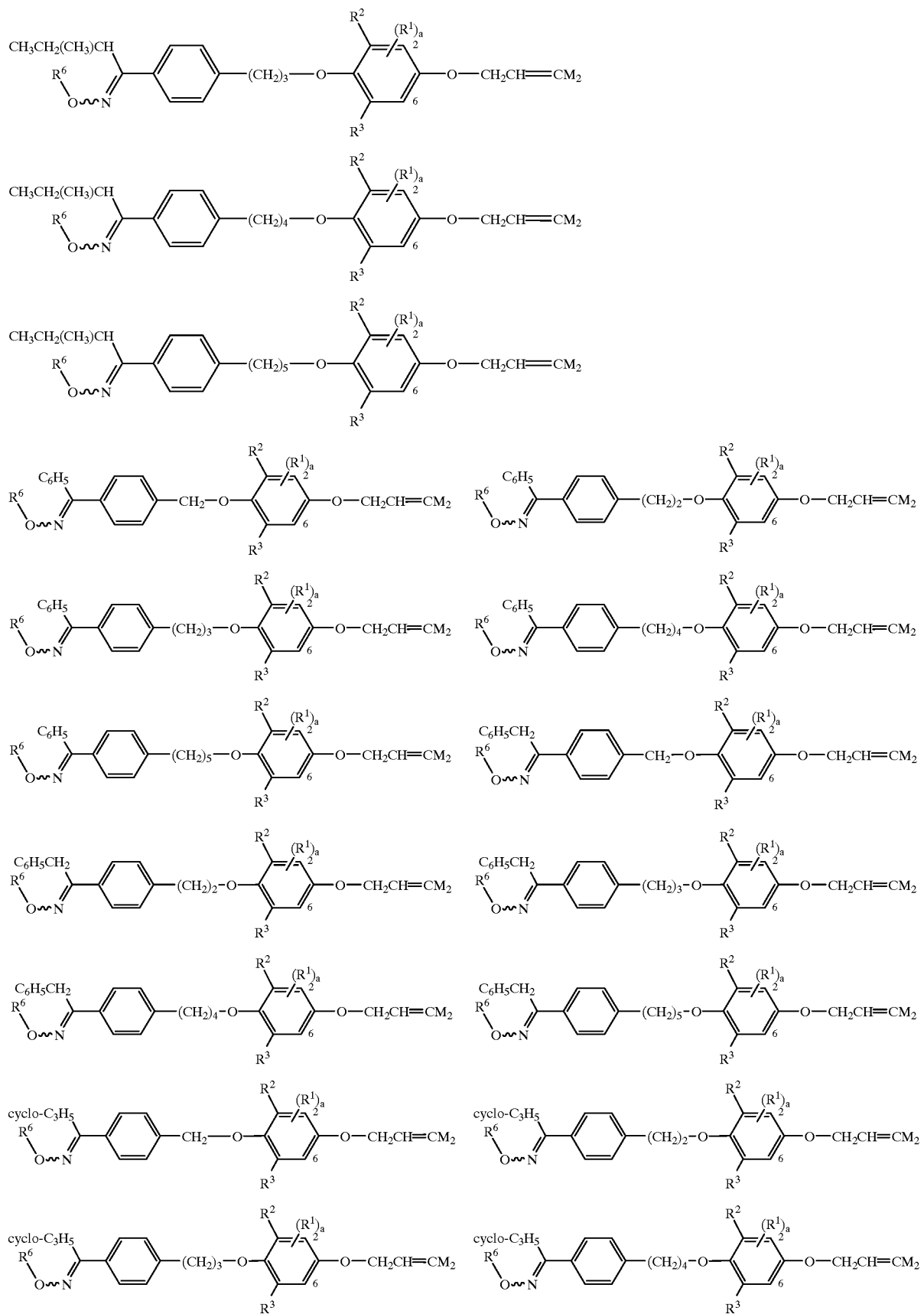

-continued
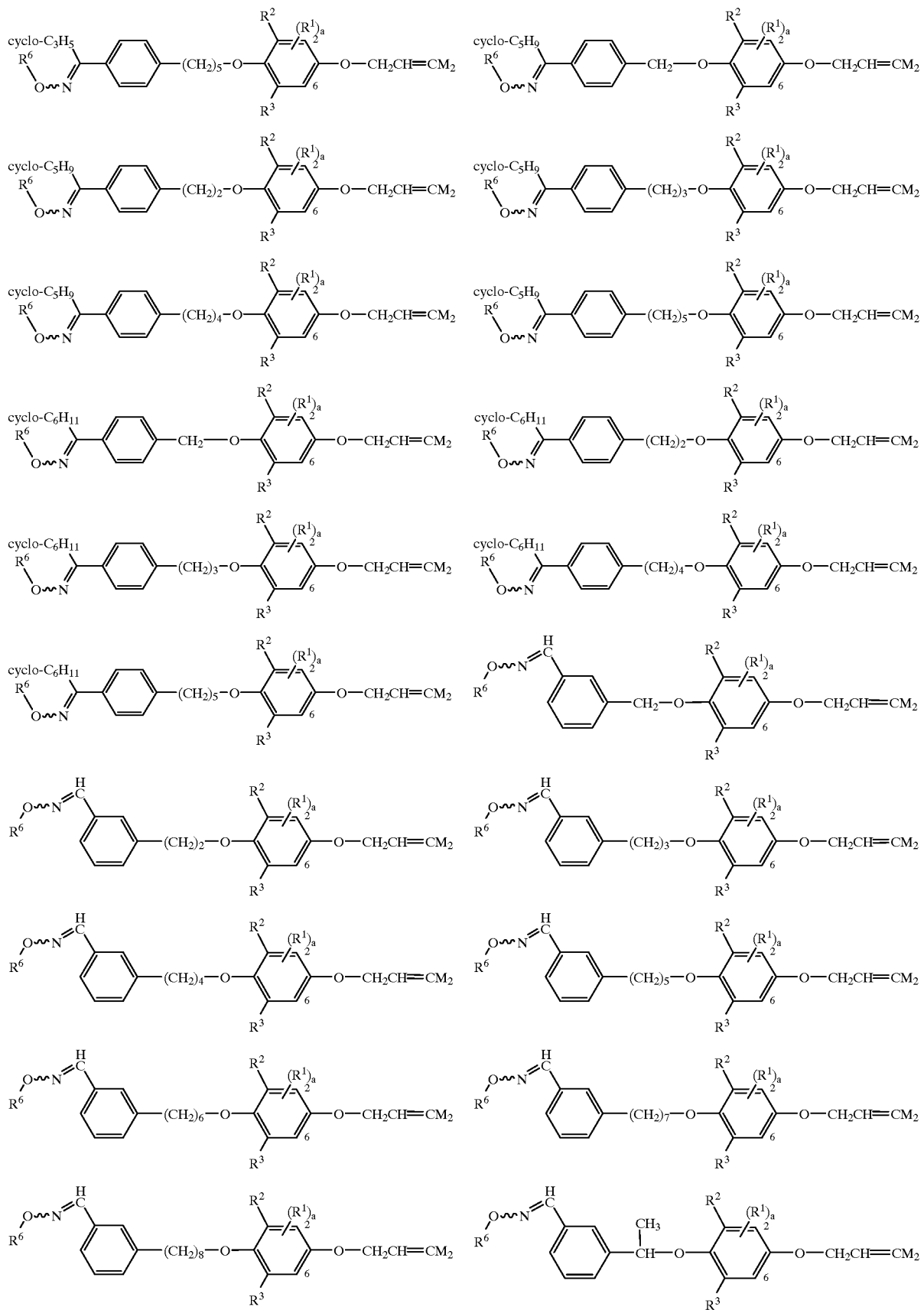

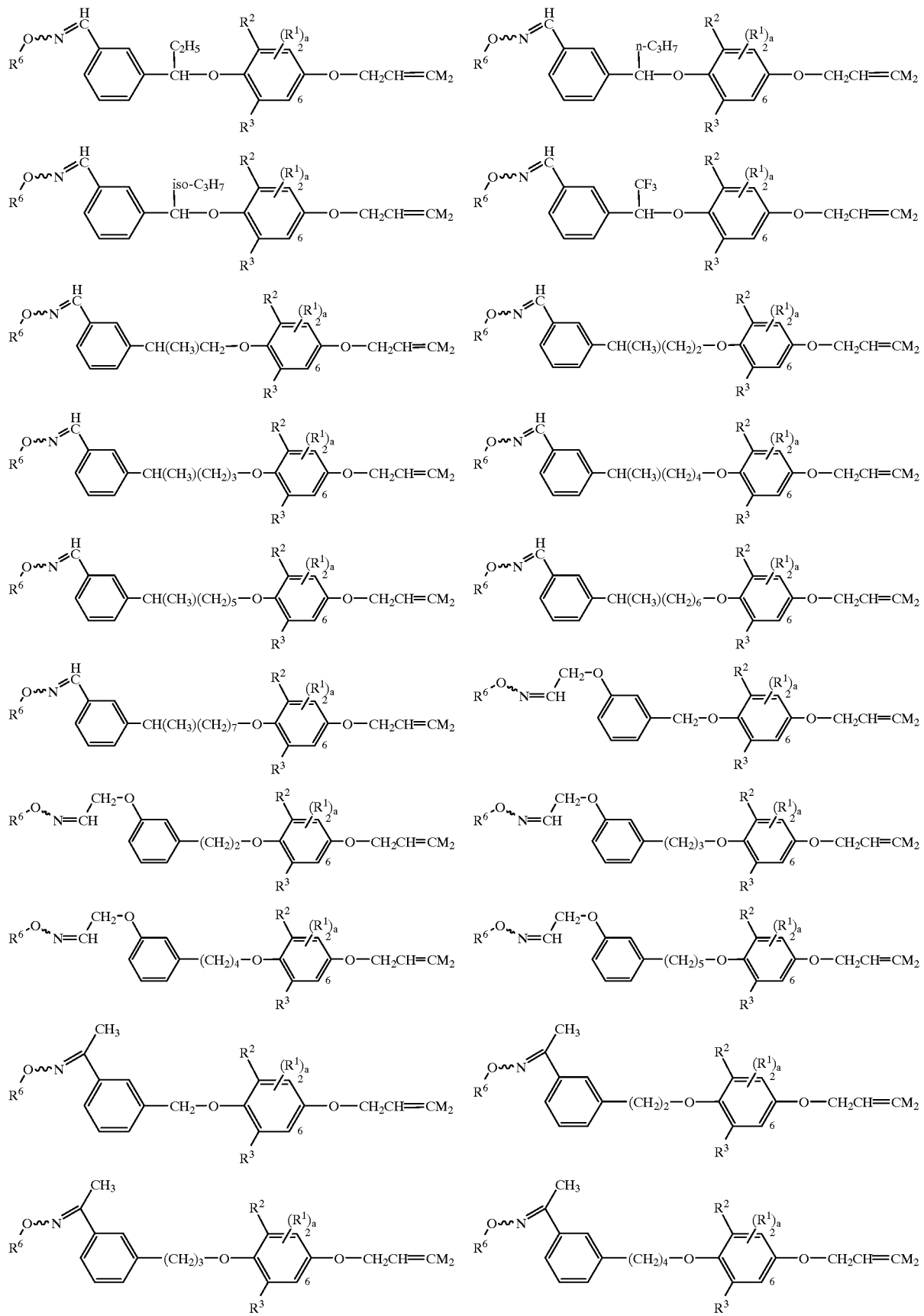

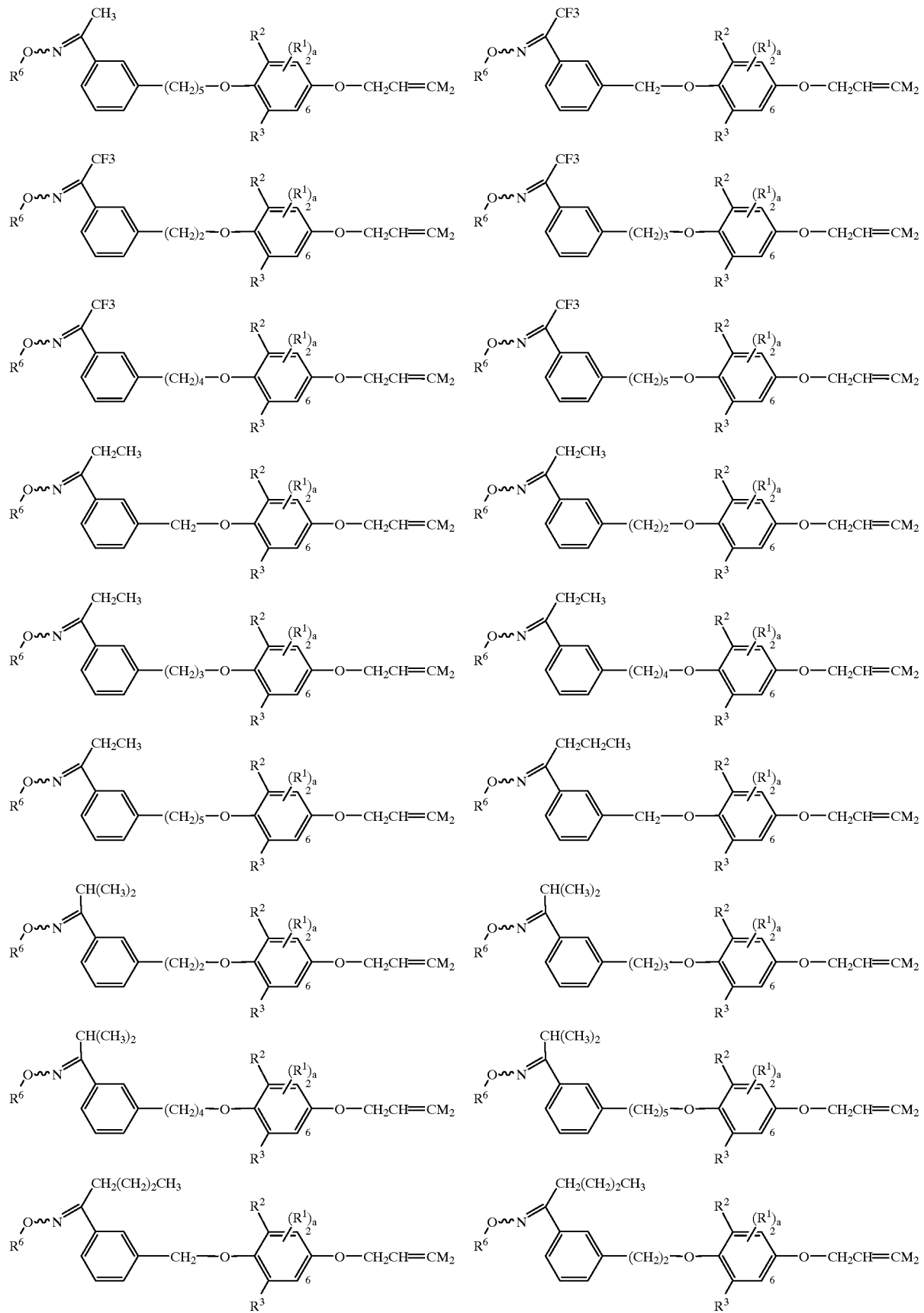

-continued
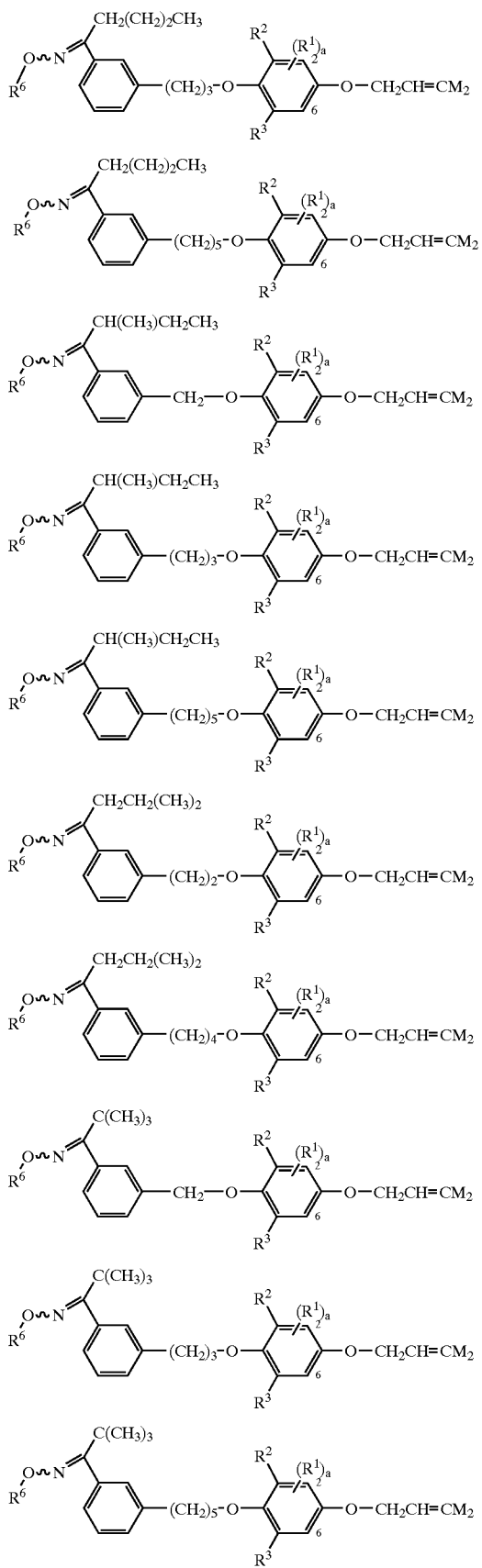
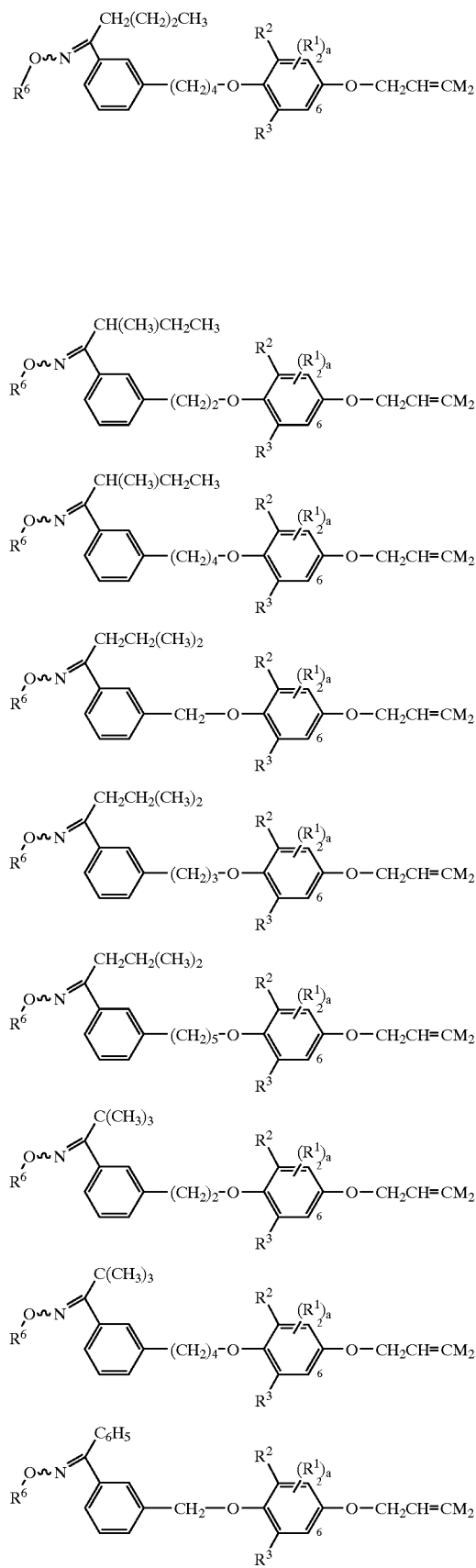

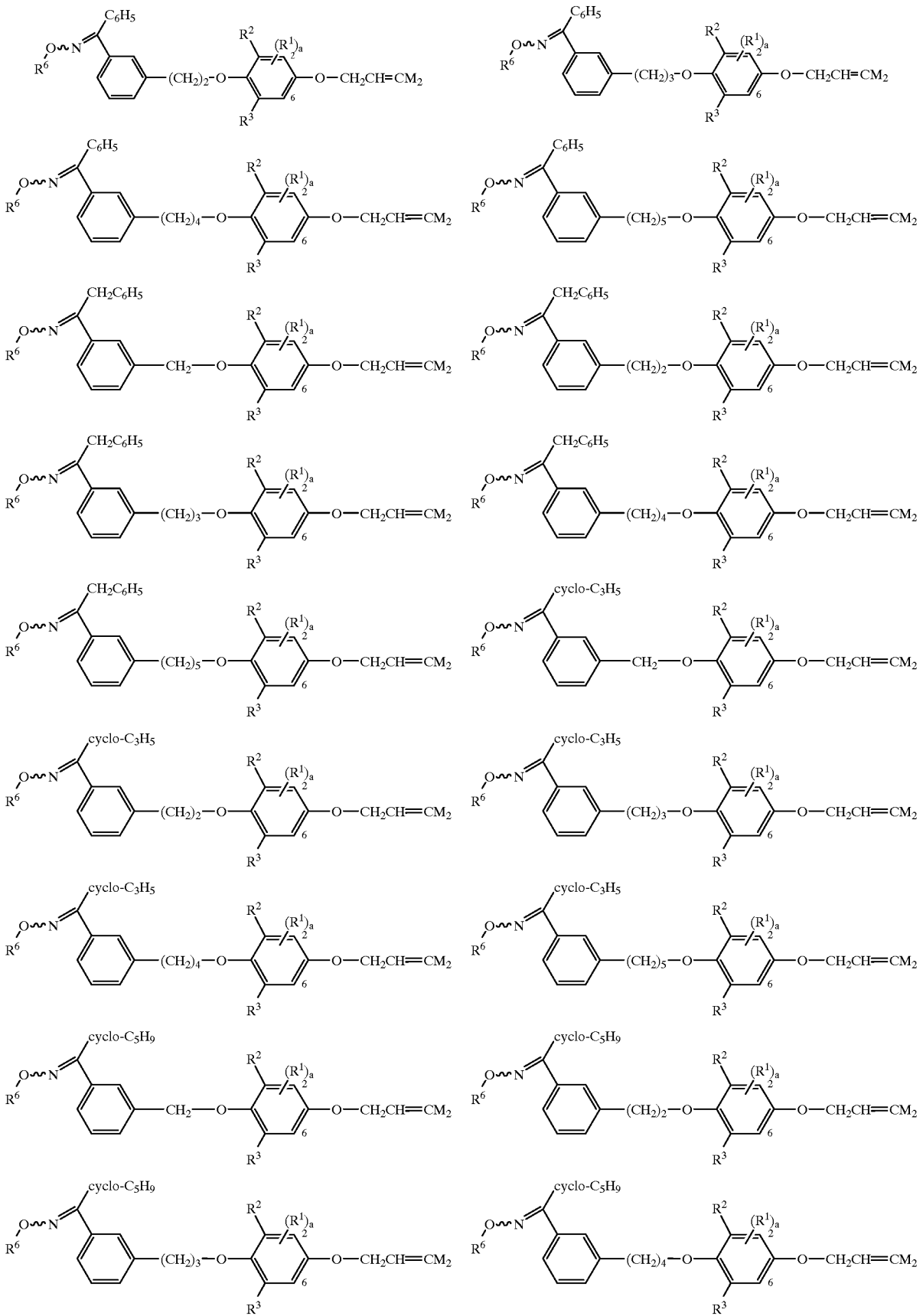

-continued
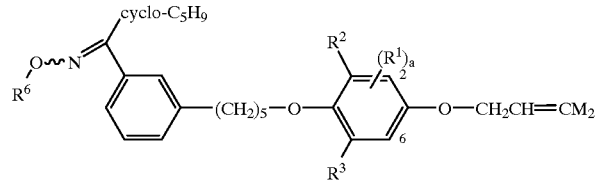
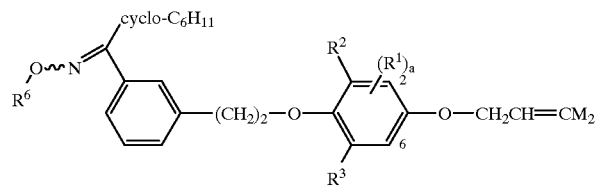
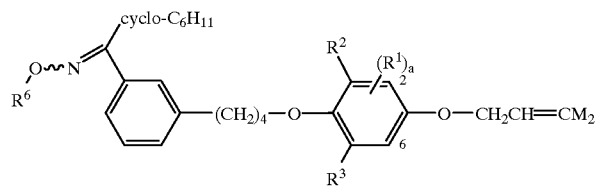
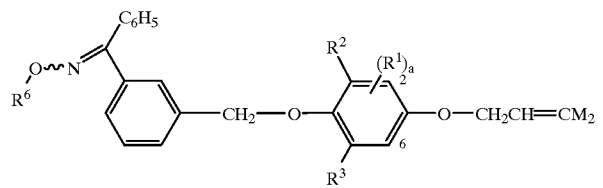
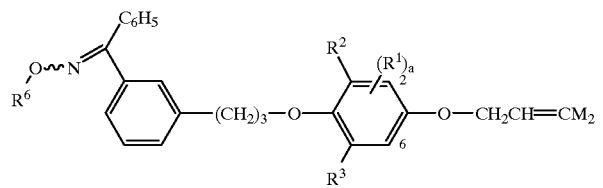
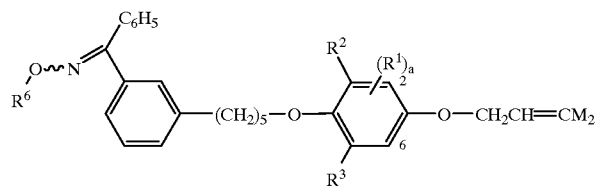
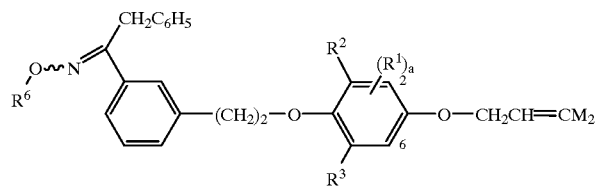
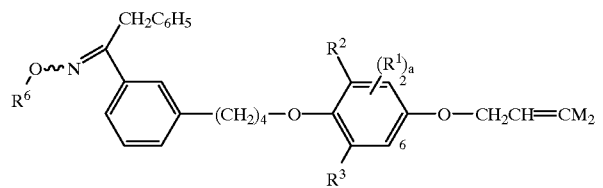
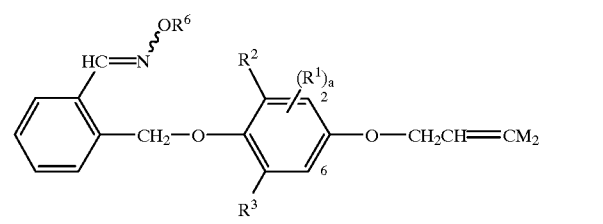
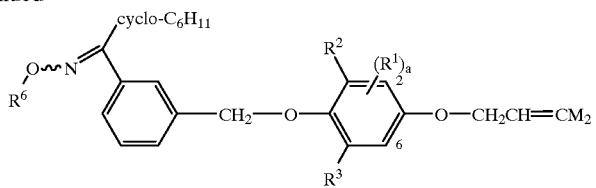
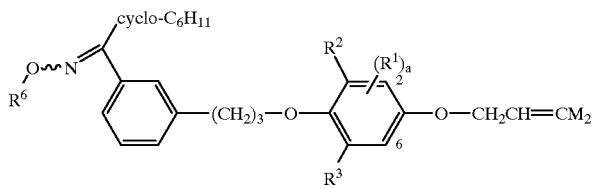
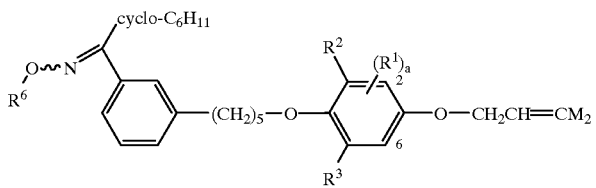
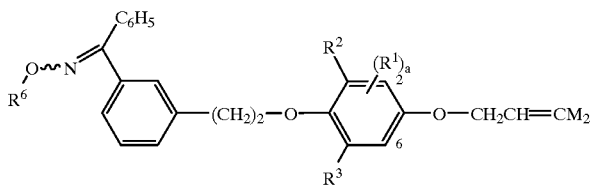
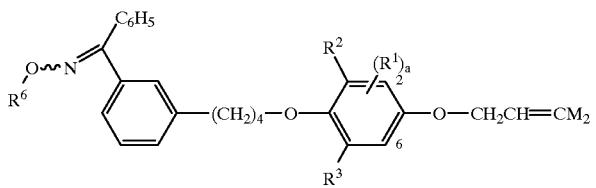
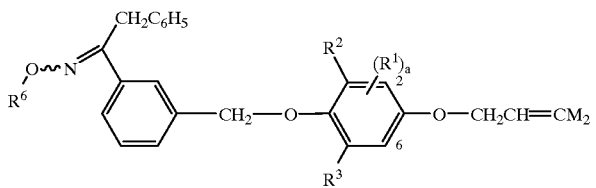
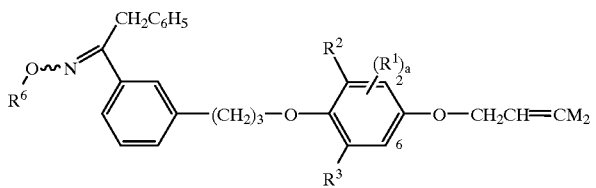
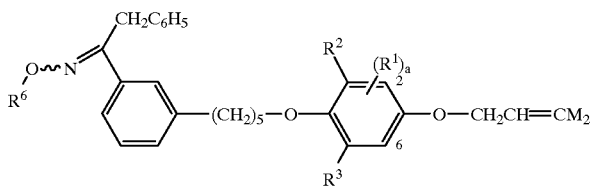
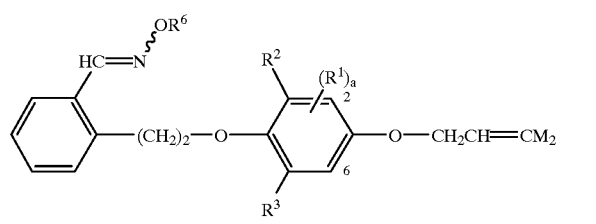

-continued
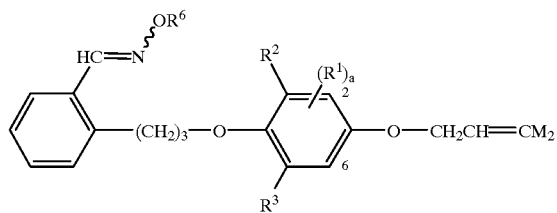
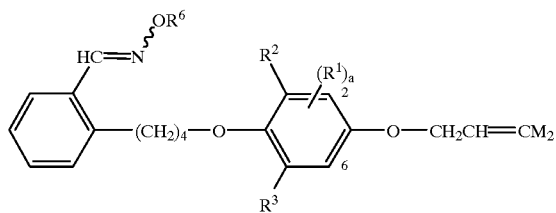
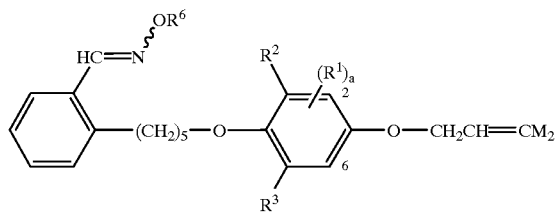
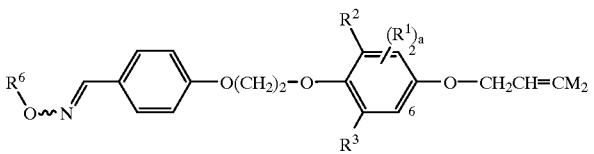
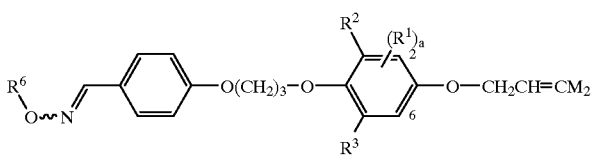
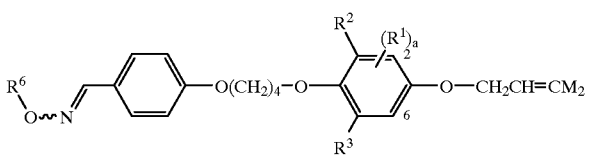
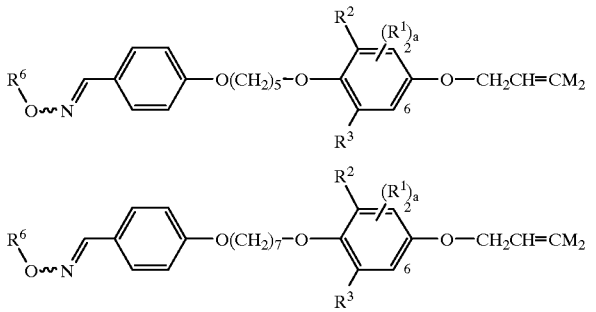
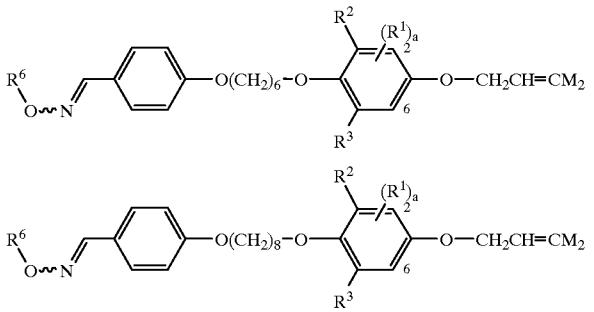
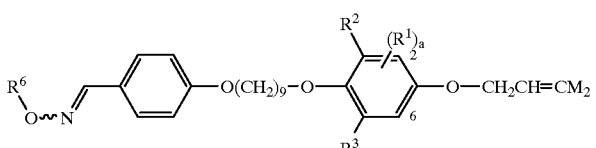
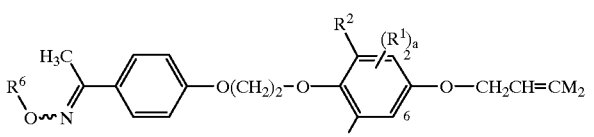
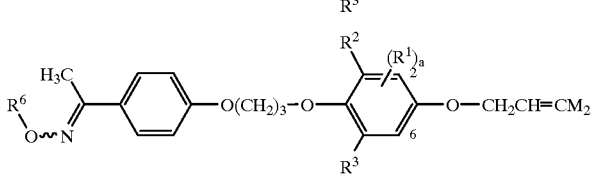
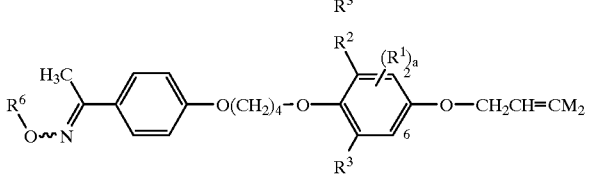
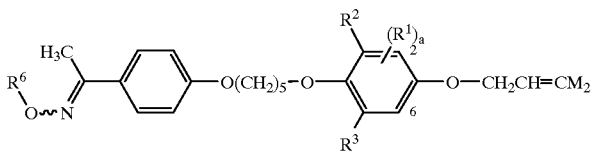
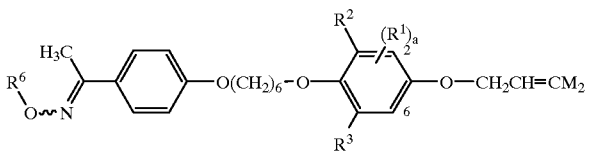
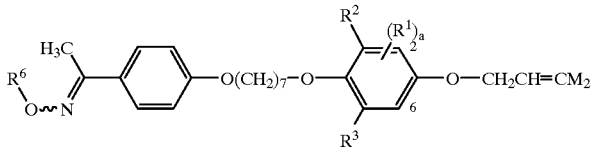
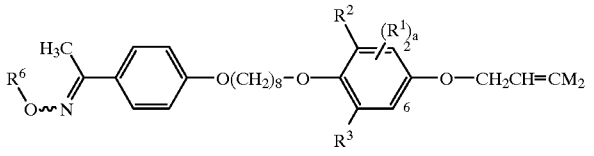
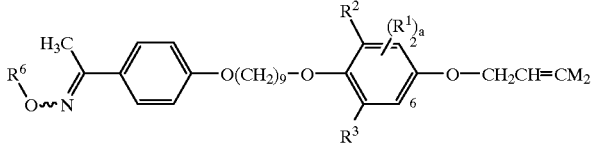
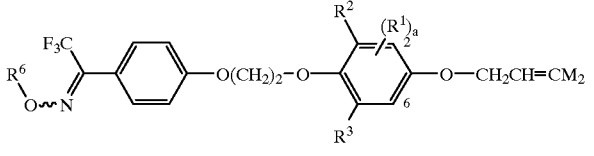

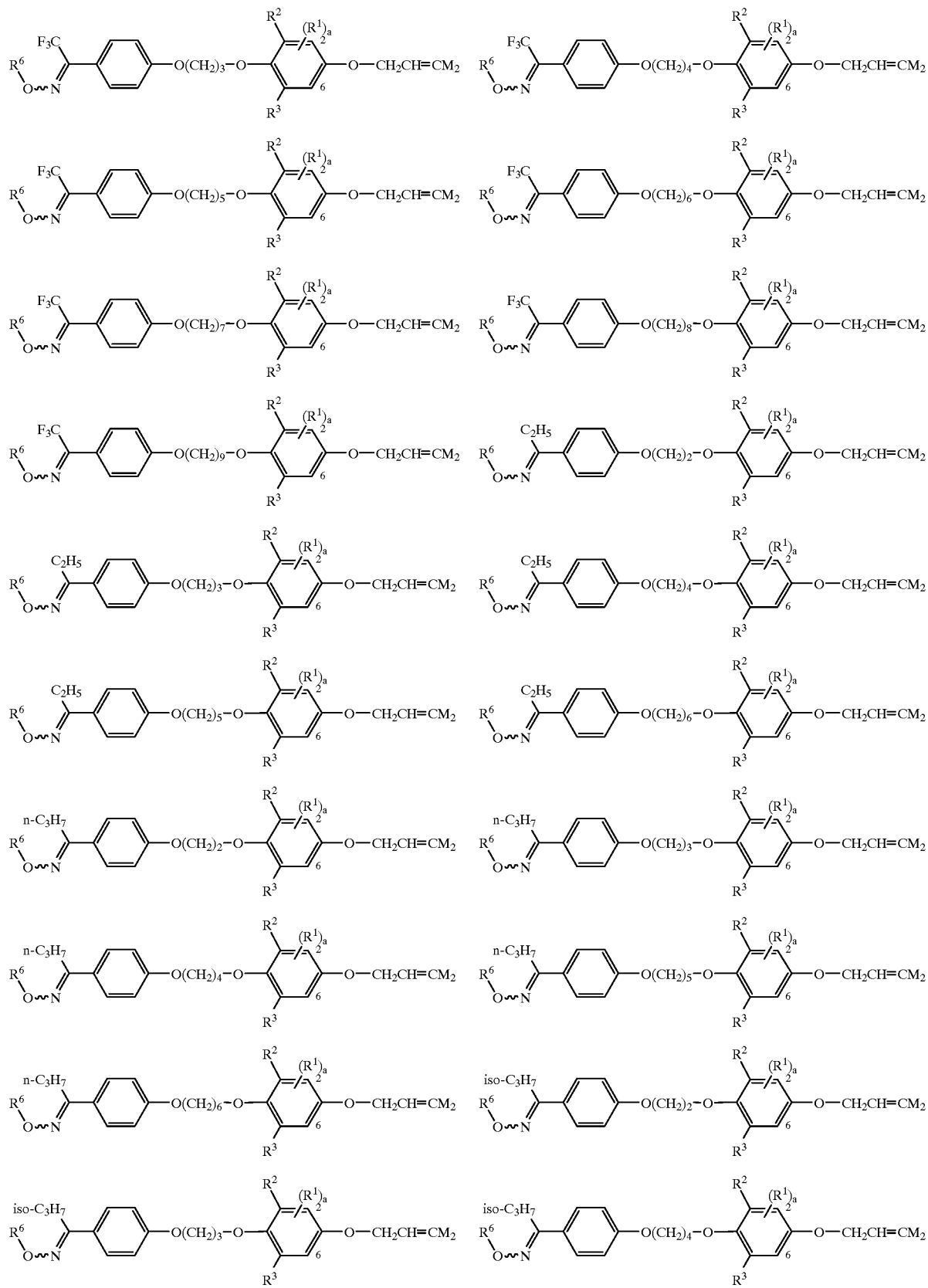

-continued
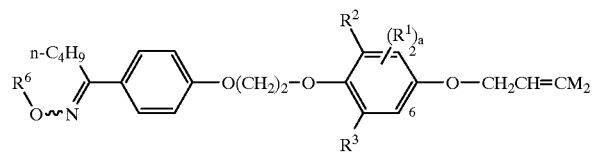
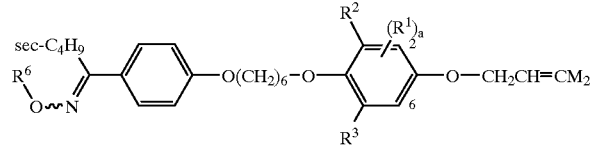
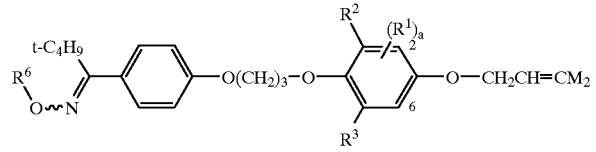

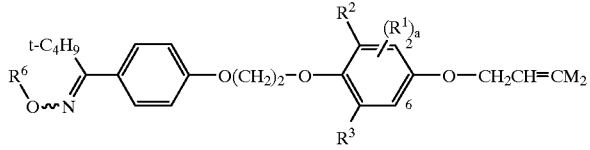
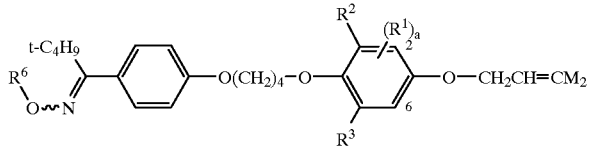

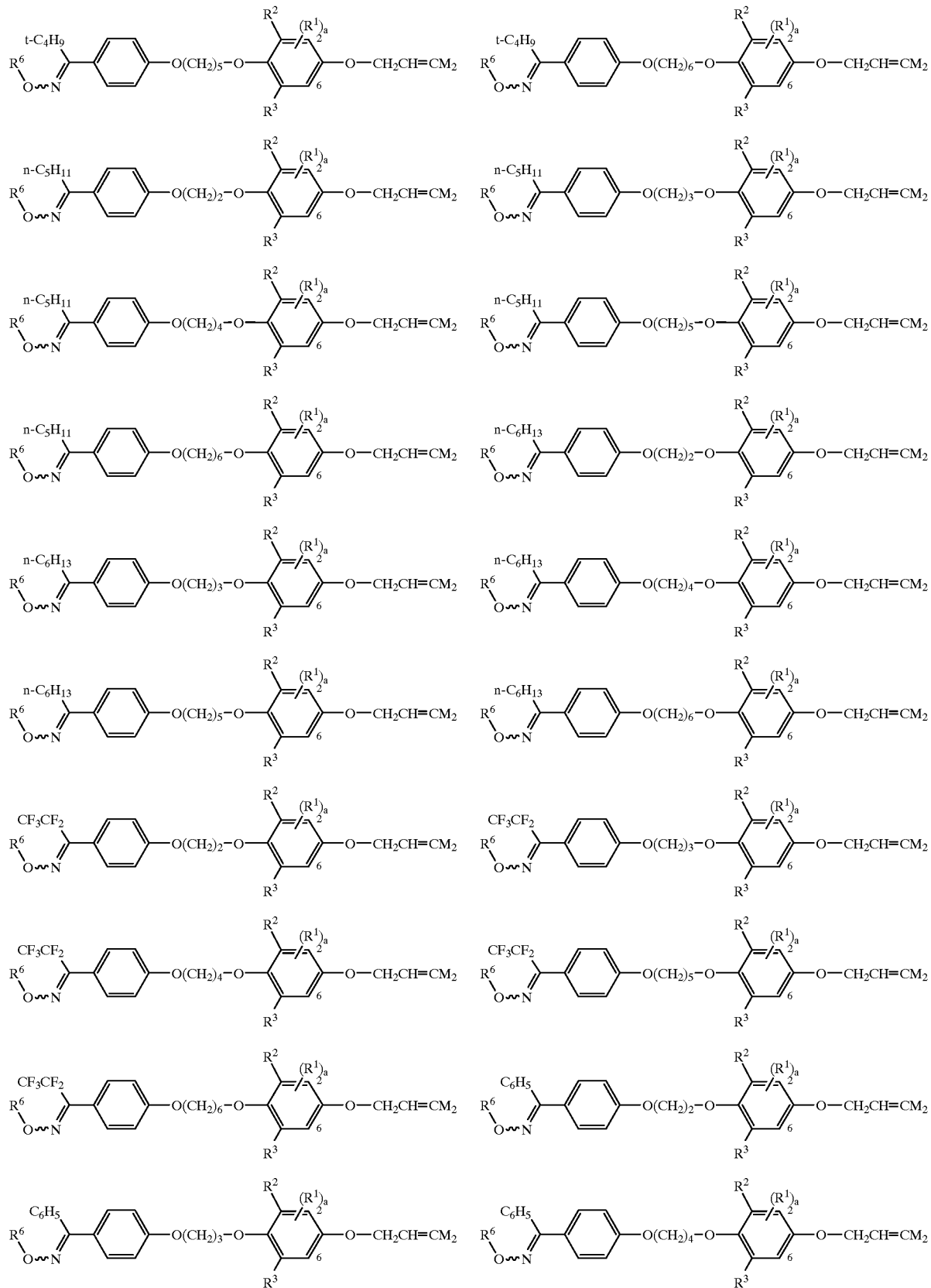

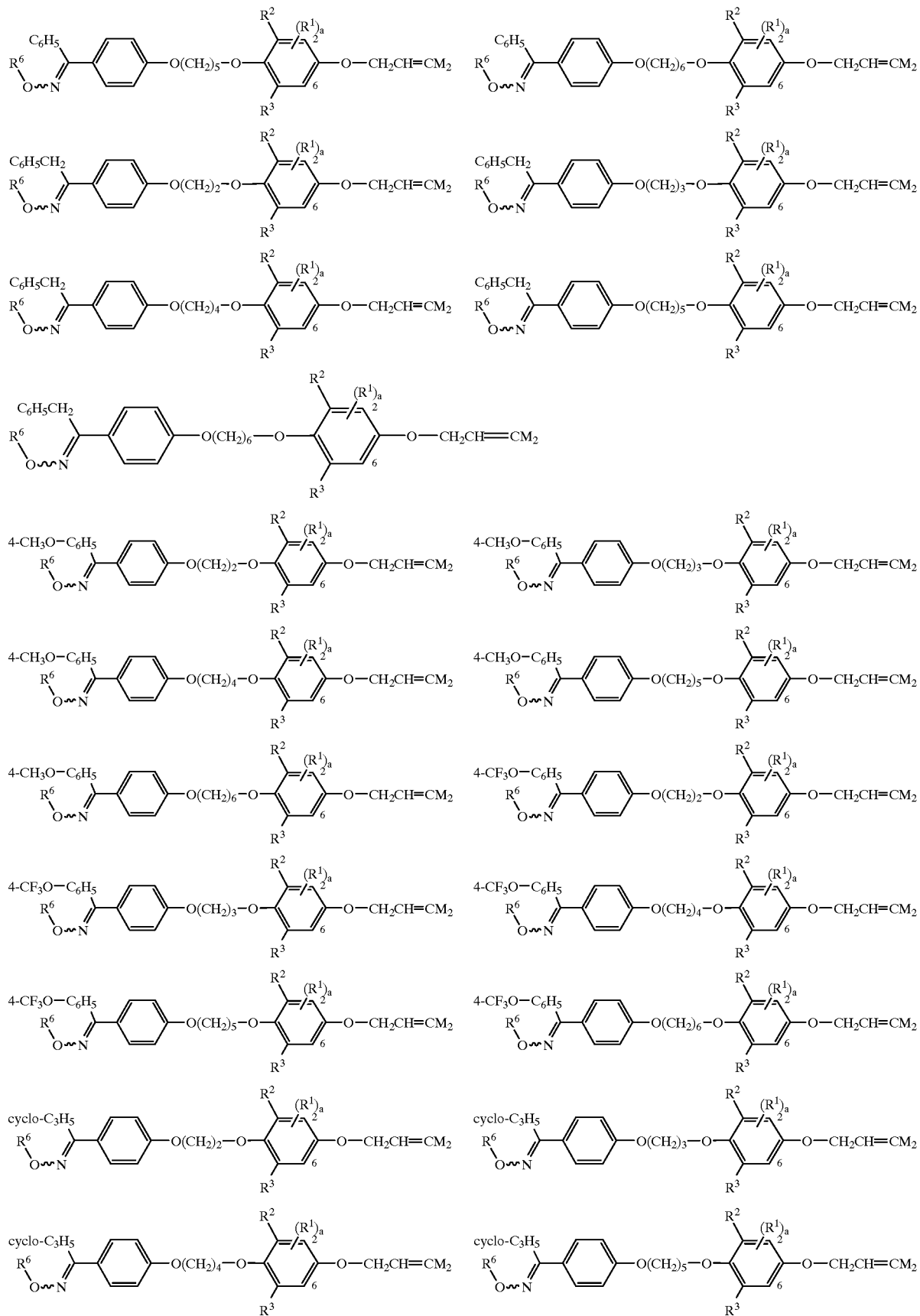

-continued
| 147 | 148 |
|---|---|
| 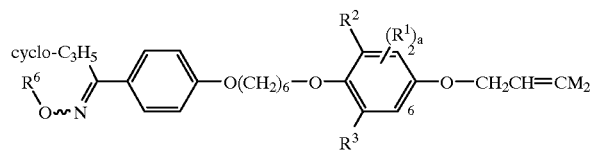 | 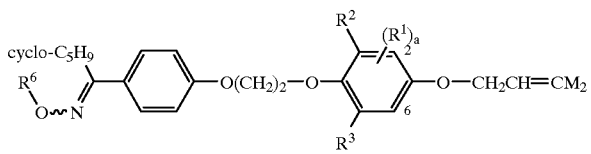 |
| 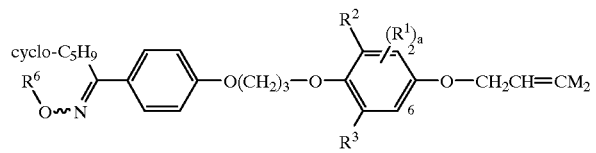 | 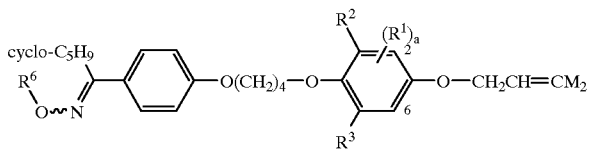 |
| 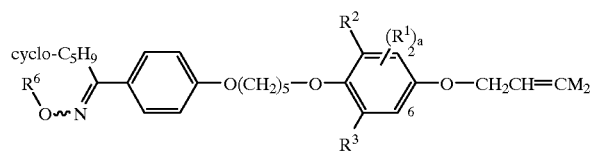 | 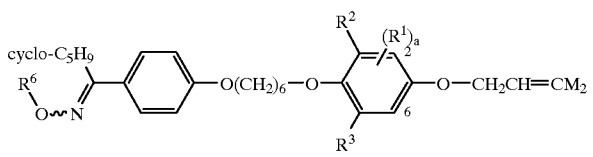 |
| 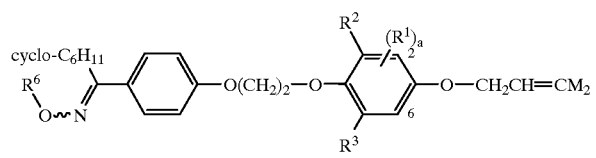 | 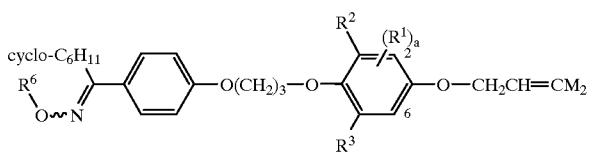 |
| 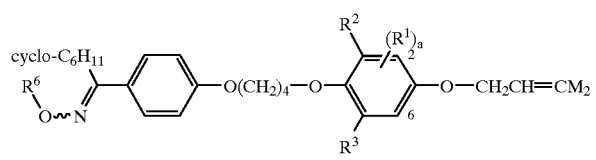 | 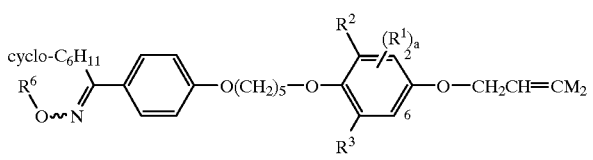 |
| 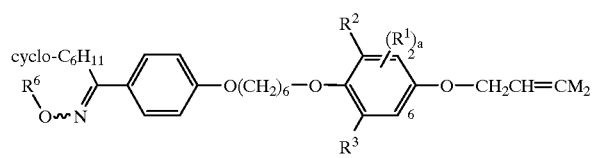 | |
| 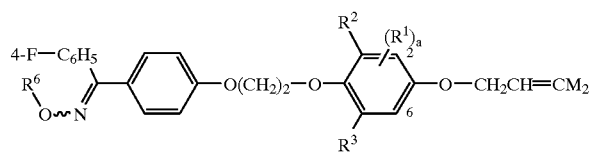 | 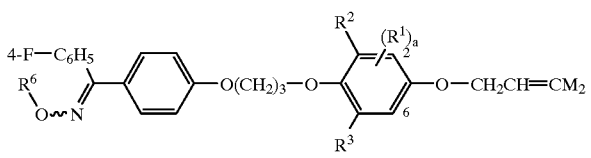 |
| 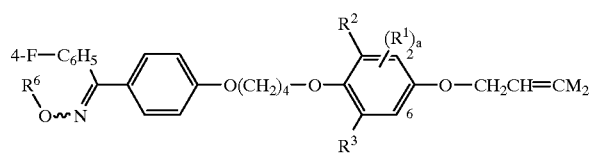 | 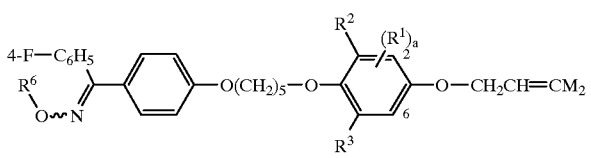 |
| 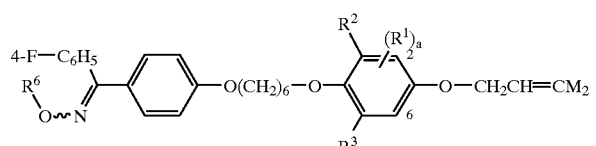 | 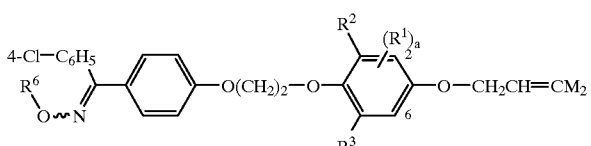 |
| 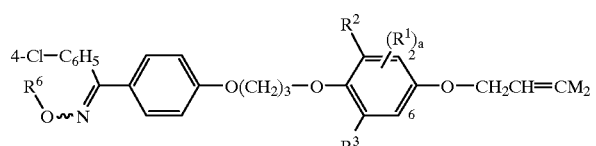 | 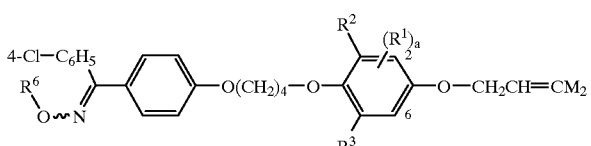 |
| 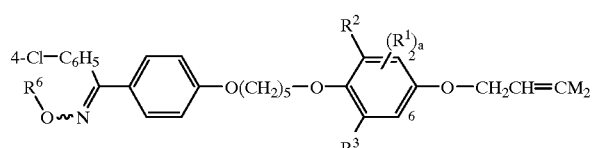 | 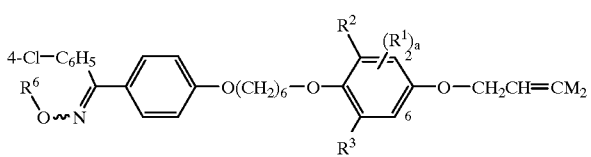 |

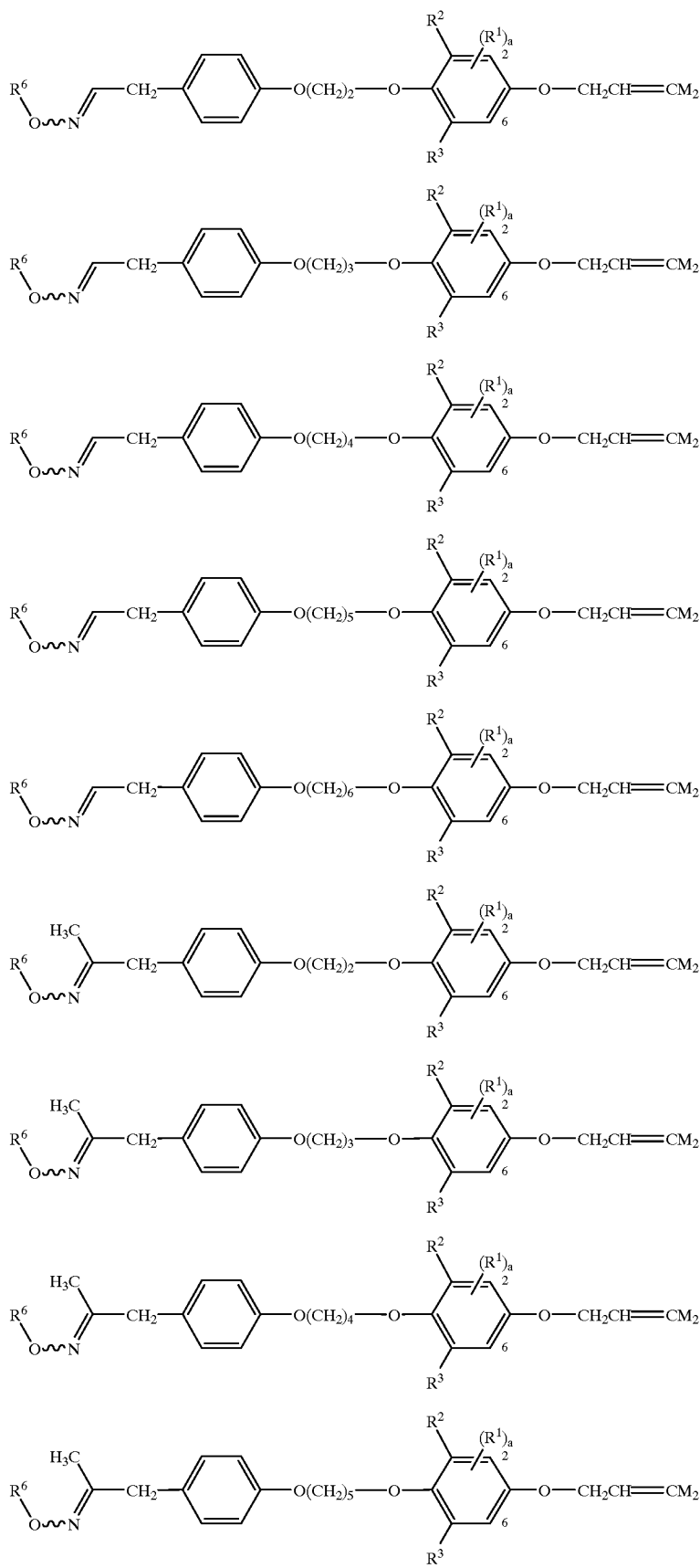

-continued
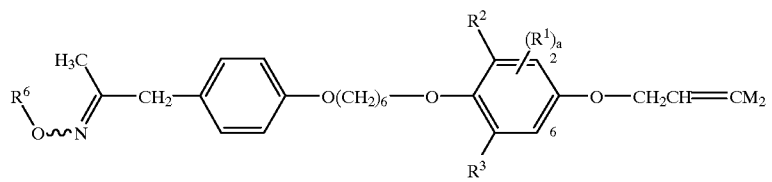
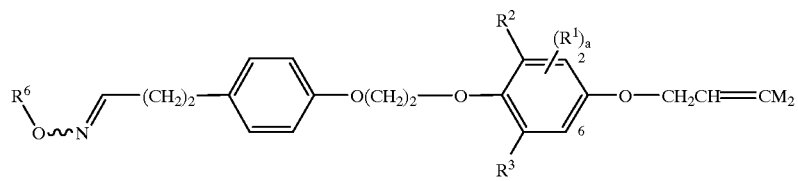
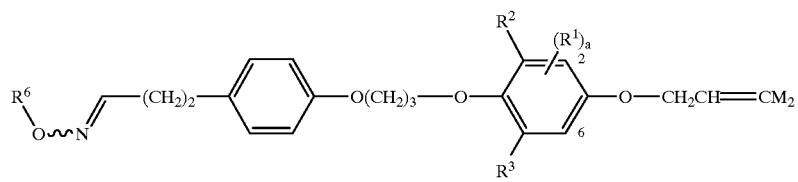
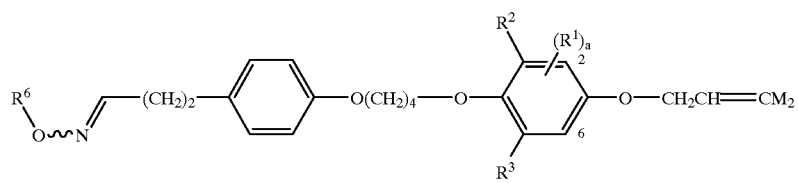
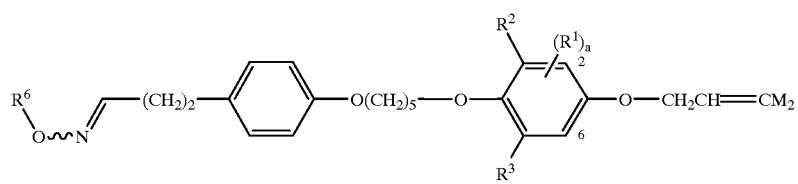
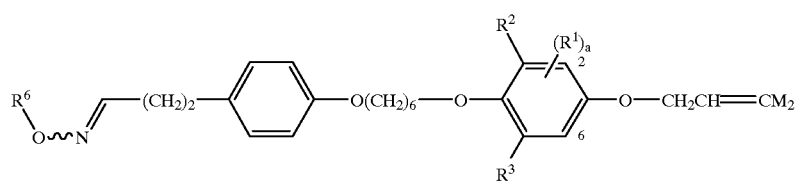
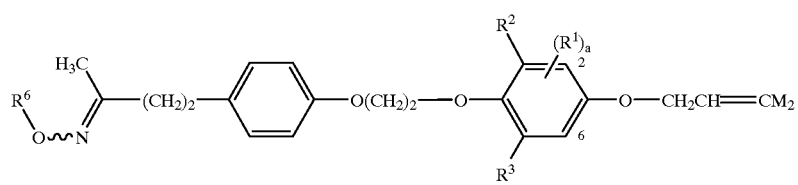
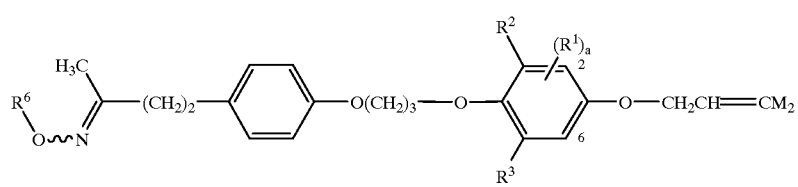
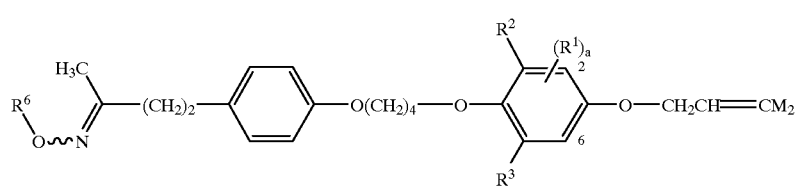

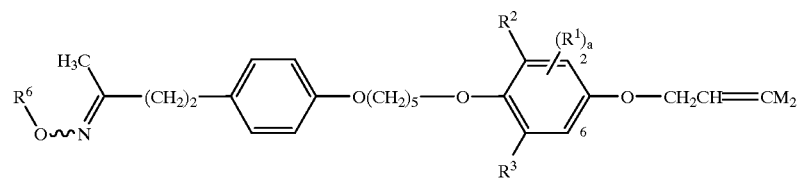
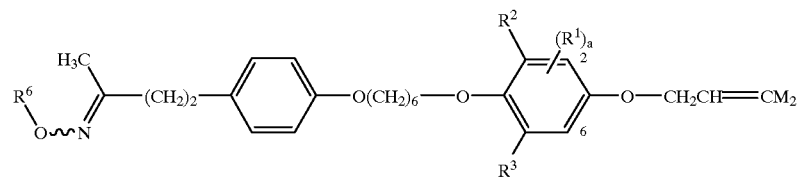
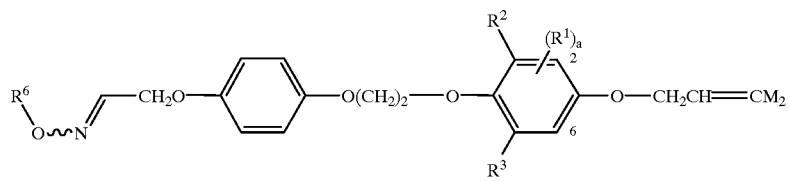
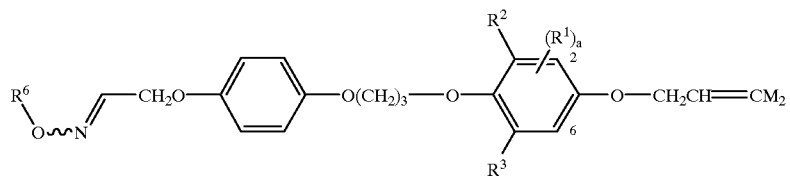
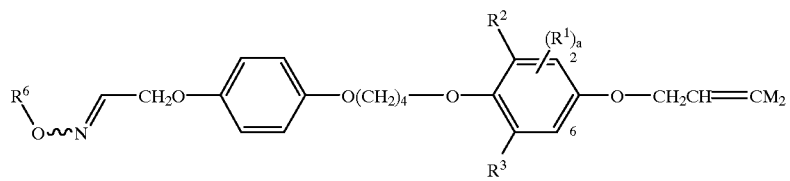
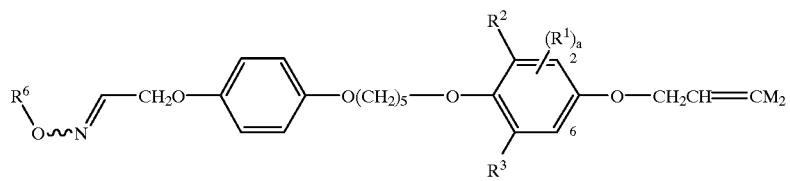
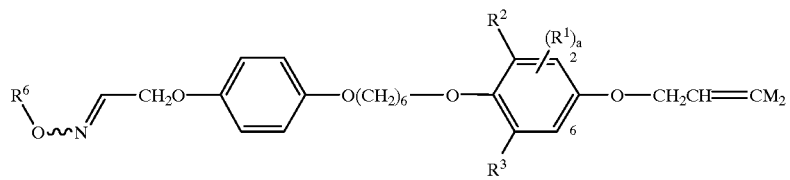
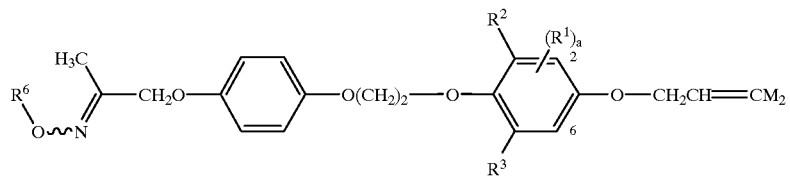
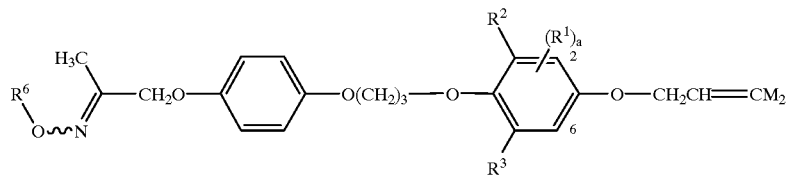

-continued
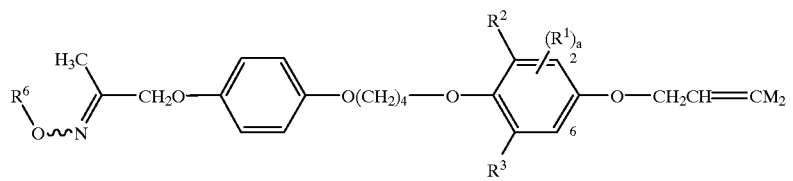
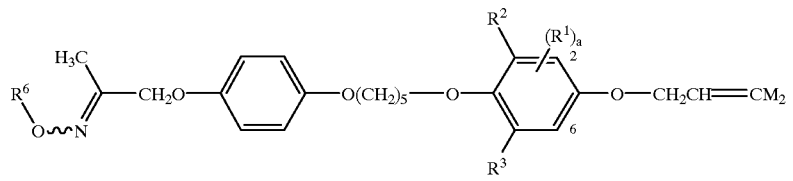
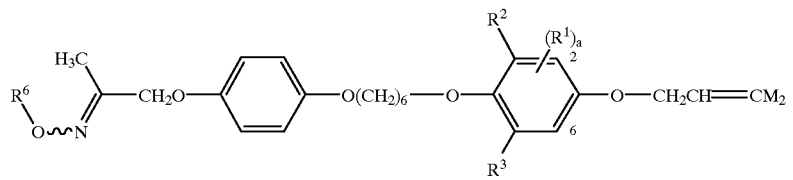
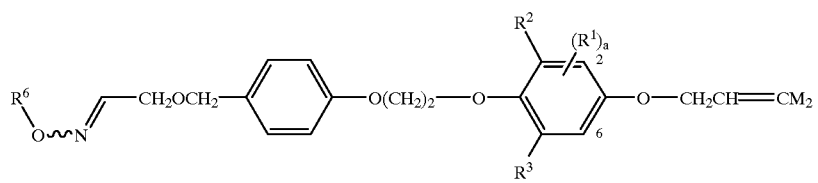
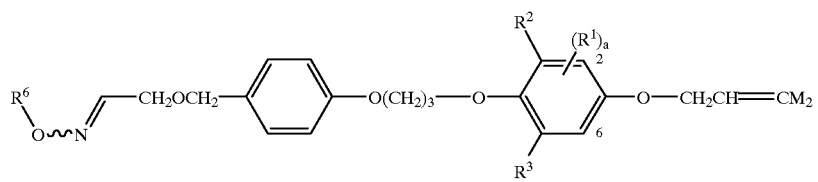
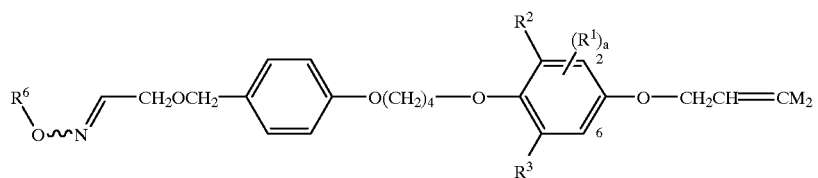
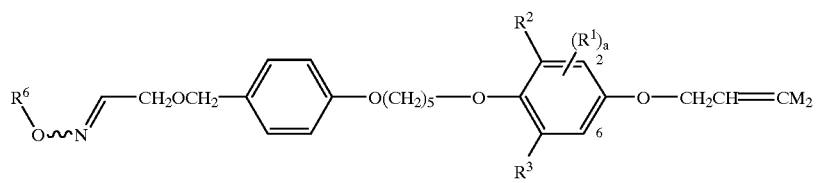
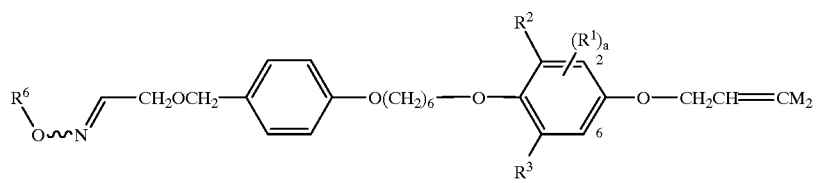
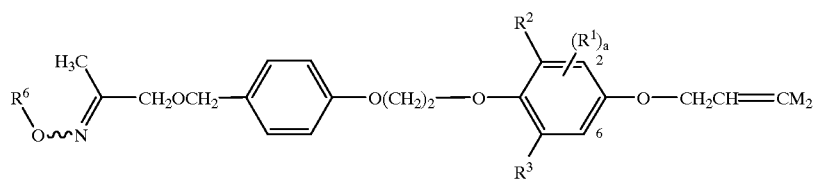

-continued
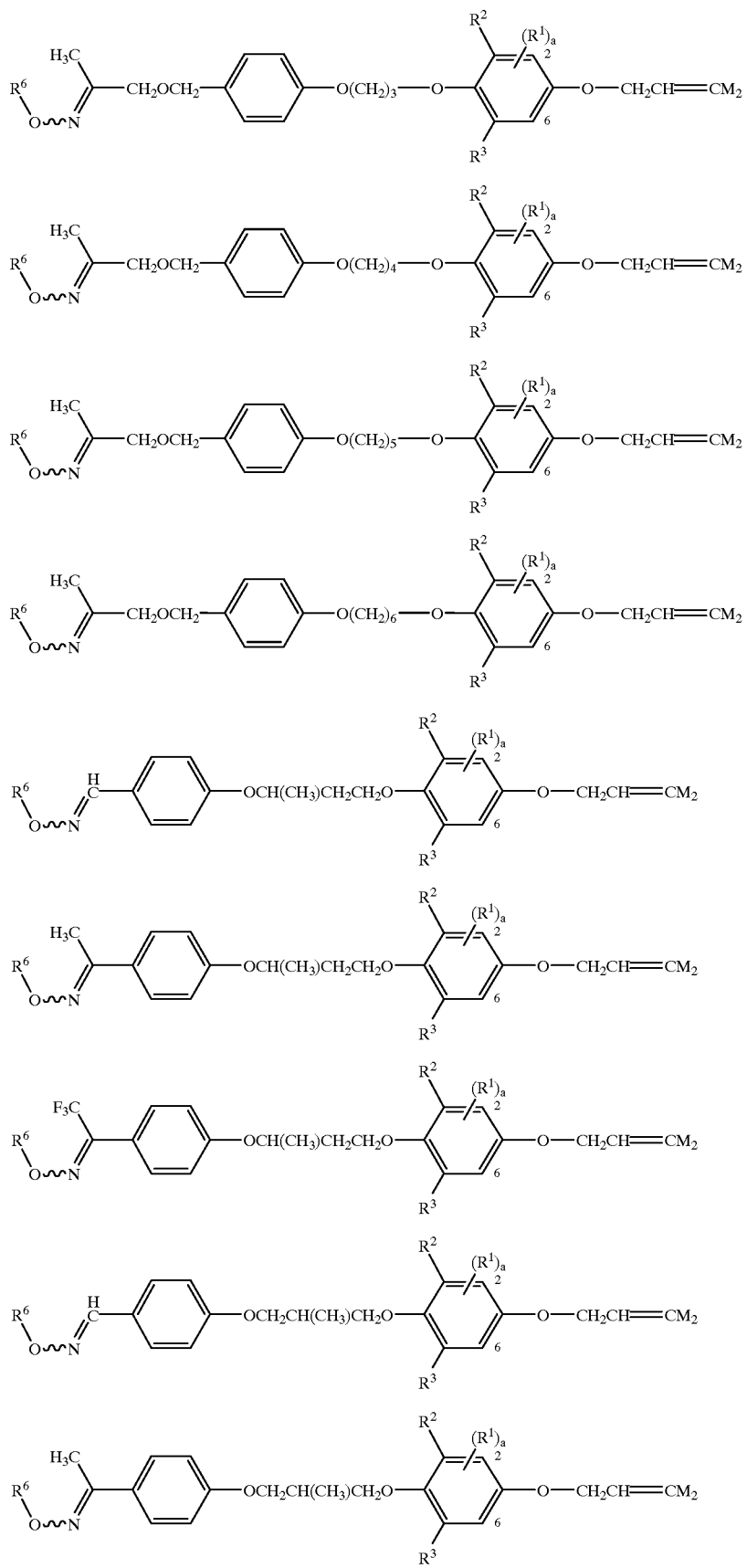

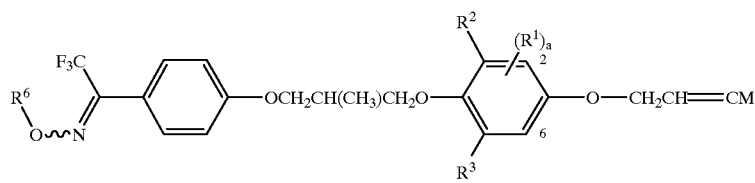
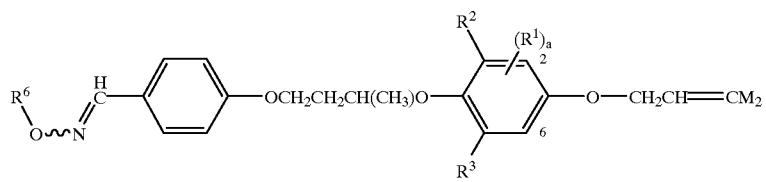
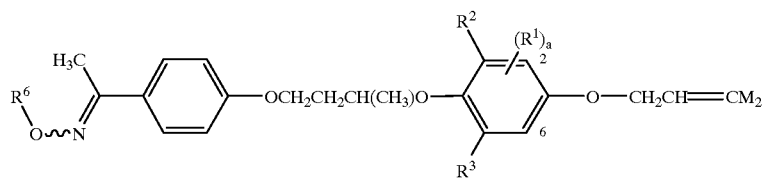
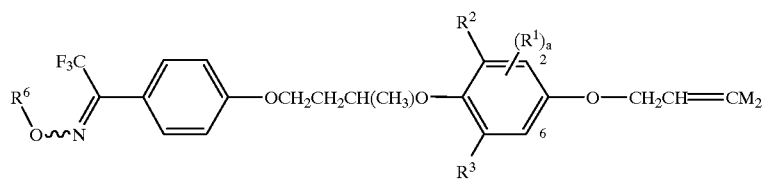
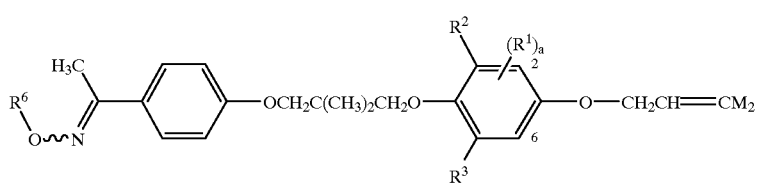
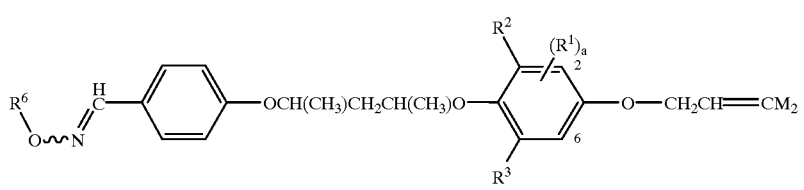
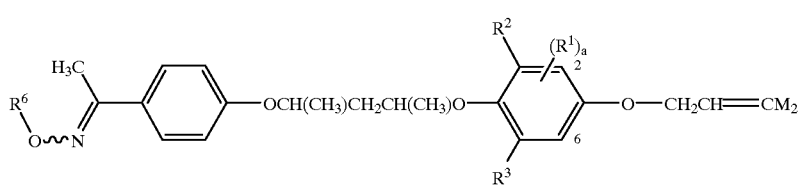

-continued
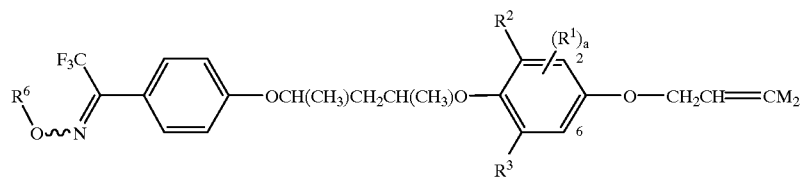
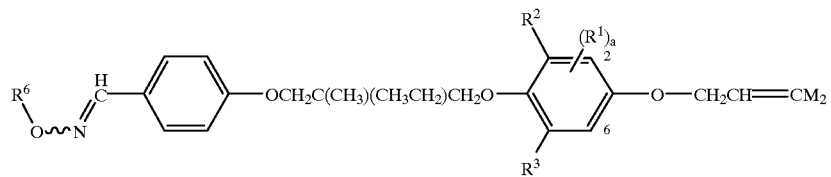
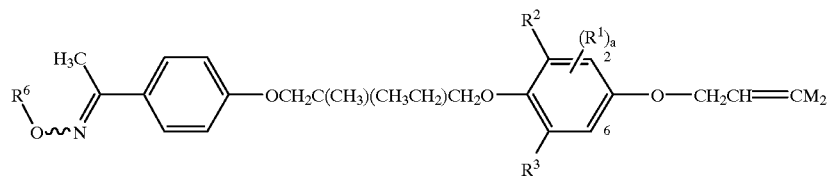
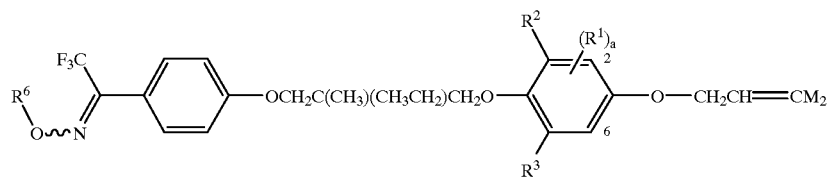
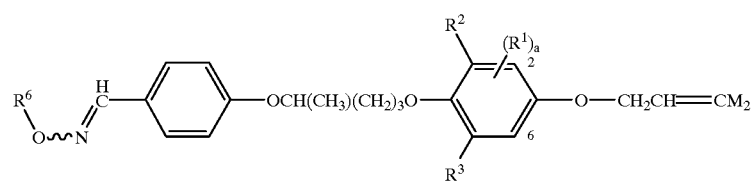
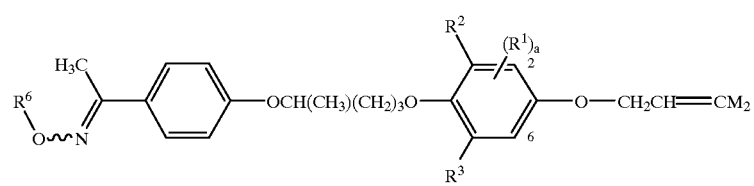
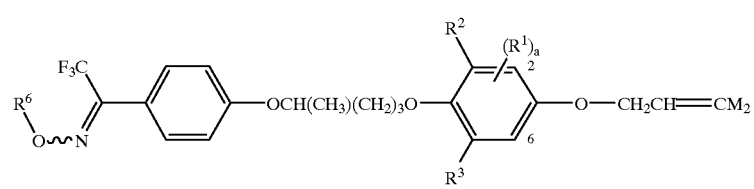
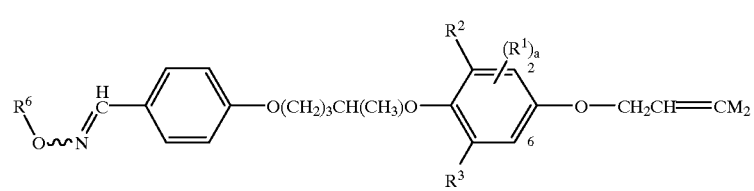
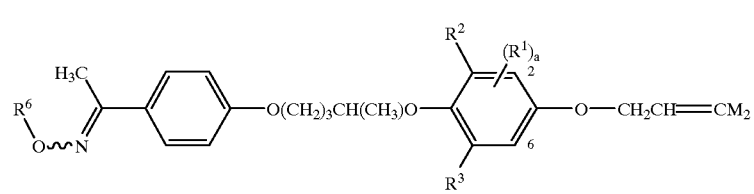

-continued
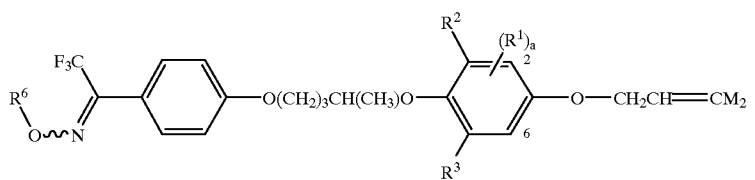
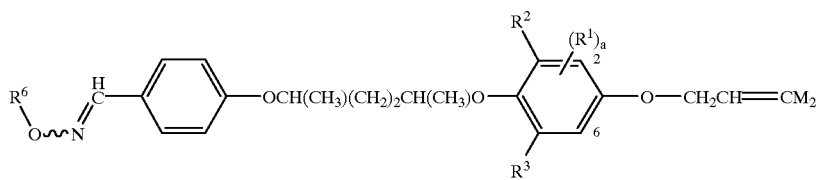
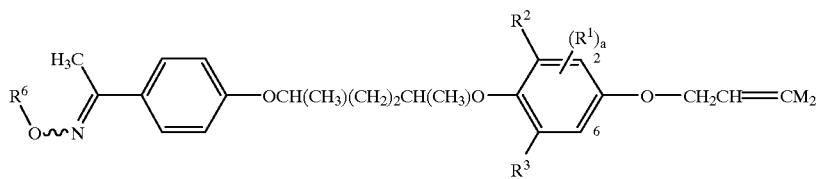
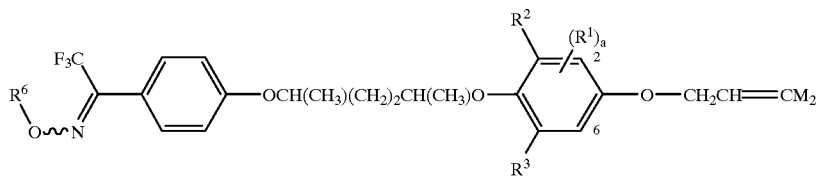
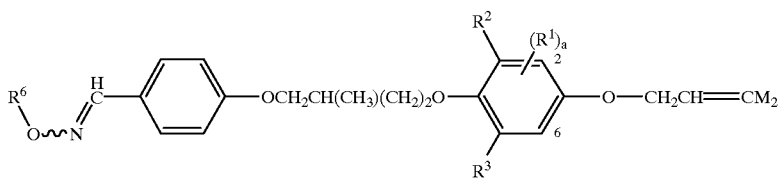
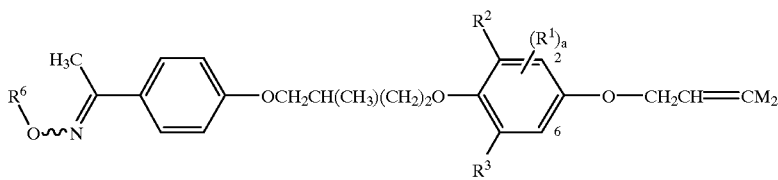
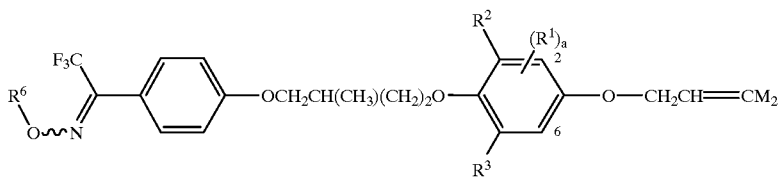
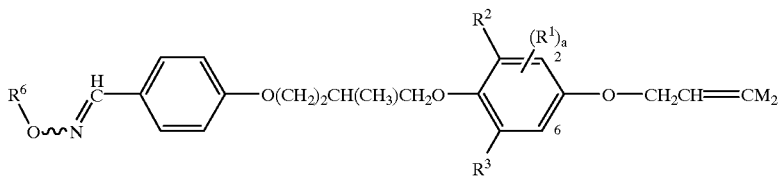
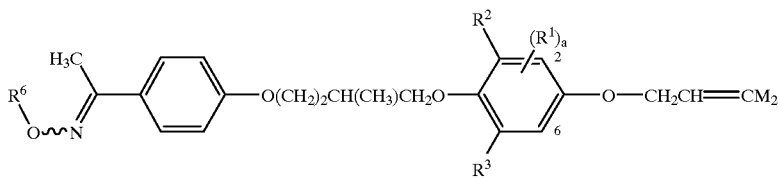

-continued
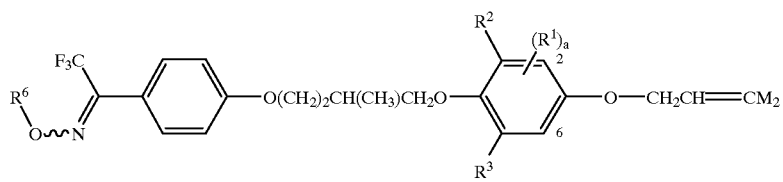
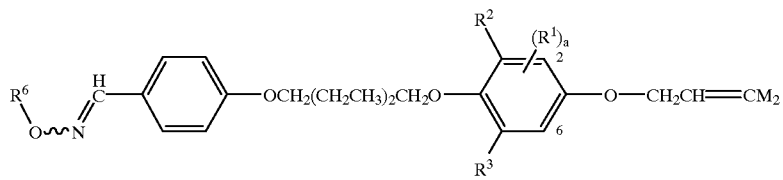
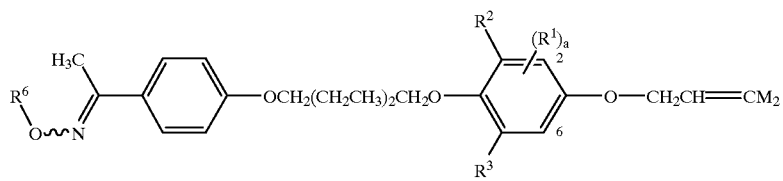
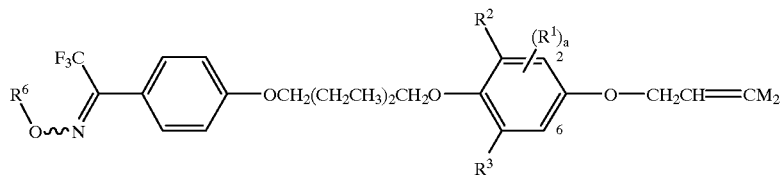
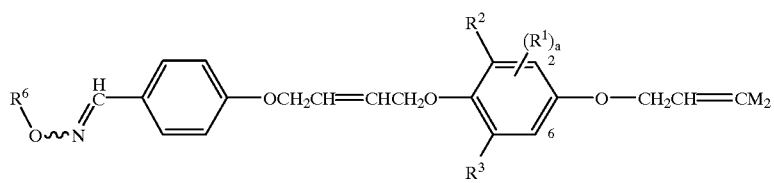
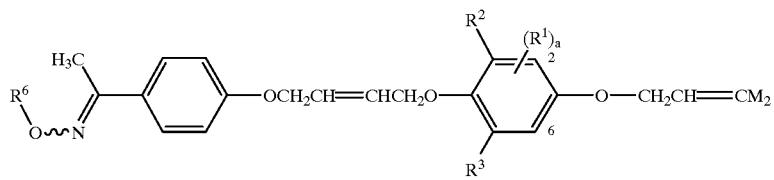
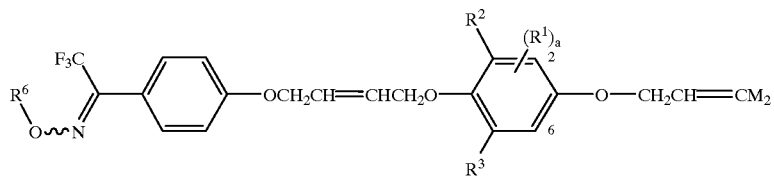
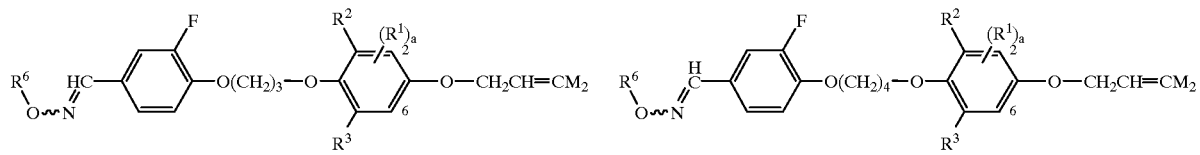
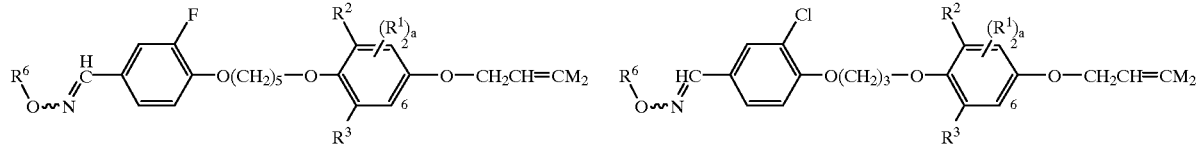

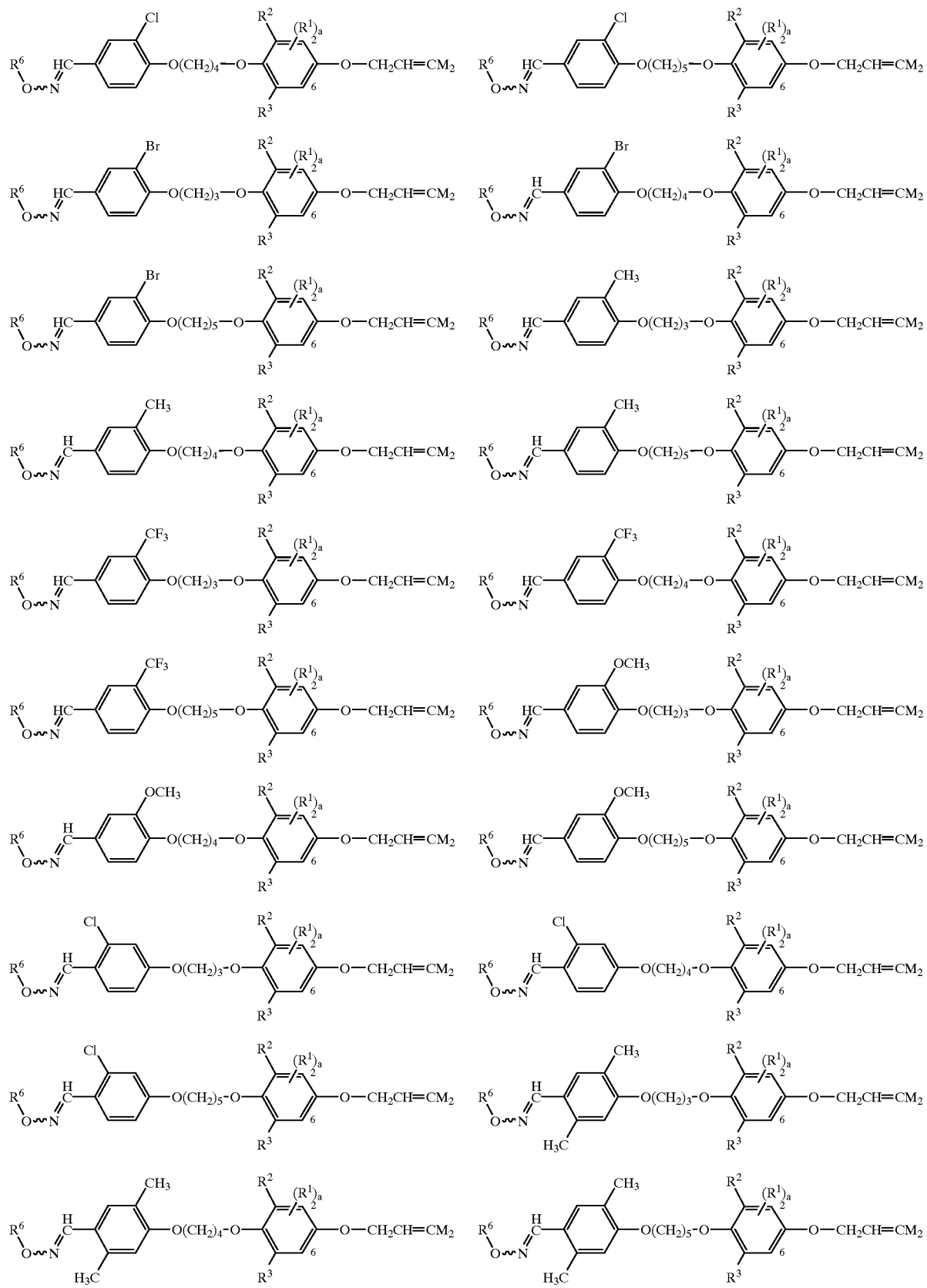

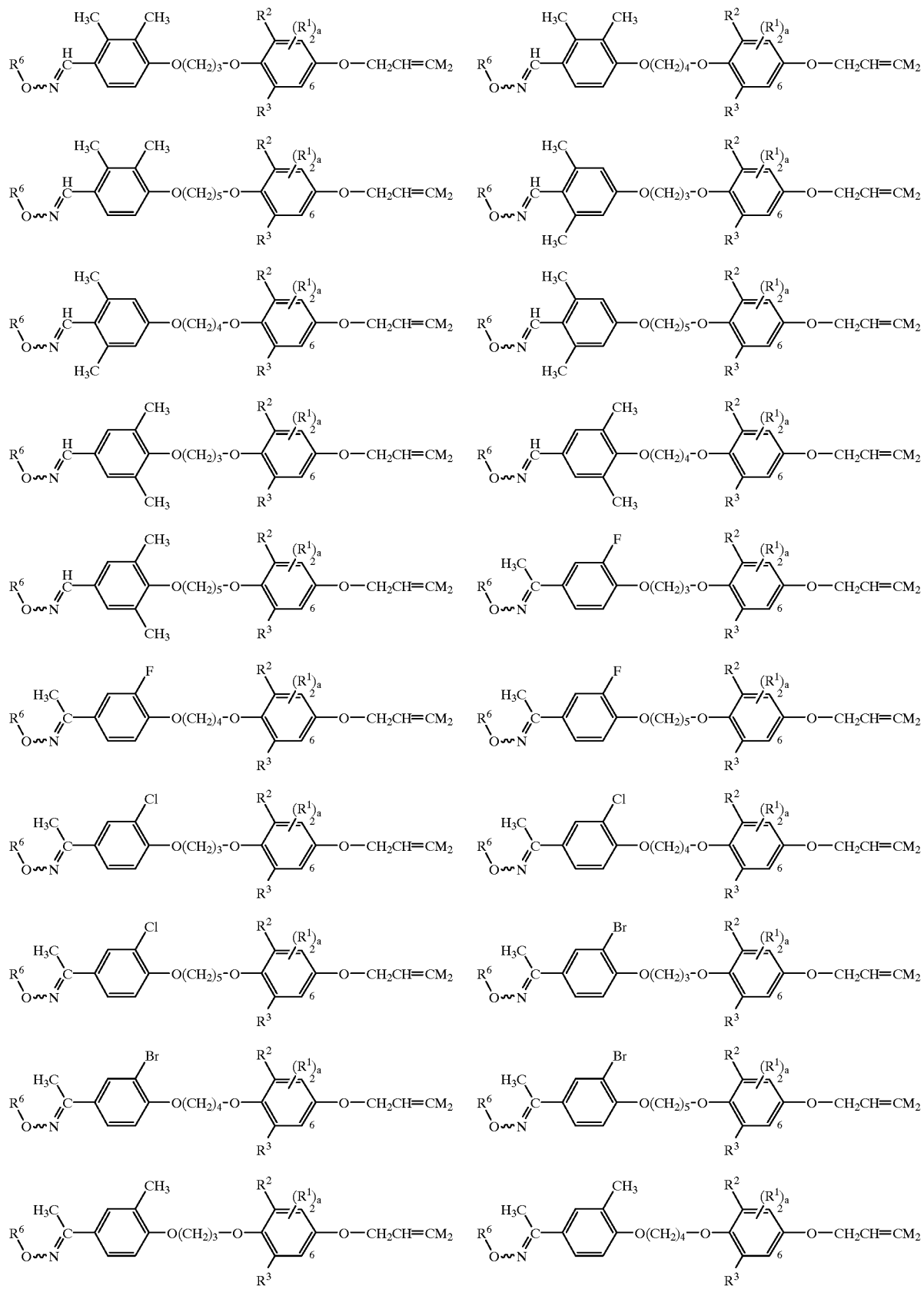

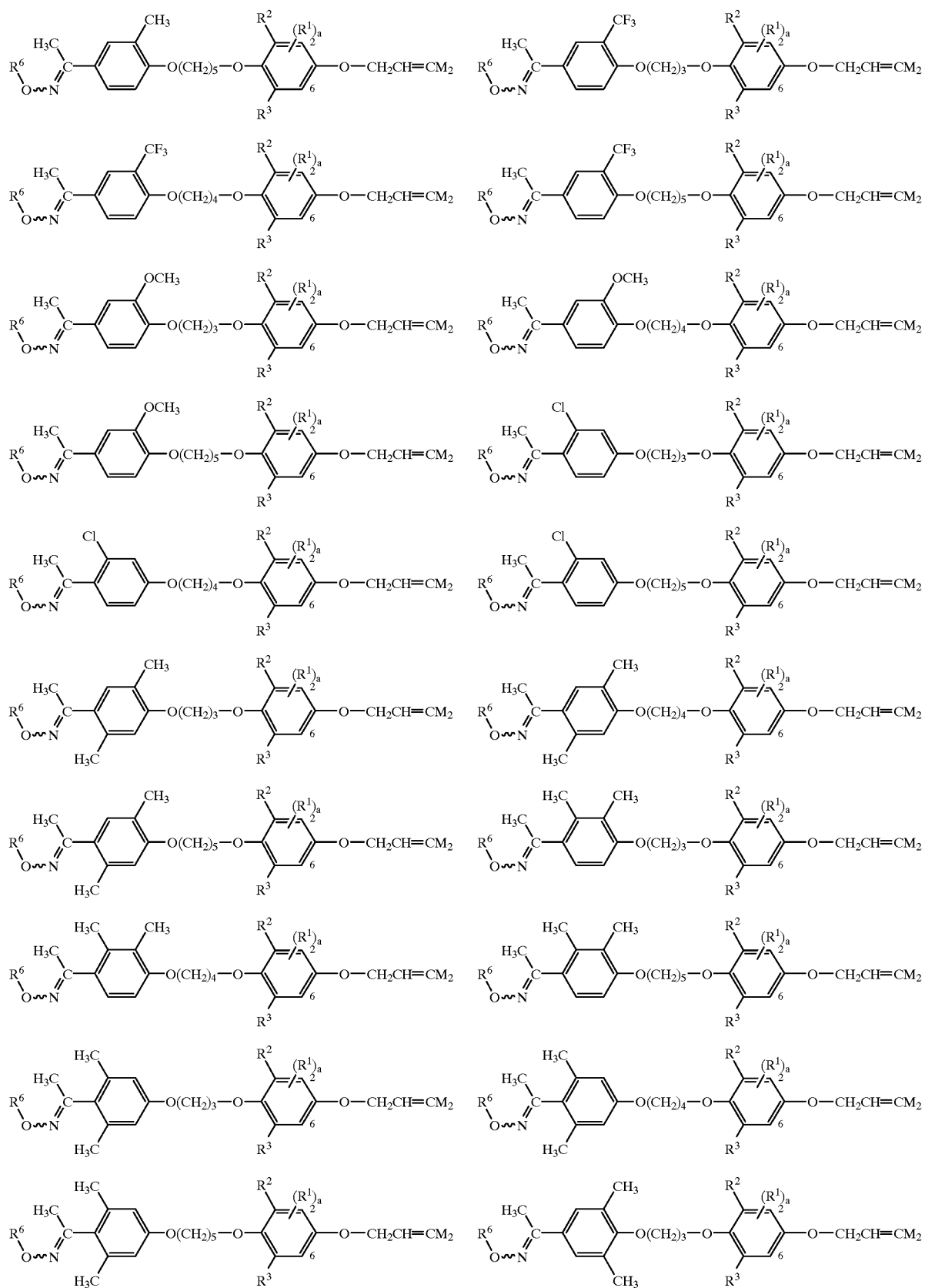

-continued
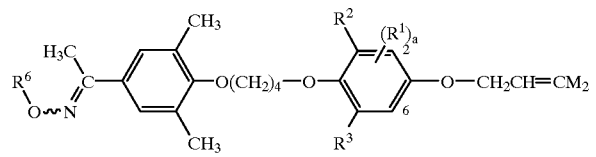
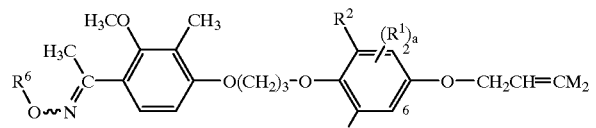
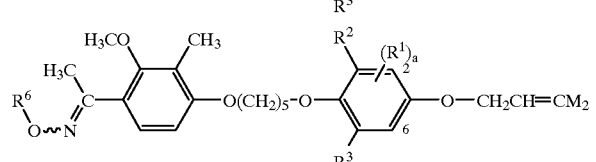
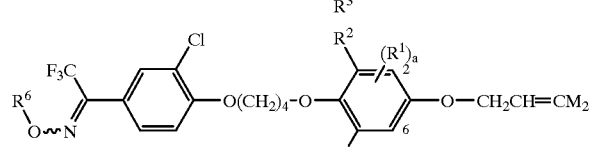
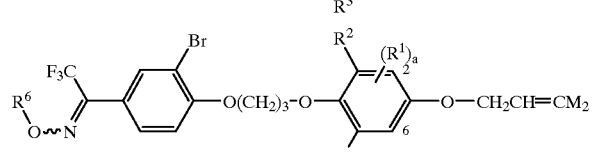
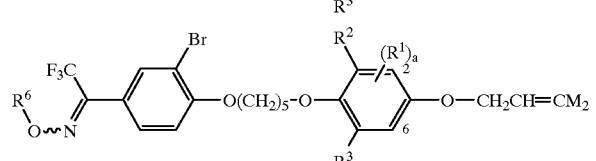
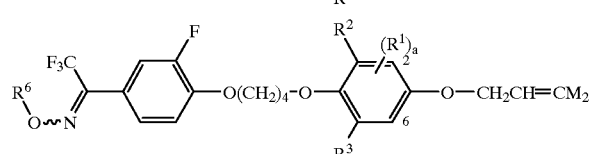
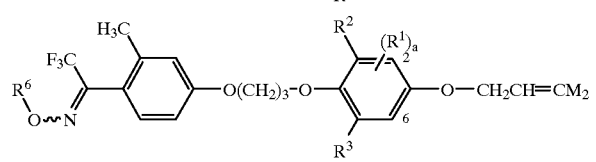
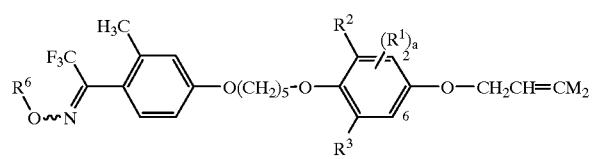
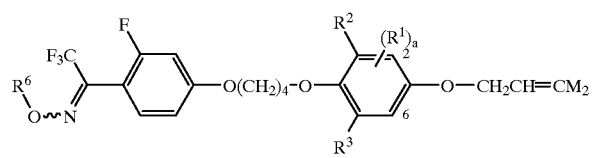
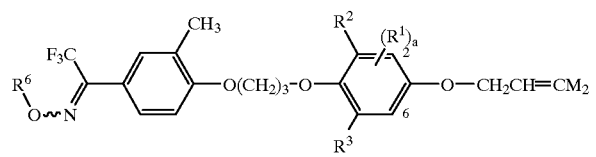
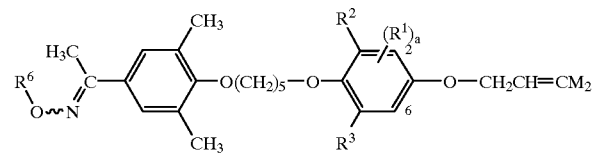
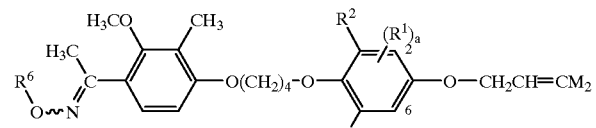
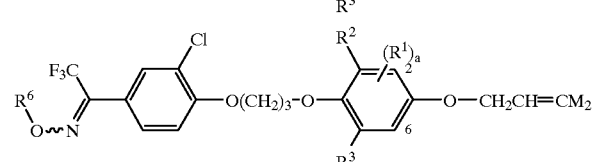
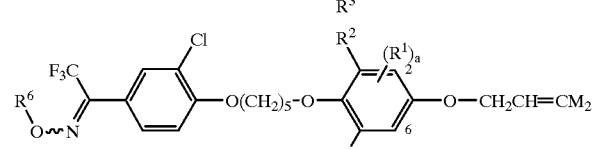
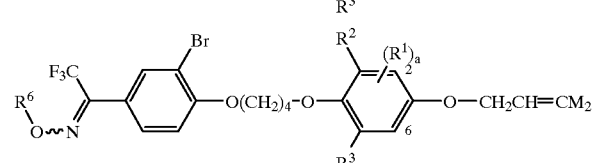
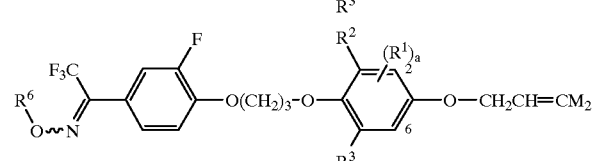
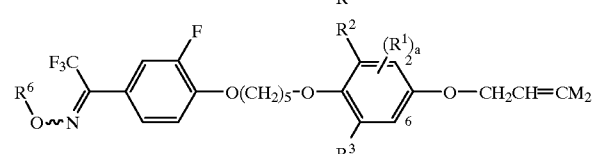
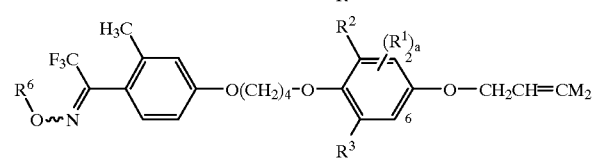
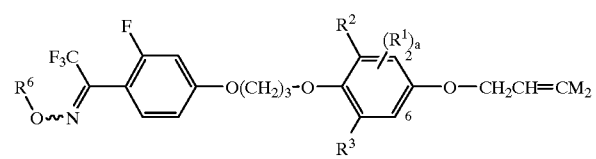
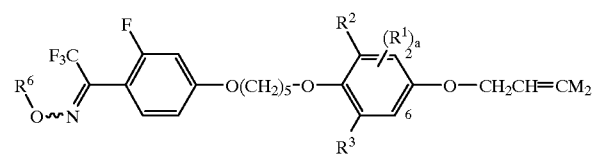
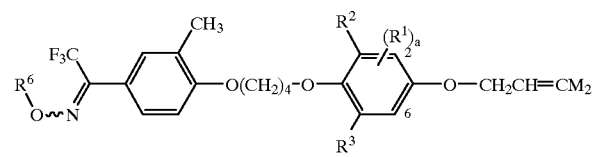

-continued
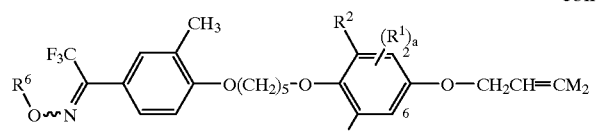
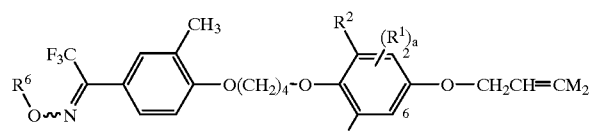
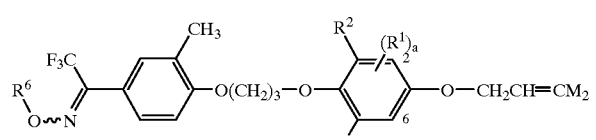
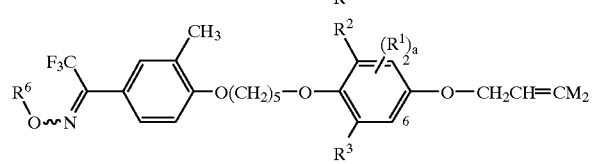
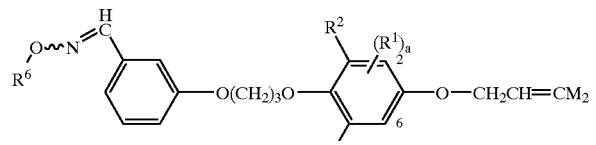
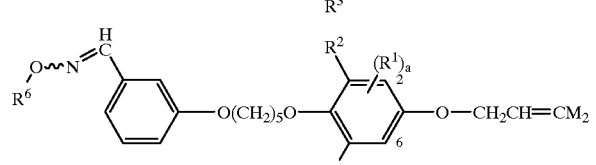
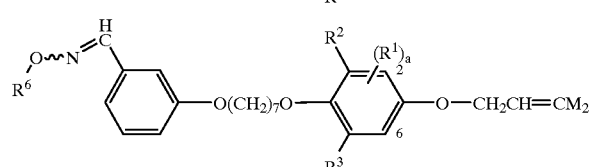
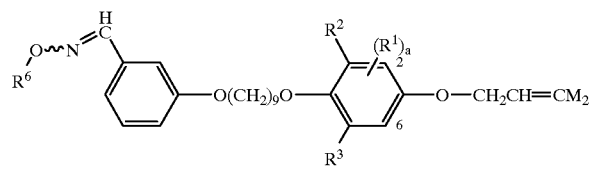
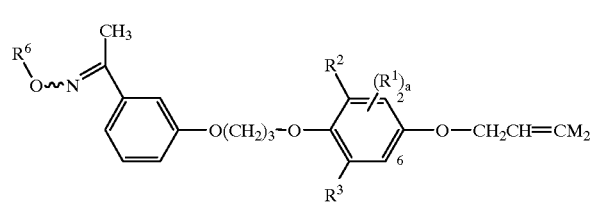
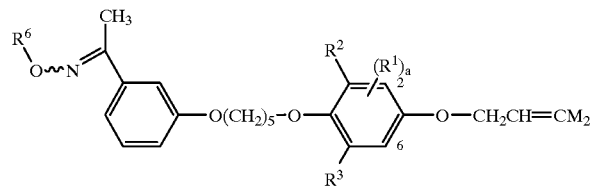
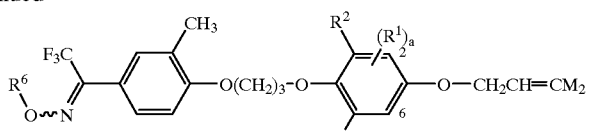
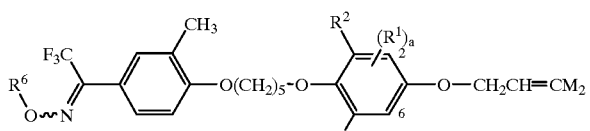
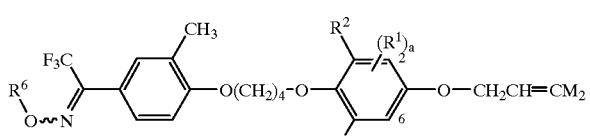
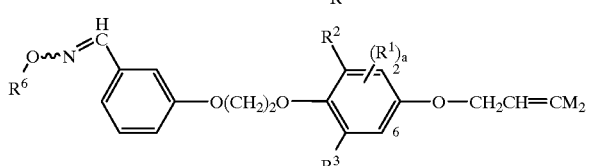
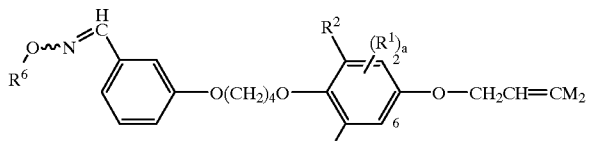
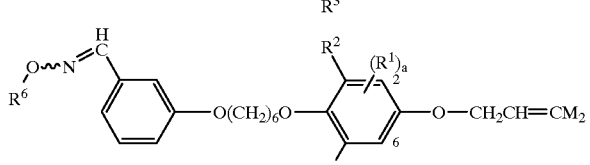
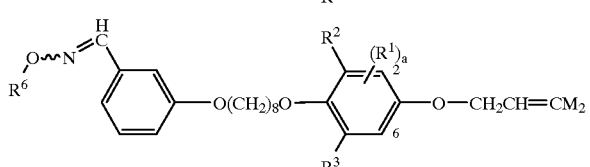
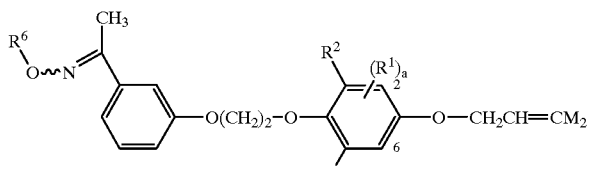
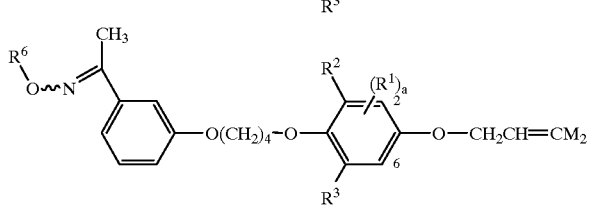
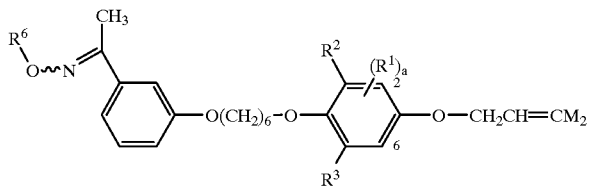

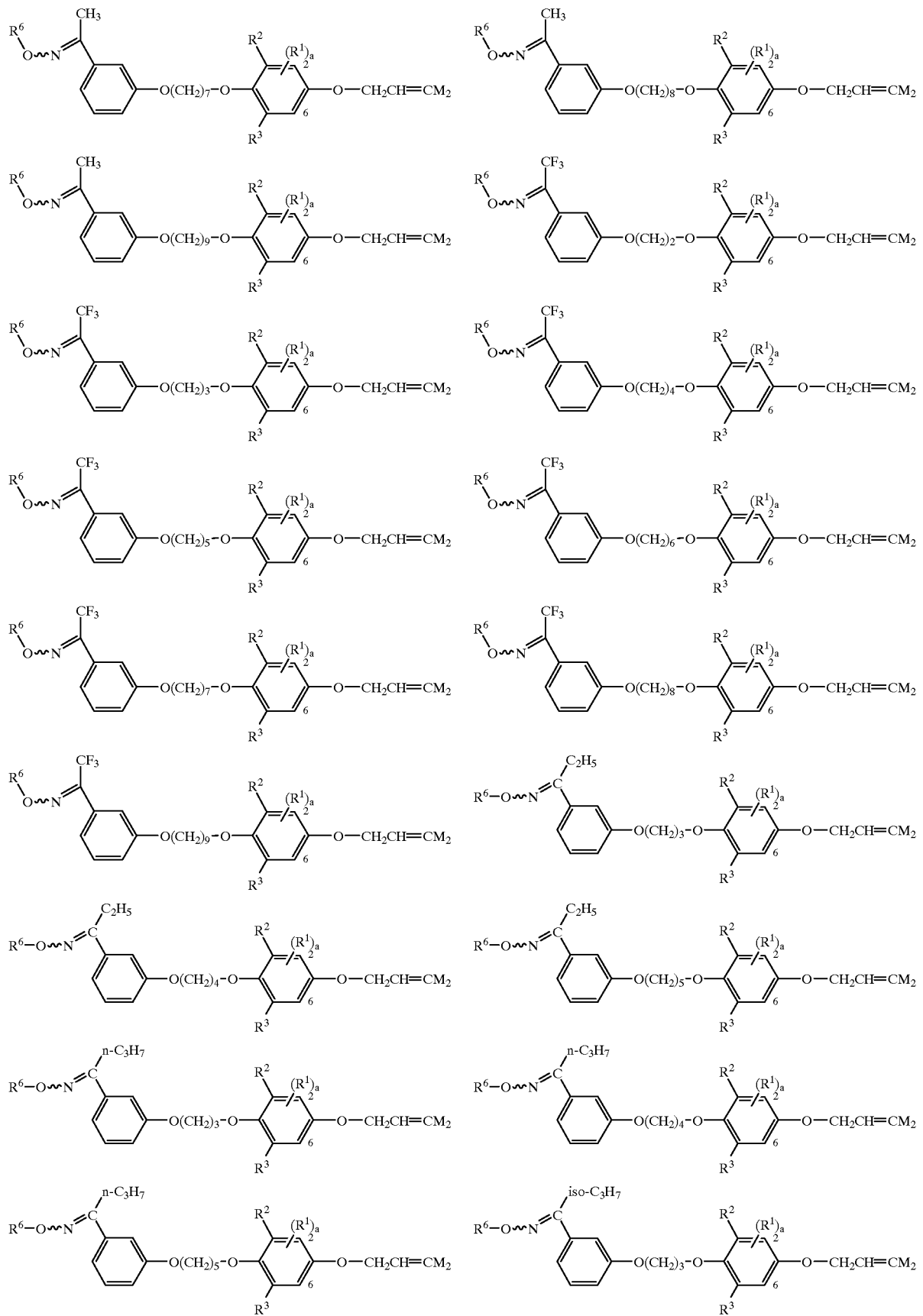

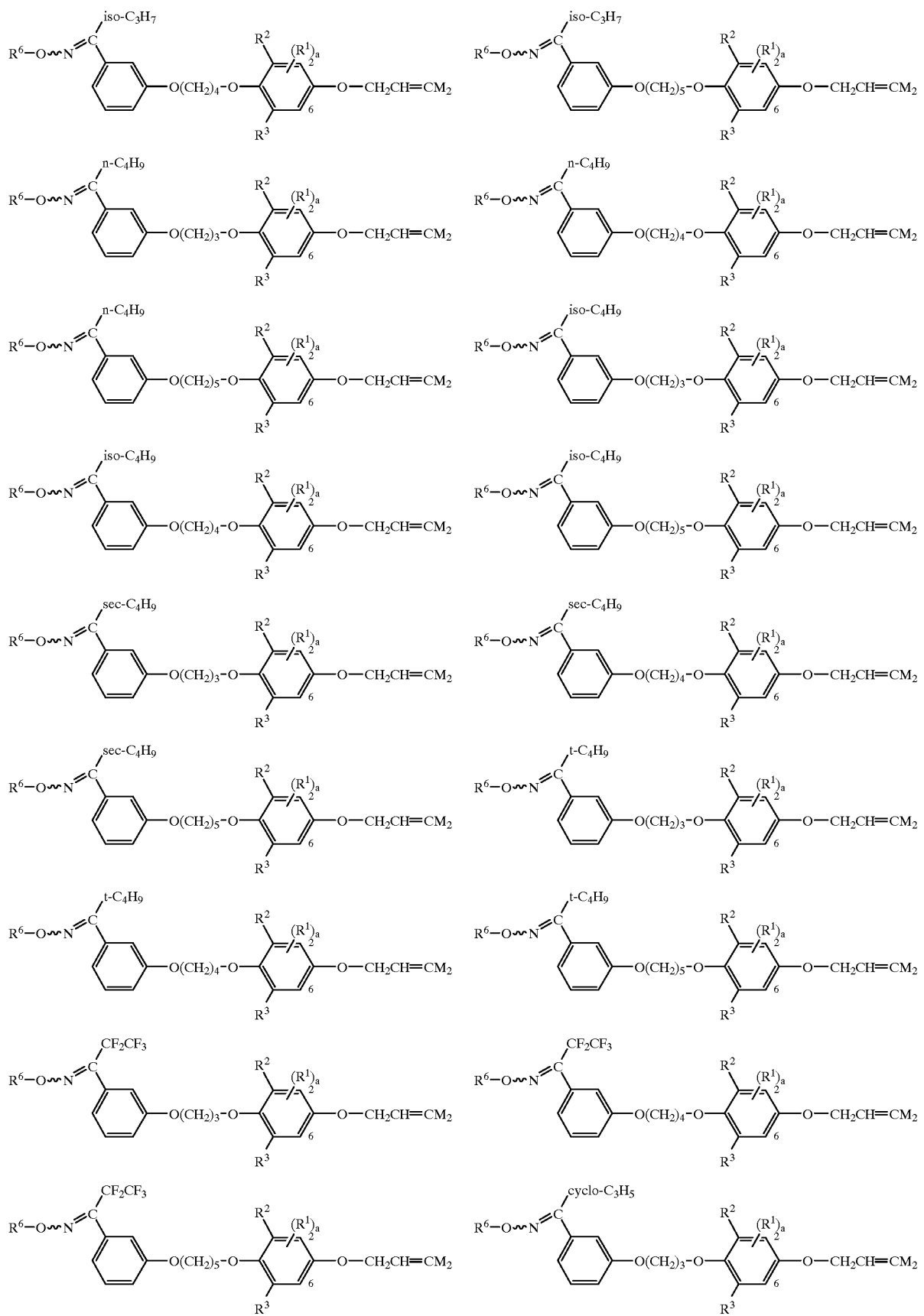

-continued
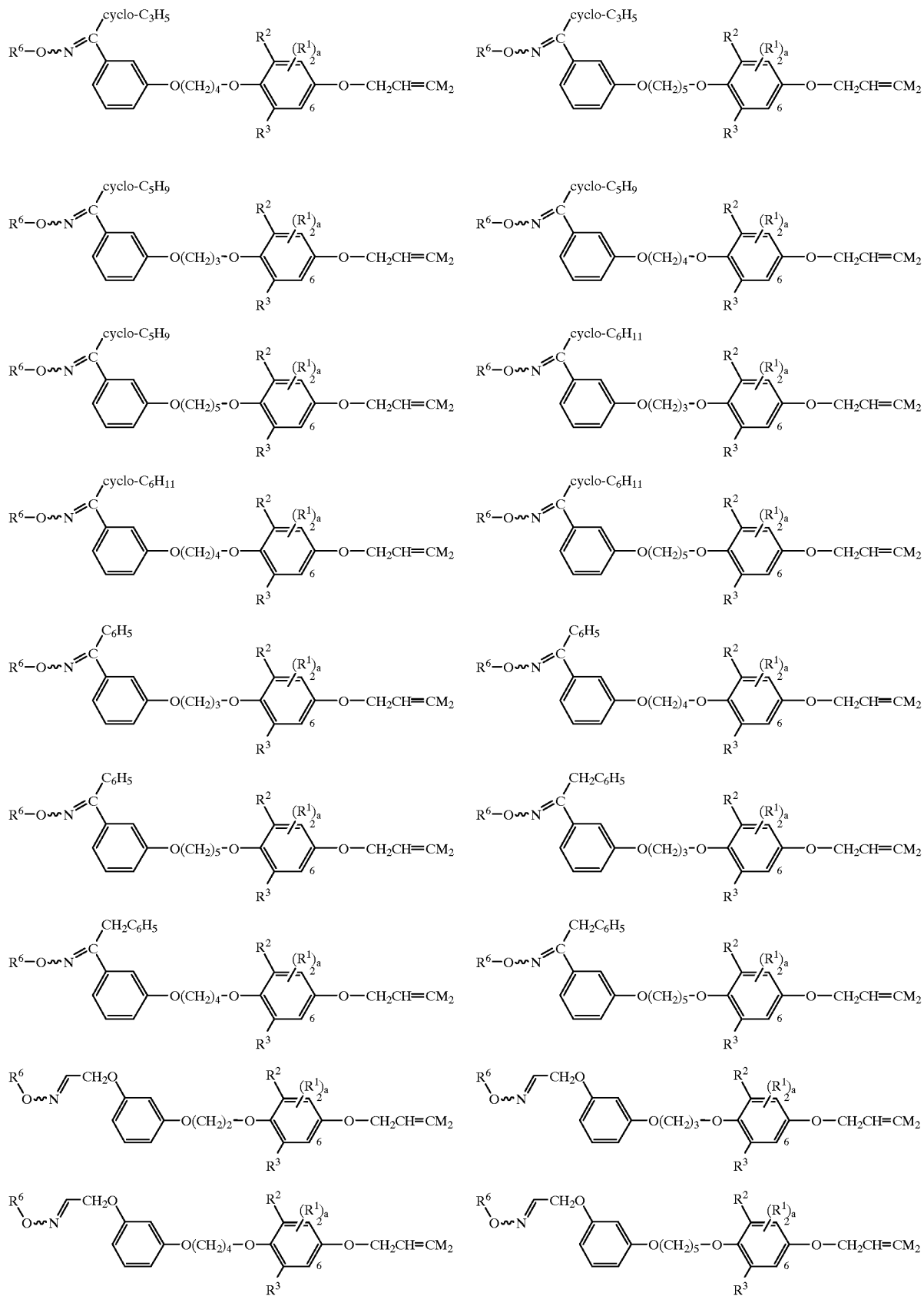

-continued
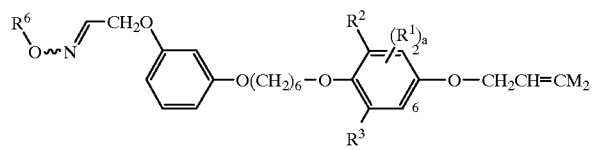
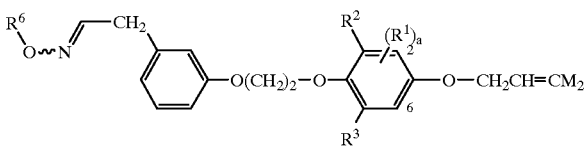
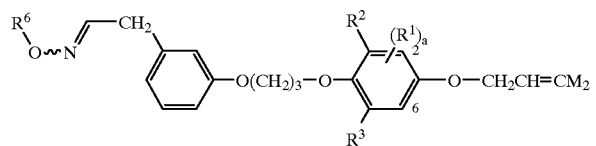
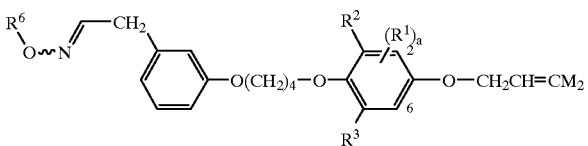
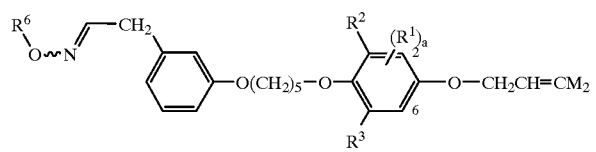
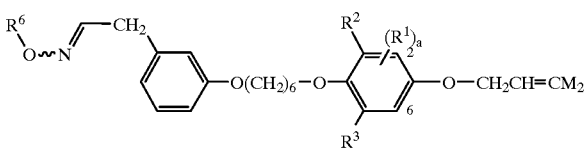
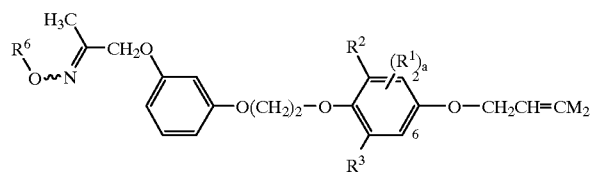
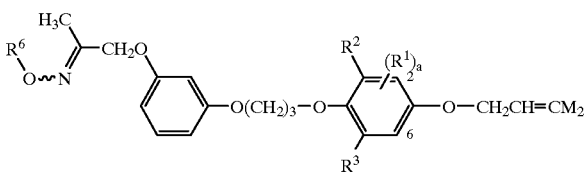
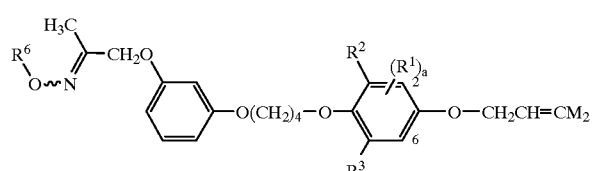
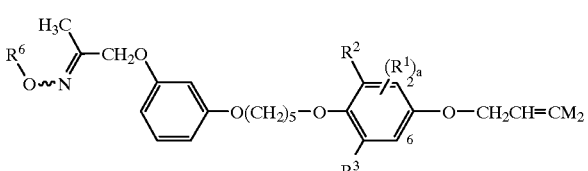
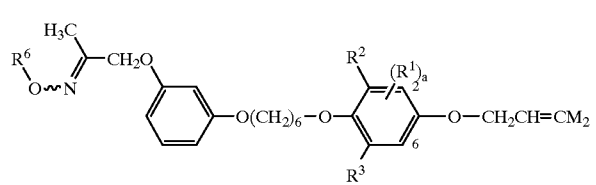
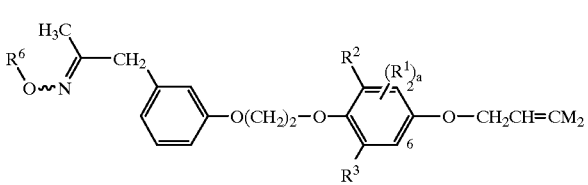
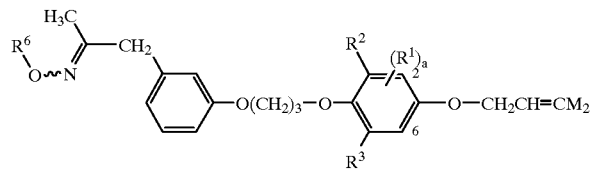
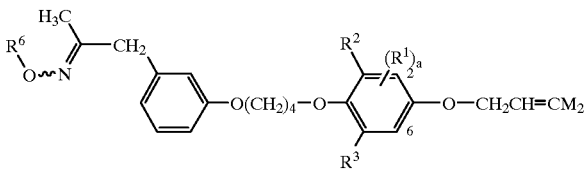
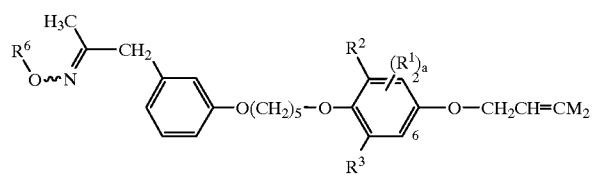
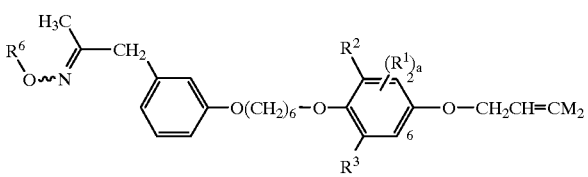
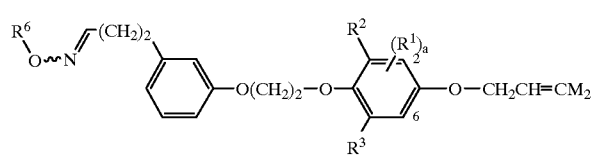
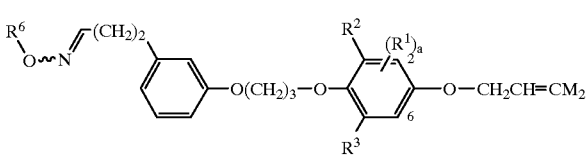
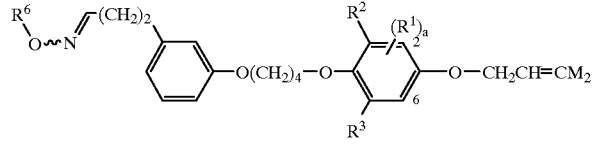
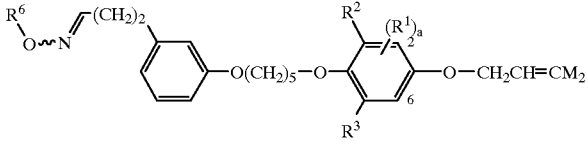

-continued
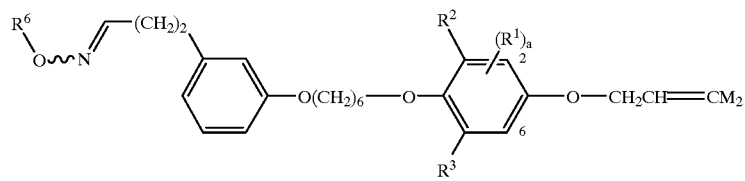
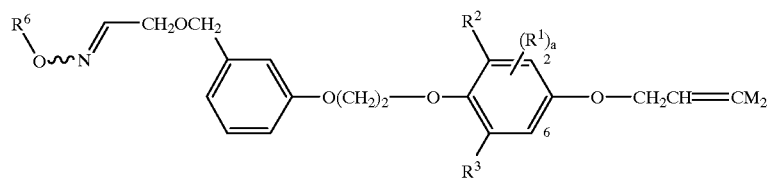
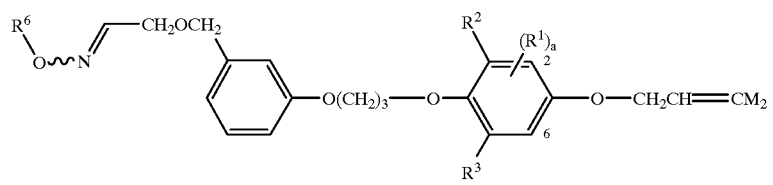
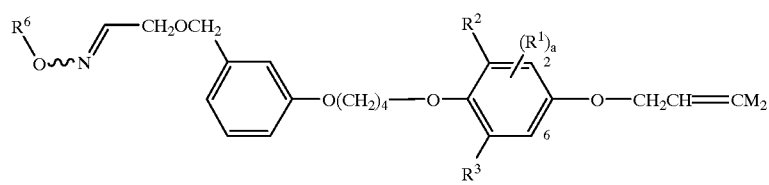
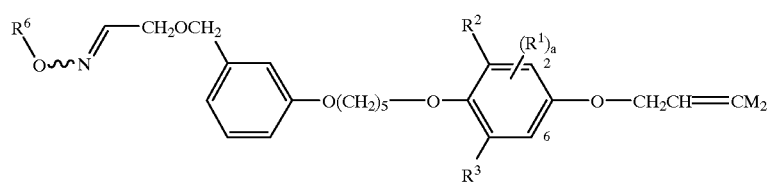
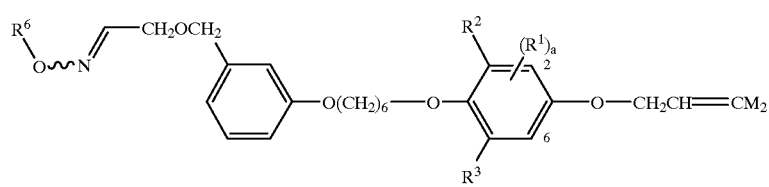
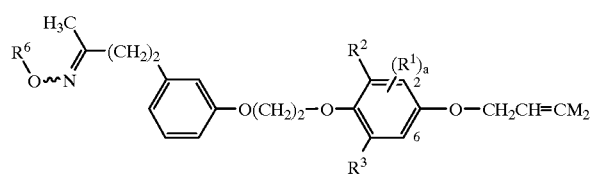
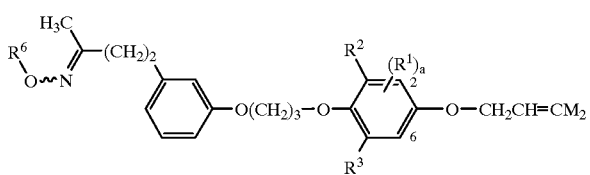
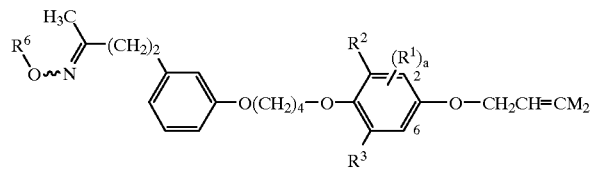
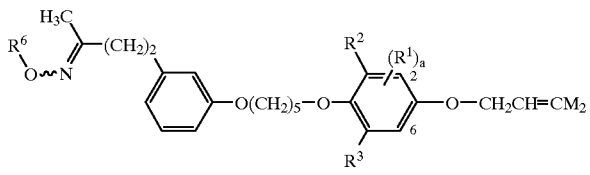
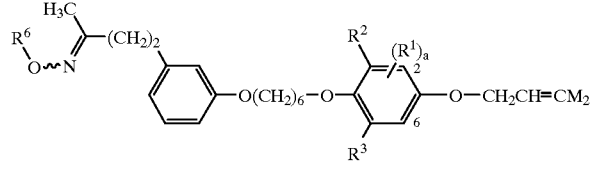

-continued
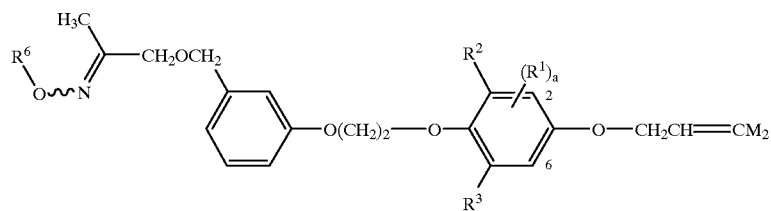
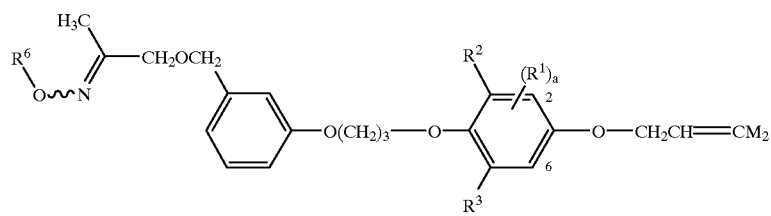
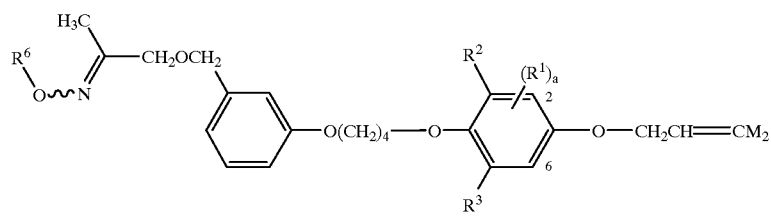
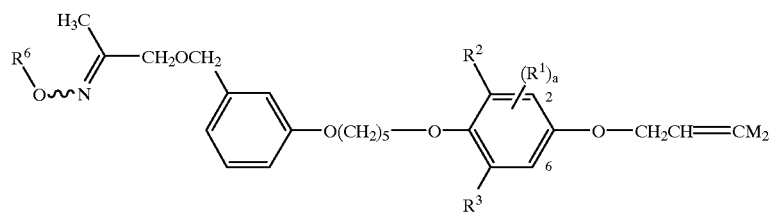
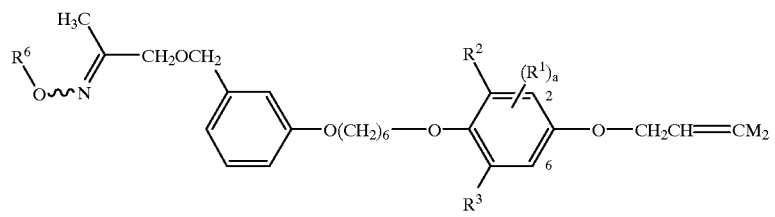
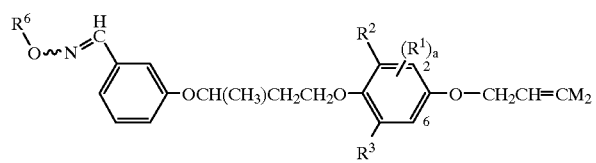
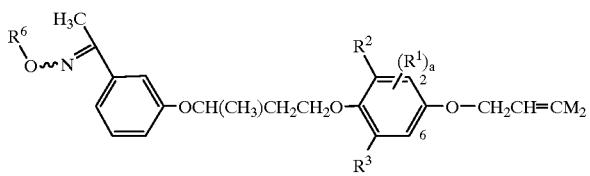
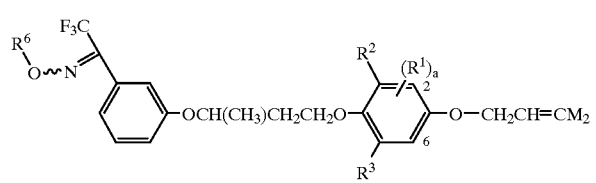
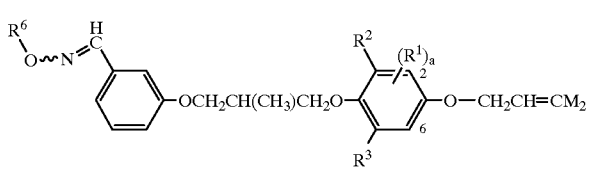
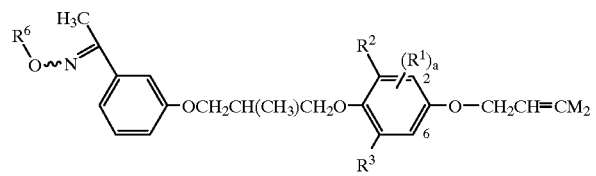
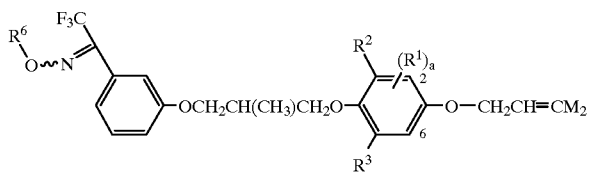

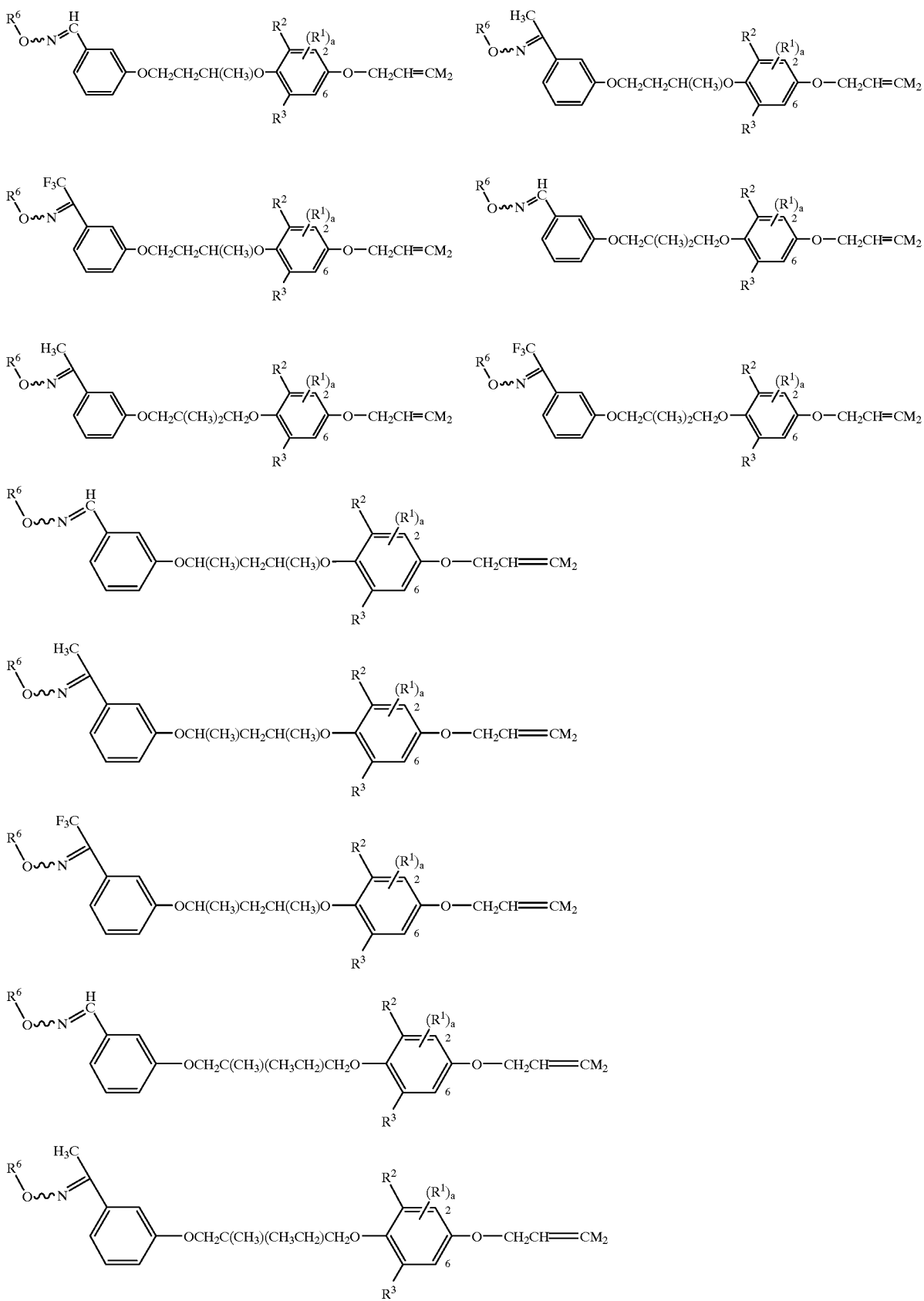

-continued
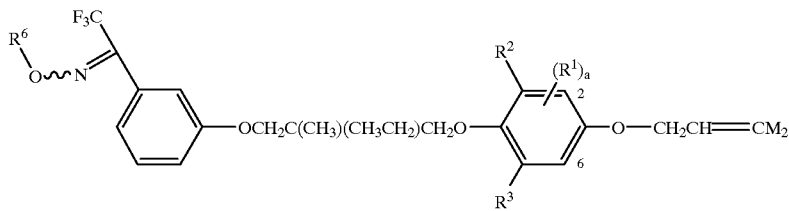
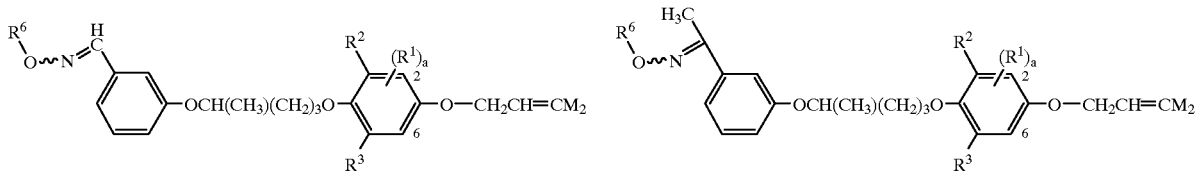
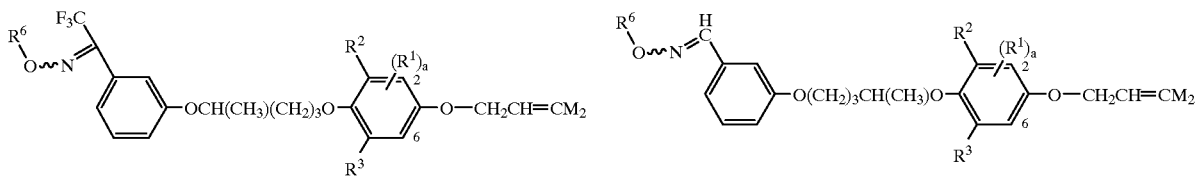
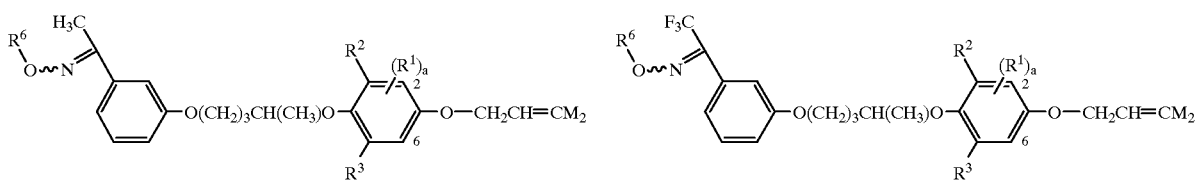
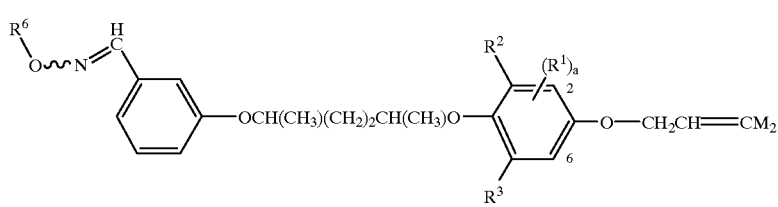
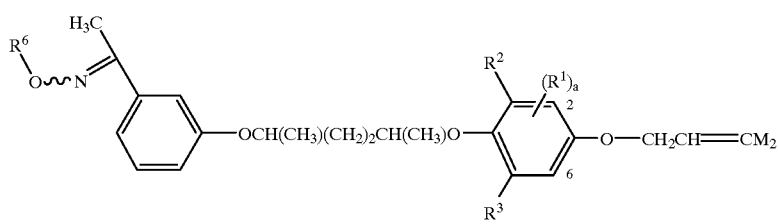
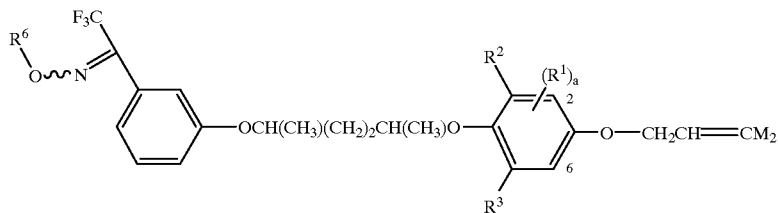
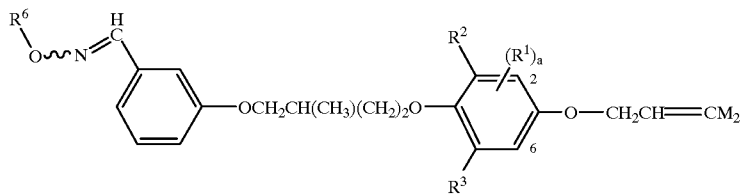

-continued
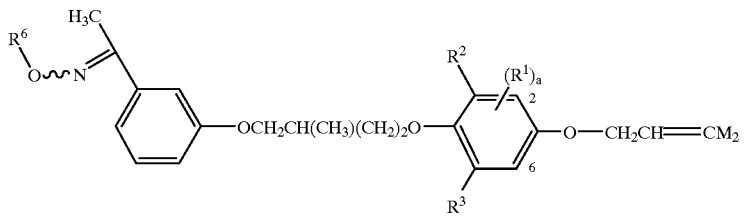
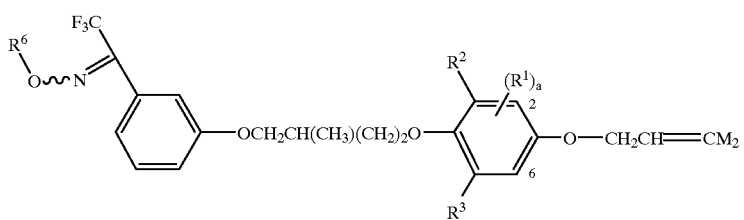
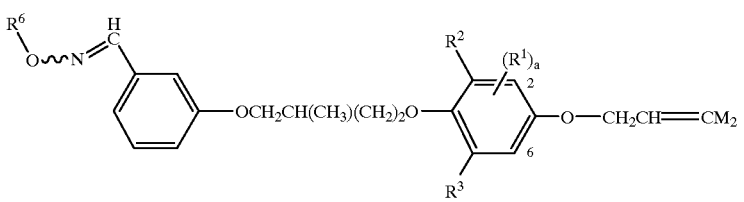
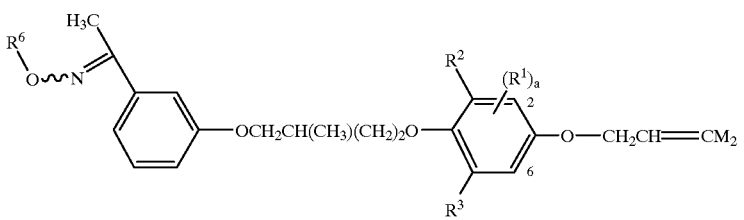
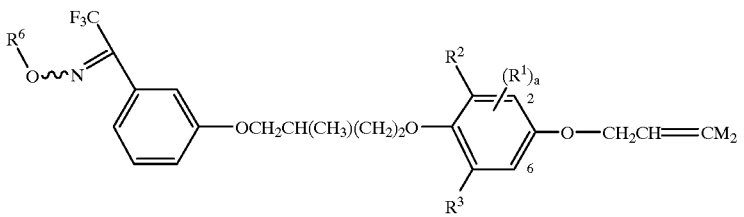
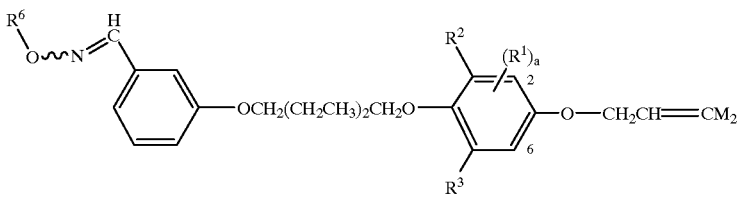
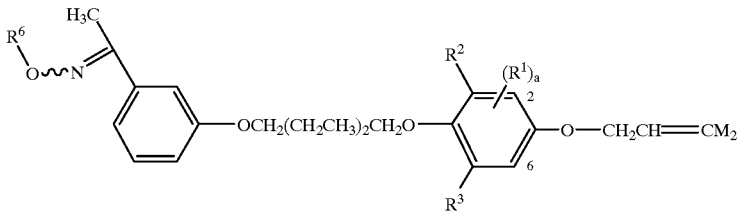
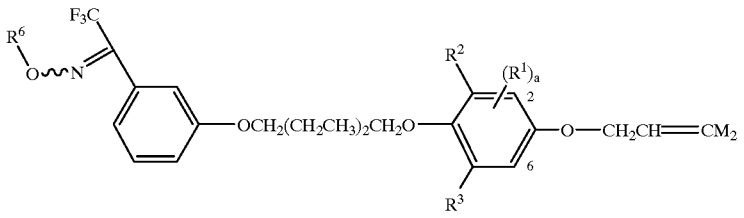

-continued
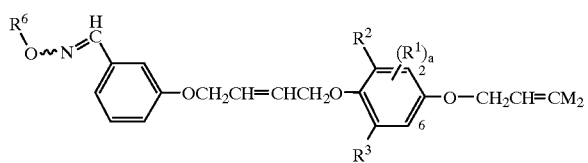
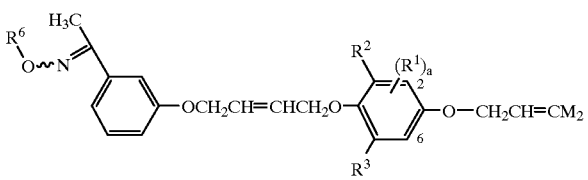
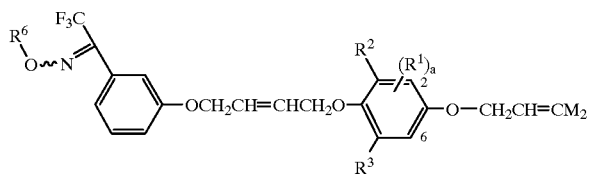
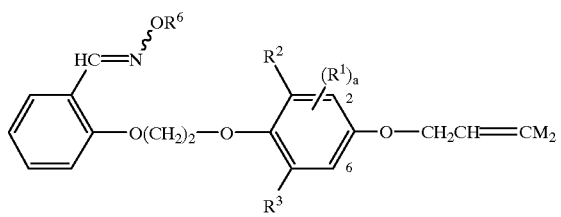
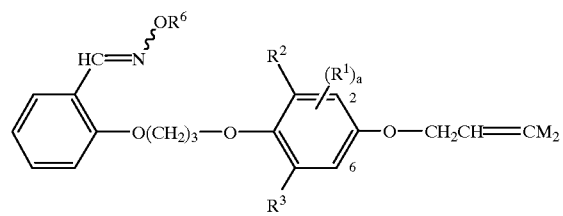
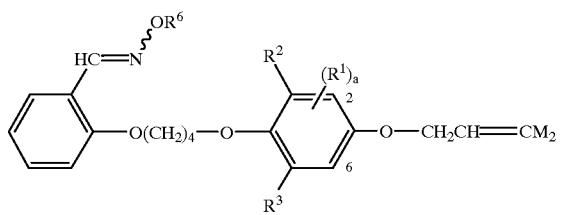
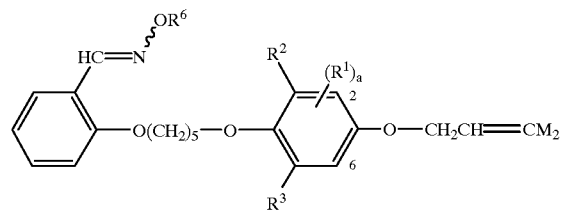
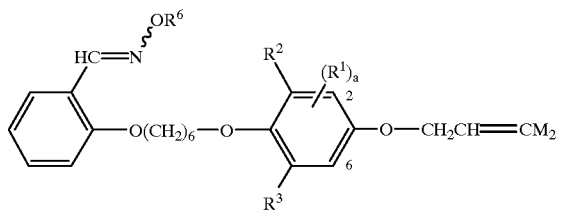
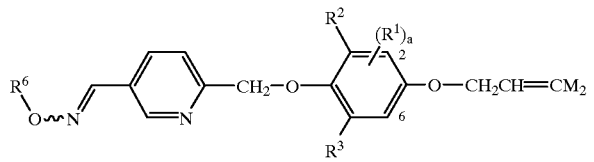
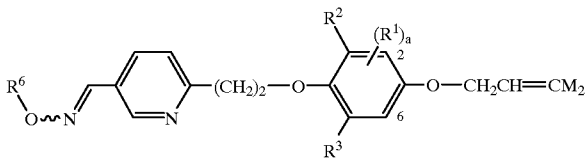
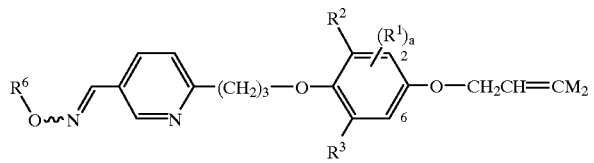
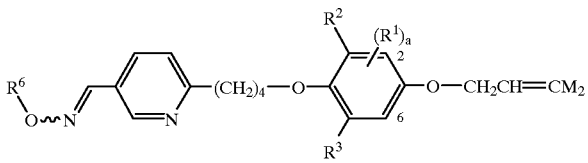
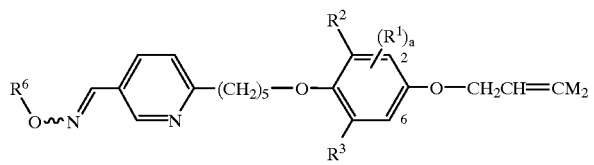
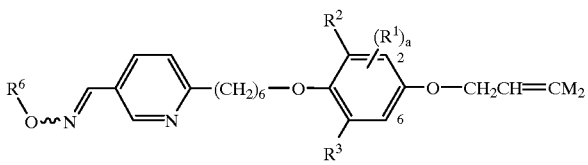
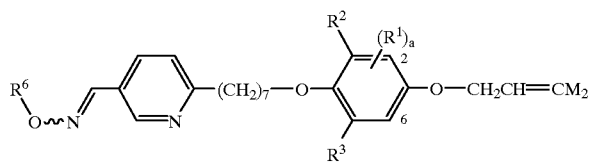
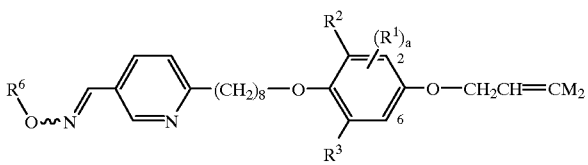
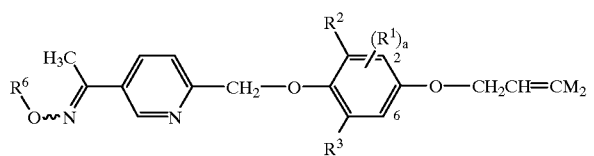
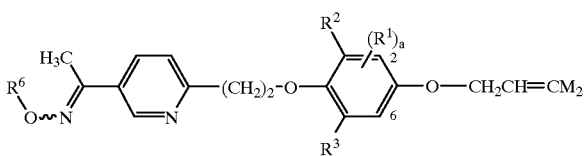

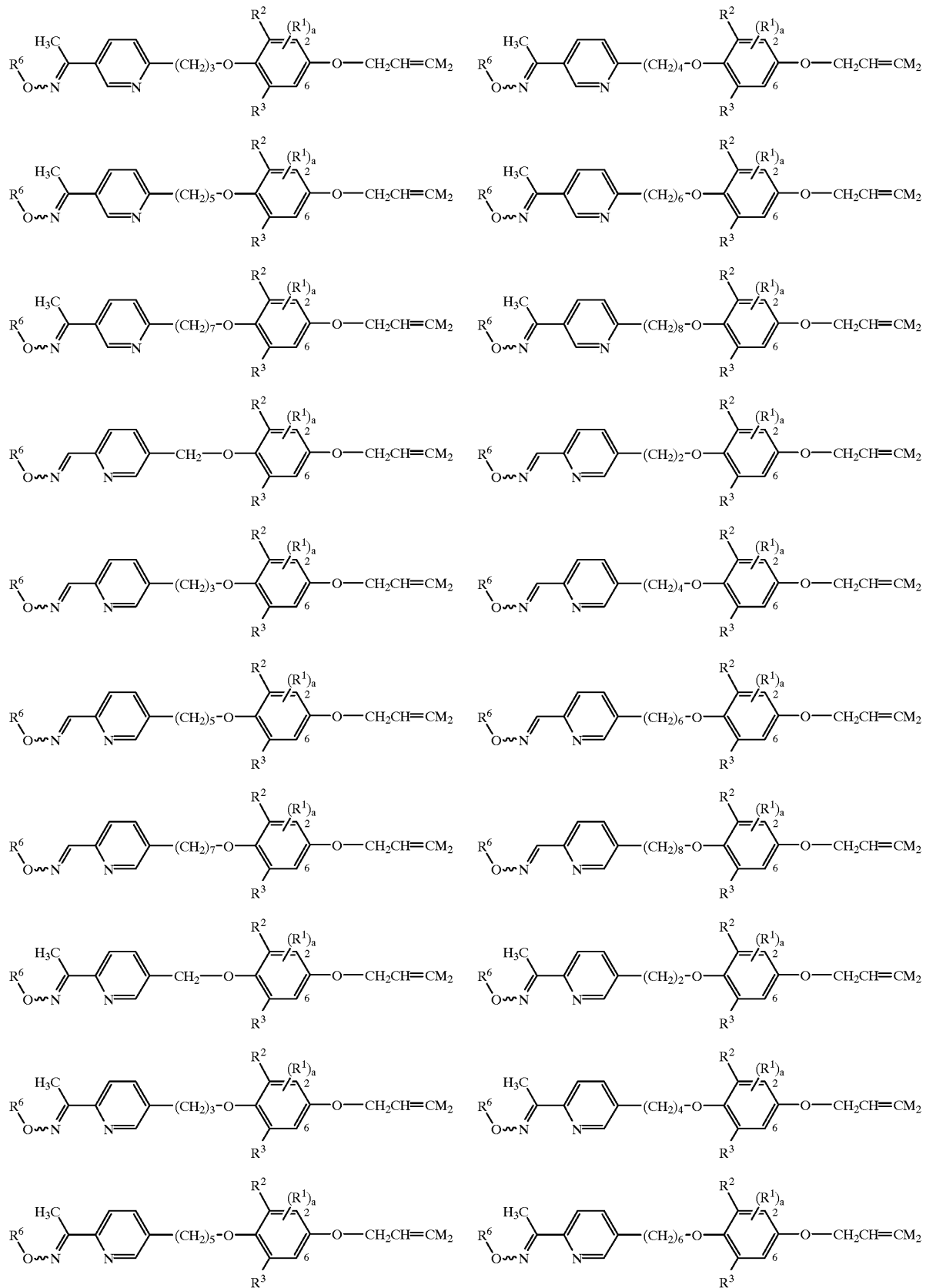

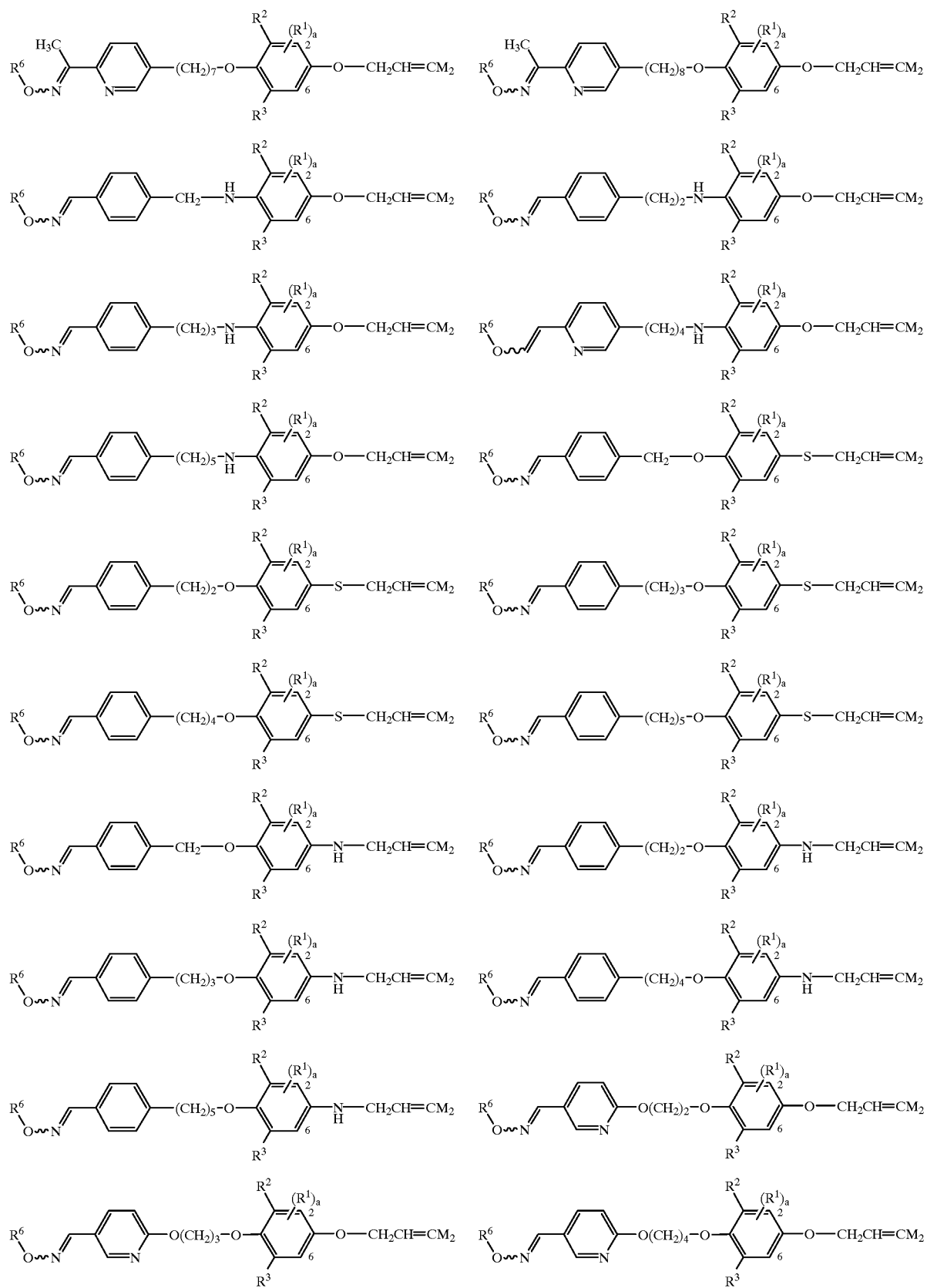

-continued

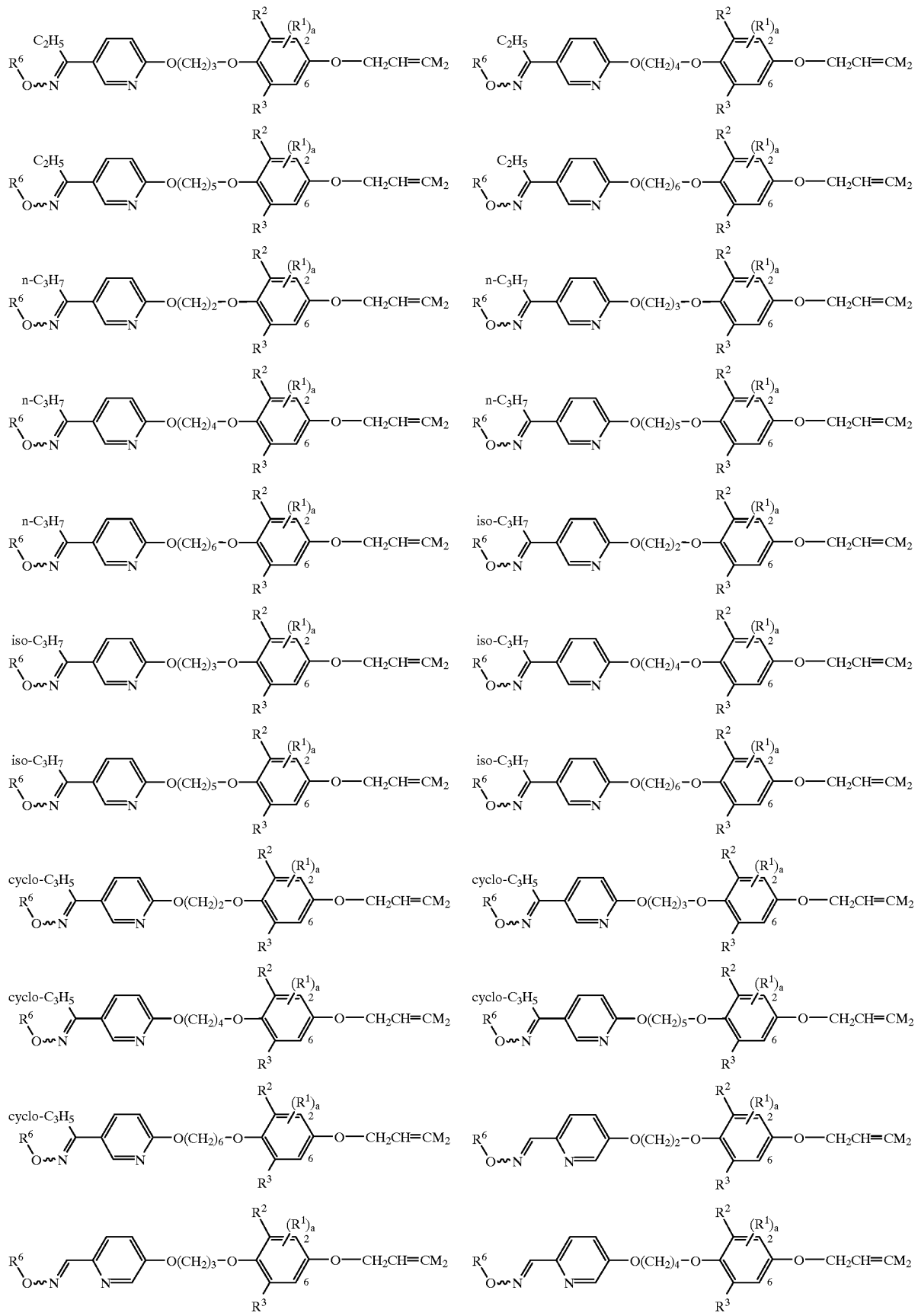

-continued
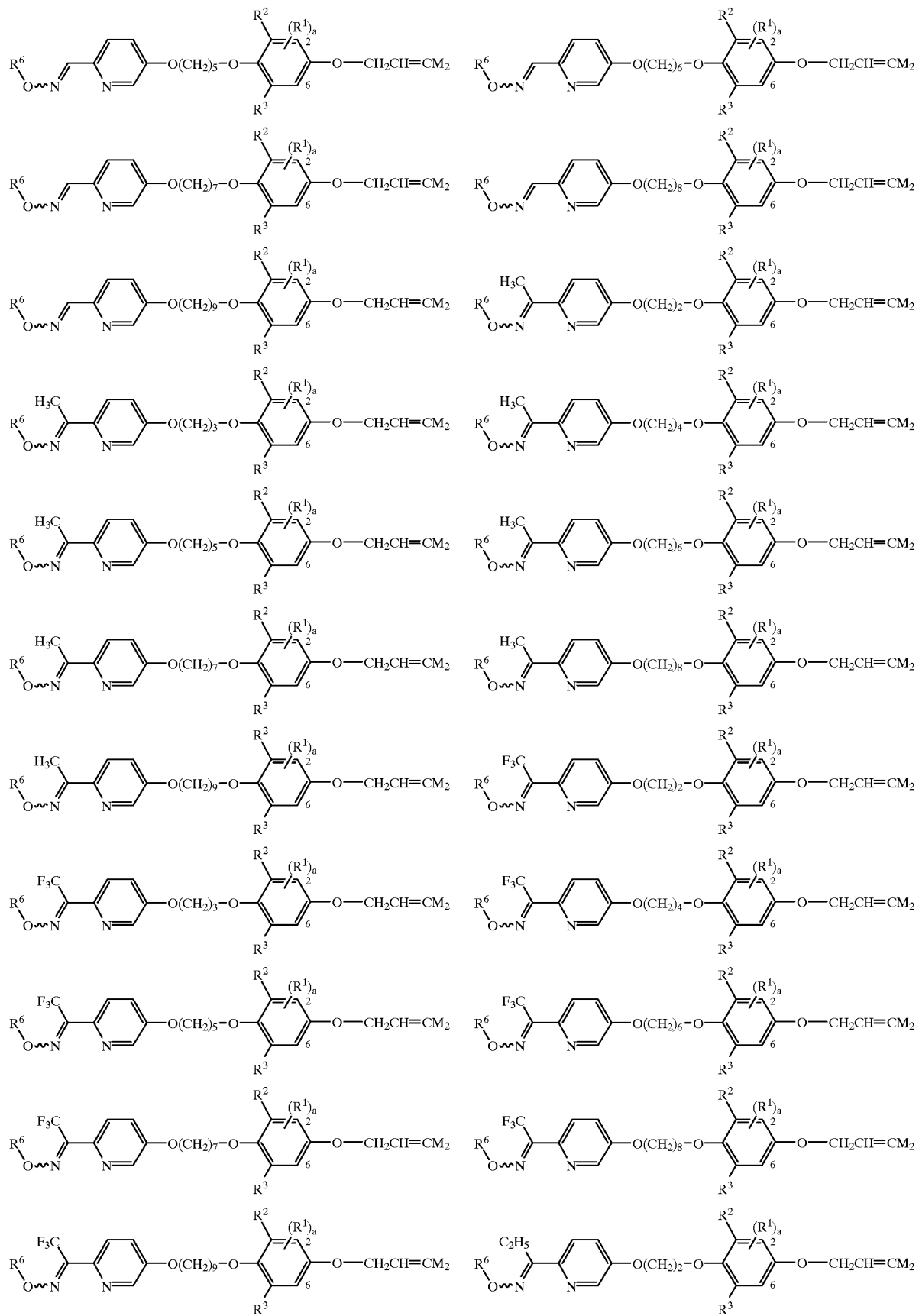

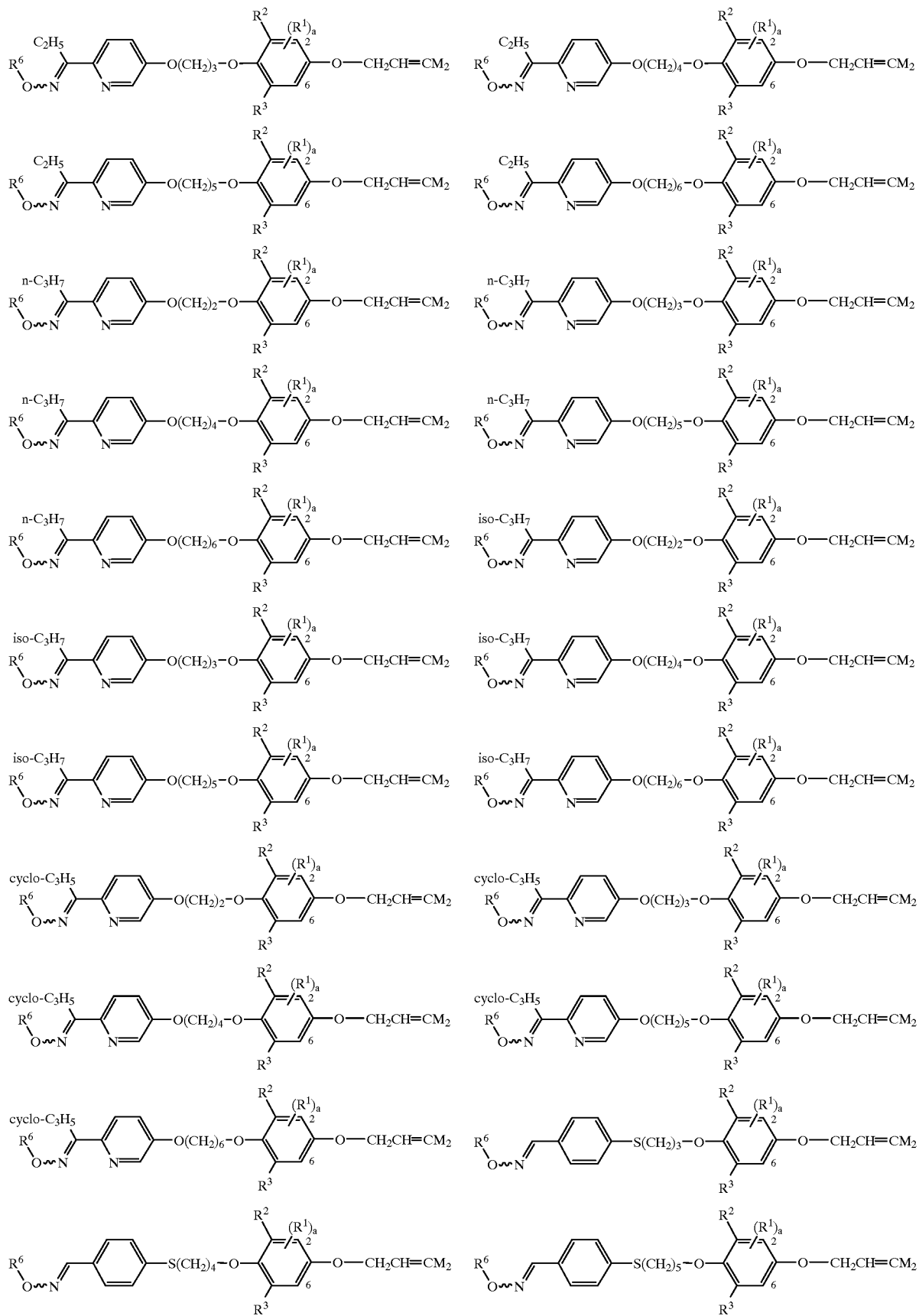

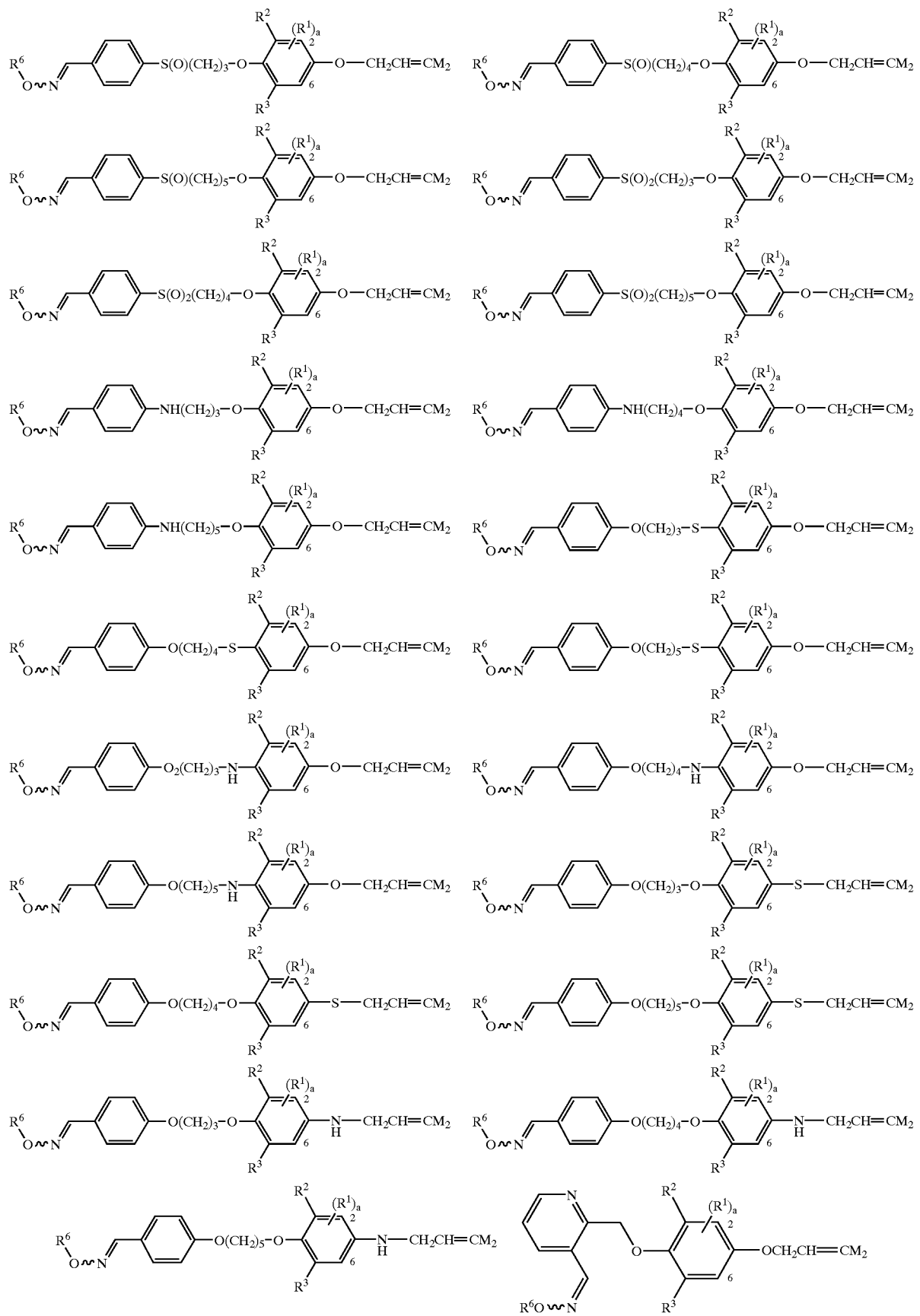

211 212
-continued
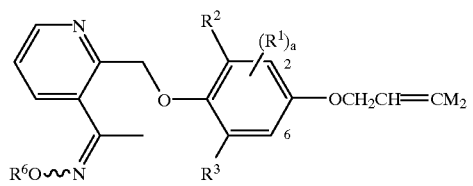
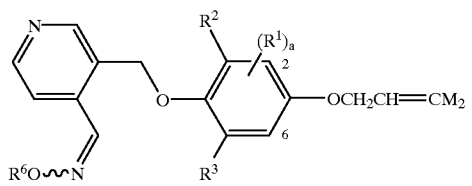
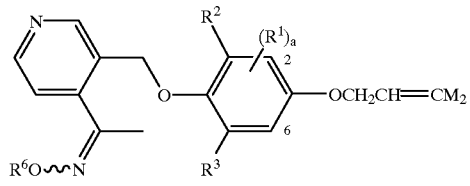
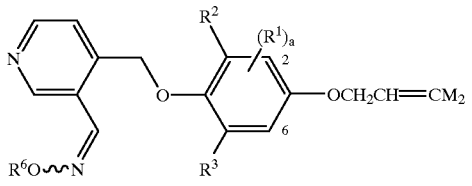
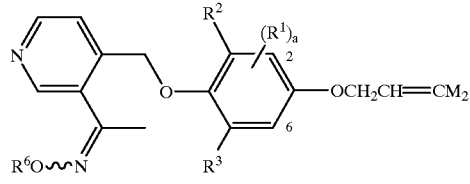
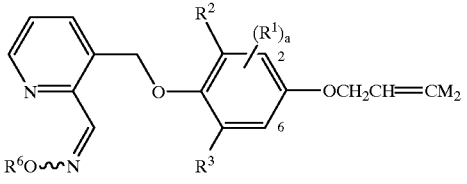
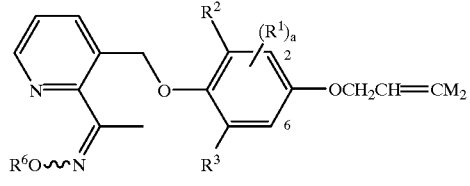
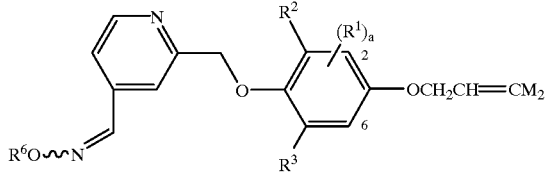
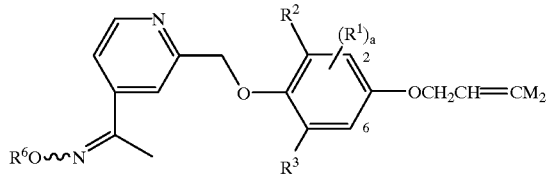
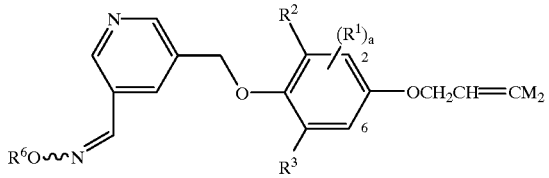
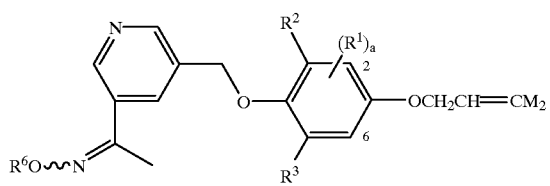
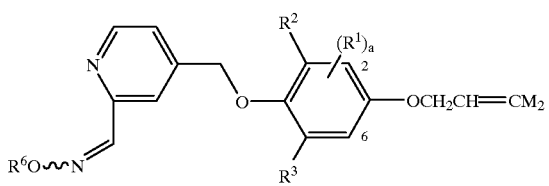
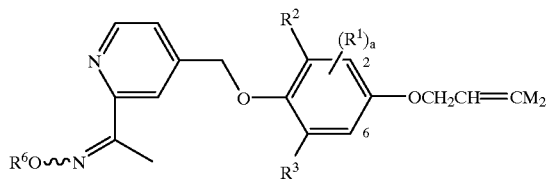
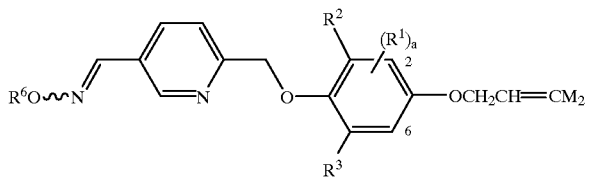
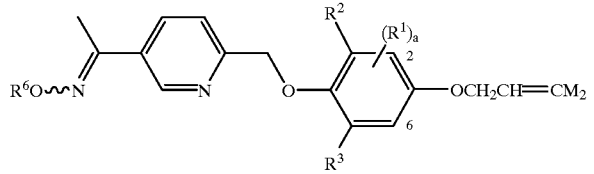
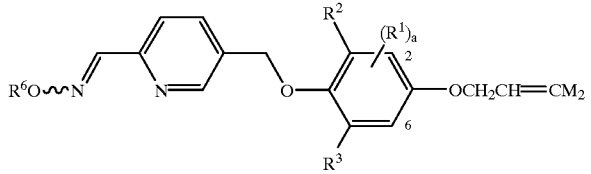
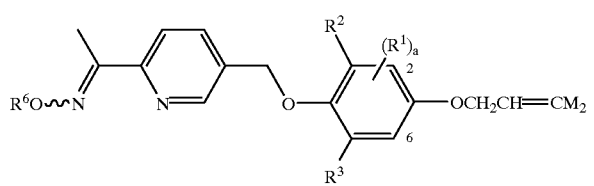
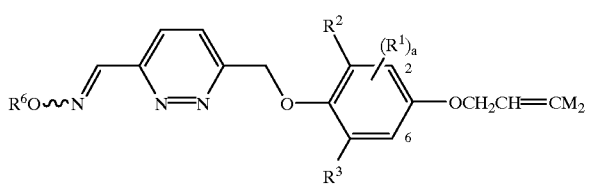

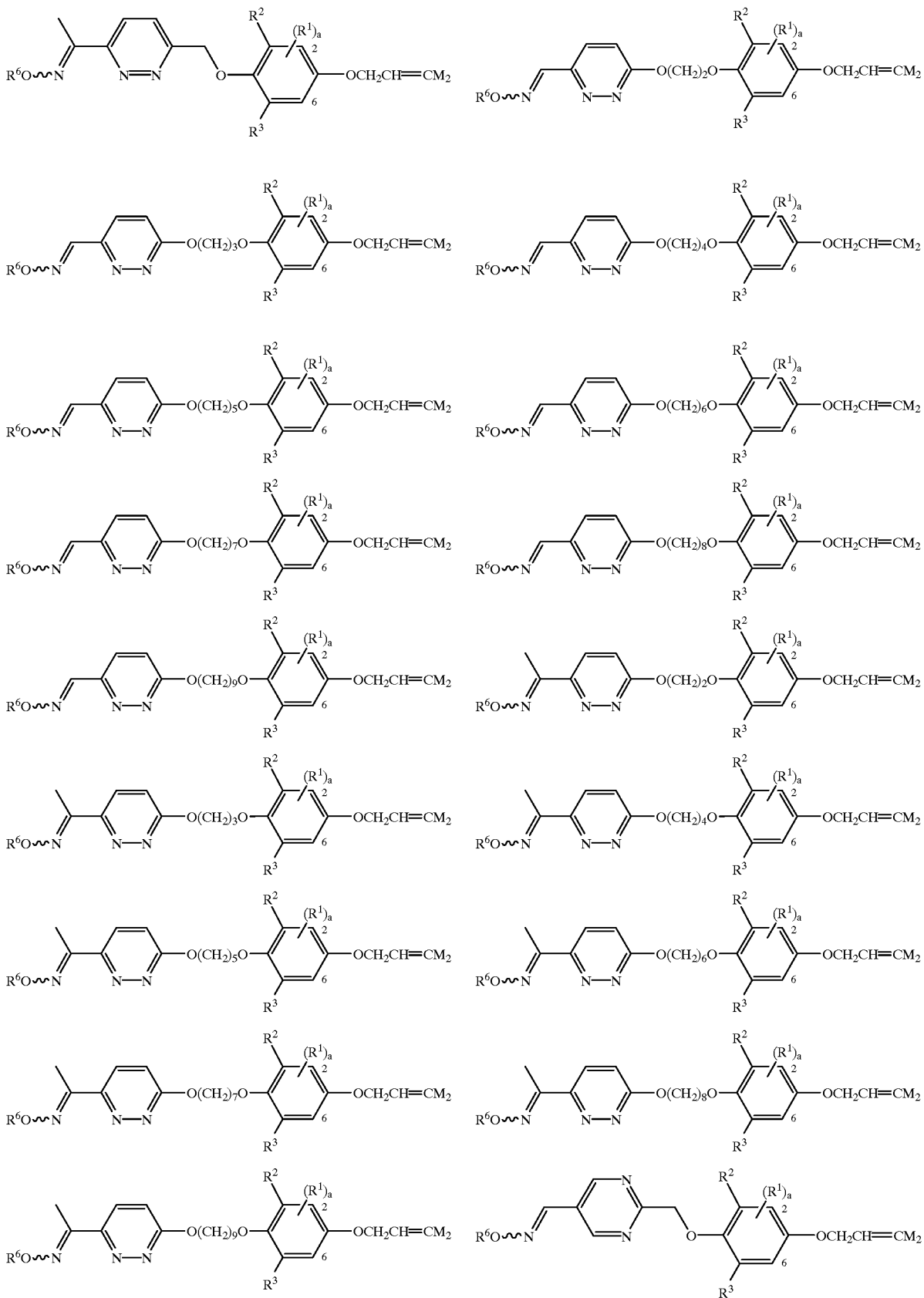

-continued
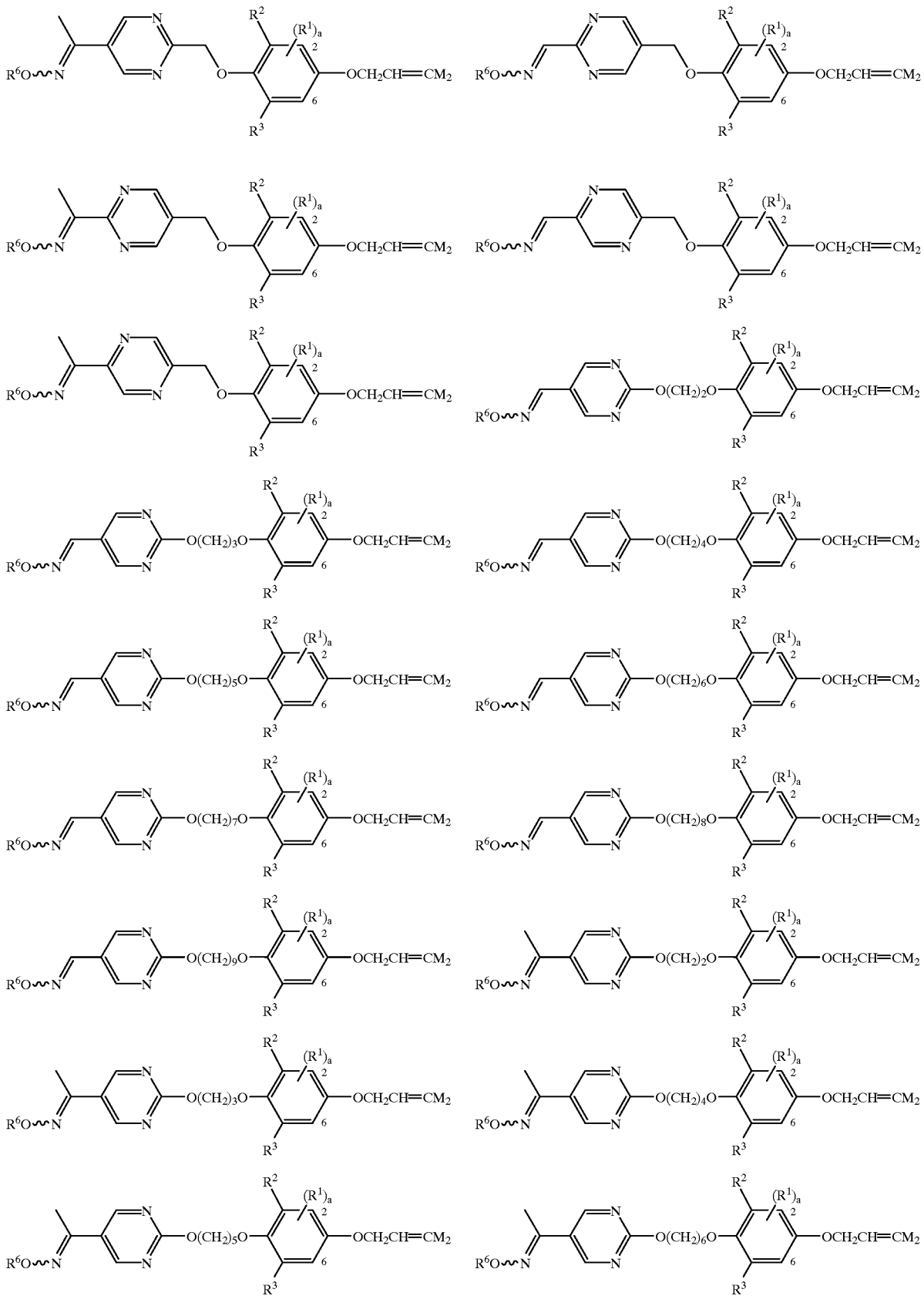

217 218
-continued
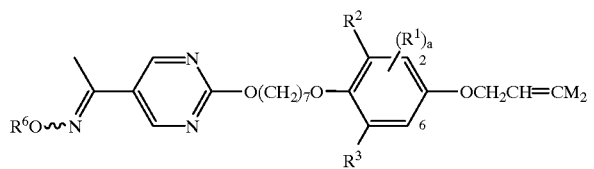
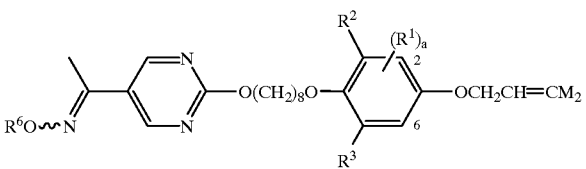
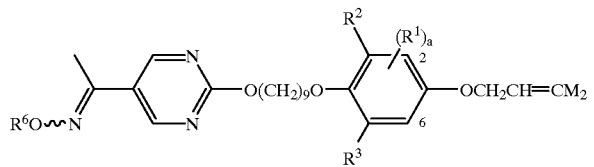
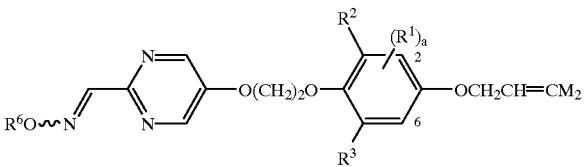
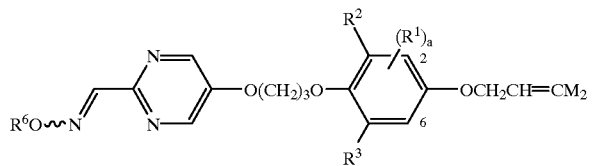
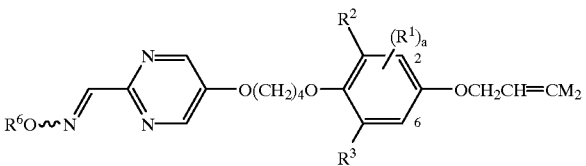
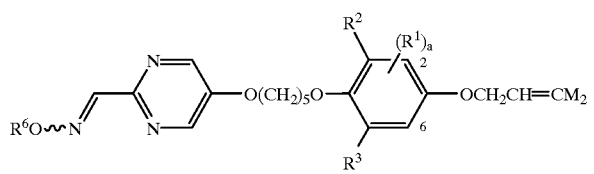
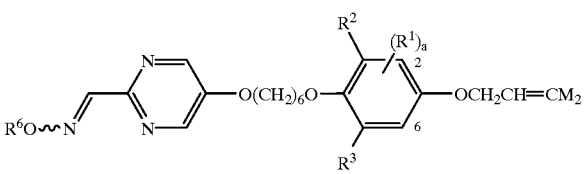
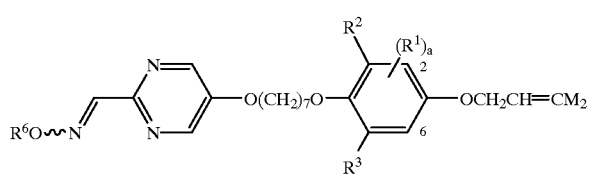
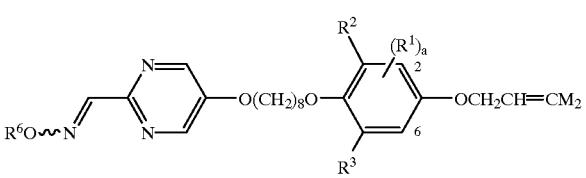
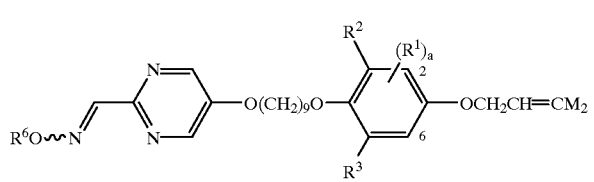
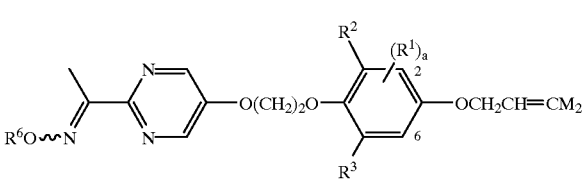
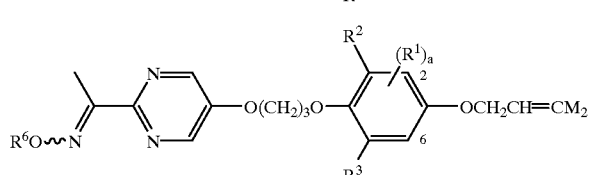
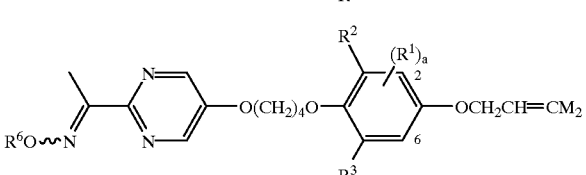
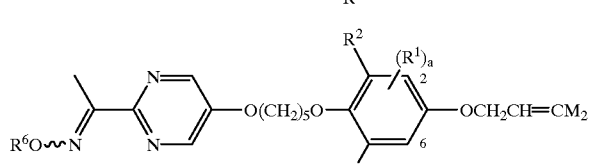
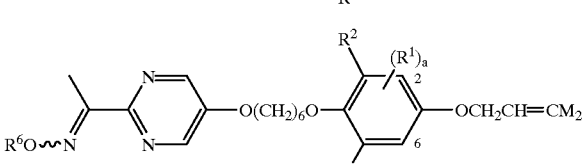
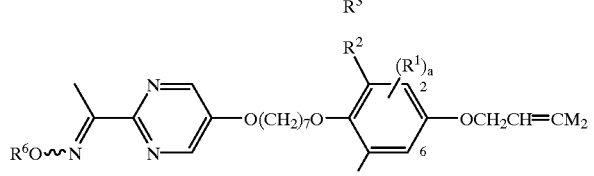
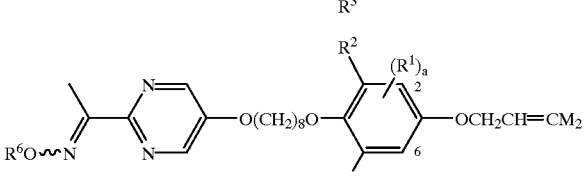

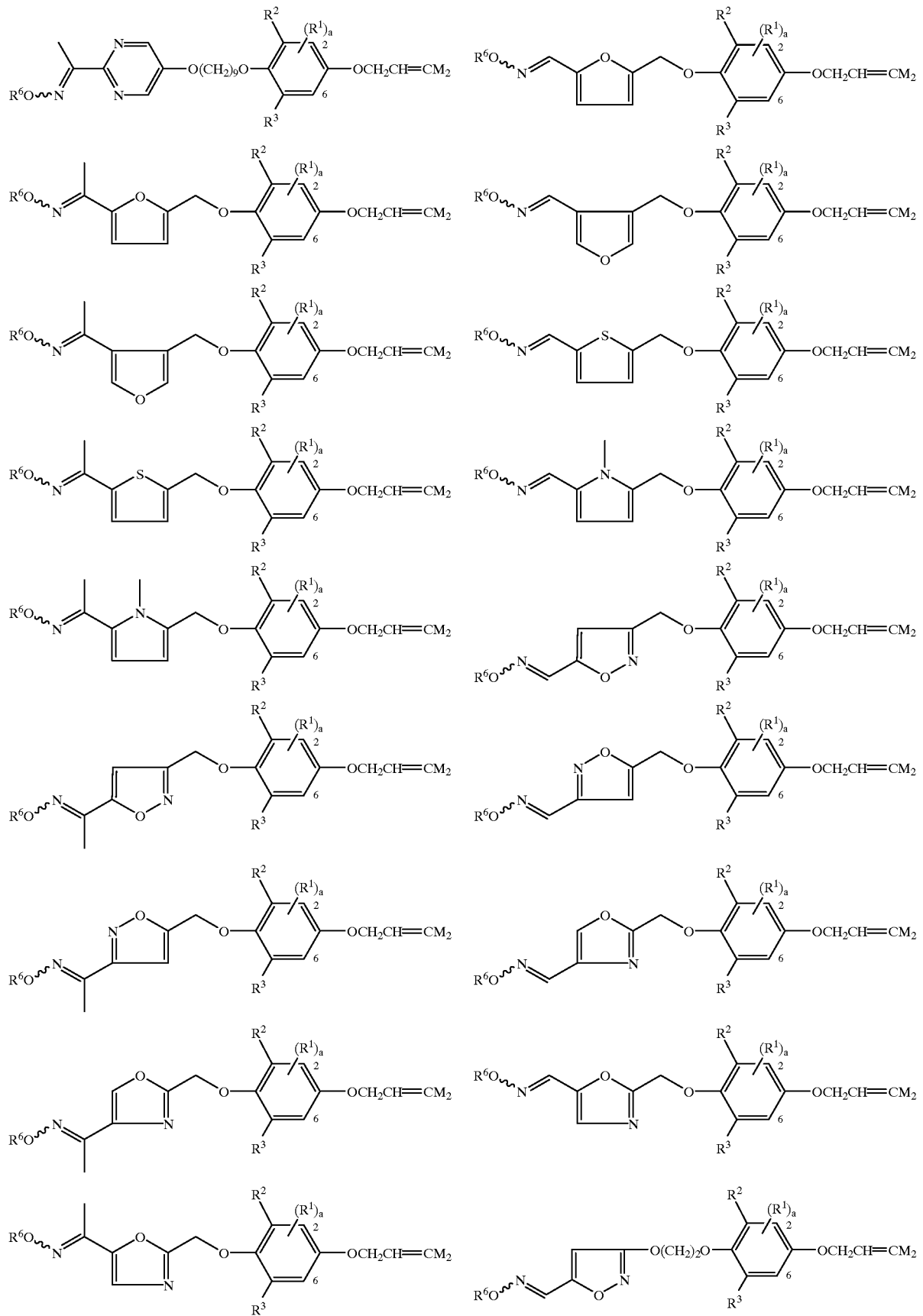

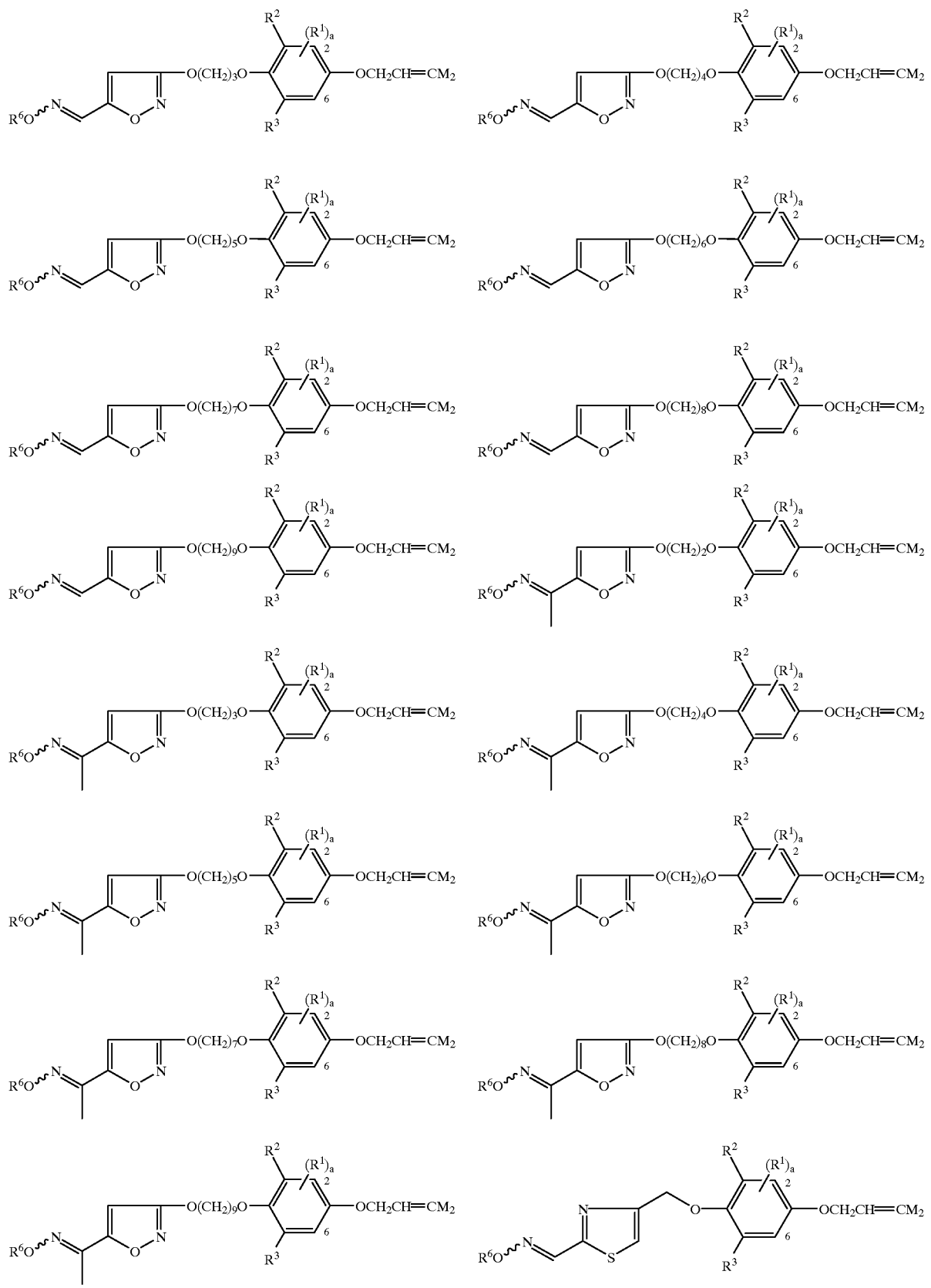

-continued
| 223 | 224 |
|---|---|
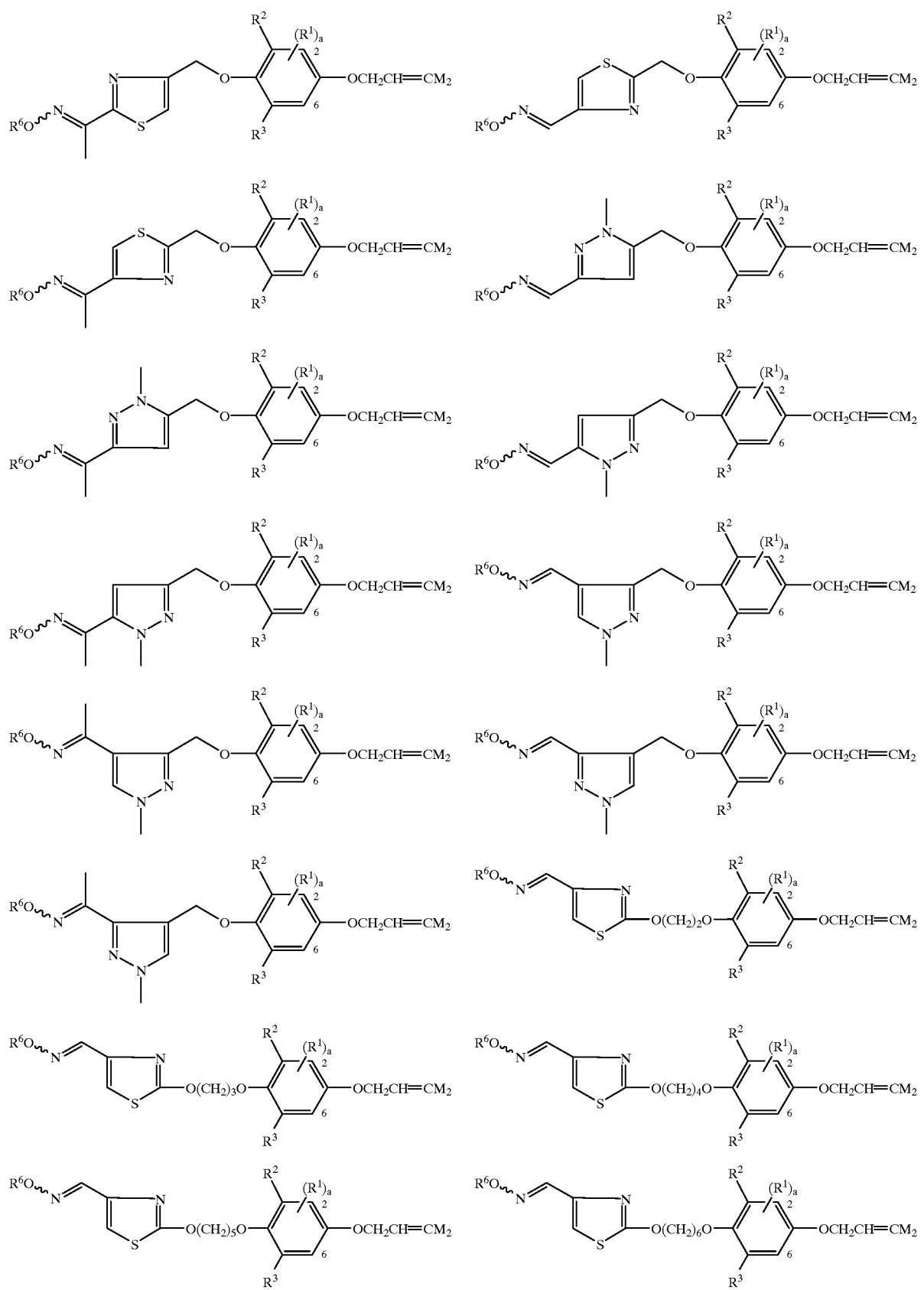

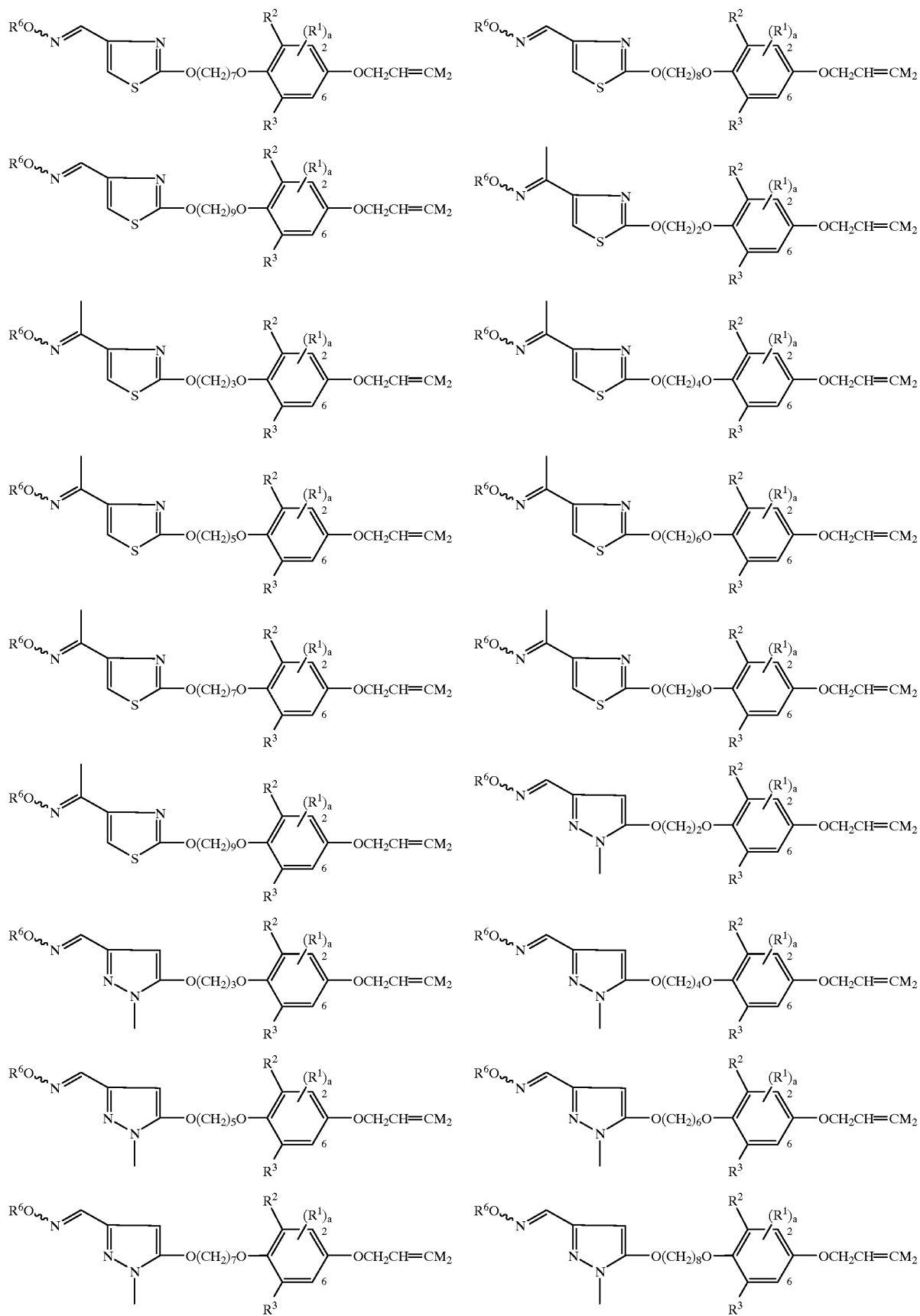
-continued

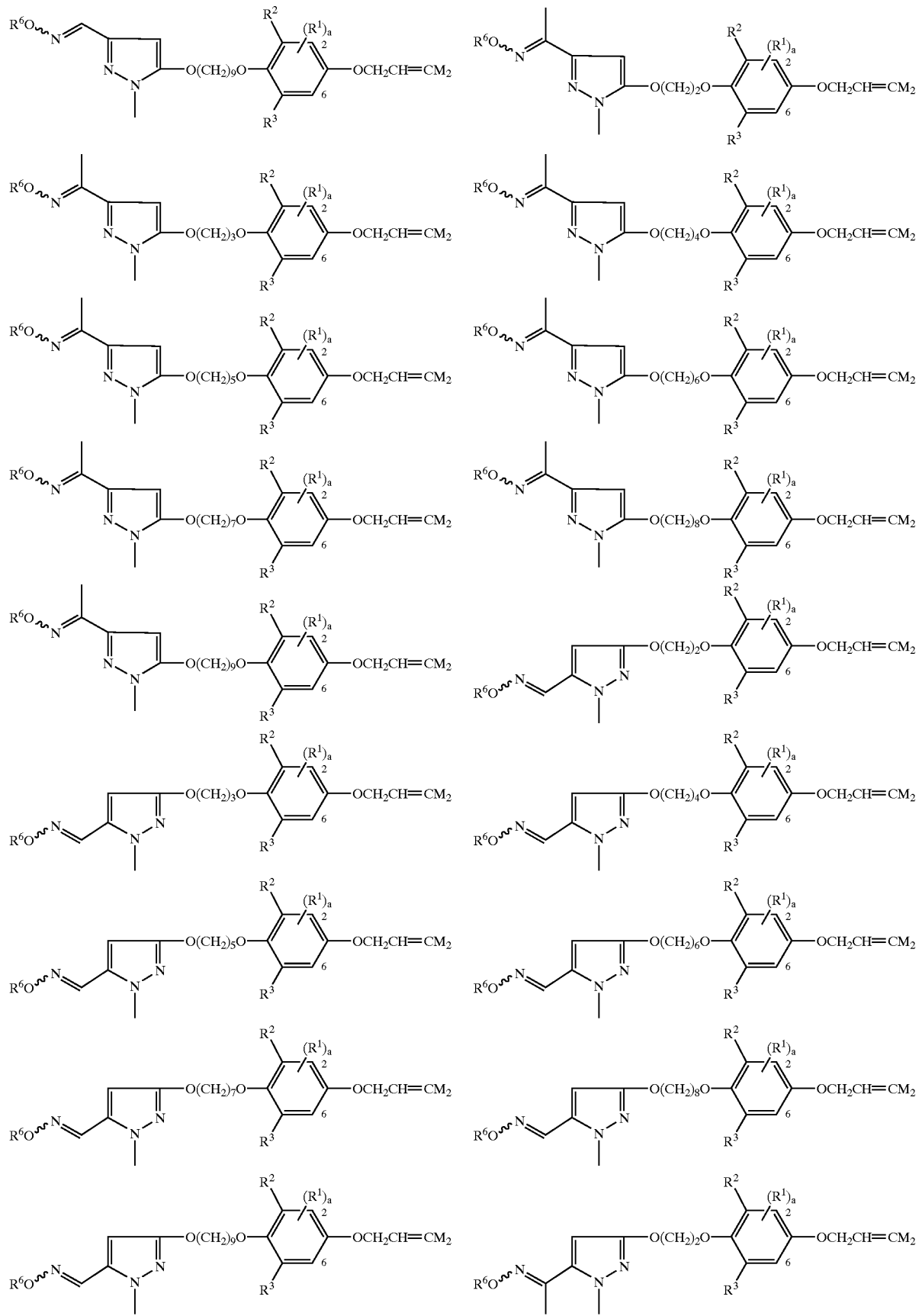

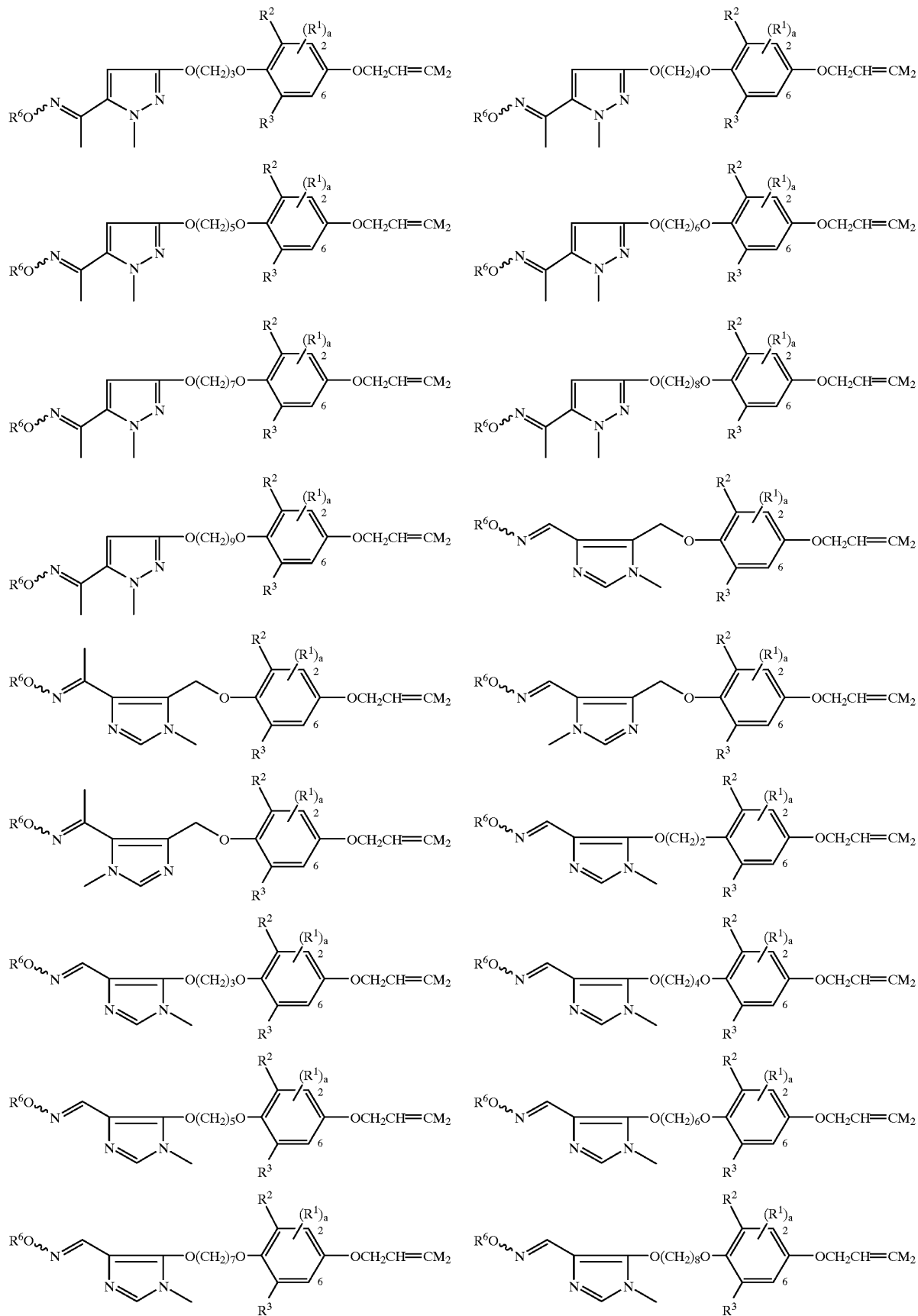

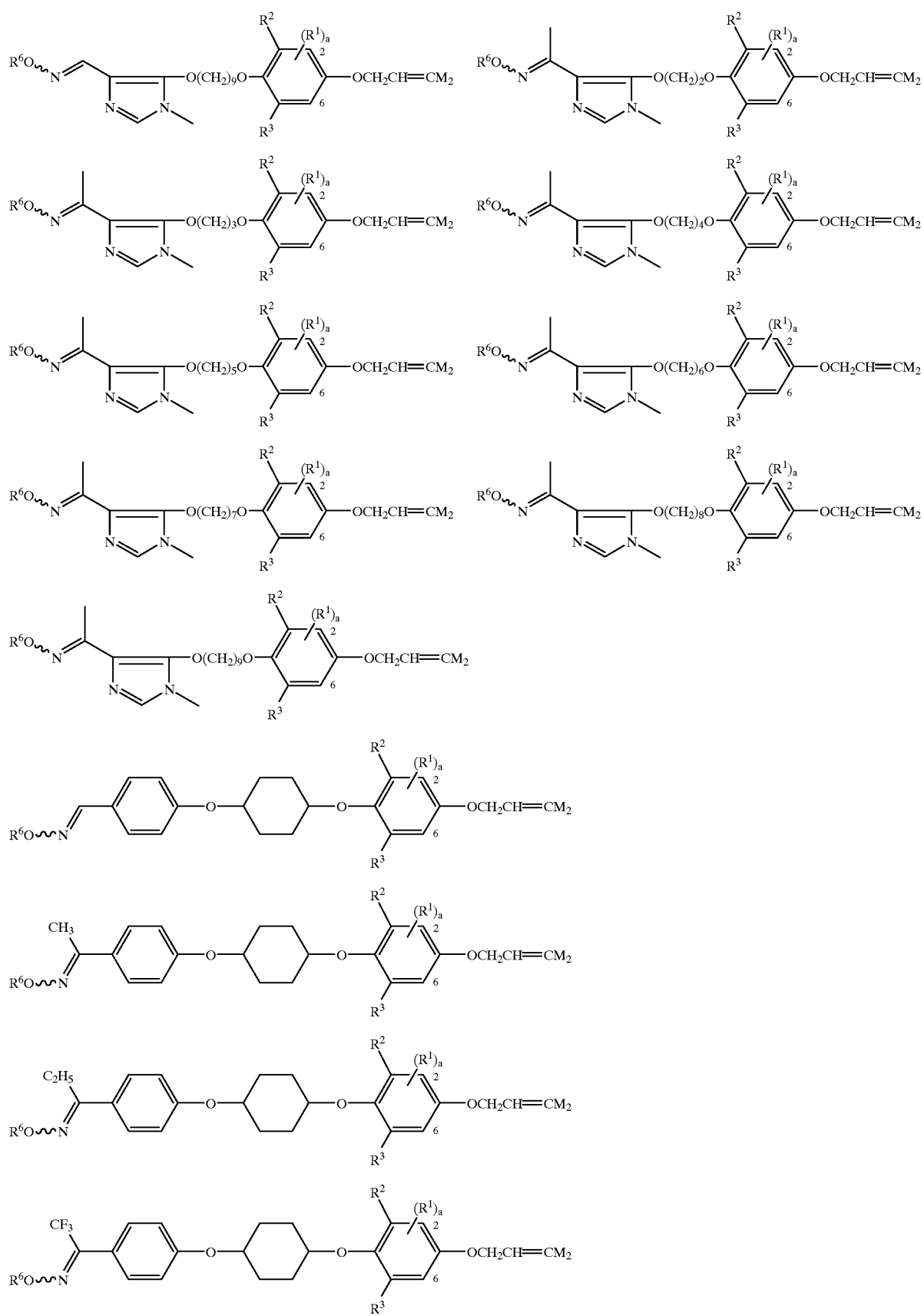

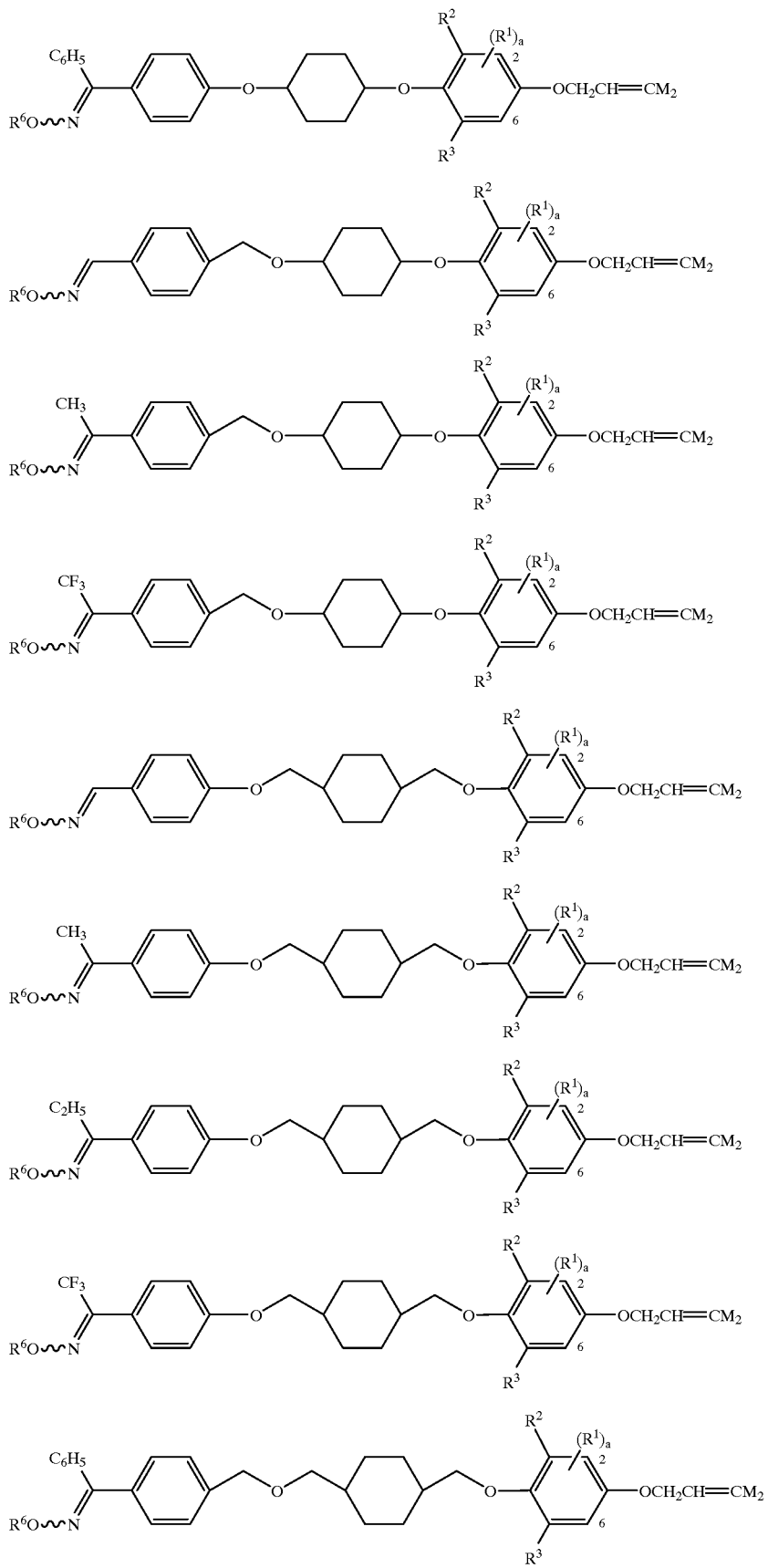

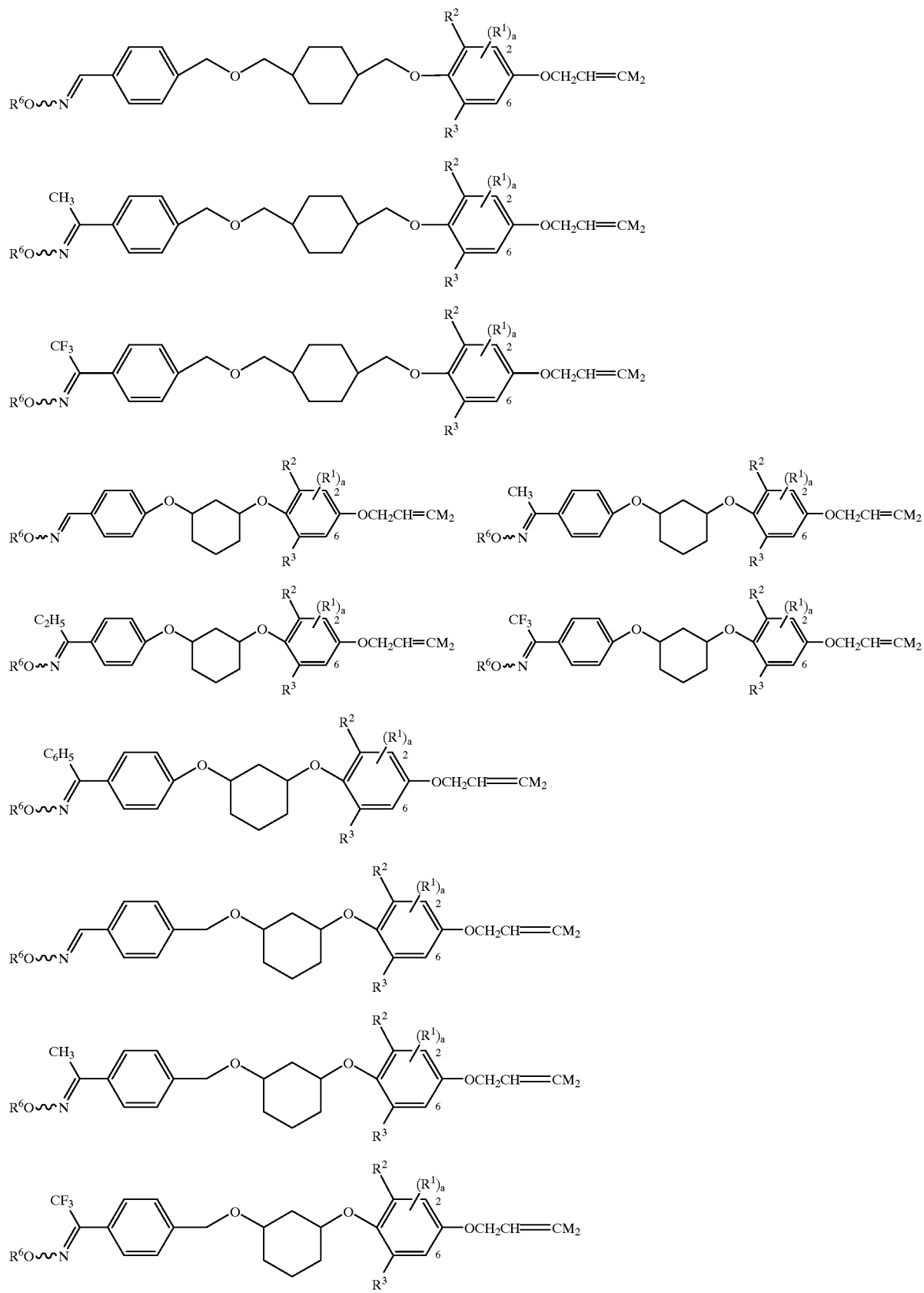

-continued
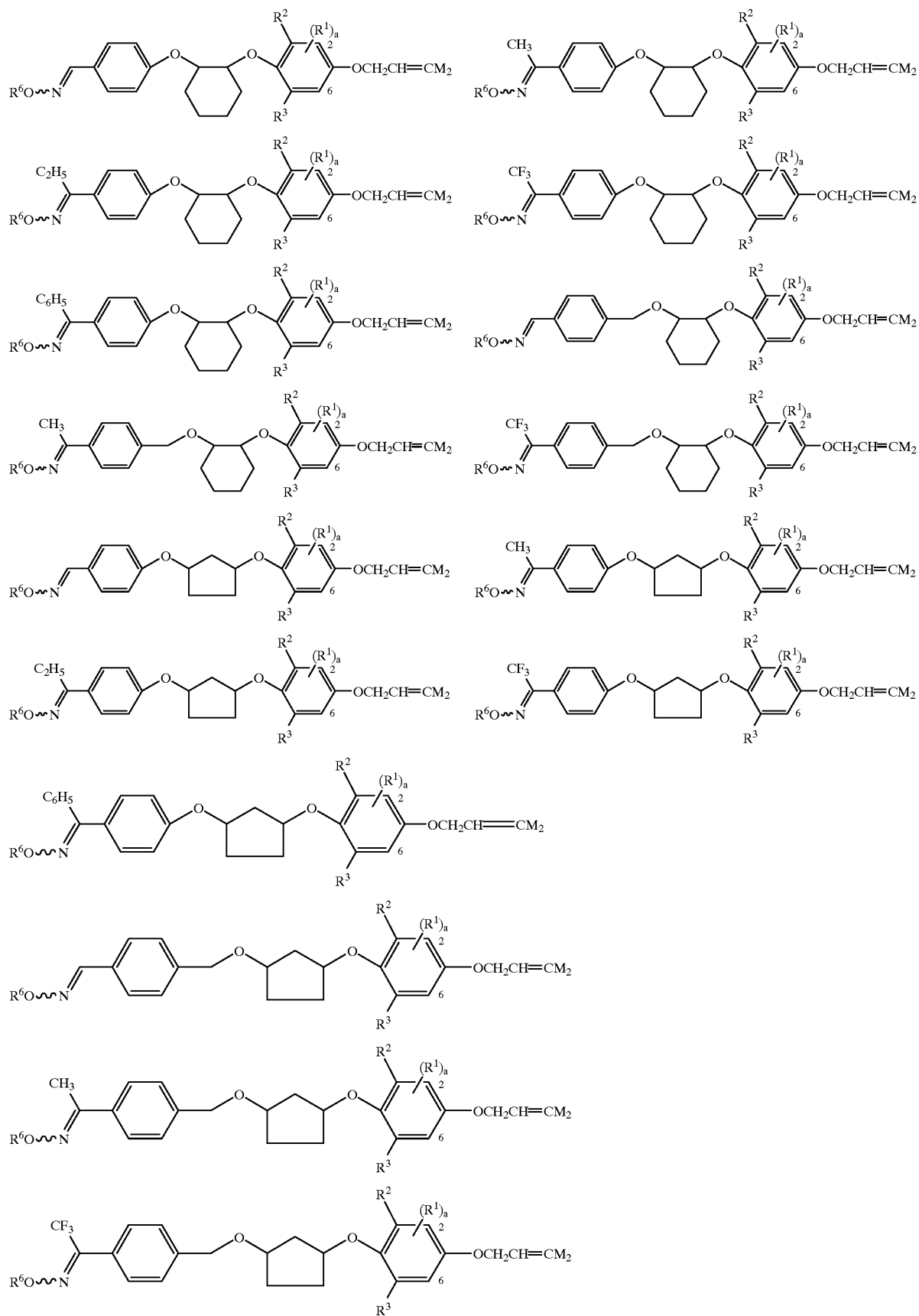

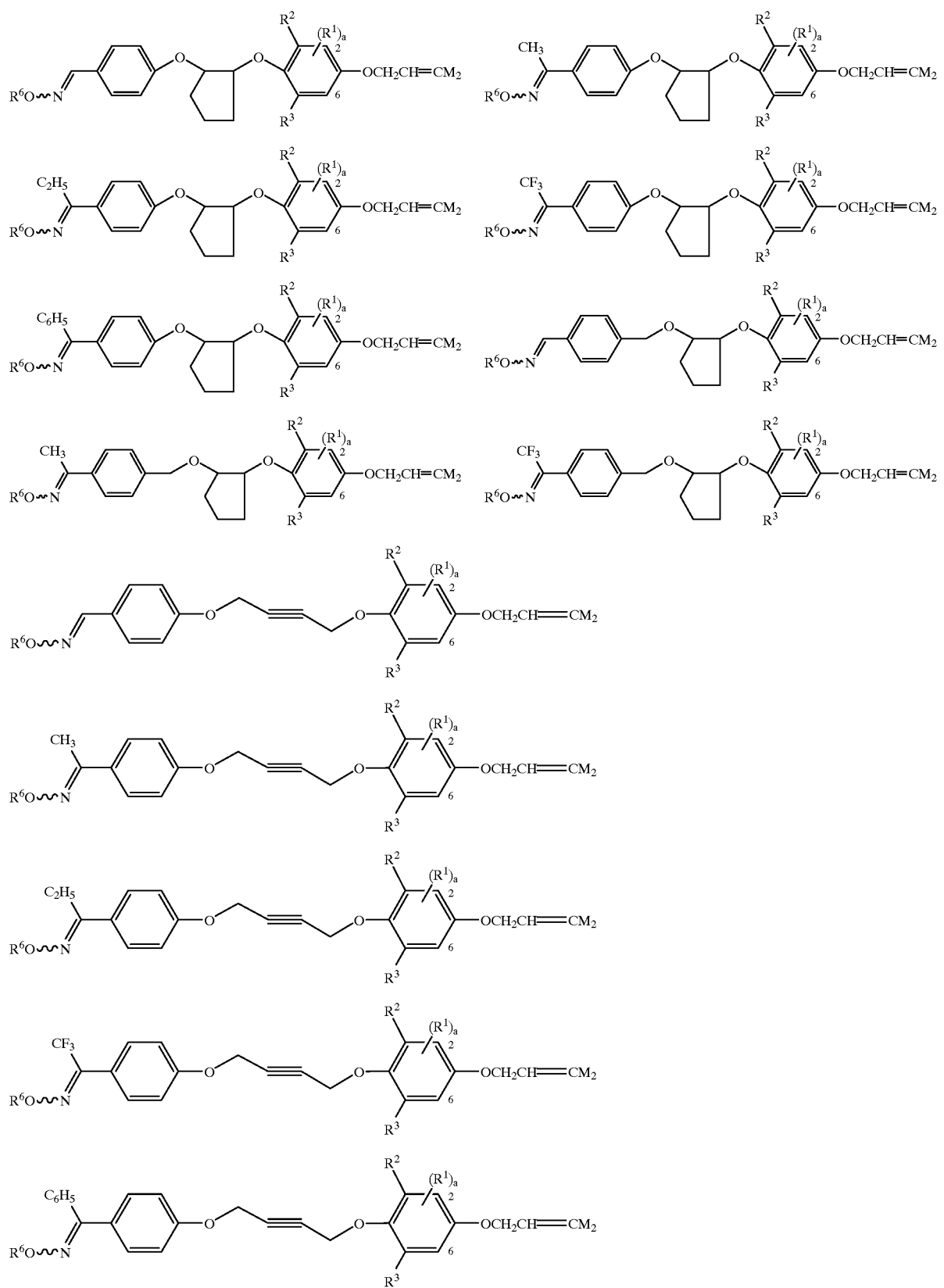

-continued
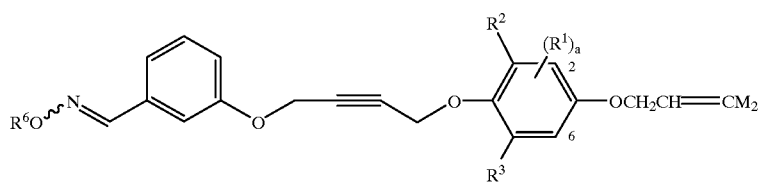
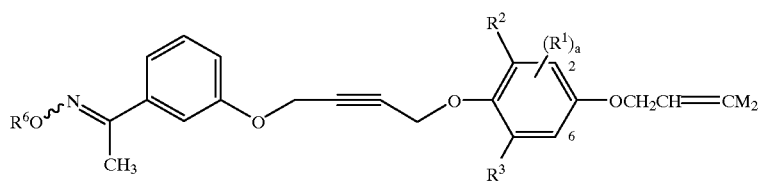
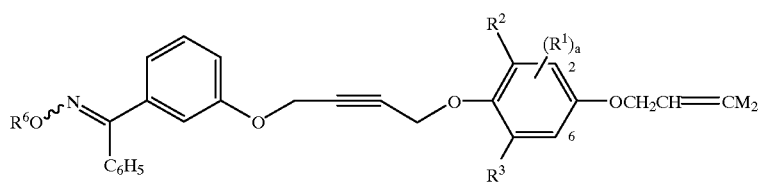
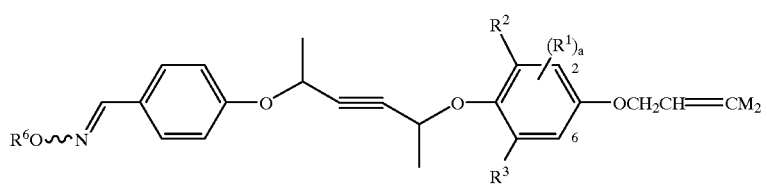
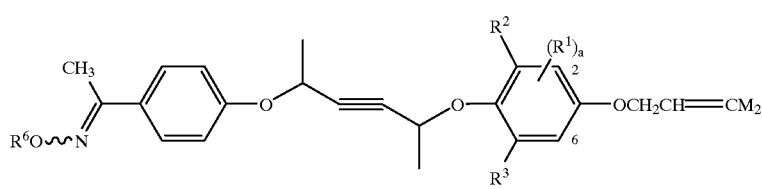
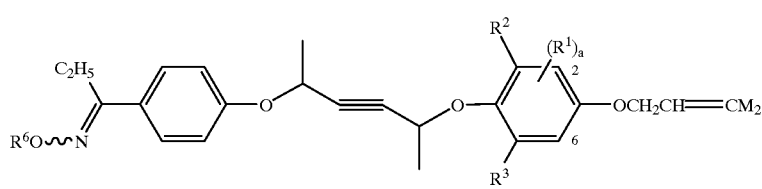
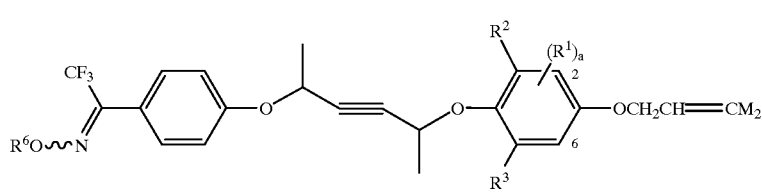
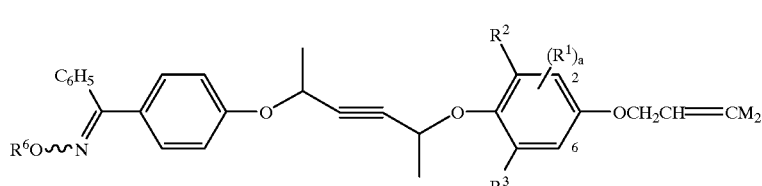
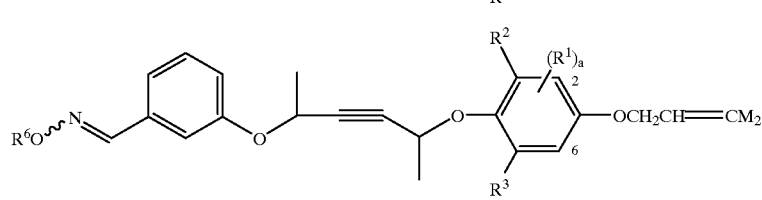

-continued

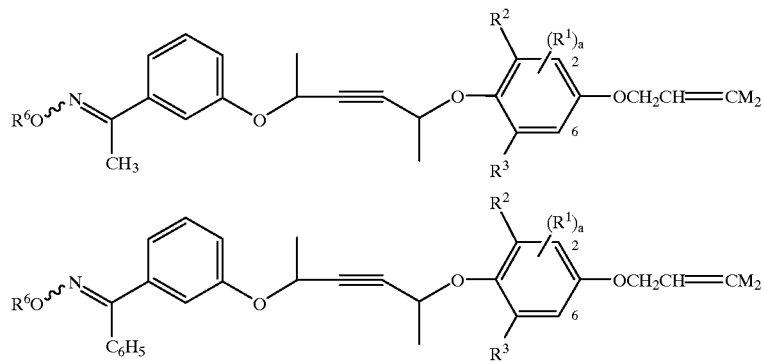

In the above formulae, $(R^1)_a$, $R^2$, $R^3$, and $M_2$ are as defined in Table 1 below, and $R^6$ is as defined in Tables 2 to 19 below.

TABLE 1

| $(R^1)_a$ | $R^2$ | $R^3$ | $M_2$ |
|---|---|---|---|
| H | Cl | Cl | $Cl_2$ |
| H | Cl | Cl | $Br_2$ |
| H | Cl | Cl | $F_2$ |
| H | Cl | Cl | Cl, F |
| H | Cl | Cl | Cl, Br |
| H | Cl | Cl | F, Br |
| H | Cl | F | $Cl_2$ |
| H | Cl | F | $Br_2$ |
| H | Cl | F | $F_2$ |
| H | Cl | F | Cl, F |
| H | Cl | F | Cl, Br |
| H | Cl | F | F, Br |
| H | Cl | Br | $Cl_2$ |
| H | Cl | Br | $Br_2$ |
| H | Cl | Br | $F_2$ |
| H | Cl | Br | Cl, F |
| H | Cl | Br | Cl, Br |
| H | Cl | Br | F, Br |
| H | Cl | $CF_3$ | $Cl_2$ |
| H | Cl | $CF_3$ | $Br_2$ |
| H | Cl | $CF_3$ | $F_2$ |
| H | Cl | $CF_3$ | Cl, F |
| H | Cl | $CF_3$ | Cl, Br |
| H | Cl | $CF_3$ | F, Br |
| H | Cl | $CH_3$ | $Cl_2$ |
| H | Cl | $CH_3$ | $Br_2$ |
| H | Cl | $CH_3$ | $F_2$ |
| H | Cl | $CH_3$ | Cl, F |
| H | Cl | $CH_3$ | Cl, Br |
| H | Cl | $CH_3$ | F, Br |
| H | Cl | $CH_3CH_2$ | $Cl_2$ |
| H | Cl | $CH_3CH_2$ | $Br_2$ |
| H | Cl | $CH_3CH_2$ | $F_2$ |
| H | Cl | $CH_3CH_2$ | Cl, F |
| H | Cl | $CH_3CH_2$ | Cl, Br |
| H | Cl | $CH_3CH_2$ | F, Br |
| H | Cl | $CH_3CH_2CH_2$ | $Cl_2$ |
| H | Cl | $CH_3CH_2CH_2$ | $Br_2$ |
| H | Cl | $CH_3CH_2CH_2$ | Cl, F |
| H | Cl | $CH_3CH_2CH_2$ | Cl, Br |
| H | Cl | $CH_3CH_2CH_2$ | F, Br |
| H | Cl | $(CH_3)_2CH$ | $Cl_2$ |
| H | Cl | $(CH_3)_2CH$ | $Br_2$ |
| H | Cl | $(CH_3)_2CH$ | Cl, F |
| H | Cl | $(CH_3)_2CH$ | Cl, Br |
| H | Cl | $(CH_3)_2CH$ | F, Br |
| H | F | F | $Cl_2$ |
| H | F | F | $Br_2$ |
| H | F | Br | $Cl_2$ |

TABLE 1-continued

| $(R^1)_a$ | $R^2$ | $R^3$ | $M_2$ |
|---|---|---|---|
| H | F | Br | $Br_2$ |
| H | F | $CF_3$ | $Cl_2$ |
| H | F | $CF_3$ | $Br_2$ |
| H | F | $CH_3$ | $Cl_2$ |
| H | F | $CH_3$ | $Br_2$ |
| H | F | $CH_3CH_2$ | $Cl_2$ |
| H | F | $CH_3CH_2$ | $Br_2$ |
| H | F | $CH_3CH_2CH_2$ | $Cl_2$ |
| H | F | $CH_3CH_2CH_2$ | $Br_2$ |
| H | F | $(CH_3)_2CH$ | $Cl_2$ |
| H | F | $(CH_3)_2CH$ | $Br_2$ |
| H | Br | Br | $Cl_2$ |
| H | Br | Br | $Br_2$ |
| H | Br | $CF_3$ | $Cl_2$ |
| H | Br | $CF_3$ | $Br_2$ |
| H | Br | $CH_3$ | $Cl_2$ |
| H | Br | $CH_3$ | $Br_2$ |
| H | Br | $CH_3CH_2$ | $Cl_2$ |
| H | Br | $CH_3CH_2$ | $Br_2$ |
| H | Br | $CH_3CH_2CH_2$ | $Cl_2$ |
| H | Br | $CH_3CH_2CH_2$ | $Br_2$ |
| H | Br | $(CH_3)_2CH$ | $Cl_2$ |
| H | Br | $(CH_3)_2CH$ | $Br_2$ |
| H | $CH_3$ | $CF_3$ | $Cl_2$ |
| H | $CH_3$ | $CF_3$ | $Br_2$ |
| H | $CH_3$ | $CH_3$ | $Cl_2$ |
| H | $CH_3$ | $CH_3$ | $Br_2$ |
| H | $CH_3$ | $CH_3CH_2$ | $Cl_2$ |
| H | $CH_3$ | $CH_3CH_2$ | $Br_2$ |
| H | $CH_3$ | $CH_3CH_2$ | $F_2$ |
| H | $CH_3$ | $CH_3CH_2$ | Cl, F |
| H | $CH_3$ | $CH_3CH_2$ | Cl, Br |
| H | $CH_3$ | $CH_3CH_2$ | F, Br |
| H | $CH_3$ | $CH_3CH_2CH_2$ | $Cl_2$ |
| H | $CH_3$ | $CH_3CH_2CH_2$ | $Br_2$ |
| H | $CH_3$ | $(CH_3)_2CH$ | $Cl_2$ |
| H | $CH_3$ | $(CH_3)_2CH$ | $Br_2$ |
| H | $CH_3CH_2$ | $CF_3$ | $Cl_2$ |
| H | $CH_3CH_2$ | $CF_3$ | $Br_2$ |
| H | $CH_3CH_2$ | $CH_3CH_2$ | $Cl_2$ |
| H | $CH_3CH_2$ | $CH_3CH_2$ | $Br_2$ |
| H | $CH_3CH_2$ | $CH_3CH_2$ | $F_2$ |
| H | $CH_3CH_2$ | $CH_3CH_2$ | Cl, F |
| H | $CH_3CH_2$ | $CH_3CH_2$ | Cl, Br |
| H | $CH_3CH_2$ | $CH_3CH_2$ | F, Br |
| H | $CH_3CH_2$ | $CH_3CH_2CH_2$ | $Cl_2$ |
| H | $CH_3CH_2$ | $CH_3CH_2CH_2$ | $Br_2$ |
| H | $CH_3CH_2$ | $(CH_3)_2CH$ | $Cl_2$ |
| H | $CH_3CH_2$ | $(CH_3)_2CH$ | $Br_2$ |
| H | $CH_3CH_2CH_2$ | $CF_3$ | $Cl_2$ |
| H | $CH_3CH_2CH_2$ | $CF_3$ | $Br_2$ |
| H | $CH_3CH_2CH_2$ | $CH_3CH_2CH_2$ | $Cl_2$ |
| H | $CH_3CH_2CH_2$ | $CH_3CH_2CH_2$ | $Br_2$ |
| H | $CH_3CH_2CH_2$ | $(CH_3)_2CH$ | $Cl_2$ |
| H | $CH_3CH_2CH_2$ | $(CH_3)_2CH$ | $Br_2$ |

TABLE 1-continued

| $(R^1)_a$ | $R^2$ | $R^3$ | $M_2$ |
|---|---|---|---|
| H | $(CH_3)_2CH$ | $CF_3$ | $Cl_2$ |
| H | $(CH_3)_2CH$ | $CF_3$ | $Br_2$ |
| H | $(CH_3)_2CH$ | $(CH_3)_2CH$ | $Cl_2$ |
| H | $(CH_3)_2CH$ | $(CH_3)_2CH$ | $Br_2$ |
| H | $CF_3$ | $CF_3$ | $Cl_2$ |
| H | $CF_3$ | $CF_3$ | $Br_2$ |
| H | $OCH_3$ | $OCH_3$ | $Cl_2$ |
| H | $OCH_3$ | $OCH_3$ | $Br_2$ |
| 2-F | Cl | Cl | $Cl_2$ |
| 2-F | Cl | Cl | $Br_2$ |
| 2-F | Cl | $CH_3$ | $Cl_2$ |
| 2-F | $CH_3CH_2$ | $CH_3CH_2$ | $Cl_2$ |
| 2-F | $CH_3CH_2$ | $CH_3CH_2$ | $Br_2$ |
| 2-F | $CH_3CH_2$ | $CH_3$ | $Cl_2$ |
| 2-F | $CH_3CH_2$ | $CH_3$ | $Br_2$ |
| 2-Cl | Cl | Cl | $Cl_2$ |
| 2-Cl | Cl | Cl | $Br_2$ |
| 2-Cl | Cl | $CH_3$ | $Cl_2$ |
| 2-Cl | $CH_3CH_2$ | $CH_3CH_2$ | $Cl_2$ |
| 2-Cl | $CH_3CH_2$ | $CH_3CH_2$ | $Br_2$ |
| 2-Cl | $CH_3CH_2$ | $CH_3$ | $Cl_2$ |
| 2-Cl | $CH_3CH_2$ | $CH_3$ | $Br_2$ |
| 2-Br | Cl | Cl | $Cl_2$ |
| 2-Br | $CH_3CH_2$ | $CH_3CH_2$ | $Cl_2$ |
| 2-Br | $CH_3CH_2$ | $CH_3$ | $Cl_2$ |
| 2-$CH_3$ | Cl | Cl | $Cl_2$ |
| 2-$CH_3$ | $CH_3CH_2$ | $CH_3CH_2$ | $Cl_2$ |
| 2-$CH_3$ | $CH_3CH_2$ | $CH_3$ | $Cl_2$ |
| 2,6-$Cl_2$ | Cl | Cl | $Cl_2$ |
| 2,6-$Cl_2$ | $CH_3CH_2$ | $CH_3CH_2$ | $Cl_2$ |
| 2,6-$Cl_2$ | $CH_3CH_2$ | $CH_3$ | $Cl_2$ |
| 2-$C_2H_5$ | Cl | Cl | $Cl_2$ |
| 2-$C_2H_5$ | $CH_3CH_2$ | $CH_3CH_2$ | $Cl_2$ |
| 2-$C_2H_5$ | $CH_3CH_2$ | $CH_3$ | $Cl_2$ |
| 2-n-$C_3H_7$ | Cl | Cl | $Cl_2$ |
| 2-n-$C_3H_7$ | $CH_3CH_2$ | $CH_3CH_2$ | $Cl_2$ |
| 2-n-$C_3H_7$ | $CH_3CH_2$ | $CH_3$ | $Cl_2$ |

TABLE 2

| $R^6$— |
|---|
| H— |
| $CH_3$— |
| $CH_3CH_2$— |
| $CH_3CH_2CH_2$— |
| $(CH_3)_2CH$— |
| $CH_3CH_2CH_2CH_2$— |
| $(CH_3)_2CHCH_2$— |
| $CH_3CH_2CH(CH_3)$— |
| $(CH_3)_3C$— |
| $CH_3CH_2CH_2CH_2CH_2$— |
| $(CH_3)_2CHCH_2CH_2$— |
| $CH_3CH_2CH(CH_3)CH_2$— |
| $(CH_3)_3CCH_2$— |
| $CH_3CH_2CH_2CH(CH_3)$— |
| $(CH_3)_2CHCH(CH_3)$— |
| $CH_3CH_2C(CH_3)_2$— |
| $(CH_3)_2CH)_2CH$— |
| $CH_3CH_2CH_2CH_2CH_2CH_2$— |
| $CH_3CH_2CH_2CH_2CH(CH_3)$— |
| $CH_3CH_2CH_2CH(CH_2CH_3)$— |
| $CH_3CH_2CH_2C(CH_3)_2$— |
| $(CH_3)_2CHC(CH_3)_2$— |
| $(CH_3CH_2)_2C(CH_3)$— |
| $CH_3CH_2CH_2CH_2CH_2CH_2CH_2$— |
| $CH_3CH_2CH_2CH_2CH_2CH(CH_3)$— |
| $CH_3CH_2CH_2CH_2CH(CH_2CH_3)$— |
| $(CH_3CH_2CH_2)_2CH$— |
| $CH_3CH_2CH_2CH_2C(CH_3)_2$— |
| $(CH_3)_3CC(CH_3)_2$— |
| $CH_3CH_2CH_2CH_2CH_2CH_2CH_2CH_2$— |
| $CH_3CH_2CH_2CH_2CH_2CH_2C(CH_3)_2$— |
| $(CH_3)_3CCH_2C(CH_3)_2$— |
| $CH_2=CHCH_2$— |
| $CH_3CH=CHCH_2$— |
| $CH_2=C(CH_3)CH_2$— |
| $CH_2=CHCH(CH_3)$— |
| $(CH_3)_2C=CHCH_2$— |
| $CH_3CH_2CH=CHCH_2$— |
| $CH_3CH_2CH_2CH=CHCH_2$— |
| $(CH_3)_2CHCH=CHCH_2$— |
| $CH_2=C(CH_2CH_3)CH_2$— |
| $CH_2=C(CH_2CH_2CH_3)CH_2$— |
| $CH_2=C(CH(CH_3)_2)CH_2$— |
| $CH_2=CHCH(CH_2CH_3)$— |
| $CH_2=CHCH(CH_2CH_2CH_3)$— |
| $CH_2=CHCH(CH(CH_3)_2)$— |
| $CH_2=CHCH_2CH_2$— |
| $CH_2=CHCH_2CH_2CH_2$— |
| $CH_2=CHCH_2CH_2CH_2CH_2$— |
| $(CH_3)_2C=CHCH_2CH_2$— |
| $HC≡CCH_2$— |
| $CH_3C≡CCH_2$— |
| $HC≡CCH(CH_3)$— |
| $HC≡CCH_2CH_2$— |
| $CH_3C≡CCH_2CH_2$— |
| $HC≡CCH_2CH(CH_3)$— |
| $CH_3CH_2C≡CCH_2$— |
| $HC≡CCH(CH_2CH_3)$— |
| $HC≡CCH_2CH_2CH_2$— |
| $HC≡CCH_2CH_2CH_2CH_2$— |
| $CH_2FCH_2$— |
| $CHF_2CH_2$— |
| $CF_3CH_2$— |
| $CH_2ClCH_2$— |
| $CHCl_2CH_2$— |
| $CCl_3CH_2$— |
| $CH_2BrCH_2$— |
| $CH_2ICH_2$— |
| $CHBr_2CH_2$— |
| $CBr_3CH_2$— |
| $CFCl_2CH_2$— |
| $CFBr_2CH_2$— |
| $BrCF_2CF_2$— |
| $CHF_2CF_2$— |
| $CHFClCF_2$— |
| $CH_2FCH_2CH_2$— |
| $CHF_2CH_2CH_2$— |
| $CF_3CH_2CH_2$— |
| $CH_2ClCH_2CH_2$— |
| $CHCl_2CH_2CH_2$— |
| $CCl_3CH_2CH_2$— |
| $CH_2BrCH_2CH_2$— |
| $CH_2ICH_2CH_2$— |
| $CHBr_2CH_2CH_2$— |
| $CBr_3CH_2CH_2$— |
| $CF_3CF_2CH_2$— |
| $CHF_2CF_2CH_2$— |
| $CH_3CHFCH_2$— |
| $CF_3CHFCF_2$— |
| $CH_3CHClCH_2$— |
| $CH_3CHBrCH_2$— |
| $CH_2ClCHClCH_2$— |
| $CH_2BrCHBrCH_2$— |
| $CH_2FCH(CH_3)$— |
| $CH_2ClCH(CH_3)$— |
| $CH_2BrCH(CH_3)$— |
| $(CH_2F)_2CH$— |
| $(CH_2Cl)_2CH$— |
| $(CH_2Br)_2CH$— |
| $CF_3CH(CH_3)$— |
| $CH_2FCH_2CH_2CH_2$— |
| $CH_2ClCH_2CH_2CH_2$— |
| $CH_2BrCH_2CH_2CH_2$— |
| $CH_3CHClCH_2CH_2$— |
| $CH_3CHBrCH_2CH_2$— |
| $CH_2ClCHClCH_2CH_2$— |
| $CH_2BrCHBrCH_2CH_2$— |
| $CF_3CF_2CF_2CH_2$— |

TABLE 2-continued

R⁶—

CF₃CF₂CH₂CH₂—
CF₃CHFCF₂CH₂—
CHF₂CF₂CF₂CH₂—
CF₃CH₂CH₂CH₂—
CH₂ClCHClCHClCH₂—
CBrF₂CF₂CH₂CH₂—
CH₂ClCH₂CH(CH₃)—
CH₂BrCH₂CH(CH₃)—
CH₃CHClCH(CH₃)—
CH₃CHBrCH(CH₃)—
(CH₃)₂CClCH₂—
(CH₃)₂CBrCH₂—
CH₃CH₂CHClCH₂—
CH₃CH₂CHBrCH₂—
CH₂FCH₂CH₂CH₂CH₂—
CH₂ClCH₂CH₂CH₂CH₂—
CH₂BrCH₂CH₂CH₂CH₂—
CH₃CHClCH₂CH₂CH₂—
CH₃CHBrCH₂CH₂CH₂—
CH₃C(CH₂Cl)₂CH₂—
CH₃C(CH₂Br)₂CH₂—
CF₃CF₂CF₂CF₂CH₂—
CF₃CH₂CH₂CH₂CH₂—
CH₂FCH₂CH₂CH₂CH₂CH₂—
CH₂ClCH₂CH₂CH₂CH₂CH₂—
CH₂BrCH₂CH₂CH₂CH₂CH₂—
C(CH₃)₃CHClCH₂—
C(CH₃)₃CHBrCH₂—
CF₃CF₂CF₂CF₂CF₂CH₂—
CF₃CH₂CH₂CH₂CH₂CH₂—
CHCl=CHCH₂—
CH₃CCl=CHCH₂—
CH₃CH₂CCl=CHCH₂—
CH₃CH₂CH₂CCl=CHCH₂—
CH(CH₃)₂CCl=CHCH₂—
CF₃CCl=CHCH₂—
CClF₂CCl=CHCH₂—
CBrF₂CCl=CHCH₂—
CF₃CF₂CCl=CHCH₂—
CF₃CF₂CF₂CCl=CHCH₂—
CHCl=C(CH₃)CH₂—
CH₃CCl=C(CH₃)CH₂—
CH₃CH₂CCl=C(CH₃)CH₂—
CF₃CCl=C(CH₃)CH₂—
CF₃CF₂CCl=C(CH₃)CH₂—
CHCl=C(CH₂CH₃)CH₂—
CH₃CCl=C(CH₂CH₃)CH₂—
CF₃CCl=C(CH₂CH₃)CH₂—
CHCl=C(CH₂CH₂CH₂CH₃)CH₂—
CHCl=C(CH(CH₃)₂)CH₂—
CHCl=C(CF₃)CH₂—
CH₃CCl=C(CF₃)CH₂—
CF₃CCl=C(CF₃)CH₂—
CH₂=CClCH₂—
CH₃CH=CClCH₂—
CH₃CH₂CH=CClCH₂—
CH₃CH₂CH₂CH=CClCH₂—
CH(CH₃)₂CH=CClCH₂—
CH₃CH₂C(CH₃)=CClCH₂—
CHBr=CHCH₂—
CH₃CBr=CHCH₂—
CH₃CH₂CBr=CHCH₂—
CH₃CH₂CH₂CBr=CHCH₂—
CH(CH₃)₂CBr=CHCH₂—
CF₃CBr=CHCH₂—
CF₃CF₂CBr=CHCH₂—
CHBr=C(CH₃)CH₂—
CH₃CBr=C(CH₃)CH₂—
CH₃CH₂CBr=C(CH₃)CH₂—
CF₃CBr=C(CH₃)CH₂—
CF₃CF₂CBr=C(CH₃)CH₂—
CHBr=C(CH₂CH₃)CH₂—
CH₃CBr=C(CH₂CH₃)CH₂—
CF₃CBr=C(CH₂CH₃)CH₂—
CHBr=C(CH₂CH₂CH₃)CH₂—
CHBr=C(CH(CH₃)₂)CH₂—
CH₂=CBrCH₂—

TABLE 2-continued

R⁶—

CH₃CH=CBrCH₂—
CH₃CH₂CH=CBrCH₂—
CH₃CH₂CH₂CH=CBrCH₂—
CH(CH₃)₂CH=CBrCH₂—
CH₃CH₂C(CH₃)=CBrCH₂—
CHF=CHCH₂—
CH₃CF=CHCH₂—
CH₃CH₂CF=CHCH₂—
CH₃CH₂CH₂CF=CHCH₂—
CH(CH₃)₂CF=CHCH₂—
CF₃CF=CHCH₂—
CF₃CF₂CF₂CF=CHCH₂—
CHF=C(CH₃)CH₂—
CH₃CF=C(CH₃)CH₂—
CH₃CH₂CF=C(CH₃)CH₂—
CF₃CF=C(CH₃)CH₂—
CF₃CF₂CF=C(CH₃)CH₂—
CHF=C(CH₂CH₃)CH₂—
CH₃CF=C(CH₂CH₃)CH₂—
CF₃CF=C(CH₂CH₃)CH₂—
CHF=C(CH₂CH₂CH₃)CH₂—
CHF=C(CH(CH₃)₂)CH₂—
CH₂=CFCH₂—
CH₃CH=CFCH₂—
CH₃CH₂CH=CFCH₂—
CH₃CH₂CH₂CH=CFCH₂—
CH(CH₃)₂CH=CFCH₂—
CH₃CH₂C(CH₃)=CFCH₂—
CCl₂=CHCH₂—
CCl₂=C(CH₃)CH₂—
CCl₂=C(CH₂CH₃)CH₂—
CCl₂=C(CH₂CH₂CH₃)CH₂—
CCl₂=C(CH(CH₃)₂)CH₂—
CCl₂=C(CF₃)CH₂—
CBr₂=CHCH₂—
CBr₂=C(CH₃)CH₂—
CBr₂=C(CH₂CH₃)CH₂—
CBr₂=C(CH₂CH₂CH₃)CH₂—
CBr₂=C(CH(CH₃)₂)CH₂—
CBr₂=C(CF₃)CH₂—
CF₂=CHCH₂—
CF₂=C(CH₃)CH₂—
CF₂=C(CH₂CH₃)CH₂—
CF₂=C(CH₂CH₂CH₃)CH₂—
CF₂=C(CH(CH₃)₂)CH₂—
CF₂=C(CF₃)CH₂—
CClBr=CHCH₂—
CClF=CHCH₂—
CBrF=CHCH₂—
CHCl=CClCH₂—
CH₃CCl=CClCH₂—
CH₃CH₂CCl=CClCH₂—
CH₃CH₂CH₂CCl=CClCH₂—
CH(CH₃)₂CCl=CClCH₂—
CHBr=CBrCH₂—
CH₃CBr=CBrCH₂—
CH₃CH₂CBr=CBrCH₂—
CH₃CH₂CH₂CBr=CBrCH₂—
CH(CH₃)₂CBr=CBrCH₂—
CCl₂=CClCH₂—
CBr₂=CBrCH₂—
CF₃CH=CHCH₂—
CF₃C(CH₃)=CHCH₂—
(CF₃)₂C=CHCH₂—
CF₃CH=C(CH₃)CH₂—
CH₂=C(CF₃)CH₂—
CHCl=CHCH₂CH₂—
CH₃CCl=CHCH₂CH₂—
CH₃CH₂CCl=CHCH₂CH₂—
CF₃CCl=CHCH₂CH₂—
CF₃CF₂CCl=CHCH₂CH₂—
CHCl=C(CH₃)CH₂CH₂—
CH₃CCl=C(CH₃)CH₂CH₂—
CF₃CCl=C(CH₃)CH₂CH₂—
CHCl=C(CH₂CH₃)CH₂CH₂—
CH₂=CClCH₂CH₂—
CH₃CH=CClCH₂CH₂—

TABLE 2-continued

| $R^6$— |
|---|
| CH$_3$CH$_2$CH=CClCH$_2$CH$_2$— |
| CHBr=CHCH$_2$CH$_2$— |
| CH$_3$CBr=CHCH$_2$CH$_2$— |
| CH$_3$CH$_2$CBr=CHCH$_2$CH$_2$— |
| CF$_3$CBr=CHCH$_2$CH$_2$— |
| CF$_3$CF$_2$CBr=CHCH$_2$CH$_2$— |
| CHBr=C(CH$_3$)CH$_2$CH$_2$— |
| CH$_3$CBr=C(CH$_3$)CH$_2$CH$_2$— |
| CF$_3$CBr=C(CH$_3$)CH$_2$CH$_2$— |
| CHBr=C(CH$_2$CH$_3$)CH$_2$CH$_2$— |
| CH$_2$=CBrCH$_2$CH$_2$— |
| CH$_3$CH$_2$=CBrCH$_2$CH$_2$— |
| CH$_3$CH$_2$CH=CBrCH$_2$CH$_2$— |
| CHF=CHCH$_2$CH$_2$— |
| CH$_3$CF=CHCH$_2$CH$_2$— |
| CH$_3$CH$_2$CF=CHCH$_2$CH$_2$— |
| CF$_3$CF=CHCH$_2$CH$_2$— |
| CF$_3$CF$_2$CF=CHCH$_2$CH$_2$— |
| CHF=C(CH$_3$)CH$_2$CH$_2$— |
| CH$_3$CF=C(CH$_3$)CH$_2$CH$_2$— |
| CF$_3$CF=C(CH$_3$)CH$_2$CH$_2$— |
| CHF=C(CH$_2$CH$_3$)CH$_2$CH$_2$— |
| CH$_2$=CFCH$_2$CH$_2$— |
| CH$_3$CH=CFCH$_2$CH$_2$— |
| CH$_3$CH$_2$CH=CFCH$_2$CH$_2$— |
| CCl$_2$=CHCH$_2$CH$_2$— |
| CCl$_2$=C(CH$_3$)CH$_2$CH$_2$— |
| CCl$_2$=C(CH$_2$CH$_3$)CH$_2$CH$_2$— |
| CBr$_2$=CHCH$_2$CH$_2$— |
| CBr$_2$=C(CH$_3$)CH$_2$CH$_2$— |
| CBr$_2$=C(CH$_2$CH$_3$)CH$_2$CH$_2$— |
| CF$_2$=CHCH$_2$CH$_2$— |
| CF$_2$=C(CH$_3$)CH$_2$CH$_2$— |
| CF$_2$=C(CH$_2$CH$_3$)CH$_2$CH$_2$— |
| CClF=CHCH$_2$CH$_2$— |
| CClF=C(CH$_3$)CH$_2$CH$_2$— |
| CClF=C(CH$_2$CH$_3$)CH$_2$CH$_2$— |
| CClF=C(CH$_3$)CH$_2$CH$_2$— |
| CClF=C(CH$_2$CH$_3$)CH$_2$CH$_2$— |
| CHCl=CClCH$_2$CH$_2$— |
| CH$_3$CCl=CClCH$_2$CH$_2$— |
| CH$_3$CH$_2$CCl=CClCH$_2$CH$_2$— |
| CHBr=CBrCH$_2$CH$_2$— |
| CH$_3$CBr=CBrCH$_2$CH$_2$— |
| CH$_3$CH$_2$CBr=CBrCH$_2$CH$_2$— |
| CCl$_2$=CClCH$_2$CH$_2$— |
| CBr$_2$=CBrCH$_2$CH$_2$— |
| CF$_3$CH=CHCH$_2$CH$_2$— |
| CF$_3$C(CH$_3$)=CHCH$_2$CH$_2$— |
| (CF$_3$)$_2$C=CHCH$_2$CH$_2$— |
| CF$_3$CH=C(CH$_3$)CH$_2$CH$_2$— |
| CHCl=CHCH$_2$CH$_2$CH$_2$— |
| CH$_3$CCl=CHCH$_2$CH$_2$CH$_2$— |
| CF$_3$CCl=CHCH$_2$CH$_2$CH$_2$— |
| CHCl=C(CH$_3$)CH$_2$CH$_2$CH$_2$— |
| CH$_2$=CClCH$_2$CH$_2$CH$_2$— |
| CH$_3$CH=CClCH$_2$CH$_2$CH$_2$— |
| CHBr=CHCH$_2$CH$_2$CH$_2$— |
| CH$_3$CBr=CHCH$_2$CH$_2$CH$_2$— |
| CF$_3$CBr=CHCH$_2$CH$_2$CH$_2$— |
| CHBr=C(CH$_3$)CH$_2$CH$_2$CH$_2$— |
| CHBr=C(CF$_3$)CH$_2$CH$_2$CH$_2$— |
| CH$_2$=CBrCH$_2$CH$_2$CH$_2$— |
| CH$_3$CH=CBrCH$_2$CH$_2$CH$_2$— |
| CCl$_2$=CHCH$_2$CH$_2$CH$_2$— |
| CCl$_2$=C(CH$_3$)CH$_2$CH$_2$CH$_2$— |
| CBr$_2$=CHCH$_2$CH$_2$CH$_2$— |
| CBr$_2$=C(CH$_3$)CH$_2$CH$_2$CH$_2$— |
| CF$_2$=CHCH$_2$CH$_2$CH$_2$— |
| CF$_2$=C(CH$_3$)CH$_2$CH$_2$CH$_2$— |
| CCl$_2$=CClCH$_2$CH$_2$CH$_2$— |
| CBr$_2$=CBrCH$_2$CH$_2$CH$_2$— |
| CF$_3$CH=CHCH$_2$CH$_2$CH$_2$— |
| ClC≡CCH$_2$— |
| BrC≡CCH$_2$— |
| FC≡CCH$_2$— |
| CF$_3$C≡CCH$_2$— |

TABLE 2-continued

| $R^6$— |
|---|
| CF$_3$CF$_2$C≡CCH$_2$— |
| CF$_3$CF$_2$CF$_2$C≡CCH$_2$— |
| ClC≡CCH$_2$CH$_2$— |
| BrC≡CCH$_2$CH$_2$— |
| CF$_3$C≡CCH$_2$CH$_2$— |
| CF$_3$CF$_2$C≡CCH$_2$CH$_2$— |
| ClC≡CCH$_2$CH$_2$CH$_2$— |
| BrC≡CCH$_2$CH$_2$CH$_2$— |
| CF$_3$C≡CCH$_2$CH$_2$CH$_2$— |
| cyclopropyl |
| cyclobutyl |
| 1-methylcyclobutyl |
| cyclopentyl |
| 1-methylcyclopentyl |
| 2-methylcyclopentyl |
| 3-methylcyclopentyl |
| cyclohexyl |
| 1-methylcyclocyclohexyl |
| 2-methylcyclocyclohexyl |
| 3-methylcyclocyclohexyl |
| 4-methylcyclocyclohexyl |
| 2-ethylcyclocyclohexyl |
| 4-ethylcyclocyclohexyl |
| 2-tert-butylcyclocyclohexyl |
| 4-tert-butylcyclocyclohexyl |
| 2,3-dimethylcyclocyclohexyl |
| 3,4-dimethylcyclocyclohexyl |
| 3,5-dimethylcyclocyclohexyl |
| 2,6-dimethylcyclocyclohexyl |
| 3,3,5,5-tetramethylmethylcyclocyclohexyl |
| menthyl |
| cycloheptyl |
| cyclopropylmethyl |
| 1-cyclopropylethyl |
| (1-methylcyclopropyl)methyl |
| (2-methylcyclopropyl)methyl |
| cyclobutylmethyl |
| cyclopentylmethyl |
| 3-cyclopentylpropyl |
| cyclohexylmethyl |
| 1-cyclohexylethyl |
| 2-cyclohexylethyl |
| 3-cyclohexylpropyl |
| 4-cyclohexylbutyl |
| 2-cyclopentenyl |
| 3-cyclopentenyl |
| 2-cyclohexenyl |
| 3-cyclohexenyl |
| 3-methyl-2-cyclohexenyl |
| 3,5,5-trimethyl-2-cyclohexenyl |
| (1-cyclopentenyl)methyl |
| (3-cyclohexenyl)methyl |
| 2-(4-methyl-3-cyclohexenyl)propyl |
| NC—CH$_2$— |
| NC—CH(CH$_3$)— |
| NC—CH$_2$CH$_2$— |
| NC—CH$_2$CH(CH$_3$)— |
| NC—CH(CH$_3$)CH$_2$— |
| NC—CH$_2$CH$_2$CH$_2$ |
| NC—CH$_2$CH$_2$CH$_2$CH$_2$ |
| NO$_2$—CH$_2$— |
| NO$_2$—CH(CH$_3$)— |
| NO$_2$—C(CH$_2$)— |
| CH$_3$OOC—CH$_2$— |
| CH$_3$OOC—CH(CH$_3$)— |
| CH$_3$OOC—C(CH$_3$)$_2$— |
| CH$_3$OOC—CH$_2$CH$_2$— |
| CH$_3$OOC—CH$_2$CH$_2$CH$_2$— |
| CH$_3$OOC—CH$_2$CH$_2$CH$_2$CH$_2$— |
| CH$_3$CH$_2$OOC—CH$_2$— |
| CH$_3$CH$_2$OOC—CH(CH$_3$)— |
| CH$_3$CH$_2$OOC—C(CH$_3$)$_2$— |
| CH$_3$CH$_2$OOC—CH$_2$CH$_2$— |
| CH$_3$CH$_2$OOC—CH$_2$CH$_2$CH$_2$— |
| CH$_3$CH$_2$OOC—CH$_2$CH$_2$CH$_2$CH$_2$— |
| (CH$_3$)$_2$CHOOC—CH$_2$— |
| (CH$_3$)$_2$CHOOC—CH(CH$_3$)— |

TABLE 2-continued

| $R^6$— |
|---|
| $(CH_3)_2CHOOC—C(CH_3)_2$— |
| $(CH_3)_2CHOOC—CH_2CH_2$— |
| $(CH_3)_2CHOOC—CH_2CH_2CH_2$— |
| $(CH_3)_2CHOOC—CH_2CH_2CH_2CH_2$— |
| $(CH_3)_3COOC—CH_2$— |
| $(CH_3)_3COOC—CH(CH_3)$— |
| $(CH_3)_3COOC—C(CH_3)_2$— |
| $(CH_3)_3COOC—CH_2CH_2$— |
| $(CH_3)_3COOC—CH_2CH_2CH_2$— |
| $(CH_3)_3COOC—CH_2CH_2CH_2CH_2$— |
| $CH_3OCH_2$— |
| $CH_3CH_2OCH_2$— |
| $CH_3OCH(CH_3)$— |
| $CH_3CH_2OCH(CH_3)$— |
| $CH_3CH_2CH_2OCH(CH_3)$— |
| $(CH_3)_2CHOCH(CH_3)$— |
| $CH_3CH_2CH_2CH_2OCH(CH_3)$— |
| $(CH_3)_2CHCH_2OCH(CH_3)$— |
| $CH_3OC(CH_3)_2$— |
| $CH_3OCH_2CH_2$— |
| $CH_3CH_2OCH_2CH_2$— |
| $(CH_3)_2CHOCH_2CH_2$— |
| $(CH_3O)_2CHCH_2$— |
| $(CH_3CH_2O)_2CHCH_2$— |
| $(CH_3CH_2CH_2O)_2CHCH_2$— |
| $(CH_3O)_2C(CH_3)CH_2$— |
| $(CH_3CH_2O)_2C(CH_3)CH_2$— |
| $(CH_3CH_2CH_2O)_2C(CH_3)CH_2$— |
| $(CH_3O)_2CHCH_2CH_2$— |
| $(CH_3CH_2O)_2CHCH_2CH_2$— |
| $(CH_3CH_2CH_2O)_2CHCH_2CH_2$— |
| $CH_3SCH_2$— |
| $CH_3SCH_2CH_2$— |
| $CH_3SCH_2CH_2CH_2$— |
| $(CH_3S)_2CHCH_2$— |
| triphenylmethyl |

TABLE 3

$R^6 = T^1\text{-}1 =$ phenyl ring with positions 2,3,4,5,6, $(R^{10})_b$ substituent (D = CH)

| $(R^{10})_b$— |
|---|
| H— |
| 2-$CH_3$— |
| 2-$CH_3CH_2$— |
| 2-$CH_3CH_2CH_2$— |
| 2-$(CH_3)_2CH$— |
| 2-$CF_3$— |
| 2-F— |
| 2-Cl— |
| 2-Br— |
| 2-$CH_3O$— |
| 3-$CH_3$— |
| 3-$CH_3CH_2$— |
| 3-$CH_3CH_2CH_2$— |
| 3-$(CH_3)_2CH$— |
| 3-$CH_3CH_2CH(CH_3)$— |
| 3-$(CH_3)_3C$— |
| 3-$CF_3$— |
| 3-F— |
| 3-Cl— |
| 3-Br— |
| 3-I— |
| 3-$CH_3O$— |
| 3-$CF_3O$— |

TABLE 3-continued $R^6 = T^1\text{-}1 =$ phenyl ring with positions 2,3,4,5,6, $(R^{10})_b$ substituent (D = CH)

| $(R^{10})_b$— |
|---|
| 4-$CH_3$— |
| 4-$CH_3CH_2$— |
| 4-$CH_3CH_2CH_2$— |
| 4-$(CH_3)_2CH$— |
| 4-$CH_3CH_2CH(CH_3)$— |
| 4-$(CH_3)_3C$— |
| 4-$CH_3CH_2C(CH_3)_2$— |
| 4-$CF_3$— |
| 4-F— |
| 4-Cl— |
| 4-Br— |
| 4-I— |
| 4-$CH_3O$— |
| 4-$CH_3CH_2O$— |
| 4-$CH_3CH_2CH_2O$— |
| 4-$(CH_3)_2CHO$— |
| 4-$CH_3CH_2CH_2CH_2O$— |
| 4-$CF_3O$— |

TABLE 4

$R^6 = T^1\text{-}1 =$ pyridine ring with positions 2,3,4,5,6, $(R^{10})_b$ substituent (D = nitrogen)

| $(R^{10})_b$— |
|---|
| H— |
| 6-$CH_3$— |
| 5-$CH_3$— |
| 3-$CH_3$— |
| 4-$CH_3$— |
| 6-Cl— |
| 5-Cl— |
| 6-Br— |
| 5-Br— |
| 6-$CF_3$— |
| 5-$CF_3$— |
| 5-$NO_2$— |
| 4,6-$(CH_3)_2$— |
| 3,5-$(CF_3)_2$— |
| 3,5-$Cl_2$— |
| 3-F—, 5-$CF_3$— |
| 3-Cl—, 5-$CF_3$— |
| 3-Br—, 5-$CF_3$— |
| 3-$NO_2$—, 5-Br— |
| 3-$NO_2$—, 4-$CH_3$— |
| 4-$CH_3$—, 5-$NO_2$— |
| 3,5,6-$F_3$— |
| 3,5,6-$F_3$—, 4-$CH_3$— |
| 3,5,6-$F_3$—, 4-Br— |
| 3,4,5,6-$F_4$— |
| 3,4,5,6-$Cl_4$— |
| 3,5-$Cl_2$—, 4,6-$F_2$— |

TABLE 5

$R^6 = T^1\text{-}1 =$ [pyridine ring with positions 2,3,4,5,6 and N, substituted with $(R^{10})_b$, 3-methyl] (D = nitrogen)

| $(R^{10})_b$— |
|---|
| H— |
| 6-CH$_3$— |
| 2-CH$_3$— |
| 5-Cl— |
| 2-Cl— |
| 2-Br— |
| 2-I—, 6-CH$_3$— |

TABLE 6

$R^6 = T^1\text{-}1 =$ [pyridine ring with positions 2,3,4,5,6 and N, substituted with $(R^{10})_b$, 4-methyl] (D = nitrogen)

| $(R^{10})_b$— |
|---|
| H— |
| 2,6-F$_2$ |

TABLE 7

$R^6 = T^1\text{-}2 =$ [phenyl ring with positions 2,3,4,5,6 substituted with $(R^{10})_b$ and $(CR^{11}R^{12})_d$] (D = CH)

| $(R^{10})_b$— | —$(CR^{11}R^{12})_d$— |
|---|---|
| H— | —CH$_2$— |
| 2-F— | —CH$_2$— |
| 3-F— | —CH$_2$— |
| 4-F— | —CH$_2$— |
| 2-Cl— | —CH$_2$— |
| 3-Cl— | —CH$_2$— |
| 4-Cl— | —CH$_2$— |
| 2-Br— | —CH$_2$— |
| 3-Br— | —CH$_2$— |
| 4-Br— | —CH$_2$— |
| 2-I— | —CH$_2$— |
| 3-I— | —CH$_2$— |
| 4-I— | —CH$_2$— |
| 2-CH$_3$— | —CH$_2$— |
| 3-CH$_3$— | —CH$_2$— |
| 4-CH$_3$— | —CH$_2$— |
| 4-CH$_3$CH$_2$— | —CH$_2$— |
| 4-CH$_3$CH$_2$CH$_2$— | —CH$_2$— |
| 4-(CH$_3$)$_2$CH— | —CH$_2$— |
| 4-CH$_3$CH$_2$CH$_2$CH$_2$— | —CH$_2$— |
| 4-(CH$_3$)$_3$C— | —CH$_2$— |
| 2-CF$_3$— | —CH$_2$— |
| 3-CF$_3$— | —CH$_2$— |
| 4-CF$_3$— | —CH$_2$— |
| 2-CH$_3$O— | —CH$_2$— |
| 3-CH$_3$O— | —CH$_2$— |
| 4-CH$_3$O— | —CH$_2$— |
| 2-CH$_3$CH$_2$O— | —CH$_2$— |
| 3-CH$_3$CH$_2$O— | —CH$_2$— |
| 4-CH$_3$CH$_2$O— | —CH$_2$— |
| 4-CH$_3$CH$_2$CH$_2$O— | —CH$_2$— |
| 4-(CH$_3$)$_2$CH—O— | —CH$_2$— |
| 4-CH$_3$CH$_2$CH$_2$CH$_2$O— | —CH$_2$— |

TABLE 7-continued $R^6 = T^1\text{-}2 =$ [phenyl ring with positions 2,3,4,5,6 substituted with $(R^{10})_b$ and $(CR^{11}R^{12})_d$] (D = CH)

| $(R^{10})_b$— | —$(CR^{11}R^{12})_d$— |
|---|---|
| 4-(CH$_3$)$_3$CO— | —CH$_2$— |
| 2-CF$_3$O— | —CH$_2$— |
| 3-CF$_3$O— | —CH$_2$— |
| 4-CF$_3$O— | —CH$_2$— |
| 4-CH$_3$OOC— | —CH$_2$— |
| 2-NO$_2$— | —CH$_2$— |
| 3-NO$_2$— | —CH$_2$— |
| 4-NO$_2$— | —CH$_2$— |
| 2-CN— | —CH$_2$— |
| 3-CN— | —CH$_2$— |
| 4-CN— | —CH$_2$— |
| 2,3-F$_2$— | —CH$_2$— |
| 2,4-F$_2$— | —CH$_2$— |
| 2,5-F$_2$— | —CH$_2$— |
| 2,6-F$_2$— | —CH$_2$— |
| 3,5-F$_2$— | —CH$_2$— |
| 3,6-F$_2$— | —CH$_2$— |
| 2,3-Cl$_2$— | —CH$_2$— |
| 2,4-Cl$_2$— | —CH$_2$— |
| 2,5-Cl$_2$— | —CH$_2$— |
| 2,6-Cl$_2$— | —CH$_2$— |
| 3,4-Cl$_2$— | —CH$_2$— |
| 3,5-Cl$_2$— | —CH$_2$— |
| 2,5-Br$_2$— | —CH$_2$— |
| 3,5-Br$_2$— | —CH$_2$— |
| 2-F—, 4-Cl— | —CH$_2$— |
| 2-Cl—, 4-F— | —CH$_2$— |
| 2-Cl—, 6-F— | —CH$_2$— |
| 3-Cl—, 4-F— | —CH$_2$— |
| 2-F—, 4-Br— | —CH$_2$— |
| 2-F—, 5-Br— | —CH$_2$— |
| 2-Br—, 4-F— | —CH$_2$— |
| 2-Br—, 5-F— | —CH$_2$— |
| 3-Br—, 4-F— | —CH$_2$— |
| 2-F—, 4-I— | —CH$_2$— |
| 2-Br—, 5-Cl— | —CH$_2$— |
| 2,3-(CH$_3$)$_2$— | —CH$_2$— |
| 2,4-(CH$_3$)$_2$— | —CH$_2$— |
| 2,5-(CH$_3$)$_2$— | —CH$_2$— |
| 2,6-(CH$_3$)$_2$— | —CH$_2$— |
| 3,4-(CH$_3$)$_2$— | —CH$_2$— |
| 3,5-(CH$_3$)$_2$— | —CH$_2$— |
| 2-Cl—, 6-CH$_3$— | —CH$_2$— |
| 2-Br—, 6-CH$_3$— | —CH$_2$— |
| 3-CH$_3$—, 5-Br— | —CH$_2$— |
| 2,3-(CH$_3$O)$_2$— | —CH$_2$— |
| 2,4-(CH$_3$O)$_2$— | —CH$_2$— |
| 2,5-(CH$_3$O)$_2$— | —CH$_2$— |
| 2,6-(CH$_3$O)$_2$— | —CH$_2$— |
| 3,4-(CH$_3$O)$_2$— | —CH$_2$— |
| 3,5-(CH$_3$O)$_2$— | —CH$_2$— |
| 3-CH$_3$CH$_2$O—, 4-CH$_3$O— | —CH$_2$— |
| 4-CH$_3$CH$_2$O—, 3-CH$_3$O— | —CH$_2$— |
| 2-CH$_3$O—, 5-Br— | —CH$_2$— |
| 3,4-(NO$_2$)$_2$— | —CH$_2$— |
| 3,5-(NO$_2$)$_2$— | —CH$_2$— |
| 2-Cl—, 5-NO$_2$— | —CH$_2$— |
| 2-NO$_2$—, 4-Cl— | —CH$_2$— |
| 2-NO$_2$—, 5-Cl— | —CH$_2$— |
| 3-NO$_2$—, 4-Cl— | —CH$_2$— |
| 2-CH$_3$—, 3-NO$_2$— | —CH$_2$— |
| 3-CH$_3$—, 4-NO$_2$— | —CH$_2$— |
| 2-NO$_2$—, 3-CH$_3$— | —CH$_2$— |
| 3-NO$_2$—, 5-CH$_3$— | —CH$_2$— |
| 3-NO$_2$—, 4-CH$_3$— | —CH$_2$— |
| 2-CH$_3$O—, 5-NO— | —CH$_2$— |
| 3-CH$_3$O—, 4-NO$_2$— | —CH$_2$— |
| 2,3,4-F$_3$— | —CH$_2$— |
| 2,4,6-(CH$_3$)$_3$— | —CH$_2$— |
| 2,3,4-(CH$_3$O)$_3$— | —CH$_2$— |

TABLE 7-continued $R^6 = T^1\text{-}2 = $ (phenyl ring with positions 2,3,4,5,6 and substituents $(R^{10})_b$)—$(CR^{11}R^{12})_d$— (D = CH)

| $(R^{10})_b$— | —$(CR^{11}R^{12})_d$— |
|---|---|
| 3,4,5-(CH$_3$O)$_3$— | —CH$_2$— |
| 2,3-(CH$_3$)$_2$—, 4-CH$_3$O— | —CH$_2$— |
| 2,4-(CH$_3$O)$_2$, 3-CH$_3$— | —CH$_2$— |
| 2,3,5,6-F$_4$— | —CH$_2$— |
| 2,3,4,5,6-F$_5$— | —CH$_2$— |
| H— | —CH(CH$_3$)— |
| H— | —CH(CH$_2$CH$_3$)— |
| H— | —CH(CH$_2$CH$_2$CH$_3$)— |
| H— | —CH(CF$_3$)— |
| 4-F— | —CH(CH$_3$)— |
| 4-Cl— | —CH(CH$_3$)— |
| 2-Br— | —CH(CH$_3$)— |
| 4-Br— | —CH(CH$_3$)— |
| 2-CF$_3$— | —CH(CH$_3$)— |
| 3-CF$_3$— | —CH(CH$_3$)— |
| 4-CF$_3$— | —CH(CH$_3$)— |
| 4-CH$_3$O— | —CH(CH$_3$)— |
| 2,4-Cl$_2$— | —CH(CH$_3$)— |
| 2,3,4,5,6-F$_5$— | —CH(CH$_3$)— |
| H— | —CH$_2$CH$_2$— |
| 2-F— | —CH$_2$CH$_2$— |
| 4-F— | —CH$_2$CH$_2$— |
| 2-Cl— | —CH$_2$CH$_2$— |
| 3-Cl— | —CH$_2$CH$_2$— |
| 4-Cl— | —CH$_2$CH$_2$— |
| 4-Br— | —CH$_2$CH$_2$— |
| 2-CH$_3$— | —CH$_2$CH$_2$— |
| 3-CH$_3$— | —CH$_2$CH$_2$— |
| 2-CF$_3$— | —CH$_2$CH$_2$— |
| 3-CF$_3$— | —CH$_2$CH$_2$— |
| 4-CH$_3$— | —CH$_2$CH$_2$— |
| 2-CH$_3$O— | —CH$_2$CH$_2$— |
| 3-CH$_3$O— | —CH$_2$CH$_2$— |
| 4-CH$_3$O— | —CH$_2$CH$_2$— |
| 2-NO$_2$— | —CH$_2$CH$_2$— |
| 3-NO$_2$— | —CH$_2$CH$_2$— |
| 4-NO$_2$— | —CH$_2$CH$_2$— |
| 2,3-(CH$_3$O)$_2$— | —CH$_2$CH$_2$— |
| 3-CH$_3$O—, 4-CH$_3$CH$_2$O— | —CH$_2$CH$_2$— |
| H— | —CH$_2$CH$_2$CH$_2$— |

In Table 7, —$(CR^{11}R^{12})_d$— is bonded at the left side to the benzene ring.

TABLE 8

$R^6 = T^1\text{-}2 = $ (pyridine ring with positions 2,3,4,5,6 and N at 1, substituents $(R^{10})_b$)—$(CR^{11}R^{12})_d$— (D = nitrogen)

| $(R^{10})_b$— | —$(CR^{11}R^{12})_d$— |
|---|---|
| H— | —CH$_2$— |
| H— | —CH$_2$CH$_2$— |
| H— | —CH$_2$CH$_2$CH$_2$— |
| H— | —CH(CH$_3$)— |
| 6-CH$_3$— | —CH$_2$— |
| 6-F— | —CH$_2$— |
| 6-F— | —CH(CH$_3$)— |
| 6-F— | —CH$_2$CH$_2$— |
| 6-Cl— | —CH$_2$— |
| 6-Cl— | —CH(CH$_3$)— |
| 6-Cl— | —CH$_2$CH$_2$— |
| 5-Cl— | —CH$_2$— |
| 3-Cl— | —CH$_2$— |
| 3-Cl— | —CH(CH$_3$)— |
| 3-Cl— | —CH$_2$CH$_2$— |
| 6-Br— | —CH$_2$— |
| 6-Br— | —CH(CH$_3$)— |
| 6-Br— | —CH$_2$CH$_2$— |
| 5-Br— | —CH$_2$— |
| 5-Br— | —CH(CH$_3$)— |
| 5-Br— | —CH$_2$CH$_2$— |
| 5-CF$_3$— | —CH$_2$— |
| 5-CF$_3$— | —CH(CH$_3$)— |
| 5-CF$_3$— | —CH$_2$CH$_2$— |
| 3,5-Cl$_2$— | —CH$_2$— |
| 3,5-Cl$_2$— | —CH(CH$_3$)— |
| 3,5-Cl$_2$— | —CH$_2$CH$_2$— |
| 3,5-(CF$_3$)$_2$— | —CH$_2$— |
| 3,5-(CF$_3$)$_2$— | —CH(CH$_3$)— |
| 3,5-(CF$_3$)$_2$— | —CH$_2$CH$_2$— |
| 4,5-(CF$_3$)$_2$— | —CH$_2$— |
| 4,5-(CF$_3$)$_2$— | —CH(CH$_3$)— |
| 4,5-(CF$_3$)$_2$— | —CH$_2$CH$_2$— |
| 3-Cl—, 5-CF$_3$— | —CH$_2$— |
| 3-Cl—, 5-CF$_3$— | —CH(CH$_3$)— |
| 3-Cl—, 5-CF$_3$— | —CH$_2$CH$_2$— |

In Table 8, —$(CR^{11}R^{12})_d$— is bonded at the left side to the pyridine ring.

TABLE 9

$R^6 = T^1\text{-}2 = $ (pyridine ring with positions 2,3,4,5,6 and N at 1, substituents $(R^{10})_b$)—$(CR^{11}R^{12})_d$— (D = nitrogen)

| $(R^{10})_b$— | —$(CR^{11}R^{12})_d$— |
|---|---|
| H— | —CH$_2$— |
| H— | —CH$_2$CH$_2$— |
| H— | —CH$_2$CH$_2$CH$_2$— |
| H— | —CH(CH$_3$)— |
| 6-CH$_3$— | —CH$_2$— |
| 6-CH$_3$— | —CH(CH$_3$)— |
| 2-CH$_3$— | —CH$_2$— |
| 2-CH$_3$— | —CH(CH$_3$)— |
| 6-Cl— | —CH$_2$— |
| 6-Cl— | —CH(CH$_3$)— |
| 5-Cl— | —CH$_2$— |
| 5-Cl— | —CH(CH$_3$)— |
| 2-Cl— | —CH$_2$— |
| 2-Cl— | —CH(CH$_3$)— |
| 6-Br— | —CH$_2$— |
| 6-Br— | —CH(CH$_3$)— |
| 5-Br— | —CH$_2$— |
| 5-Br— | —CH(CH$_3$)— |
| 6-I— | —CH$_2$— |
| 6-I— | —CH(CH$_3$)— |
| 5,6-Cl$_2$— | —CH$_2$— |
| 5,6-Cl$_2$— | —CH(CH$_3$)— |
| 2,6-Cl$_2$— | —CH$_2$— |
| 2,6-Cl$_2$— | —CH(CH$_3$)— |
| 2-Cl—, 6-CH$_3$— | —CH$_2$— |
| 2-Cl—, 6-CH$_3$— | —CH(CH$_3$)— |

In Table 9, —$(CR^{11}R^{12})_d$— is bonded at the left side to the pyridine ring.

TABLE 10

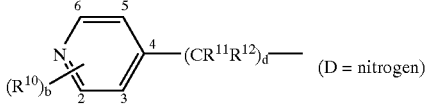

$R^6 = T^1\text{-}2 =$ (D = nitrogen)

| $(R^{10})_b$— | —$(CR^{11}R^{12})_d$— |
|---|---|
| H— | —CH$_2$— |
| H— | —CH(CH$_3$)— |
| H— | —CH$_2$CH$_2$— |
| H— | —CH$_2$CH$_2$CH$_2$— |
| 2,3,5,6-F$_4$— | —CH$_2$— |

In Table 10, —(CR$^{11}$R$^{12}$)$_d$— is bonded at the left side to the pyridine ring.

TABLE 11

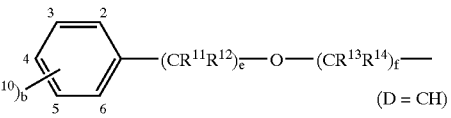

$R^6 = T^1\text{-}3 =$ (D = CH)

| $(R^{10})_b$— | —(CR$^{11}$R$^{12}$)$_e$—O—(CR$^{13}$R$^{14}$)$_f$ |
|---|---|
| H— | —O—CH$_2$CH$_2$— |
| H— | —O—CH$_2$CH$_2$CH$_2$— |
| H— | —O—CH$_2$CH$_2$CH$_2$CH$_2$— |
| 4-F— | —O—CH$_2$CH$_2$CH$_2$— |
| 4-F— | —O—CH$_2$CH$_2$CH$_2$CH$_2$— |
| 4-Cl— | —O—CH$_2$CH$_2$CH$_2$— |
| 4-Cl— | —O—CH$_2$CH$_2$CH$_2$CH$_2$— |
| 4-Br— | —O—CH$_2$CH$_2$CH$_2$— |
| 4-Br— | —O—CH$_2$CH$_2$CH$_2$CH$_2$— |
| 4-CF$_3$— | —O—CH$_2$CH$_2$CH$_2$— |
| 4-CF$_3$— | —O—CH$_2$CH$_2$CH$_2$CH$_2$— |
| 4-CH$_3$O— | —O—CH$_2$CH$_2$CH$_2$— |
| 4-CH$_3$O— | —O—CH$_2$CH$_2$CH$_2$CH$_2$— |
| 4-CF$_3$O— | —O—CH$_2$CH$_2$CH$_2$— |
| 4-CF$_3$O— | —O—CH$_2$CH$_2$CH$_2$CH$_2$— |
| H— | —CH$_2$—O—CH$_2$CH$_2$— |
| H— | —CH$_2$—O—CH$_2$CH$_2$CH$_2$— |
| H— | —CH$_2$—O—CH$_2$CH$_2$CH$_2$CH$_2$— |
| 4-F— | —CH$_2$—O—CH$_2$CH$_2$CH$_2$— |
| 4-F— | —CH$_2$—O—CH$_2$CH$_2$CH$_2$CH$_2$— |
| 4-Cl— | —CH$_2$O—CH$_2$CH$_2$CH$_2$— |
| 4-Cl— | —CH$_2$—O—CH$_2$CH$_2$CH$_2$CH$_2$— |
| 4-Br— | —CH$_2$—O—CH$_2$CH$_2$CH$_2$— |
| 4-Br— | —CH$_2$—O—CH$_2$CH$_2$CH$_2$CH$_2$— |
| 4-CF$_3$— | —CH$_2$—O—CH$_2$CH$_2$CH$_2$— |
| 4-CF$_3$— | —CH$_2$—O—CH$_2$CH$_2$CH$_2$CH$_2$— |
| 4-CH$_3$O— | —CH$_2$—O—CH$_2$CH$_2$CH— |
| 4-CH$_3$O— | —CH$_2$—O—CH$_2$CH$_2$CH$_2$CH$_2$— |

In Table 11, —(CR$^{11}$R$^{12}$)$_e$—O—(CR$^{13}$R$^{14}$)$_f$— is bonded at the left side to the benzene ring.

TABLE 12

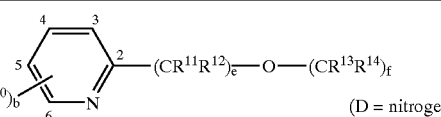

$R^6 = T^1\text{-}3 =$ (D = nitrogen)

| $(R^{10})_b$— | —(CR$^{11}$R$^{12}$)$_e$—O—(CR$^{13}$R$^{14}$)$_f$ |
|---|---|
| H— | —O—CH$_2$CH$_2$CH$_2$— |
| H— | —O—CH$_2$CH$_2$CH$_2$CH$_2$— |
| 5-Cl— | —O—CH$_2$CH$_2$CH$_2$— |

TABLE 12-continued

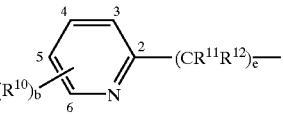

$R^6 = T^1\text{-}3 =$ (D = nitrogen)

| $(R^{10})_b$— | —(CR$^{11}$R$^{12}$)$_e$—O—(CR$^{13}$R$^{14}$)$_f$ |
|---|---|
| 5-Cl— | —O—CH$_2$CH$_2$CH$_2$CH$_2$— |
| 5-Br— | —O—CH$_2$CH$_2$CH$_2$— |
| 5-Br— | —O—CH$_2$CH$_2$CH$_2$CH$_2$— |
| 5-CF$_3$— | —O—CH$_2$CH$_2$CH$_2$— |
| 5-CF$_3$— | —O—CH$_2$CH$_2$CH$_2$CH$_2$— |
| 3,5-(CF$_3$)$_2$— | —O—CH$_2$CH$_2$CH$_2$— |
| 3,5-(CF$_3$)$_2$— | —O—CH$_2$CH$_2$CH$_2$CH$_2$— |
| 3,5-Cl$_2$— | —O—CH$_2$CH$_2$CH$_2$— |
| 3,5-Cl$_2$— | —O—CH$_2$CH$_2$CH$_2$CH$_2$— |
| 3-Cl—, 5-CF$_3$— | —O—CH$_2$CH$_2$CH$_2$— |
| 3-Cl—, 5-CF$_3$— | —O—CH$_2$CH$_2$CH$_2$CH$_2$— |
| H— | —CH$_2$—O—CH$_2$CH$_2$CH$_2$— |
| H— | —CH$_2$—O—CH$_2$CH$_2$CH$_2$CH$_2$— |

In Table 12, —(CR$^{11}$R$^{12}$)$_e$—O—(CR$^{13}$R$^{14}$)$_f$— is bonded at the left side to the pyridine ring.

TABLE 13

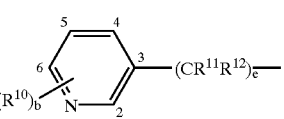

$R^6 = T^1\text{-}3 =$ (D = nitrogen)

| $(R^{10})_b$— | —(CR$^{11}$R$^{12}$)$_e$—O—(CR$^{13}$R$^{14}$)$_f$ |
|---|---|
| H— | —O—CH$_2$CH$_2$CH$_2$— |
| H— | —O—CH$_2$CH$_2$CH$_2$CH$_2$— |
| 5-Cl— | —O—CH$_2$CH$_2$CH$_2$— |
| 5-Cl— | —O—CH$_2$CH$_2$CH$_2$CH$_2$— |
| H— | —CH$_2$—O—CH$_2$CH$_2$CH$_2$— |
| H— | —CH$_2$—O—CH$_2$CH$_2$CH$_2$CH$_2$— |

In Table 13, —(CR$^{11}$R$^{12}$)$_e$—O—(CR$^{13}$R$^{14}$)$_f$— is bonded at the left side to the pyridine ring.

TABLE 14

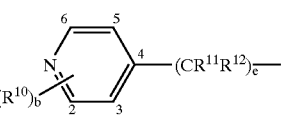

$R^6 = T^1\text{-}3 =$ (D = nitrogen)

| $(R^{10})_b$— | —(CR$^{11}$R$^{12}$)$_e$—O—(CR$^{13}$R$^{14}$)$_f$ |
|---|---|
| H— | —O—CH$_2$CH$_2$CH$_2$— |
| H— | —O—CH$_2$CH$_2$CH$_2$CH$_2$— |
| H— | —CH$_2$—O—CH$_2$CH$_2$CH$_2$— |
| H— | —CH$_2$—O—CH$_2$CH$_2$CH$_2$CH$_2$— |

In Table 14, —(CR$^{11}$R$^{12}$)$_e$—O—(CR$^{13}$R$^{14}$)$_f$— is bonded at the left side to the pyridine ring.

TABLE 15

In the case where $R^6$ is $T^1$-4:

$R^6$—

CH$_3$C(=O)—
CH$_3$CH$_2$C(=O)—
CH$_3$CH$_2$CH$_2$C(=O)—
(CH$_3$)$_2$CHC(=O)—
CH$_3$CH$_2$CH$_2$CH$_2$C(=O)—
(CH$_3$)$_2$CHCH$_2$C(=O)—
CH$_3$CH$_2$CH(CH$_3$)C(=O)—
(CH$_3$)$_3$CC(=O)—
CH$_2$=CHC(=O)—
CH$_3$CH=CHC(=O)—
CH$_2$=C(CH$_3$)C(=O)—
(CH$_3$)$_2$C=CHC(=O)—
CH$_2$FC(=O)—
CHF$_2$C(=O)—
CF$_3$C(=O)—
CH$_2$ClC(=O)—
CHCl$_2$C(=O)—
CCl$_3$C(=O)—
CH$_2$BrC(=O)—
CHBr$_2$C(=O)—
CBr$_3$C(=O)—

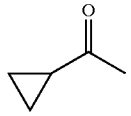

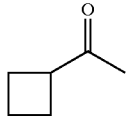

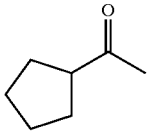

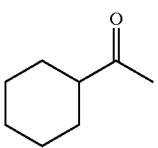

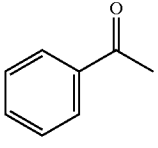

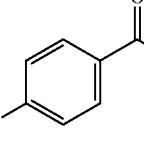

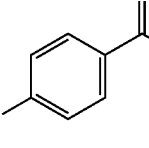

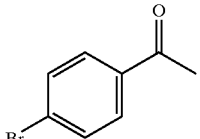

TABLE 15-continued

In the case where $R^6$ is $T^1$-4:

$R^6$—

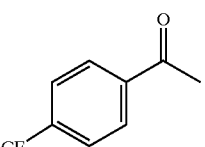

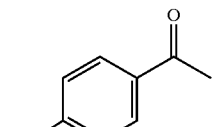

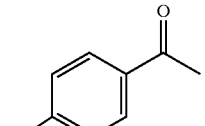

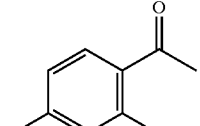

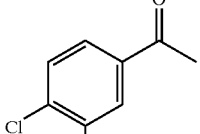

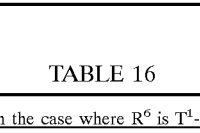

TABLE 16

In the case where $R^6$ is $T^1$-5:

$R^6$—

(CH$_3$)$_2$NC(=O)—
(CH$_3$CH$_2$)$_2$NC(=O)—
((CH$_3$)$_2$CH)$_2$NC(=O)—

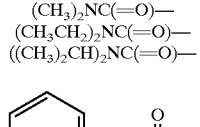

TABLE 16-continued

In the case where $R^6$ is $T^1$-5:

$R^6$—

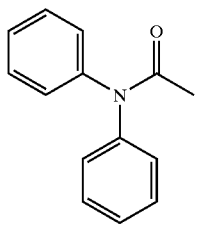

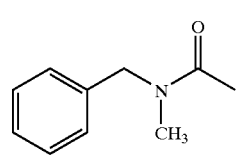

TABLE 17

In the case where $R^6$ is $T^1$-6:

$R^6$—

CH$_3$NHC(=O)—
CH$_3$CH$_2$NHC(=O)—
CH$_3$CH$_2$CH$_2$NHC(=O)—
(CH$_3$)$_2$CHNHC(=O)—
CH$_3$CH$_2$CH$_2$CH$_2$NHC(=O)—
(CH$_3$)$_3$CNHC(=O)—
CH$_2$=CHCH$_2$NHC(=O)—
CH$_2$ClCH$_2$NHC(=O)—

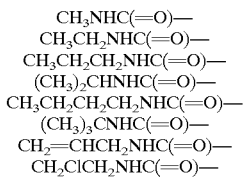

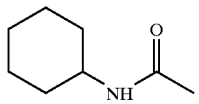

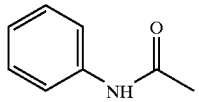

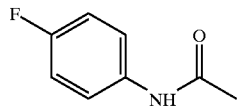

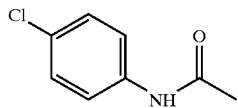

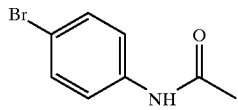

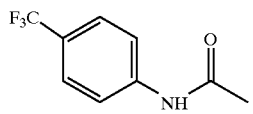

TABLE 17-continued

In the case where $R^6$ is $T^1$-6:

$R^6$—

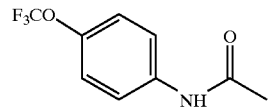

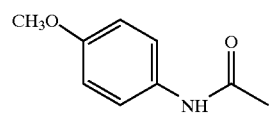

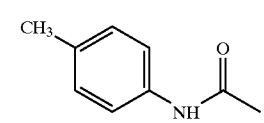

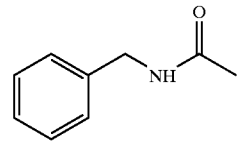

TABLE 18

In the case where $R^6$ is $T^1$-6:

$R^6$—

CH$_3$NHC(=S)—
CH$_3$CH$_2$NHC(=S)—
CH$_3$CH$_2$CH$_2$NHC(=S)—
(CH$_3$)$_2$CHNHC(=S)—
CH$_3$CH$_2$CH$_2$CH$_2$NHC(=S)—
(CH$_3$)$_3$CNHC(=S)—
CH$_2$=CHCH$_2$NHC(=S)—

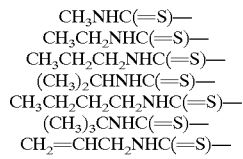

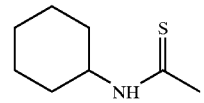

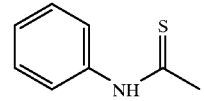

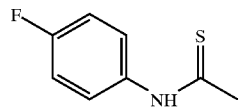

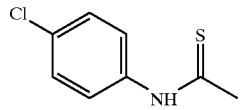

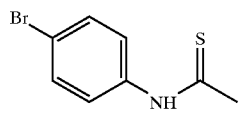

TABLE 18-continued
In the case where $R^6$ is $T^1$-6:
$R^6$—
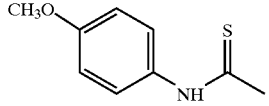
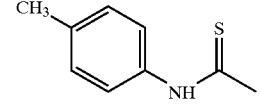
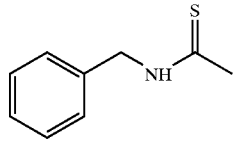
TABLE 19
In the case where $R^6$ is $T^1$-7:
$R^6$—
$CH_3S(=O)_2$—
$CH_3CH_2S(=O)_2$—
$CH_3CH_2CH_2S(=O)_2$—
$(CH_3)_2CHS(=O)_2$—
$CCl_3S(=O)_2$—
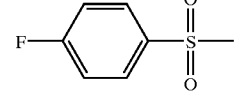
TABLE 19-continued
In the case where $R^6$ is $T^1$-7:
$R^6$—
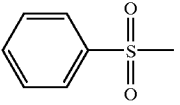
Formula 2
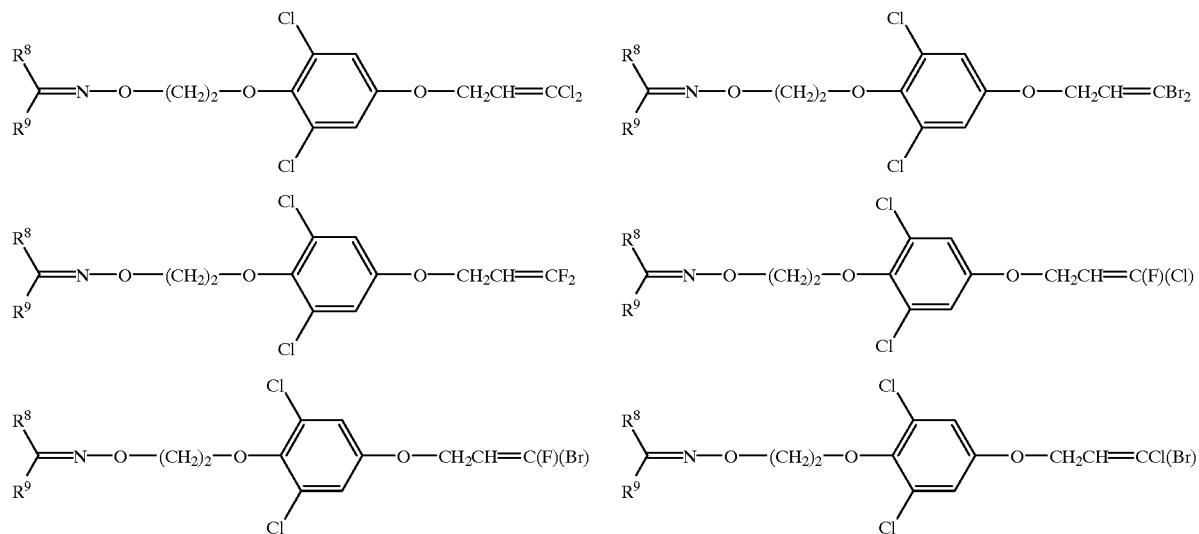

265 266
-continued
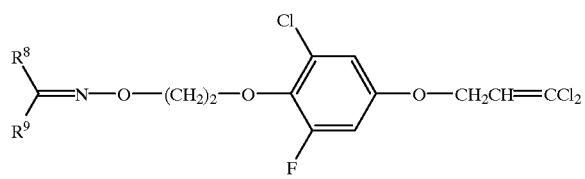 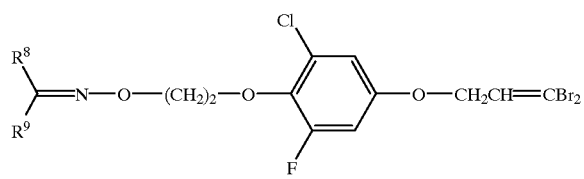
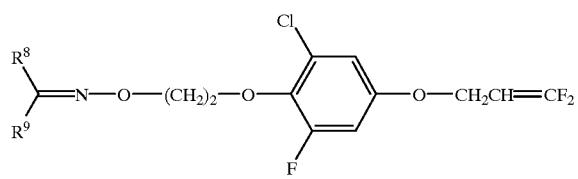 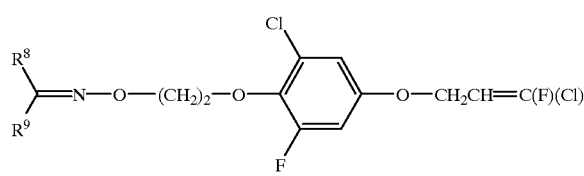
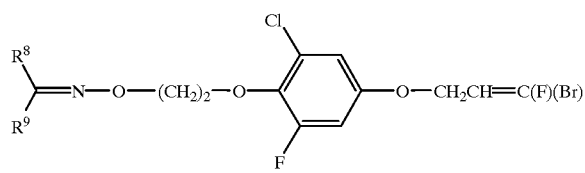 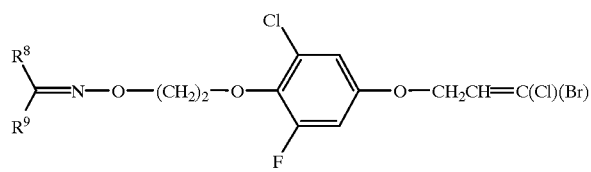
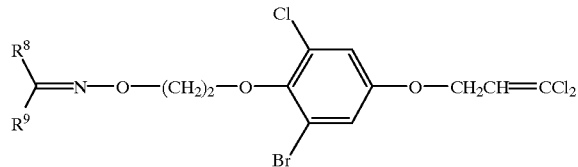 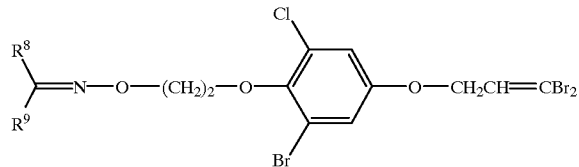
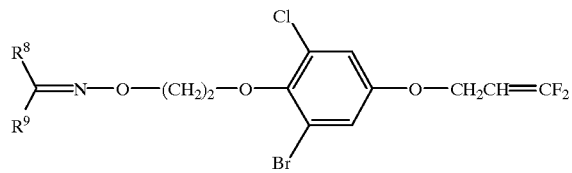 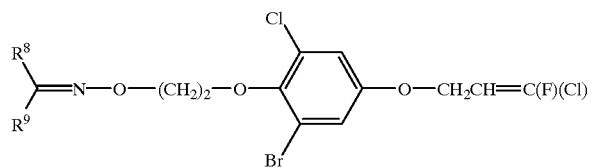
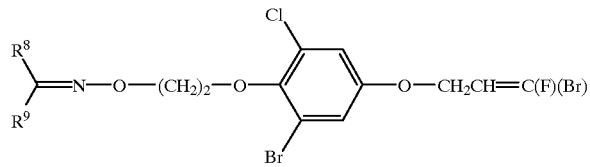 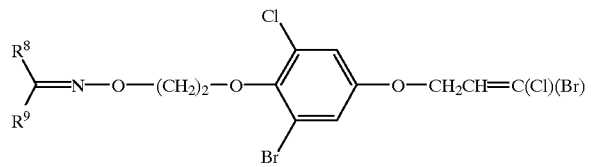
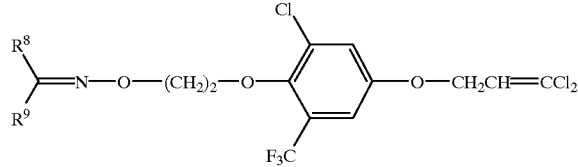 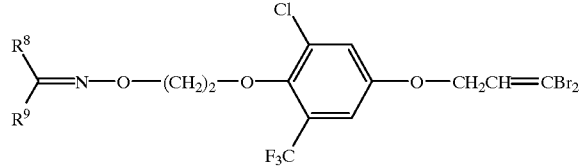
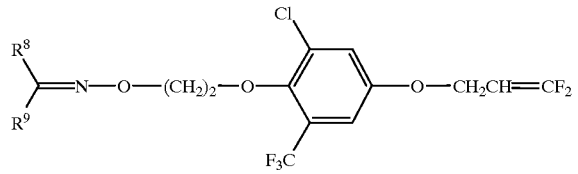 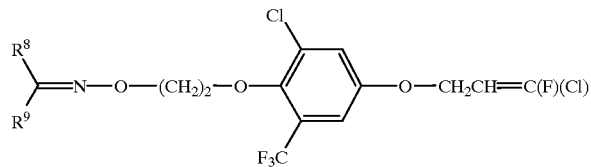
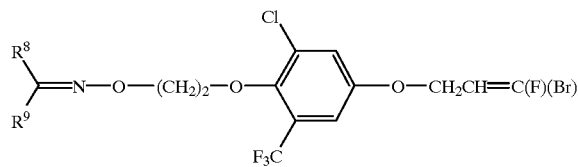 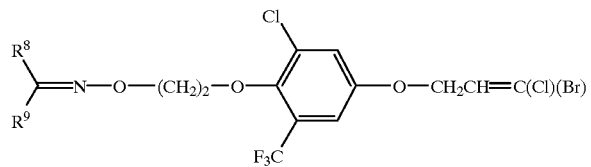

267 268
-continued
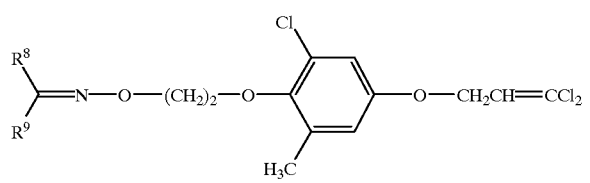
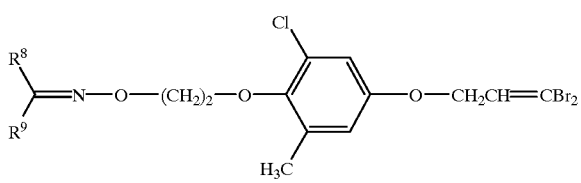
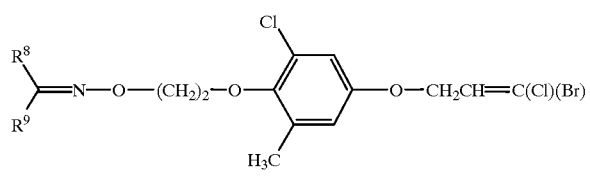
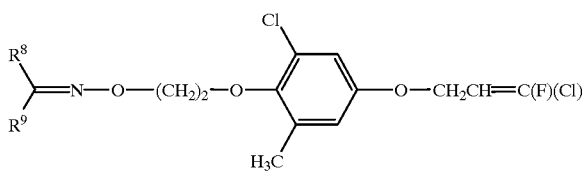
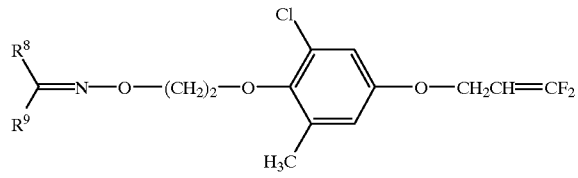
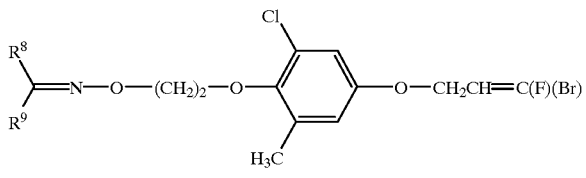
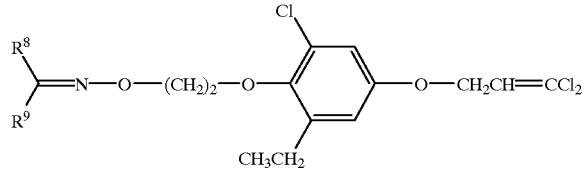
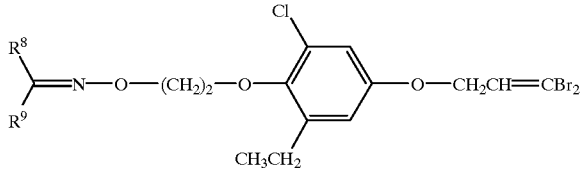
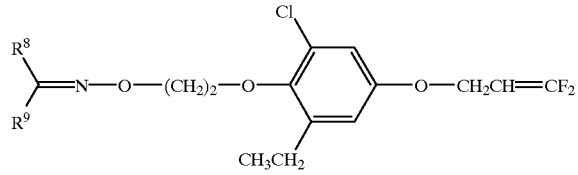
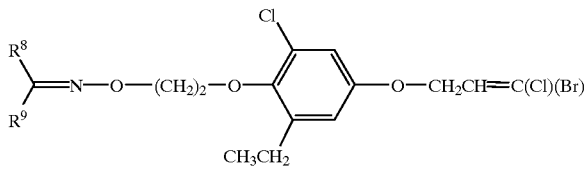
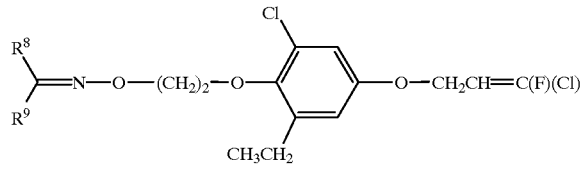
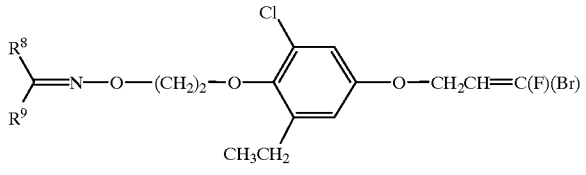
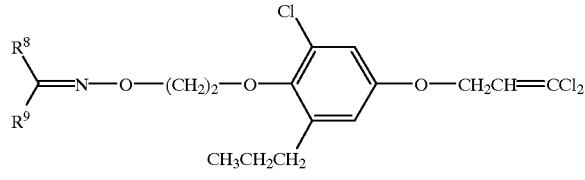
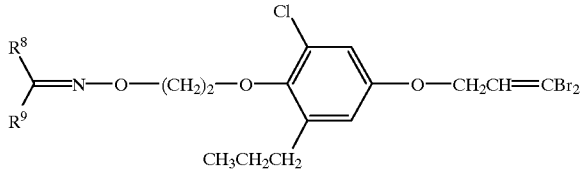
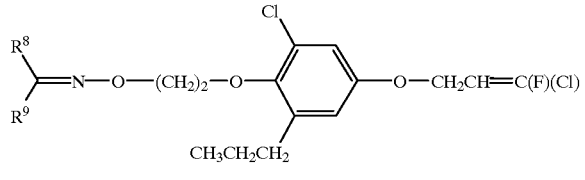
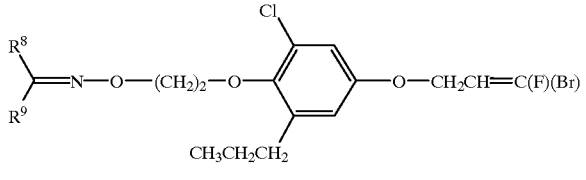
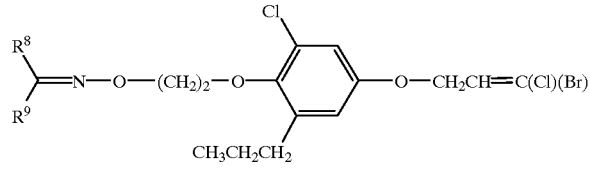
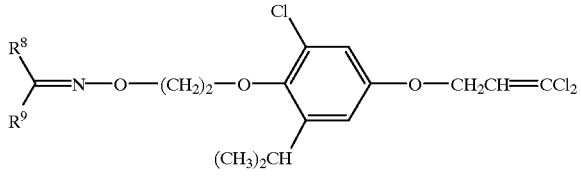

269 270
-continued
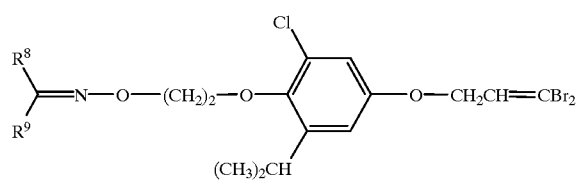
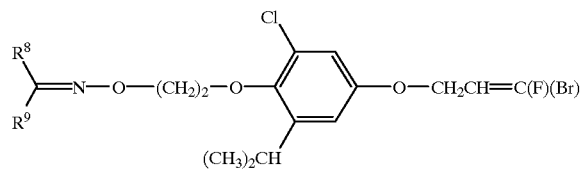
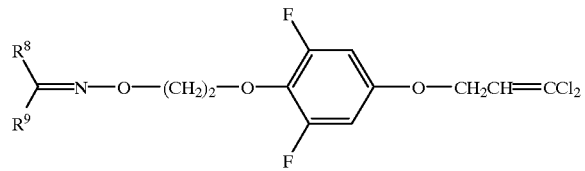
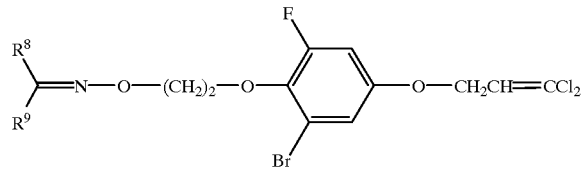
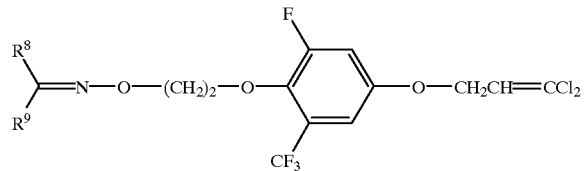
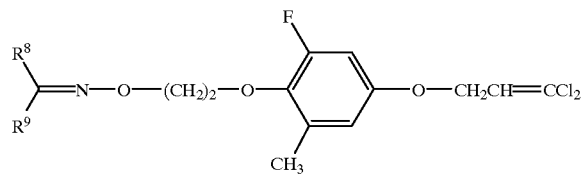
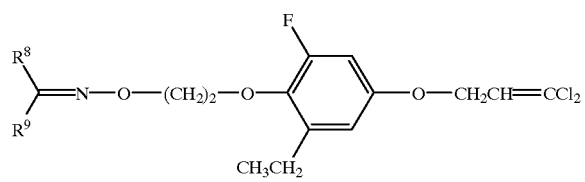
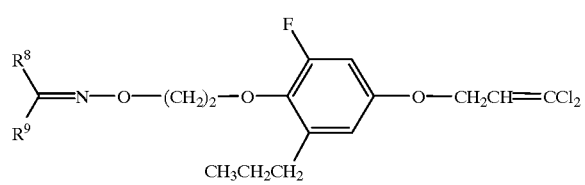
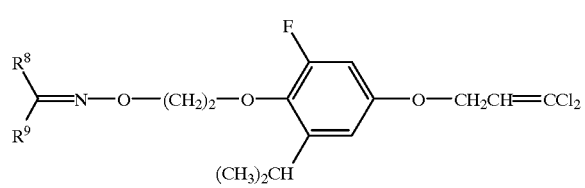
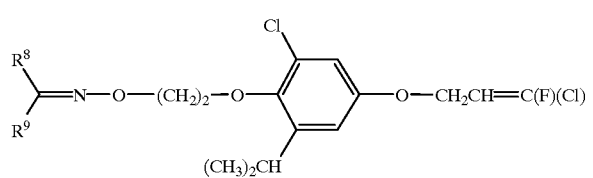
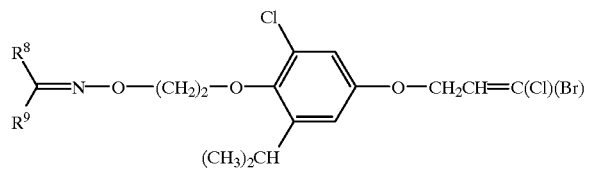
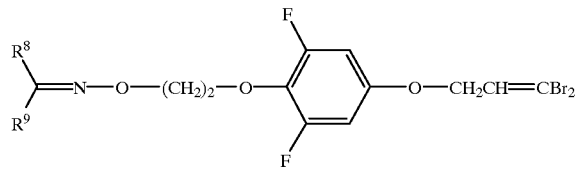
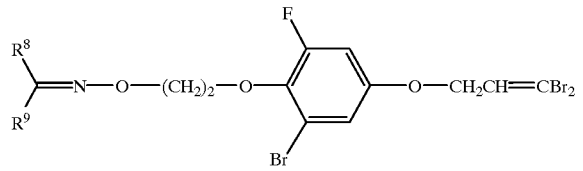
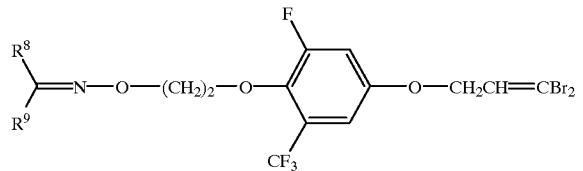
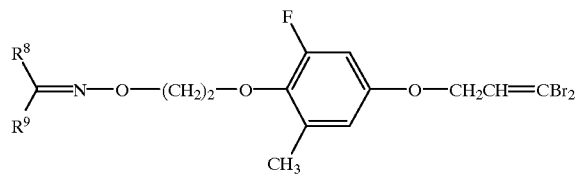
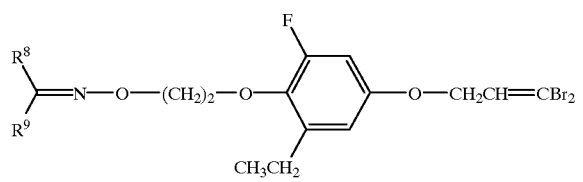
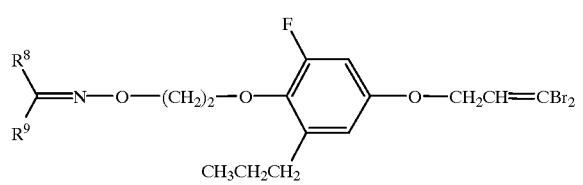
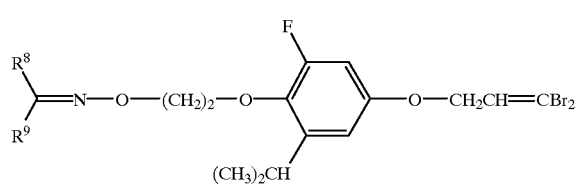

-continued
271
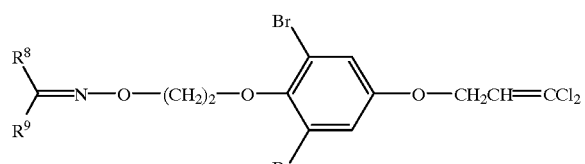
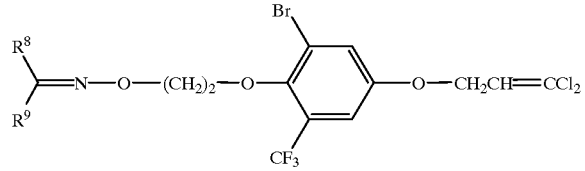
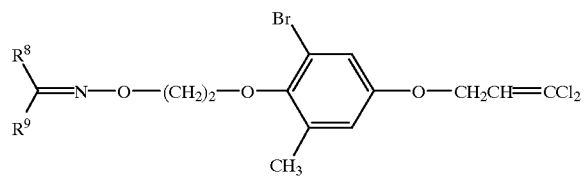
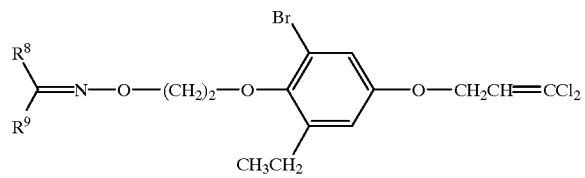
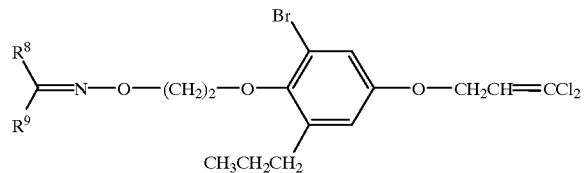
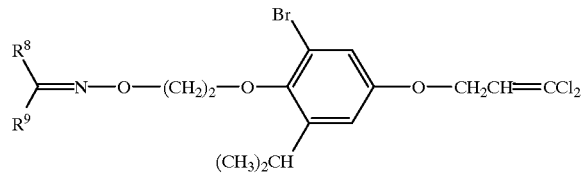
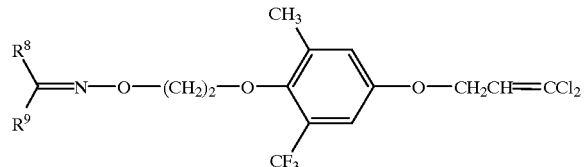
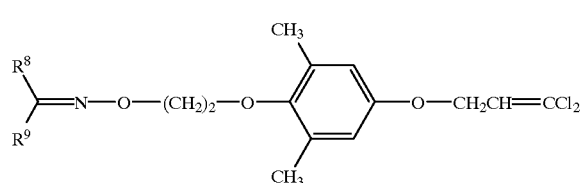
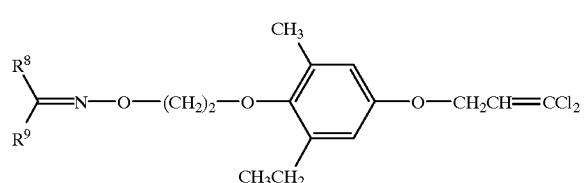
272
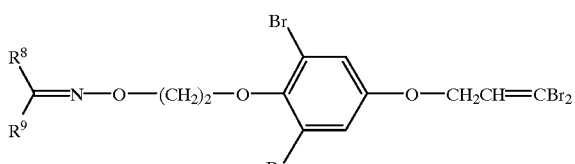
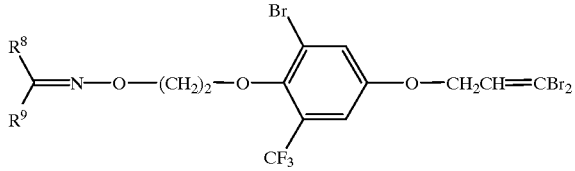
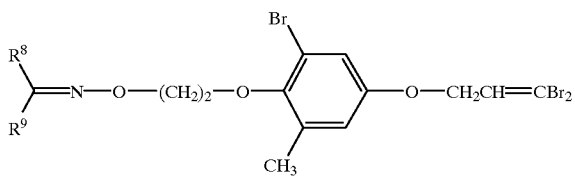
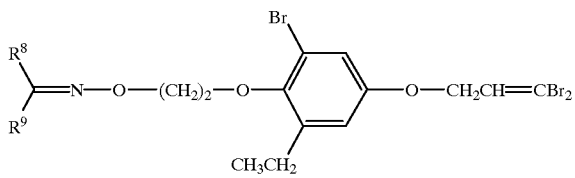
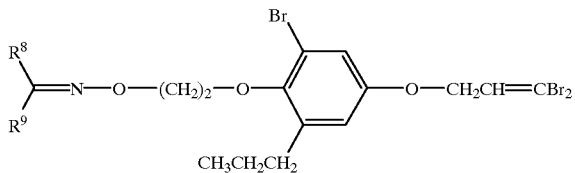
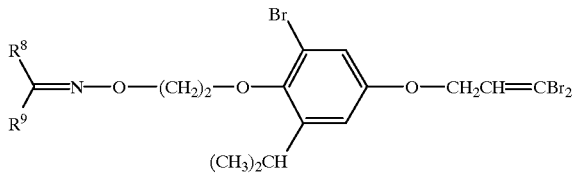
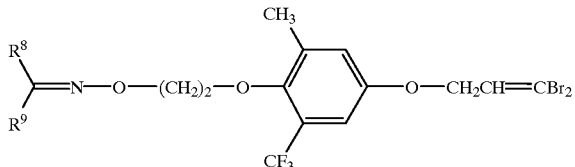
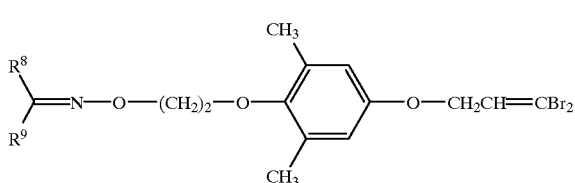
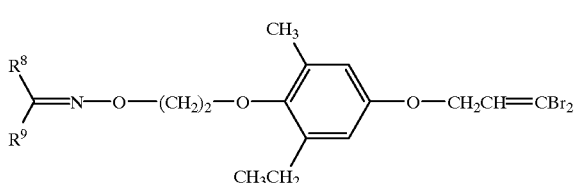

273
274
-continued
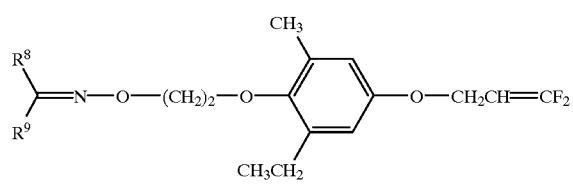
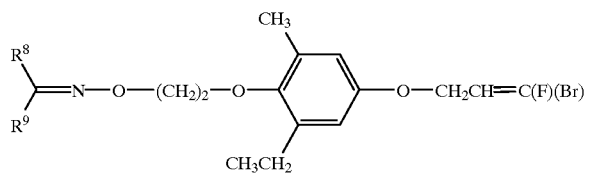
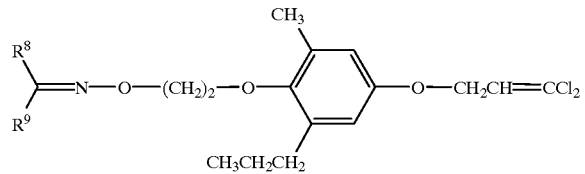
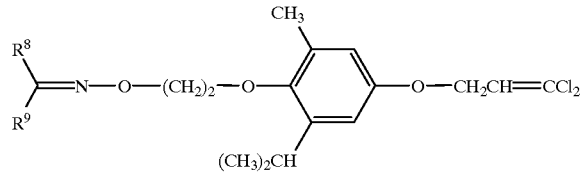
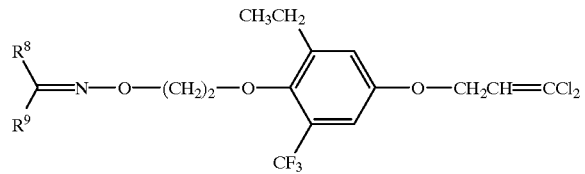
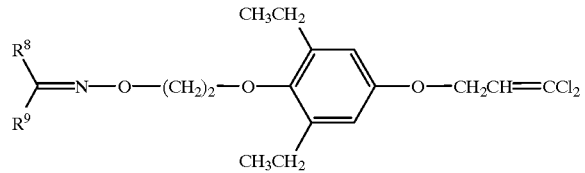
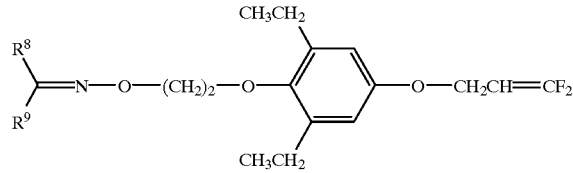
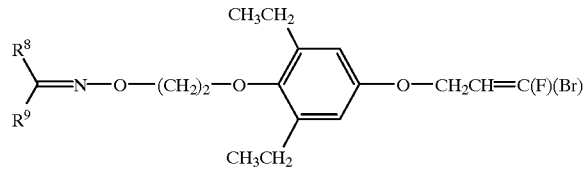
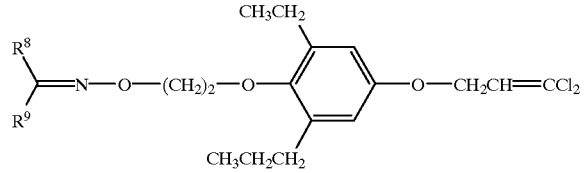
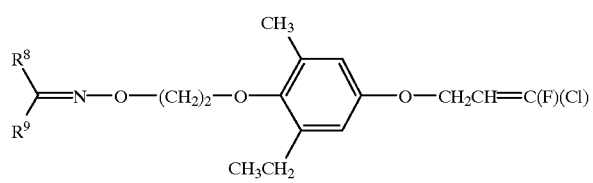
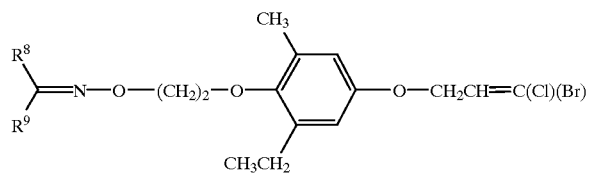
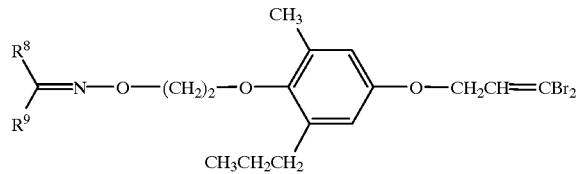
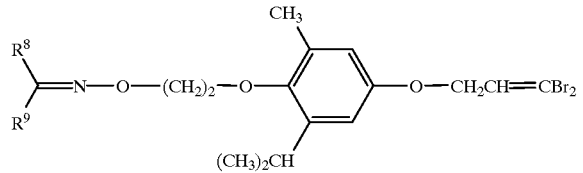
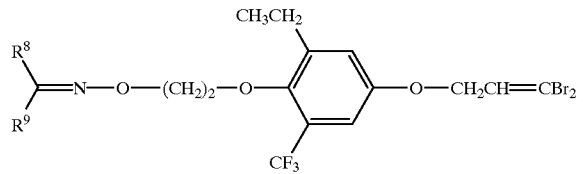
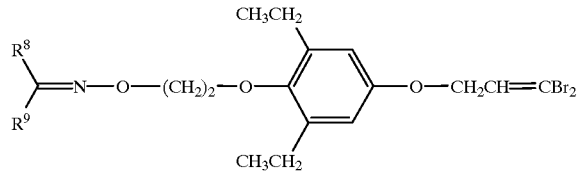
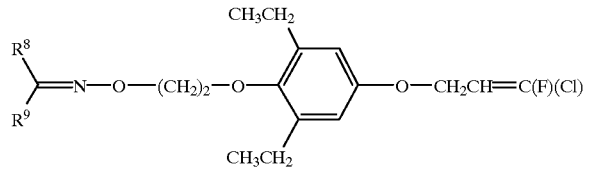
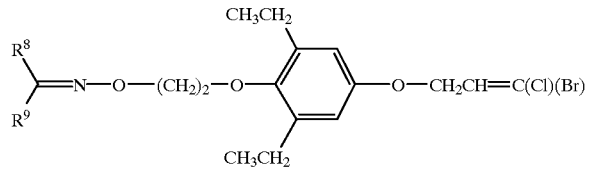
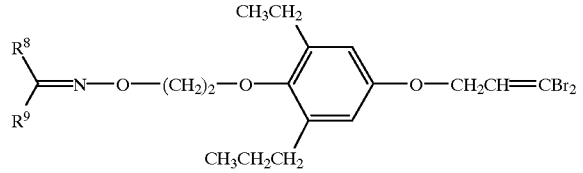

275
276
-continued
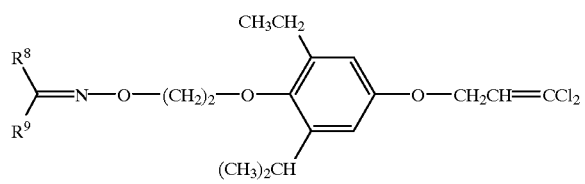
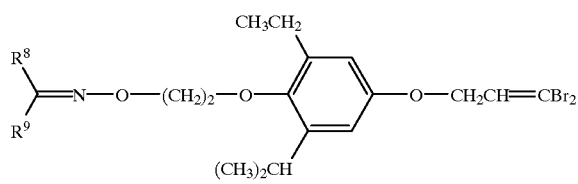
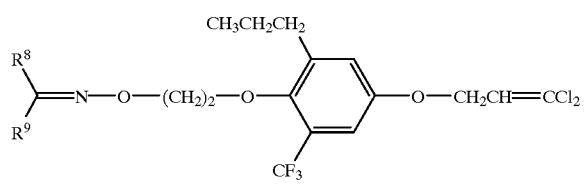
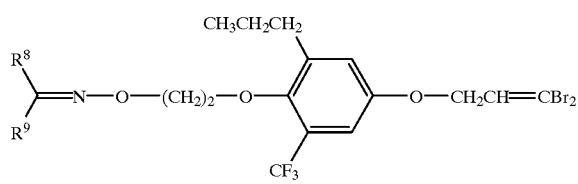
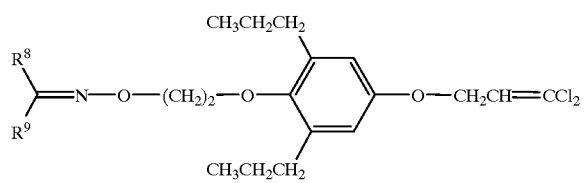
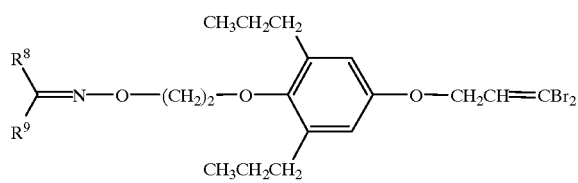
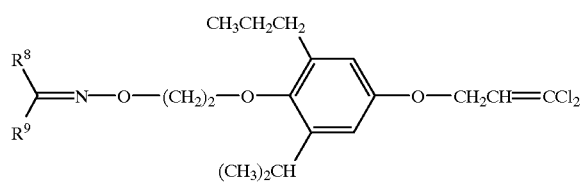
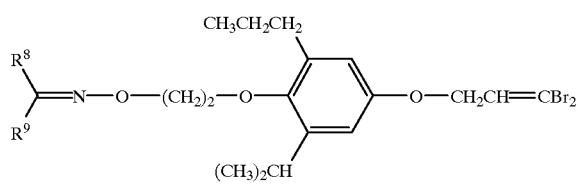
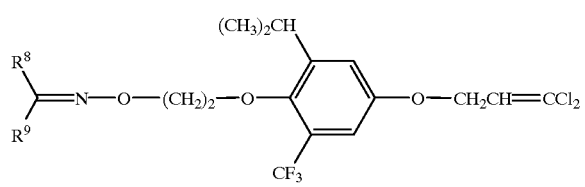
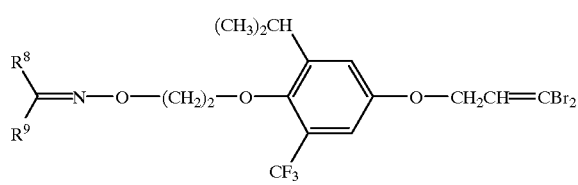
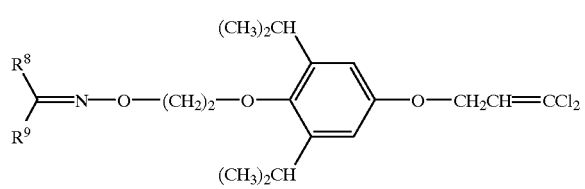
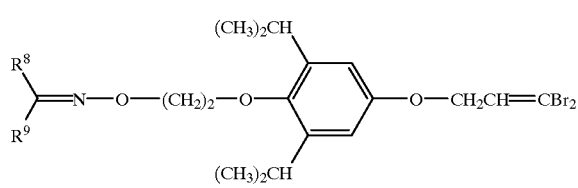
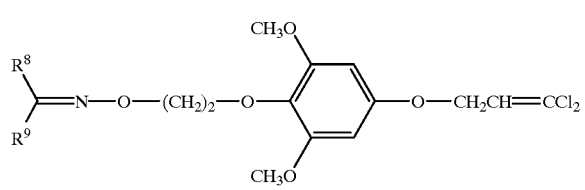
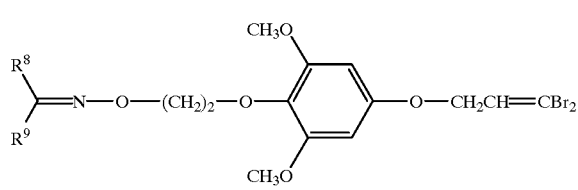
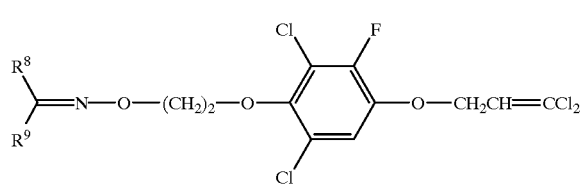
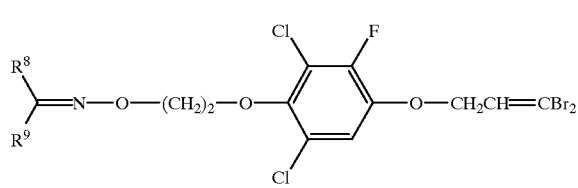
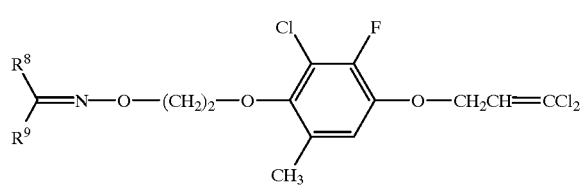
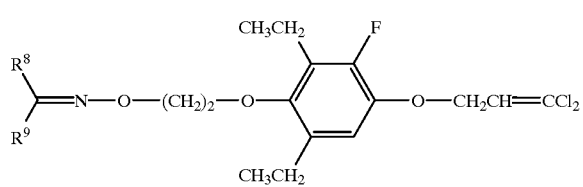

-continued
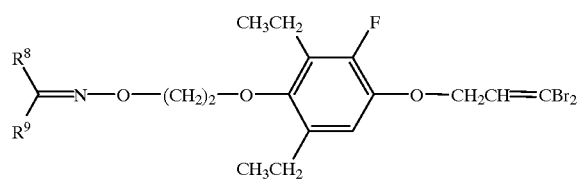
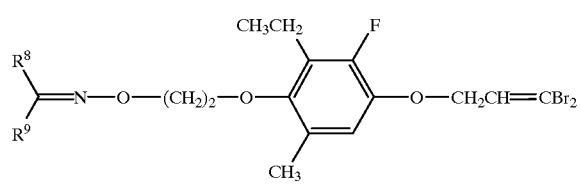
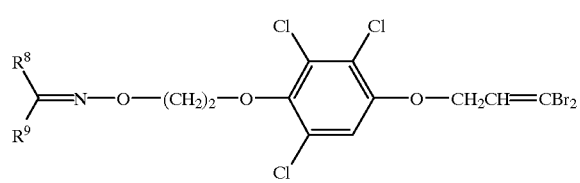
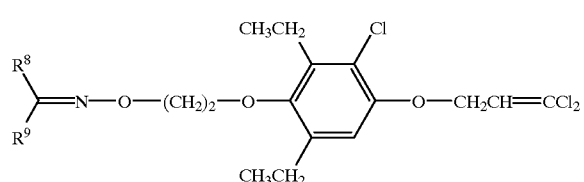
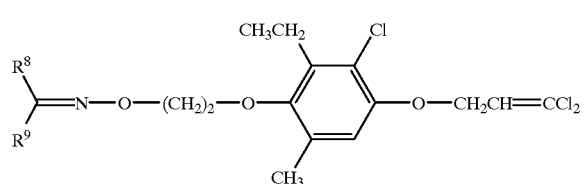
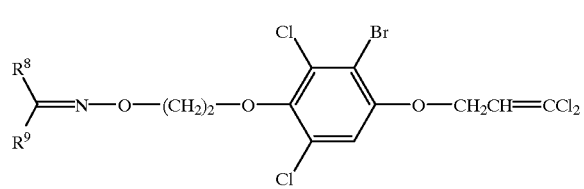
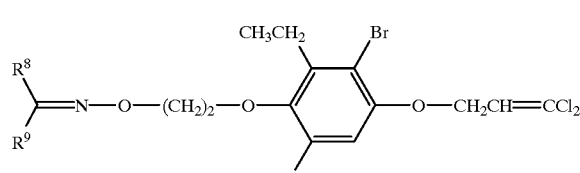
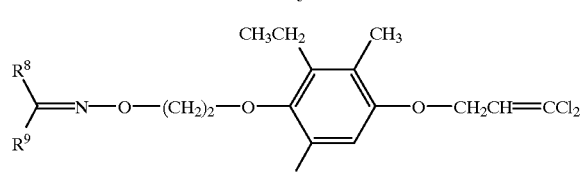
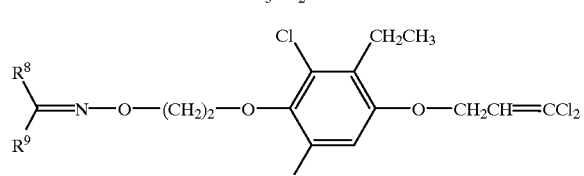
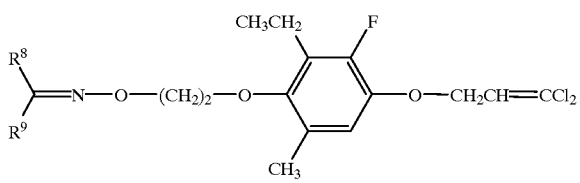
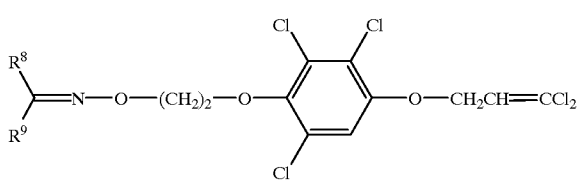
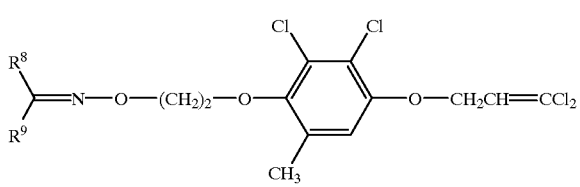
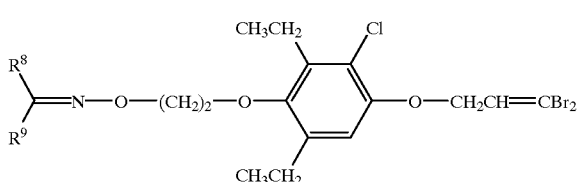
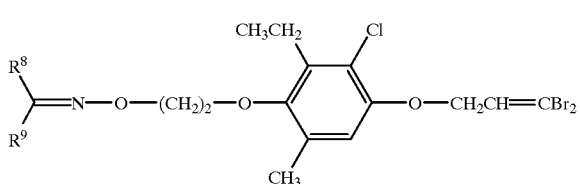
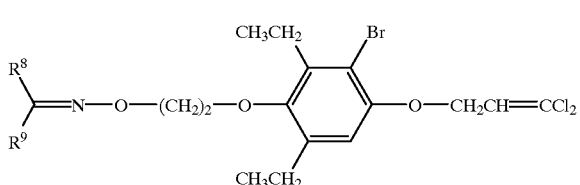
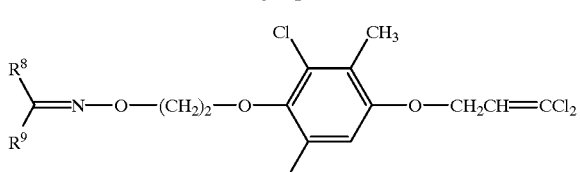
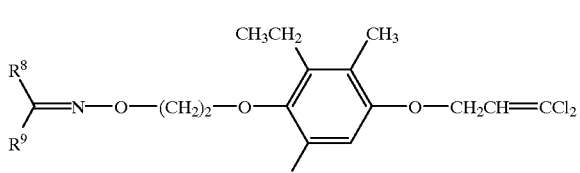
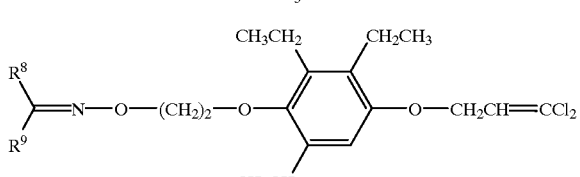

-continued 281 282
-continued
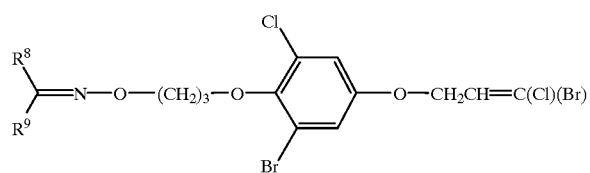 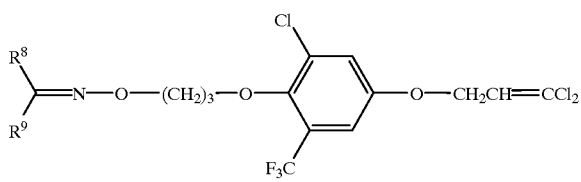
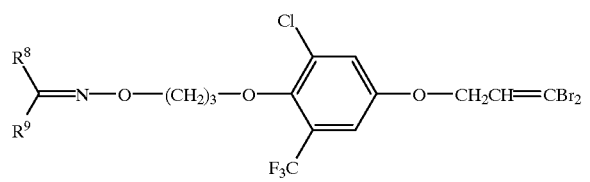 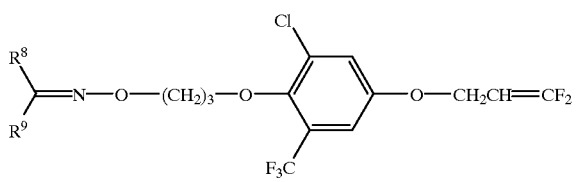
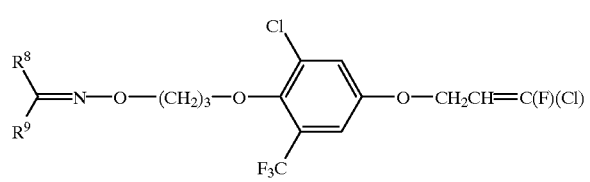 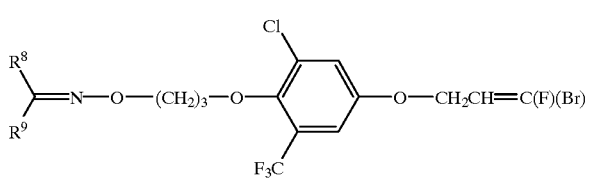
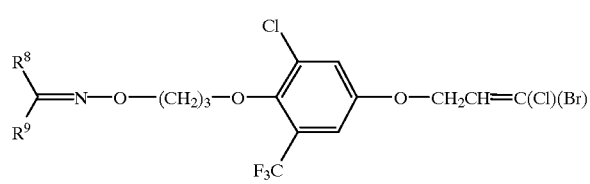 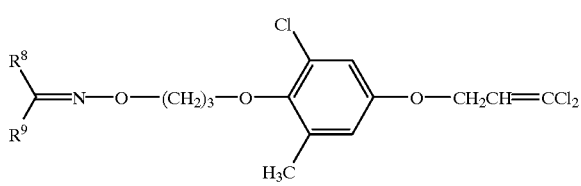
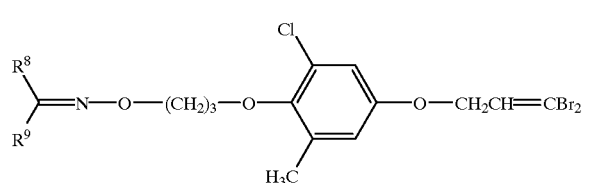 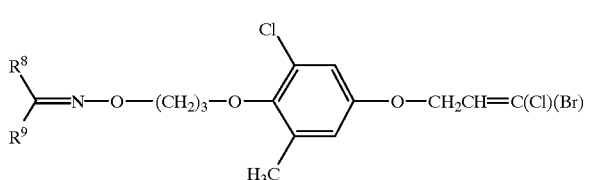
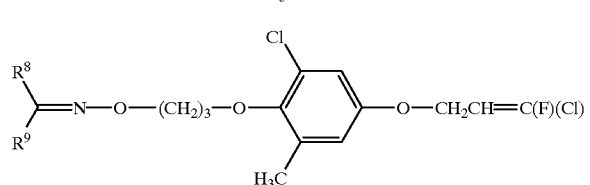 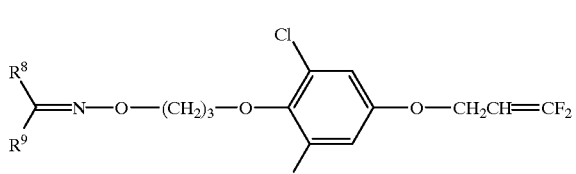
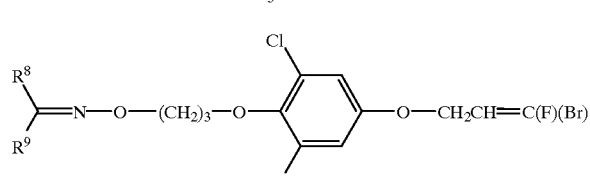 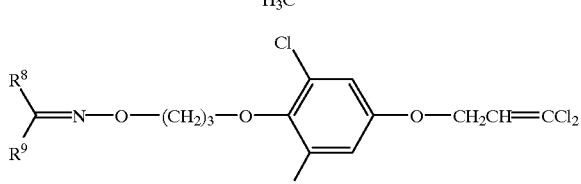
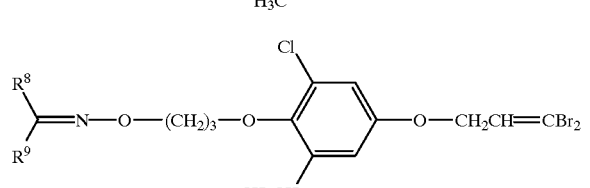 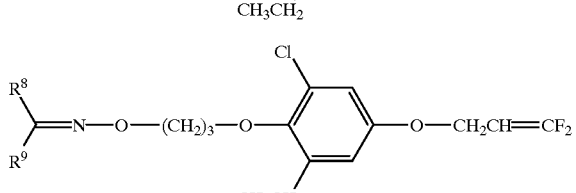
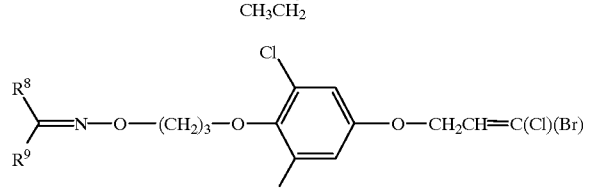 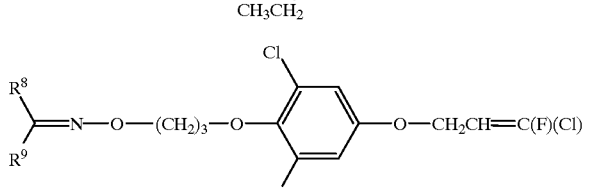

-continued
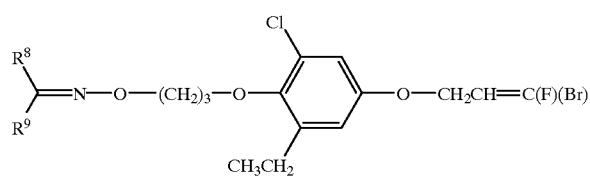
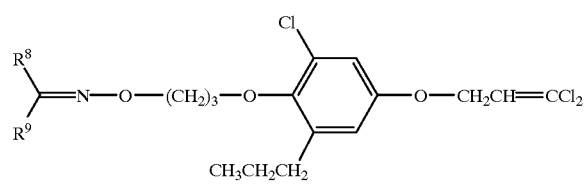
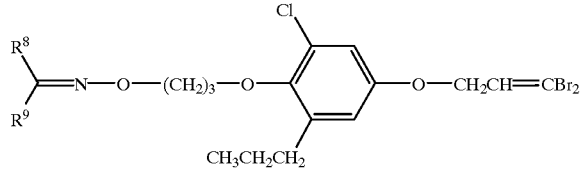
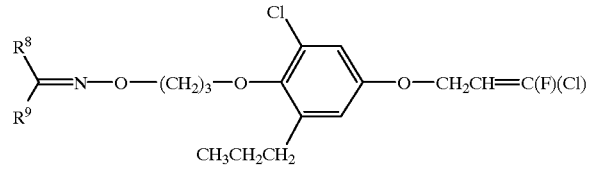
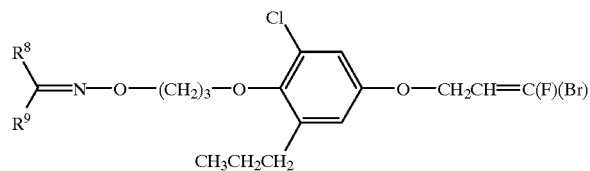
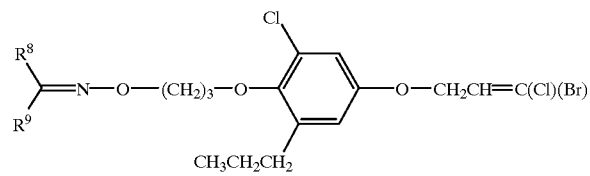
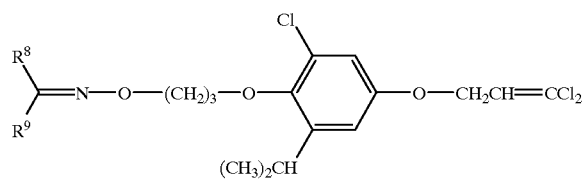
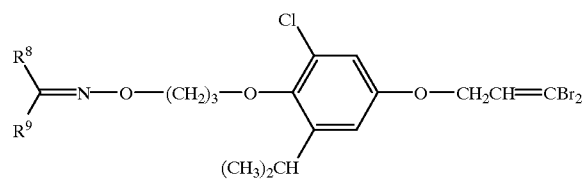
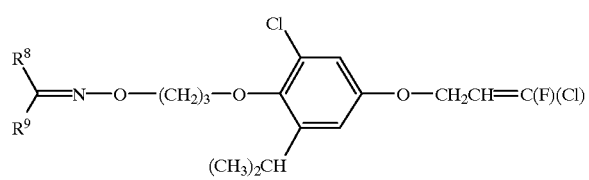
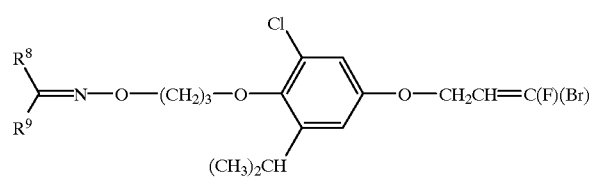
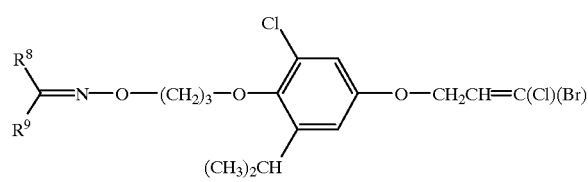
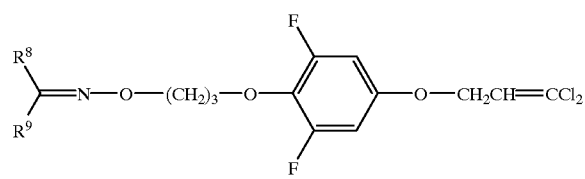
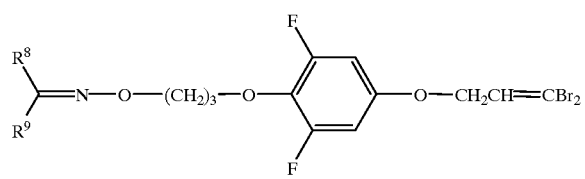
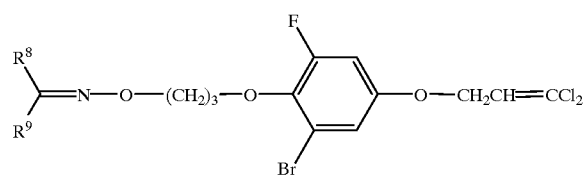
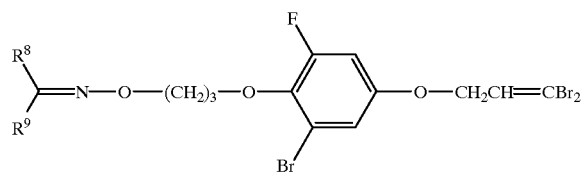
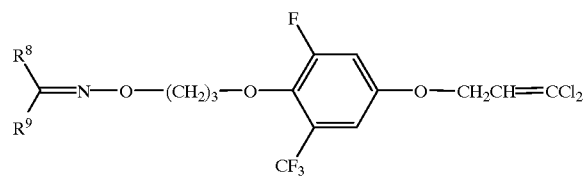
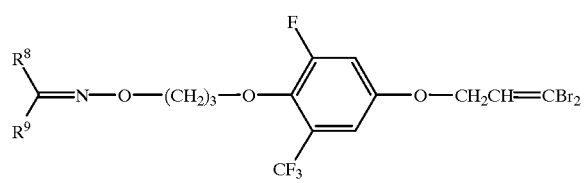
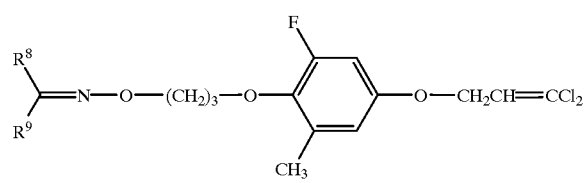

-continued
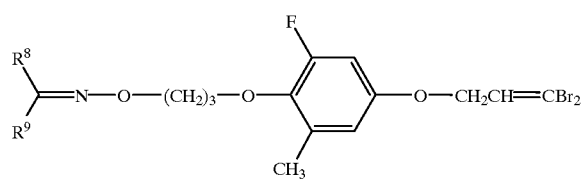
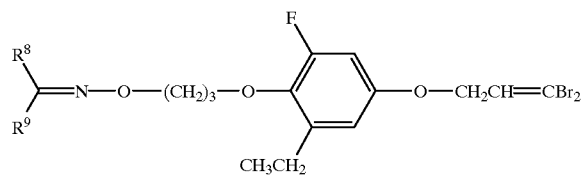
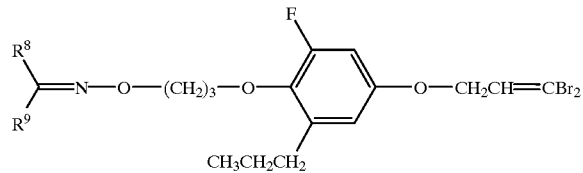
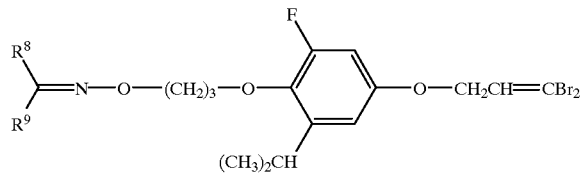
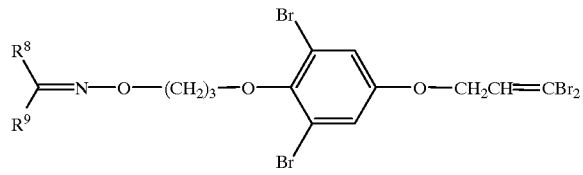
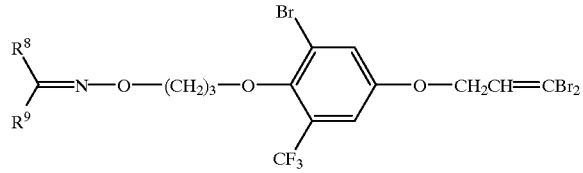
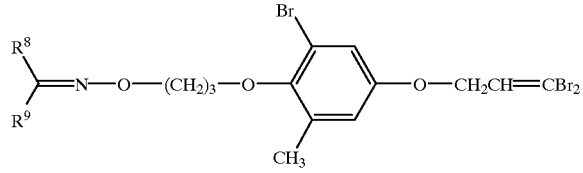
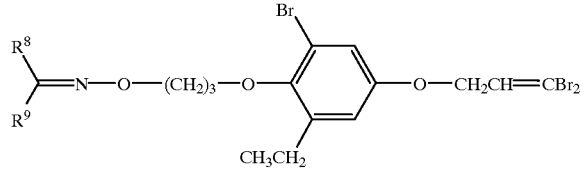
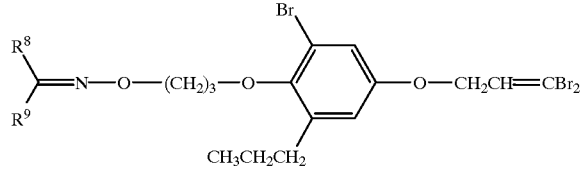
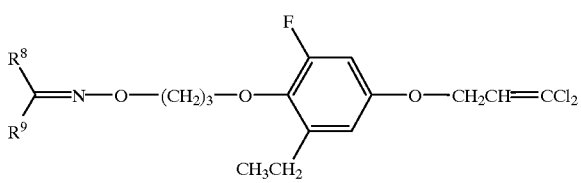
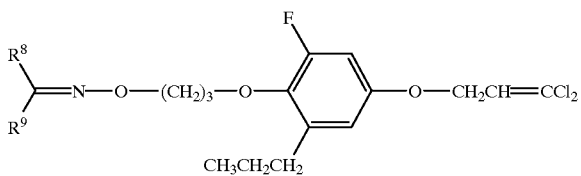
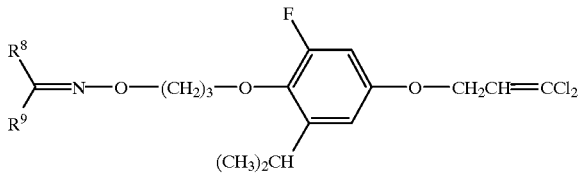
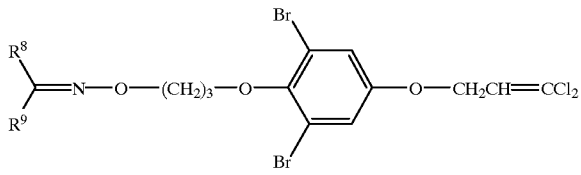
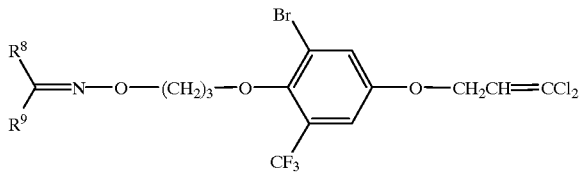
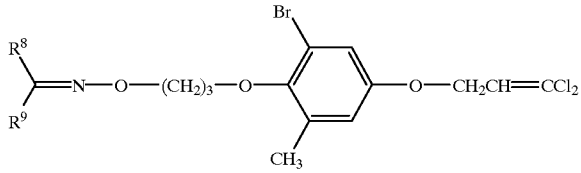
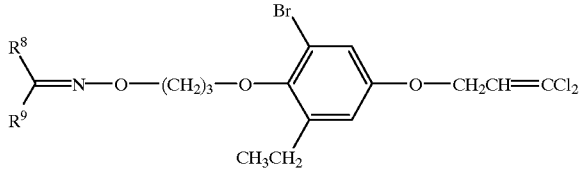
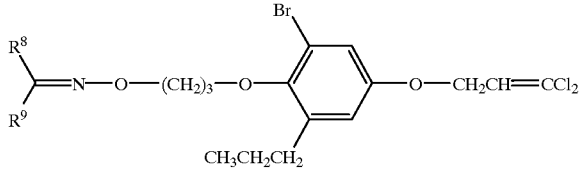
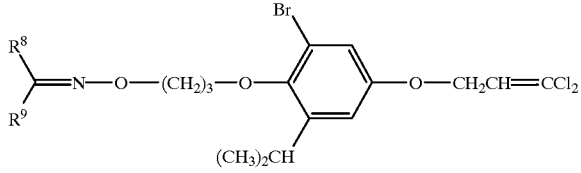

287
288
-continued
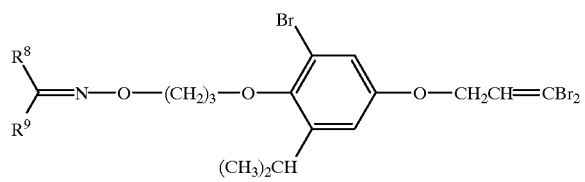
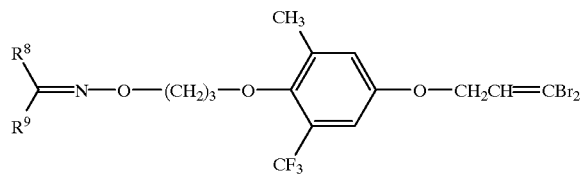
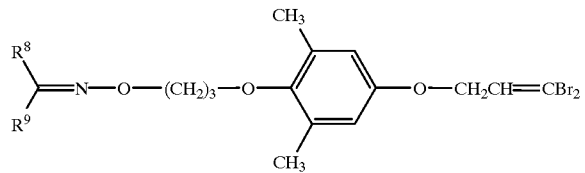
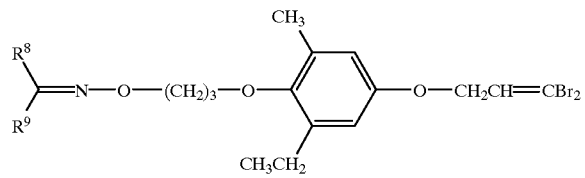
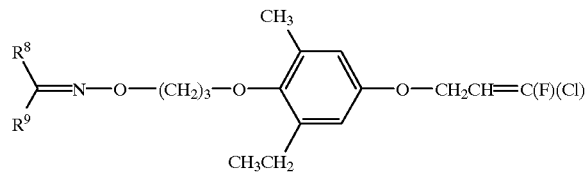
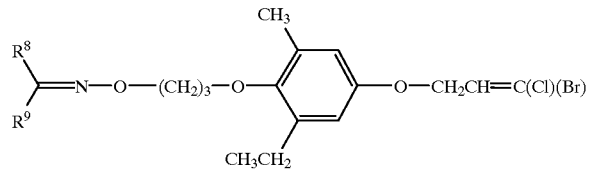
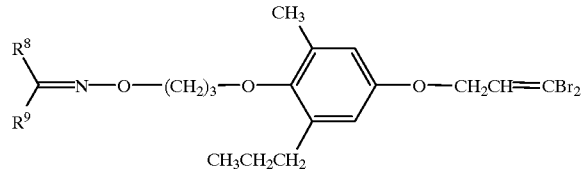
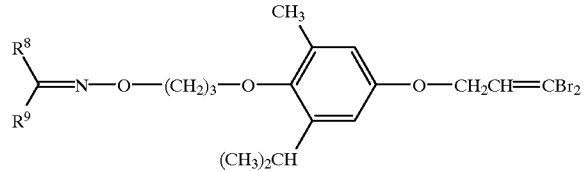
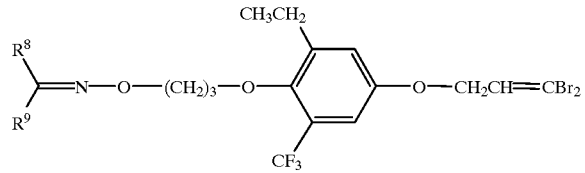
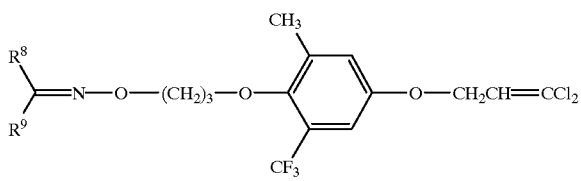
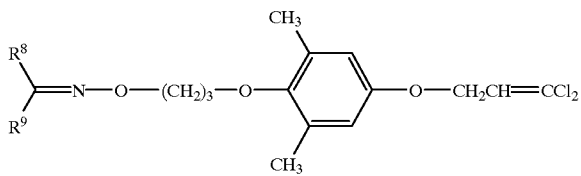
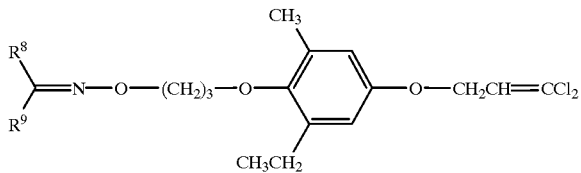
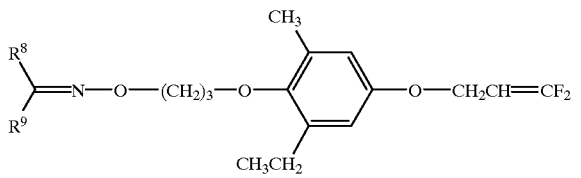
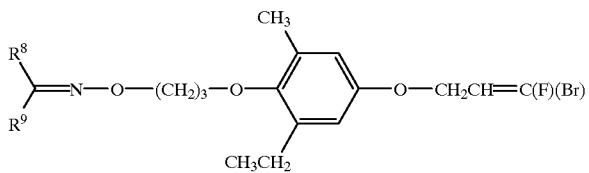
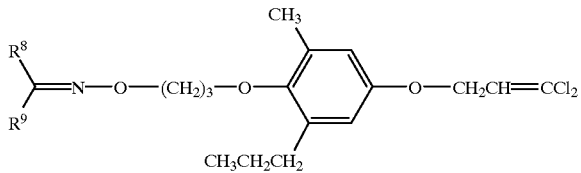
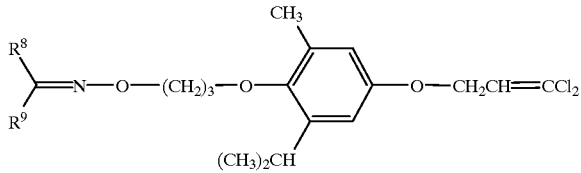
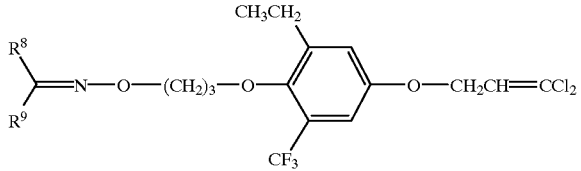
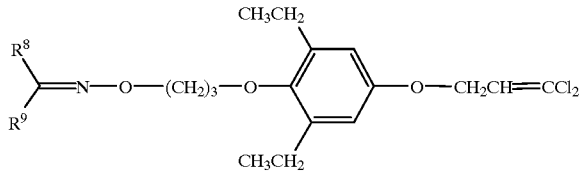

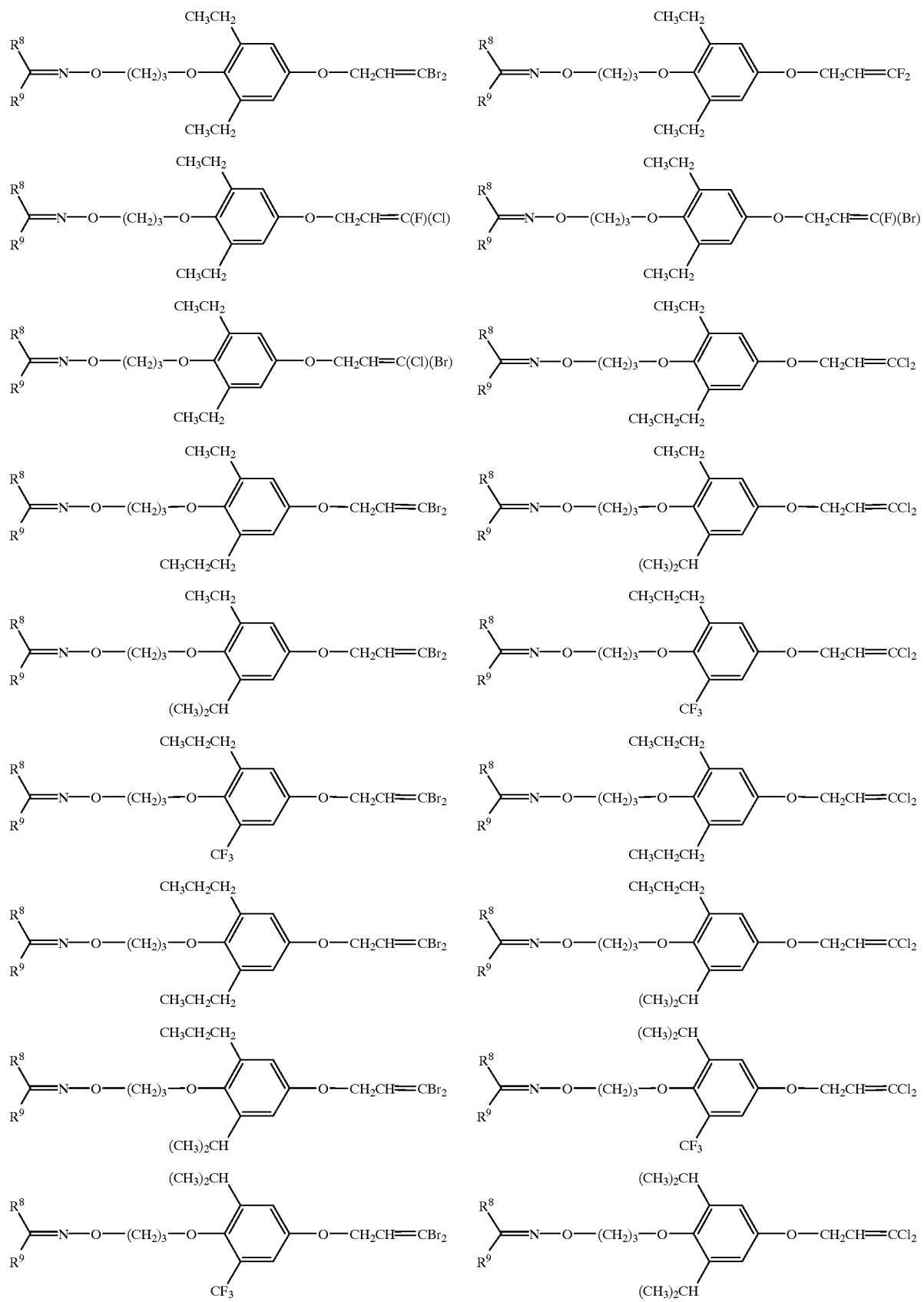

291 292
-continued
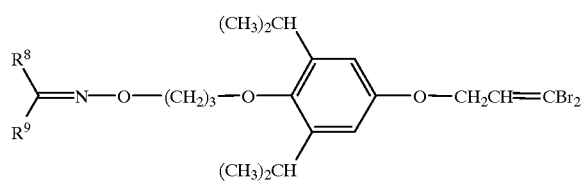
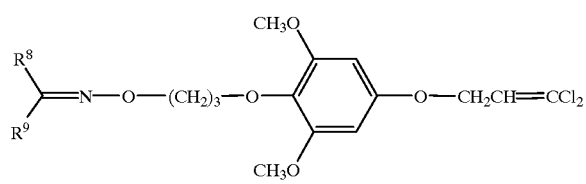
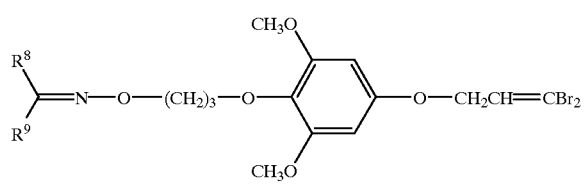
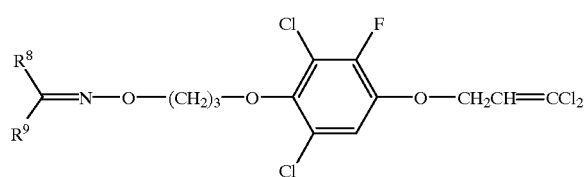
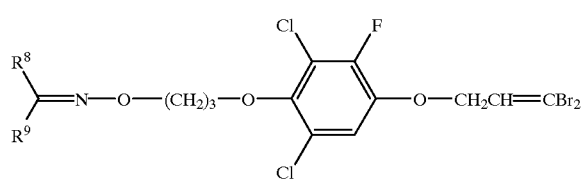
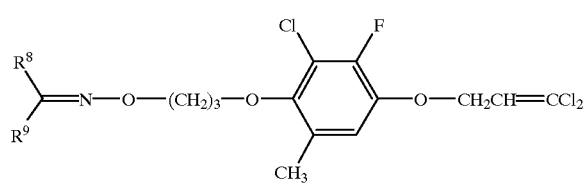
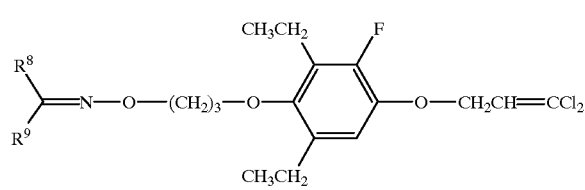
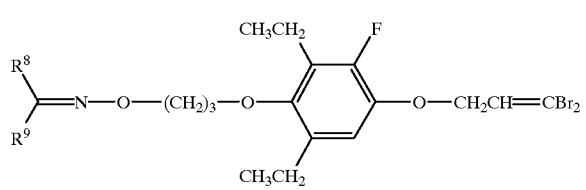
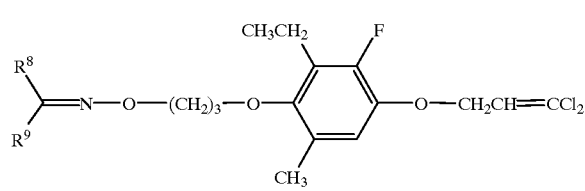
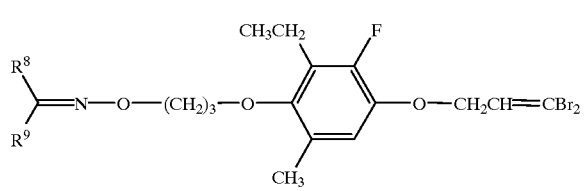
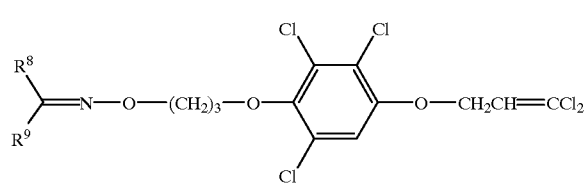
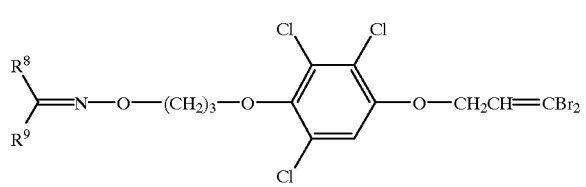
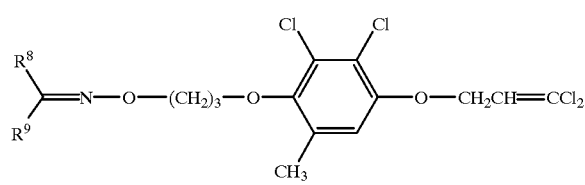
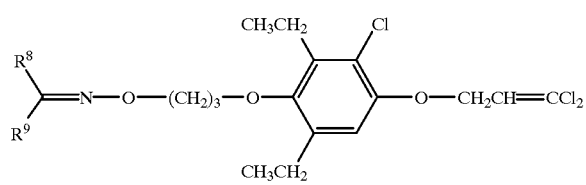
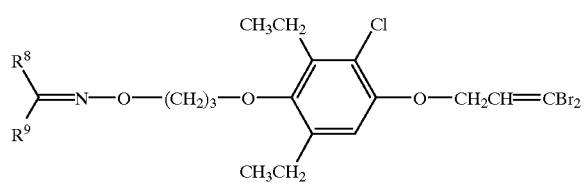
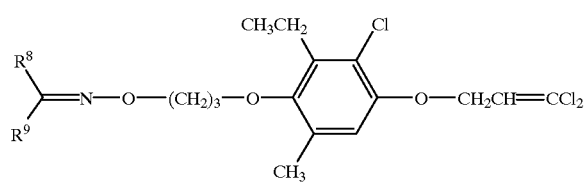
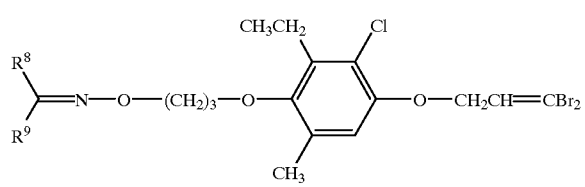
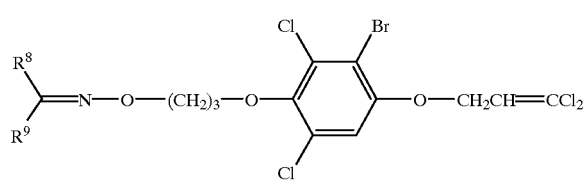

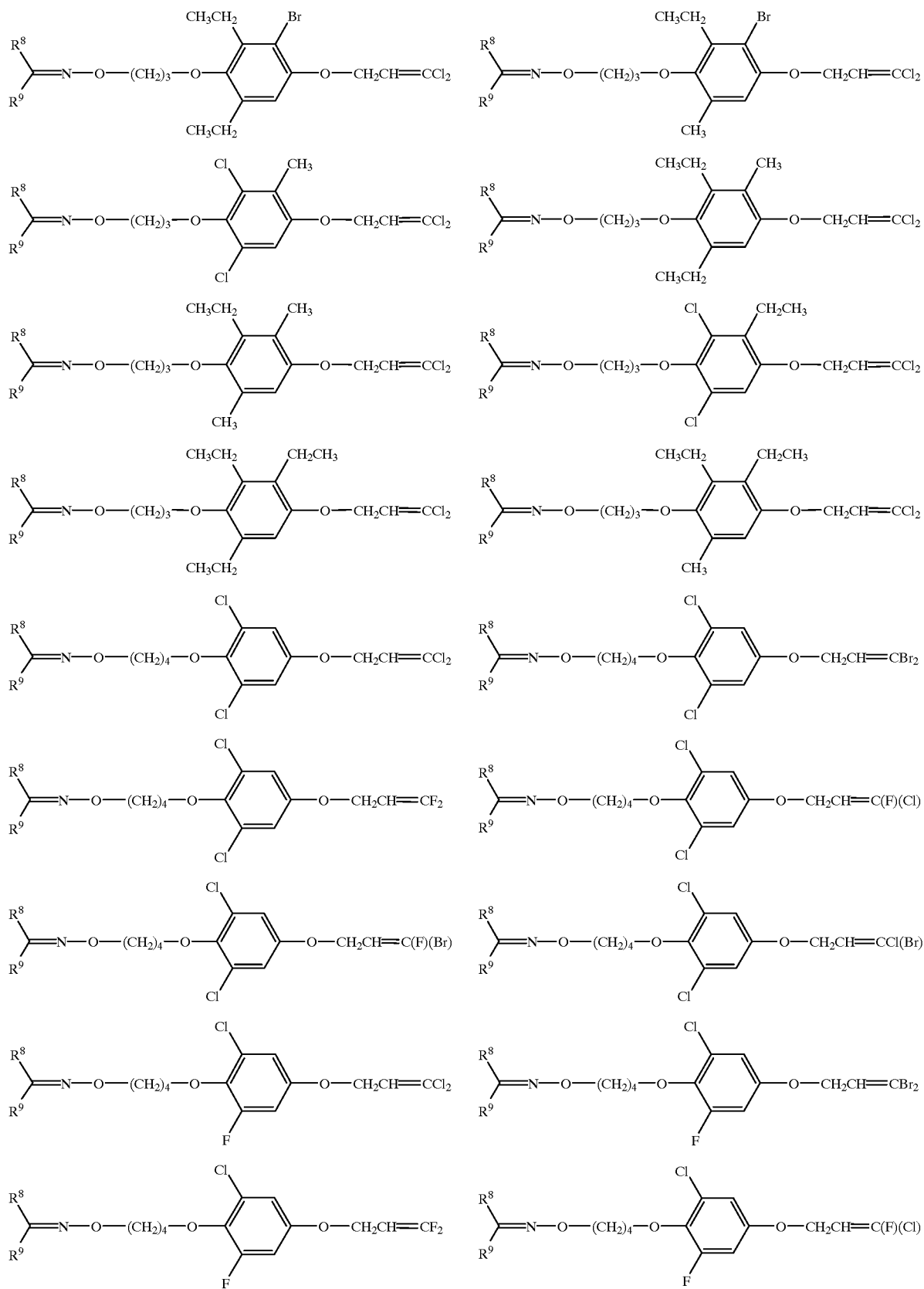

295
296
-continued
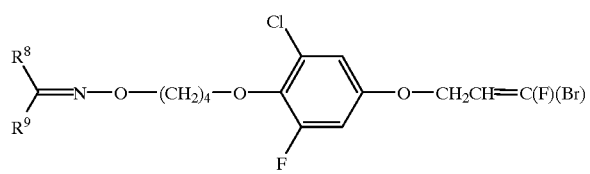
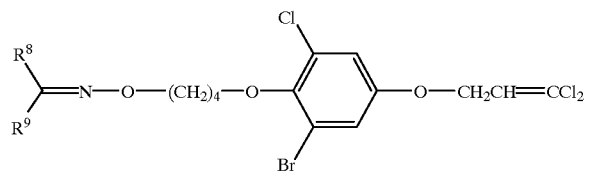
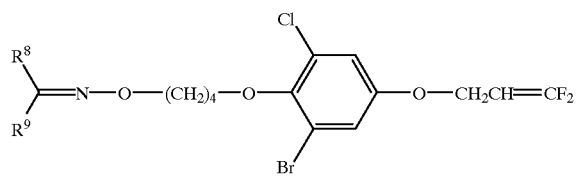
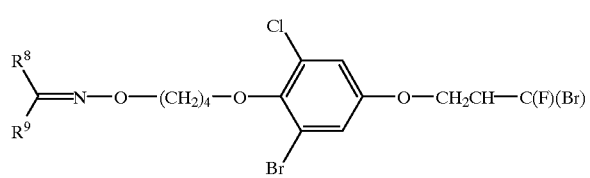
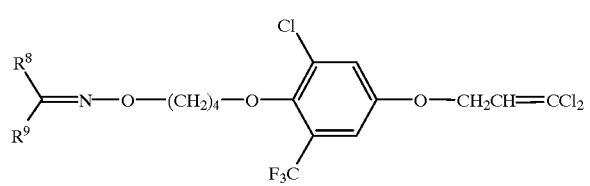
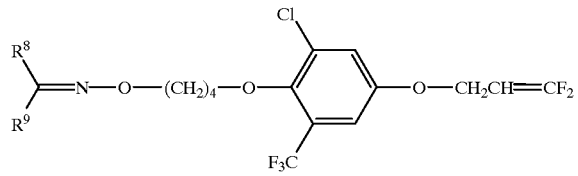
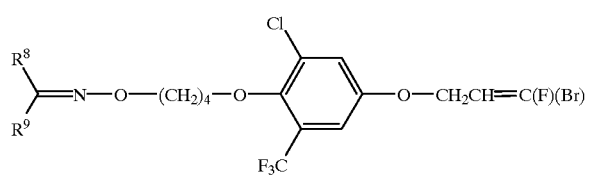
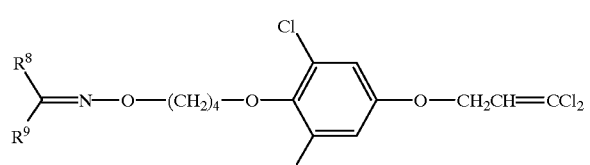
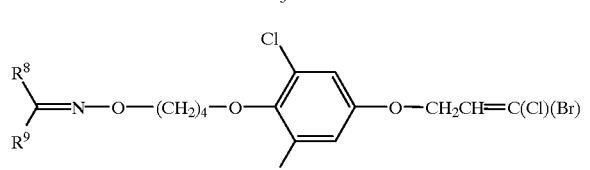
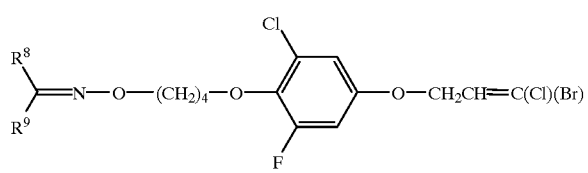
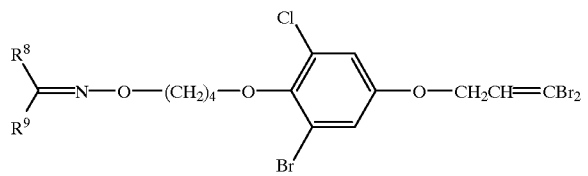
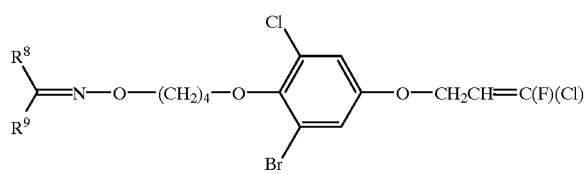
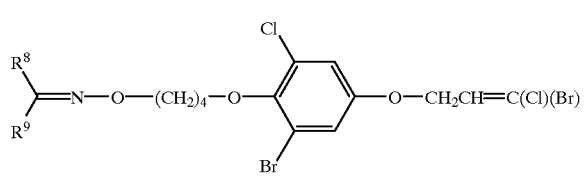
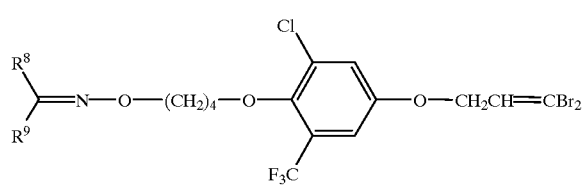
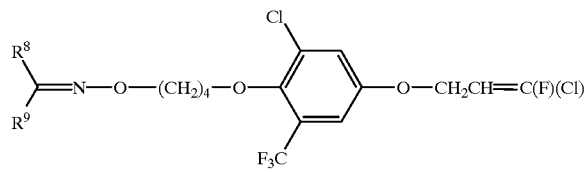
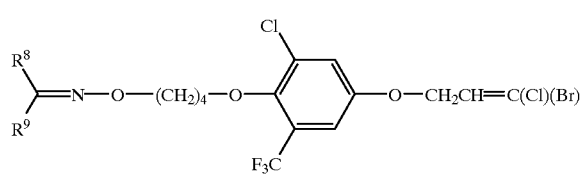
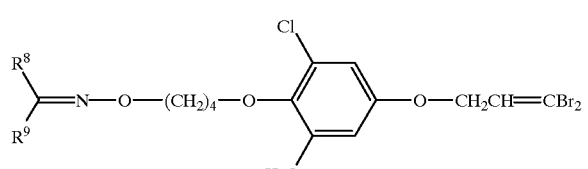
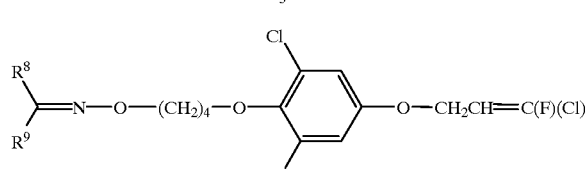

297 298
-continued
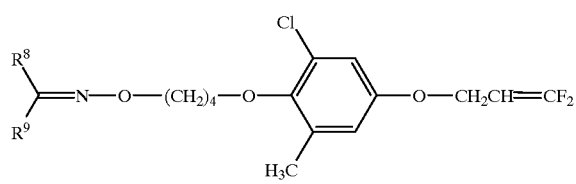
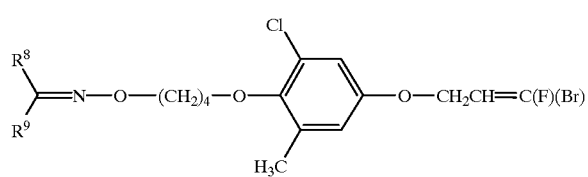
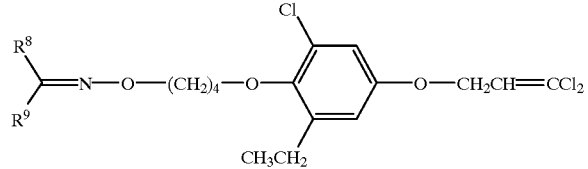
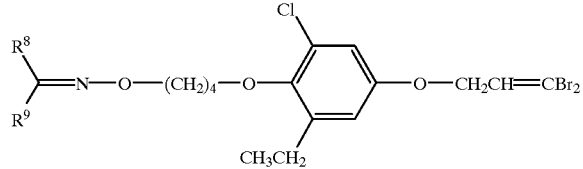
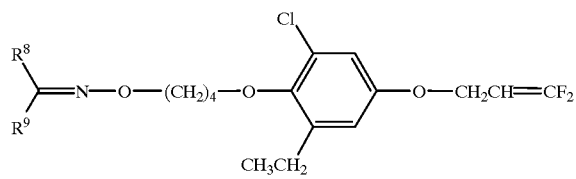
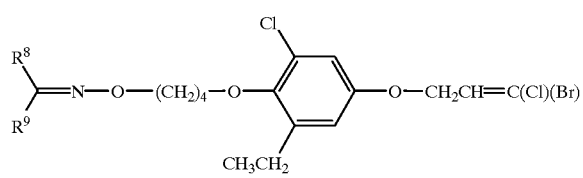
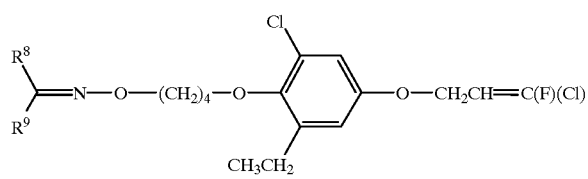
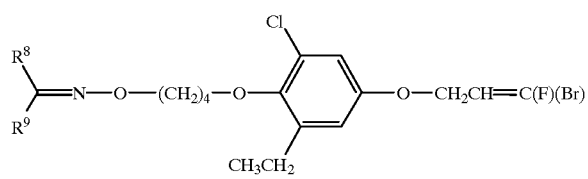
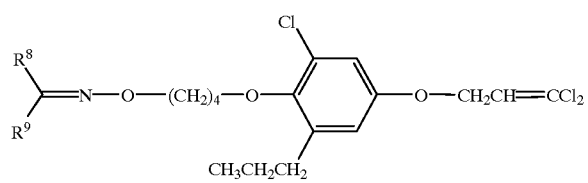
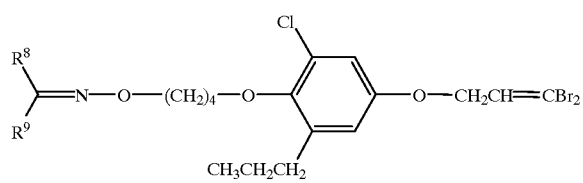
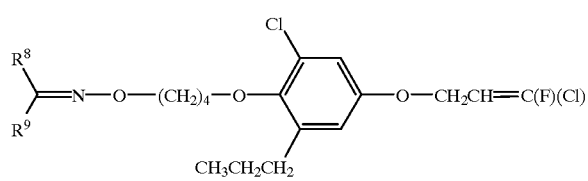
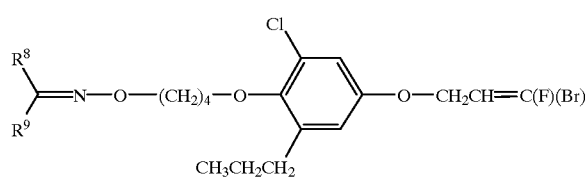
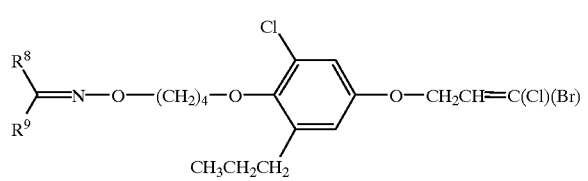
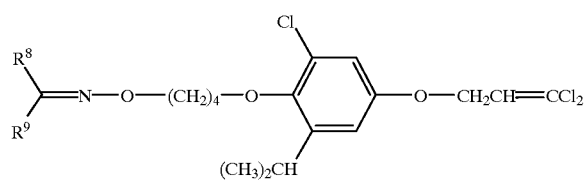
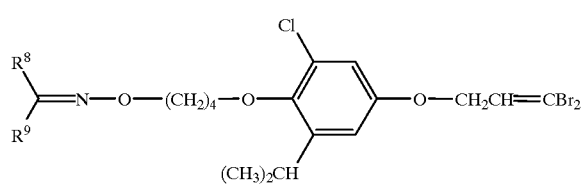
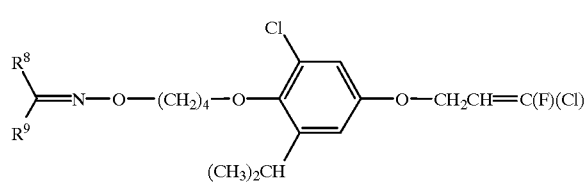
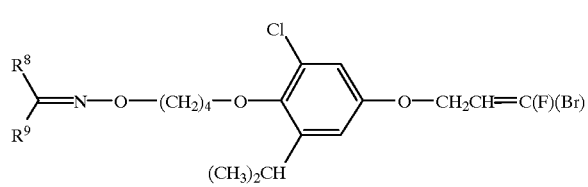
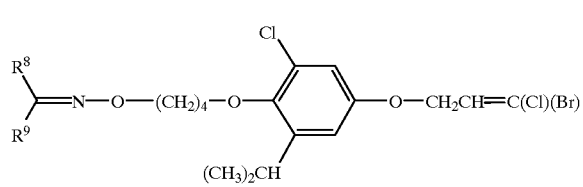

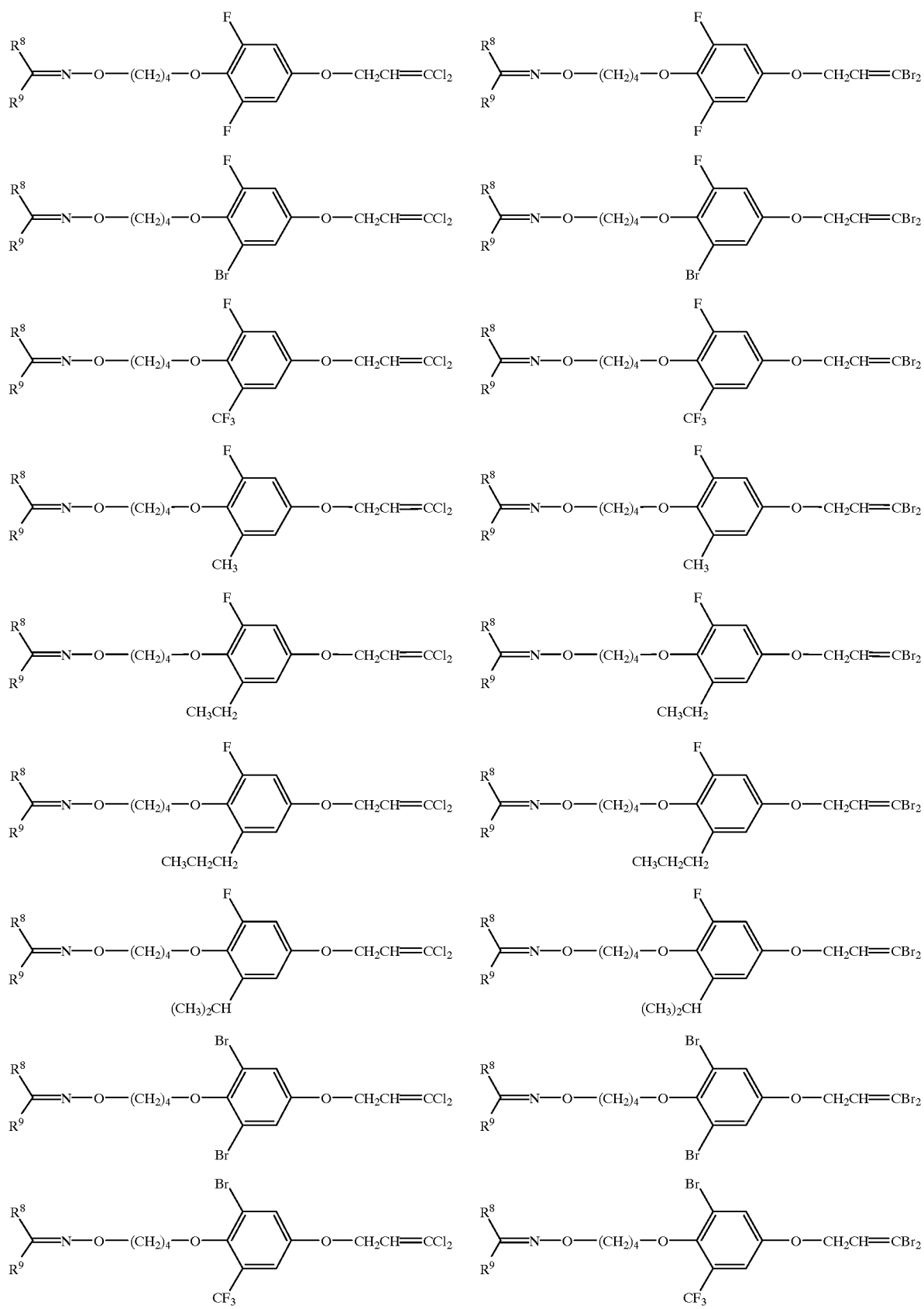

-continued
| 301 | 302 |
|---|---|
| 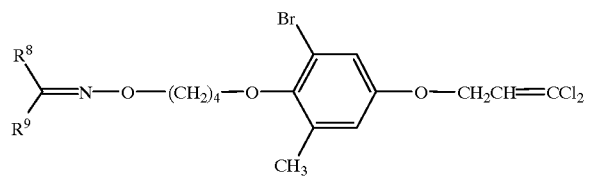 | 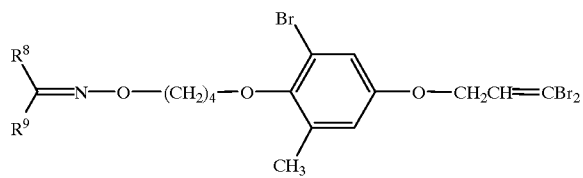 |
| 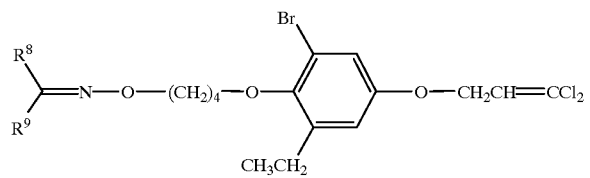 | 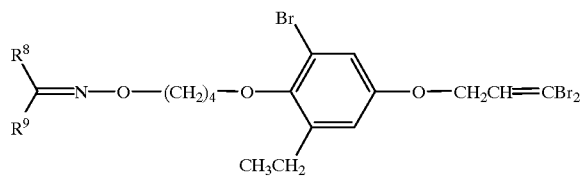 |
| 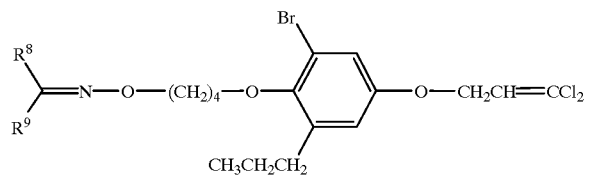 | 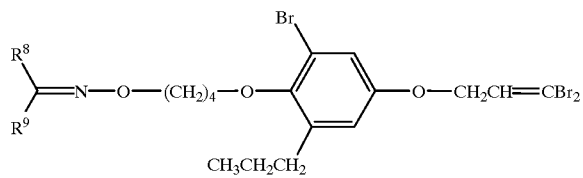 |
| 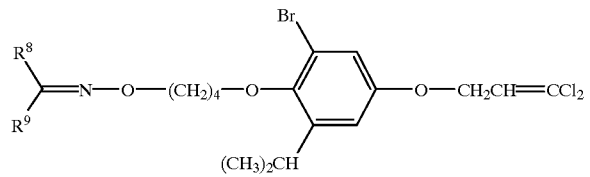 | 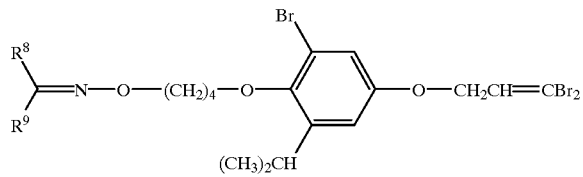 |
| 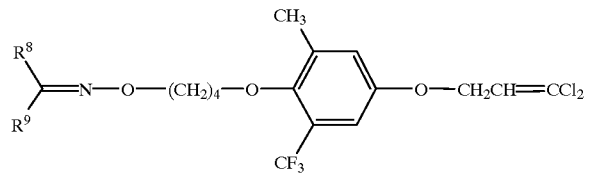 | 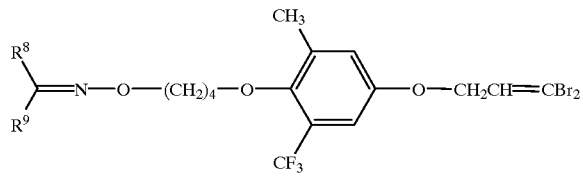 |
| 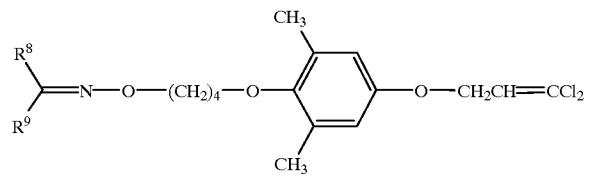 | 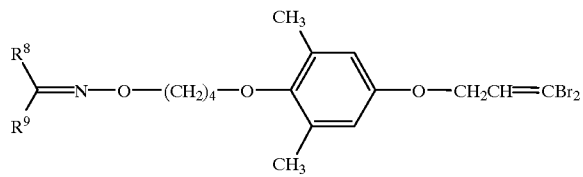 |
| 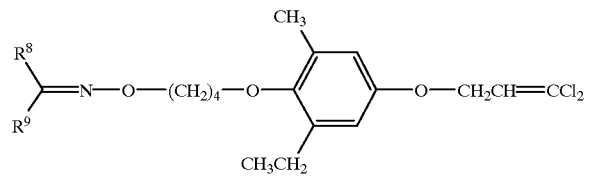 | 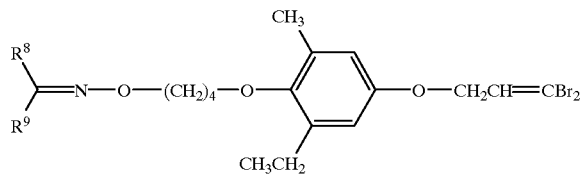 |
| 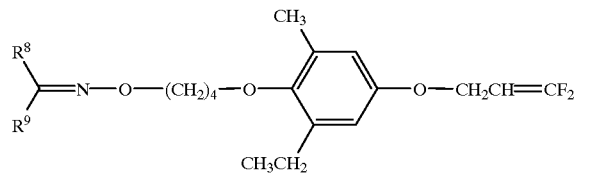 | 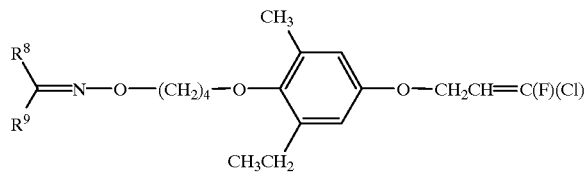 |
| 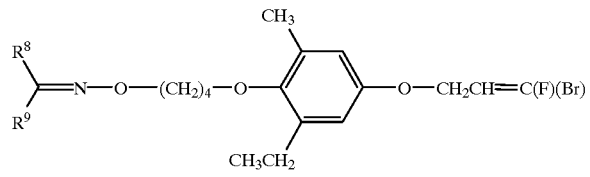 | 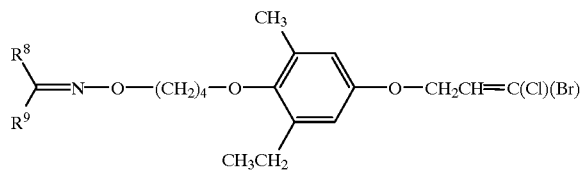 |

-continued
303
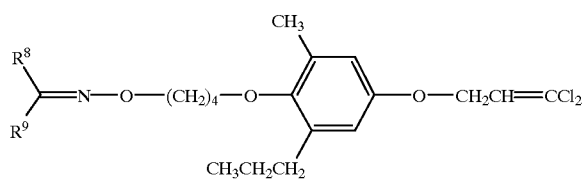
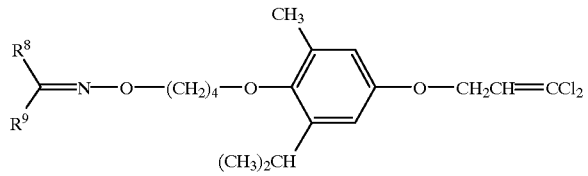
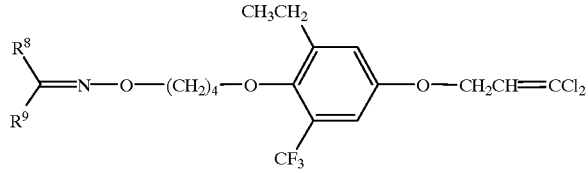
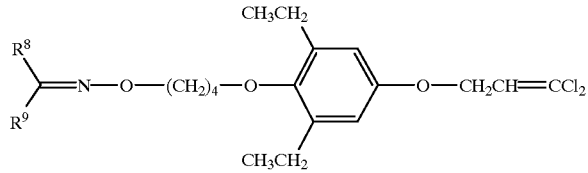
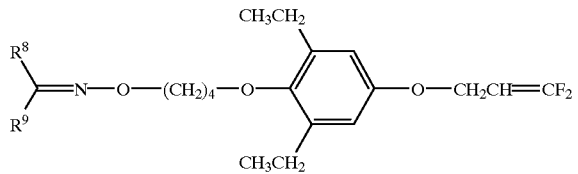
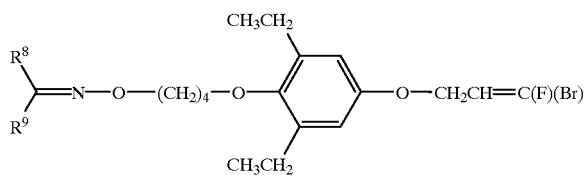
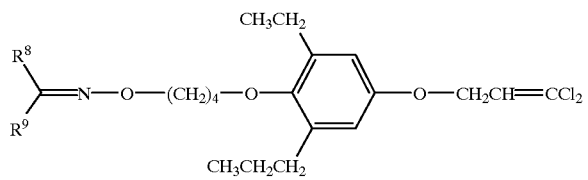
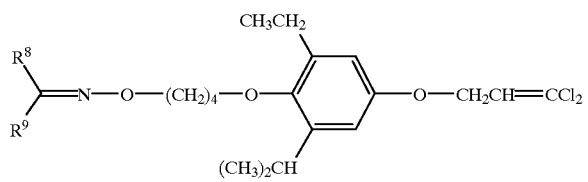
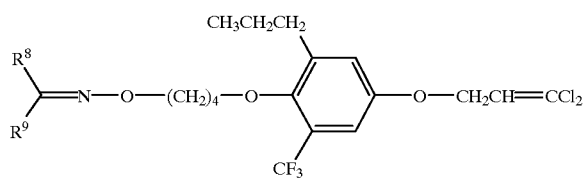
304
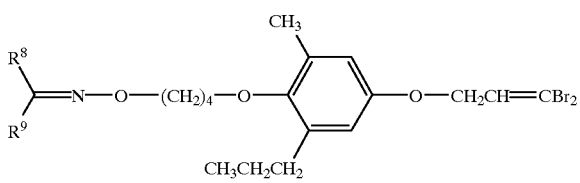
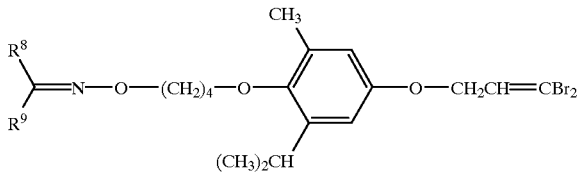
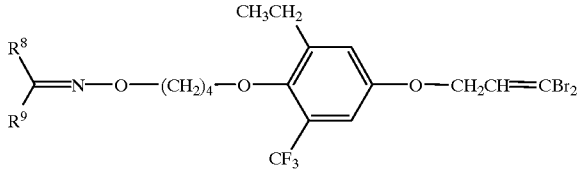
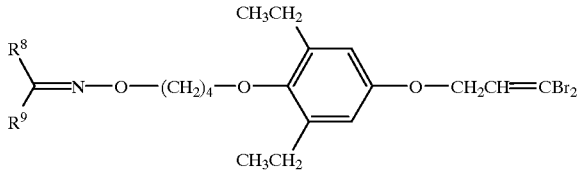
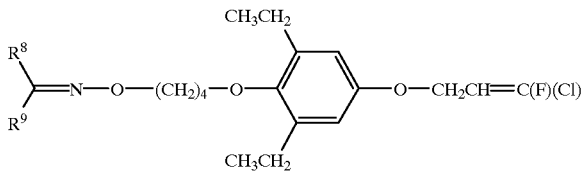
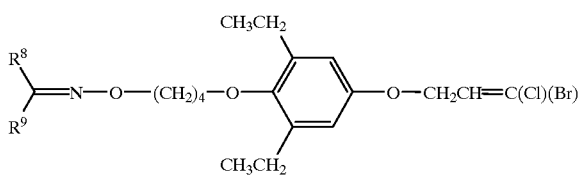
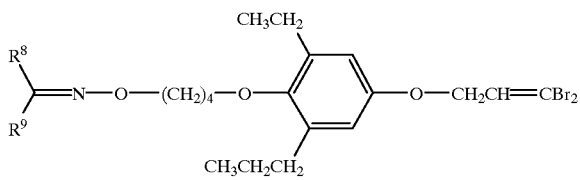
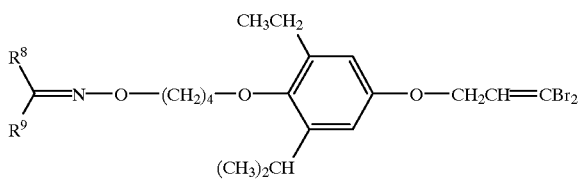
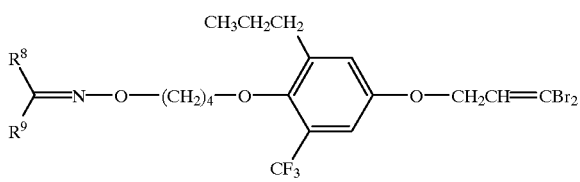

305 306
-continued
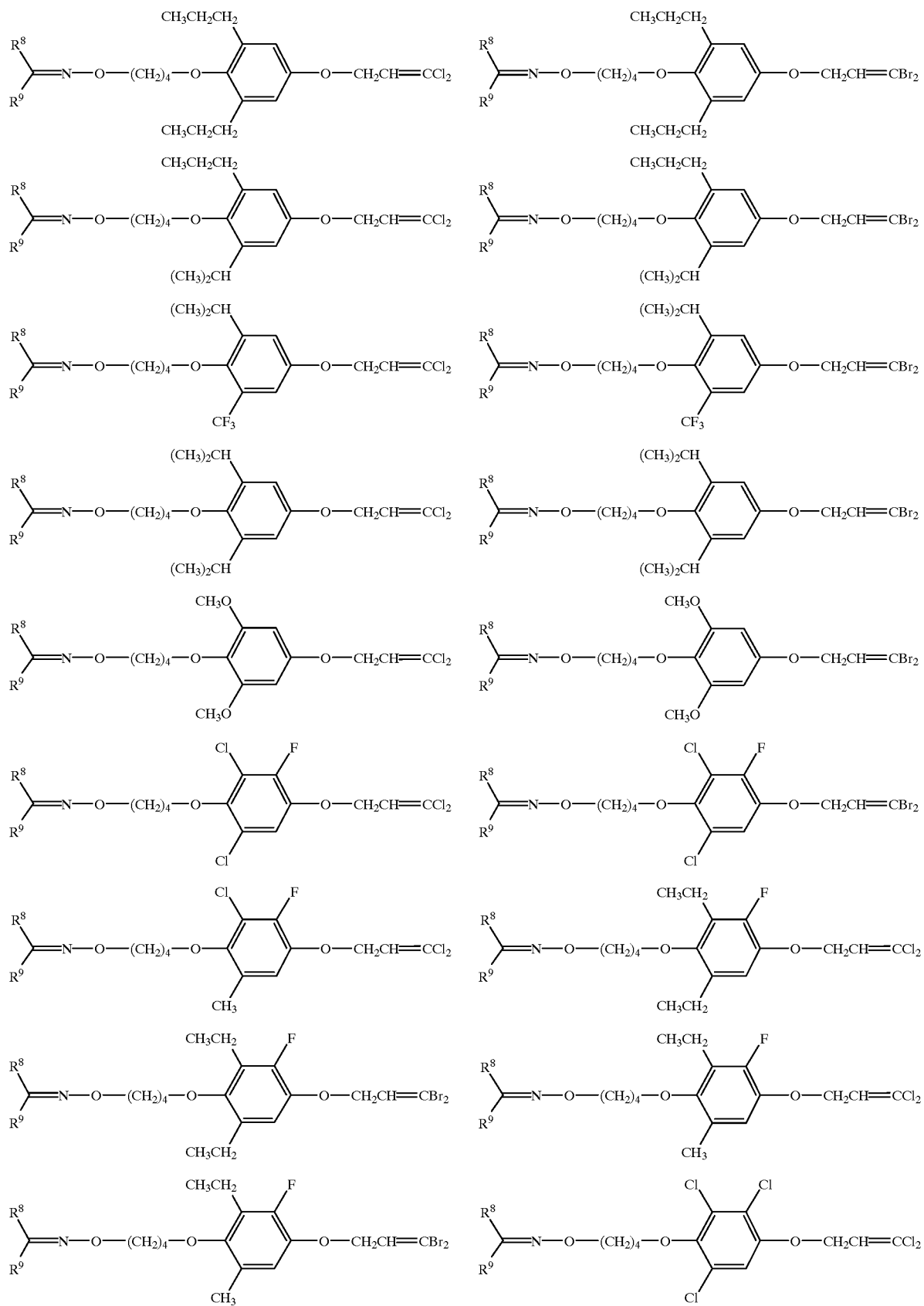

-continued
| 307 | 308 |
|---|---|
| 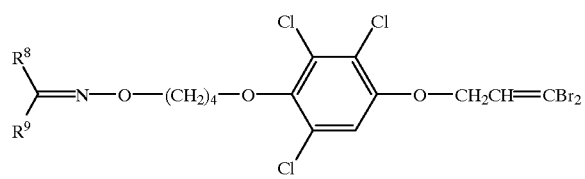 | 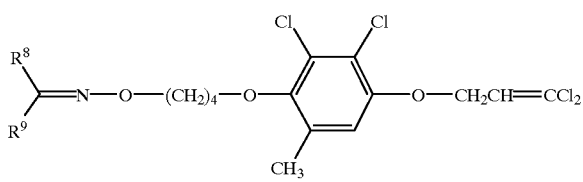 |
| 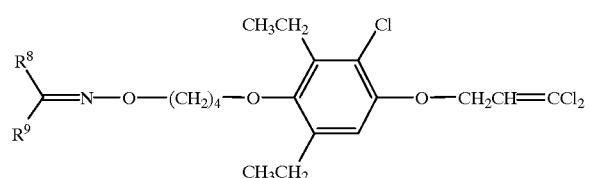 | 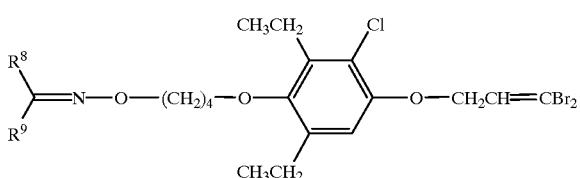 |
| 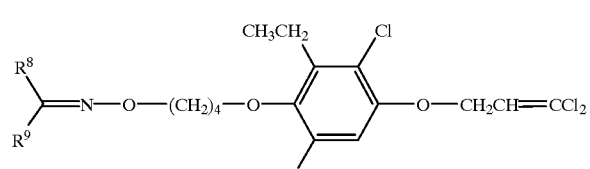 | 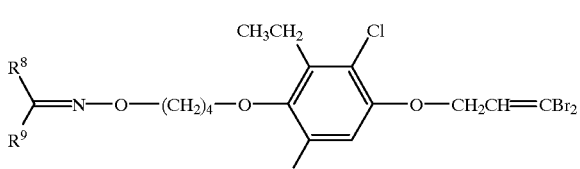 |
| 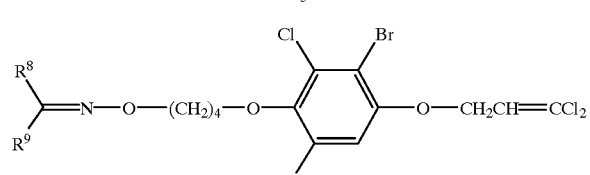 | 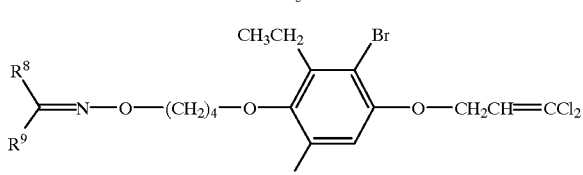 |
| 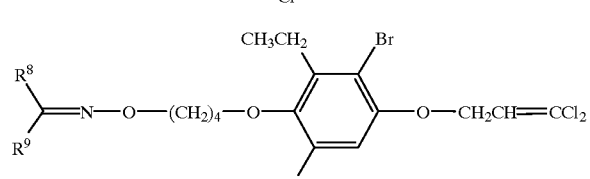 | 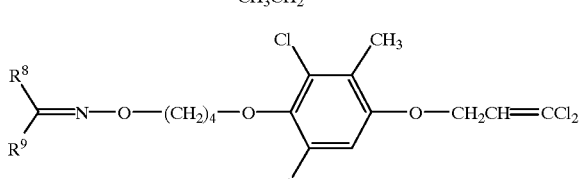 |
| 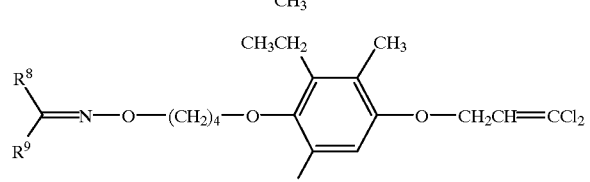 | 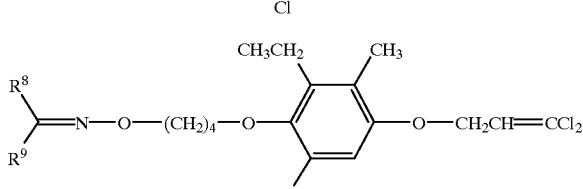 |
| 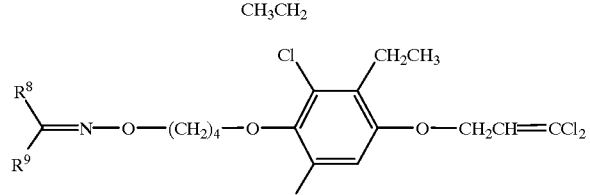 | 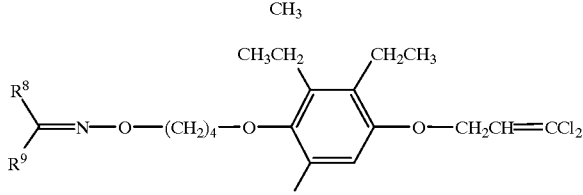 |
| 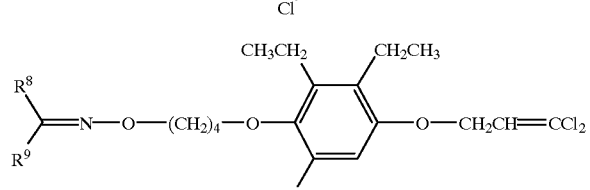 | 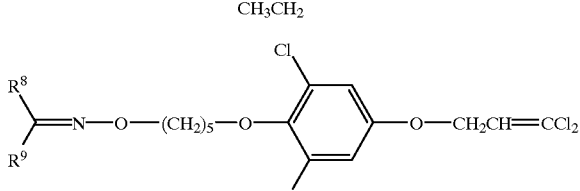 |
| 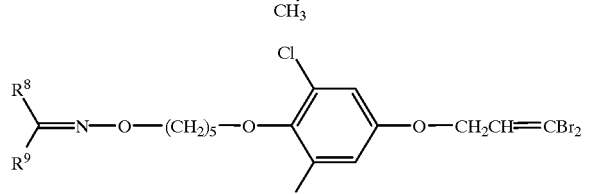 | 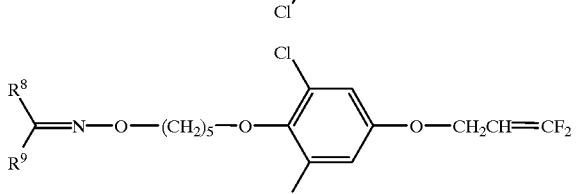 |

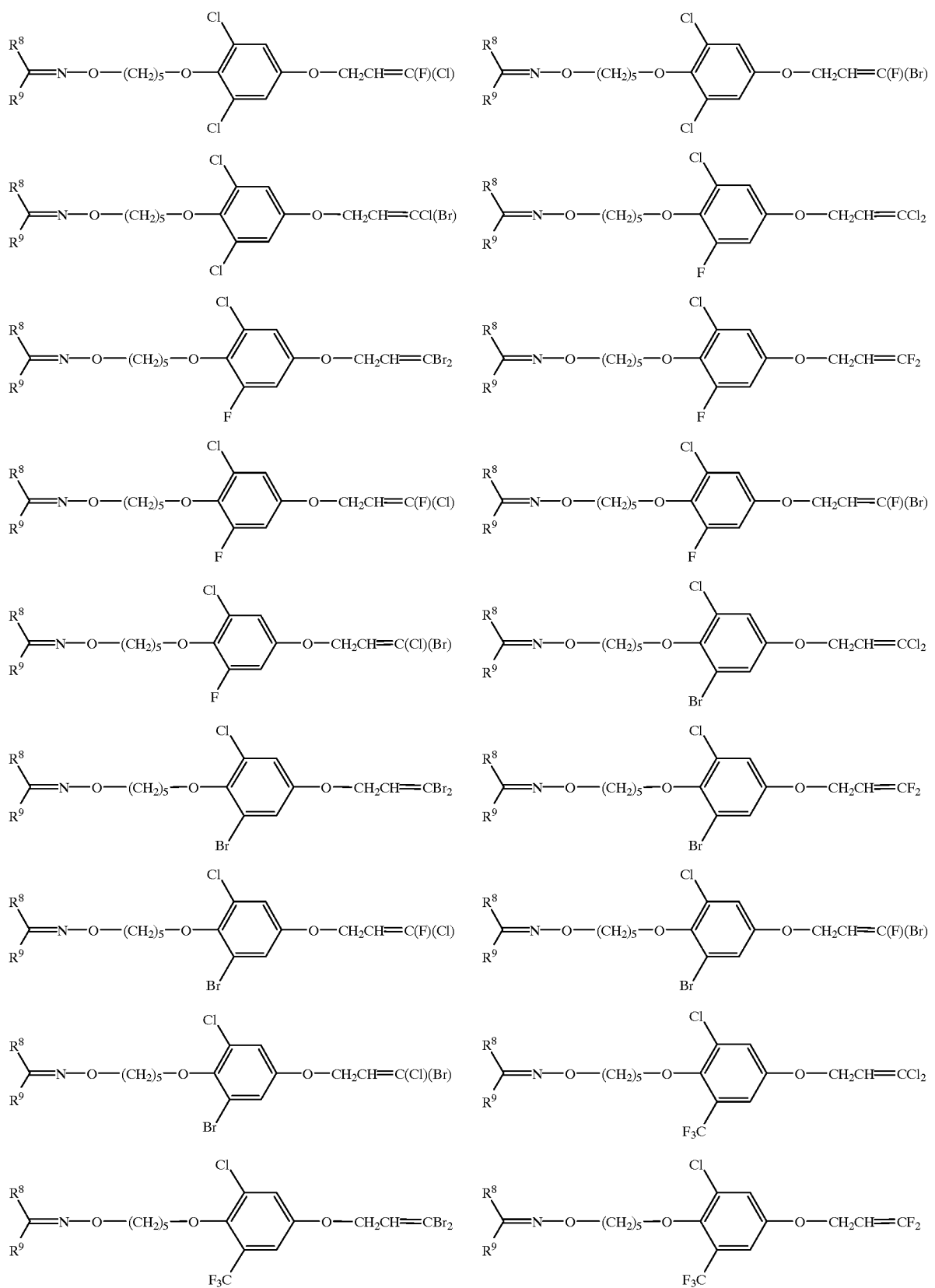

-continued
| 311 | 312 |
|---|---|
| 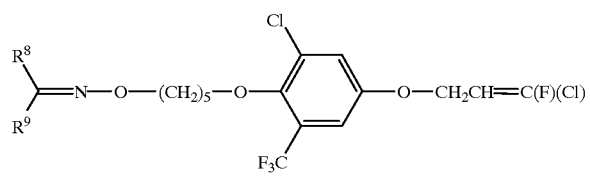 | 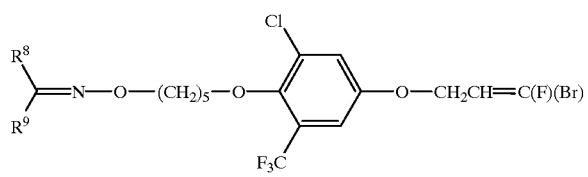 |
| 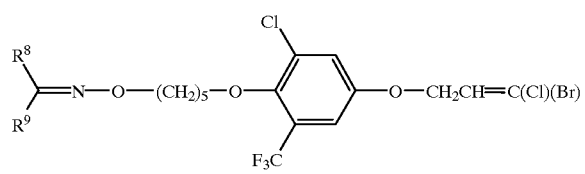 | 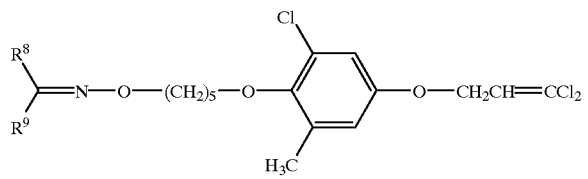 |
| 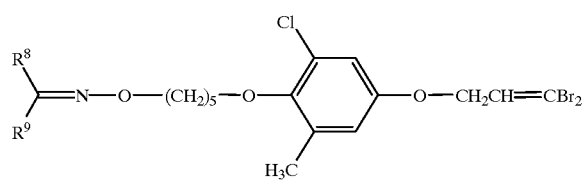 | 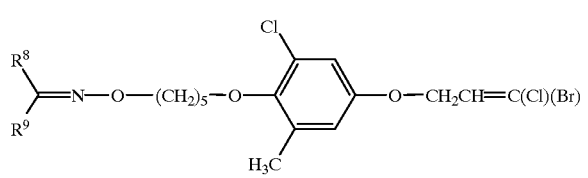 |
| 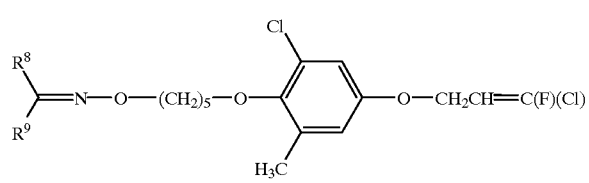 | 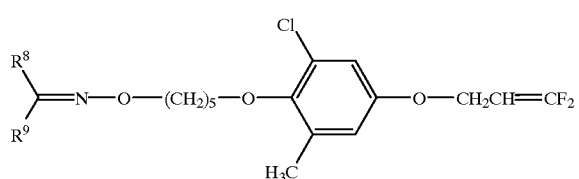 |
| 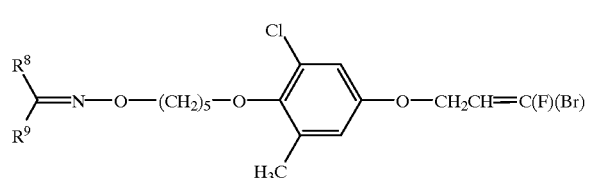 | 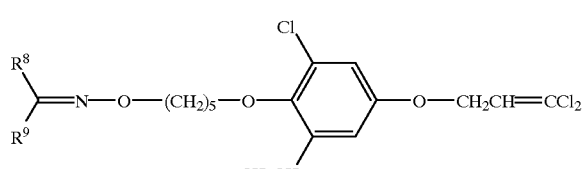 |
| 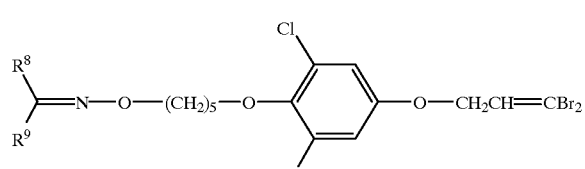 | 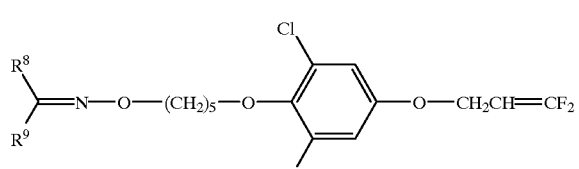 |
| 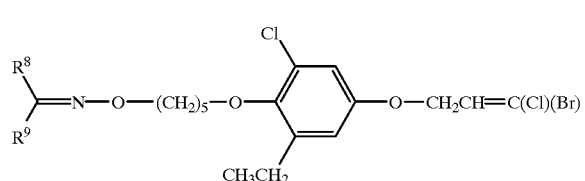 | 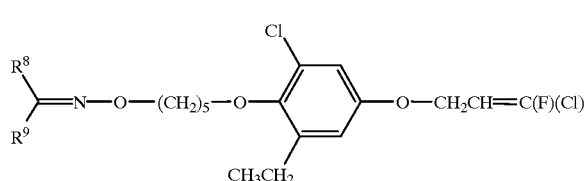 |
| 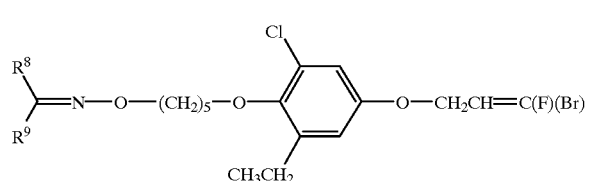 | 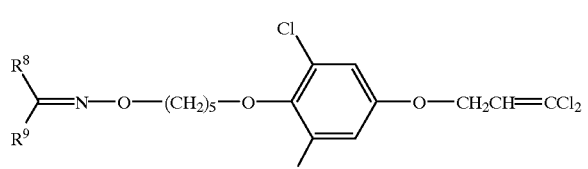 |
| 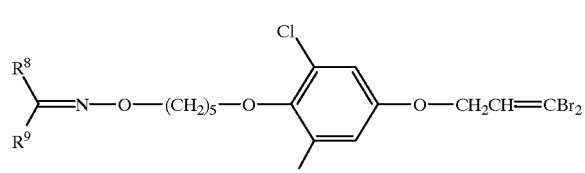 | 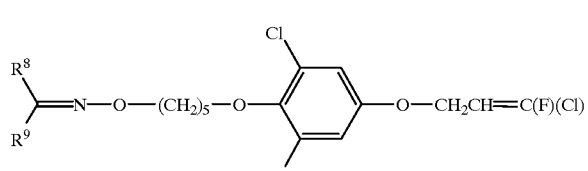 |

313 314
-continued
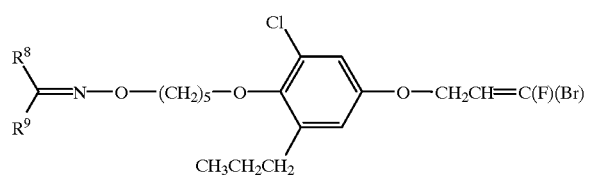 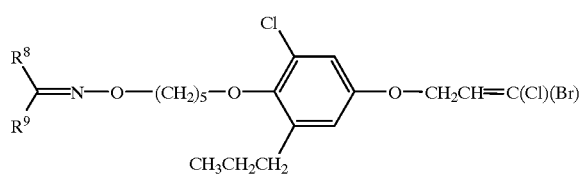
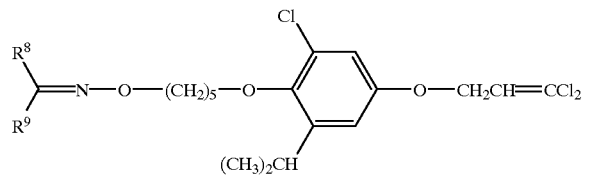 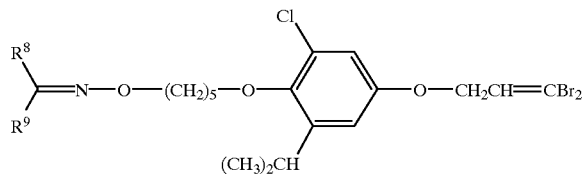
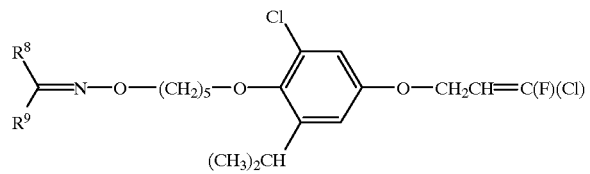 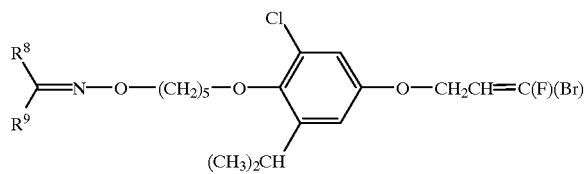
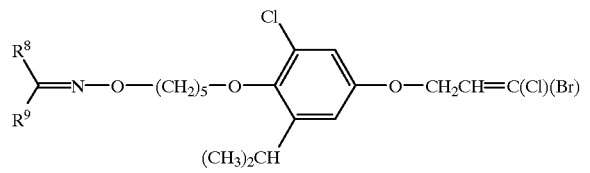 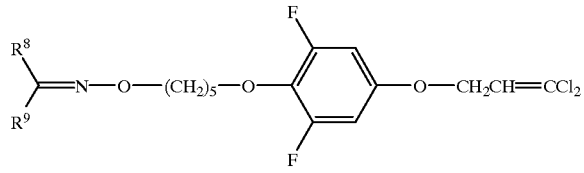
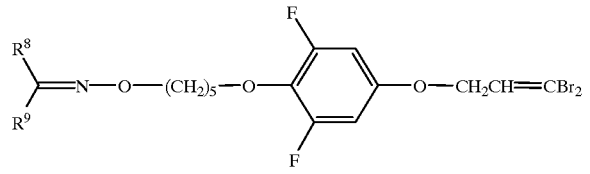 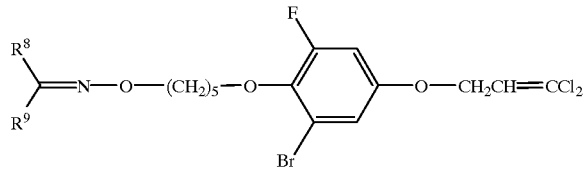
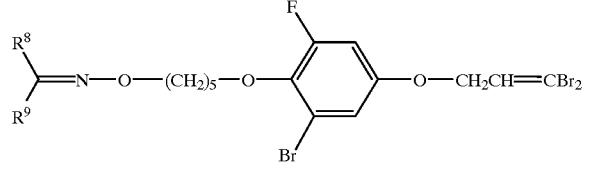 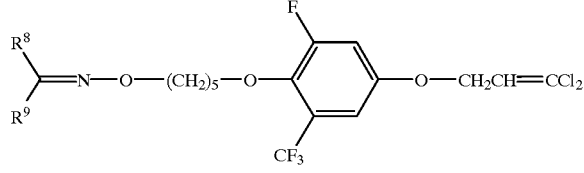
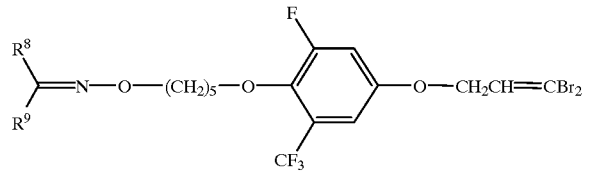 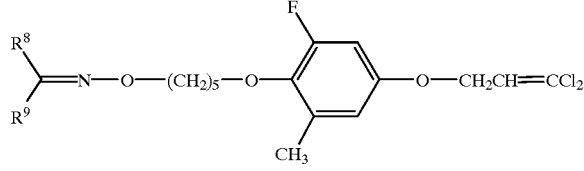
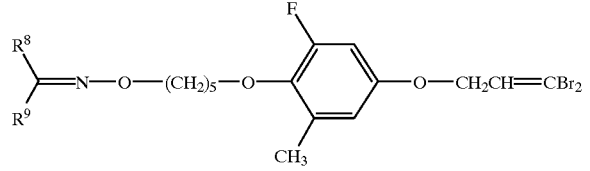 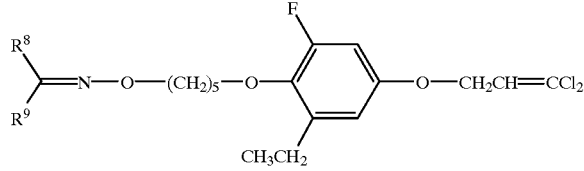
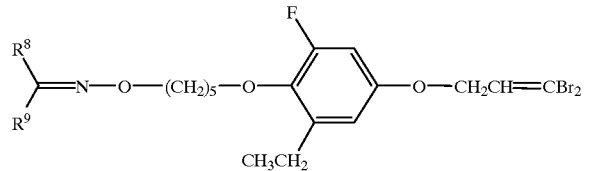 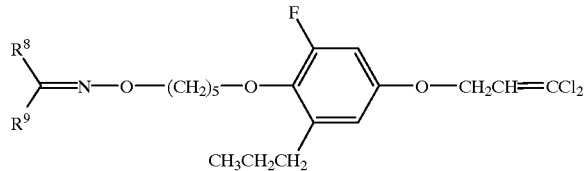

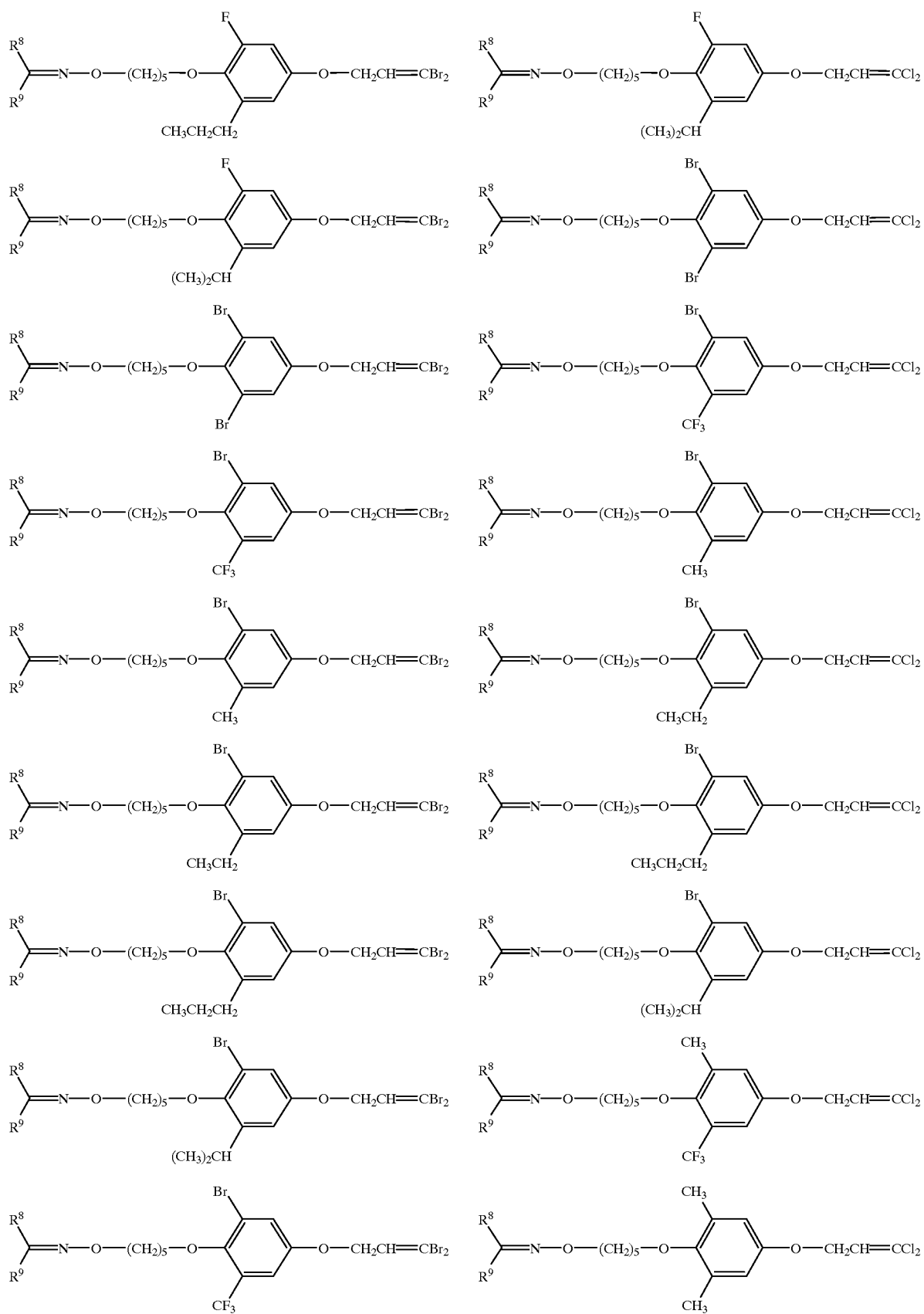

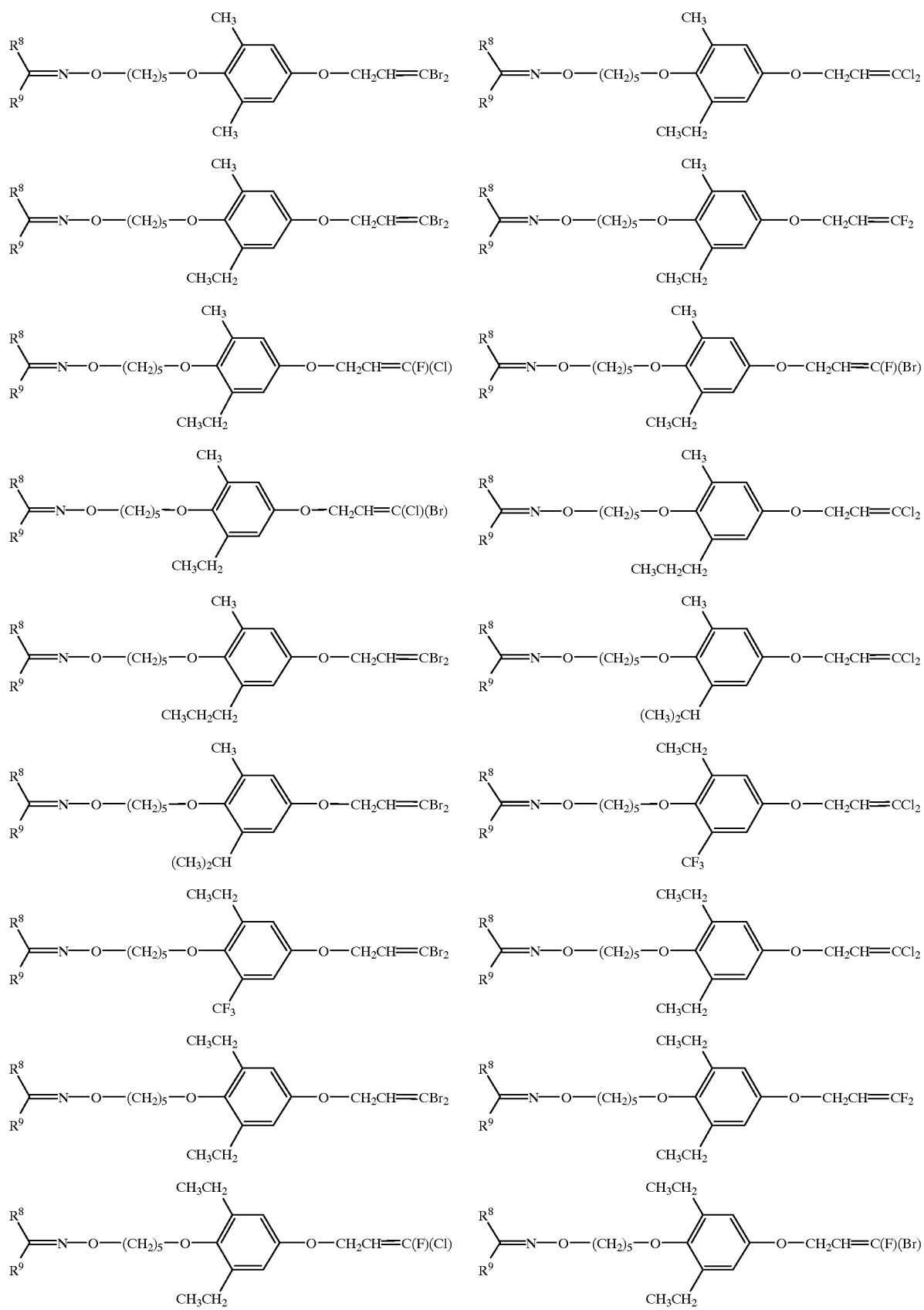

319
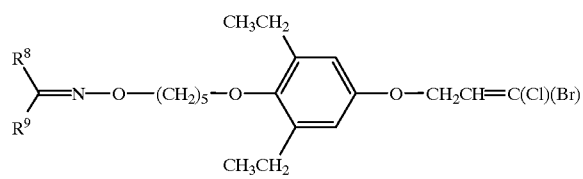
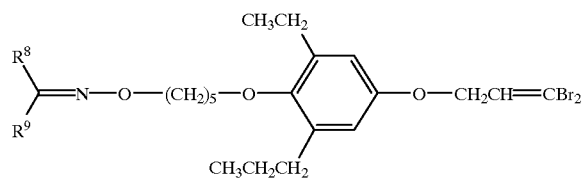
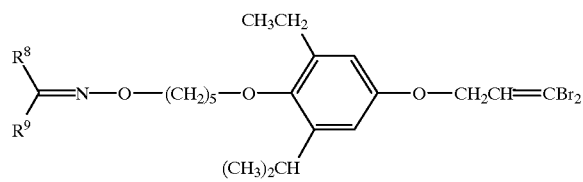
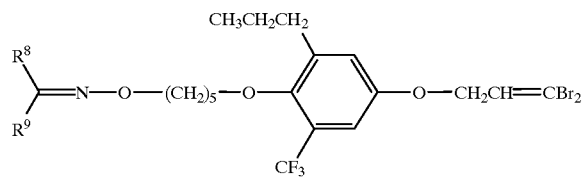
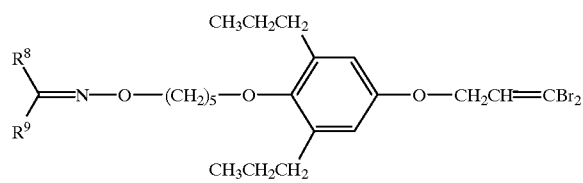
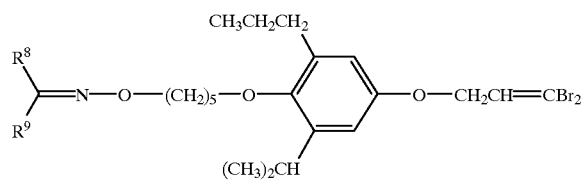
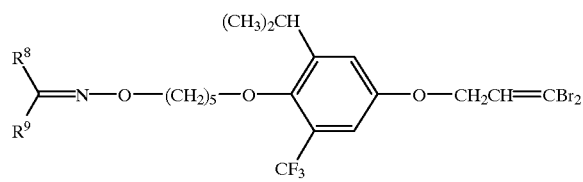
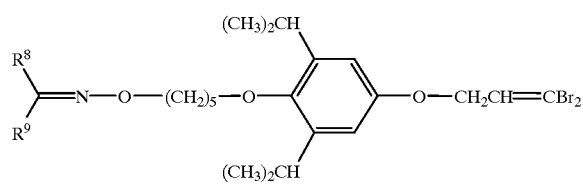
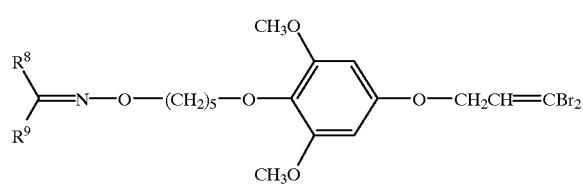
320
-continued
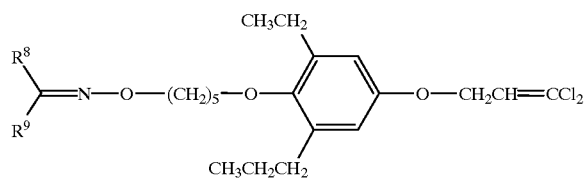
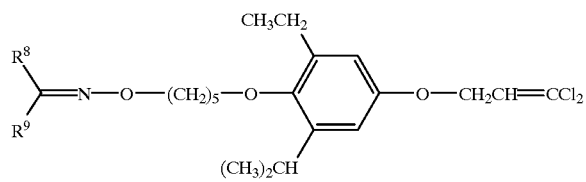
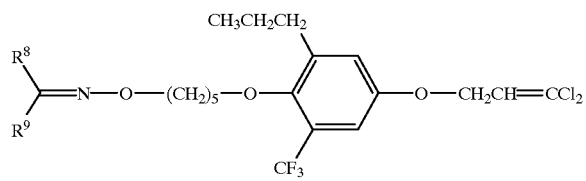
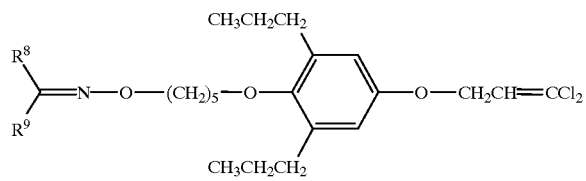
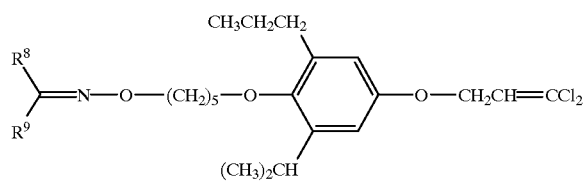
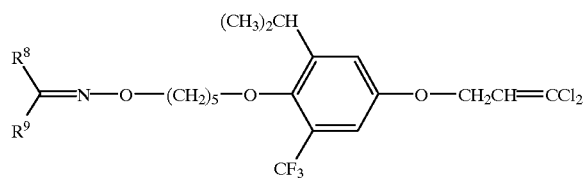
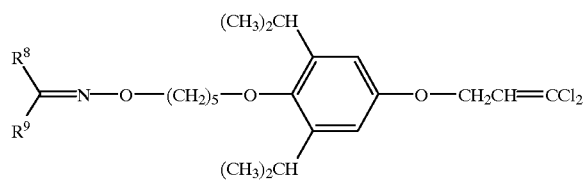
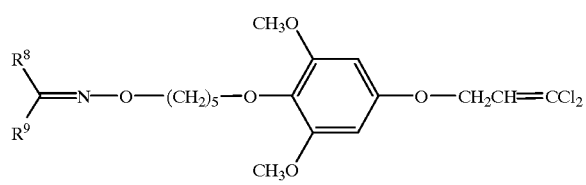
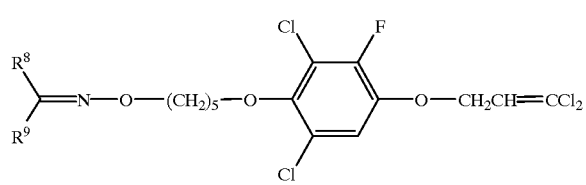

-continued
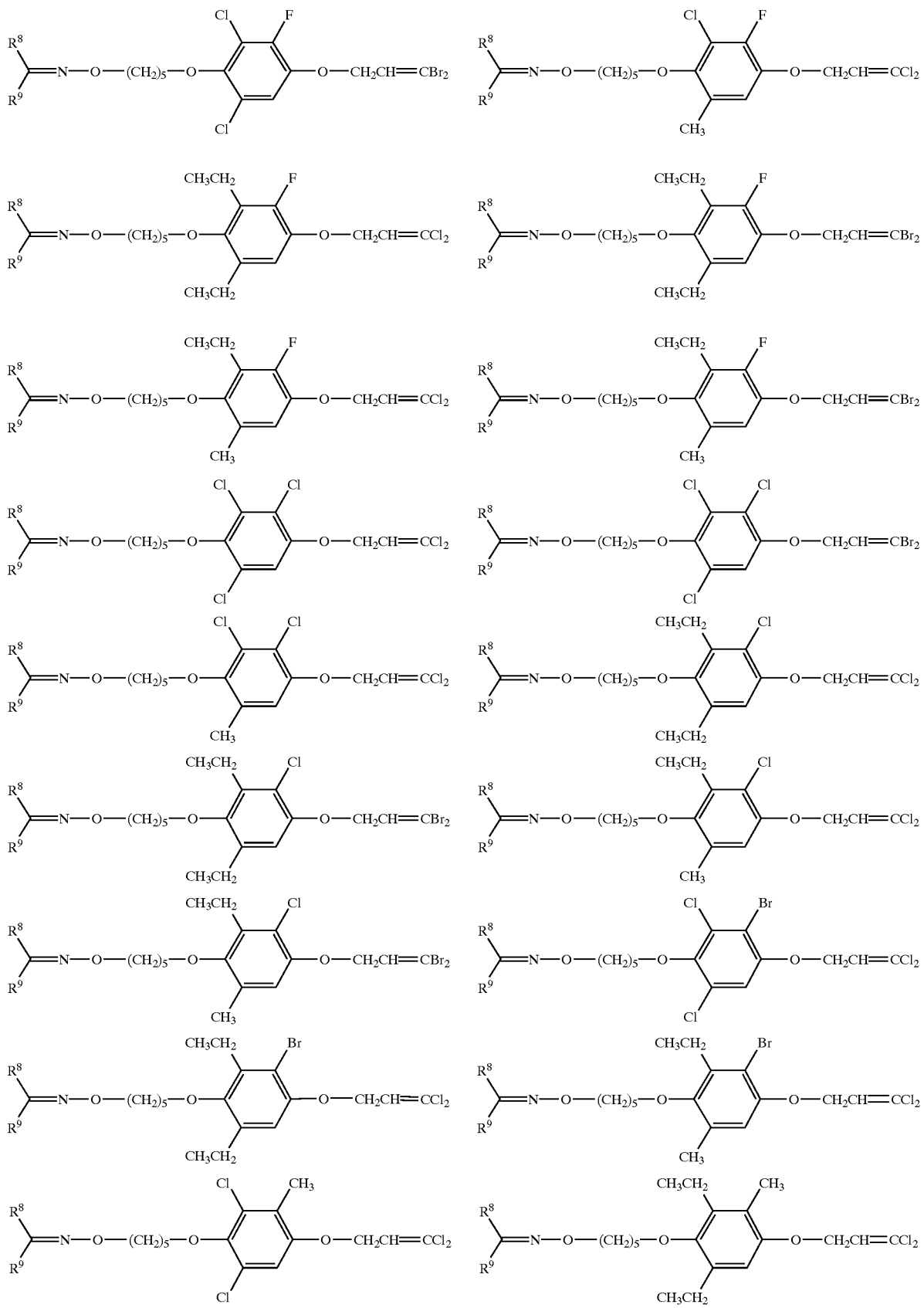

323 324
-continued
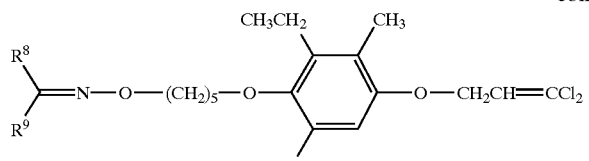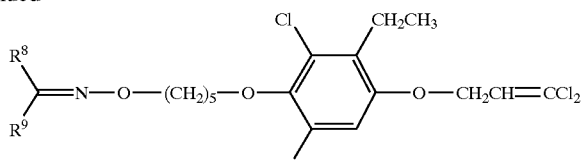
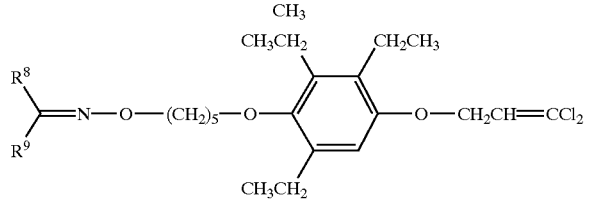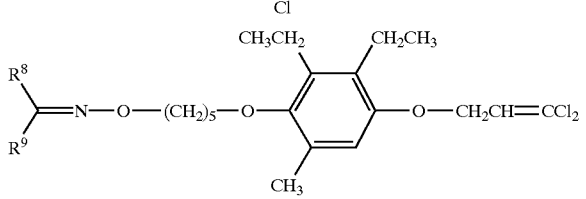
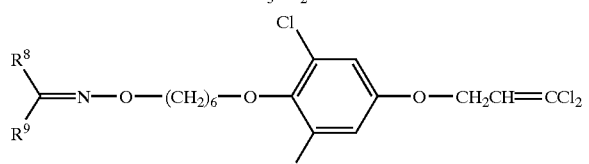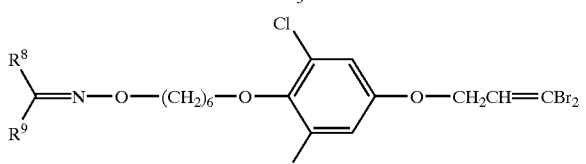
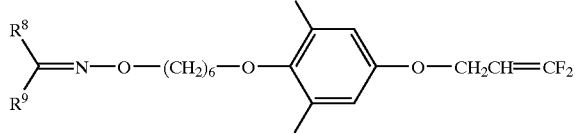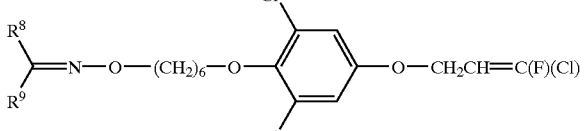
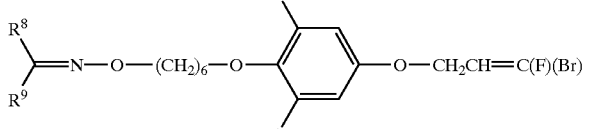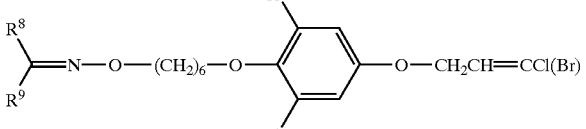
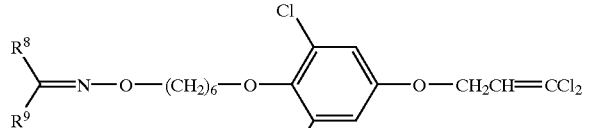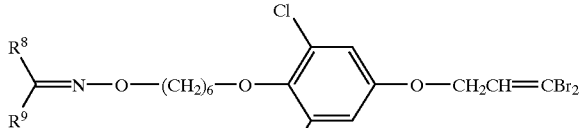
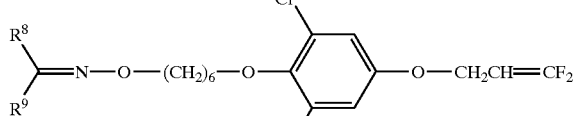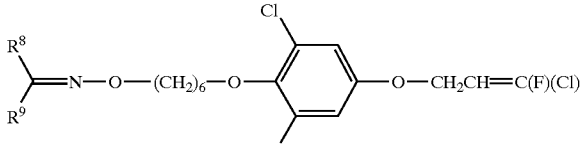
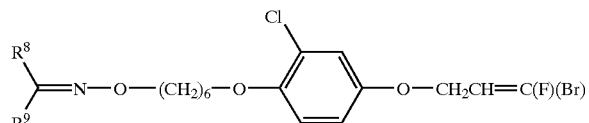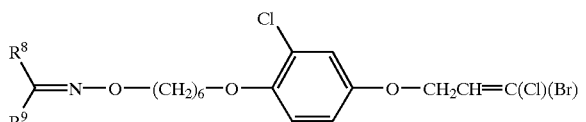
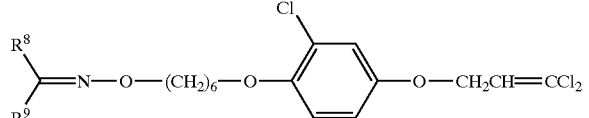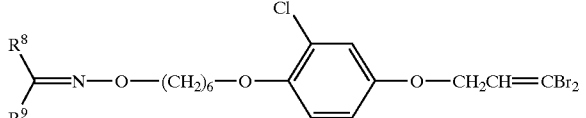
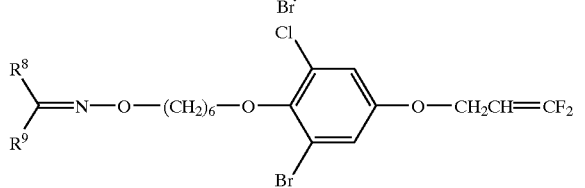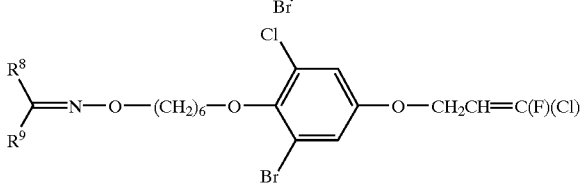

325  326
-continued
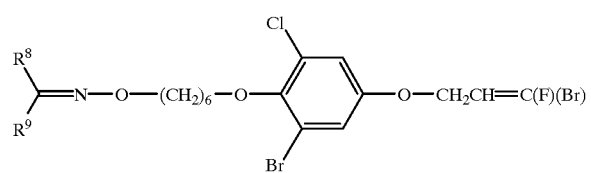
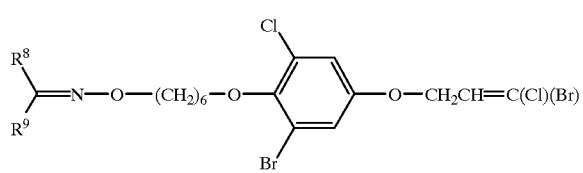
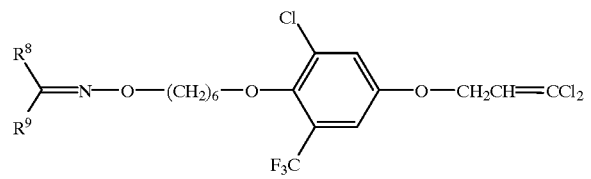
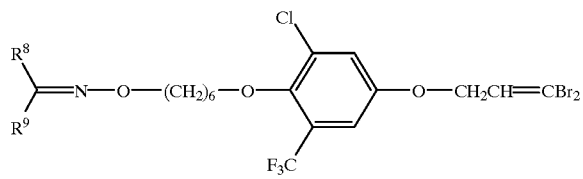
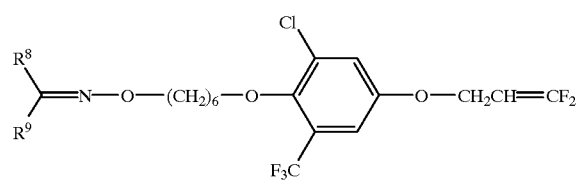
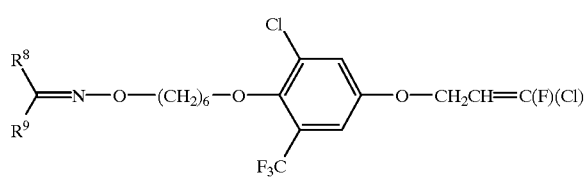
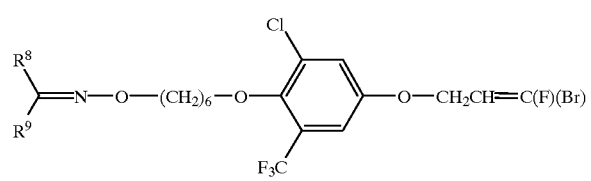
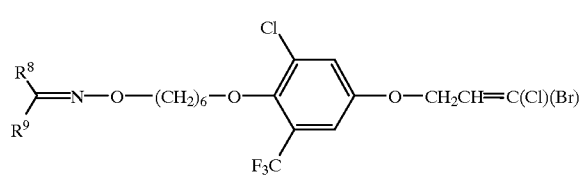
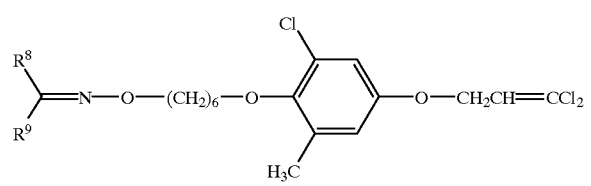
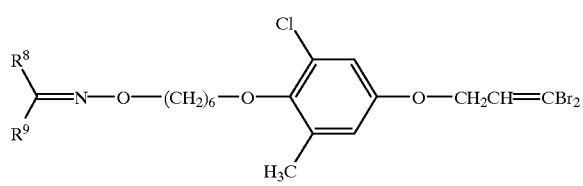
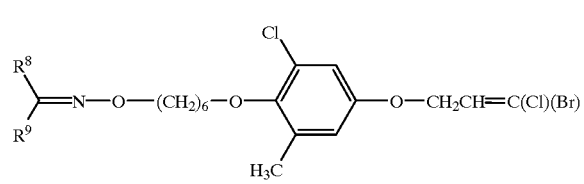
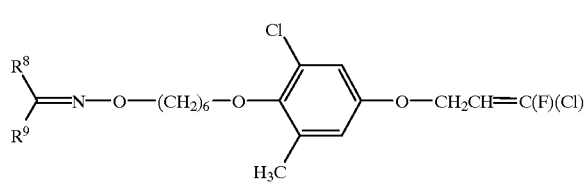
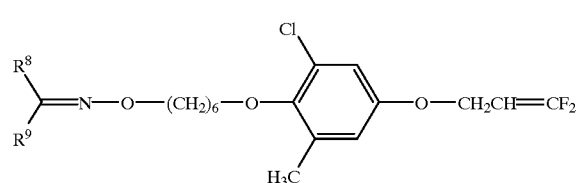
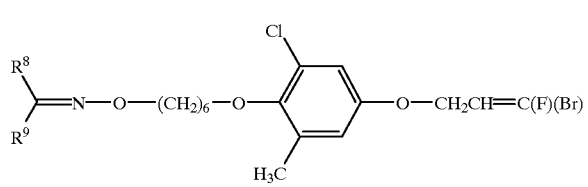
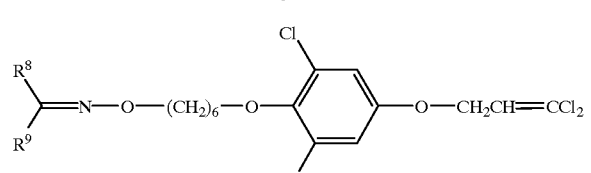
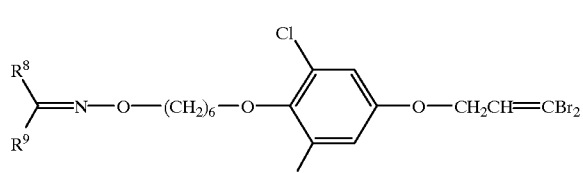
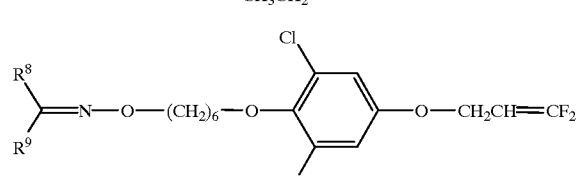
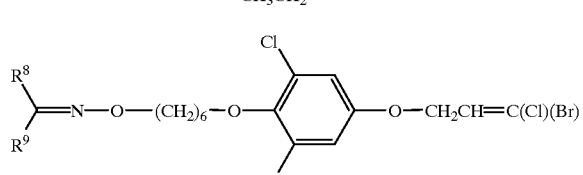

327  328
-continued
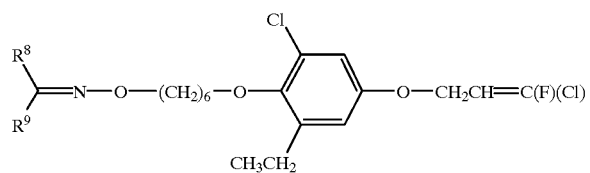
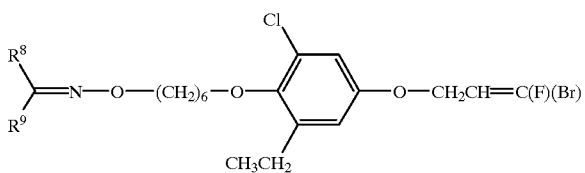
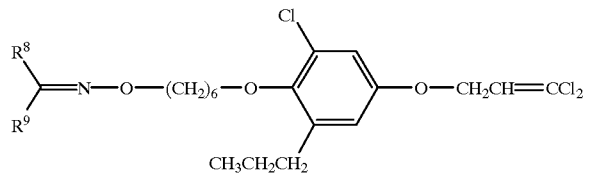
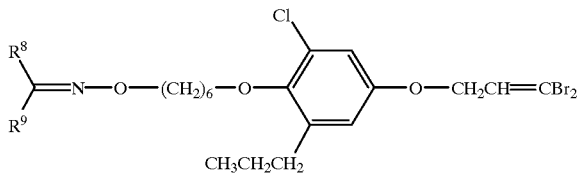
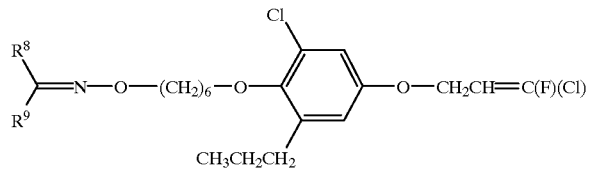
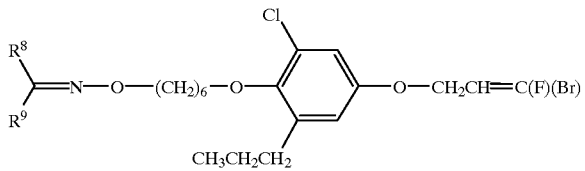
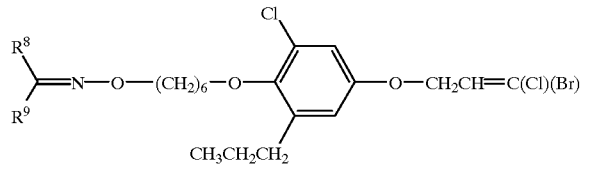
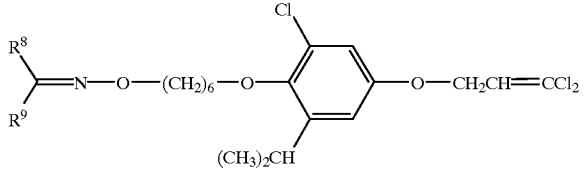
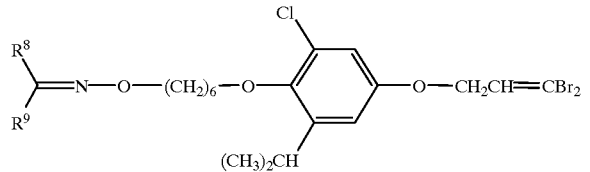
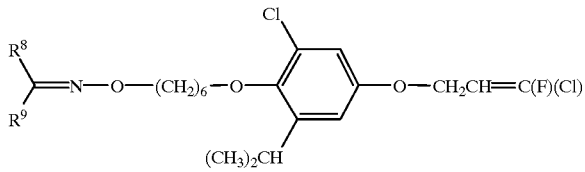
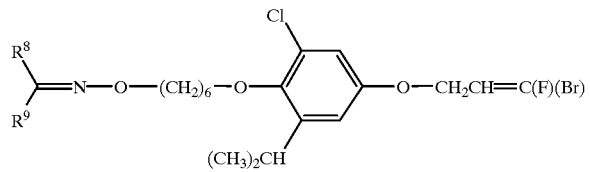
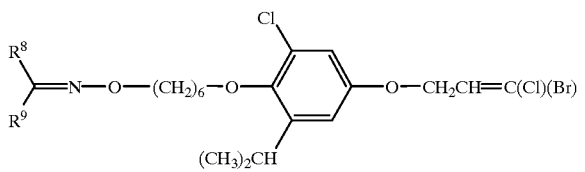
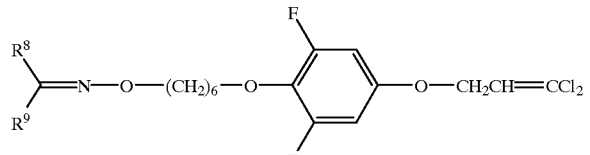
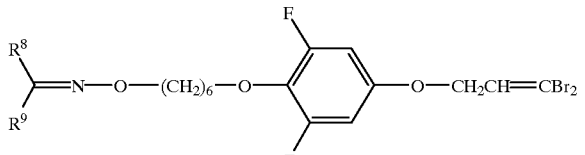
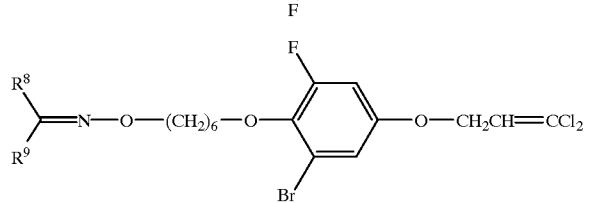
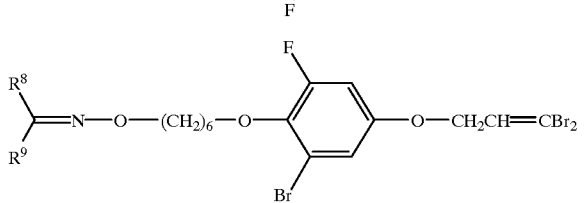

329 330

-continued
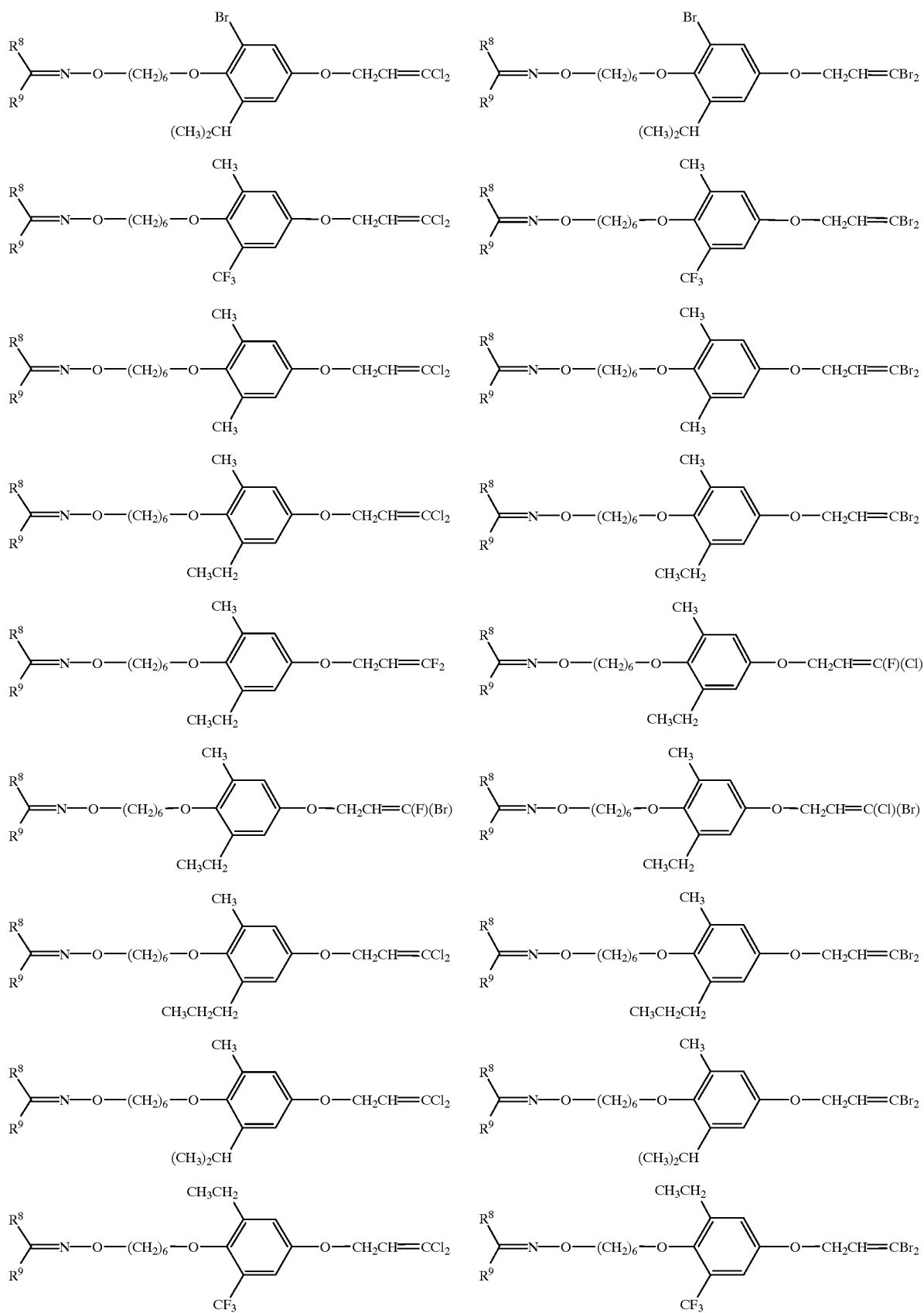

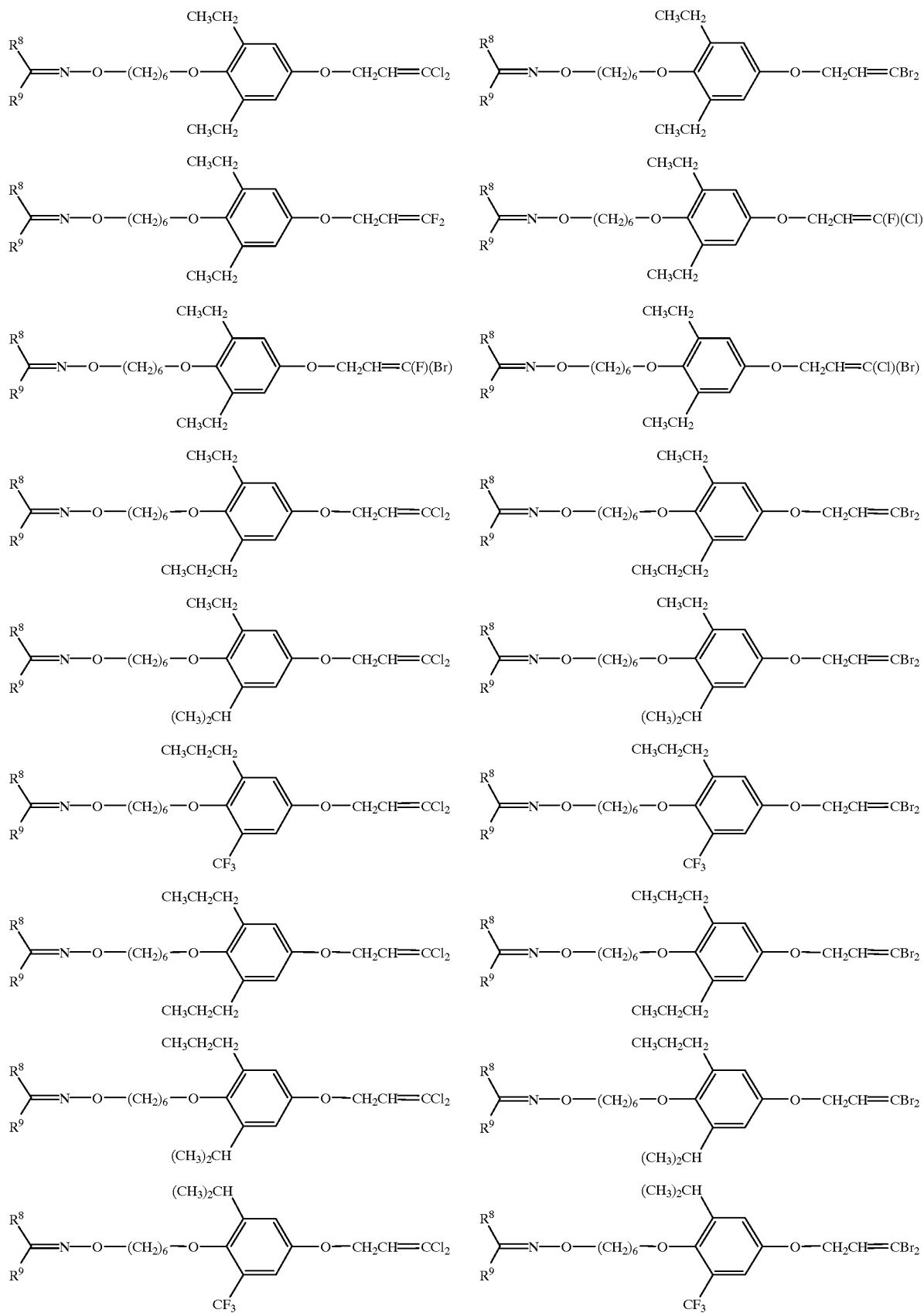

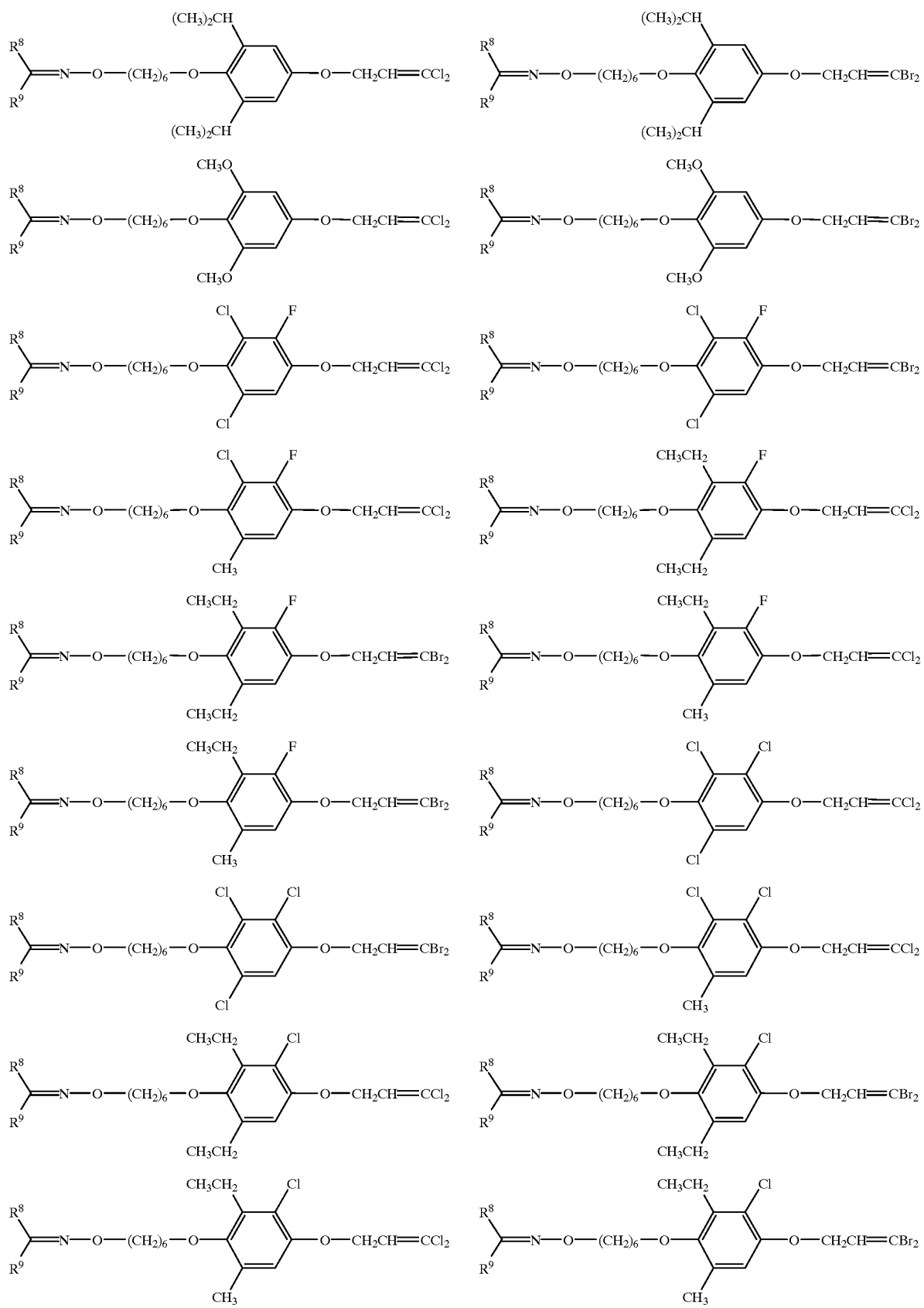

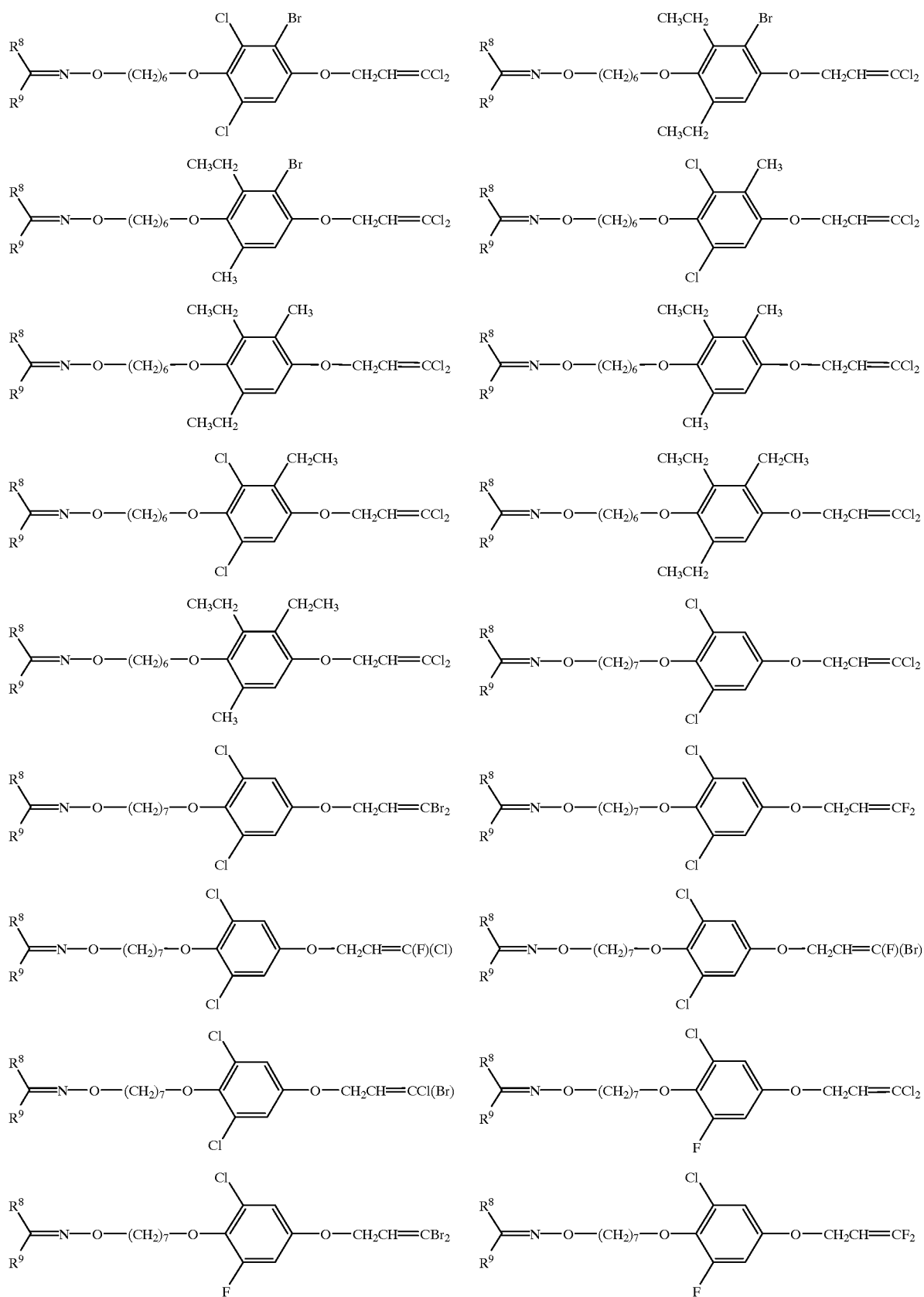

339 340
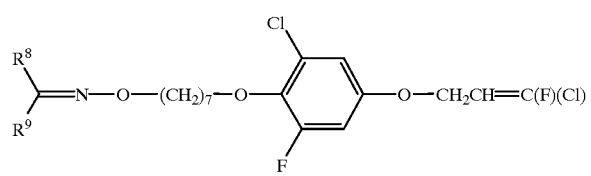 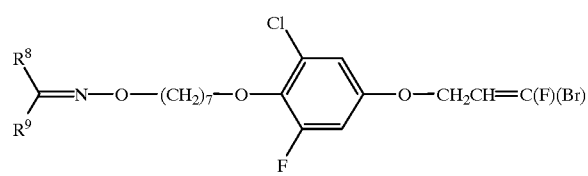
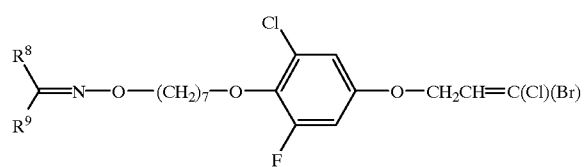 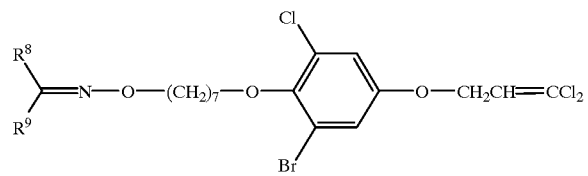
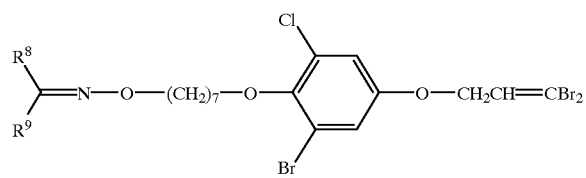 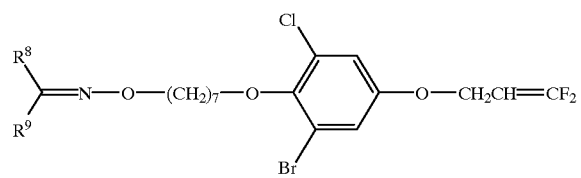
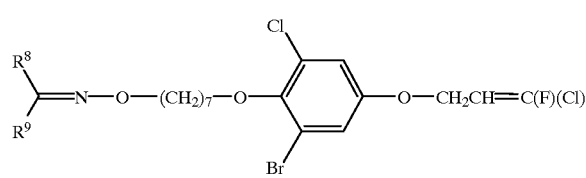 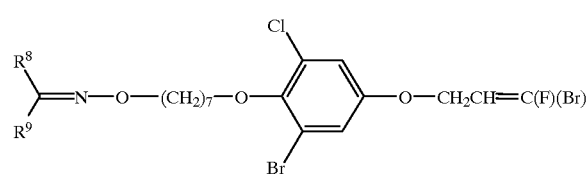
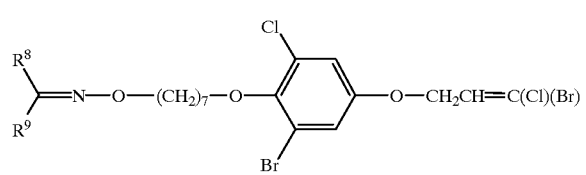 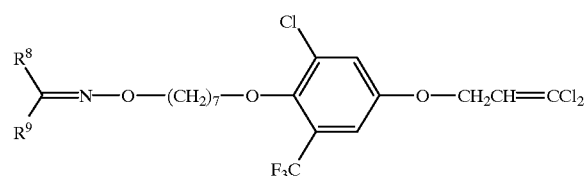
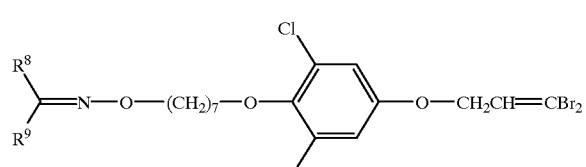 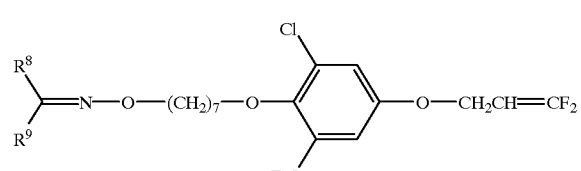
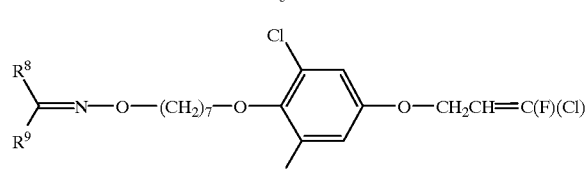 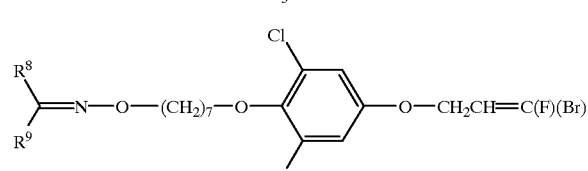
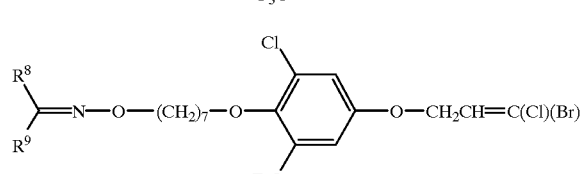 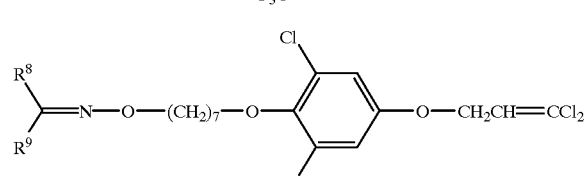
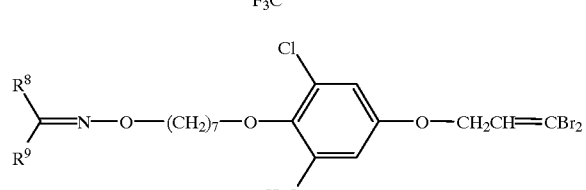 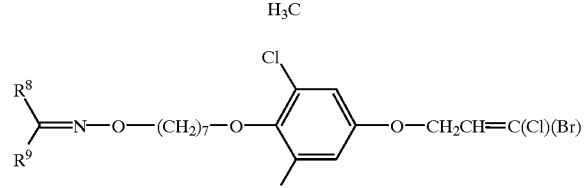

-continued
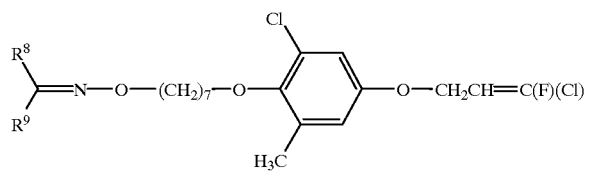
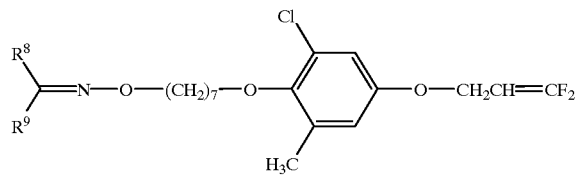
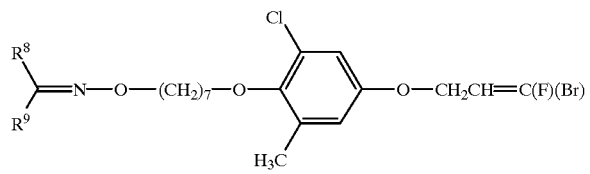
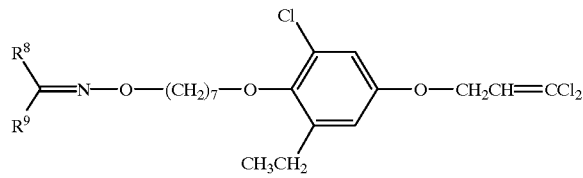
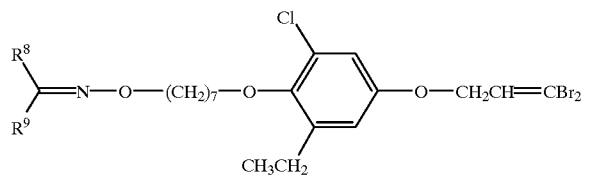
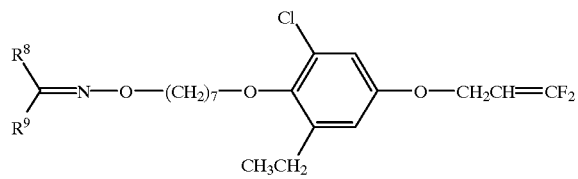
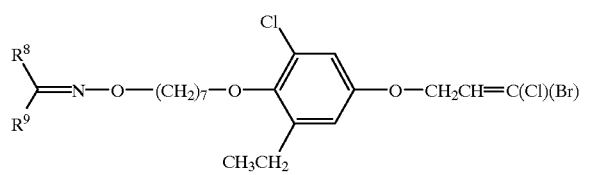
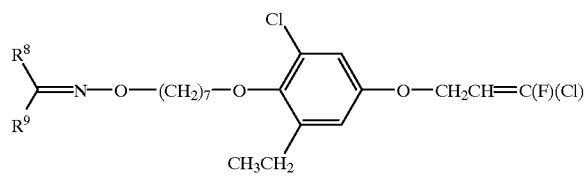
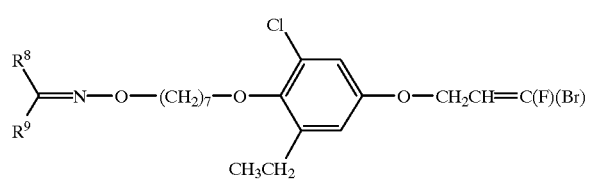
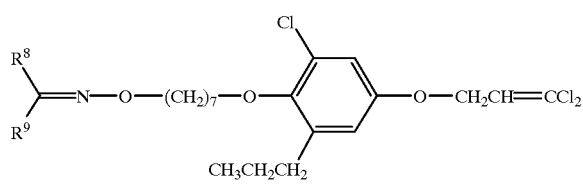
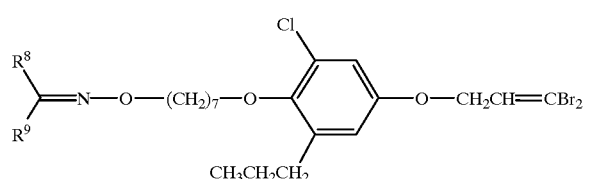
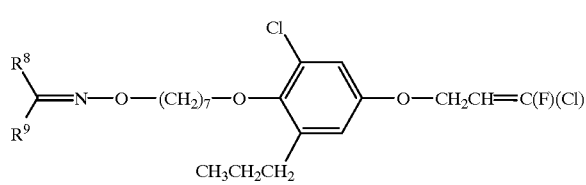
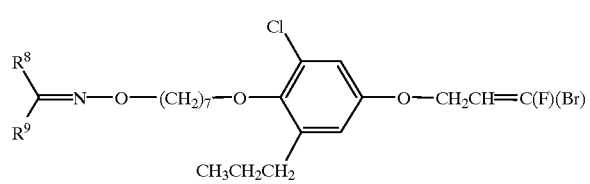
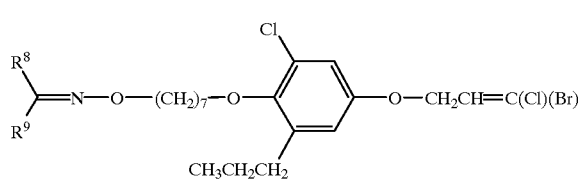
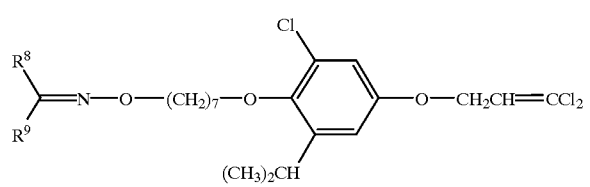
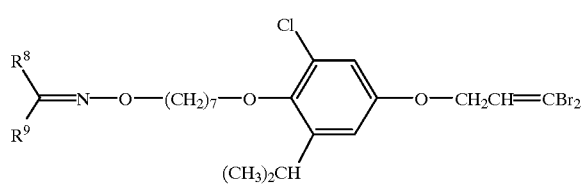
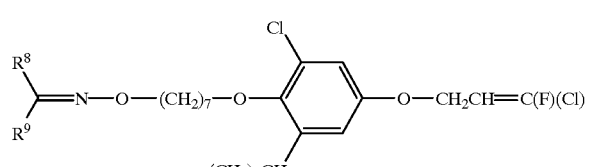
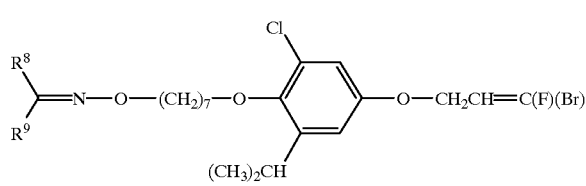

-continued
343
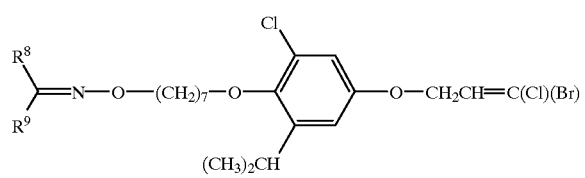
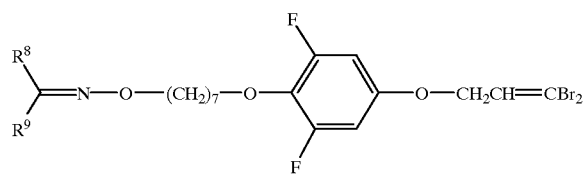
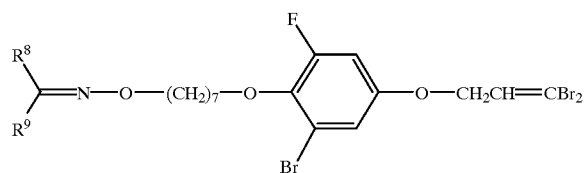
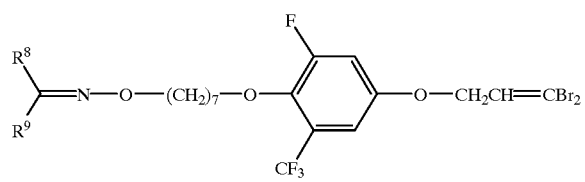
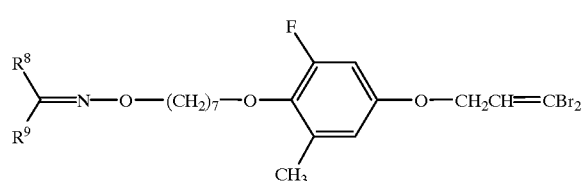
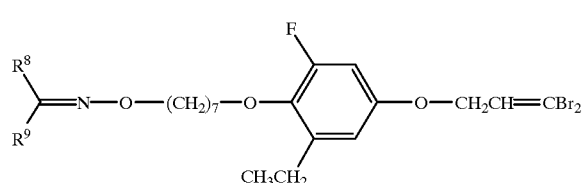
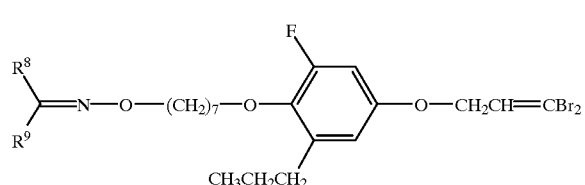
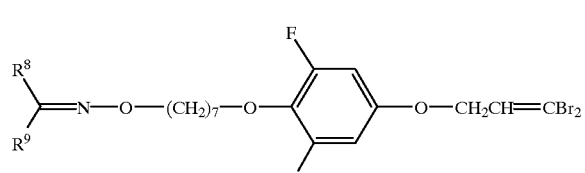
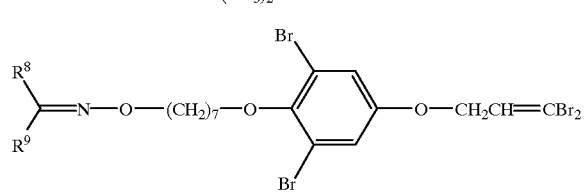
344
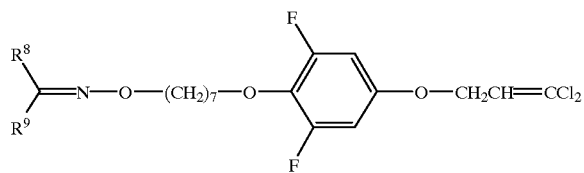
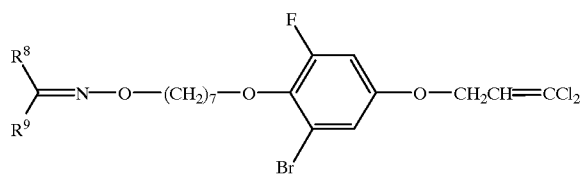
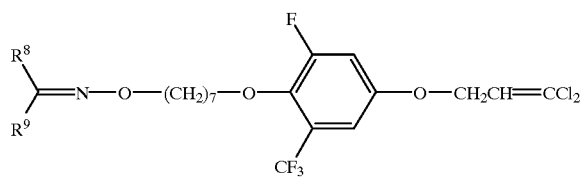
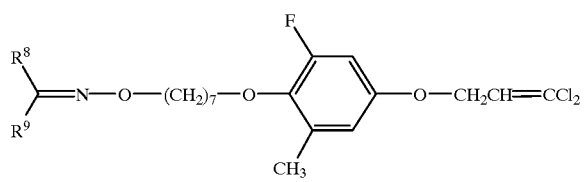
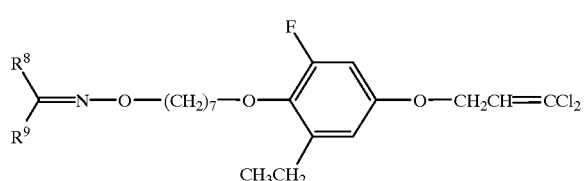
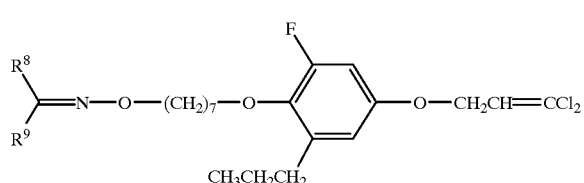
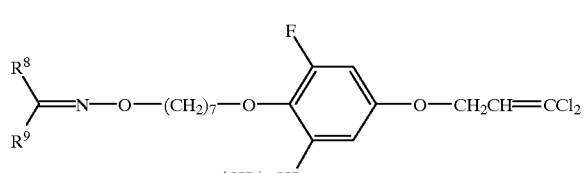
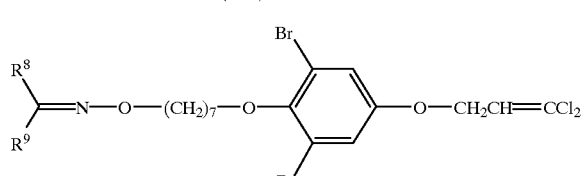
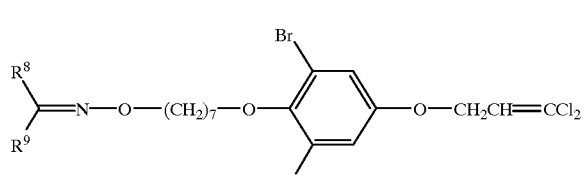

-continued
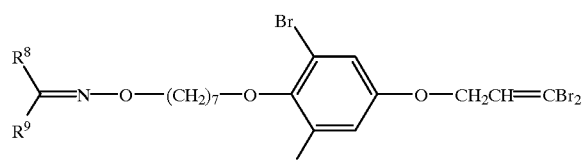
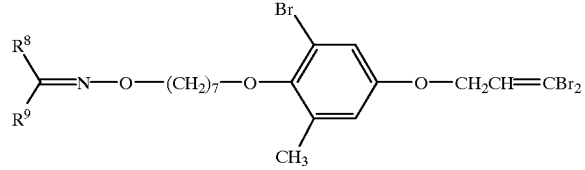
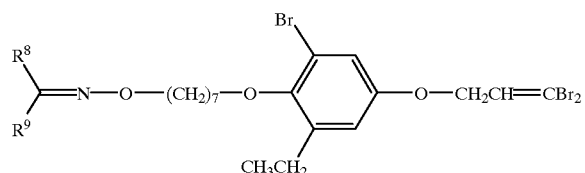
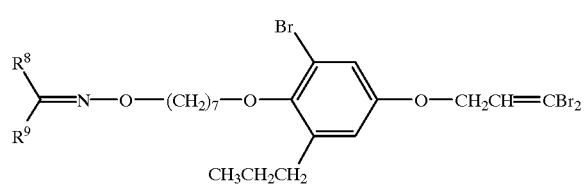
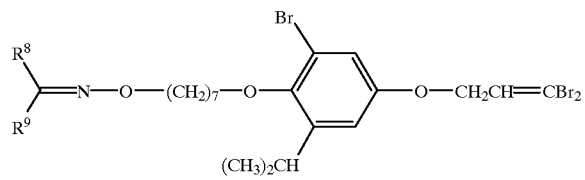
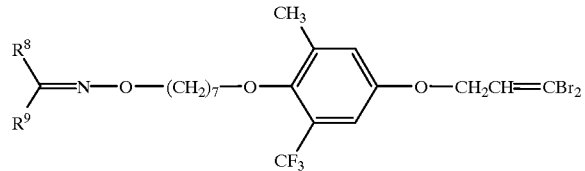
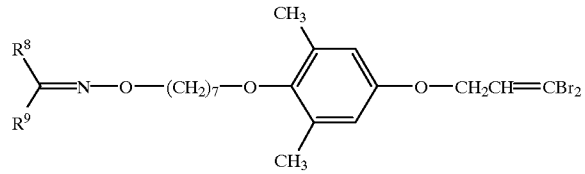
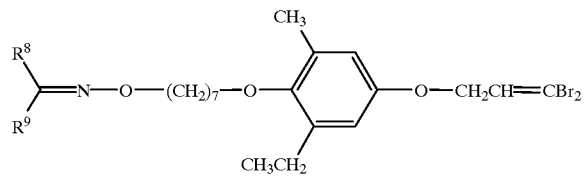
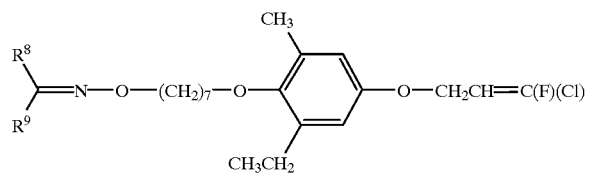
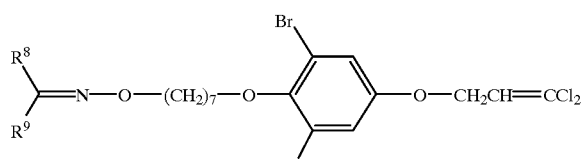
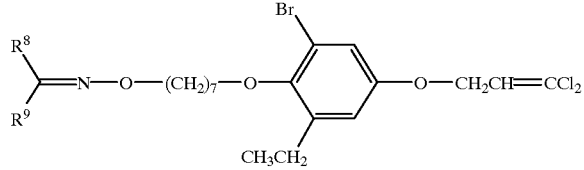
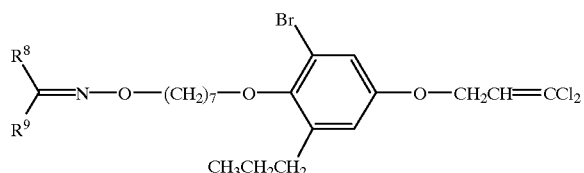
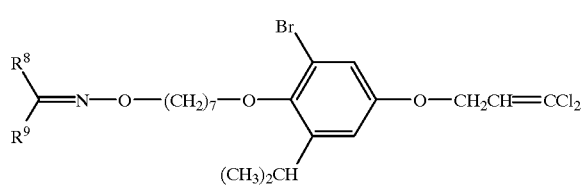
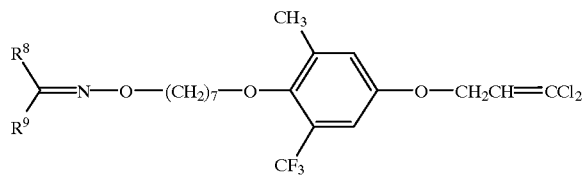
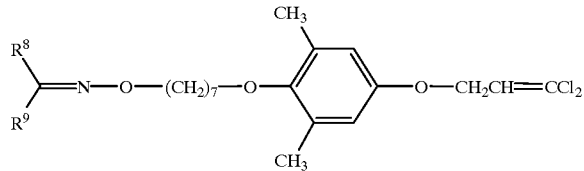
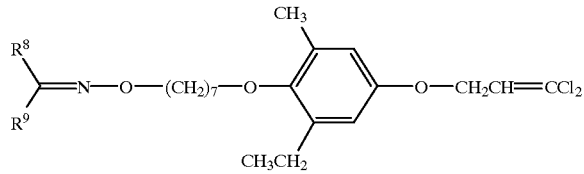
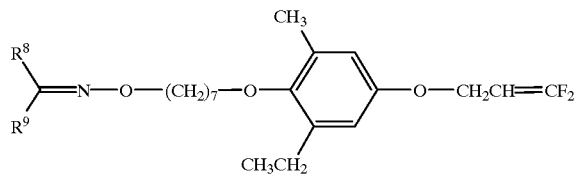
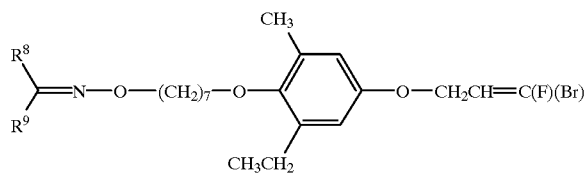

-continued
| 347 | 348 |
|---|---|
| 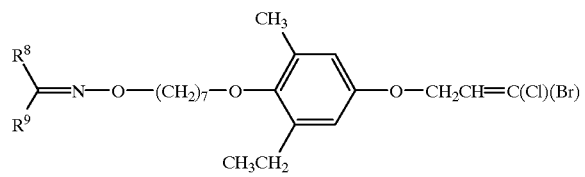 | 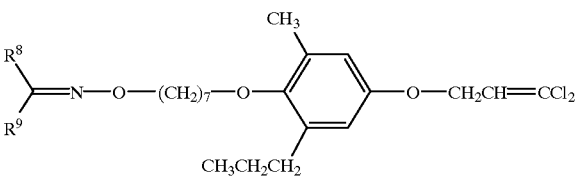 |
| 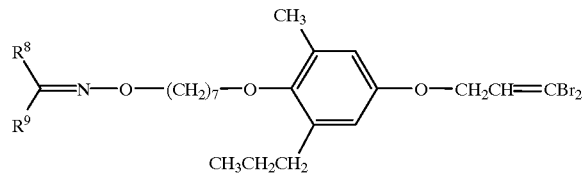 | 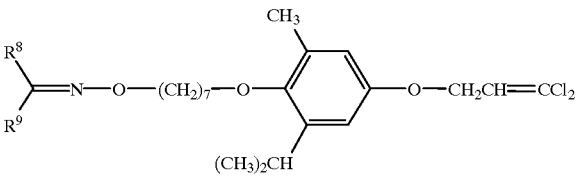 |
| 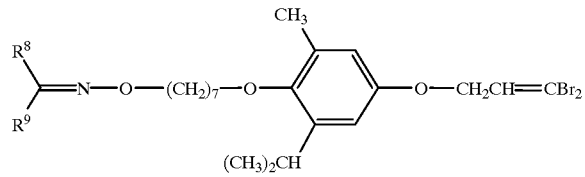 | 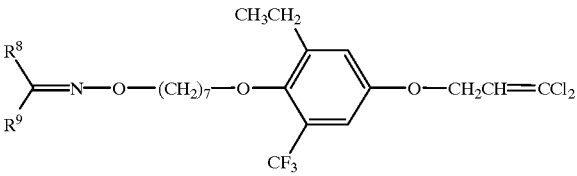 |
| 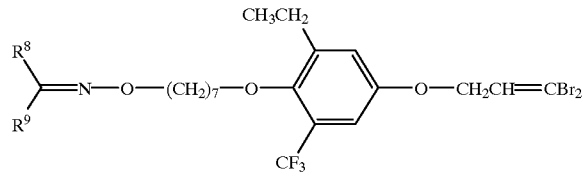 | 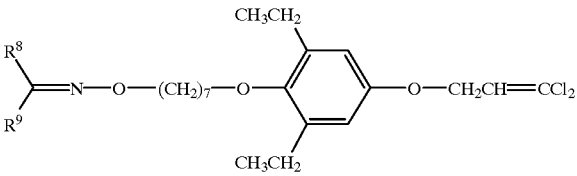 |
| 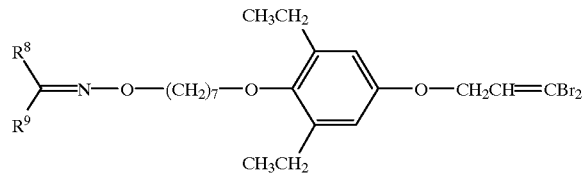 | 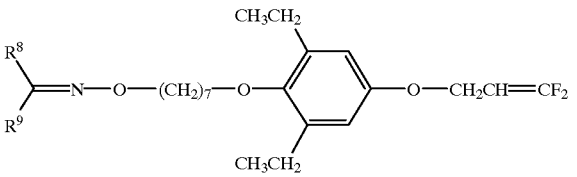 |
| 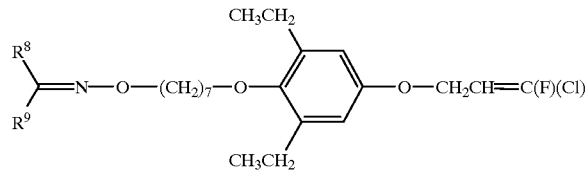 | 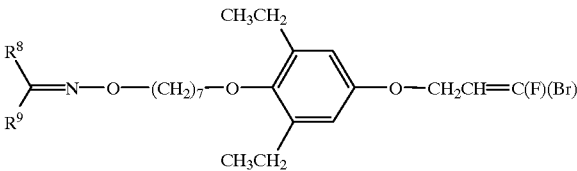 |
| 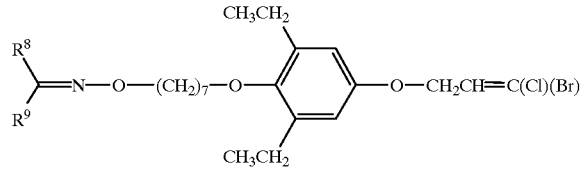 | 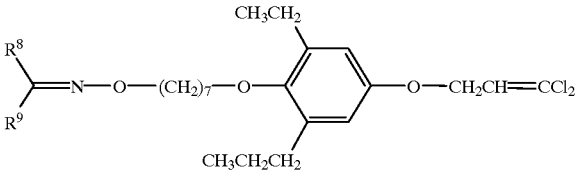 |
| 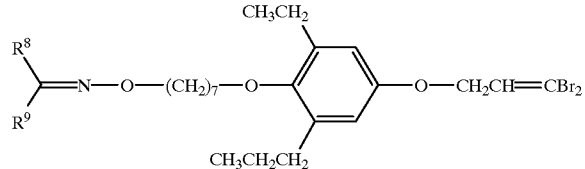 | 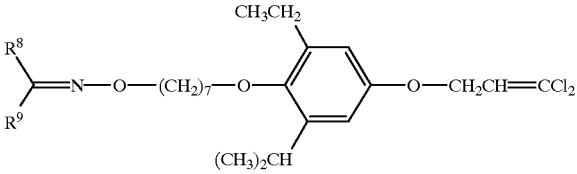 |
| 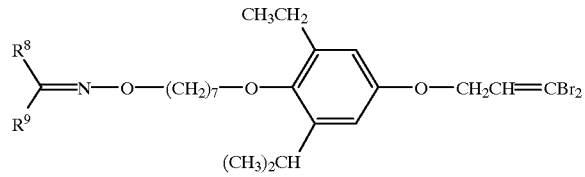 | 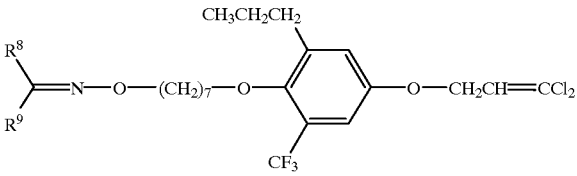 |

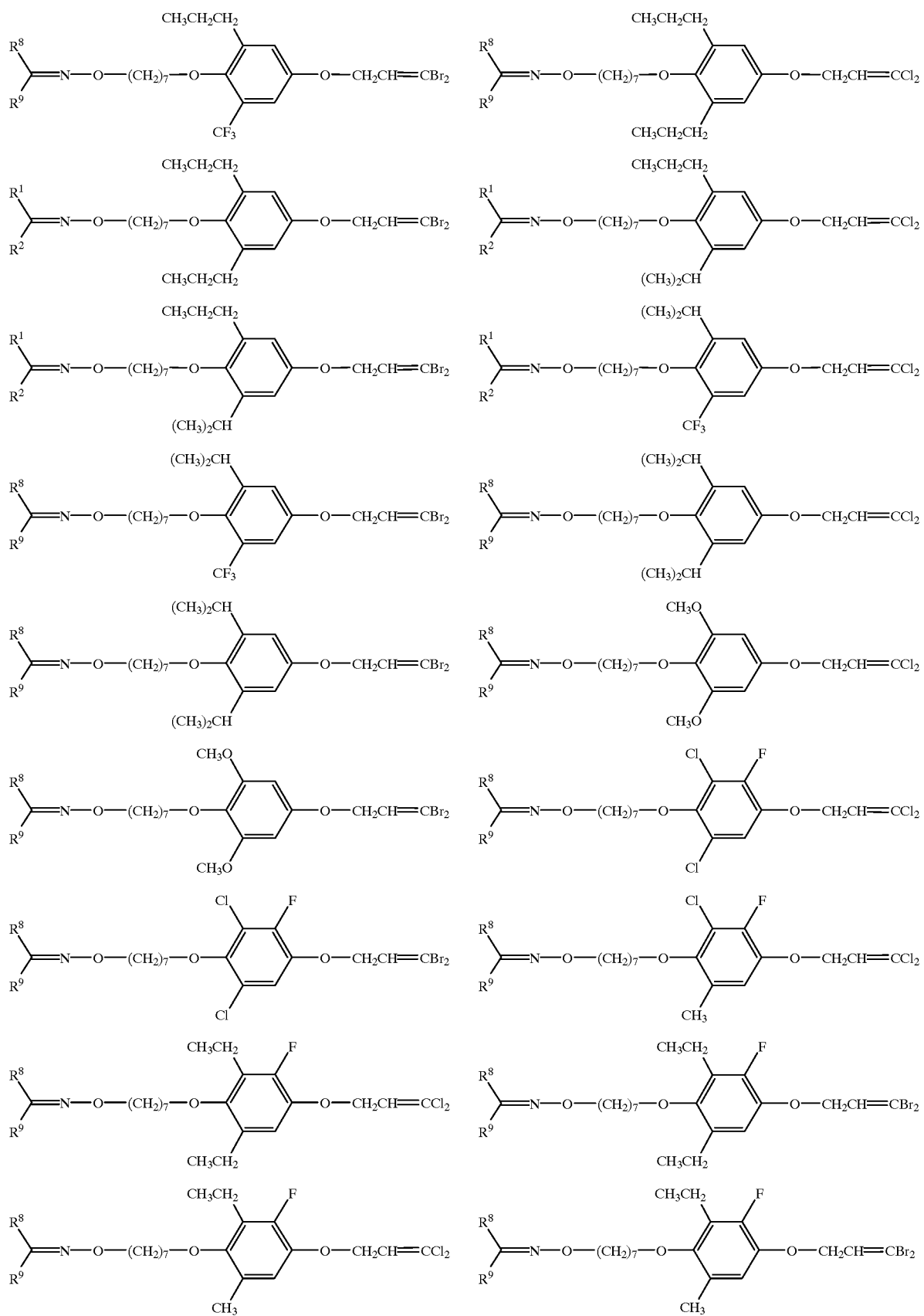

351 352

-continued

-continued
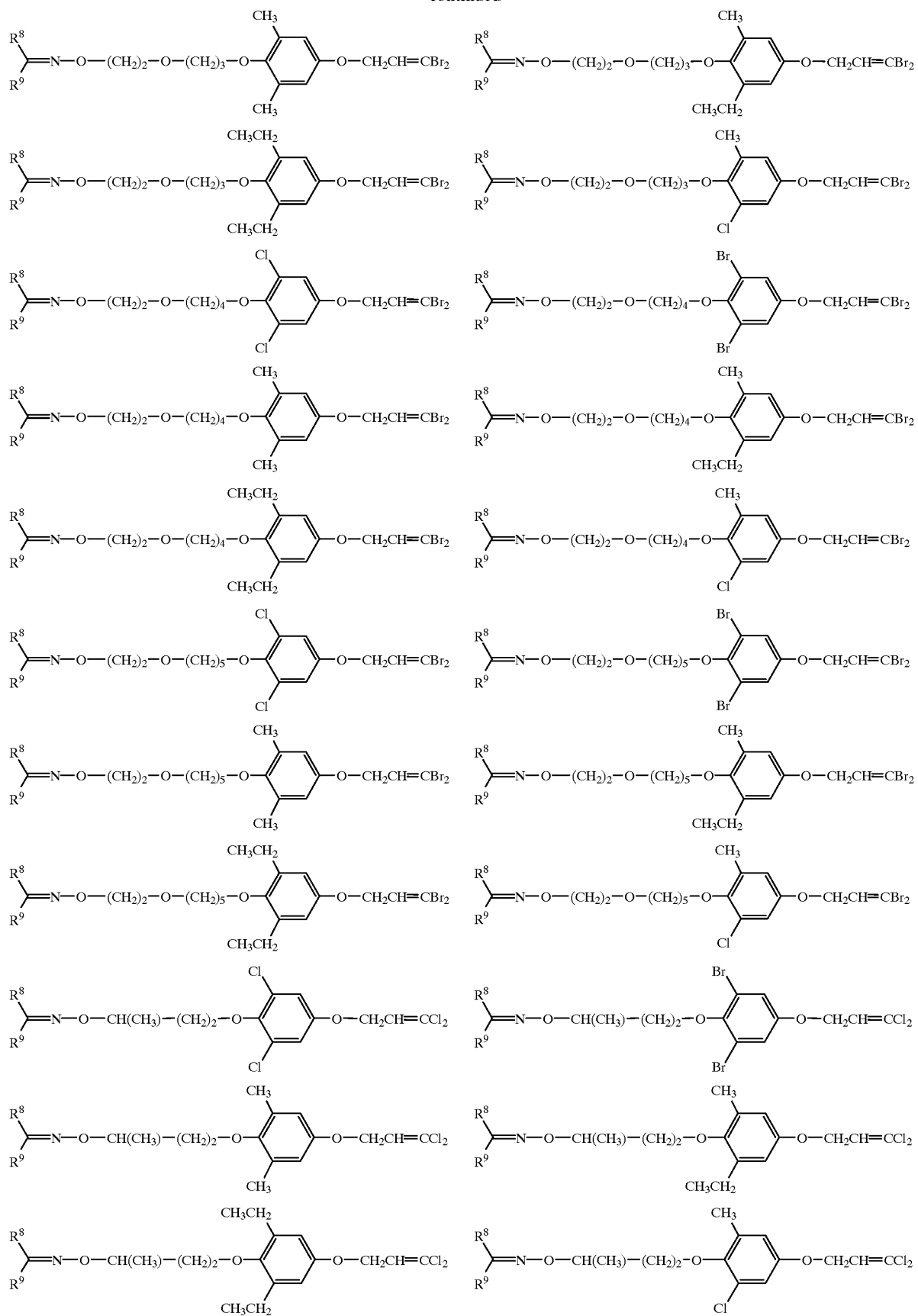

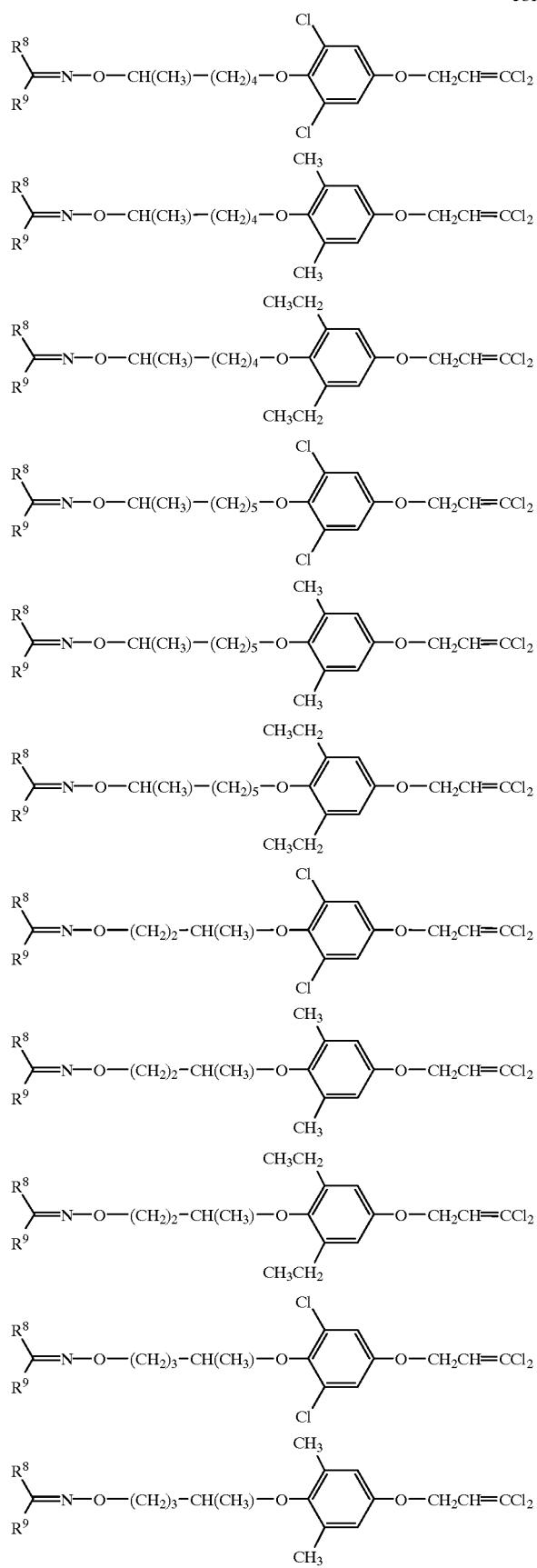
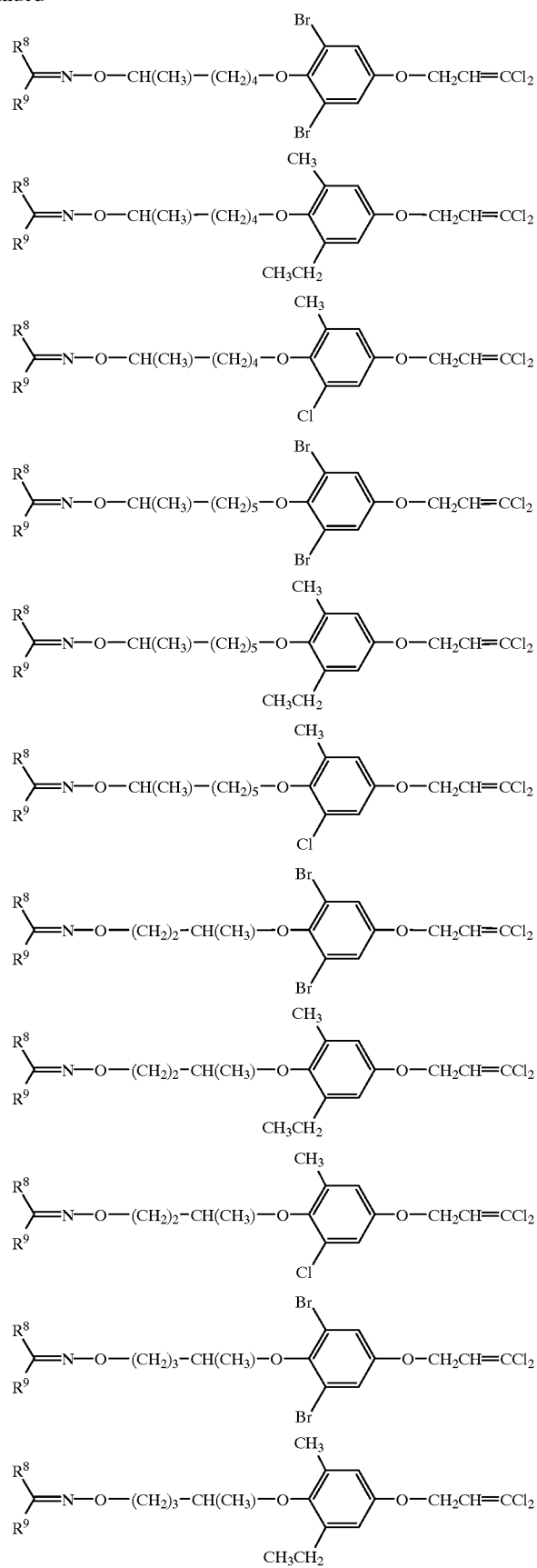

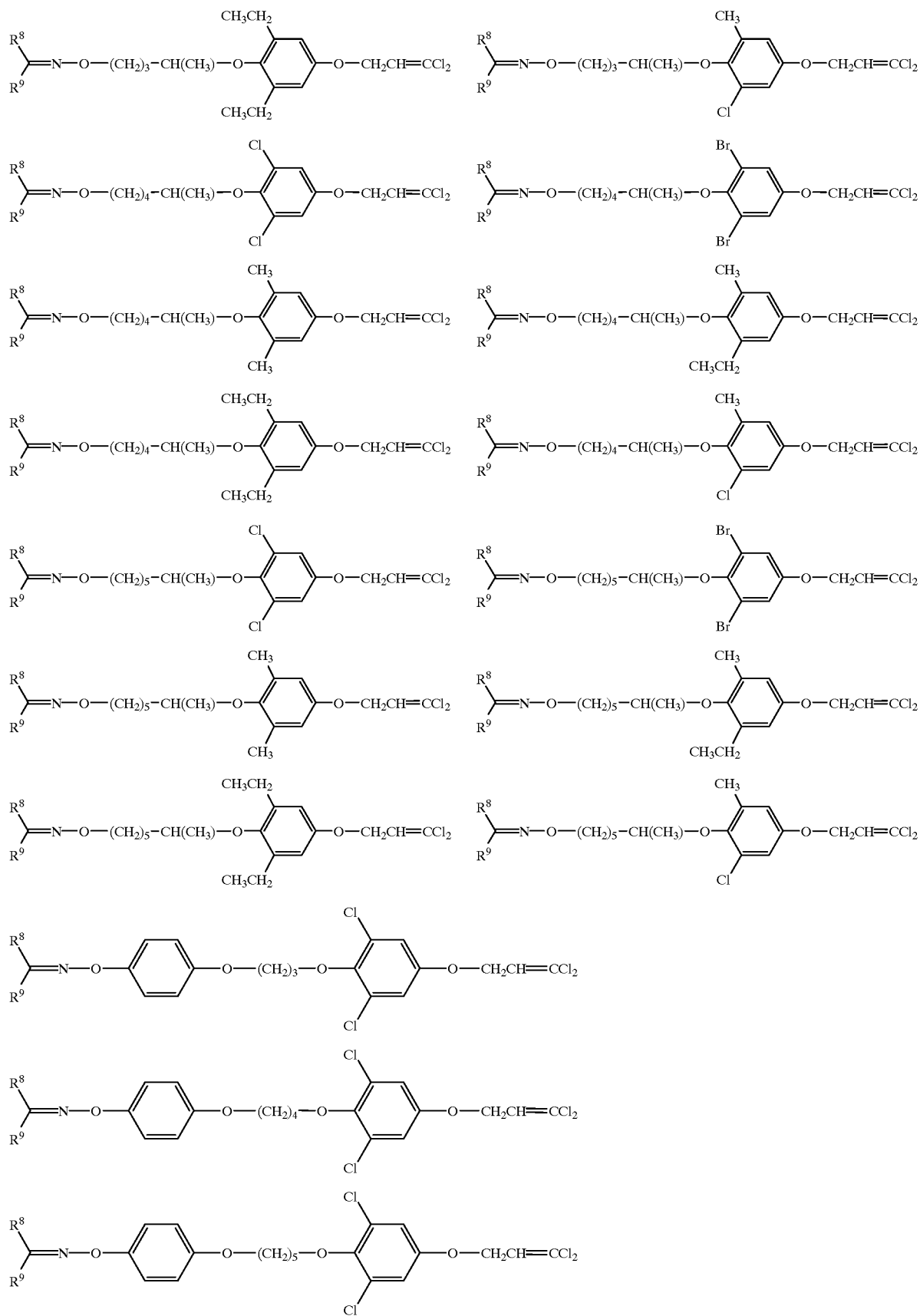

-continued
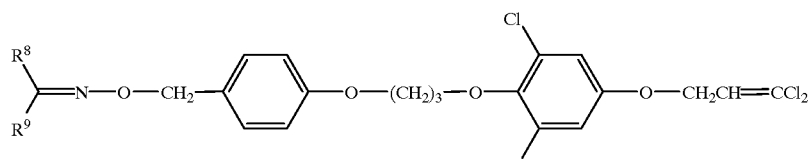
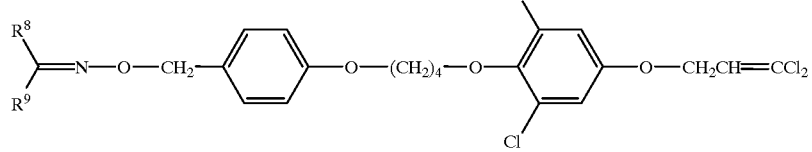
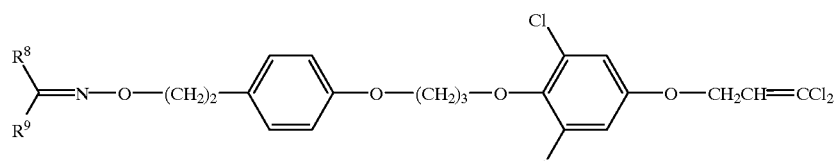
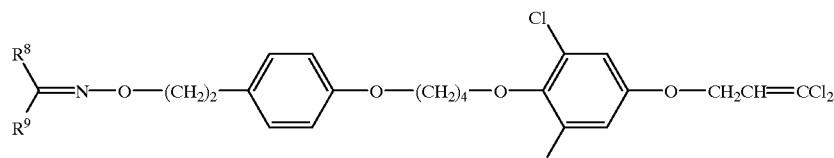
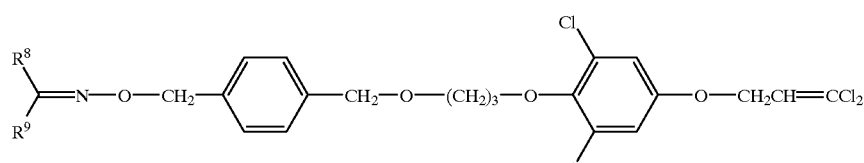
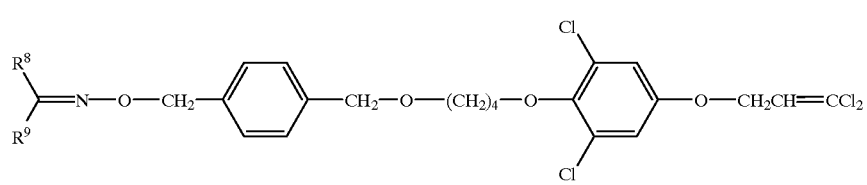
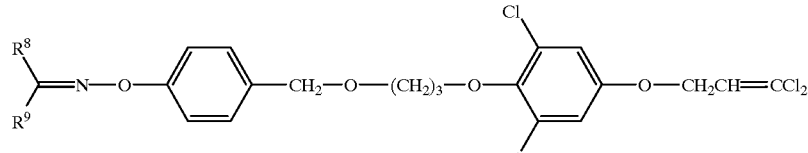
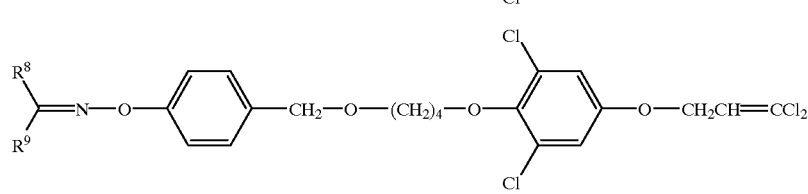
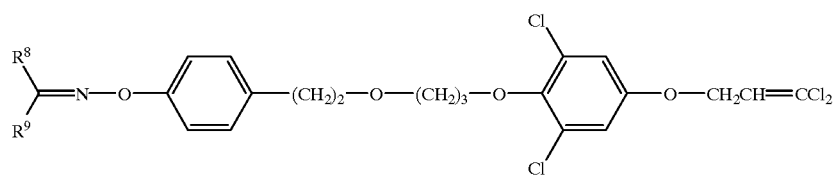

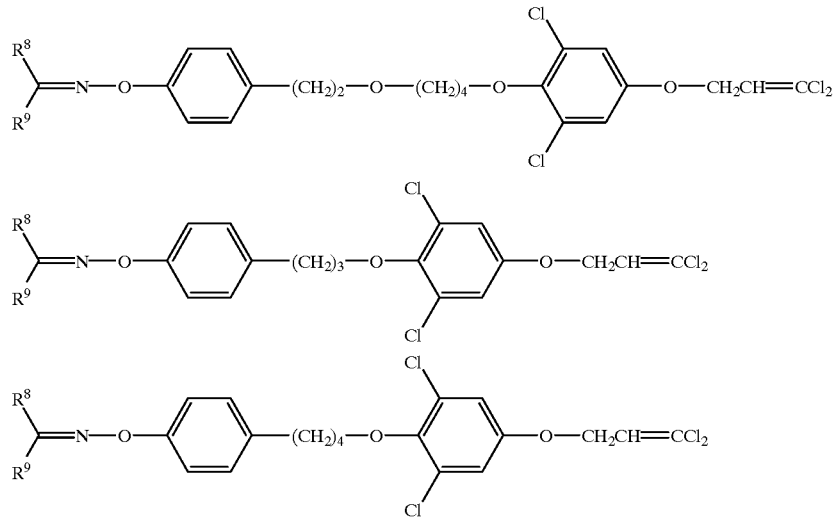

In the above formulae, R⁸ and R⁹ are as defined in Tables 20 to 47.

TABLE 20

| R⁸ | R⁹ |
|---|---|
| CH₃— | H |
| CH₃CH₂— | H |
| CH₃CH₂CH₂— | H |
| (CH₃)₂CH— | H |
| CH₃CH₂CH₂CH₂— | H |
| (CH₃)₂CHCH₂— | H |
| CH₃CH₂CH(CH₃)— | H |
| (CH₃)₃C— | H |
| CH₃CH₂CH₂CH₂CH₂— | H |
| (CH₃)₂CHCH₂CH₂— | H |
| CH₃CH₂CH(CH₃)CH₂— | H |
| (CH₃)₃CCH₂— | H |
| CH₃CH₂CH₂CH(CH₃)— | H |
| (CH₃)₂CHCH(CH₃)— | H |
| (CH₃CH₂)₂CH— | H |
| CH₃CH₂CH₂CH₂CH₂CH₂— | H |
| CH₃CH₂CH₂CH₂CH(CH₃)— | H |
| CH₃CH₂CH₂CH(CH₂CH₃)— | H |
| (CH₃CH₂)₂C(CH₃)— | H |
| CH₃CH₂CH₂CH₂CH₂CH₂CH₂— | H |
| CH₃CH₂CH₂CH₂CH₂CH(CH₃)— | H |
| (CH₃CH₂CH₂)₂CH— | H |
| CH₃(CH₂)₆CH₂— | H |
| CH₃(CH₂)₇CH₂— | H |
| CH₃(CH₂)₈CH₂— | H |
| CH₃(CH₂)₉CH₂— | H |
| CH₂F— | H |
| CHF₂— | H |
| CF₃— | H |
| CH₂Cl— | H |
| CHCl₂— | H |
| CCl₃— | H |
| CH₂Br— | H |
| CHBr₂— | H |
| CBr₃— | H |
| CFCl₂— | H |
| CFBr₂— | H |
| CH₂FCH₂— | H |
| CH₂ICH₂— | H |
| CHF₂CH₂— | H |
| CF₃CH₂— | H |
| CH₂ClCH₂— | H |
| CHCl₂CH₂— | H |
| CCl₃CH₂— | H |
| CH₂BrCH₂— | H |

TABLE 20-continued

| R⁸ | R⁹ |
|---|---|
| CHBr₂CH₂— | H |
| CBr₃CH₂— | H |
| CF₃CF₂— | H |
| CHF₂CF₂— | H |
| CH₃CHF— | H |
| CH₃CHCl— | H |
| CH₃CHBr— | H |
| CH₂ClCHCl— | H |
| CH₂BrCHBr— | H |
| CH₂FCH₂CH₂— | H |
| CH₂ClCH₂CH₂— | H |
| CH₂BrCH₂CH₂— | H |
| CH₃CHClCH₂— | H |
| CH₃CHBrCH₂— | H |
| CH₂ClCHClCH₂— | H |
| CH₂BrCHBrCH₂— | H |
| CF₃CF₂CH₂— | H |
| CF₃CHFCF₂— | H |
| CHF₂CF₂CF₂— | H |
| CF₃CH₂CH₂— | H |
| CH₂ClCHClCHCl— | H |
| CBrF₂CF₂CH₂— | H |
| (CH₃)₂CCl— | H |
| (CH₃)₂CBr— | H |
| CH₃CH₂CHCl— | H |
| CH₃CH₂CHBr— | H |
| CH₂FCH₂CH₂CH₂— | H |
| CH₂ClCH₂CH₂CH₂— | H |
| CH₂BrCH₂CH₂CH₂— | H |
| CH₃CHClCH₂CH₂— | H |
| CH₃CHBrCH₂CH₂— | H |
| CH₃C(CH₂Cl)₂— | H |
| CH₃C(CH₂Br)₂— | H |
| CF₃CH₂CH₂CH₂— | H |
| CH₂ClCH₂CH₂CH₂CH₂— | H |
| C(CH₃)₃CHCl— | H |
| CF₃CH₂CH₂CH₂CH₂— | H |
| CHCl=CHCH₂CH₂— | H |
| CH₃CCl=CHCH₂CH₂— | H |
| CH₃CH₂CCl=CHCH₂CH₂— | H |
| CF₃CCl=CHCH₂CH₂— | H |
| CF₃CF₂CCl=CHCH₂CH₂— | H |
| CHBr=CHCH₂CH₂— | H |
| CH₃CBr=CHCH₂CH₂— | H |
| CH₃CH₂CBr=CHCH₂CH₂— | H |
| CF₃CBr=CHCH₂CH₂— | H |
| CF₃CF₂CBr=CHCH₂CH₂— | H |
| CHF=CHCH₂CH₂— | H |

TABLE 20-continued

| R⁸ | R⁹ |
|---|---|
| CH₃CF=CHCH₂CH₂— | H |
| CH₃CH₂CF=CHCH₂CH₂— | H |
| CF₃CF=CHCH₂CH₂— | H |
| CF₃CF₂CF=CHCH₂CH₂— | H |
| CCl₂=CHCH₂CH₂— | H |
| CBr₂=CHCH₂CH₂— | H |
| CF₂=CHCH₂CH₂— | H |
| CClF=CHCH₂CH₂— | H |
| CF₃CH=CHCH₂CH₂— | H |
| CF₃C(CH₃)=CHCH₂CH₂— | H |
| (CF₃)₂C=CHCH₂CH₂— | H |
| CH₃OCH₂— | H |
| CH₃CH₂OCH₂— | H |
| CH₃CH₂CH₂OCH₂— | H |
| CH₃CH₂CH₂CH₂OCH₂— | H |
| CH₃SCH(CH₃)— | H |
| CH₃SC(CH₃)₂— | H |
| CH₃SCH₂CH₂— | H |
| cyclopropyl | H |
| cyclobutyl | H |
| 1-methylcyclobutyl | H |
| cyclopentyl | H |
| 1-methylcyclopentyl | H |
| 2-methylcyclopentyl | H |
| 3-methylcyclopentyl | H |
| cyclohexyl | H |
| 1-methylcyclohexyl | H |
| 2-methylcyclohexyl | H |
| 3-methylcyclohexyl | H |
| 4-methylcyclohexyl | H |
| 2-ethylcyclohexyl | H |
| 4-ethylcyclohexyl | H |
| 2-tert-butylcyclohexyl | H |
| 4-tert-butylcyclohexyl | H |
| 2,3-dimethylcyclohexyl | H |
| 3,4-dimethylcyclohexyl | H |
| 3,5-dimethylcyclohexyl | H |
| 2,6-dimethylcyclohexyl | H |
| menthyl | H |
| cycloheptyl | H |
| cyclopropylmethyl | H |
| 1-cyclopropylethyl | H |
| (1-methylcyclopropyl)methyl | H |
| (2-methylcyclopropyl)methyl | H |
| cyclobutylmethyl | H |
| cyclopentylmethyl | H |
| 3-cyclopentylpropyl | H |
| cyclohexylmethyl | H |
| 1-cyclohexylethyl | H |
| 2-cyclohexylethyl | H |
| 3-cyclohexylpropyl | H |
| 4-cyclohexylbutyl | H |
| 2-cyclopentenyl | H |
| 3-cyclopentenyl | H |
| 2-cyclohexenyl | H |
| 3-cyclohexenyl | H |
| 3-methyl-2-cyclohexenyl | H |
| (1-cyclopentenyl)methyl | H |
| (3-cyclohexenyl)methyl | H |
| CH₃— | CH₃ |
| CH₃CH₂— | CH₃ |
| CH₃CH₂CH₂— | CH₃ |
| (CH₃)₂CH— | CH₃ |
| CH₃CH₂CH₂CH₂— | CH₃ |
| (CH₃)₂CHCH₂— | CH₃ |
| CH₃CH₂CH(CH₃)— | CH₃ |
| (CH₃)₃C— | CH₃ |
| CH₃CH₂CH₂CH₂CH₂— | CH₃ |
| (CH₃)₂CHCH₂CH₂— | CH₃ |
| CH₃CH₂CH(CH₃)CH₂— | CH₃ |
| (CH₃)₃CCH₂— | CH₃ |
| CH₃CH₂CH₂CH(CH₃)— | CH₃ |
| (CH₃)₂CHCH(CH₃)— | CH₃ |
| (CH₃CH₂)₂CH— | CH₃ |
| CH₃CH₂CH₂CH₂CH₂CH₂— | CH₃ |
| CH₃CH₂CH₂CH₂CH(CH₃)— | CH₃ |
| CH₃CH₂CH₂CH(CH₂CH₃)— | CH₃ |
| (CH₃CH₂)₂C(CH₃)— | CH₃ |
| CH₃CH₂CH₂CH₂CH₂CH₂CH₂— | CH₃ |
| CH₃CH₂CH₂CH₂CH₂CH(CH₃)— | CH₃ |
| (CH₃CH₂CH₂)₂CH— | CH₃ |
| CH₃(CH₂)₆CH₂— | CH₃ |
| CH₃(CH₂)₇CH₂— | CH₃ |
| CH₃(CH₂)₈CH₂— | CH₃ |
| CH₃(CH₂)₉CH₂— | CH₃ |
| CH₂F— | CH₃ |
| CHF₂— | CH₃ |
| CF₃— | CH₃ |
| CH₂Cl— | CH₃ |
| CHCl₂— | CH₃ |
| CCl₃— | CH₃ |
| CH₂Br— | CH₃ |
| CHBr₂— | CH₃ |
| CBr₃— | CH₃ |
| CFCl₂— | CH₃ |
| CFBr₂— | CH₃ |
| CH₂FCH₂— | CH₃ |
| CH₂ICH₂— | CH₃ |
| CHF₂CH₂— | CH₃ |
| CF₃CH₂— | CH₃ |
| CH₂ClCH₂— | CH₃ |
| CHCl₂CH₂— | CH₃ |
| CCl₃CH₂— | CH₃ |
| CH₂BrCH₂— | CH₃ |
| CHBr₂CH₂— | CH₃ |
| CBr₃CH₂— | CH₃ |
| CF₃CF₂— | CH₃ |
| CHF₂CF₂— | CH₃ |
| CH₃CHF— | CH₃ |
| CH₃CHCl— | CH₃ |
| CH₃CHBr— | CH₃ |
| CH₂ClCHCl— | CH₃ |
| CH₂BrCHBr— | CH₃ |
| CH₂FCH₂CH₂— | CH₃ |
| CH₂ClCH₂CH₂— | CH₃ |
| CH₂BrCH₂CH₂— | Cl13 |
| CH₃CHClCH₂— | CH₃ |
| CH₃CHBrCH₂— | CH₃ |
| CH₂ClCHClCH₂— | CH₃ |
| CH₂BrCHBrCH₂— | CH₃ |
| CF₃CF₂CH₂— | CH₃ |
| CF₃CHFCF₂— | CH₃ |
| CHF₂CF₂CF₂— | CH₃ |
| CF₃CH₂CH₂— | CH₃ |
| CH₂ClCHClCHCl— | CH₃ |
| CBrF₂CF₂CH₂— | CH₃ |
| (CH₃)₂CCl— | CH₃ |
| (CH₃)₂CBr— | CH₃ |
| CH₃CH₂CHCl— | CH₃ |
| CH₃CH₂CHBr— | CH₃ |
| CH₂FCH₂CH₂CH₂— | CH₃ |
| CH₂ClCH₂CH₂CH₂— | CH₃ |
| CH₂BrCH₂CH₂CH₂— | CH₃ |
| CH₃CHClCH₂CH₂— | CH₃ |
| CH₃CHBrCH₂CH₂— | CH₃ |
| CH₃C(CH₂Cl)₂— | CH₃ |
| CH₃C(CH₂Br)₂— | CH₃ |
| CF₃CH₂CH₂CH₂— | CH₃ |
| CH₂ClCH₂CH₂CH₂CH₂— | CH₃ |
| C(CH₃)₃CHCl— | CH₃ |
| CF₃CH₂CH₂CH₂CH₂— | CH₃ |
| CHCl=CHCH₂CH₂— | CH₃ |
| CH₃CCl=CHCH₂CH₂— | CH₃ |
| CH₃CH₂CCl=CHCH₂CH₂— | CH₃ |
| CF₃CCl=CHCH₂CH₂— | CH₃ |
| CF₃CF₂CCl=CHCH₂CH₂— | CH₃ |
| CHBr=CHCH₂CH₂— | CH₃ |
| CH₃CBr=CHCH₂CH₂— | CH₃ |
| CH₃CH₂CBr=CHCH₂CH₂— | CH₃ |
| CF₃CBr=CHCH₂CH₂— | CH₃ |
| CF₃CF₂CBr=CHCH₂CH₂— | CH₃ |
| CHF=CHCH₂CH₂— | CH₃ |
| CH₃CF=CHCH₂CH₂— | CH₃ |
| CH₃CH₂CF=CHCH₂CH₂— | CH₃ |

TABLE 20-continued

| R⁸ | R⁹ |
|---|---|
| CF₃CF=CHCH₂CH₂— | CH₃ |
| CF₃CF₂CF=CHCH₂CH₂— | CH₃ |
| CCl₂=CHCH₂CH₂— | CH₃ |
| CBr₂=CHCH₂CH₂— | CH₃ |
| CF₂=CHCH₂CH₂— | CH₃ |
| CClF=CHCH₂CH₂— | CH₃ |
| CF₃CH=CHCH₂CH₂— | CH₃ |
| CF₃C(CH₃)=CHCH₂CH₂— | CH₃ |
| (CF₃)₂C=CHCH₂CH₂— | CH₃ |
| CH₃OCH₂— | CH₃ |
| CH₃CH₂OCH₂— | CH₃ |
| CH₃CH₂CH₂OCH₂— | CH₃ |
| CH₃CH₂CH₂CH₂OCH₂— | CH₃ |
| CH₃SCH(CH₃)— | CH₃ |
| CH₃SCH₂CH₂— | CH₃ |
| cyclopropyl | CH₃ |
| cyclobutyl | CH₃ |
| 1-methylcyclobutyl | CH₃ |
| cyclopentyl | CH₃ |
| 1-methylcyclopentyl | CH₃ |
| 2-methylcyclopentyl | CH₃ |
| 3-methylcyclopentyl | CH₃ |
| cyclohexyl | CH₃ |
| 1-methylcyclohexyl | CH₃ |
| 2-methylcyclohexyl | CH₃ |
| 3-methylcyclohexyl | CH₃ |
| 4-methylcyclohexyl | CH₃ |
| 2-ethylcyclohexyl | CH₃ |
| 4-ethylcyclohexyl | CH₃ |
| 2-tert-butylcyclohexyl | CH₃ |
| 4-tert-butylcyclohexyl | CH₃ |
| 2,3-dimethylcyclohexyl | CH₃ |
| 3,4-dimethylcyclohexyl | CH₃ |
| 3,5-dimethylcyclohexyl | CH₃ |
| 2,6-dimethylcyclohexyl | CH₃ |
| menthyl | CH₃ |
| cycloheptyl | CH₃ |
| cyclopropylmethyl | CH₃ |
| 1-cyclopropylethyl | CH₃ |
| (1-methylcyclopropyl)methyl | CH₃ |
| (2-methylcyclopropyl)methyl | CH₃ |
| cyclobutylmethyl | CH₃ |
| cyclopentylmethyl | CH₃ |
| 3-cyclopentylpropyl | CH₃ |
| cyclohexylmethyl | CH₃ |
| 1-cyclohexylethyl | CH₃ |
| 2-cyclohexylethyl | CH₃ |
| 3-cyclohexylpropyl | CH₃ |
| 4-cyclohexylbutyl | CH₃ |
| 2-cyclopentenyl | CH₃ |
| 3-cyclopentenyl | CH₃ |
| 2-cyclohexenyl | CH₃ |
| 3-cyclohexenyl | CH₃ |
| 3-methyl-2-cyclohexenyl | CH₃ |
| (1-cyclopentenyl)methyl | CH₃ |
| (3-cyclohexenyl)methyl | CH₃ |
| CH₃CH₂— | CH₃CH₂ |
| CH₃CH₂CH₂— | CH₃CH₂ |
| (CH₃)₂CH— | CH₃CH₂ |
| CH₃CH₂CH₂CH₂— | CH₃CH₂ |
| (CH₃)₂CHCH₂— | CH₃CH₂ |
| CH₃CH₂CH(CH₃)— | CH₃CH₂ |
| (CH₃)₃C— | CH₃CH₂ |
| CH₃CH₂CH₂CH₂CH₂— | CH₃CH₂ |
| (CH₃)₂CHCH₂CH₂— | CH₃CH₂ |
| CH₃CH₂CH(CH₃)CH₂ | CH₃CH₂ |
| (CH₃)₃CCH₂— | CH₃CH₂ |
| CH₃CH₂CH₂CH(CH₃)— | CH₃CH₂ |
| (CH₃)₂CHCH(CH₃)— | CH₃CH₂ |
| (CH₃CH₂)₂CH— | CH₃CH₂ |
| CH₃CH₂CH₂CH₂CH₂CH₂— | CH₃CH₂ |
| CH₃CH₂CH₂CH₂CH(CH₃)— | CH₃CH₂ |
| CH₃CH₂CH₂CH(CH₂CH₃)— | CH₃CH₂ |
| (CH₃CH₂)₂C(CH₃)— | CH₃CH₂ |
| CH₃CH₂CH₂CH₂CH₂CH₂CH₂— | CH₃CH₂ |
| CH₃CH₂CH₂CH₂CH₂CH(CH₃)— | CH₃CH₂ |
| (CH₃CH₂CH₂)₂CH— | CH₃CH₂ |

| R⁸ | R⁹ |
|---|---|
| CH₃(CH₂)₆CH₂— | CH₃CH₂ |
| CH₃(CH₂)₇CH₂— | CH₃CH₂ |
| CH₃(CH₂)₈CH₂— | CH₃CH₂ |
| CH₃(CH₂)₉CH₂— | CH₃CH₂ |
| CH₂F— | CH₃CH₂ |
| CHF₂— | CH₃CH₂ |
| CF₃— | CH₃CH₂ |
| CH₂Cl— | CH₃CH₂ |
| CHCl₂— | CH₃CH₂ |
| CCl₃— | CH₃CH₂ |
| CH₂Br— | CH₃CH₂ |
| CHBr₂— | CH₃CH₂ |
| CBr₃— | CH₃CH₂ |
| CFCl₂— | CH₃CH₂ |
| CFBr₂— | CH₃CH₂ |
| CH₂FCH₂— | CH₃CH₂ |
| CH₂ICH₂— | CH₃CH₂ |
| CHF₂CH₂— | CH₃CH₂ |
| CF₃CH₂— | CH₃CH₂ |
| CH₂ClCH₂— | CH₃CH₂ |
| CHCl₂CH₂— | CH₃CH₂ |
| CCl₃CH₂— | CH₃CH₂ |
| CH₂BrCH₂— | CH₃CH₂ |
| CHBr₂CH₂— | CH₃CH₂ |
| CBr₃CH₂— | CH₃CH₂ |
| CF₃CF₂— | CH₃CH₂ |
| CHF₂CF₂— | CH₃CH₂ |
| CH₃CHF— | CH₃CH₂ |
| CH₃CHCl— | CH₃CH₂ |
| CH₃CHBr— | CH₃CH₂ |
| CH₂ClCHCl— | CH₃CH₂ |
| CH₂BrCHBr— | CH₃CH₂ |
| CH₂FCH₂CH₂— | CH₃CH₂ |
| CH₂ClCH₂CH₂— | CH₃CH₂ |
| CH₂BrCH₂CH₂— | CH₃CH₂ |
| CH₃CHClCH₂— | CH₃CH₂ |
| CH₃CHBrCH₂— | CH₃CH₂ |
| CH₂ClCHClCH₂— | CH₃CH₂ |
| CH₂BrCHBrCH₂— | CH₃CH₂ |
| CF₃CF₂CH₂— | CH₃CH₂ |
| CF₃CHFCF₂— | CH₃CH₂ |
| CHF₂CF₂CF₂— | CH₃CH₂ |
| CF₃CH₂CH₂— | CH₃CH₂ |
| CH₂ClCHClCHCl— | CH₃CH₂ |
| CBrF₂CF₂CH₂— | CH₃CH₂ |
| (CH₃)₂CCl— | CH₃CH₂ |
| (CH₃)₂CBr— | CH₃CH₂ |
| CH₃CH₂CHCl— | CH₃CH₂ |
| CH₃CH₂CHBr— | CH₃CH₂ |
| CH₂FCH₂CH₂CH₂— | CH₃CH₂ |
| CH₂ClCH₂CH₂CH₂— | CH₃CH₂ |
| CH₂BrCH₂CH₂CH₂— | CH₃CH₂ |
| CH₃CHClCH₂CH₂— | CH₃CH₂ |
| CH₃CHBrCH₂CH₂— | CH₃CH₂ |
| CH₃C(CH₂Cl)₂— | CH₃CH₂ |
| CH₃C(CH₂Br)₂— | CH₃CH₂ |
| CF₃CH₂CH₂CH₂— | CH₃CH₂ |
| CH₂ClCH₂CH₂CH₂CH₂— | CH₃CH₂ |
| C(CH₃)₃CHCl— | CH₃CH₂ |
| CF₃CH₂CH₂CH₂CH₂— | CH₃CH₂ |
| CHCl=CHCH₂CH₂— | CH₃CH₂ |
| CH₃CCl=CHCH₂CH₂— | CH₃CH₂ |
| CH₃CH₂CCl=CHCH₂CH₂— | CH₃CH₂ |
| CF₃CCl=CHCH₂CH₂— | CH₃CH₂ |
| CF₃CF₂CCl=CHCH₂CH₂— | CH₃CH₂ |
| CHBr=CHCH₂CH₂— | CH₃CH₂ |
| CH₃CBr=CHCH₂CH₂— | CH₃CH₂ |
| CH₃CH₂CBr=CHCH₂CH₂— | CH₃CH₂ |
| CF₃CBr=CHCH₂CH₂— | CH₃CH₂ |
| CF₃CF₂CBr=CHCH₂CH₂— | CH₃CH₂ |
| CHF=CHCH₂CH₂— | CH₃CH₂ |
| CH₃CF=CHCH₂CH₂— | CH₃CH₂ |
| CH₃CH₂CF=CHCH₂CH₂— | CH₃CH₂ |
| CF₃CF=CHCH₂CH₂— | CH₃CH₂ |

TABLE 20-continued

| R⁸ | R⁹ |
|---|---|
| CF₃CF₂CF=CHCH₂CH₂— | CH₃CH₂ |
| CCl₂=CHCH₂CH₂— | CH₃CH₂ |
| CBr₂=CHCH₂CH₂— | CH₃CH₂ |
| CF₂=CHCH₂CH₂— | CH₃CH₂ |
| CClF=CHCH₂CH₂— | CH₃CH₂ |
| CF₃CH=CHCH₂CH₂— | CH₃CH₂ |
| CF₃C(CH₃)=CHCH₂CH₂— | CH₃CH₂ |
| (CF₃)₂C=CHCH₂CH₂— | CH₃CH₂ |
| CH₃OCH₂— | CH₃CH₂ |
| CH₃CH₂OCH₂— | CH₃CH₂ |
| CH₃CH₂CH₂OCH₂— | CH₃CH₂ |
| CH₃CH₂CH₂CH₂OCH₂— | CH₃CH₂ |
| CH₃SCH(CH₃)— | CH₃CH₂ |
| CH₃SCH₂CH₂— | CH₃CH₂ |
| cyclopropyl | CH₃CH₂ |
| cyclobutyl | CH₃CH₂ |
| 1-methylcyclobutyl | CH₃CH₂ |
| cyclopentyl | CH₃CH₂ |
| 1-methylcyclopentyl | CH₃CH₂ |
| 2-methylcyclopentyl | CH₃CH₂ |
| 3-methylcyclopentyl | CH₃CH₂ |
| cyclohexyl | CH₃CH₂ |
| 1-methylcyclohexyl | CH₃CH₂ |
| 2-methylcyclohexyl | CH₃CH₂ |
| 3-methylcyclohexyl | CH₃CH₂ |
| 4-methylcyclohexyl | CH₃CH₂ |
| 2-ethylcyclohexyl | CH₃CH₂ |
| 4-ethylcyclohexyl | CH₃CH₂ |
| 2-tert-butylcyclohexyl | CH₃CH₂ |
| 4-tert-butylcyclohexyl | CH₃CH₂ |
| 2,3-dimethylcyclohexyl | CH₃CH₂ |
| 3,4-dimethylcyclohexyl | CH₃CH₂ |
| 3,5-dimethylcyclohexyl | CH₃CH₂ |
| 2,6-dimethylcyclohexyl | CH₃CH₂ |
| menthyl | CH₃CH₂ |
| cycloheptyl | CH₃CH₂ |
| cyclopropylmethyl | CH₃CH₂ |
| 1-cyclopropylethyl | CH₃CH₂ |
| (1-methylcyclopropyl)methyl | CH₃CH₂ |
| (2-methylcyclopropyl)methyl | CH₃CH₂ |
| cyclobutylmethyl | CH₃CH₂ |
| cyclopentylmethyl | CH₃CH₂ |
| 3-cyclopentylpropyl | CH₃CH₂ |
| cyclohexylmethyl | CH₃CH₂ |
| 1-cyclohexylethyl | CH₃CH₂ |
| 2-cyclohexylethyl | CH₃CH₂ |
| 3-cyclohexylpropyl | CH₃CH₂ |
| 4-cyclohexylbutyl | CH₃CH₂ |
| 2-cyclopentenyl | CH₃CH₂ |
| 3-cyclopentenyl | CH₃CH₂ |
| 2-cyclohexenyl | CH₃CH₂ |
| 3-cyclohexenyl | CH₃CH₂ |
| 3-methyl-2-cyclohexenyl | CH₃CH₂ |
| (1-cyclopentenyl)methyl | CH₃CH₂ |
| (3-cyclohexenyl)methyl | CH₃CH₂ |
| CH₃CH₂CH₂— | CH₃CH₂CH₂ |
| (CH₃)₂CH— | CH₃CH₂CH₂ |
| CH₃CH₂CH₂CH₂— | CH₃CH₂CH₂ |
| (CH₃)₂CHCH₂— | CH₃CH₂CH₂ |
| CH₃CH₂CH(CH₃)— | CH₃CH₂CH₂ |
| (CH₃)₃C— | CH₃CH₂CH₂ |
| CH₃CH₂CH₂CH₂CH₂— | CH₃CH₂CH₂ |
| (CH₃)₂CHCH₂CH₂— | CH₃CH₂CH₂ |
| CH₃CH₂CH(CH₃)₂CH₂— | CH₃CH₂CH₂ |
| (CH₃)₃CCH₂— | CH₃CH₂CH₂ |
| CH₃CH₂CH₂CH(CH₃)— | CH₃CH₂CH₂ |
| (CH₃)₂CHCH(CH₃)— | CH₃CH₂CH₂ |
| (CH₃CH₂)₂CH— | CH₃CH₂CH₂ |
| CH₃CH₂CH₂CH₂CH₂CH₂— | CH₃CH₂CH₂ |
| CH₃CH₂CH₂CH₂CH(CH₃)— | CH₃CH₂CH₂ |
| CH₃CH₂CH₂CH(CH₂CH₃)— | CH₃CH₂CH₂ |
| (CH₃CH₂)₂C(CH₃)— | CH₃CH₂CH₂ |
| CH₃CH₂CH₂CH₂CH₂CH₂CH₂— | CH₃CH₂CH₂ |
| CH₃CH₂CH₂CH₂CH₂CH(CH₃)— | CH₃CH₂CH₂ |
| (CH₃CH₂CH₂)₂CH— | CH₃CH₂CH₂ |
| CH₃(CH₂)₆CH₂— | CH₃CH₂CH₂ |
| CH₃(CH₂)₇CH₂— | CH₃CH₂CH₂ |
| CH₃(CH₂)₈CH₂— | CH₃CH₂CH₂ |
| CH₃(CH₂)₉CH₂— | CH₃CH₂CH₂ |
| CH₂F— | CH₃CH₂CH₂ |
| CHF₂— | CH₃CH₂CH₂ |
| CF₃— | CH₃CH₂CH₂ |
| CH₂Cl— | CH₃CH₂CH₂ |
| CHCl₂— | CH₃CH₂CH₂ |
| CCl₃— | CH₃CH₂CH₂ |
| CH₂Br— | CH₃CH₂CH₂ |
| CHBr₂— | CH₃CH₂CH₂ |
| CBr₃— | CH₃CH₂CH₂ |
| CFCl₂ | CH₃CH₂CH₂ |
| CFBr₂— | CH₃CH₂CH₂ |
| CH₂FCH₂— | CH₃CH₂CH₂ |
| CH₂ICH₂— | CH₃CH₂CH₂ |
| CHF₂CH₂— | CH₃CH₂CH₂ |
| CF₃CH₂— | CH₃CH₂CH₂ |
| CH₂ClCH₂— | CH₃CH₂CH₂ |
| CHCl₂CH₂— | CH₃CH₂CH₂ |
| CCl₃CH₂— | CH₃CH₂CH₂ |
| CH₂BrCH₂— | CH₃CH₂CH₂ |
| CHBr₂CH₂— | CH₃CH₂CH₂ |
| CBr₃CH₂— | CH₃CH₂CH₂ |
| CF₃CF₂— | CH₃CH₂CH₂ |
| CHF₂CF₂— | CH₃CH₂CH₂ |
| CH₃CHF— | CH₃CH₂CH₂ |
| CH₃CHCl— | CH₃CH₂CH₂ |
| CH₃CHBr— | CH₃CH₂CH₂ |
| CH₂ClCHCl— | CH₃CH₂CH₂ |
| CH₂BrCHBr— | CH₃CH₂CH₂ |
| CH₂FCH₂CH₂— | CH₃CH₂CH₂ |
| CH₂ClCH₂CH₂— | CH₃CH₂CH₂ |
| CH₂BrCH₂CH₂— | CH₃CH₂CH₂ |
| CH₃CHClCH₂— | CH₃CH₂CH₂ |
| CH₃CHBrCH₂— | CH₃CH₂CH₂ |
| CH₂ClCHClCH₂— | CH₃CH₂CH₂ |
| CH₂BrCHBrCH₂— | CH₃CH₂CH₂ |
| CF₃CF₂CH₂— | CH₃CH₂CH₂ |
| CF₃CHFCF₂— | CH₃CH₂CH₂ |
| CHF₂CF₂CF₂— | CH₃CH₂CH₂ |
| CF₃CH₂CH₂— | CH₃CH₂CH₂ |
| CH₂ClCHClCHCl— | CH₃CH₂CH₂ |
| CBrF₂CF₂CH₂— | CH₃CH₂CH₂ |
| (CH₃)₂CCl— | CH₃CH₂CH₂ |
| (CH₃)₂CBr— | CH₃CH₂CH₂ |
| CH₃CH₂CHCl— | CH₃CH₂CH₂ |
| CH₃CH₂CHBr— | CH₃CH₂CH₂ |
| CH₂FCH₂CH₂CH₂— | CH₃CH₂CH₂ |
| CH₂ClCH₂CH₂CH₂— | CH₃CH₂CH₂ |
| CH₂BrCH₂CH₂CH₂— | CH₃CH₂CH₂ |
| CH₃CHClCH₂CH₂— | CH₃CH₂CH₂ |
| CH₃CHBrCH₂CH₂— | CH₃CH₂CH₂ |
| CH₃C(CH₂Cl)₂— | CH₃CH₂CH₂ |
| CH₃C(CH₂Br)₂— | CH₃CH₂CH₂ |
| CF₃CH₂CH₂CH₂— | CH₃CH₂CH₂ |
| CH₂ClCH₂CH₂CH₂CH₂— | CH₃CH₂CH₂ |
| C(CH₃)₃CHCl— | CH₃CH₂CH₂ |
| CF₃CH₂CH₂CH₂CH₂— | CH₃CH₂CH₂ |
| CHCl=CHCH₂CH₂— | CH₃CH₂CH₂ |
| CH₃CCl=CHCH₂CH₂— | CH₃CH₂CH₂ |
| CH₃CH₂CCl=CHCH₂CH₂— | CH₃CH₂CH₂ |
| CF₃CCl=CHCH₂CH₂— | CH₃CH₂CH₂ |
| CF₃CF₂CCl=CHCH₂CH₂— | CH₃CH₂CH₂ |
| CHBr=CHCH₂CH₂— | CH₃CH₂CH₂ |
| CH₃CBr=CHCH₂CH₂— | CH₃CH₂CH₂ |
| CH₃CH₂CBr=CHCH₂CH₂— | CH₃CH₂CH₂ |
| CF₃CBr=CHCH₂CH₂— | CH₃CH₂CH₂ |
| CF₃CF₂CBr=CHCH₂CH₂— | CH₃CH₂CH₂ |
| CHF=CHCH₂CH₂— | CH₃CH₂CH₂ |
| CH₃CF=CHCH₂CH₂— | CH₃CH₂CH₂ |
| CH₃CH₂CF=CHCH₂CH₂— | CH₃CH₂CH₂ |
| CF₃CF=CHCH₂CH₂— | CH₃CH₂CH₂ |
| CF₃CF₂CF=CHCH₂CH₂— | CH₃CH₂CH₂ |
| CCl₂=CHCH₂CH₂— | CH₃CH₂CH₂ |
| CBr₂=CHCH₂CH₂— | CH₃CH₂CH₂ |
| CF₂=CHCH₂CH₂— | CH₃CH₂CH₂ |
| CClF=CHCH₂CH₂— | CH₃CH₂CH₂ |

TABLE 20-continued

| R⁸ | R⁹ |
|---|---|
| CF₃CH=CHCH₂CH₂— | CH₃CH₂CH₂ |
| CF₃C(CH₃)=CHCH₂CH₂— | CH₃CH₂CH₂ |
| (CF₃)₂C=CHCH₂CH₂— | CH₃CH₂CH₂ |
| CH₃OCH₂— | CH₃CH₂CH₂ |
| CH₃CH₂OCH₂— | CH₃CH₂CH₂ |
| CH₃CH₂CH₂OCH₂— | CH₃CH₂CH₂ |
| CH₃CH₂CH₂CH₂OCH₂— | CH₃CH₂CH₂ |
| CH₃SCH(CH₃)— | CH₃CH₂CH₂ |
| CH₃SCH₂CH₂— | CH₃CH₂CH₂ |
| cyclopropyl | CH₃CH₂CH₂ |
| cyclobutyl | CH₃CH₂CH₂ |
| 1-methylcyclobutyl | CH₃CH₂CH₂ |
| cyclopentyl | CH₃CH₂CH₂ |
| 1-methylcyclopentyl | CH₃CH₂CH₂ |
| 2-methylcyclopentyl | CH₃CH₂CH₂ |
| 3-methylcyclopentyl | CH₃CH₂CH₂ |
| cyclohexyl | CH₃CH₂CH₂ |
| 1-methylcyclohexyl | CH₃CH₂CH₂ |
| 2-methylcyclohexyl | CH₃CH₂CH₂ |
| 3-methylcyclohexyl | CH₃CH₂CH₂ |
| 4-methylcyclohexyl | CH₃CH₂CH₂ |
| 2-ethylcyclohexyl | CH₃CH₂CH₂ |
| 4-ethylcyclohexyl | CH₃CH₂CH₂ |
| 2-tert-butylcyclohexyl | CH₃CH₂CH₂ |
| 4-tert-butylcyclohexyl | CH₃CH₂CH₂ |
| 2,3-dimethylcyclohexyl | CH₃CH₂CH₂ |
| 3,4-dimethylcyclohexyl | CH₃CH₂CH₂ |
| 3,5-dimethylcyclohexyl | CH₃CH₂CH₂ |
| 2,6-dimethylcyclohexyl | CH₃CH₂CH₂ |
| menthyl | CH₃CH₂CH₂ |
| cycloheptyl | CH₃CH₂CH₂ |
| cyclopropylmethyl | CH₃CH₂CH₂ |
| 1-cyclopropylethyl | CH₃CH₂CH₂ |
| (1-methylcyclopropyl)methyl | CH₃CH₂CH₂ |
| (2-methylcyclopropyl)methyl | CH₃CH₂CH₂ |
| cyclobutylmethyl | CH₃CH₂CH₂ |
| cyclopentylmethyl | CH₃CH₂CH₂ |
| 3-cyclopentylpropyl | CH₃CH₂CH₂ |
| cyclohexylmethyl | CH₃CH₂CH₂ |
| 1-cyclohexylethyl | CH₃CH₂CH₂ |
| 2-cyclohexylethyl | CH₃CH₂CH₂ |
| 3-cyclohexylpropyl | CH₃CH₂CH₂ |
| 4-cyclohexylbutyl | CH₃CH₂CH₂ |
| 2-cyclopentenyl | CH₃CH₂CH₂ |
| 3-cyclopentenyl | CH₃CH₂CH₂ |
| 2-cyclohexenyl | CH₃CH₂CH₂ |
| 3-cyclohexenyl | CH₃CH₂CH₂ |
| 3-methyl-2-cyclohexenyl | CH₃CH₂CH₂ |
| (1-cyclopentenyl)methyl | CH₃CH₂CH₂ |
| (3-cyclohexenyl)methyl | CH₃CH₂CH₂ |

TABLE 21

$R^8 = T^2\text{-}2 =$ phenyl-CH₂— with $(R^{17})_b$ at positions 3,4,5,6 (2 is also on ring)

| R¹⁷ | R⁹ |
|---|---|
| H— | H |
| H— | CH₃ |

TABLE 22

$R^8 = T^2\text{-}2 =$ phenyl-CH(CH₃)— with $(R^{17})_b$

| R¹⁷ | R⁹ |
|---|---|
| H— | H |
| H— | CH₃ |

TABLE 23

$R^8 = T^2\text{-}2 =$ phenyl-CH₂CH₂— with $(R^{17})_b$

| R¹⁷ | R⁹ |
|---|---|
| H— | H |
| 4-F— | H |
| 4-Cl— | H |
| 4-Br— | H |
| 4-CH₃ | H |
| 4-CF₃— | H |
| 4-CH₃O— | H |

TABLE 24

$R^8 = T^2\text{-}2 =$ phenyl-CH₂CH₂CH₂— with $(R^{17})_b$

| R¹⁷ | R⁹ |
|---|---|
| H— | H |

TABLE 25

$R^8 = T^2\text{-}1 =$ phenyl— with $(R^{17})_b$

| R¹⁷ | R⁹ |
|---|---|
| H | H |
| 2-CH₃— | H |
| 2-CH₃CH₂— | H |
| 2-CH₃CH₂CH₂— | H |
| 2-(CH₃)₂CH— | H |
| 2-CF₃— | H |
| 2-F— | H |
| 2-Cl— | H |
| 2-Br— | H |
| 2-CH₃O— | H |
| 3-CH₃— | H |
| 3-CH₃CH₂— | H |
| 3-CH₃CH₂CH₂— | H |
| 3-(CH₃)₂CH— | H |
| 3-(CH₃)₃C— | H |
| 3-CF₃— | H |
| 3-F— | H |
| 3-Cl— | H |
| 3-Br— | H |
| 3-I— | H |

TABLE 25-continued

R⁸ = T²-1 = [4-position substituted phenyl-CH₃ with (R¹⁷)ᵦ at positions 3,4,5,6]

| R¹⁷ | R⁹ |
|---|---|
| 3-CH₃O— | H |
| 3-CFO— | H |
| 4-CH₃— | H |
| 4-CH₃CH₂— | H |
| 4-CH₃CH₂CH₂— | H |
| 4-(CH₃)₂CH— | H |
| 4-(CH₃)₃C— | H |
| 4-CF₃— | H |
| 4-F— | H |
| 4-Cl— | H |
| 4-Br— | H |
| 4-I— | H |
| 4-CH₃O— | H |
| 4-CH₃CH₂O— | H |
| 4-CH₃CH₂CH₂O— | H |
| 4-(CH₃)₂CHO— | H |
| 4-CH₃CH₂CH₂CH₂O— | H |
| 4-CFO— | H |
| 4-CH₃S— | H |
| 4-NO₂— | H |
| 2,6-F₂— | H |
| 3,4-F₂— | H |
| 2,4-F₂— | H |
| 3,4-Cl₂— | H |
| H | CH₃ |
| 2-CH₃— | CH₃ |
| 2-CH₃CH₂— | CH₃ |
| 2-CH₃CH₂CH₂— | CH₃ |
| 2-(CH₃)₂CH— | CH₃ |
| 2-CF₃— | CH₃ |
| 2-F— | CH₃ |
| 2-Cl— | CH₃ |
| 2-Br— | CH₃ |
| 2-CH₃O— | CH₃ |
| 3-CH₃— | CH₃ |
| 3-CH₃CH₂— | CH₃ |
| 3-CH₃CH₂CH₂— | CH₃ |
| 3-(CH₃)₂CH— | CH₃ |
| 3-(CH₃)₃C— | CH₃ |
| 3-CF₃— | CH₃ |
| 3-F— | CH₃ |
| 3-Cl— | CH₃ |
| 3-Br— | CH₃ |
| 3-I— | CH₃ |
| 3-CH₃O— | CH₃ |
| 3-CFO— | CH₃ |
| 4-CH₃— | CH₃ |
| 4-CH₃CH₂— | CH₃ |
| 4-CH₃CH₂CH₂— | CH₃ |
| 4-(CH₃)₂CH— | CH₃ |
| 4-(CH₃)₃O— | CH₃ |
| 4-CF₃— | CH₃ |
| 4-F— | CH₃ |
| 4-Cl— | CH₃ |
| 4-Br— | CH₃ |
| 4-I— | CH₃ |
| 4-CH₃O— | CH₃ |
| 4-CH₃CH₂O— | CH₃ |
| 4-CH₃CH₂CH₂O— | CH₃ |
| 4-(CH₃)₂CHO— | CH₃ |
| 4-CH₃CH₂CH₂CH₂O— | CH₃ |
| 4-CFO— | CH₃ |
| 4-CH₃S— | CH₃ |
| 4-NO₂— | CH₃ |
| 2,6-F₂— | CH₃ |
| 3,4-F₂— | CH₃ |
| 2,4-F₂— | CH₃ |
| 3,4-Cl₂— | CH₃ |
| H | CH₃CH₂ |
| 2-F— | CH₃CH₂ |
| 3-Cl— | CH₃CH₂ |

TABLE 25-continued

R⁸ = T²-1 =

| R¹⁷ | R⁹ |
|---|---|
| 3-Br— | CH₃CH₂ |
| 4-CH₃— | CH₃CH₂ |
| 4-CH₃CH₂— | CH₃CH₂ |
| 4-CH₃CH₂CH₂— | CH₃CH₂ |
| 4-(CH₃)₂CH— | CH₃CH₂ |
| 4-(CH₃)₃C— | CH₃CH₂ |
| 4-CF₃— | CH₃CH₂ |
| 4-F— | CH₃CH₂ |
| 4-Cl— | CH₃CH₂ |
| 4-Br— | CH₃CH₂ |
| 4-I— | CH₃CH₂ |
| 4-CH₃O— | CH₃CH₂ |
| 4-CH₃CH₂O— | CH₃CH₂ |
| 4-CH₃CH₂CH₂O— | CH₃CH₂ |
| 4-(CH₃)₂CHO— | CH₃CH₂ |
| 4-CH₃CH₂CH₂CH₂O— | CH₃CH₂ |
| 4-CFO— | CH₃CH₂ |
| 3,4-Cl₂— | CH₃CH₂ |
| H— | CH₃CH₂CH₂ |
| H— | CH₃CH(CH₃) |
| H— | cyclopropyl |
| H— | CH₃OCH₂ |
| H— | CF₃ |
| 4-Cl— | CH₃CH₂CH₂ |
| 4-Cl— | CH₃CH(CH₃) |
| 4-Cl— | cyclopropyl |
| 4-Br— | CH₃CH₂CH₂ |
| 4-Br— | CH₃CH(CH₃) |
| 4-Br— | cyclopropyl |

TABLE 26

R⁸ = T²-2 = [pyridyl-CH₂—]

| R¹⁷ | R⁹ |
|---|---|
| H | H |

TABLE 27

R⁸ = T²-2 = [pyridyl-CH₂CH₂CH₂—]

| R¹⁷ | R² |
|---|---|
| H | H |

TABLE 28

R⁸ = T²-2 = [pyridine-3-yl-CH₂CH₂-, (R¹⁷)ᵦ on N position, numbered 2,3,4,5,6]

| R¹⁷ | R² |
|---|---|
| H | H |

TABLE 29

R⁸ = T²-1 = [pyridine-3-yl-methyl, (R¹⁷)ᵦ, numbered 2,3,4,5,6]

| R¹⁷ | R² |
|---|---|
| H | H |
| 6-Cl— | H |
| 6-Br— | H |
| 6-CH₃— | H |
| 6-CH₃O— | H |
| 2-CH₃— | H |
| 2-Cl— | H |
| 5-Br— | H |
| 2-Cl—6-CH₂— | H |
| 2,6-Cl₂— | H |
| 5,6-Cl₂— | H |
| H | CH₃ |
| 6-Cl— | CH₃ |

TABLE 30

R⁸ = T²-2 = [pyridin-4-yl-CH₂-, (R¹⁷)ᵦ, numbered 2,3,4,5,6]

| R¹⁷ | R⁹ |
|---|---|
| H | H |
| H | H |

TABLE 31

R⁸ = T²-2 = [pyridin-4-yl-CH₂CH₂-, (R¹⁷)ᵦ, numbered 2,3,4,5,6]

| R¹⁷ | R⁹ |
|---|---|
| H | H |

TABLE 32

R⁸ = T²-2 = [pyridin-4-yl-CH₂CH₂CH₂-, (R¹⁷)ᵦ, numbered 2,3,4,5,6]

| R¹⁷ | R⁹ |
|---|---|
| H | H |

TABLE 33

R⁸ = T²-1 = [pyridin-4-yl-methyl, (R¹⁷)ᵦ, numbered 2,3,4,5,6]

| R¹⁷ | R⁹ |
|---|---|
| H | H |
| H | CH₃ |

TABLE 34

R⁸ = T²-2 = [pyridin-2-yl-CH₂-, (R¹⁷)ᵦ, numbered 2,3,4,5,6]

| R¹⁷ | R⁹ |
|---|---|
| H | H |

TABLE 35

R⁸ = T²-2 = [pyridin-2-yl-CH₂CH₂-, (R¹⁷)ᵦ, numbered 2,3,4,5,6]

| R¹⁷ | R⁹ |
|---|---|
| H | H |

TABLE 36

R⁸ = T²-2 = [pyridin-2-yl-CH₂CH₂CH₂-, (R¹⁷)ᵦ, numbered 2,3,4,5,6]

| R¹⁷ | R⁹ |
|---|---|
| H | H |

TABLE 37

$R^8 = T^2-1 =$ [pyridine ring with positions 2,3,4,5,6; $(R^{17})_b$ at position 5, N at position 1]

| $R^{17}$ | $R^9$ |
|---|---|
| H | H |
| H | $CH_3$ |

TABLE 38

| —$R^8$—$R^9$— |
|---|
| tetramethylene |
| 1-methyltetramethylene |
| 2-methyltetramethylene |
| 1,1-dimethyltetramethylene |
| 1,3-dimethyltetramethylene |
| pentamethylene |
| 1-methylpentamethylene |
| 2-methylpentamethylene |
| 3-methylpentamethylene |
| 3-ethylpentamethylene |
| 3-tert-butylpentamethylene |
| 1,1-dimethylpentamethylene |
| 1,5-dimethylpentamethylene |
| 1-chloropentamethylene |
| 1-methoxypentamethylene |
| 2-oxa-1-methyltetramethylene |
| 3-oxapentamethylene |
| 2-thiatetramethylene |
| 3-thiapentamethylene |

TABLE 39

$R^8 =$ [furan ring with $(R^{18})_g$ substituent]

| $R^{18}$ | $R^9$ |
|---|---|
| H | H |
| 5-$CH_3$ | H |
| 5-$CH_3CH_2$ | H |
| 5-$NO_2$ | H |
| H | $CH_3$ |
| 5-$CH_3$ | $CH_3$ |

TABLE 40

$R^8 =$ [3-methylfuran ring with $(R^{18})_g$ substituent]

| $R^{18}$ | $R^9$ |
|---|---|
| H | H |
| 2,5-$(CH_3)_2$ | $CH_3$ |

TABLE 41

$R^8 =$ [thiophene ring with $(R^{18})_g$ substituent]

| $R^{18}$ | $R^9$ |
|---|---|
| H | H |
| 3-$CH_3$ | H |
| 5-$CH_3$ | H |
| 4-Br | H |
| 5-Br | H |
| 5-$NO_2$ | H |
| H | $CH_3$ |
| 3-$CH_3$ | $CH_3$ |
| 5-Cl | $CH_3$ |
| 5-Br | $CH_3$ |
| H | $CH_3CH_2$ |
| H | cyclopropyl |

TABLE 42

$R^8 =$ [3-methylthiophene ring with $(R^{18})_g$ substituent]

| $R^{18}$ | $R^9$ |
|---|---|
| H | H |
| H | $CH_3$ |
| 2,5-$(CH_3)_2$ | $CH_3$ |

TABLE 43

$R^8 =$ [pyrrole ring with $(R^{18})_g$ substituent]

| $R^{18}$ | $R^9$ |
|---|---|
| 1-$CH_3$ | H |
| 1-$CH_3$ | $CH_3$ |

TABLE 44

$R^8 =$ [3-methylpyrrole ring with $(R^{18})_g$ substituent]

| $R^{18}$ | $R^9$ |
|---|---|
| 1-$CH_3$ | $CH_3$ |

TABLE 45

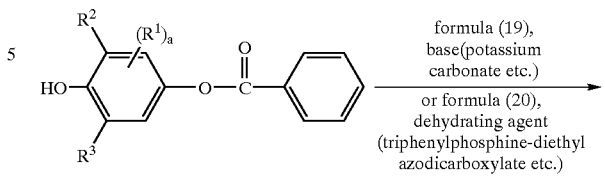

| R[18] | R[9] |
|---|---|
| H | CH$_3$ |

TABLE 46

R$^8$ = [thiazole structure with (R$^{18}$)$_g$]

| R[18] | R[9] |
|---|---|
| 2,4-(CH$_3$)$_2$ | CH$_3$ |

TABLE 47

R$^8$ = [pyrazole structure with (R$^{18}$)$_g$]

| R[18] | R[9] |
|---|---|
| 1-CH$_3$CH$_2$-3-CH$_3$-5-Cl | CH$_3$ |

The following will describe various processes for producing the intermediates in the production of the present compounds.

The compounds of formula (15) as the intermediates for the production of the present compounds can be produced, for example, according to the following schemes I to VI.

Scheme I
(when Y and Z are both oxygen)

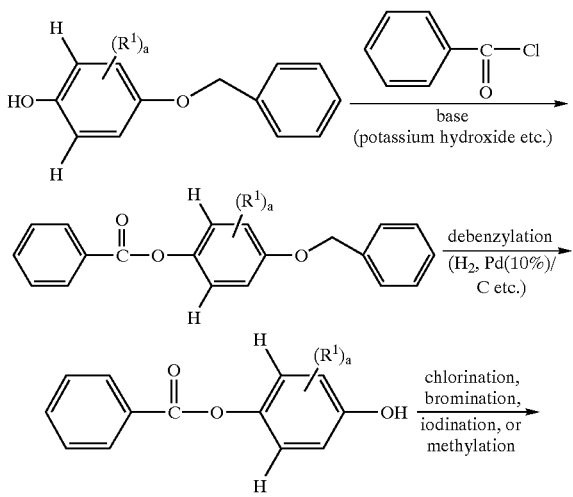

wherein all the variables are as defined above, with the proviso that R$^6$ is not hydrogen.

Scheme II
(when Y and Z are both oxygen)

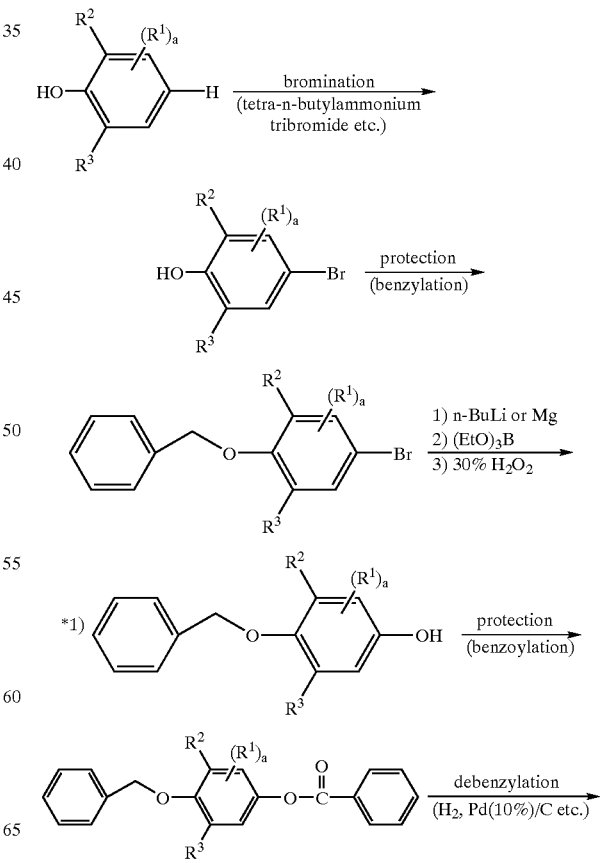

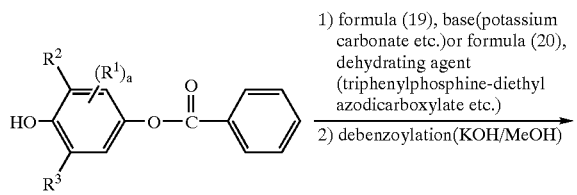

1) formula (19), base(potassium carbonate etc.)or formula (20), dehydrating agent (triphenylphosphine-diethyl azodicarboxylate etc.)
2) debenzoylation(KOH/MeOH)

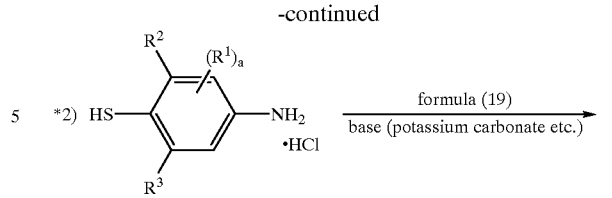

formula (19)
base (potassium carbonate etc.)

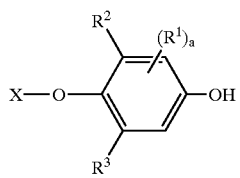

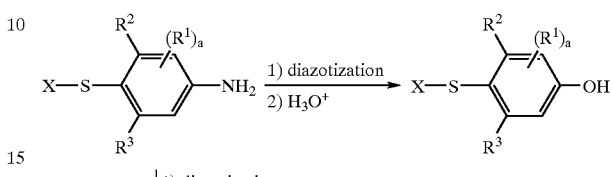

1) diazotization
2) $H_3O^+$

*1): J. Org.Chem.,22,1001(1957)

1) diazotization
2) EtOCSSK
3) $H_3O^+$ wherein all the variable are as defined above, with the proviso that $R^6$ is not hydrogen.

<u>Scheme III</u>
(when Y and Z are not both oxygen)

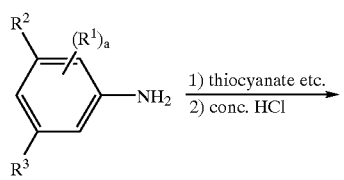

1) thiocyanate etc.
2) conc. HCl

*2): JP-A 60-181067 wherein all the variable are as defined above, with the proviso that $R^6$ is not hydrogen.

<u>Scheme IV</u>

(when Y and Z are not both oxygen)

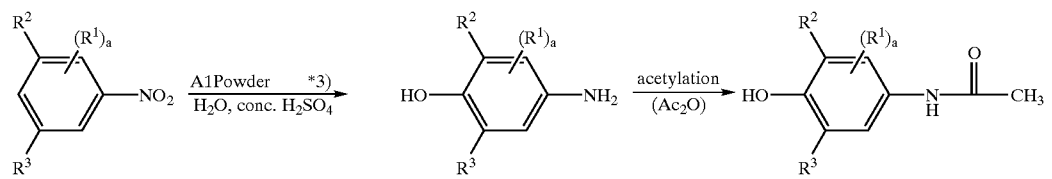

formula (19), base(potassium carbonate etc.)

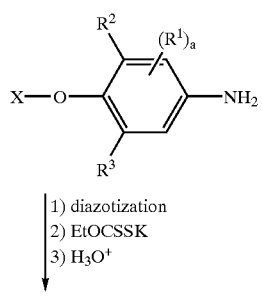

deacetylation hydrolysis formula (19), base(potassium carbonate etc.) or formula (20), dehydrating agent(triphenylphosphine-diethylazodicarboxylate etc.)

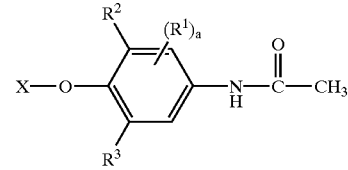

1) diazotization
2) EtOCSSK
3) $H_3O^+$

-continued

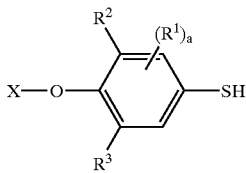

*3): H.J. Shine," Aromatic Rearrangement",
Elsevier.182(1967)

wherein all the variable are as defined above, with the proviso that $R^6$ is not hydrogen.

Scheme V (when Y is oxygen)

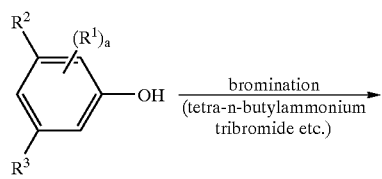

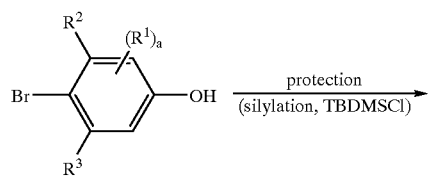

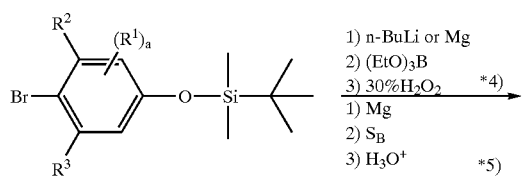

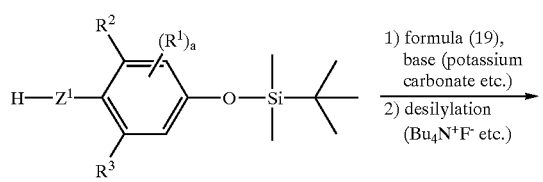

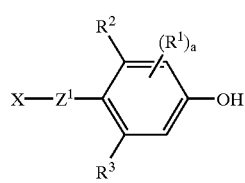

*4): J.Org.Chem., 22,1001(1957)
*5): Ber., 72,594(1939)

wherein TBDMSCl is tert-butyldimethylsillyl chloride, $Z^1$ is oxygen or sulfur, and the other variables are as defined above, with the proviso that $R^6$ is not hydrogen.

Scheme VI (when Y is oxygen)

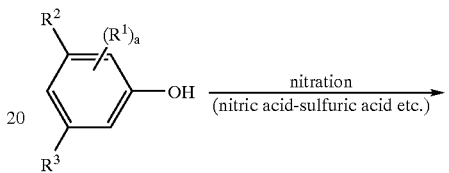

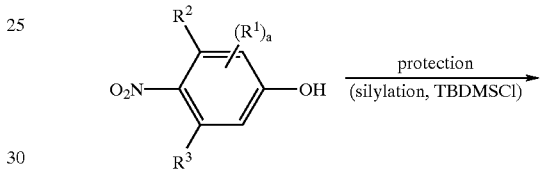

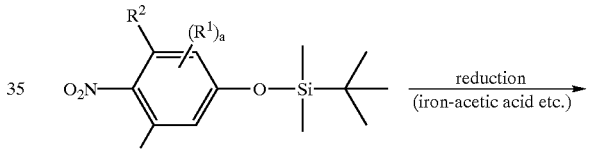

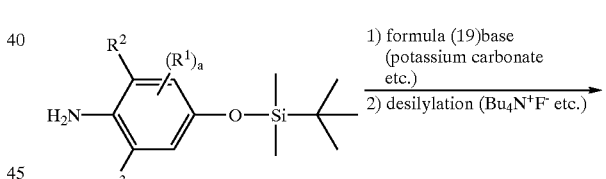

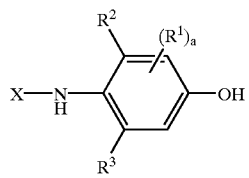

wherein all the variables are as defined above, with the proviso that $R^6$ is not hydrogen.

The compounds of formula (18) as the intermediates for the production of the present compounds can be produced, for example, according to the following scheme VII.

Scheme VII

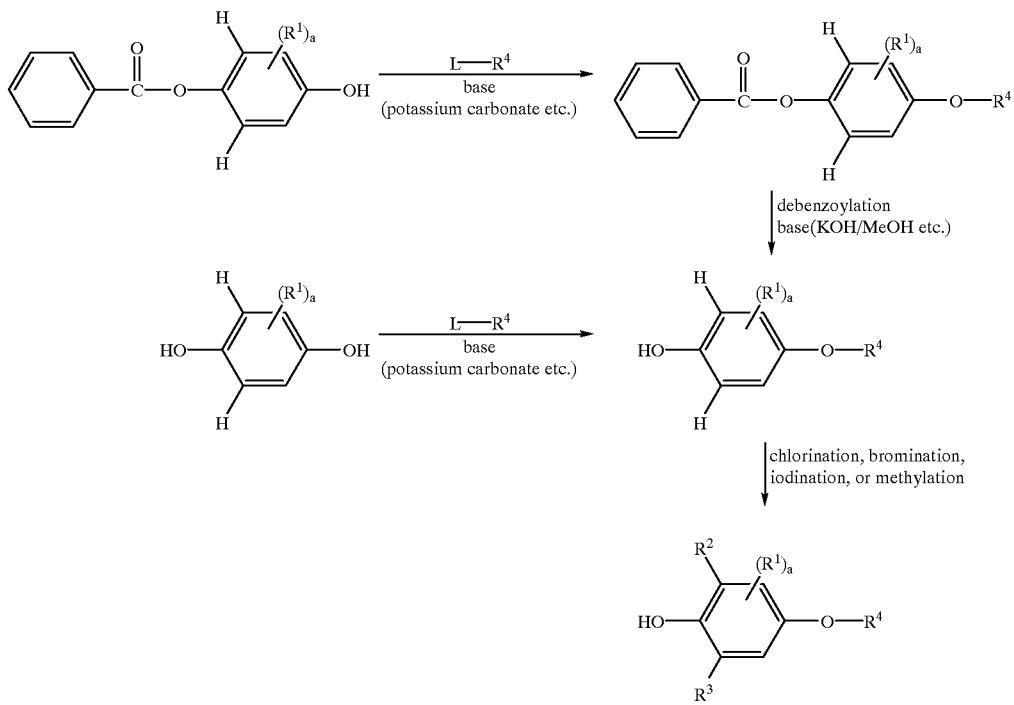

wherein all the variables are as defined above.

The halide compounds of formula (16) and alcohol compounds of formula (17), both as the intermediates for the production of the present compounds, are commercially available or can be produced, for example, according to the publications: J. Org. Chem., 56, 1037–1041 (1991); Izvest. Akad. Nauk S.S.S.R., Otdel. Khim. Nauk, 1960, 447–451 [CA (Chemical Abstracts) vol. 54, 22344d]; and Doklady Akad. Nauk S.S.S.R. in, 606–608 (1960) [CA (Chemical Abstracts) vol. 54, 22331h], or according to the following scheme VIII.

Scheme VIII

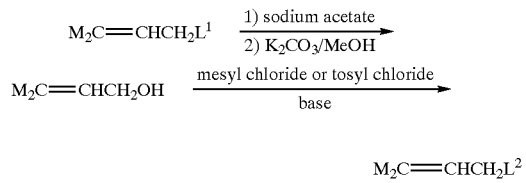

-continued wherein $L^1$ is chlorine or bromine, $L^2$ is mesyloxy or tosyloxy, and M is halogen.

The compounds of formula (19) or (20) as the intermediates for the production of the present compounds can be produced, for example, according to the following scheme IX or X.

Scheme IX
(in the case where X is $X^1$, and $A^1$ is $A^1$-1, $A^1$-2, $A^1$-3, $A^1$-4, $A^1$-5, or $A^1$-6)

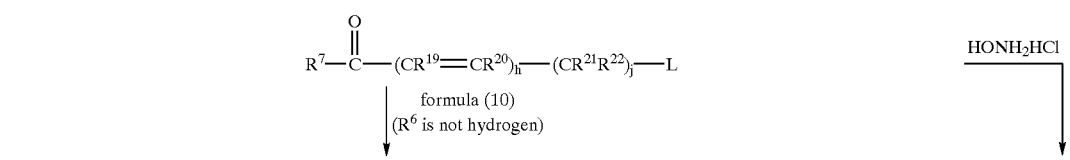

-continued

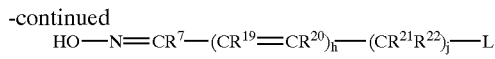

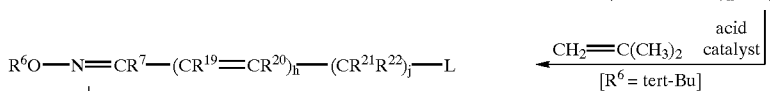

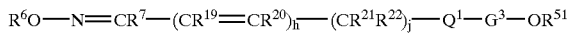

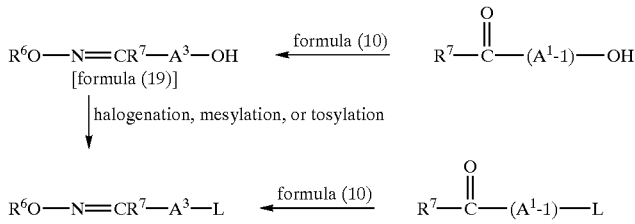

wherein $R^{51}$ is a protecting group for alcohols, such as benzoyl or acetyl, $Q^{10}$ is oxygen, sulfur, or $NR^{33}$ wherein $R^{33}$ is as defined above, $A^3$ is $A^1$-1, $A^1$-2, $A^1$-3, $A^1$-4, $A^1$-5, or A-6, $G^3$ is $G^3$-2, $G^3$-3, $G^3$-4, $G^3$-5, or $G^3$-6 of formula (38) when $A^1$ is $A^1$-2, $A^1$-3, $A^1$-4, $A^1$-5, or $A^1$-6, $G^3$-2: —$(CR^{23}R^{24})_k$— (when $A^1$ is $A^1$-2)

$G^3$-3: —$(CR^{23}R^{24})_m$—$CR^{25}$=$CR^{26}$—$(CR^{27}R^{28})_n$— (when $A^1$ is $A^1$-3)

$G^3$-4: —$(CR^{23}R^{24})_m$—C≡C—$(CR^{25}R^{26})_n$— (when $A^1$ is $A^1$-4)

$G^3$-5: —$(CR^{23}R^{24})_p$—E—$(CR^{25}R^{26})_q$— (when $A^1$ is $A^1$-5)

$G^3$-6: —$(CR^{23}R^{24})_r$—$Q^2$—$(CR^{25}R^{26})_s$— (when $A^1$ is $A^1$-6)

wherein all the variables are as defined above, and the other variables are as defined above.

Scheme X
(in the case where X is $X^1$, $A^1$ is $A^1$-2, $A^1$-3, $A^1$-4, $A^1$-5, or $A^1$-6, and $Q^1$ is oxygen)

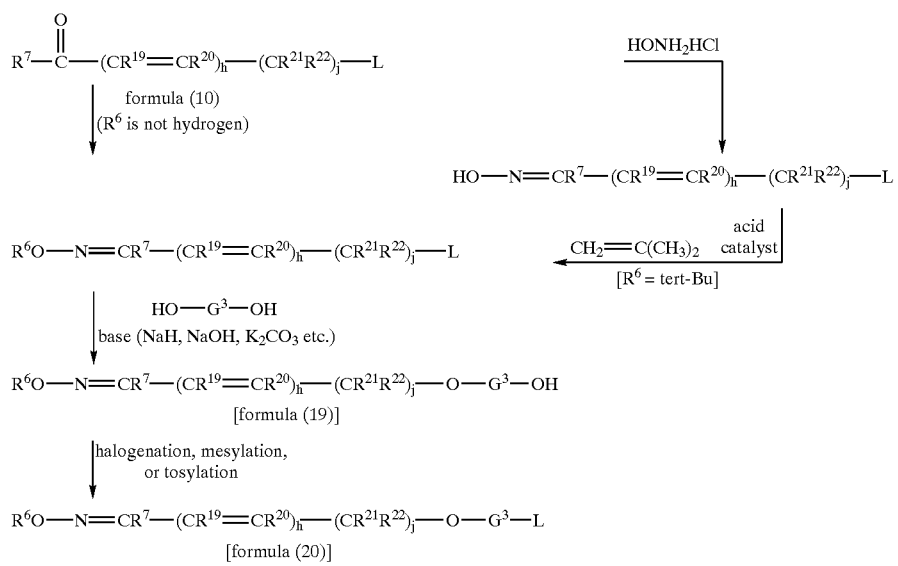

wherein all the variables are as defined above.

The compounds of formula (22) as the intermediates for the production of the present compounds can be produced, for example, according to the following scheme XI, XII, XIII, XIV, or XV.

wherein $Y^1$ is oxygen or NH, $R^{52}$ is a protecting group for the hydroxyl group of phenol or for the amino group of aniline, such as benzoyl, acetyl, or tert-butylmethylsillyl (TBDMS), and the other variables are as defined above.

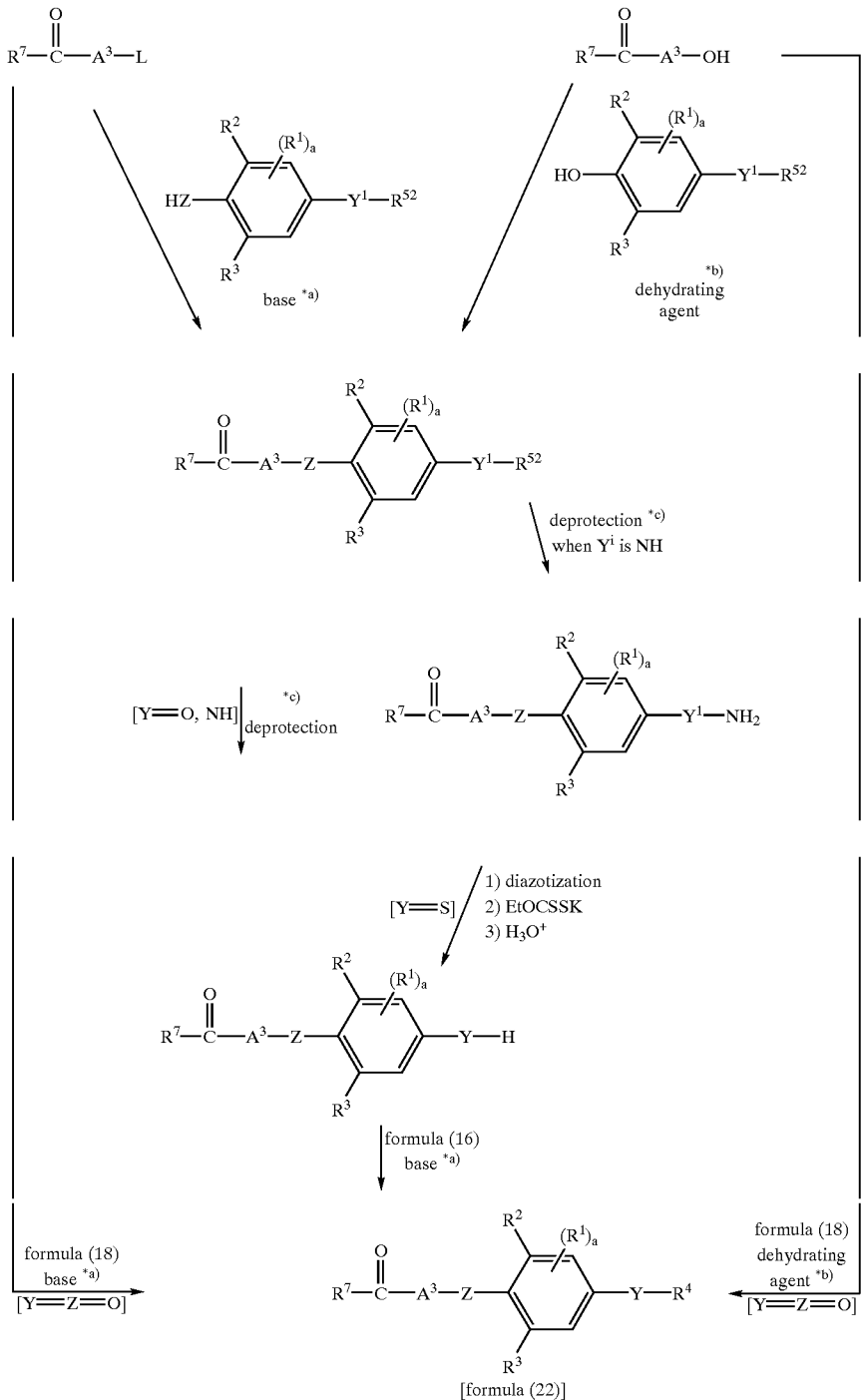

Scheme XII
(in the case where X is $X^1$, $A^1$ is $A^1$-1, $A^1$-2, $A^1$-3, $A^1$-4, $A^1$-5, or $A^1$-6, and $Q^1$, Y, and Z are all oxygen)
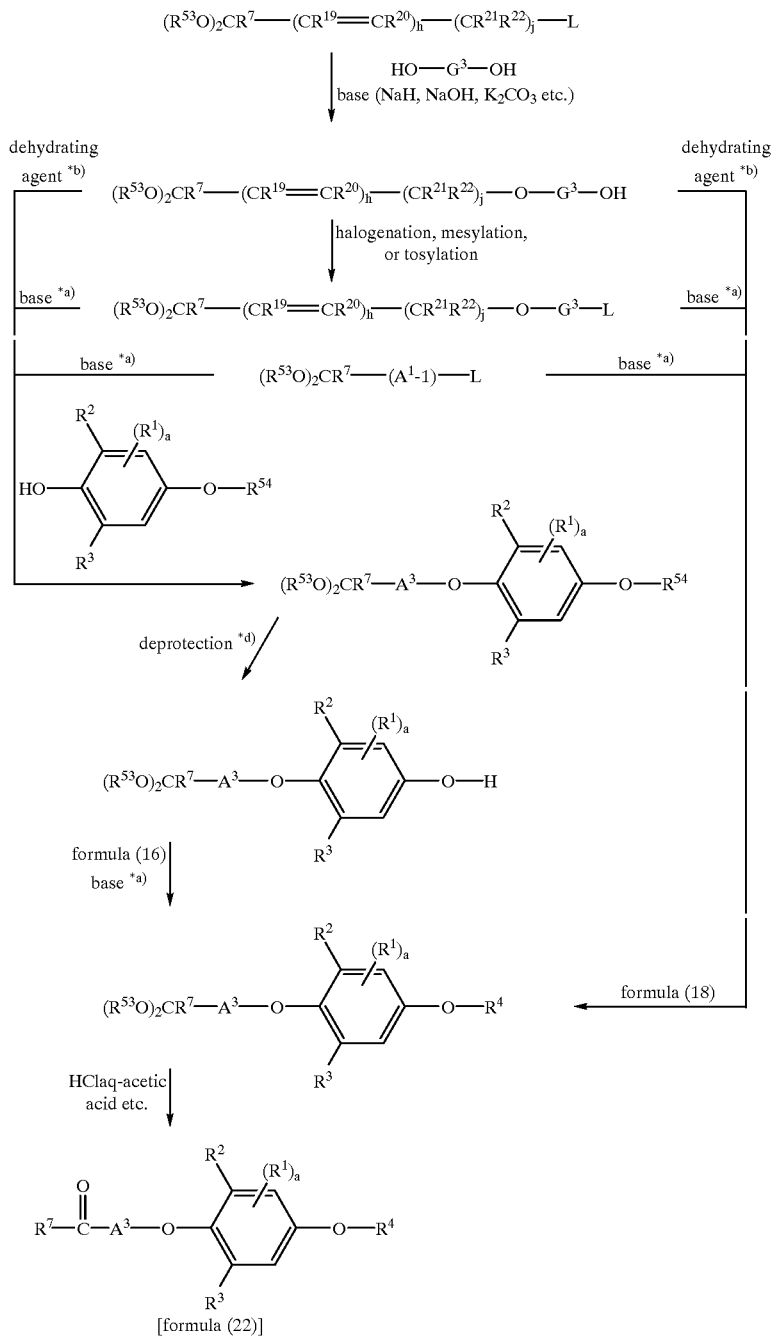
[formula (22)]
*a) $K_2CO_3$ etc.
*b) $PPh_3$-diethyl azodicarboxylate etc.
*d) e.g., KOH—MeOH etc., when $R^{54}$ is $C_6H_5CO$
wherein $R^{53}$ is methyl or ethyl, $R^{54}$ is a protecting group for the hydroxyl group of phenol, such as benzoyl or acetyl, and the other variables are as defined above.

Scheme XIII
(in the case where X is $X^1$, $A^1$ is $A^1$-2, $A^1$-3, $A^1$-4, $A^1$-5, or $A^1$-6, $Q^1$, Y, and Z are all oxygen, and $R^7$ is methyl)
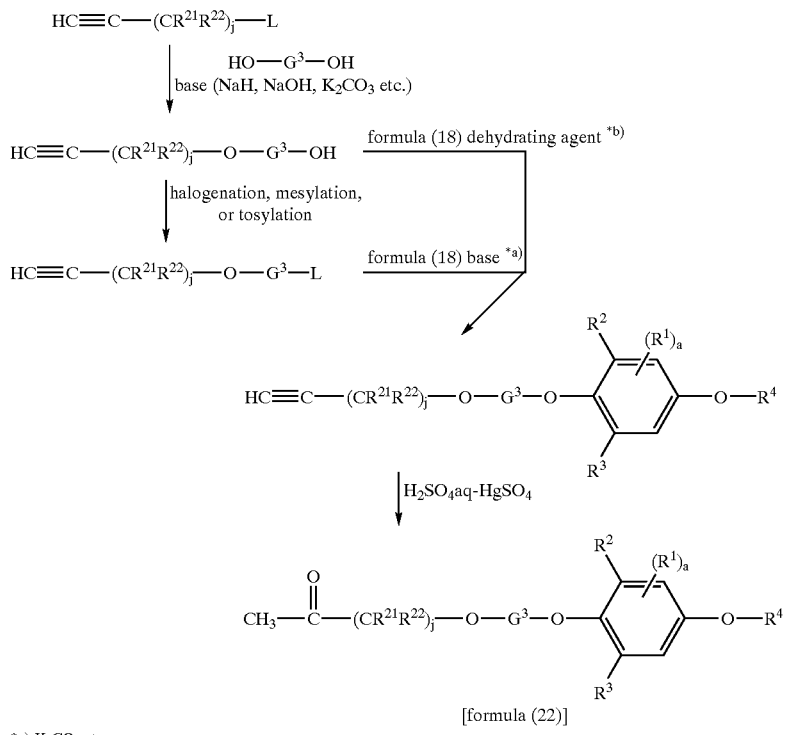
*a) $K_2CO_3$ etc.
*b) $PPh_3$-diethyl azodicarboxylate etc.
wherein all the variables are as defined above.
Scheme XIV
(in the case where X is $X^1$, $A^1$ is $A^1$-1, Y and Z are both oxygen, and $R^7$ is hydrogen)
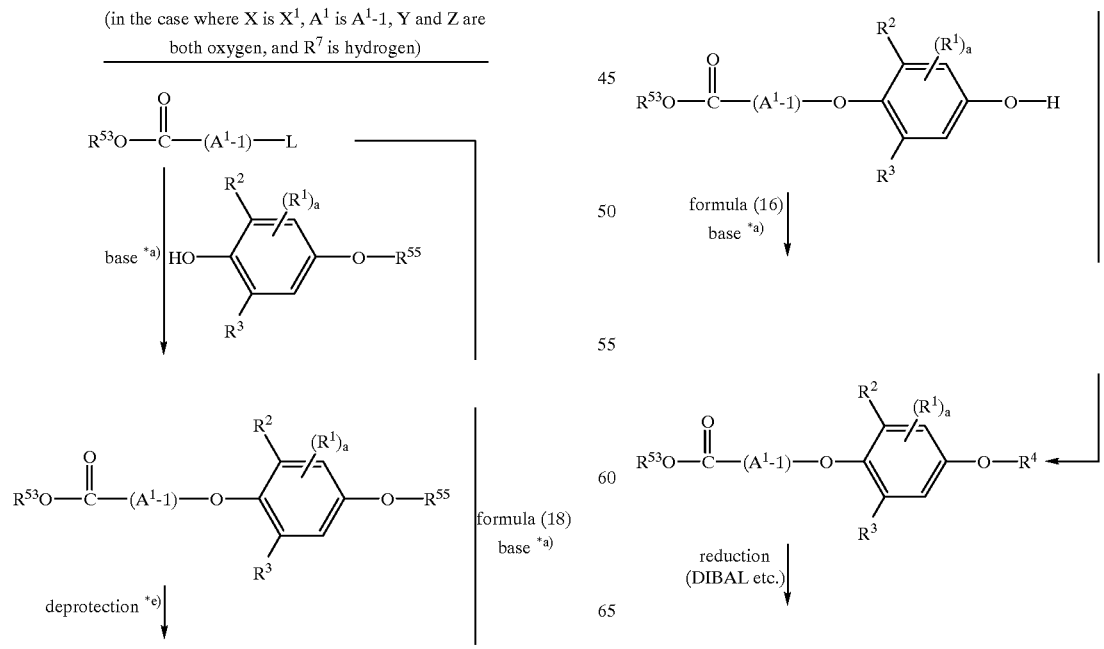

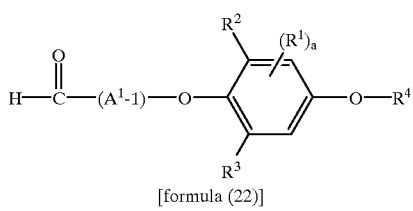
[formula (22)]
*a) $K_2CO_3$ etc.
*e) e.g., $H_2$—Pd (10%)/C etc. (wherein h is 0), when $R^{55}$ is $C_6H_5CH_2$
wherein $R^{53}$ is methyl or ethyl, $R^{55}$ is a protecting group for the hydroxyl group of phenol, such as benzyl, DIBAL means dusobutylaluminum hydride, and the other variables are as defined above.
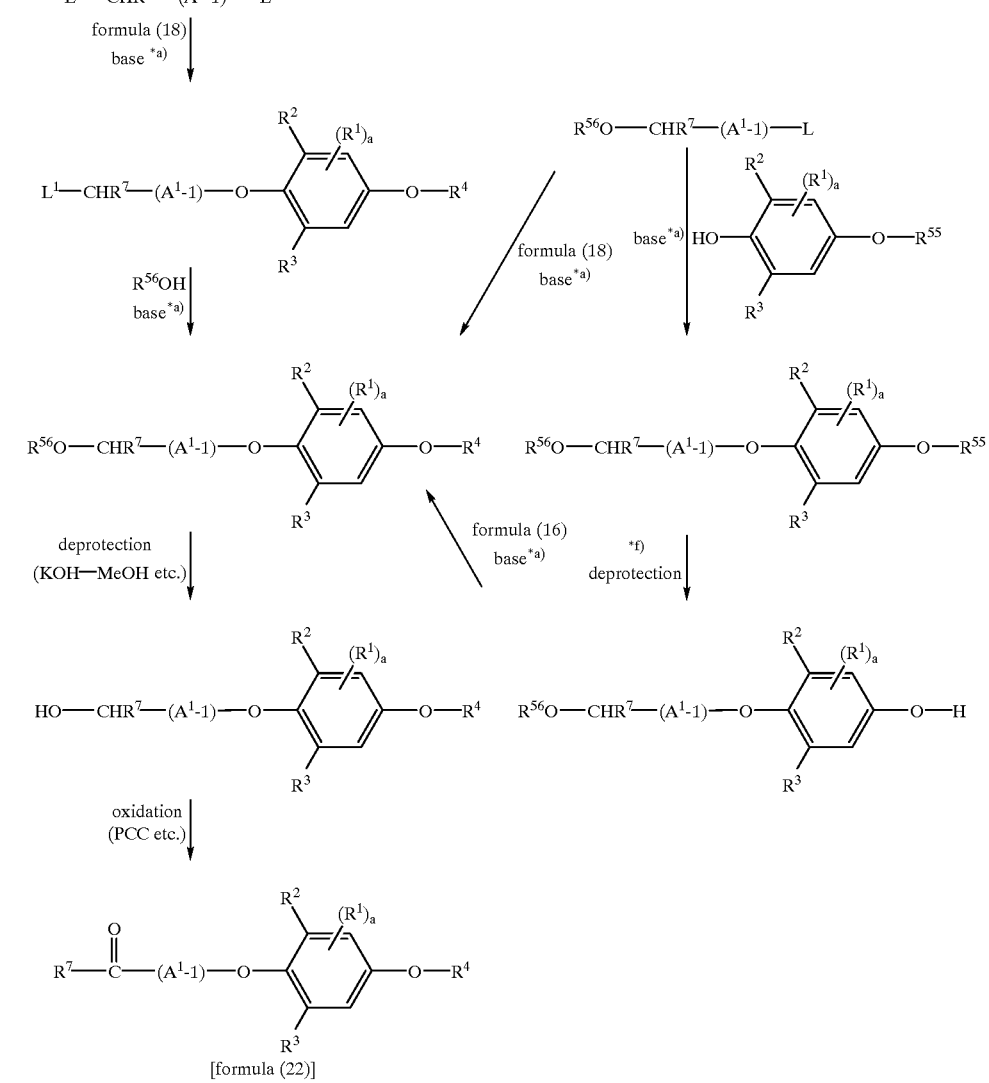
*a) $K_2CO_3$ etc.
*f) e.g., $H_2$—Pd (10%)/C etc. (wherein h is 0), when $R^{55}$ is $C_6H_5CH_2$ wherein $R^{55}$ is a protecting group for the hydroxyl group of phenol, such as benzyl, $R^{56}$ is acetyl or benzoyl, PCC means pyridinium chlorocromate, and the other variables are as defined above.

The compounds of formula (21) as the intermediates for the production of the present compounds are commercially available or can be produced, for example, according to the following scheme XVI.

Scheme XVI
(with the proviso that $R^6$ is not hydrogen)

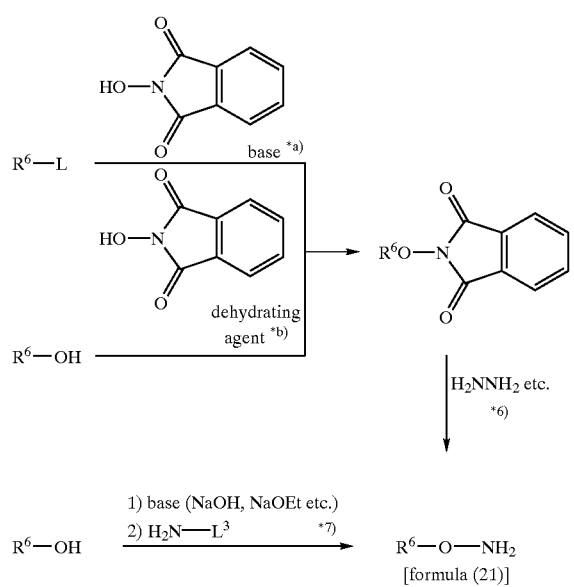

*a) $K_2CO_3$ etc.
*b) $PPh_3$-diethyl azodicarboxylate etc.
*6) Bull. Acad. Pol. Sci., Ser. Sci. Chim., 22, 195 (1974) etc.
*7) Synthesis, 461 (1980) etc.

wherein $L^3$ is a leaving group such as halogen, hydroxysulfonyloxy, or 2,4,6-trimethylbenzenesulfonyloxy, and the other variables are as defined above.

The compounds of formula (33), (34), (35), (36), or (37), as the intermediates for the production of the present compounds, are commercially available or can be produced by the methods widely known in the art or by the methods as described in the publications: [compounds of formula (33) wherein J is sulfur] J. Org. Chem., 30, 1284 (1965); [compounds of formula (35) wherein J is oxygen] J. Am. Chem. Soc., 81, 714 (1959); [compounds of formula (35) wherein J is sulfur] Justus Liebigs Ann. Chem., 590, 123 (1954).

The compounds of formula (19) or (20) as the intermediates for the production of the present compounds can be produced, for example, according to the following scheme XVII.

Scheme XVII
(in the case where X is $X^1$, and $A^1$ is $A^1$-7, $A^1$-8, $A^1$-9, $A^1$-10, $A^1$-11, or $A^1$-12)

formula (39)

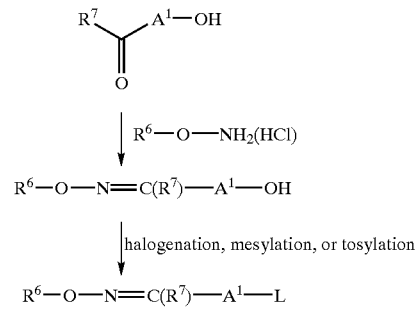

wherein all the variables are as defined above.

The compounds of formula (39) can be produced, for example, according to the following schemes XVIII-1 to XVIII-9.

Scheme XVIII-1
(in the case where $G^1$ is $G^1$-2)

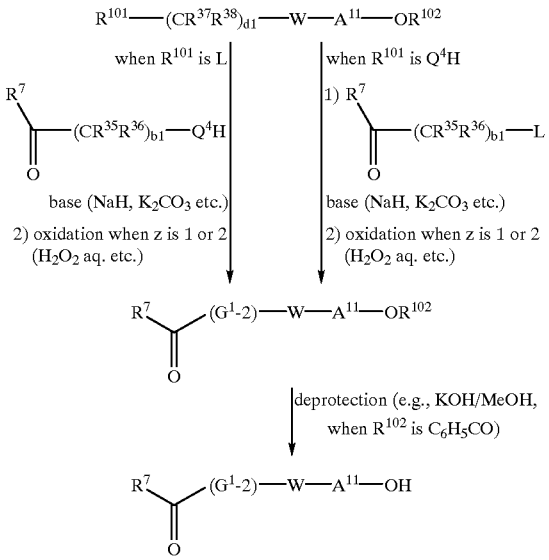

wherein $R^{101}$ is L or $Q^4H$, $Q^4$ is oxygen, sulfur, or $NR^{34}$, $R^{34}$ is hydrogen or $C_1$-$C_3$ alkyl, $R^{102}$ is a protecting group for alcohols, such as benzoyl, $A^{11}$ is $A^{11}$-7, $A^{11}$-8, $A^{11}$-9, $A^{11}$-10, $A^{11}$-11, or $A^{11}$-12 of formula (40)

$A^{11}$-7:  —$(CR^{19}R^{20})_t$—$(CR^{23}=CR^{24})_h$—$(CR^{25}R^{26})_u$—$(CR^{27}=CR^{28})_p$—$(CR^{29}R^{30})_j$—

$A^{11}$-8:  —$G^2$—$(CR^{19}R^{20})_j$—$(CR^{23}=CR^{24})_h$—$(CR^{25}R^{26})_u$—$(CR^{27}=CR^{28})_p$—$(CR^{29}R^{30})_v$—

$A^{11}$-9:  —$(CR^{19}R^{20})_t$—$(CR^{23}=CR^{24})_h$—$(CR^{25}R^{26})_j$—$Q^1$—$(CR^{27}R^{28})_v$—$(CR^{29}=CR^{30})_p$—$(CR^{31}R^{32})_w$—

$A^{11}$-10:  —$G^2$—$(CR^{19}R^{20})_j$—$(CR^{23}=CR^{24})_h$—$(CR^{25}R^{26})_v$—$Q^1$—$(CR^{27}R^{28})_w$—$(CR^{29}=CR^{30})_p$—$(CR^{31}R^{32})_x$—

$A^{11}$-11:  —$(CR^{19}R^{20})_t$—$Q^1$—$(CR^{23}R^{24})_h$—E—$(CR^{25}R^{26})_p$—p1  $A^{11}$-12:  —$(CR^{19}R^{20})_t$—$Q^1$—$(CR^{23}R^{24})_j$—C≡C—$(CR^{25}R^{26})_m$— and the other variables are as defined above.

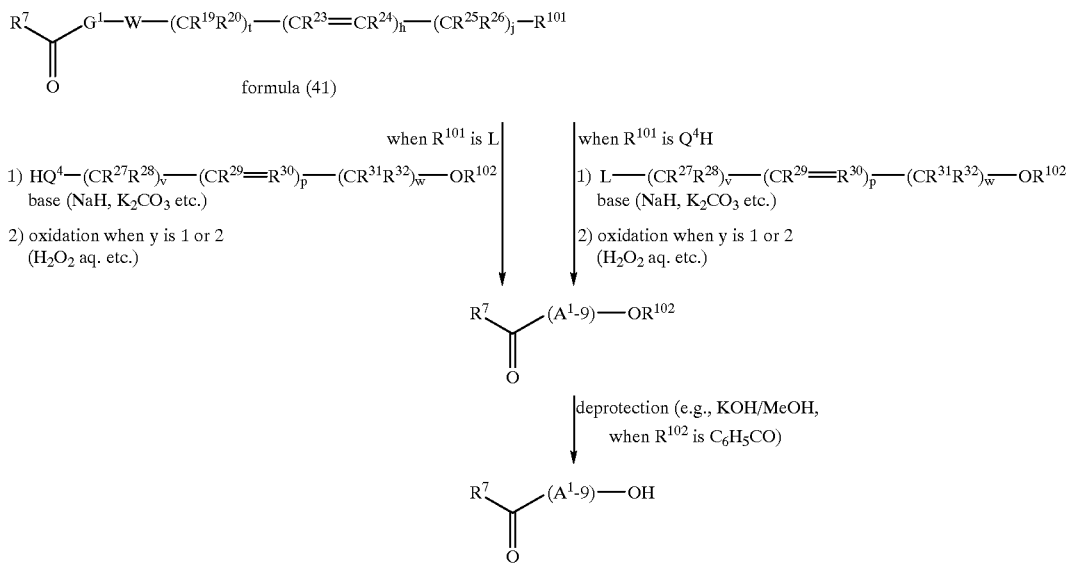
wherein all the variables are as defined above.
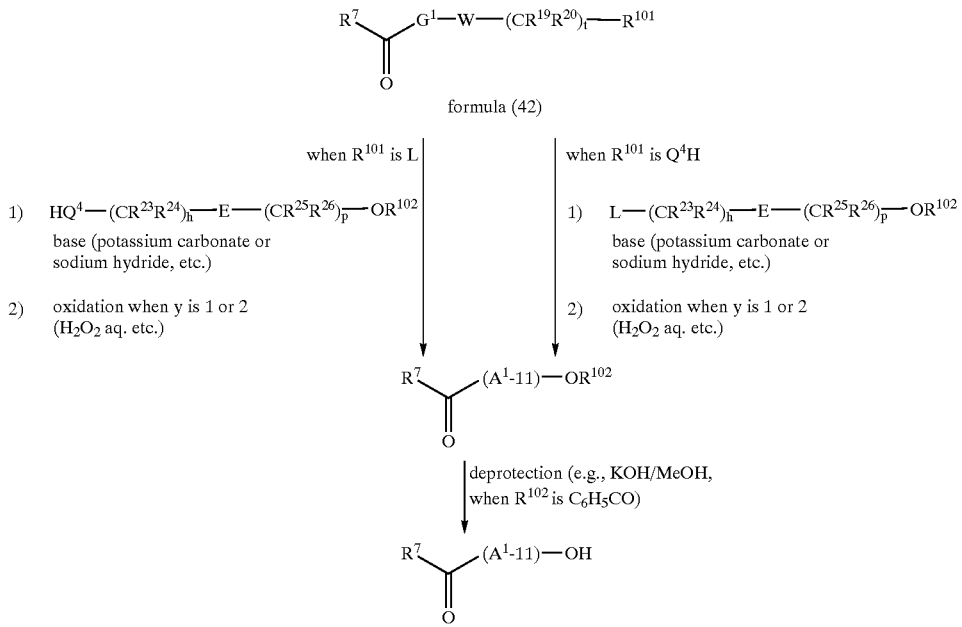
wherein all the variables are as defined above.

Scheme XVIII-4
(in the case where $A^1$ is $A^1$-12)
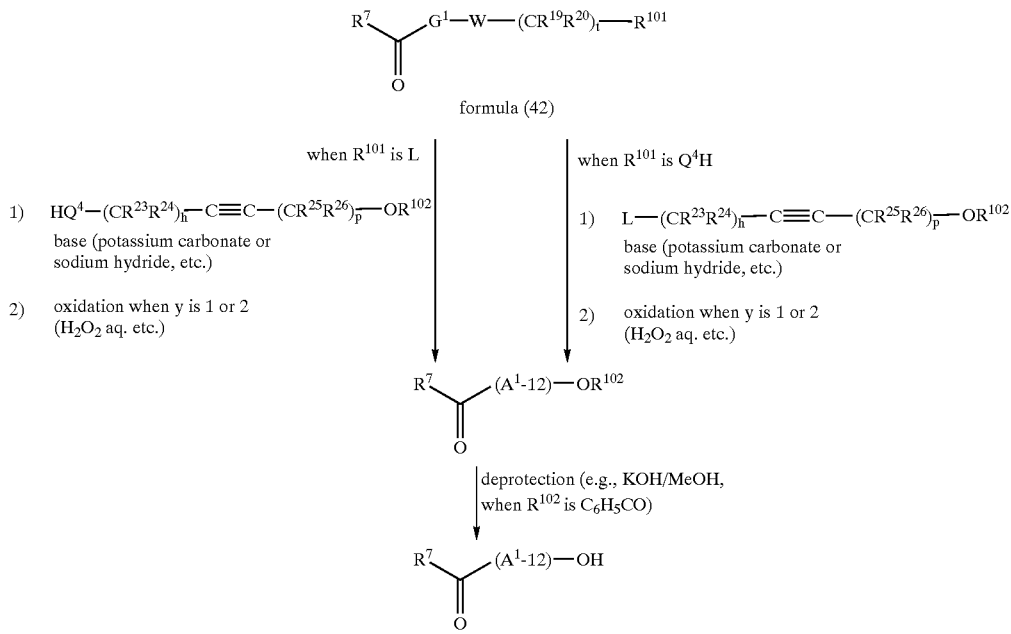
wherein all the variables are as defined above.
Scheme XVIII-5
(in the case where $A^1$ is $A^1$-8)
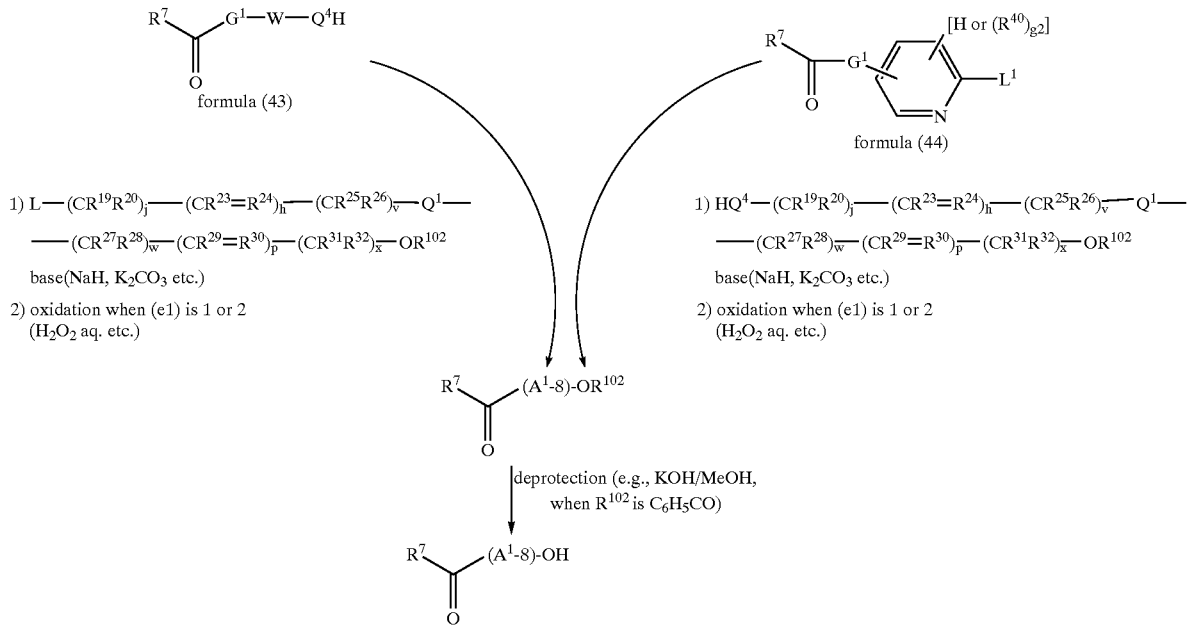
wherein all the variables are as defined above.

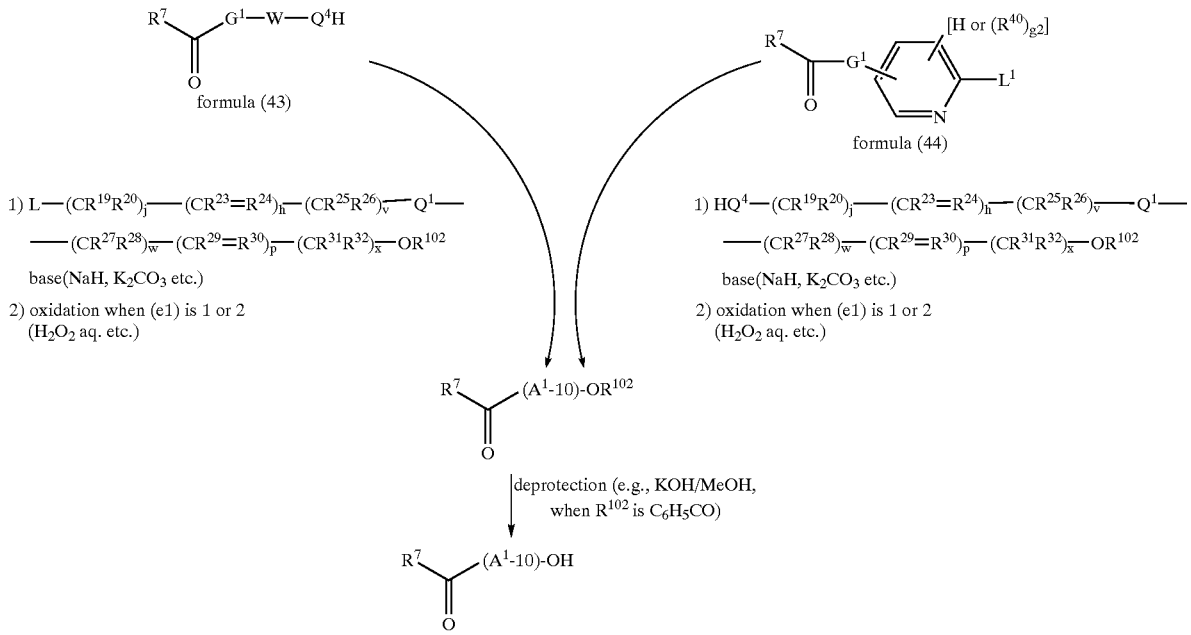
wherein all the variables are as defined above.
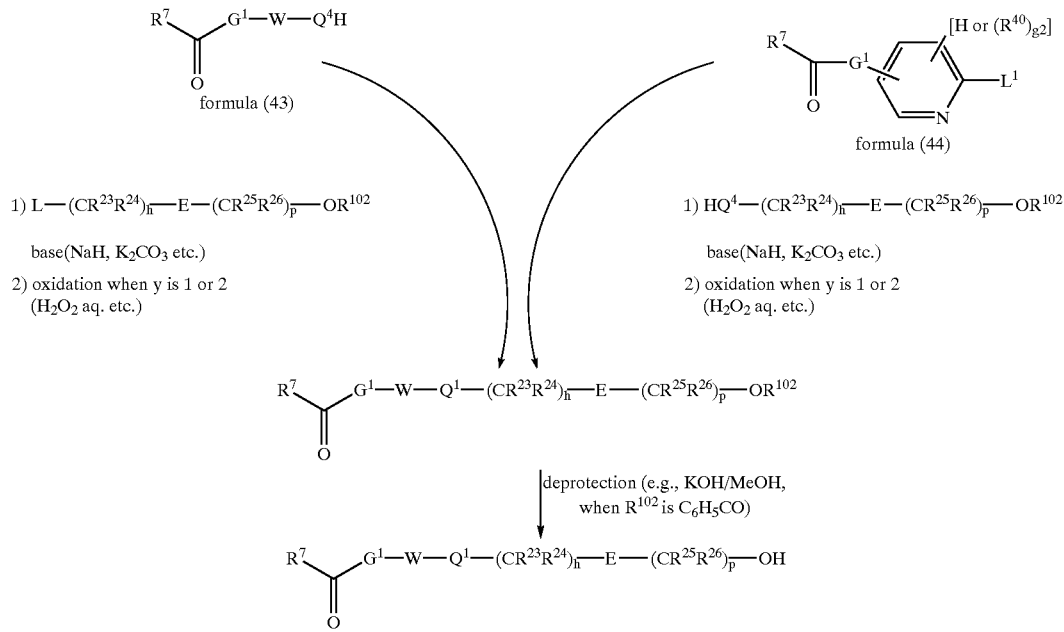
wherein all the variables are as defined above.

Scheme XVIII-8
(in the case where $A^1$ is $A^1$-12 and t is 0)
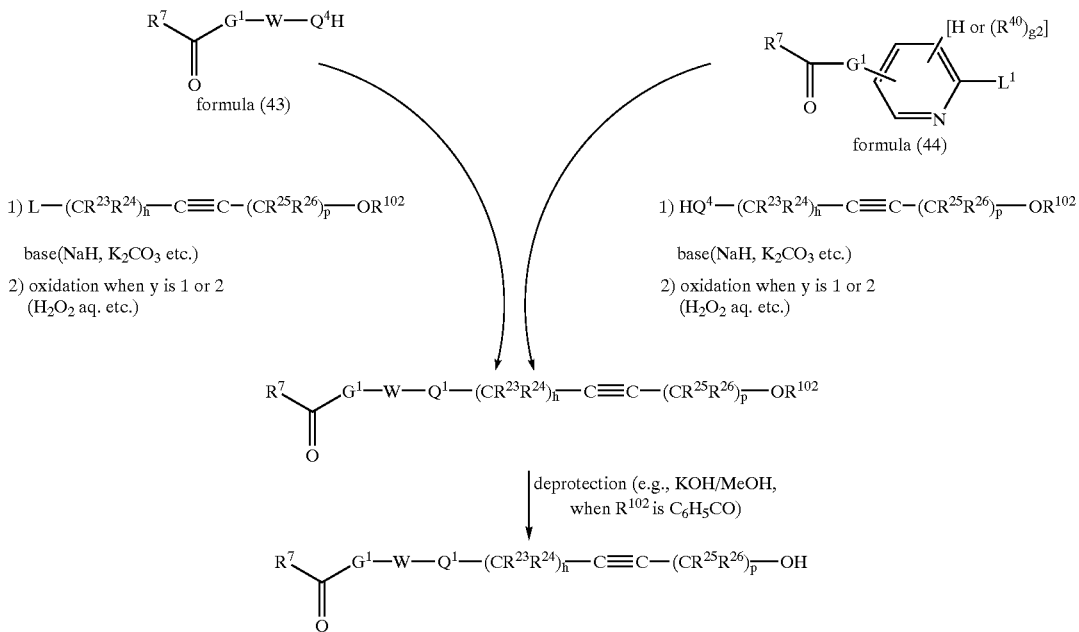
wherein all the variables are as defined above.
Scheme XVIII-9
(in the case where $A^1$ is $A^1$-10)
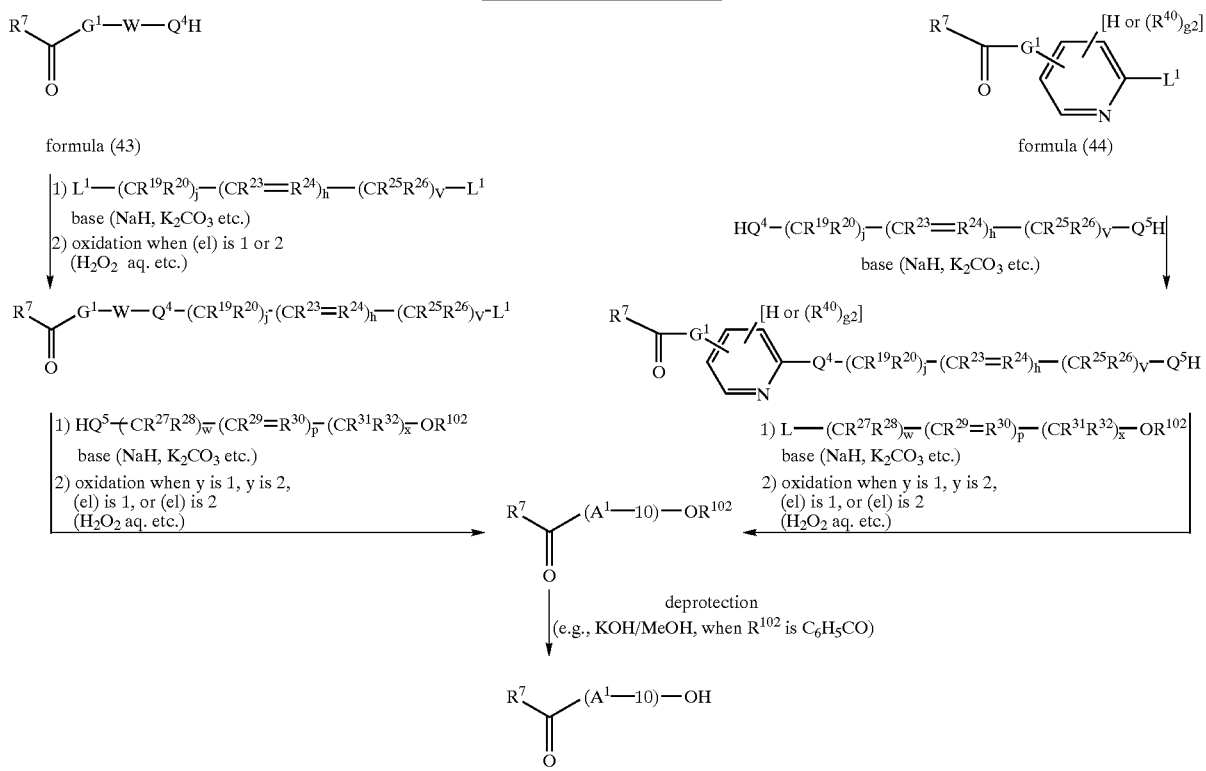

wherein $Q^5$ is oxygen, sulfur, or $NR^{33}$, and the other variables are as defined above.

The compounds of formula (25) as the intermediates for the production of the present compounds can be produced, for example, according to scheme XIV.

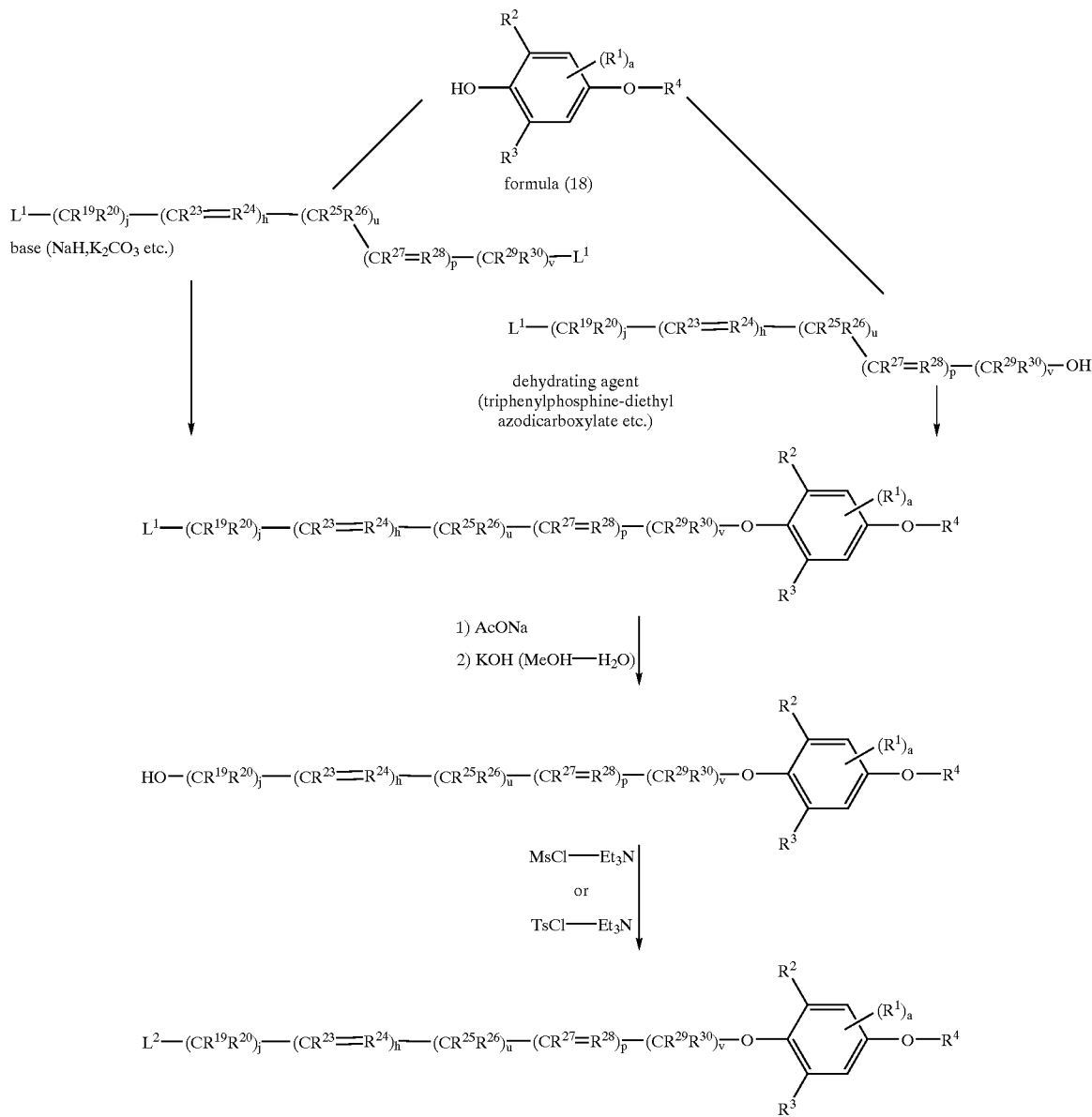

where all the variables are as defined above.

The compounds of formula (26) as the intermediates for the production of the present compounds can be produced, for example, according to the following scheme XX.

Scheme XX

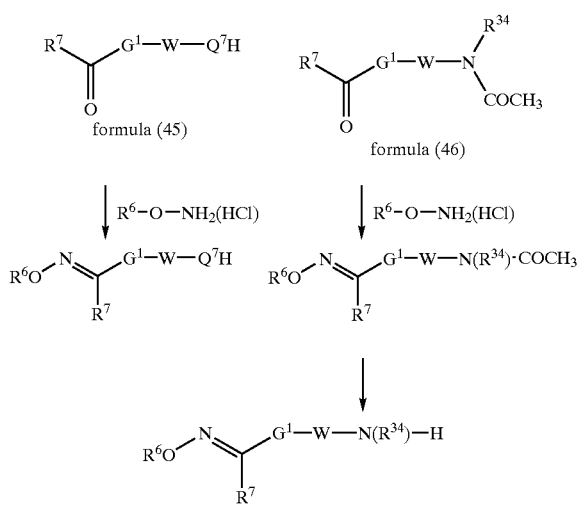

wherein $Q^7$ is oxygen or sulfur, and the other variables are as defined above.

The compounds of formula (21) as the intermediates for the production of the present compounds are commercially available or can be produced, for example, according to the following scheme XXI.

wherein $R^{103}$ and $R^{104}$ are $C_1$–$C_3$ alkyl, and the other variables are as defined above, with the proviso that $R^6$ is not hydrogen.

The carbonyl compounds of formula (22) as the intermediates for the production of the present compounds can be produced, for example, according to the following schemes XXI-1 to XXII-5.

Scheme XXI

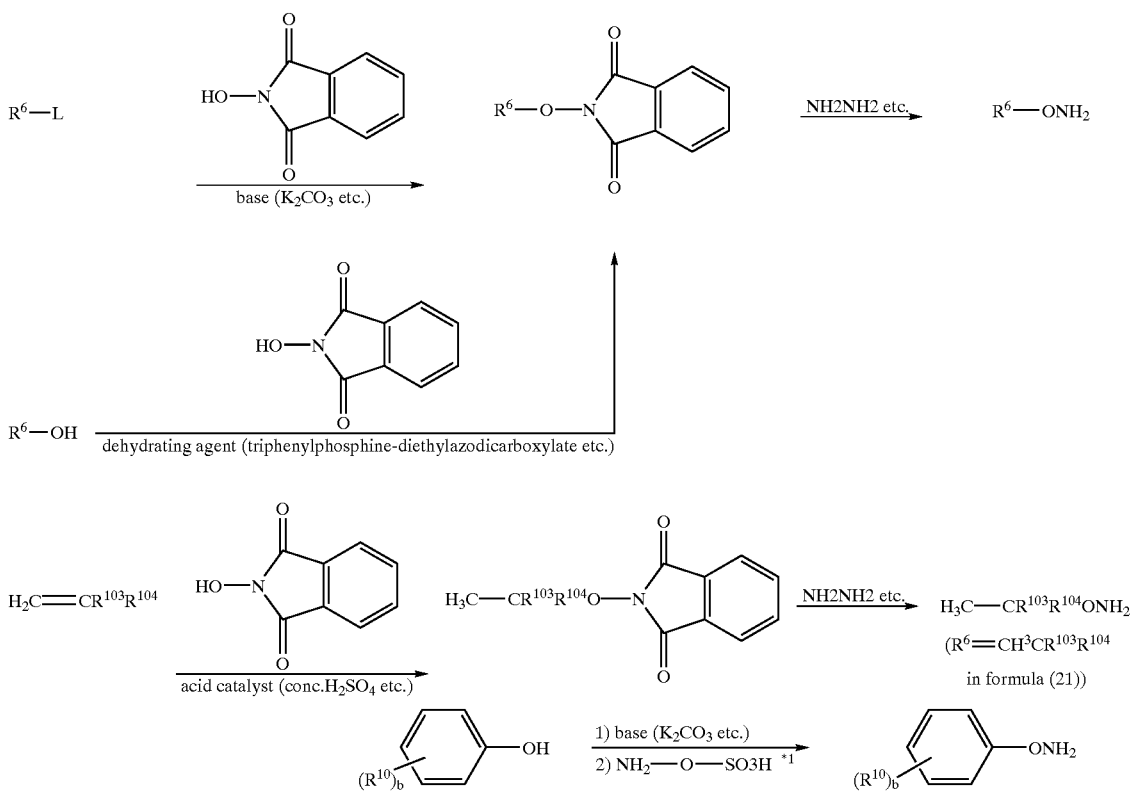

*1: e.g., JP-A 04-368360 etc.

Scheme XXII-1
(in the case where X is $X^1$, and $A^1$ is $A^1$-7, $A^1$-8, $A^1$-9, $A^1$-10, $A^1$-11, or $A^1$-12)
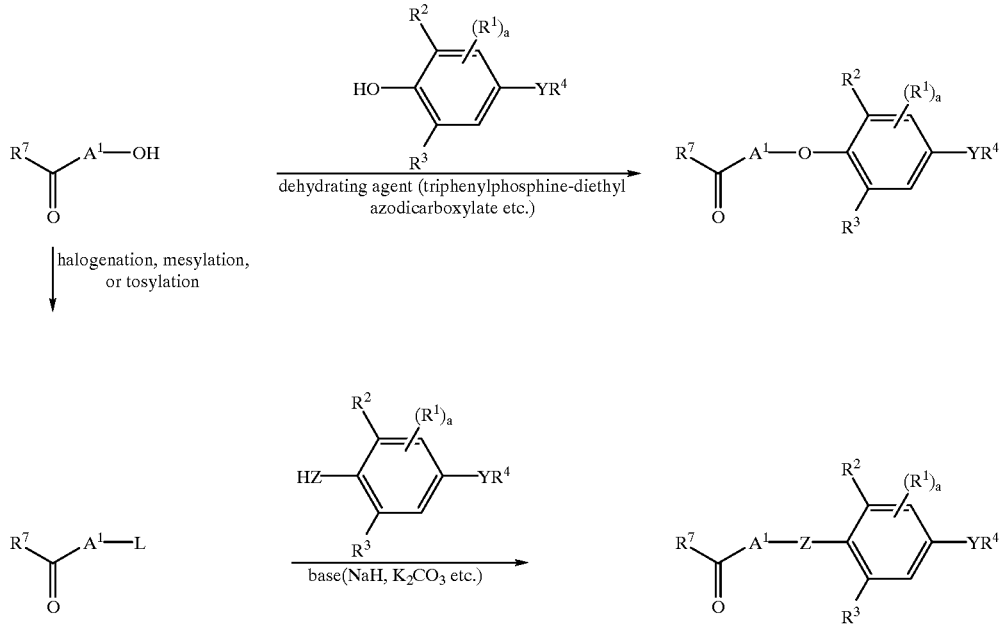
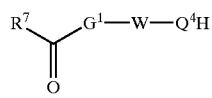
wherein all the variables are as defined above.
Scheme XXII-2
(in the case where X is $X^1$, $A^1$ is $A^1$-8, and Y and Z are both oxygen)
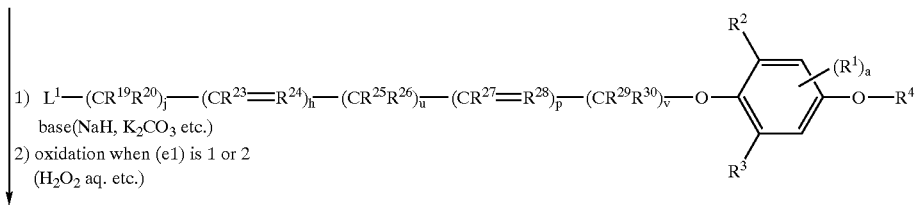

-continued

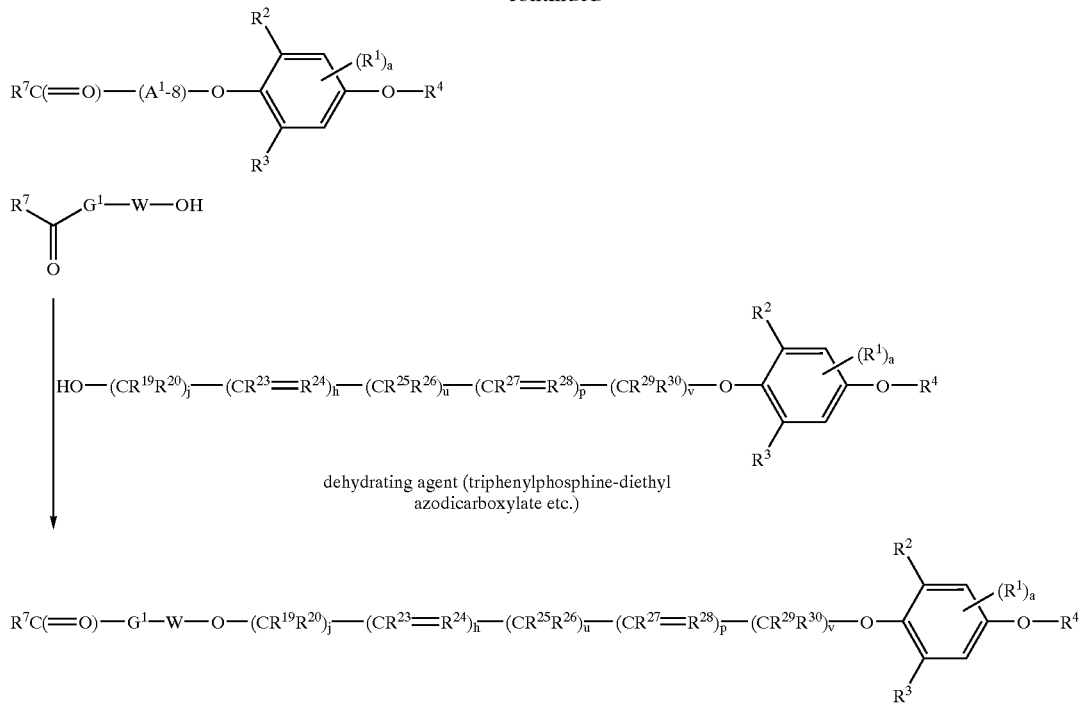

wherein all the variables are as defined above.

Scheme XXII-3
(in the case where X is $X^1$, $R^7$ is hydrogen, W is $W^1$, $A^1$ is $A^1$-8, $G^1$ is $G^1$-1, a1 is 0, and Y and Z are both oxygen)

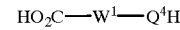

↓ methyl esterification or ethyl esterification

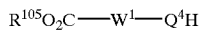

↓ 1) formula (25), base (potassium carbonate or sodium hydride, etc.)
2) oxidation when (e1) is 1 or 2 ($H_2O_2$ aq. etc.)

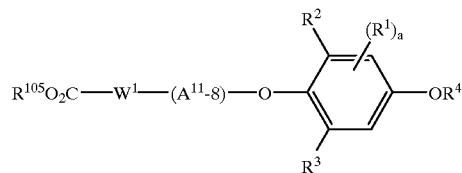

↓ 1) isobutyl aluminium hydride
2) $H_3O^+$

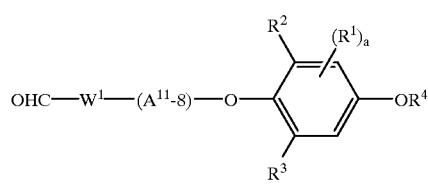

wherein $R^{105}$ is methyl or ethyl, $W^1$ is a benzene ring or a heterocyclic ring containing no —NH— linkage in the ring thereof, and the other variables are as defined above.

Scheme XXII-4
(in the case where X is $X^1$, $R^7$ is hydrogen, W is $W^1$, $A^1$ is $A^1$-8, $G^1$ is $G^1$-1, a1 is 0, and Y and Z are both oxygen)

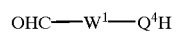

↓ acetalization

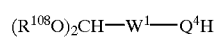

↓ 1) formula (25), base (potassium carbonate or sodium hydride, etc.)
2) oxidation when (e1) is 1 or 2 ($H_2O_2$ aq. etc.)

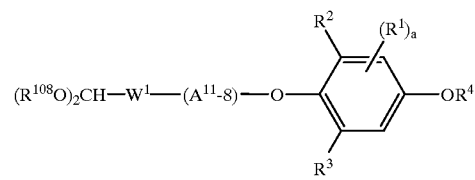

↓ deasetalization ($H_3O^+$)

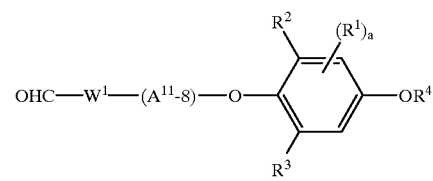

wherein $R^{108}$ is methyl or ethyl, or two $R^{108}$'s are combined together at their ends to form ethylene or trimethylene, and the other variables are as defined above.

Scheme XXII-5
(in the case where X is $X^1$, $R^7$ is hydrogen, $A^1$ is $A^1$-7, $G^1$ is $G^1$-1, a1 is 0, W is $W^1$, t, h, u, and p are 0, j is 1, $R^{29}$ and $R^{30}$ are both hydrogen, and Y and Z are both oxygen)

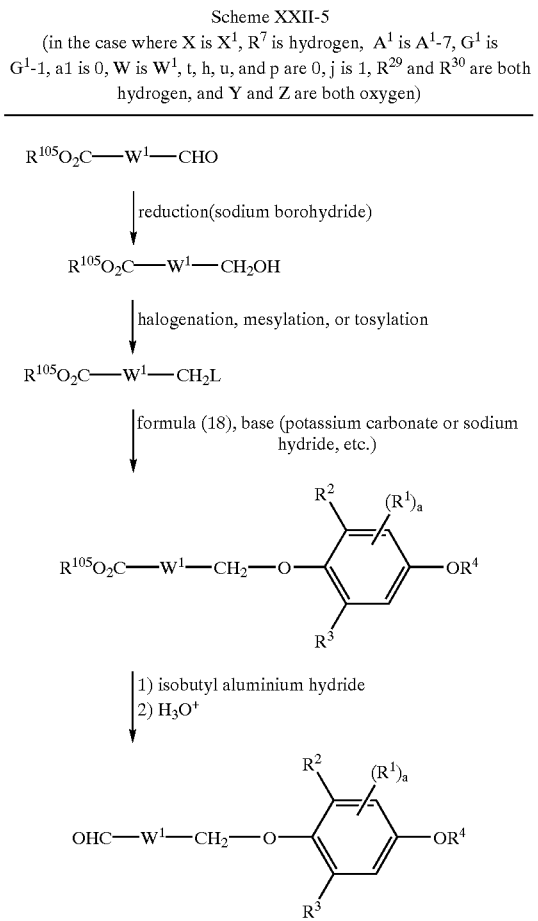

wherein all the variables are as defined above.

The compounds of formula (24) as the intermediates for the production of the present compounds can be produced, for example, according to the following scheme XXIII.

Scheme XXIII
(in the case where X is $X^1$)

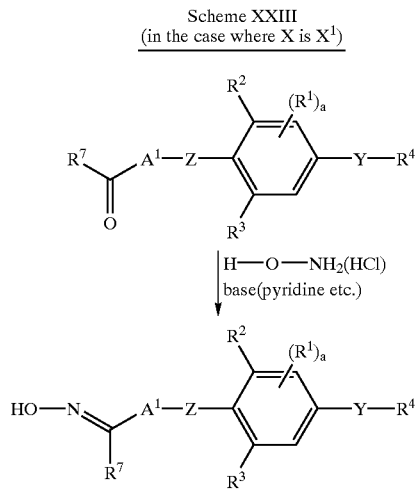

wherein all the variables are as defined above.

Some of the compounds of formula (41), (42), or (43) are commercially available or can be produced according to the following schemes XXIV-1 to XXIV-4.

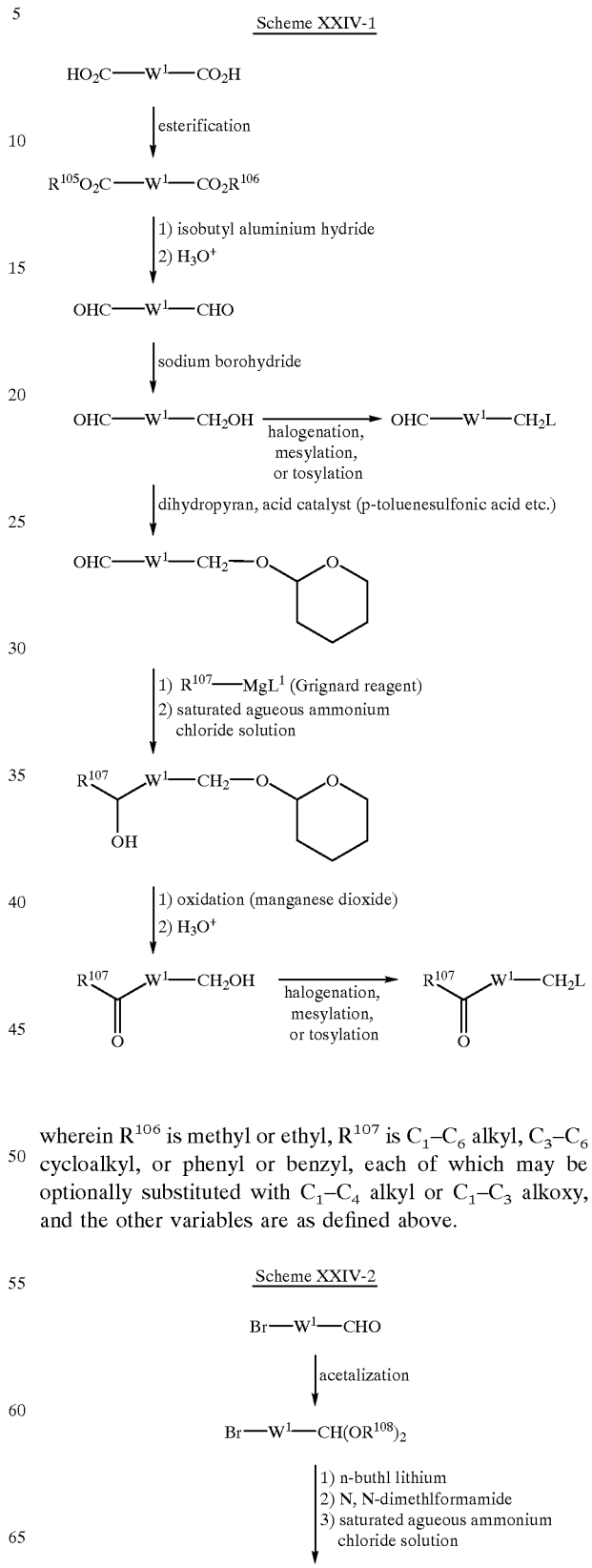

wherein $R^{106}$ is methyl or ethyl, $R^{107}$ is $C_1$–$C_6$ alkyl, $C_3$–$C_6$ cycloalkyl, or phenyl or benzyl, each of which may be optionally substituted with $C_1$–$C_4$ alkyl or $C_1$–$C_3$ alkoxy, and the other variables are as defined above.

Scheme XXIV-2

Br—$W^1$—CHO

↓ acetalization

Br—$W^1$—CH(OR$^{108}$)$_2$ 1) n-buthl lithium
2) N, N-dimethlformamide
3) saturated agueous ammonium chloride solution -continued

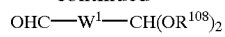

↓ reduction (sodium borohydride)

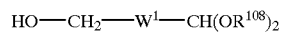

↓ deacetalization $HO-CH_2-W^1-CHO$

↓ halogenation, mesylation, or tosylation $L-CH_2-W^1-CHO$ wherein all the variables are as defined above.

Scheme XXIV-3

$CH_3CO-W^1-COCH_3$

↓ reduction (sodium borohydride)

$CH_3CO-W^1-CH(OH)-CH_3$

↓ halogenation, mesylation, or tosylation $CH_3CO-W^1-CH(L)-CH_3$ wherein all the variables are as defined above.

Scheme XXIV-4

$Br-W^1-Q^7H$

↓ benzyl chloride or benzyl bromide
base (potassium carbonate or sodium hydride, etc.)

$Br-W^1-Q^7-CH_2C_6H_5$

↓ 1) n-butyl lithium
2) dry ice
3) $H_3O^+$ $HO_2C-W^1-Q^7-CH_2C_6H_5$

↓ esterification $R^{105}O_2C-W^1-Q^7-CH_2C_6H_5$

↓ 1) isobuthl aluminium hydride
2) $H_3O^+$ $OHC-W^1-Q^7-CH_2C_6H_5$

↓ debenzylation (catalytic hydragenation)

-continued $OHC-W^1-Q^7-H$ wherein all the variables are as defined above.

The starting compounds of formula (47)

$R^{109}-W^1-R^{110}$ wherein $R^{109}$ and $R^{110}$ are $L^1$, $Q^4H$, CHO, $CH(OR^{108})_2$, $CO_2H$, $CO_2R^{105}$, $COCH_3$, or $CH_2L^1$, and the other variables are as defined above, which are used in the schemes XXII-3, XXII-4, XXII-5, XXIV-1, XXIV-2, XXIV-3, and XXIV-4, and other compounds are commercially available or can be produced, for example, by the methods as described in the following publications.

In the case where $W^1$ is a pyridazine ring:

*J. Heterocyclic Chem.*, 5, 845 (1968);
*Monatschefte fur Chem.*, 110, 365 (1979), etc.

In the case where $W^1$ is a pyrimidine ring:

*Justus Liebigs Ann. Chem.*, 684, 209 (1965);
*J. Heterocyclic Chem.*, 28, 1281 (1991);
*Chem. Ber.*, 97, 3407 (1964);
*J. Chem. Soc.*, 1965, 5467;
*Aust. J. Chem.*, 19, 2321 (1966), etc.

In the case where $W^1$ is a pyradine ring:

*J. Org. Chem.*, 54, 640 (1089) etc.

In the case where $W^1$ is an oxazole ring:

*J. Org. Chem.*, 57, 4797 (1992) etc.

In the case where $W^1$ is an isoxazole ring:

*Chem. Pharm. Bull.*, 14, 92 (1966);
*Chem. Pharm. Bull.*, 14, 1277 (1966);
*Chem. Pharm. Bull.*, 19, 46 (1971);
*J. Chem. Res. Synop.*, 1994, 116;
*Synthesis*, 1976, 992, etc.

In the case where $W^1$ is a thiazole ring:

*J. Am. Chem. Soc.*, 72, 5221 (1950) etc.

In the case where $W^1$ is an isothiazole ring:

*J. Chem. Soc.*, 1959, 3061 etc.

In the case where $W^1$ is an imidazole ring:

*Tetrahedron Lett.*, 26, 1915 (1985) etc.

In the case where $W^1$ is a pyrazole ring:

*Chem. Ber.*, 112, 1712 (1979);
*Chem. Ber.*, 116, 1520 (1983);
JP-A 63-185964/1988;
*Tetrahedron*, 29, 441 (1973);
*J. Chem. Soc., Chem. Commun.*, 1969, 66;
*J. Org. Chem.*, 35, 3451 (1970);
*Chem. Ber.*, 103, 2356 (1970), etc.

The compounds of formula (19) or (20) wherein X is $X^2$, as the intermediates for the production of the present compounds, can be produced, for example, according to the following scheme XXV.

Scheme XXV

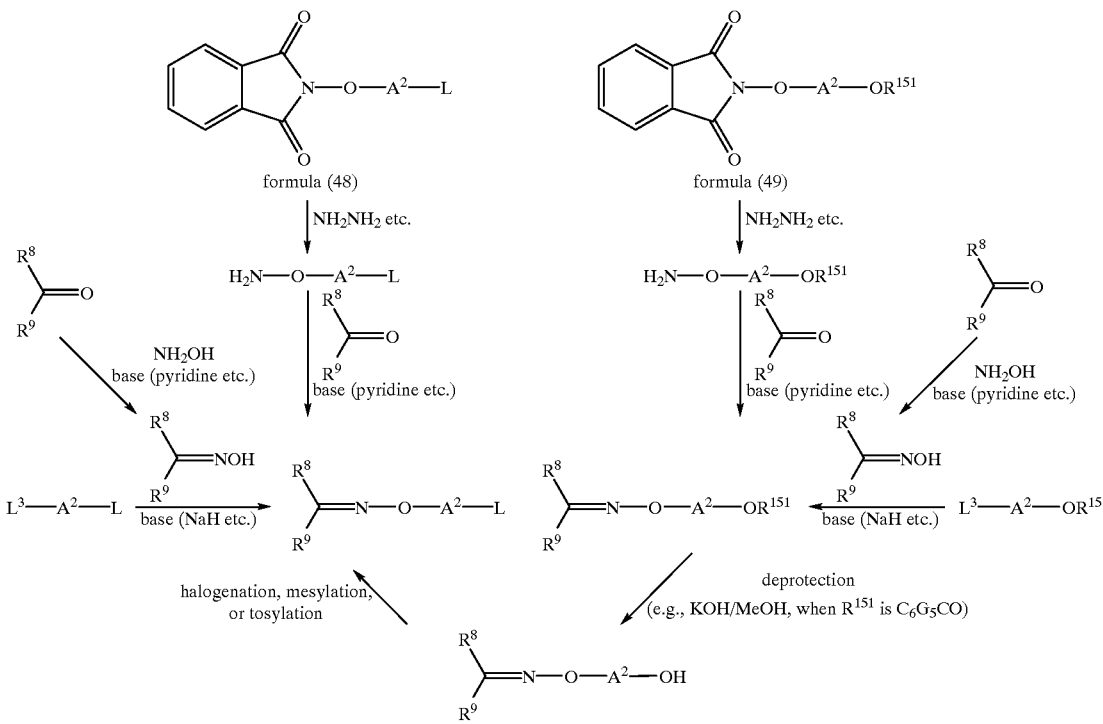

wherein $L^3$ is halogen (e.g., chlorine, bromine, iodine), mesyloxy, or tosyloxy, $R^{151}$ is a protecting group for alcohols, such as described in PROTECTIVE GROUPS IN ORGANIC SYNTHESIS, T. W. Greene, P. G. M. Wuts, A WILEY-INTERSCIENCE PUBLICATION, JOHN WILEY & SONS, INC., pp. 10–142; e.g., benzoyl, and the other variables are as defined above.

The compounds of formula (48) or (49) in the scheme XXV can be produced, for example, according to the following schemes XXVI to XXXXIII.

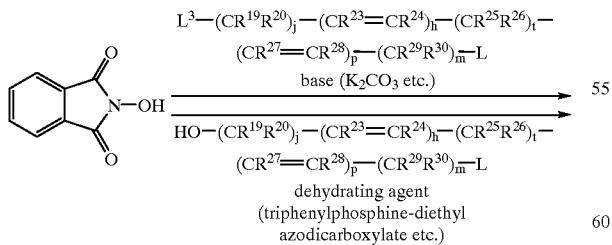

Scheme XXVI
(in the case where $A^2$ is $A^2$-1)

wherein all the variables are as defined above.

Scheme XXVII
(in the case where $A^2$ is $A^2$-2)
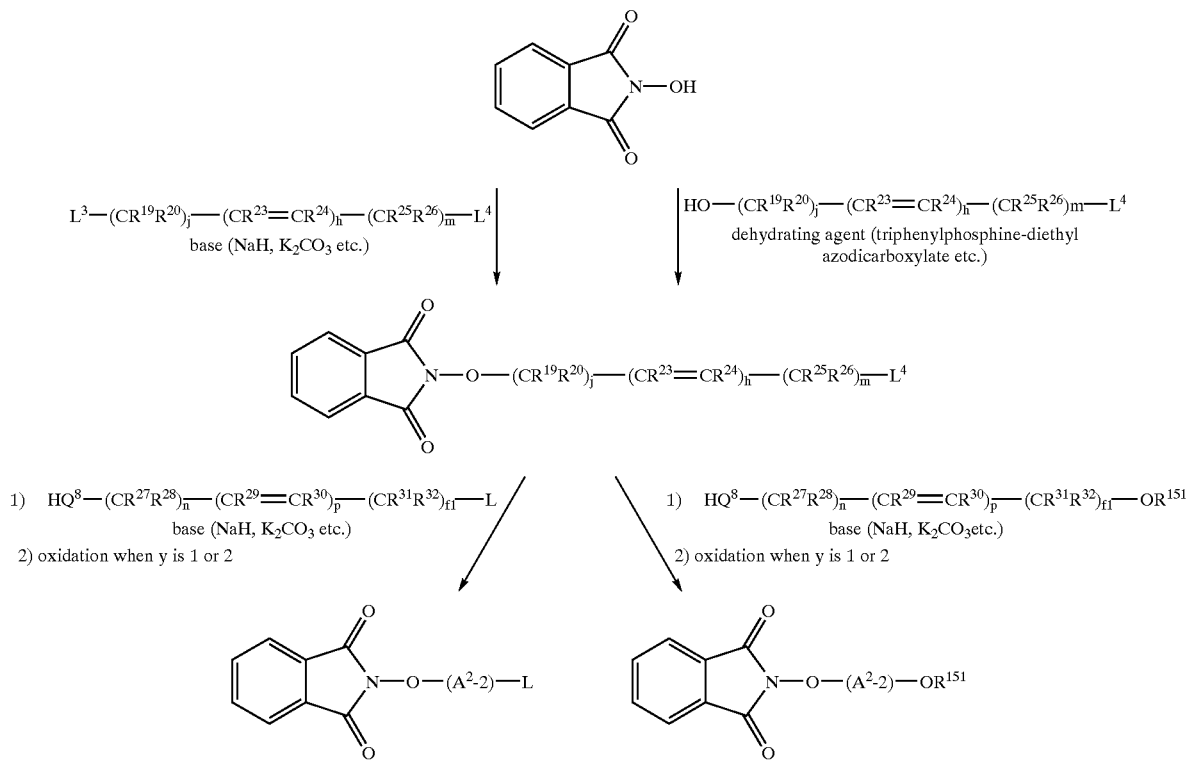
wherein $L^4$ is halogen (e.g., chlorine, bromine, iodine), mesyloxy, or tosyloxy, $Q^8$ is oxygen, sulfur, or $NR^{33}$, $R^{33}$ is hydrogen or $C_1$–$C_3$ alkyl, and the other variables are as defined above.
Scheme XXVIII
(in the case where $A^2$ is $A^2$-3 and $U^3$ is $U^3$-2)
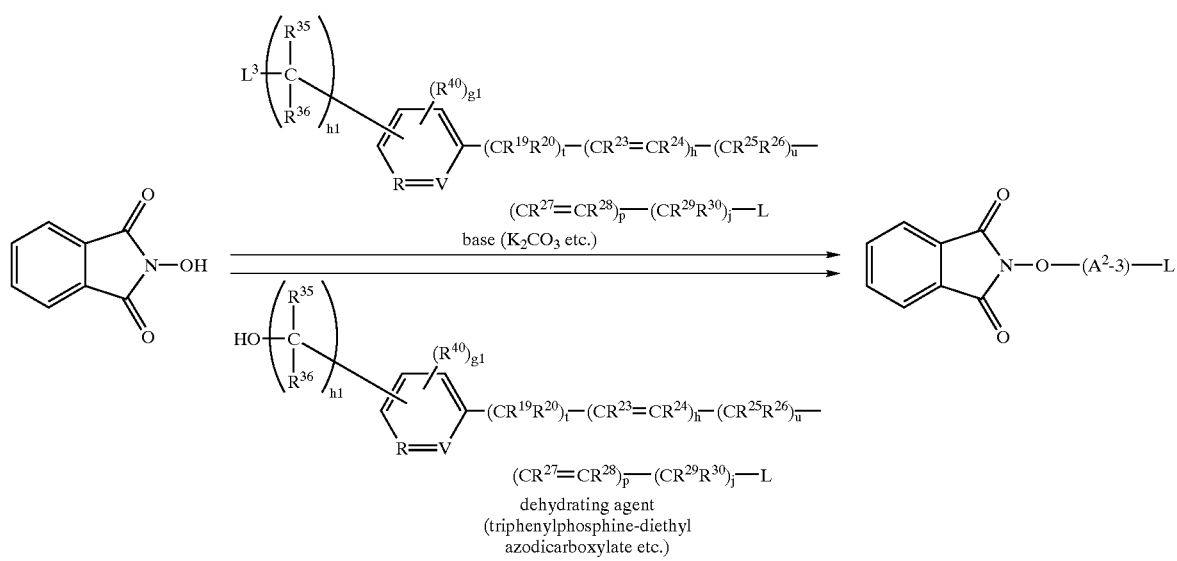

wherein all the variables are as defined above.
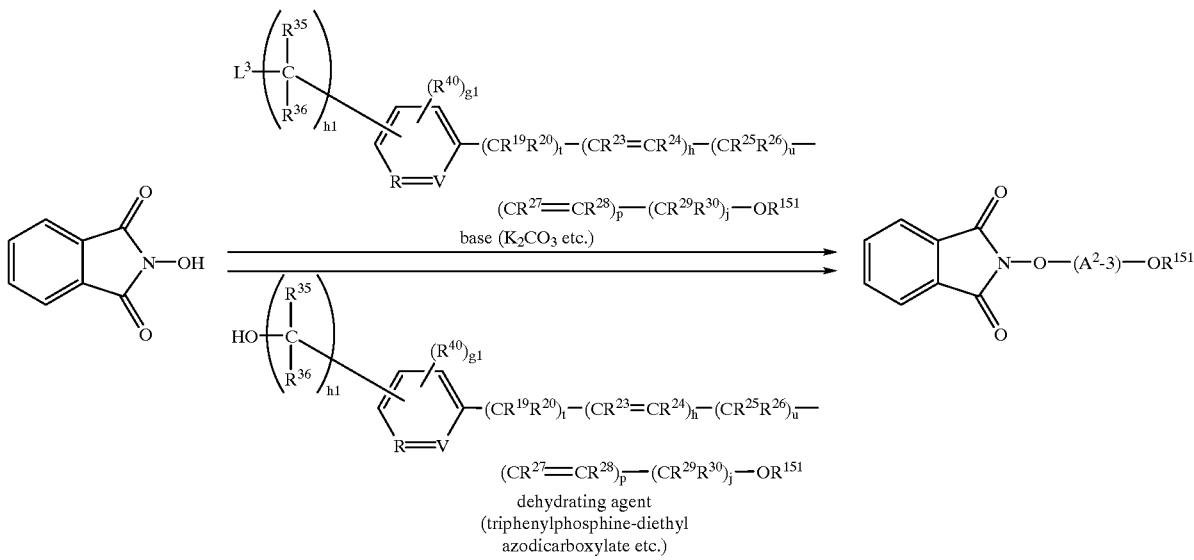
wherein all the variables are as defined above.
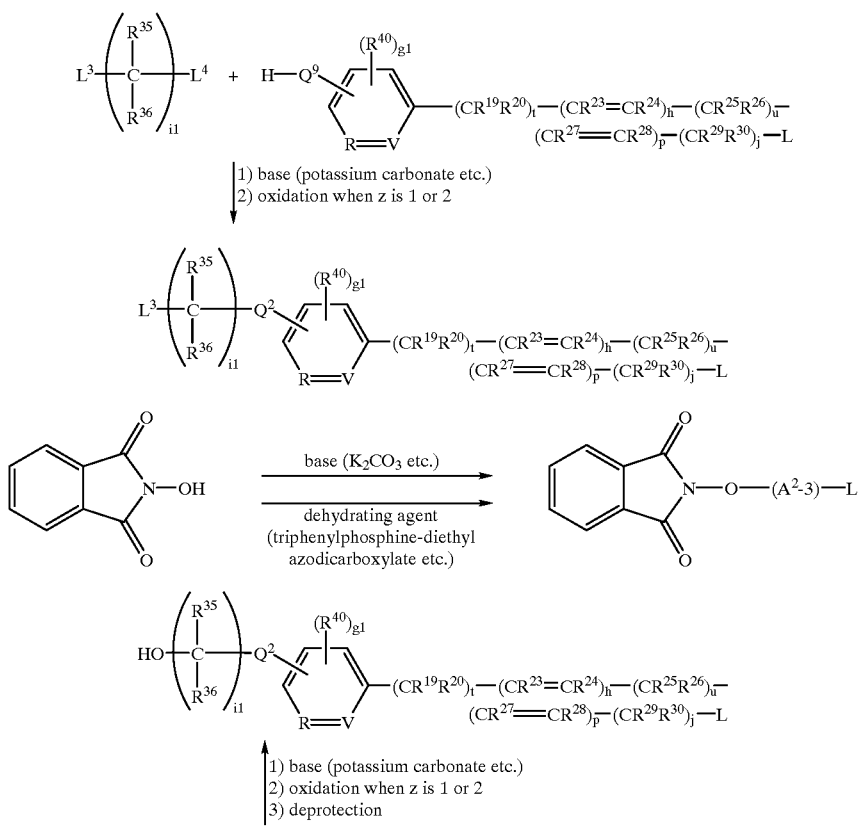

-continued

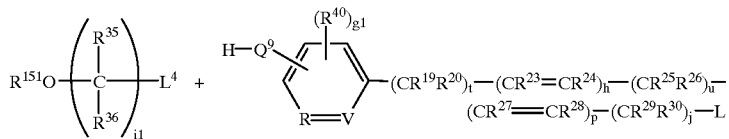

wherein $Q^9$ is oxygen, sulfur, or $NR^{34}$, $R^{34}$ is hydrogen or $C_1$–$C_3$ alkyl, and the other variables are as defined above.

Scheme XXXI
(in the case where $A^2$ is $A^2$-3 and $U^3$ is $U^3$-3)

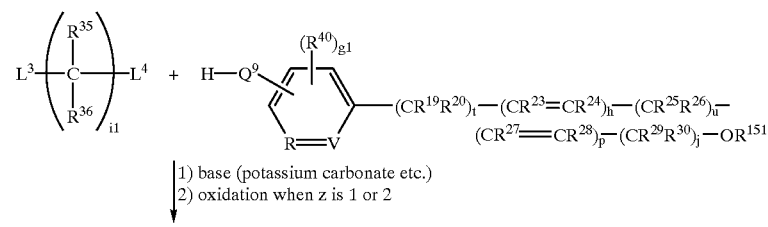

1) base (potassium carbonate etc.)
2) oxidation when z is 1 or 2

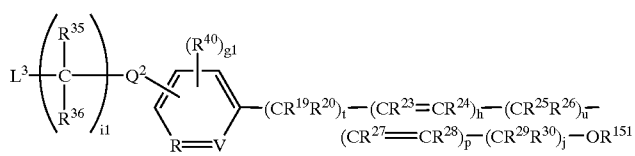

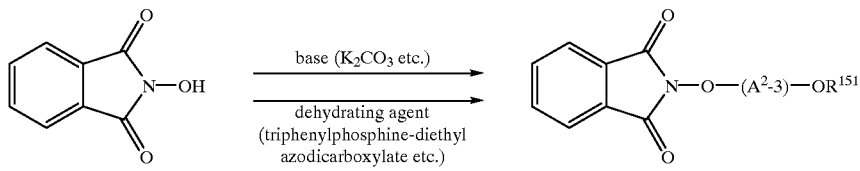

base ($K_2CO_3$ etc.)
⇌
dehydrating agent
(triphenylphosphine-diethyl azodicarboxylate etc.)

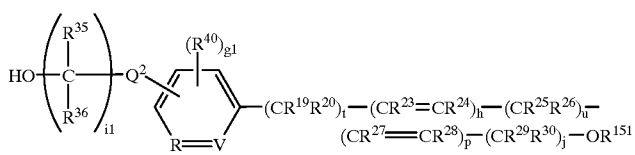

1) base (potassium carbonate etc.)
2) oxidation when z is 1 or 2
3) deprotection

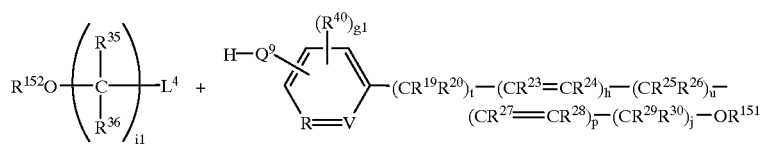

wherein $R^{152}$ is a protecting group for alcohols (as described in PROTECTIVE GROUPS IN ORGANIC SYNTHESIS, T. W. Greene, P. G. M. Wuts, A WILEY-INTERSCIENCE PUBLICATION, JOHN WILEY & SONS, INC., pp. 10–142; as a protecting group selectively removable for $R^{151}$, for example, when $R^{151}$ is benzoyl, $R^{152}$ is tetrahydropyranyl), and the other variables are as defined above.

Scheme XXXII
(in the case where $A^2$ is $A^2$-4 and $U^4$ is $U^4$-2)

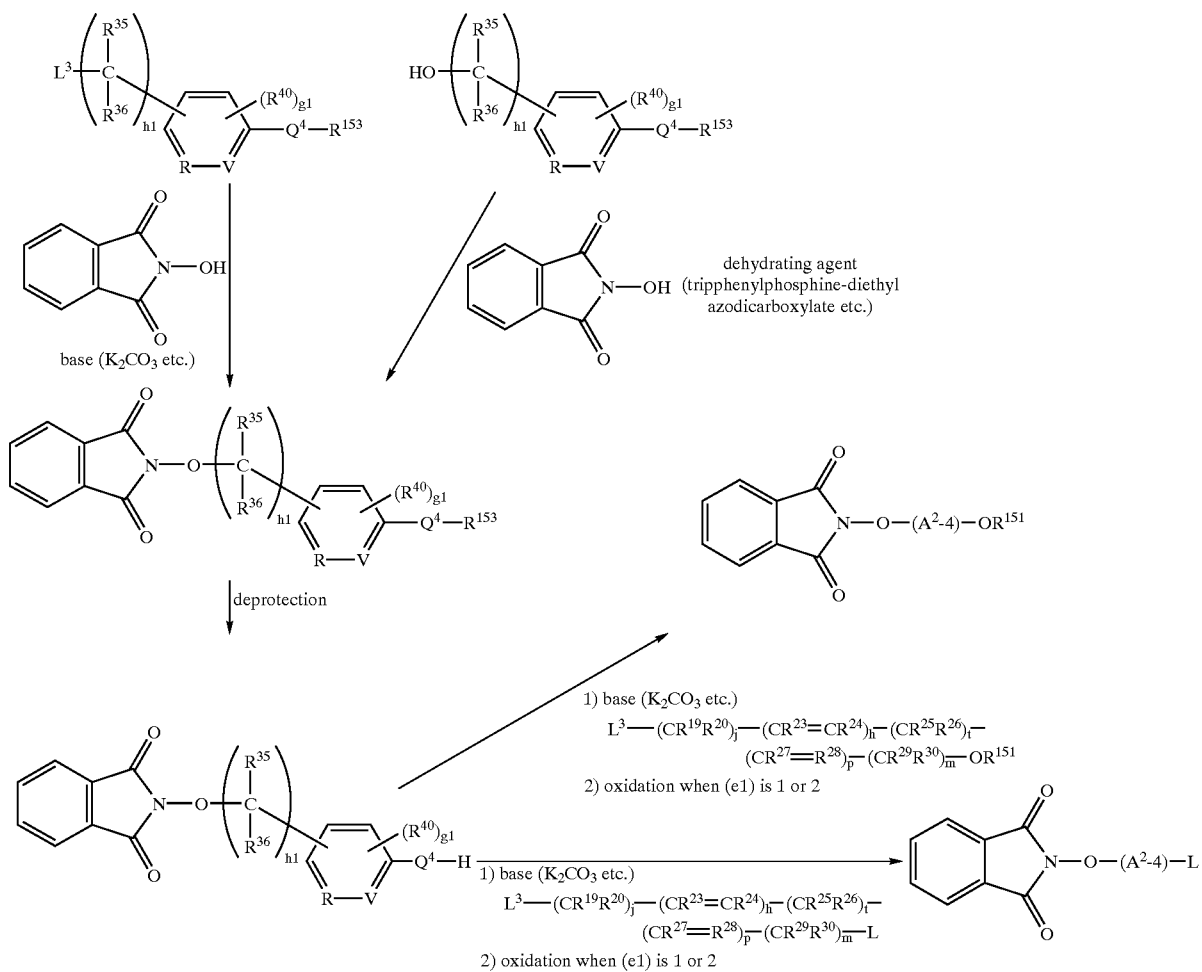

wherein $R^{153}$ is a protecting group (as described in PROTECTIVE GROUPS IN ORGANIC SYNTHESIS, T. W. Greene, P. G. M. Wuts, A WILEY-INTERSCIENCE PUBLICATION, JOHN WILEY & SONS, INC., pp. 143–170 and 277–405; for example, when $Q^4$ is oxygen, $R^{153}$ is benzoyl), and the other variables are as defined above.

Scheme XXXIII
(in the case where $A^2$ is $A^2$-4 and $U^4$ is $U^4$-3)

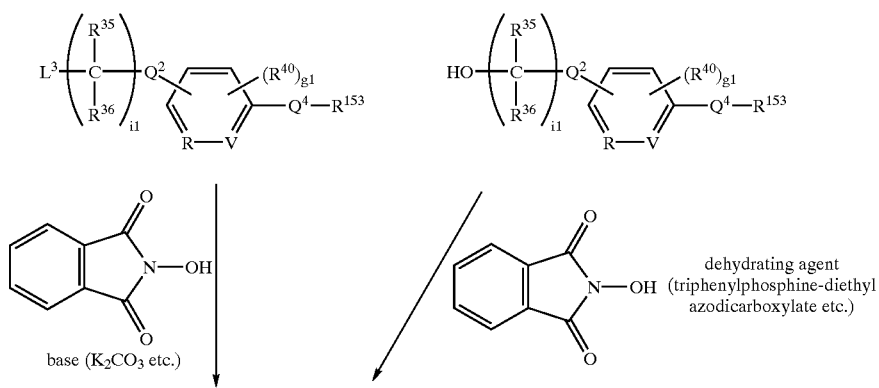

-continued
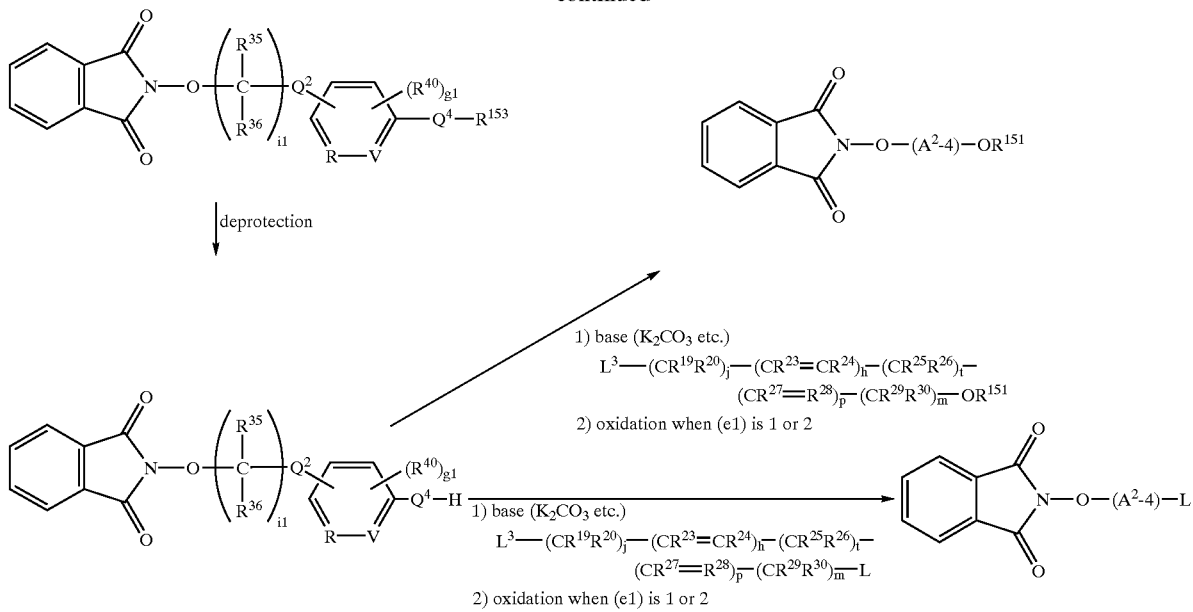
wherein all the variables are as defined above.
Scheme XXXIV
(in the case where $A^2$ is $A^2$-5 and $U^3$ is $U^3$-2)
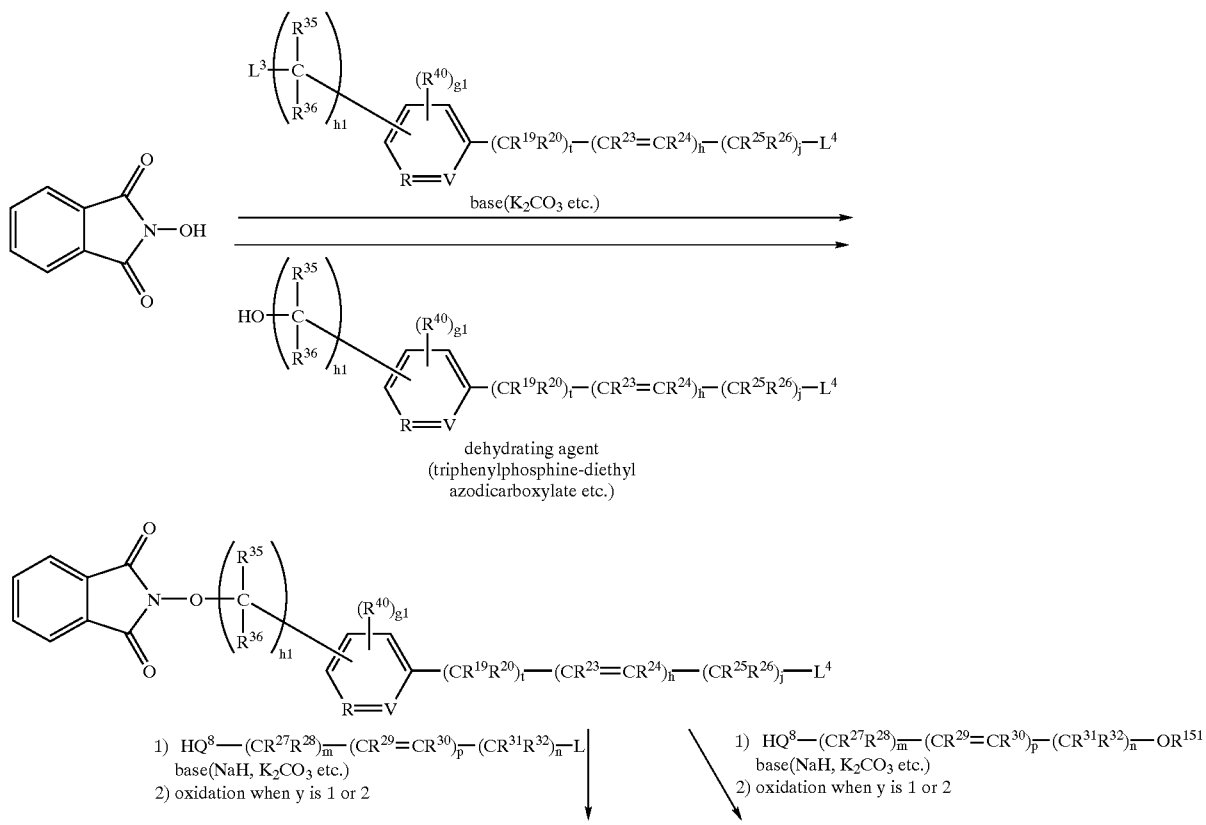

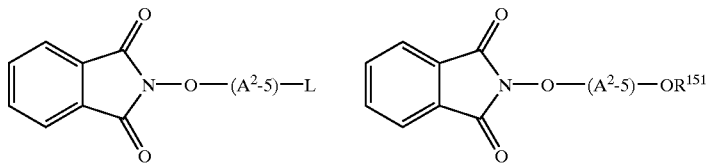
wherein all the variables are as defined above.
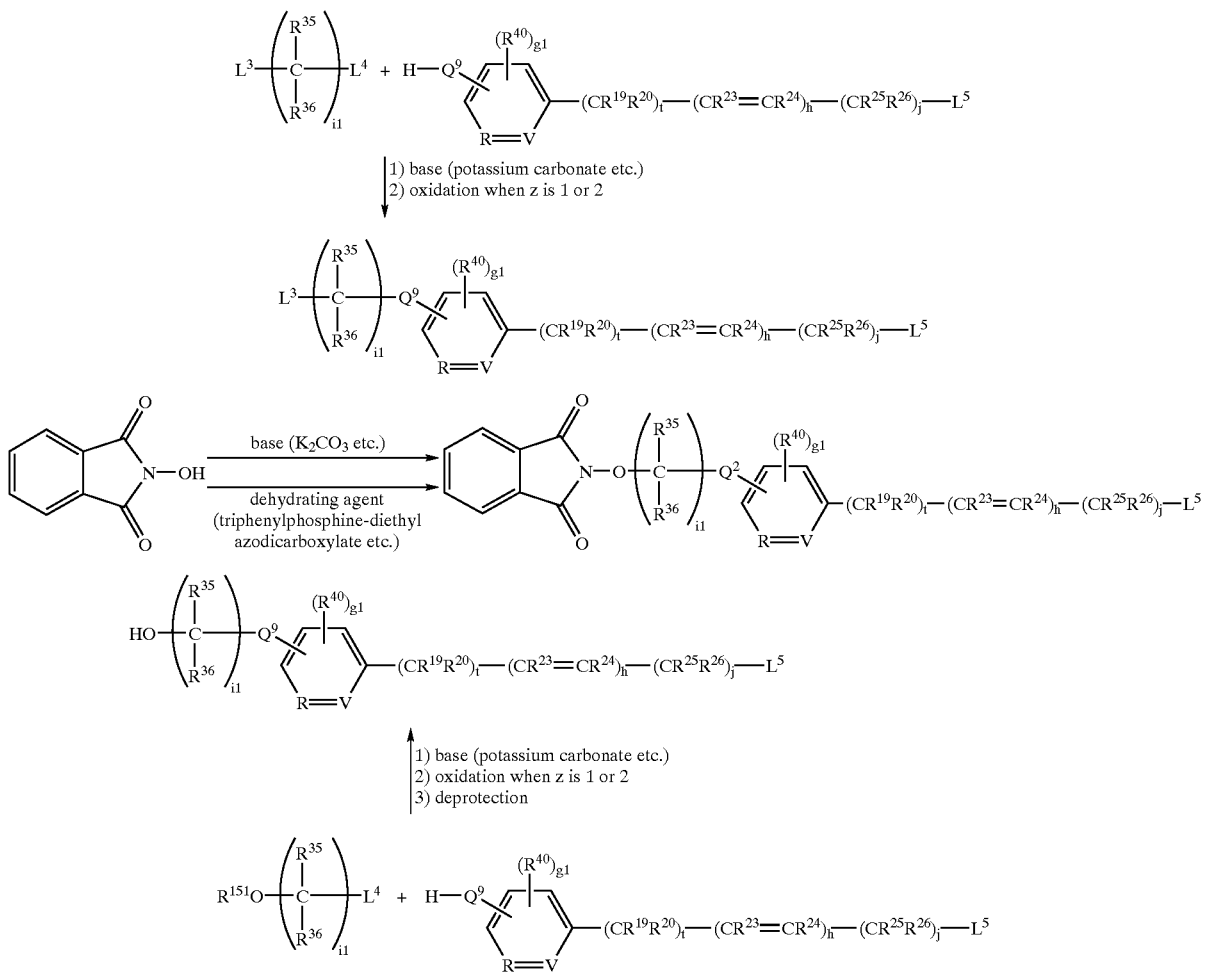
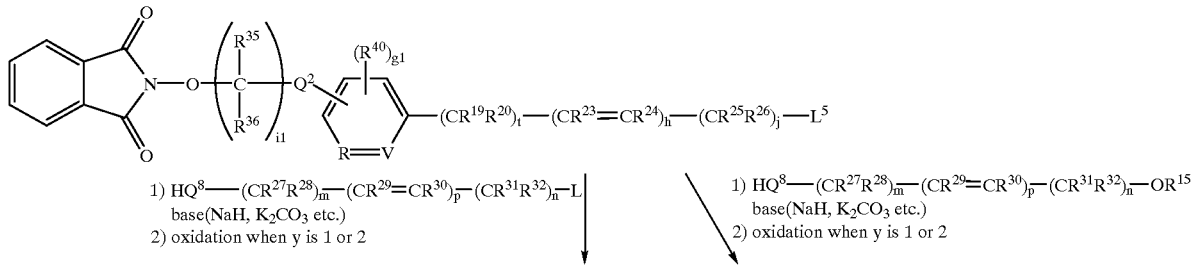

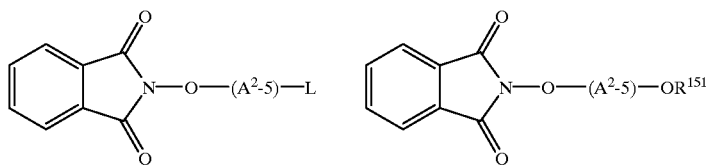
wherein $L^5$ is halogen (e.g., chlorine, bromine, iodine), mesyloxy, or tosyloxy, and the other variables are as defined above.
Scheme XXXVI
(in the case where $A^2$ is $A^2$-6 and $U^4$ is $U^4$-2)
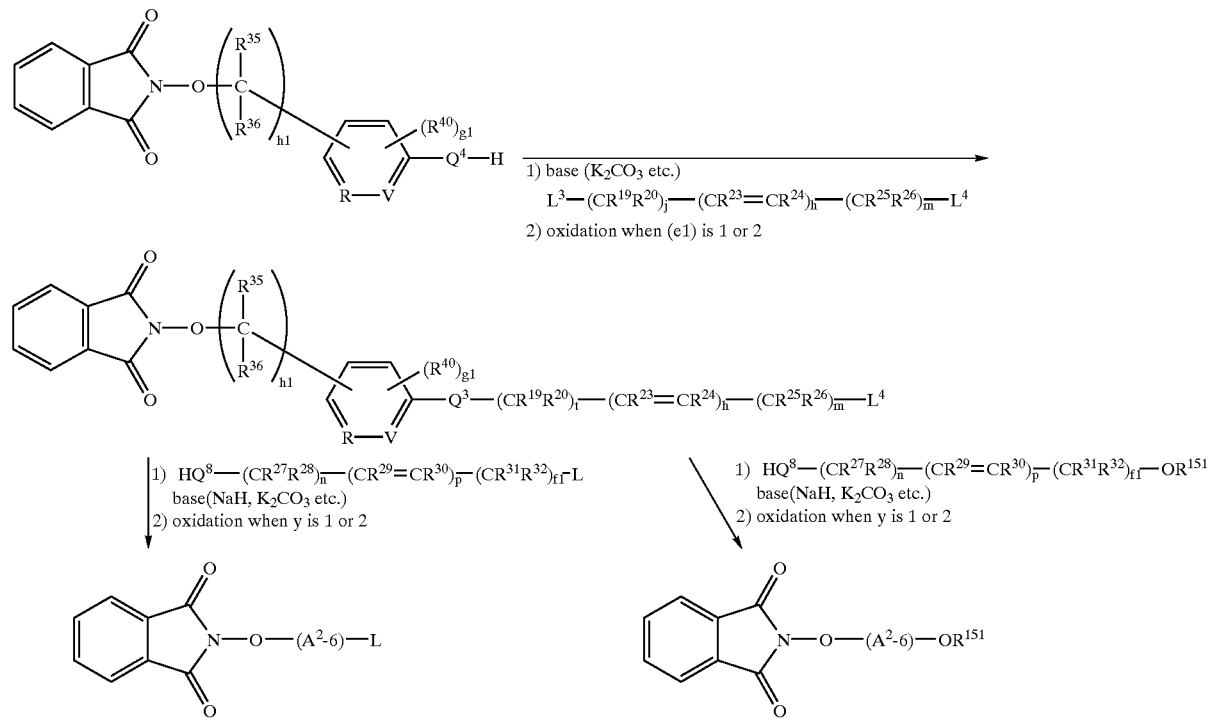
wherein all the variables are as defined above.
Scheme XXXVII
(in the case where $A^2$ is $A^2$-6 and $U^4$ is $U^4$-3)
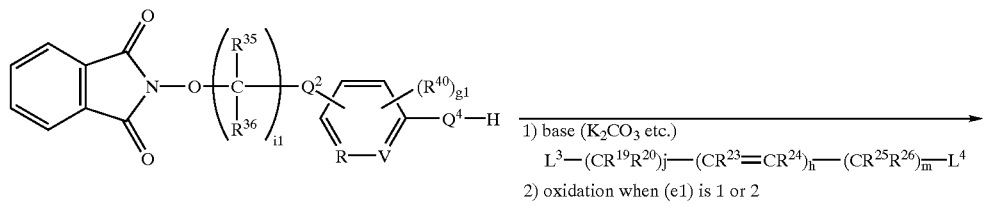

-continued
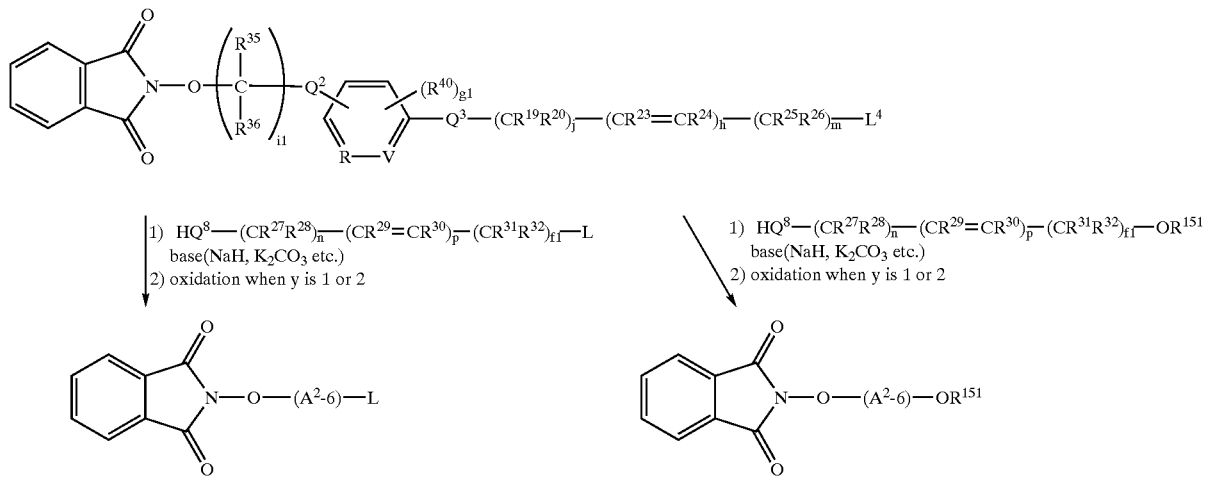
wherein all the variables are as defined above.
Scheme XXXVIII
(in the case where $A^2$ is $A^2$-7 and $U^3$ is $U^3$-2)
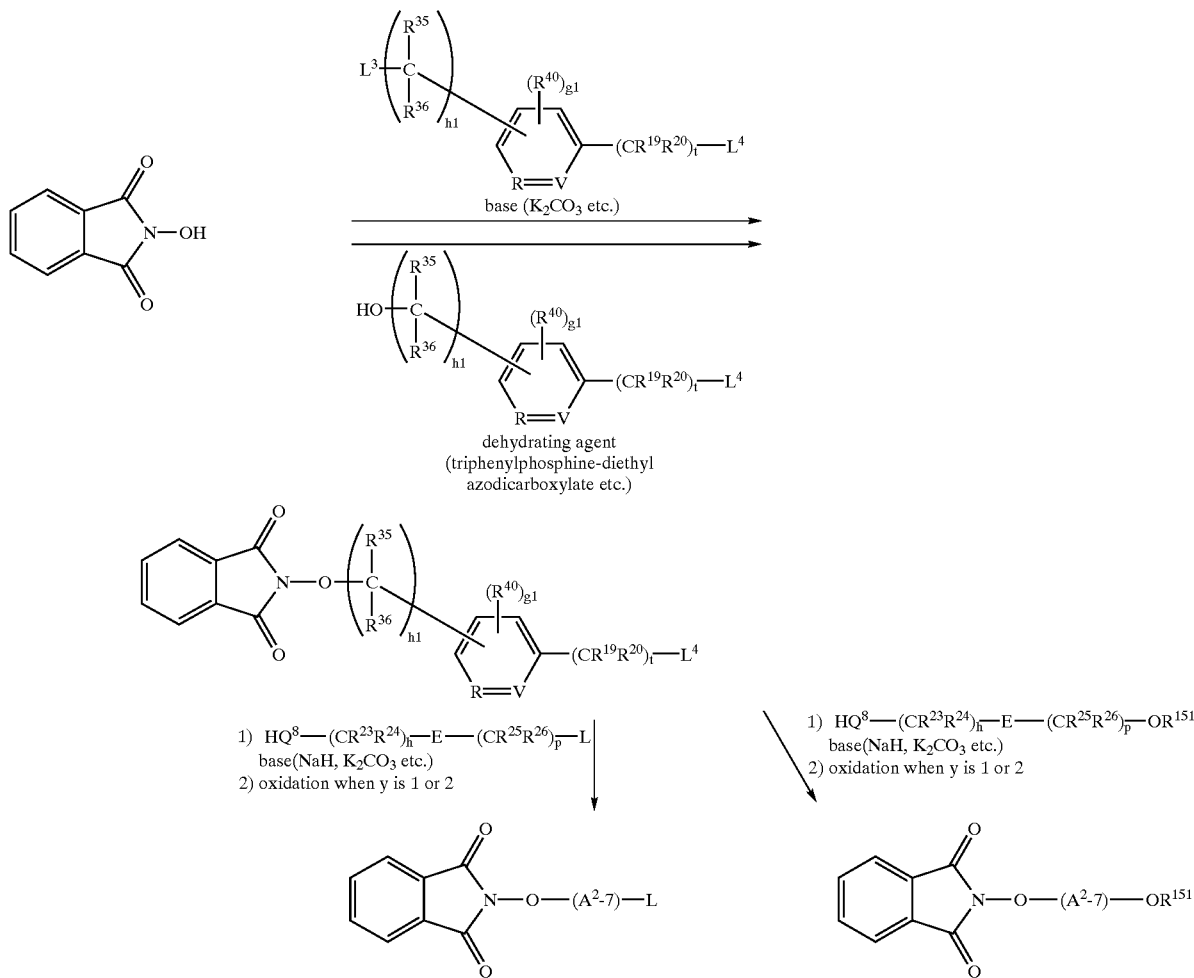

wherein all the variables are as defined above.
Scheme XXXIX-1
(in the case where $A^2$ is $A^2$-7 and $U^3$ is $U^3$-3)
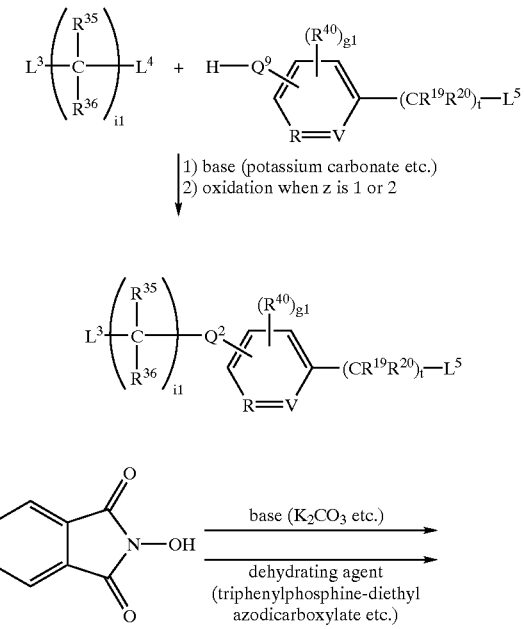
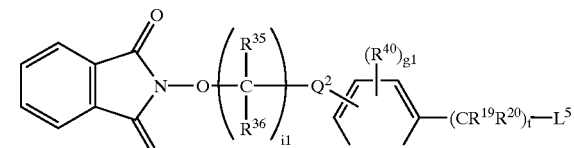
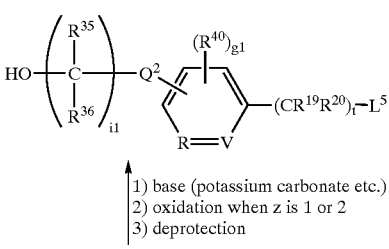
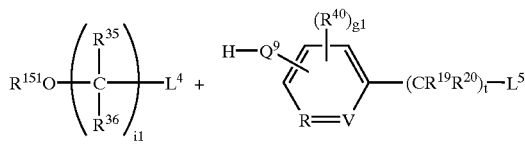
Scheme XXXIX-2
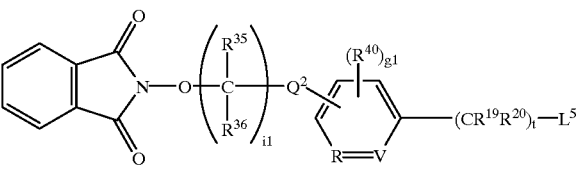
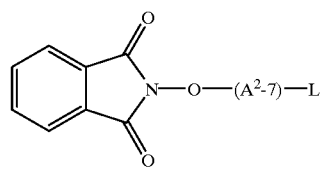
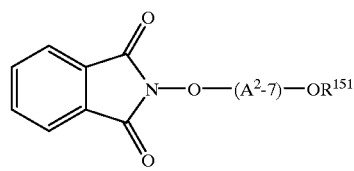
wherein all the variables are as defined above.

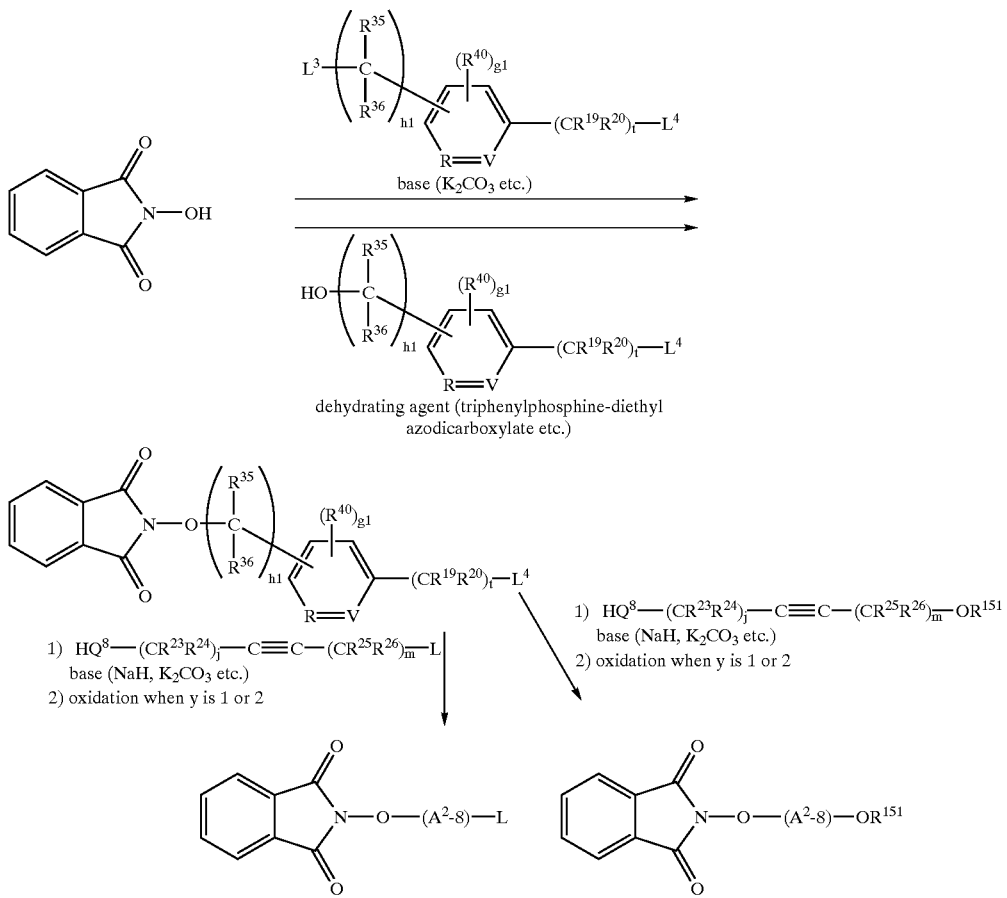
wherein all the variables are as defined above.
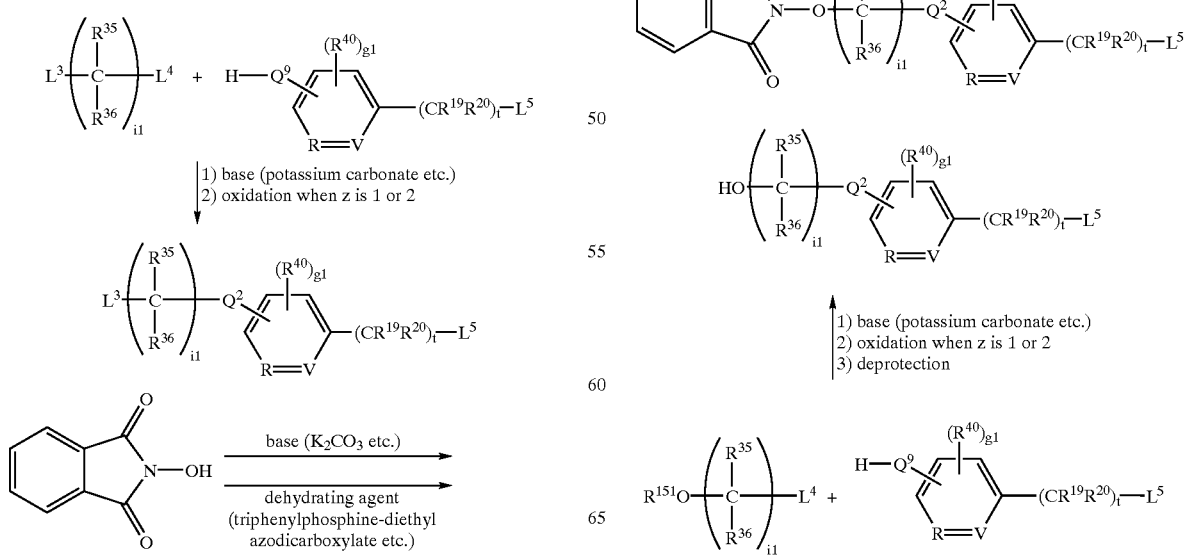

Scheme XXXXI-2
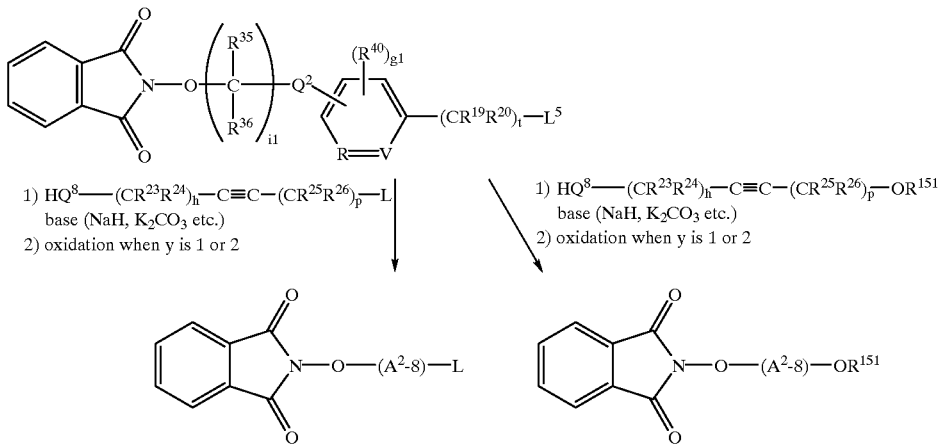
wherein all the variables are as defined above.
Scheme XXXXII
(in the case where $A^2$ is $A^2$-9)
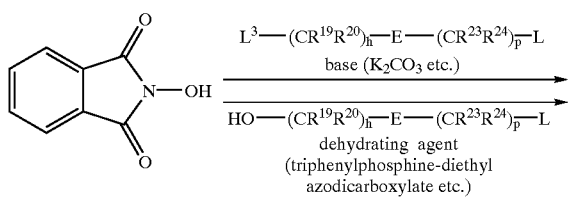
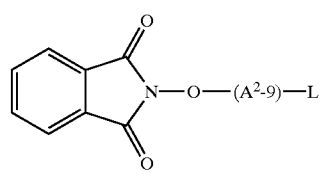
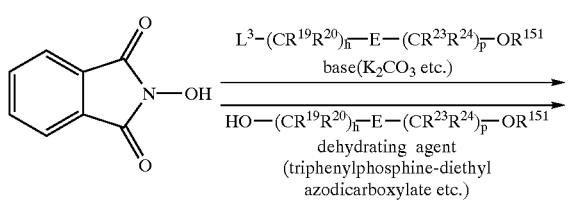
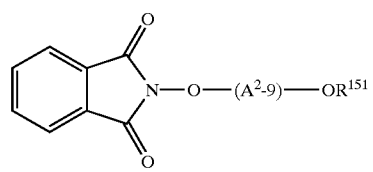
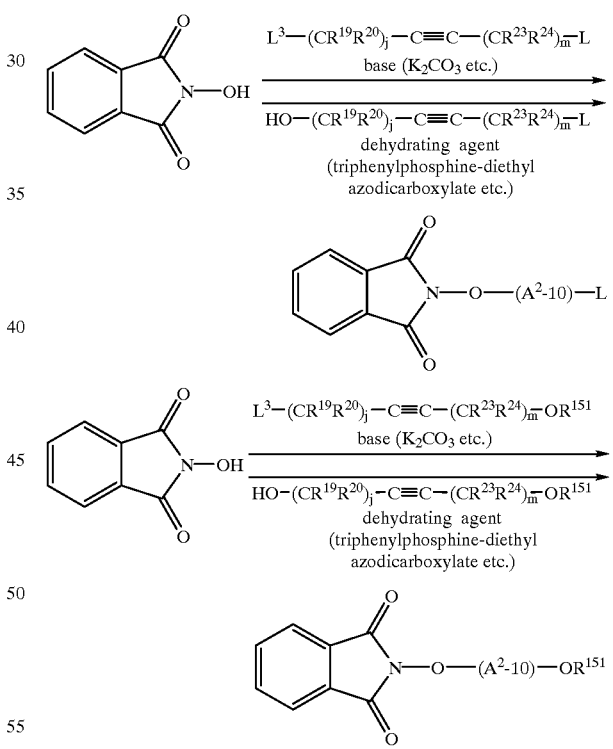
wherein all the variables are as defined above.
The compounds of formula (27) as the intermediates for the production of the present compounds can be produced, for example, according to the following scheme XXXXIV.

Scheme XXXXIV
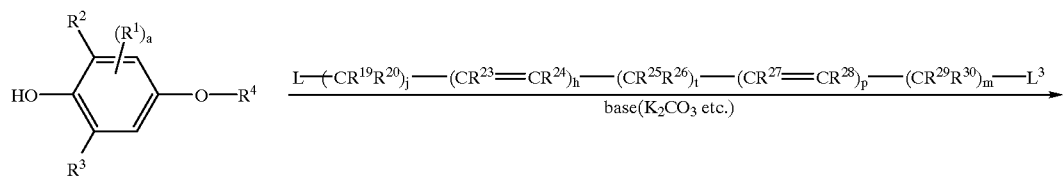
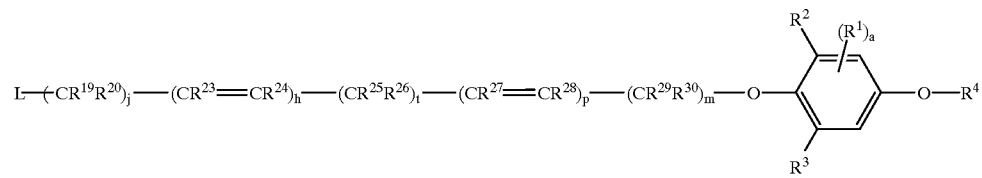
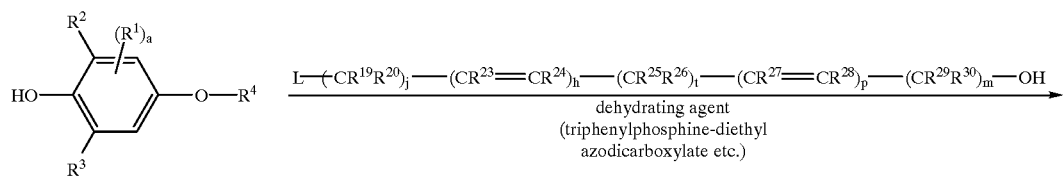
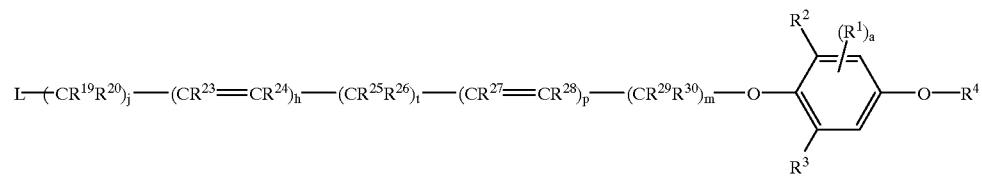
wherein all the variables are as defined above.
The compounds of formula (28) as the intermediates for the production of the present compounds can be produced, for example, according to the following schemes XXXXV to XXXXVII.
Scheme XXXXV
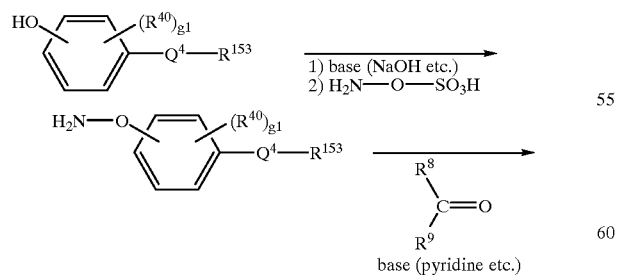
-continued
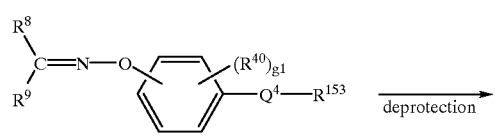
wherein all the variables are as defined above.

Scheme XXXXVI
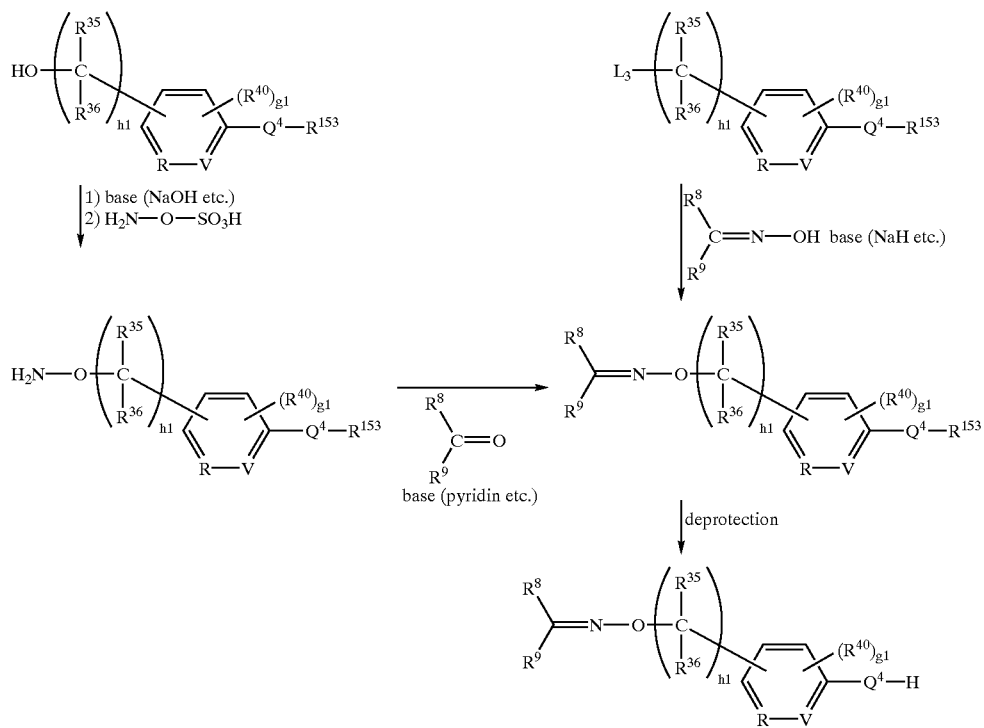
wherein all the variable are as defined above.
Scheme XXXXVII
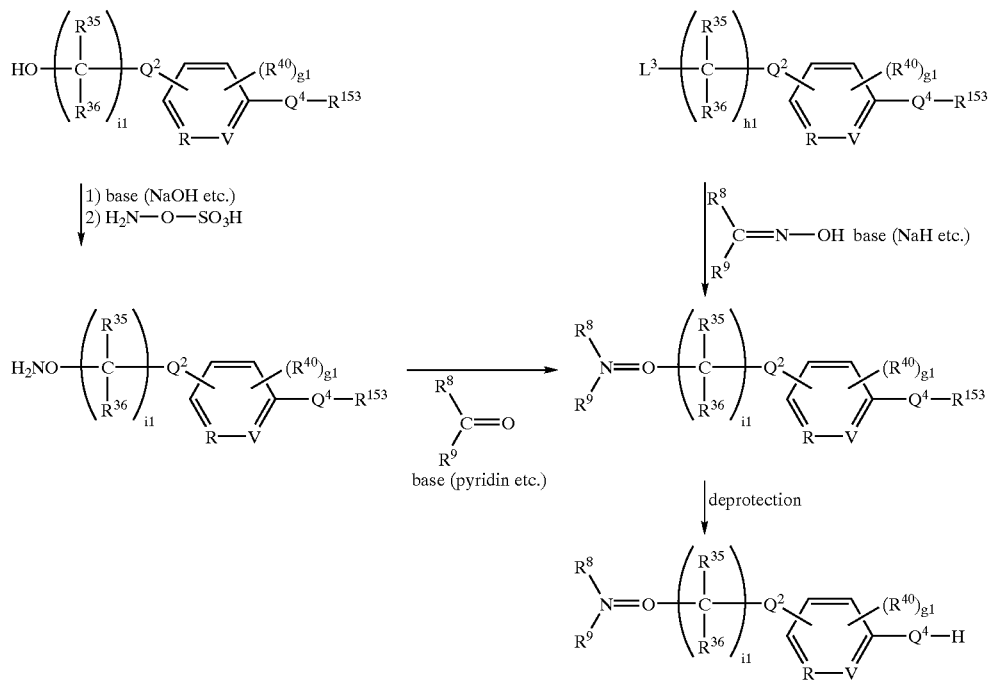

wherein all the variable are as defined above.

The compounds of formula (29) as the intermediates for the production of the present compounds can be produced, for example, according to the following scheme XXXXVIII.

Scheme XXXXVIII

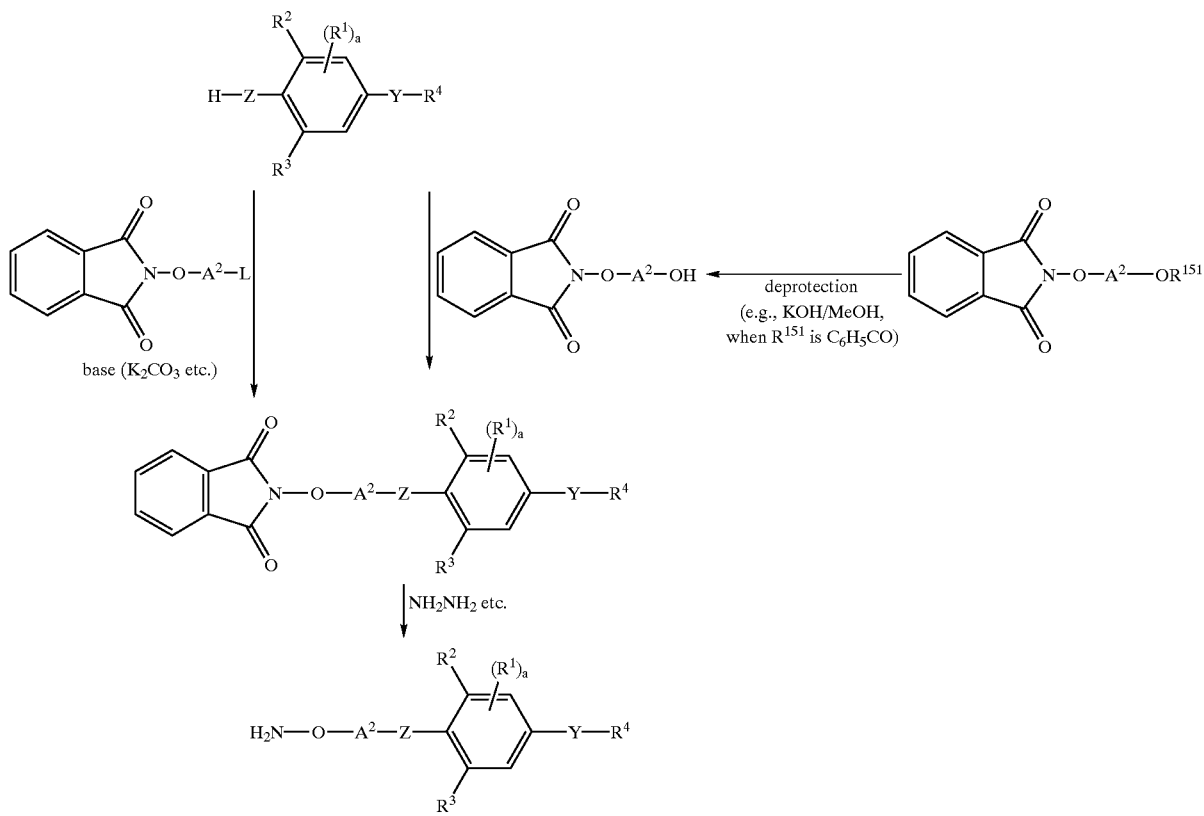

wherein all the variables are as defined above.

The compounds of formula (32) as the intermediates for the production of the present compounds can be produced, for example, according to the following scheme XXXXIX.

Scheme XXXXIX

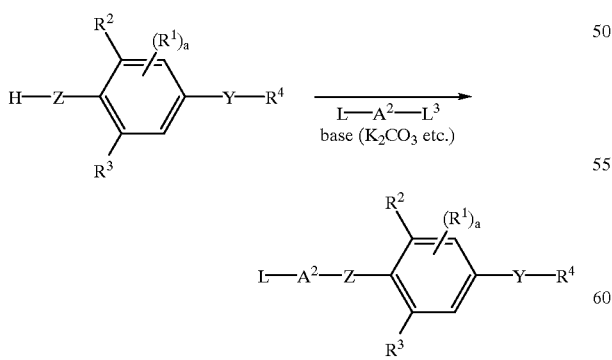

wherein all the variables are as defined above.

The harmful insects and harmful ticks and mites, against which the present compounds exhibit controlling activity, may include, for example, the following:

The present compounds are satisfactorily effective for the control of various noxious insects, mites and ticks, examples of which are as follows:

Hemiptera:
Delphacidae such as *Laodelphax striatellus, Nilaparvata lugens,* and *Sogatella furcifera,* Deltocephalidae such as *Nephotettix cincticeps* and *Empoasca onukii,* Aphididae such as *Aphis gossypii* and *Myzus persicae,* Pentatomidae, Aleyrodidae such as *Trialeurodes vaporariorum, Bemisia tabaci,* and *Bemisia argentifolii,* Coccidae, Tingidae, Psyllidae, etc.

Lepidoptera:
Pyralidae such as *Chilo suppressalis, Cnaphalocrocis medinalis, Ostrinia nubilalis,* and *Parapediasia teterrella,* Noctuidae such as *Spodoptera litura, Spodoptera exigua, Pseudaletia separata, Mamestra brassicae, Agrotis ipsilon,* Trichoplusia spp., Heliothis spp., Helicoverpa spp. and Earias spp., Pieridae such as *Pieris rapae crucivora,* Tortricidae such as *Adoxophyes orana fasciata, Grapholita molesta,* and *Cydia pomonella,* Carposinidae such as *Carposina niponensis,* Lyonetiidae such as *Lyonetia clerkella,* Graciflariidae such as *Phyllonorycter ringoniella,*

Phyllocnistidae such as *Phyllocnistis citrella*, Yponomeutidae such as *Plutella xylostella*, Gelechiidae such as *Pectinophora gossypiella*, Arctiidae, Tineidae, etc.

Diptera:

Calicidae, Aedes spp., Anopheles spp., Chironomidae, Muscidae, Calliphoridae, Sarcophagidae, Anthomyiidae, Cecidomyiidae, Agromyzidae, Tephritidae, Drosophilidae, Psychodidae, Simuliidae, Tabanidae, Stomoxyidae, etc.

Coleoptera:

Chrysomelidae, Scarahaeidae, Curculionidae, Attelabidae, Coccinellidae, Cerambycidae, Tenebrionidae, etc.

Thysanoptera:

Thnipidae such as Thrips spp., e.g., Thrips palmi, Frankliniella spp., e.g., *Frankliniella occidentalis*, Sciltothrips spp., e.g., *Sciltothnips dorsalis*, and Phlaeothezipidae, etc.

Hymenoptera:

Tenthredinidae, Pormicidae, Vespidae, etc.

Dictyoptera:

Blattidae, Blattellidae, etc.

Orthoptera:

Acrididae, Gryllotalpidae, etc.

Aphaniptera:

Purex irritans etc.

Anoplura:

*Pediculus humanus capitis* etc.

Isoptera:

Termitidae etc.

Acarina:

Tetranychidae such as Tetranychus spp. and Panonychus spp., Tarsonemidae, Eriophyidae, Acaridae, Ixodidae, etc.

The present compounds are also effective for the control of various noxious insects, mites and ticks with resistance to conventional insecticides or acaricides.

When the present compounds are used as the active ingredients of insecticidal/acaricidal agents, they may be used as such without addition of any other ingredients. The present compounds are, however, usually mixed with solid carriers, liquid carriers, gaseous carriers, or baits, and if necessary, with surfactants and other auxiliaries, and formulated into various forms, such as oil sprays, emulsifiable concentrates, wettable powders, flowables, granules, dusts, aerosols, fumigants (e.g., foggings), or poison baits.

Each of these formulations may usually contain at least one of the present compounds as an active ingredient in an amount of 0.01% to 95% by weight.

The solid carrier which can be used in the formulation may include, for example, fine powder or granules of clay materials such as kaolin clay, diatomaceous earth, synthetic hydrated silicon oxide, bentonite, Fubasami clay, and acid clay; various kinds of talc, ceramics, and other inorganic minerals such as sericite, quartz, sulfur, activated carbon, calcium carbonate, and hydrated silica; and chemical fertilizers such as ammonium sulfate, ammonium phosphate, ammonium nitrate, urea, and ammonium chloride.

The liquid carrier may include, for example, water; alcohols such as methanol and ethanol; ketones such as acetone and methyl ethyl ketone; hydrocarbons such as hexane, cyclohexane, kerosene, and light oil; esters such as ethyl acetate and butyl acetate; nitrites such as acetonitrile and isobutyronitrile; ethers such as diisopropyl ether and dioxane; acid amides such as N,N-dimethylformamide and N,N-dimethylacetamide; halogenated hydrocarbons such as dichloromethane, trichloroethane, and carbon tetrachloride; dimethyl sulfoxide; and vegetable oils such as soybean oil and cottonseed oil.

The gaseous carrier or propellant may include, for example, Freon gas, butane gas, LPG (liquefied petroleum gas), dimethyl ether, and carbon dioxide.

The surfactant may include, for example, alkyl sulfates, alkyl sulfonates, alkyl arylsulfonates, alkyl aryl ethers and their polyoxyethylene derivatives, polyethylene glycol ethers, polyhydric alcohol esters, and sugar alcohol derivatives.

The auxiliaries such as fixing agents or dispersing agents may include, for example, casein, gelatin, polysaccharides such as starch, gum arabic, cellulose derivatives, and alginic acid, lignin derivatives, bentonite, sugars, and synthetic water-soluble polymers such as polyvinyl alcohol, polyvinyl pyrrolidone, and polyacrylic acid.

The stabilizer may include, for example, PAP (isopropyl acid phosphate), BHT (2,6-di-tert-butyl-4-methylphenol), BHA (mixtures of 2-tert-butyl-4-methoxyphenol and 3-tert-butyl-4-methoxyphenol), vegetable oils, mineral oils, surfactants, fatty acids, and their esters.

The base material for used in poison baits may include, for example, bait materials such as grain powder, vegetable oils, sugars, and crystalline cellulose; antioxidants such as dibutylhydroxytoluene and nordihydroguaiaretic acid; preservatives such as dehydroacetic acid; substances for preventing erroneous eating, such as red pepper powder; attractant flavors such as cheese flavor or onion flavor.

The formulations thus obtained are used as such or after diluted with water. Furthermore, they may be used in admixture with or separately but simultaneously with other insecticides, nematocides, acaricides, bactericides, fungicides, herbicides, plant growth regulators, synergists, fertilizers, soil conditioners and/or animal.

The insecticide, nematocide and/or acaricide which can be used may include, for example, organophosphorus compounds such as Fenitrothion [O,O-dimethyl O-(3-methyl-4-nitrophenyl)phosphorothioate], Fenthion [O,O-dimethyl O-(3-methyl-4-(methylthio)phenyl)phophorothioate], Diazinon [O,O-diethyl-O-2-isopropyl-6-methylpyrimidin-4-ylphosphorothioate], Chlorpyriphos [O,O-diethyl-O-3,5,6-trichloro-2-pyridylphosphorothioate], Acephate [O,S-dimethylacetylphosphoramidothioate], Methidathion [S-2,3-di-hydro-5-methoxy-2-oxo-1,3,4-thiadiazol-3-ylmethyl O,O-dimethylphosphorodithioate], Disulfoton [O,O-diethyl S-2-ethylthioethylphosphorothioate], DDVP [2,2-dichlorovinyldimethylphosphate], Sulprofos [O-ethyl O-4-(methylthio)phenyl S-propyl phosphorodithioate], Cyanophos [O-4-cyanophenyl O,O-dimethylphosphorothioate], Dioxabenzofos [2-methoxy-4H-1,3,2-benzodioxaphosphinine-2-sulfide], Dimethoate [O,O-dimethyl-S-(N-methylcarbamoylmethyl)dithiophosphate], Phenthoate [ethyl 2-dimethoxyphosphinothioylthio(phenyl) acetate], Malathion [diethyl(dimethoxyphosphinothioylthio) succinate], Trichlorfon [dimethyl 2,2,2-trichloro-1-hydroxyethylphosphonate], Azinphos-methyl [S-3,4-dihydro-4-oxo-1,2,3-benzotriazin-3-yl-methyl O,O-dimethylphosphorodithioate], Monocrotophos [dimethyl (E)-1-methyl-2-(methylcarbamoyl)vinylphosphate], Ethion [O,O,O',O'-tetraethyl S,S'-methylenebis (phosphorodithioate)], and Profenofos [O-4-bromo-2-chlorophenyl O-ethyl S-propyl phosphorothioate]; carbamate compounds such as BPMC (2-sec-butylphenylmethylcarbamate), Benfuracarb [ethyl N-[2,3- dihydro-2,2-dimethylbenzofuran-7-yloxycarbonyl(methyl) aminothio]-N-isopropyl-β-alaninate], Propoxur [2-isopropoxyphenyl N-methylcarbamate], Carbosulfan [2,3-dihydro-2,2-dimethyl-7-benzo[b]furanyl N-dibutylaminothio-N-methylcarbamate], Carbaril [1-naphthyl-N-methylcarbamate], Methomyl [S-methyl-N-[(methylcarbamoyl)oxy]thioacetimidate], Ethiofencarb [2-(ethylthiomethyl)phenylmethylcarbamate], Aldicarb [2-methyl-2-(methylthio)propionaldehyde O-methylcarbamoyloxime], Oxamyl [N,N-dimethyl-2-methylcarbamoyloxyimino-2-(methylthio)acetamide], Fenothiocarb [S-4-phenoxybutyl]-N,N-dimethylthiocarbamate], Thiodicarb [3,7,9,13-tetramethyl-5,11-dioxa-2,8,14-trithia-4,7,9,12-tetraazapentadeca-3,12-diene-6,10-dione], and Alanycarb [ethyl (Z)-N-benzyl-N-{[methyl(1-methylthioethylideneaminooxycarbonyl)amino]thio}-β-alaninate]; pyrethroid compounds such as Etofenprox [2-(4-ethoxyphenyl)-2-methylpropyl-3-phenoxybenzylether], Fenvalerate [(RS)-α-cyano-3-phenoxybenzyl (RS)-2-(4-chlorophenyl)-3-methylbutyrate], Esfenvalerate [(S)-α-cyano-3-phenoxybenzyl (S)-2-(4-chlorophenyl)-3-methylbutyrate], Fenpropathrin [(RS)-α-cyano-3-phenoxybenzyl 2,2,3,3-tetramethylcyclopropanecarboxylate], Cypermethrin [(RS)-α-cyano-3-phenoxybenzyl (1RS, 3RS)-3-(2,2-dichlorovinyl)-2,2-dimethylcyclopropanecarboxylate], Permethrin [3-phenoxybenzyl (1RS,3RS)-3-(2,2-dichlorovinyl)-2,2-dimethylcyclopropanecarboxylate], Cyhalothrin [(RS)-α-cyano-3-phenoxybenzyl (Z)-(1RS)-cis-3-(2-chloro-3,3,3-trifluoroprop-1-enyl)-2,2-dimethylcyclopropanecarboxylate], Deltamethrin [(S)-α-cyano-3-phenoxybenzyl (1R,3R)-3-(2,2-dibromovinyl)-2,2-dimethylcycloprop anecarboxylate], Cycloprothrin [(RS)-α-cyano-3-phenoxybenzyl (RS)-2,2-dichloro-1-(4-ethoxyphenyl)cyclopropanecarboxylate], Fluvalinate (α-cyano-3-phenoxybenzyl N-(2-chloro-α,α,α-trifluoro-p-tolyl)-D-valinate), Bifenthrin (2-methylbiphenyl-3-yl-methyl) (Z)-(1RS)-cis-3-(2-chloro-3,3,3-trifluoroprop-1-enyl)-2,2-dimethylcyclopropanecarboxylate), Acrinathrin [(S)-α-cyano-(3-phenoxyphenyl)-methyl [1R-{1α(S*),3α (Z)}]-2,2-dimethyl-3-[3-oxo-3-(2,2,2-trifluoro-1-fluoromethyl)ethoxy-1-propenyl)cyclopropanecarboxylate], 2-methyl-2-(4-bromodifluoromethoxyphenyl)propyl (3-phenoxybenzyl) ether, Traromethrin [(S)-α-cyano-3-phenoxylbenzyl (1R,3R)-3-[(1'RS)(1',1',2',2'-tetrabromoethyl)]-2,2-dimethylcyclopropanecarboxylate], and Silafluofen [4-ethoxylphenyl [3-(4-fluoro-3-phenoxyphenyl)propyl]dimethylsilane]; thiadiazine derivatives such as Buprofezin (2-tert-butylimino-3-isopropyl-5-phenyl-1,3,5-thiadiazin-4-one; nitroimidazolidine derivatives such as Imidacloprid [1-(6-chloro-3-pyridylmethyl)-N-nitroimidazolidin-2-ylidenamine]; Nereistoxin derivatives such as Cartap [S,S'-(2-dimethylaminotrimethylene)bis(thiocarbamate)], Thiocyclam [N,N-dimethyl-1,2,3-trithian-5-ylamine], and Bensultap [S,S'-2-dimethylaminotrimethylene di(benzenethiosulfonate)]; N-cyanoamidine derivatives such as acetamiprid [N-cyano-N'-methyl-N'-(6-chloro-3-pyridylmethyl)acetamidine]; chlorinated hydrocarbon compounds such as Endosulfan [6,7,8,9,10,10-hexachloro-1,5,5a,6,9,9a-hexahydro-6,9-methano-2,4,3-benzodioxathiepinoxide], γ-BHC (1,2,3,4,5,6-hexachlorocyclohexane), and 1,1-bis(chlorophenyl)-2,2,2-trichloroethanol; benzoylphenylurea compounds such as Chlorfluazuron [1-(3,5-dichloro-4-(3-chloro-5-trifluoromethylpyridin-2-yloxy)phenyl)-3-(2,6-difluorobenzoyl)urea], Teflubenzuron [1-(3,5-dichloro-2,4-difluorophenyl)-3-(2,6-difluorobenzoyl)urea], and Fulphenoxron [1-(4-(2-chloro-4-trifluoromethylphenoxy)-2-fluorophenyl)-3-(2,6-difluorobenzoyl)urea]; formamidine derivatives such as Amitraz [N,N'-[(methylimino) dimethylidine]-di-2,4-xylidine], and Chlordimeform [N'-(4-chloro-2-methylphenyl)-N,N-dimethylmethanimidamide]; thiourea derivatives such as Diafenthiuron [N-(2,6-diisopropyl-4-phenoxyphenyl)-N'-tert-butylcarbodiimide]; Bromopropylate [isopropyl 4,4'-dibromobenzylate], Tetradifon [4-chlorophenyl 2,4,5-trichlorophenylsulfone], Quinomethionate [S,S-6-methylquinoxaline-2,3-diyldithiocarbonate], Propargate [2-(4-tert-butyl-phenoxy) cyclohexyl prop-2-yl sulfite], Fenbutatin oxide [bis[tris(2-methyl-2-phenylpropyl)tin]oxide], Hexythiazox [(4RS, 5RS)-5-(4-chlorophenyl)-N-chlorohexyl-4-methyl-2-oxo-1, 3-thiazolidine-3-carboxamide], Chlofentezine [3,6-bis(2-chlorophenyl)-1,2,4,5-tetrazine], Pyridaben [2-tert-butyl-5-(4-tert-butylbenzylthio)-4-chloropyridazin-3(2H)-one], Fenpyroximate [tert-butyl (E)-4-[(1,3-dimethyl-5-phenoxypyrazol-4-yl)methyleneaminooxymethyl]-benzoate], Tebfenpyrad [N-4-tert-butylbenzyl]-4-chloro-3-ethyl-1-methyl-5-pyrazolecarboxamide], polynactin complexes [e.g., tetranactin, dinactin, trinactin]; Milbemectin, Avermectin, Ivermectin, Azadilactin [AZAD], Pyrimidifen [5-chloro-N-[2-{4-(2-ethoxyethyl)-2,3-dimethylphenoxy}ethyl]-6-ethylpyrimidin-4-amine], Chlorfenapyr [4-bromo-2-(4-chlorophenyl)-1-ethoxymethyl-5-trifluoromethylpyrrole-3-carbonitrile], Tebfenozide [N-tert-butyl-N'-(4-ethylbenzoyl)-3,5-dimethylbenzohydrazide], and phenylpyrazole derivatives.

When the present compounds are used as the active ingredients of insecticidal/acaricidal agents for agriculture, the application amount thereof is usually in the range of 0.1 to 100 g per 10 ares. When they are used after diluted with water in the case of emulsifiable concentrates, wettable powders, flowables, or similar formulations, the application concentration thereof is usually in the range of 1 to 10,000 ppm. In the case of granules, dusts, or similar formulations, they are applied as such formulations without any dilution. When the present compounds are used as the active ingredients of insecticidal/acaricidal agents for epidemic prevention, they are usually applied after diluted with water to a typical concentration of 0.1 to 500 ppm in the case of emulsifiable concentrates, wettable powders, flowable, or similar formulations; or they are applied as such in the case of oil sprays, aerosols, fumigants, poisonous baits, or similar formulations.

The application amount and concentration may vary depending upon the conditions including types of formulations, times, places and methods of application, kinds of noxious insects, mites and ticks, and degree of damage, and they can be increased or decreased without limitation to the above range.

EXAMPLES

The present invention will be further illustrated by the following production examples, formulation examples, and test examples; however, the present invention is not limited to these examples.

The following are production examples for the present compounds.

Production Example 1

Production of the Present Compound (2) by Production Process (E)

To a mixture of 0.37 g of 4-(2,6-dichloro-4-(3,3-dichloro-2-propenyloxy)phenoxy)butyloxyacetaldehyde and 10 ml of pyridine was added 0.20 g of O-(3,3-dichloro-2-propenyl) hydroxylamine hydrochloride. After stirring at room temperature for 24 hours, the reaction mixture was poured into diluted hydrochloric acid and extracted twice with diethyl ether. The diethyl ether layers were combined, washed with water, dried over anhydrous magnesium sulfate, and concentrated to give a crude product. This crude product was subjected to silica gel chromatography, which afforded 0.39 g (yield, 74%) of 4-(2,6-dichloro-4-(3,3-dichloro-2-propenyloxy)phenoxy)butyloxyacetaldehyde O-(3,3-dichloro-2-propenyl)oxime, $n_D^{24.0}$ 1.5489.

Production Example 2

Production of the Present Compound (12) by Production Process F

First, 0.27 g of 4-(2,6-diethyl-4-(3,3-dichloro-2-propenyloxy)phenoxy)butyloxyacetaldehyde oxime, 0.10 g of potassium carbonate, 0.16 g of benzyl bromide, and 10 ml of N,N-dimethylformamide were placed in a reaction vessel. After stirring at room temperature for 24 hours, the reaction mixture was poured into water, and extracted twice with diethyl ether. The diethyl ether layers were combined, washed with water, dried over anhydrous magnesium sulfate, and concentrated to give a crude product. This crude product was subjected to silica gel chromatography, which afforded 0.21 g (yield, 56%) of 4-(2,6-diethyl-4-(3,3-dichloro-2-propenyloxy)phenoxy)butyloxyacetaldehyde O-benzyloxime, $n_D^{22.5}$ 1.5402.

Production Example 3

Production of the Present Compound (16) by Production Process E

To a mixture of 0.37 g of 5-(2,6-dichloro-4-(3,3-dichloro-2-propenyloxy)phenoxy)pentanal and 10 ml of pyridine was added 0.13 g of O-tert-butylhydroxylamine hydrochloride. After stirring at room temperature for 24 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which afforded 0.22 g (yield, 50%) of 4-(2,6-dichloro-4-(3,3-dichloro-2-propenyloxy)phenoxy)pentanal O-tert-butyloxime, $n_D^{25.2}$ 1.5275.

Production Example 4

Production of the Present Compound (30) by Production Process E

To a mixture of 0.34 g of (2,6-dichloro-4-(3,3-dichloro-2-propenyloxy)phenoxy)acetone and 10 ml of pyridine was added 0.11 g of O-ethylhydroxylamine hydrochloride. After stirring at room temperature for 24 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which afforded 0.32 g (yield, 81%) of (2,6-dichloro-4-(3,3-dichloro-2-propenyloxy)phenoxy)acetone O-ethyloxime, m.p., 65.4° C.

Production Example 5

Production of the Present Compound (14) by Production Process E

To a mixture of 0.42 g of 5-(2,6-dichloro-4-(3,3-dichloro-2-propenyloxy)phenoxy)pentyloxyacetaldehyde and 10 ml of pyridine was added 0.13 g of O-tert-butylhydroxylamine hydrochloride. After stirring at room temperature for 24 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which afforded 0.45 g (yield, 92%) of 5-(2,6-dichloro-4-(3,3-dichloro-2-propenyloxy)phenoxy)pentyloxyacetaldehyde O-tert-butyloxime, $n_D^{25.2}$ 1.5185.

Production Example 6

Production of the Present Compound (17) by Production Process E

To a mixture of 0.37 g of 5-(2,6-dichloro-4-(3,3-dichloro-2-propenyloxy)phenoxy)pentanal and 10 ml of pyridine was added 0.20 g of O-(3,3-dichloro-2-propenyl)hydroxylamine hydrochloride. After stirring at room temperature for 24 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which afforded 0.23 g (yield, 48%) of 5-(2,6-dichloro-4-(3,3-dichloro-2-propenyloxy)phenoxy)pentanal O-(3,3-dichloro-2-propenyl)oxime, $n_D^{25.2}$ 1.5559.

Production Example 7

Production of the Present Compound (74) by Production Process C

First, 0.58 g of 2,6-dichloro-4-(3,3-dichloro-2-propenyloxy)phenol (which had been produced according to the method as disclosed in JP-A 8-337549/1996), 0.30 g of potassium carbonate, 0.43 g of chloroacetaldehyde O-(3,3-dichloro-2-propenyl)oxime, and 10 ml of N,N-dimethylformamide were placed in a reaction vessel. After stirring at room temperature for 24 hours, the reaction mixture was poured into water, and extracted twice with diethyl ether. The diethyl ether layers were combined, washed with water, dried over anhydrous magnesium sulfate, and concentrated to give a crude product. This crude product was subjected to silica gel chromatography, which afforded 0.74 g (yield, 82%) of (2,6-dichloro-4-(3,3-dichloro-2-propenyloxy)phenoxy)acetaldehyde O-(3,3-dichloro-2-propenyl)oxime, $n_D^{22.3}$ 1.5680.

Production Example 8

Production of the Present Compound (147) by Production Process E

To a mixture of 0.75 g of 4-(2,6-diethyl-4-(3,3-dichloro-2-propenyloxy)phenoxy)butyloxyacetaldehyde and 10 ml of pyridine was added 0.15 g of hydroxylamine hydrochloride. After stirring at room temperature for 24 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which afforded 0.67 g (yield, 75%) of 4-(2,6-diethyl-4-(3,3-dichloro-2-propenyloxy)phenoxy)butyloxyacetaldehyde oxime, $n_D^{24.5}$ 1.5278.

Production Example 9

Production of the Present Compound (152) by Production Process E

To a mixture of 5.58 g of 5-(2,6-dichloro-4-(3,3-dichloro-2-propenyloxy)phenoxy)pentanal and 50 ml of pyridine was added 1.25 g of hydroxylamine hydrochloride. After stirring at room temperature for 24 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which afforded 2.44 g (yield, 41%) of 5-(2,6-dichloro-4-(3,3-dichloro-2-propenyloxy)phenoxy)pentanal oxime, $n_D^{23.4}$ 1.5600.

Production Example 10

Production of the Present Compound (234) by Production Process E

To a mixture of 1.67 g of 5-(2,6-dichloro-4-(3,3-dichloro-2-propenyloxy)phenoxy)pentyloxyacetone and 30 ml of pyridine was added 8.60 g of hydroxylamine hydrochloride. After stirring at room temperature for 1 hour, the reaction mixture was poured into diluted hydrochloric acid, and extracted twice with diethyl ether. The diethyl ether layers were combined, washed with water, dried over anhydrous magnesium sulfate, and concentrated, which afforded 8.81 g (yield, 99%) of 5-(2,6-dichloro-4-(3,3-dichloro-2-propenyloxy)phenoxy)pentyloxyacetone oxime, $n_D^{25.0}$ 1.5460.

Production Example 11

Production of the Present Compound (104) by Production Process E

To a mixture of 0.43 g of 5-(2,6-dichloro-4-(3,3-dichloro-2-propenyloxy)phenoxy)pentyloxyacetone and 10 ml of pyridine was added 0.15 g of O-tert-butylhydroxylamine hydrochloride. After stirring at room temperature for 24 hours, the reaction mixture was poured into diluted hydrochloric acid, and extracted twice with diethyl ether. The diethyl ether layers were combined, washed with water, dried over anhydrous magnesium sulfate, and concentrated, which afforded 0.45 g (yield, 90%) of 5-(2,6-dichloro-4-(3,3-dichloro-2-propenyloxy)phenoxy)pentyloxyacetone O-tert-butyloxime, $n_D^{25.5}$ 1.5170.

Production Example 12

Production of the Present Compound (177) by Production Process K

First, 0.45 g of 5-(2,6-dichloro-4-(3,3-dichloro-2-propenyloxy)phenoxy)pentyloxyacetone oxime, 0.12 g of triethylamine, and 10 ml of tetrahydrofuran were placed in a reaction vessel, to which 0.12 g of acetic anhydride was slowly added dropwise with stirring at room temperature. After completion of the addition, the reaction mixture was further stirred at room temperature for 30 minutes, poured into diluted hydrochloric acid, and extracted twice with diethyl ether. The diethyl ether layers were combined, washed with saturated aqueous sodium hydrogencarbonate solution and water in this order, dried over anhydrous magnesium sulfate, and concentrated to give a crude product. This crude product was subjected to silica gel chromatography, which afforded 0.21 g (yield, 43%) of 5-(2,6-dichloro-4-(3,3-dichloro-2-propenyloxy)phenoxy)pentyloxyacetone O-acetyloxime, $n_D^{25.6}$ 1.5318.

Production Example 13

Production of the Present Compound (179) by Production Process K

First, 0.45 g of 5-(2,6-dichloro-4-(3,3-dichloro-2-propenyloxy)phenoxy)pentyloxyacetone oxime, 0.12 g of triethylamine, and 10 ml of tetrahydrofuran were placed in a reaction vessel, to which 0.25 g of 4-trifluoromethylbenzoyl chloride was slowly added dropwise with stirring at room temperature. After completion of the addition, the reaction mixture was further stirred at room temperature for 30 minutes, poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which afforded 0.59 g (yield, 96%) of 5-(2,6-dichloro-4-(3,3-dichloro-2-propenyloxy)phenoxy)pentyloxyacetone O-(4-trifluoromethylbenzoyl)oxime, $n_D^{25.6}$ 1.5300.

Production Example 14

Production of the Present Compound (180) by Production Process K

First, 0.45 g of 5-(2,6-dichloro-4-(3,3-dichloro-2-propenyloxy)phenoxy)pentyloxyacetone oxime and 10 ml of tetrahydrofuran were placed in a reaction vessel, to which 0.12 g of tert-butylisocyannate was slowly added dropwise with stirring at room temperature. After completion of the addition, the reaction mixture was further stirred at room temperature for 30 minutes, poured into water, and extracted twice with diethyl ether. The diethyl ether layers were combined, washed with water, dried over anhydrous magnesium sulfate, and concentrated to give a crude product. This crude product was subjected to silica gel chromatography, which afforded 0.47 g Wield, 86%) of 5-(2,6-dichloro-4-(3,3-dichloro-2-propenyloxy)phenoxy)pentyloxyacetone O-(N-tert-butylcarbamoyl)oxime, $n_D^{25.6}$ 1.5191.

Production Example 15

Production of the Present Compound (216) by Production Process K

First, 0.45 g of 5-(2,6-dichloro-4-(3,3-dichloro-2-propenyloxy)phenoxy)pentyloxyacetone oxime, 0.12 g of triethylamine, and 10 ml of tetrahydrofuran are placed in a reaction vessel, to which a solution of 0.23 g of p-toluenesulfonyl chloride dissolved in 5 ml of tetrahydrofuran is slowly added dropwise with stirring under ice cooling. After completion of the addition, the reaction mixture is further stirred at room temperature for 30 minutes, poured into diluted hydrochloric acid, and extracted twice with diethyl ether. The diethyl ether layers are combined, washed with water, dried over anhydrous magnesium sulfate, and concentrated to give a crude product. This crude product is subjected to silica gel chromatography, which affords 5-(2,6-dichloro-4-(3,3-dichloro-2-propenyloxy)phenoxy)pentyloxyacetone O-(p-toluenesulfonyl)oxime.

Production Example 16

Production of the Present Compound (217) by Production Process K

First, 0.45 g of 5-(2,6-dichloro-4-(3,3-dichloro-2-propenyloxy)phenoxy)pentyloxyacetone oxime, 0.12 g of triethylamine, and 10 ml of tetrahydrofuran are placed in a reaction vessel, to which 0.16 g of N,N-diethylcarbamoyl chloride is slowly added dropwise with stirring under ice cooling. After completion of the addition, the reaction mixture is further stirred at room temperature for 30 minutes, poured into diluted hydrochloric acid, and extracted twice with diethyl ether. The diethyl ether layers are combined, washed with water, dried over anhydrous magnesium sulfate, and concentrated to give a crude product. This crude product is subjected to silica gel chromatography, which affords 5-(2,6-dichloro-4-(3,3-dichloro-2-propenyloxy)phenoxy)pentyloxyacetone O-(N,N-diethylcarbamoyl)oxime.

Production Example 17

Production of the Present Compound (218) by Production Process L

First, 0.45 g of 5-(2,6-dichloro-4-(3,3-dichloro-2-propenyloxy)phenoxy)pentyloxyacetone oxime and 10 ml of tetrahydrofuran are placed in a reaction vessel, to which 0.14 g of tert-butylisocyannate is slowly added dropwise with stirring at room temperature. After completion of the addition, the reaction mixture is further stirred at a temperature ranging from room temperature to 65° C., poured into water, and extracted twice with diethyl ether. The diethyl ether layers are combined, washed with water, dried over anhydrous magnesium sulfate, and concentrated to give a crude product. This crude product is subjected to silica gel chromatography, which affords 5-(2,6-dichloro-4-(3,3-dichloro-2-propenyloxy)phenoxy)pentyloxyacetone O-(N-tert-butylthiocarbamoyl)oxime.

Production Example 18

Production of the Present Compound (213) by Production Process F

First, 0.45 g of 5-(2,6-dichloro-4-(3,3-dichloro-2-propenyloxy)phenoxy)pentyloxyacetone oxime and 10 ml of tert-butyl methyl ether are placed in a reaction vessel, to which 48 mg of 60% sodium hydride (in oil) is slowly added with stirring at room temperature in a stream of nitrogen gas. The mixture is stirred at room temperature until the evolution of hydrogen gas ceases, to which 0.11 g of chloroacetonitrile is added at room temperature, and the mixture is further stirred with heating under reflux. After completion of the reaction, the reaction mixture is poured into diluted hydrochloric acid, and extracted twice with diethyl ether. The diethyl ether layers are combined, washed with water, dried over anhydrous magnesium sulfate, and concentrated to give a crude product. This crude product is subjected to silica gel chromatography, which affords 5-(2,6-dichloro-4-(3,3-dichloro-2-propenyloxy)phenoxy)pentyloxyacetone O-cyanomethyloxime.

Production Example 19

Production of the Present Compound (214) y Production Process F

First, 0.45 g of 5-(2,6-dichloro-4-(3,3-dichloro-2-propenyloxy)phenoxy)pentyloxyacetone oxime and 10 ml of tert-butyl methyl ether are placed in a reaction vessel, to which 48 mg of 60% sodium hydride (in oil) is slowly added with stirring at room temperature in a stream of nitrogen gas. The mixture is stirred at room temperature until the evolution of hydrogen gas ceases, to which 0.29 g of tert-butyl bromoacetate is added at room temperature, and the mixture is further stirred with heating under reflux. After completion of the reaction, the reaction mixture is poured into diluted hydrochloric acid, and extracted twice with diethyl ether. The diethyl ether layers are combined, washed with water, dried over anhydrous magnesium sulfate, and concentrated to give a crude product. This crude product is subjected to silica gel chromatography, which affords 5-(2,6-dichloro-4-(3,3-dichloro-2-propenyloxy)phenoxy)pentyloxyacetone O-(tert-butoxycarbonylmethyl)oxime.

Production Example 20

Production of the Present Compound (211) by Production Process A

First, 0.39 g of 5-(2,6-dichloro-4-hydroxyphnoxy)pentyloxyacetone O-tert-butyloxime, 0.12 g of 1,1,3-tribromo-1-propene, 0.17 g of potassium carbonate, and 10 ml of N,N-dimethylformamide are placed in a reaction vessel. After stirring at room temperature for 24 hours, the reaction mixture is poured into diluted hydrochloric acid, and extracted twice with diethyl ether. The diethyl ether layers are combined, washed with water, dried over anhydrous magnesium sulfate, and concentrated to give a crude product. This crude product is subjected to silica gel chromatography, which affords 5-(2,6-dichloro-4-(3,3-dibromo-2-propenyloxy)phenoxy)pentyloxyacetone O-tert-butyloxime.

Production Example 21

Production of the Present Compound (207) by Production Process C

First, 0.46 g of 2,6-dichloro-4-(3,3-dichloro-2-propenyloxy)phenol, 0.25 g of potassium carbonate, 0.58 g of 1-(5-(methanesulfonyloxy)pentyloxy)-2-butanone O-tert-butyloxime, and 15 ml of N,N-dimethylformamide are placed in a reaction vessel. After stirring at 55° C. to 60° C. for 24 hours, the reaction mixture is poured into diluted hydrochloric acid, and extracted twice with ethyl acetate. The ethyl acetate layers are combined, washed with water, dried over anhydrous magnesium sulfate, and concentrated to give a crude product. This crude product is subjected to silica gel chromatography, which affords 0.69 g (yield, 84%) of 1-(5-(2,6-dichloro-4-(3,3-dichloro-2-propenyloxy) phenoxy)pentyloxy)-2-butanone O-tert-butyloxime, $n_D^{23.4}$ 1.5140.

Production Example 22

Production of the Present Compound (210) by Production Process D

To a mixture of 0.45 g of 2-(5-hydroxypentyloxy) cyclohexane O-tert-butyloxime, 0.43 g of 2,6-dichloro-4-(3,3-dichloro-2-propenyloxy)phenol, 0.39 g of triphenylphosphine, and 15 ml of tetrahydrofuran is slowly added dropwise 0.30 g of diisopropyl azodicarboxylate with stirring under ice cooling in a stream of nitrogen gas. After stirring at room temperature for 24 hours, the reaction mixture is concentrated to give a residue. This residue is subjected to silica gel chromatography, which affords 2-(5-(2,6-dichloro-4-(3,3-dichloro-2-propenyloxy)phenoxy) pentyloxy)cyclohexanone O-tert-butyloxime.

Production Example 23

Production of the Present Compound (103) by Production Process C

First, 0.55 g of 2,6-dichloro-4-(3,3-dichloro-2-propenyloxy)phenol, 0.30 g of potassium carbonate, 0.59 g of 4-(methanesulfonyloxy)butyloxyacetone O-tert-butyloxime, and 10 ml of N,N-dimethylformamide are placed in a reaction vessel. After stirring at 60° C. for 6 hours, the reaction mixture is poured into diluted hydrochloric acid, and extracted twice with ethyl acetate. The ethyl acetate layers are combined, washed with water, dried over anhydrous magnesium sulfate, and concentrated to give a crude product. This crude product is subjected to silica gel chromatography, which affords 0.71 g (yield, 77%) of 4-(2,6-dichloro-4-(3,3-dichloro-2-propenyloxy)phenoxy) butyloxyacetone O-tert-butyloxime, $n_D^{25.0}$ 1.5170.

Production Example 24

Production of the Present Compound (203) by Production Process D

To a mixture of 0.51 g of 2-(2-hydroxyethoxy)ethoxyacetone O-tert-butyloxime, 0.58 g of 2,6-dichloro-4-(3,3-dichloro-2-propenyloxy)phenol, 0.58 g of triphenylphosphine, and 20 ml of tetrahydrofuran is slowly added dropwise 0.49 g of diisopropyl azodicarboxylate with stirring under ice cooling in a stream of nitrogen gas. After stirring at room temperature for 4 hours, the reaction mixture is concentrated to give a residue. This residue is subjected to silica gel chromatography, which affords 0.68 g (yield, 68%) of 2-(2-(2,6-dichloro-4-(3,3-dichloro-2-propenyloxy)phenoxy)ethoxy)ethoxyacetone O-tert-butyloxime, $n_D^{23.0}$ 1.5172.

Production Example 25

Production of the Present Compound (104) by Production Process M

First, 0.45 g of 5-(2,6-dichloro-4-(3,3-dichloro-2-propenyloxy)phenoxy)pentyloxyacetone oxime, 0.3 ml of concentrated sulfuric acid, and 10 ml of toluene are placed in a reaction vessel, into which isobutene gas is blown with stirring under ice cooling, and the mixture is further stirred at room temperature. After completion of the reaction, the reaction mixture is slowly poured into a saturated aqueous sodium hydrogencarbonate solution, and extracted twice with diethyl ether. The diethyl ether layers are combined, washed with water, dried over anhydrous magnesium sulfate, and concentrated to give a crude product. This crude product is subjected to silica gel chromatography, which affords 5-(2,6-dichloro-4-(3,3-dichloro-2-propenyloxy)phenoxy)pentyloxyacetone O-tert-butyloxime.

Production Example 26

Production of the Present Compound (185) by Production Process E

To a mixture of 1.29 g of O-(2,4,6-trimethylbenzenesulfonyl)hydroxylamine (which had been produced according to the method as described in Synthesis, 1-17 (1977)) and 10 ml of diethyl ether was added 1.14 g of sodium 1,1,1,3,3,3-hexafluoro-2-propyloxide with stirring under ice cooling, and the mixture was stirred for 2 hours. The suspended reaction mixture was filtered through Celite to give a filtrate which was a solution of O-(1,1,1, 3,3,3-hexafluoro-2-propyl)hydroxylamine in diethyl ether. The addition of diethyl ether to this filtrate made the diethyl ether solution have the weight of 30 g. Then, 10 g of the diethyl ether solution and 0.1 ml of concentrated hydrochloric acid were poured into a reaction vessel containing 0.37 g of 5-(2,6-dichloro-4-(3,3-dichloro-2-propenyloxy)phenoxy) pentanal. After stirring at room temperature for 2 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to preparative thin layer chromatography, which afforded 0.27 g (yield, 50%) of 5-(2,6-dichloro-4-(3,3-dichloro-2-propenyloxy) phenoxy)pentanal O-(1,1,1,3,3,3-hexafluoro-2-propyl)oxime, $n_D^{24.5}$ 1.4850.

Production Example 27

Production of the Present Compound (186) by Production Process E

A mixture of 0.34 g of (2,6-dichloro-4-(3,3-dichloro-2-propenyloxy)phenoxy)acetone, 0.24 g of O-(3-(5-trifluoromethyl-2-pyridyloxy)propyl)hydroxylamine, 0.14 g of pyridinium chloride, and 10 ml of pyridine was stirred at room temperature for 2 hours. The reaction mixture was poured into diluted hydrochloric acid, and extracted twice with diethyl ether. The diethyl ether layers were combined, washed with water, dried over anhydrous magnesium sulfate, and concentrated to give a crude product. The crude product was subjected to silica gel chromatography, which afforded 0.40 g (yield, 71%) of (2,6-dichloro-4-(3,3-dichloro-2-propenyloxy)phenoxy)acetone O-(3-(5-trifluoromethyl-2-pyridyloxy)propyl)oxime, $n_D^{23.0}$ 1.5310.

Production Example 28

Production of Compound (279) by Production Process D

To a mixture of 0.35 g of 2,6-dichloro-4-(3,3-dichloro-2-propenyloxy)phenol, 0.32 g of 4-(hydroxymethyl)benzaldehyde O-(3,3-dichloro-2-propenyl)oxime, 0.32 g of triphenylphosphine, and 10 ml of dichloromethane was slowly added dropwise 0.25 g of diisopropyl azodicarboxylate. After stirring at room temperature for 12 hours, the reaction mixture was concentrated to give a residue. This residue was subjected to silica gel chromatography, which afforded 0.43 g (yield, 67%) of 4-((2,6-dichloro-4-(3,3-dichloro-2-propenyloxy)phenoxy)methyl)benzaldehyde O-(3,3-dichloro-2-propenyl)oxime, m.p., 76.2° C.

Production Example 29

Production of Compound (293) by Production Process E

To a mixture of 0.31 g of 4'-(3-(2,6-dichloro-4-(3,3-dichloro-2-propenyloxy)phenoxy)propyloxy)acetophenone (which had been produced in Intermediate Production Example 2 as described below) and 10 ml of pyridine was added 0.07 g of O-ethylhydroxylamine hydrochloride. After stirring at room temperature for 24 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which afforded 0.33 g (yield, 99%) of 4'-(3-(2,6-dichloro-4-(3,3-dichloro-2-propenyloxy) phenoxy)propyloxy)acetophenone O-ethyloxime, $n_D^{24.5}$ 1.5948.

Production Example 30

Production of Compound (303) by Production Process E

To a mixture of 0.21 g of 3-(3-(2,6-dichloro-4-(3,3-dichloro-2-propenyloxy)phenoxy)propyloxy)benzaldehyde and 10 ml of pyridine was added 0.09 g of O-ethylhydroxylamine hydrochloride. After stirring at room temperature for 24 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which afforded 0.21 g (yield, 92%) of 3-(3-(2,6-dichloro-4-(3,3-dichloro-2-propenyloxy)phenoxy)propyloxy)benzaldehyde O-ethyloxime, m.p., 42.6° C.

Production Example 31

Production of Compound (353) by Production Process E

To a mixture of 0.55 g of 4-(2-(2,6-dichloro-4-(3,3-dichloro-2-propenyloxy)phenoxy)ethyl)benzaldehyde (which had been produced in Intermediate Production Example 3 as described below) and 5 ml of pyridine was added 0.18 g of O-propylhydroxylamine hydrochloride. After stirring at room temperature for 24 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which afforded 0.45 g (yield, 72%) of 4-(2-(2,6-dichloro-4-(3,3-dichloro-2-propenyloxy)phenoxy) ethyl)benzaldehyde O-propyloxime, m.p., $n_D^{24.5}$ 1.5773.

Production Example 32

Production of Compound (364) by Production Process E

To a mixture of 0.41 g of 5-acetyl-2-(3-(2,6-dichloro-4-(3,3-dichloro-2-propenyloxy)phenoxy)propyloxy)pyridine and 10 ml of pyridine was added 0.17 g of O-ethylhydroxylamine hydrochloride. After stirring at room temperature for 24 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which afforded 0.40 g (yield, 89%) of 5-(1-(N-ethoxyimino)ethyl)-2-(3-(2,6-dichloro-4-(3,3-dichloro-2-propenyloxy)phenoxy) propyloxy)pyridine, $n_D^{24.5}$ 1.5701.

Production Example 33

Production of Compound (369) by Production Process E

To a mixture of 0.43 g of 4-(3-(2,6-dichloro-4-(3,3-dichloro-2-propenyloxy)phenoxy)propyl)benzaldehyde and 5 ml of pyridine was added 0.15 g of O-tert-butylhydroxylamine hydrochloride. After stirring at room temperature for 24 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which afforded 0.38 g (yield, 75%) of 4-(3-(2,6-dichloro-4-(3,3-dichloro-2-propenyloxy)phenoxy)propyl)benzaldehyde O-tert-butyloxime, $n_D^{25.5}$ 1.5673.

Production Example 34

Production of Compound (481) by Production Process D

To a mixture of 0.62 g of 2,6-dichloro-4-(3,3-dichloro-2-propenyloxy)phenol, 0.54 g of 5-(hydroxymethyl)-2-furfural O-(3,3-dichloro- 2-propenyl)oxime, 0.57 g of triphenylphosphine, and 10 ml of dichloromethane was slowly added dropwise 0.44 g of diisopropyl azodicarboxylate with stirring under ice cooling. After stirring at room temperature for 12 hours, the reaction mixture was concentrated to give a residue. This residue was subjected to silica gel chromatography, which afforded 0.43 g (yield, 69%) of 5-((2,6-dichloro-4-(3,3-dichloro-2-propenyloxy)phenoxy) methyl)-2-furfural O-(3,3-dichloro-2-propenyl)oxime, m.p., 65.0° C.

Production Example 35

Production of Compound (523) by Production Process I

To a mixture of 0.15 g of benzaldehyde and 10 ml of pyridine was added 0.56 g of O-(3-(2,6-dichloro-4-(3,3-dichloro-2-propenyloxy)phenoxy)propyl)hydroxylamine hydrochloride. After stirring at room temperature for 1 hour, the reaction mixture was poured into 5% aqueous citric acid solution, and extracted twice with ethyl acetate. The ethyl acetate layers were combined, washed with water, dried over anhydrous magnesium sulfate, and concentrated to give a crude product. This crude product was subjected to silica gel chromatography, which afforded 0.50 g (yield, 79.4%) of benzaldehyde O-(3-(2,6-dichloro-4-(3,3-dichloro-2-propenyloxy)phenoxy)propyl)oxime, $n_D^{22.5}$ 1.5797.

Production Example 36

Production of Compound (529) by Production Process I

To a mixture of 0.14 g of 4-(trifluoromethyl)benzaldehyde and 10 ml of pyridine was added 0.30 g of O-(4-(2,6-dichloro-4-(3,3-dichloro-2-propenyloxy)phenoxy)butyl) hydroxylamine hydrochloride. After stirring at room temperature for 1 hour, the reaction mixture was poured into 5% aqueous citric acid solution, and extracted twice with ethyl acetate. The ethyl acetate layers were combined, washed with water, dried over anhydrous magnesium sulfate, and concentrated to give a crude product. This crude product was subjected to silica gel chromatography, which afforded 0.37 g (yield, 95.6%) of 4-(trifluoromethyl)benzaldehyde O-(4-(2,6-dichloro-4-(3,3-dichloro-2-propenyloxy)phenoxy) butyl)oxime, $n_D^{21.0}$ 1.5387.

Production Example 37

Production of Compound (531) by Production Process I

To a mixture of 0.15 g of 4'-(trifluoromethyl) acetophenone and 10 ml of pyridine was added 0.30 g of O-(4-(2,6-dichloro-4-(3,3-dichloro-2-propenyloxy) phenoxy)butyl)hydroxylamine hydrochloride. After stirring at room temperature for 1 hour, the reaction mixture was poured into 5% aqueous citric acid solution, and extracted twice with ethyl acetate. The ethyl acetate layers were combined, washed with water, dried over anhydrous magnesium sulfate, and concentrated to give a crude product. This crude product was subjected to silica gel chromatography, which afforded 0.30 g (yield, 75.5%) of 4'-(trifluoromethyl)acetophenone O-(4-(2,6-dichloro-4-(3,3-dichloro-2-propenyloxy)phenoxy)butyl)oxime, $n_D^{21.5}$ 1.5420.

Production Example 38

Production of Compound (545) by Production Process I

To a mixture of 0.07 g of trimethylacetaldehyde and 5 ml of pyridine was added 0.30 g of O-(5-(2,6-dichloro-4-(3,3-dichloro-2-propenyloxy)phenoxy)pentyl)hydroxylamine hydrochloride. After stirring at room temperature for 1 hour, the reaction mixture was poured into 5% aqueous citric acid solution, and extracted twice with ethyl acetate. The ethyl acetate layers were combined, washed with water, dried over anhydrous magnesium sulfate, and concentrated to give a crude product. This crude product was subjected to silica gel chromatography, which afforded 0.31 g (yield, 96.8%) of trimethylacetaldehyde O-(5-(2,6-dichloro-4-(3,3-dichloro-2-propenyloxy)phenoxy)pentyl)oxime, $n_D^{23.0}$ 1.5178.

Production Example 39

Production of Compound (564) by production Process I

To a mixture of 0.10 g of 4-methyl-2-pentanone and 5 ml of pyridine was added 0.40 g of O-(5-(2,6-dichloro-4-(3,3-dichloro-2-propenyloxy)phenoxy)pentyl)hydroxylamine hydrochloride. After stirring at room temperature for 1 hour, the reaction mixture was poured into 5% aqueous citric acid solution, and extracted twice with ethyl acetate. The ethyl acetate layers were combined, washed with water, dried over anhydrous magnesium sulfate, and concentrated to give a crude product. This crude product was subjected to silica gel chromatography, which afforded 0.42 g (yield, 95.4%) of 4-methyl-2-pentanone O-(5-(2,6-dichloro-4-(3,3-dichloro-2-propenyloxy)phenoxy)pentyl)oxime, $n_D^{24.5}$ 1.5230.

Some specific examples of the present compounds are shown below with their compound numbers and physical properties, if any.

(1) 4-(2,6-dichloro-4-(3,3-dichloro-2-propenyloxy)phenoxy)butyloxyacetaldehyde O-ethyloxime, $n_D^{24.0}$ 1.5310

(2) 4-(2,6-dichloro-4-(3,3-dichloro-2-propenyloxy)phenoxy)butyloxyacetaldehyde O-(3,3-dichloro-2-propenyl)oxime, $n_D^{24.0}$ 1.5489

(3) 4-(2,6-dichloro-4-(3,3-dichloro-2-propenyloxy)phenoxy)butyloxyacetaldehyde O-(3,3-dibromo-2-propenyl)oxime, $n_D^{24.5}$ 1.5661

(4) 4-(2,6-dichloro-4-(3,3-dichloro-2-propenyloxy)phenoxy)butyloxyacetaldehyde O-(2-propenyl)oxime, $n_D^{23.5}$ 1.5326

(5) 4-(2,6-dichloro-4-(3,3-dichloro-2-propenyloxy)phenoxy)butyloxyacetaldehyde O-benzyloxime, $n_D^{23.5}$ 1.5471

(6) 4-(2,6-dichloro-4-(3,3-dichloro-2-propenyloxy)phenoxy)butyloxyacetaldehyde O-tert-butyloxime, $n_D^{23.5}$ 1.5229

(7) 4-(2,6-dichloro-4-(3,3-dichloro-2-propenyloxy)phenoxy)butyloxyacetaldehyde O-methyloxime, $n_D^{23.5}$ 1.5374

(8) (Z)-4-(2,6-dichloro-4-(3,3-dichloro-2-propenyloxy)phenoxy)butyloxyacetaldehyde O-(3,3-dichloro-2-propenyl)oxime, $n_D^{24.6}$ 1.5498

(9) (E)-4-(2,6-dichloro-4-(3,3-dichloro-2-propenyloxy)phenoxy)butyloxyacetaldehyde O-(3,3-dichloro-2-propenyl)oxime, $n_D^{24.6}$ 1.5490

(10) 4-(2,6-diethyl-4-(3,3-dichloro-2-propenyloxy)phenoxy)butyloxyacetaldehyde O-(3,3-dichloro-2-propenyl)oxime, $n_D^{24.5}$ 1.5213

(11) 4-(2,6-diethyl-4-(3,3-dichloro-2-propenyloxy)phenoxy)butyloxyacetaldehyde O-tert-butyloxime, $n_D^{24.5}$ 1.4974

(12) 4-(2,6-diethyl-4-(3,3-dichloro-2-propenyloxy)phenoxy)butyloxyacetaldehyde O-benzyloxime, $n_D^{22.5}$ 1.5402

(13) 4-(2,6-diethyl-4-(3,3-dichloro-2-propenyloxy)phenoxy)butyloxyacetaldehyde O-(4-(trifluoromethyl)benzyl)oxime, $n_D^{22.5}$ 1.5166

(14) 5-(2,6-dichloro-4-(3,3-dichloro-2-propenyloxy)phenoxy)pentyloxyacetaldehyde O-tert-butyloxime, $n_D^{25.2}$ 1.5185

(15) 5-(2,6-dichloro-4-(3,3-dichloro-2-propenyloxy)phenoxy)pentyloxyacetaldehyde O-(3,3-dichloro-2-propenyl)oxime, $n_D^{25.2}$ 1.5450

(16) 5-(2,6-dichloro-4-(3,3-dichloro-2-propenyloxy)phenoxy)pentanal O-tert-butyloxime, $n_D^{25.2}$ 1.5275

(17) 5-(2,6-dichloro-4-(3,3-dichloro-2-propenyloxy)phenoxy)pentanal O-(3,3-dichloro-2-propenyl)oxime, $n_D^{25.2}$ 1.5559

(18) 5-(2,6-dichloro-4-(3,3-dichloro-2-propenyloxy)phenoxy)pentanal O-n-propyloxime, $n_D^{19.5}$ 1.5373

(19) 5-(2,6-dichloro-4-(3,3-dichloro-2-propenyloxy)phenoxy)pentanal O-(2-propenyl)oxime, $n_D^{19.5}$ 1.5468

(20) 5-(2,6-dichloro-4-(3,3-dichloro-2-propenyloxy)phenoxy)pentanal O-(3,3-dibromo-2-propenyl)oxime, $n_D^{23.7}$ 1.5742

(21) 5-(2,6-dichloro-4-(3,3-dichloro-2-propenyloxy)phenoxy)pentanal O-benzyloxime, $n_D^{23.7}$ 1.5605

(22) 5-(2,6-dichloro-4-(3,3-dichloro-2-propenyloxy)phenoxy)pentanal O-(4-methoxybenzyl)oxime, $n_D^{21.5}$ 1.5587

(23) 5-(2,6-dichloro-4-(3,3-dichloro-2-propenyloxy)phenoxy)pentanal O-(2,4-dinitrophenyl)oxime, m.p., 65.2° C.

(24) 4-(2,6-dichloro-4-(3,3-dichloro-2-propenyloxy)phenoxy)butanal O-(3,3-dichloro-2-propenyl)oxime, $n_D^{22.6}$ 1.5602

(25) 4-(2,6-dichloro-4-(3,3-dichloro-2-propenyloxy)phenoxy)butanal O-(3,3-dibromo-2-propenyl)oxime, $n_D^{22.6}$ 1.5797

(26) 4-(2,6-dichloro-4-(3,3-dichloro-2-propenyloxy)phenoxy)butanal O-tert-butyloxime, $n_D^{22.6}$ 1.5309

(27) 4-(2,6-dichloro-4-(3,3-dichloro-2-propenyloxy)phenoxy)butanal O-benzyloxime, $n_D^{22.6}$ 1.5700

(28) 4-(2,6-dichloro-4-(3,3-dichloro-2-propenyloxy)phenoxy)butanal O-ethyloxime, $n_D^{24.6}$ 1.5427

(29) 4-(2,6-dichloro-4-(3,3-dichloro-2-propenyloxy)phenoxy)butanal O-methyloxime, $n_D^{22.6}$ 1.5496

(30) (2,6-dichloro-4-(3,3-dichloro-2-propenyloxy)phenoxy)acetone O-ethyloxime, m.p., 65.4° C.

(31) (2,6-dichloro-4-(3,3-dichloro-2-propenyloxy)phenoxy)acetone O-(3,3-dichloro-2-propenyl)oxime, $n_D^{23.2}$ 1.5658

(32) 2-(2,6-dichloro-4-(3,3-dichloro-2-propenyloxy)phenoxy)ethoxyacetaldehyde O-(3,3-dichloro-2-propenyl)oxime

(33) 3-(2,6-dichloro-4-(3,3-dichloro-2-propenyloxy)phenoxy)propyloxyacetaldehyde O-(3,3-dichloro-2-propenyl)oxime, $n_D^{25.6}$ 1.5513

(34) 6-(2,6-dichloro-4-(3,3-dichloro-2-propenyloxy)phenoxy)hexyloxyacetaldehyde O-(3,3-dichloro-2-propenyl)oxime, $n_D^{26.0}$ 1.5390

(35) 2-(2,6-diethyl-4-(3,3-dichloro-2-propenyloxy)phenoxy)ethoxyacetaldehyde O-(3,3-dichloro-2-propenyl)oxime

(36) 3-(2,6-diethyl-4-(3,3-dichloro-2-propenyloxy)phenoxy)propyloxyacetaldehyde O-(3,3-dichloro-2-propenyl)oxime

(37) 5-(2,6-diethyl-4-(3,3-dichloro-2-propenyloxy)phenoxy)pentyloxyacetaldehyde O-(3,3-dichloro-2-propenyl)oxime

(38) 6-(2,6-diethyl-4-(3,3-dichloro-2-propenyloxy)phenoxy)hexyloxyacetaldehyde O-(3,3-dichloro-2-propenyl)oxime

(39) 2-(2-ethyl-6-methyl-4-(3,3-dichloro-2-propenyloxy)phenoxy)ethoxyacetaldehyde O-(3,3-dichloro-2-propenyl)oxime

(40) 3-(2-ethyl-6-methyl-4-(3,3-dichloro-2-propenyloxy)phenoxy)propyloxyacetaldehyde O-(3,3-dichloro-2-propenyl)oxime

(41) 4-(2-ethyl-6-methyl-4-(3,3-dichloro-2-propenyloxy)phenoxy)butyloxyacetaldehyde O-(3,3-dichloro-2-propenyl)oxime

(42) 5-(2-ethyl-6-methyl-4-(3,3-dichloro-2-propenyloxy)phenoxy)pentyloxyacetaldehyde O-(3,3-dichloro-2-propenyl)oxime

(43) 6-(2-ethyl-6-methyl-4-(3,3-dichloro-2-propenyloxy)phenoxy)hexyloxyacetaldehyde O-(3,3-dichloro-2-propenyl)oxime

(44) 2-(2,6-dichloro-4-(3,3-dichloro-2-propenyloxy)phenoxy)ethoxyacetone O-(3,3-dichloro-2-propenyl)oxime

(45) 3-(2,6-dichloro-4-(3,3-dichloro-2-propenyloxy)phenoxy)propyloxyacetone O-(3,3-dichloro-2-propenyl)oxime

(46) 4-(2,6-dichloro-4-(3,3-dichloro-2-propenyloxy)phenoxy)butyloxyacetone O-(3,3-dichloro-2-propenyl)oxime

(47) 5-(2,6-dichloro-4-(3,3-dichloro-2-propenyloxy)phenoxy)pentyloxyacetone O-(3,3-dichloro-2-propenyl)oxime, $n_D^{25.5}$ 1.5408

(48) 6-(2,6-dichloro-4-(3,3-dichloro-2-propenyloxy)phenoxy)hexyloxyacetone O-(3,3-dichloro-2-propenyl)oxime

(49) 2-(2,6-diethyl-4-(3,3-dichloro-2-propenyloxy)phenoxy)ethoxyacetone O-(3,3-dichloro-2-propenyl)oxime

(50) 3-(2,6-diethyl-4-(3,3-dichloro-2-propenyloxy)phenoxy)propyloxyacetone O-(3,3-dichloro-2-propenyl)oxime

(51) 4-(2,6-diethyl-4-(3,3-dichloro-2-propenyloxy)phenoxy)butyloxyacetone O-(3,3-dichloro-2-propenyl)oxime

(52) 5-(2,6-diethyl-4-(3,3-dichloro-2-propenyloxy)phenoxy)pentyloxyacetone O-(3,3-dichloro-2-propenyl)oxime

(53) 6-(2,6-diethyl-4-(3,3-dichloro-2-propenyloxy)phenoxy)hexyloxyacetone O-(3,3-dichloro-2-propenyl)oxime

(54) 2-(2-ethyl-6-methyl-4-(3,3-dichloro-2-propenyloxy)phenoxy)ethoxyacetone O-(3,3-dichloro-2-propenyl)oxime

(55) 3-(2-ethyl-6-methyl-4-(3,3-dichloro-2-propenyloxy)phenoxy)propyloxyacetone O-(3,3-dichloro-2-propenyl)oxime

(56) 4-(2-ethyl-6-methyl-4-(3,3-dichloro-2-propenyloxy)phenoxy)butyloxyacetone O-(3,3-dichloro-2-propenyl)oxime

(57) 5-(2-ethyl-6-methyl-4-(3,3-dichloro-2-propenyloxy)phenoxy)pentyloxyacetone O-(3,3-dichloro-2-propenyl)oxime

(58) 6-(2-ethyl-6-methyl-4-(3,3-dichloro-2-propenyloxy)phenoxy)hexyloxyacetone O-(3,3-dichloro-2-propenyl)oxime

(59) 3-(2-(2,6-dichloro-4-(3,3-dichloro-2-propenyloxy)phenoxy)ethoxy)propionaldehyde O-(3,3-dichloro-2-propenyl)oxime

(60) 3-(3-(2,6-dichloro-4-(3,3-dichloro-2-propenyloxy)phenoxy)propyloxy)propionaldehyde O-(3,3-dichloro-2-propenyl)oxime

(61) 3-(4-(2,6-dichloro-4-(3,3-dichloro-2-propenyloxy)phenoxy)butyloxy)propionaldehyde O-(3,3-dichloro-2-propenyl)oxime

(62) 3-(5-(2,6-dichloro-4-(3,3-dichloro-2-propenyloxy)phenoxy)pentyloxy)propionaldehyde O-(3,3-dichloro-2-propenyl)oxime

(63) 3-(6-(2,6-dichloro-4-(3,3-dichloro-2-propenyloxy)phenoxy)hexyloxy)propionaldehyde O-(3,3-dichloro-2-propenyl)oxime

(64) 3-(2-(2,6-diethyl-4-(3,3-dichloro-2-propenyloxy)phenoxy)ethoxy)propionaldehyde O-(3,3-dichloro-2-propenyl)oxime

(65) 3-(3-(2,6-diethyl-4-(3,3-dichloro-2-propenyloxy)phenoxy)propyloxy)propionaldehyde O-(3,3-dichloro-2-propenyl)oxime

(66) 3-(4-(2,6-diethyl-4-(3,3-dichloro-2-propenyloxy)phenoxy)butyloxy)propionaldehyde O-(3,3-dichloro-2-propenyl)oxime

(67) 3-(5-(2,6-diethyl-4-(3,3-dichloro-2-propenyloxy)phenoxy)pentyloxy)propionaldehyde O-(3,3-dichloro-2-propenyl)oxime

(68) 3-(6-(2,6-diethyl-4-(3,3-dichloro-2-propenyloxy)phenoxy)hexyloxy)propionaldehyde O-(3,3-dichloro-2-propenyl)oxime

(69) 3-(2-(2-ethyl-6-methyl-4-(3,3-dichloro-2-propenyloxy)phenoxy)ethoxy)propionaldehyde O-(3,3-dichloro-2-propenyl)oxime

(70) 3-(3-(2-ethyl-6-methyl-4-(3,3-dichloro-2-propenyloxy)phenoxy)propyloxy)propionaldehyde O-(3,3-dichloro-2-propenyl)oxime

(71) 3-(4-(2-ethyl-6-methyl-4-(3,3-dichloro-2-propenyloxy)phenoxy)butyloxy)propionaldehyde O-(3,3-dichloro-2-propenyl)oxime

(72) 3-(5-(2-ethyl-6-methyl-4-(3,3-dichloro-2-propenyloxy)phenoxy)pentyloxy)propionaldehyde O-(3,3-dichloro-2-propenyl)oxime

(73) 3-(6-(2-ethyl-6-methyl-4-(3,3-dichloro-2-propenyloxy)phenoxy)hexyloxy)propionaldehyde O-(3,3-dichloro-2-propenyl)oxime

(74) (2,6-dichloro-4-(3,3-dichloro-2-propenyloxy)phenoxy)acetaldehyde O-(3,3-dichloro-2-propenyl)oxime, $n_D^{22.3}$ 1.5680

(75) 3-(2,6-dichloro-4-(3,3-dichloro-2-propenyloxy) phenoxy)propionaldehyde O-(3,3-dichloro-2-propenyl)oxime, $n_D^{23.3}$ 1.5646

(76) 6-(2,6-dichloro-4-(3,3-dichloro-2-propenyloxy) phenoxy)hexanal O-(3,3-dichloro-2-propenyl)oxime, $n_D^{24.5}$ 1.5509

(77) (2,6-diethyl-4-(3,3-dichloro-2-propenyloxy) phenoxy)acetaldehyde O-(3,3-dichloro-2-propenyl) oxime

(78) (2,6-diethyl-4-(3,3-dichloro-2-propenyloxy) phenoxy)acetone O-(3,3-dichloro-2-propenyl)oxime

(79) 3-(2,6-diethyl-4-(3,3-dichloro-2-propenyloxy) phenoxy)propionaldehyde O-(3,3-dichloro-2-propenyl)oxime

(80) 4-(2,6-diethyl-4-(3,3-dichloro-2-propenyloxy) phenoxy)butanal O-(3,3-dichloro-2-propenyl)oxime

(81) 5-(2,6-diethyl-4-(3,3-dichloro-2-propenyloxy) phenoxy)pentanal O-(3,3-dichloro-2-propenyl)oxime

(82) 6-(2,6-diethyl-4-(3,3-dichloro-2-propenyloxy) phenoxy)hexanal O-(3,3-dichloro-2-propenyl)oxime

(83) (2-ethyl-6-methyl-4-(3,3-dichloro-2-propenyloxy) phenoxy)acetaldehyde O-(3,3-dichloro-2-propenyl) oxime

(84) (2-ethyl-6-methyl-4-(3,3-dichloro-2-propenyloxy) phenoxy)acetone O-(3,3-dichloro-2-propenyl)oxime

(85) 3-(2-ethyl-6-methyl-4-(3,3-dichloro-2-propenyloxy) phenoxy)propionaldehyde O-(3,3-dichloro-2-propenyl)oxime

(86) 4-(2-ethyl-6-methyl-4-(3,3-dichloro-2-propenyloxy) phenoxy)butanal O-(3,3-dichloro-2-propenyl)oxime

(87) 5-(2-ethyl-6-methyl-4-(3,3-dichloro-2-propenyloxy) phenoxy)pentanal O-(3,3-dichloro-2-propenyl)oxime

(88) 6-(2-ethyl-6-methyl-4-(3,3-dichloro-2-propenyloxy) phenoxy)hexanal O-(3,3-dichloro-2-propenyl)oxime

(89) 2-(2,6-dichloro-4-(3,3-dichloro-2-propenyloxy) phenoxy)ethoxyacetaldehyde O-tert-butyloxime

(90) 3-(2,6-dichloro-4-(3,3-dichloro-2-propenyloxy) phenoxy)propyloxyacetaldehyde O-tert-butyloxime, $n_D^{25.6}$ 1.5253

(91) 6-(2,6-dichloro-4-(3,3-dichloro-2-propenyloxy) phenoxy)hexyloxyacetaldehyde O-tert-butyloxime, $n_D^{26.0}$ 1.5181

(92) 2-(2,6-diethyl-4-(3,3-dichloro-2-propenyloxy) phenoxy)ethoxyacetaldehyde O-tert-butyloxime

(93) 3-(2,6-diethyl-4-(3,3-dichloro-2-propenyloxy) phenoxy)propyloxyacetaldehyde O-tert-butyloxime

(94) 5-(2,6-diethyl-4-(3,3-dichloro-2-propenyloxy) phenoxy)pentyloxyacetaldehyde O-tert-butyloxime

(95) 6-(2,6-diethyl-4-(3,3-dichloro-2-propenyloxy) phenoxy)hexyloxyacetaldehyde O-tert-butyloxime

(96) 2-(2-ethyl-6-methyl-4-(3,3-dichloro-2-propenyloxy) phenoxy)ethoxyacetaldehyde O-tert-butyloxime

(97) 3-(2-ethyl-6-methyl-4-(3,3-dichloro-2-propenyloxy) phenoxy)propyloxyacetaldehyde O-tert-butyloxime

(98) 4-(2-ethyl-6-methyl-4-(3,3-dichloro-2-propenyloxy) phenoxy)butyloxyacetaldehyde O-tert-butyloxime

(99) 5-(2-ethyl-6-methyl-4-(3,3-dichloro-2-propenyloxy) phenoxy)pentyloxyacetaldehyde O-tert-butyloxime (100) 6-(2-ethyl-6-methyl-4-(3,3-dichloro-2-propenyloxy)phenoxy)hexyloxyacetaldehyde O-tert-butyloxime (101) 2-(2,6-dichloro-4-(3,3-dichloro-2-propenyloxy) phenoxy)ethoxyacetone O-tert-butyloxime (102) 3-(2,6-dichloro-4-(3,3-dichloro-2-propenyloxy) phenoxy)propyloxyacetone O-tert-butyloxime (103) 4-(2,6-dichloro-4-(3,3-dichloro-2-propenyloxy) phenoxy)butyloxyacetone O-tert-butyloxime, $n_D^{25.0}$ 1.5170

(104) 5-(2,6-dichloro-4-(3,3-dichloro-2-propenyloxy) phenoxy)pentyloxyacetone O-tert-butyloxime, $n_D^{25.5}$ 1.5170

(105) 6-(2,6-dichloro-4-(3,3-dichloro-2-propenyloxy) phenoxy)hexyloxyacetone O-tert-butyloxime (106) 2-(2,6-diethyl-4-(3,3-dichloro-2-propenyloxy) phenoxy)ethoxyacetone O-tert-butyloxime (107) 3-(2,6-diethyl-4-(3,3-dichloro-2-propenyloxy) phenoxy)propyloxyacetone O-tert-butyloxime (108) 4-(2,6-diethyl-4-(3,3-dichloro-2-propenyloxy) phenoxy)butyloxyacetone O-tert-butyloxime (109) 5-(2,6-diethyl-4-(3,3-dichloro-2-propenyloxy) phenoxy)pentyloxyacetone O-tert-butyloxime (110) 6-(2,6-diethyl-4-(3,3-dichloro-2-propenyloxy) phenoxy)hexyloxyacetone O-tert-butyloxime (111) 2-(2-ethyl-6-methyl-4-(3,3-dichloro-2-propenyloxy)phenoxy)ethoxyacetone O-tert-butyloxime (112) 3-(2-ethyl-6-methyl-4-(3,3-dichloro-2-propenyloxy)phenoxy)propyloxyacetone O-tert-butyloxime (113) 4-(2-ethyl-6-methyl-4-(3,3-dichloro-2-propenyloxy)phenoxy)butyloxyacetone O-tert-butyloxime (114) 5-(2-ethyl-6-methyl-4-(3,3-dichloro-2-propenyloxy)phenoxy)pentyloxyacetone O-tert-butyloxime (115) 6-(2-ethyl-6-methyl-4-(3,3-dichloro-2-propenyloxy)phenoxy)hexyloxyacetone O-tert-butyloxime (116) 3-(2-(2,6-dichloro-4-(3,3-dichloro-2-propenyloxy) phenoxy)ethoxy)propionaldehyde O-tert-butyloxime (117) 3-(3-(2,6-dichloro-4-(3,3-dichloro-2-propenyloxy) phenoxy)propyloxy)propionaldehyde O-tert-butyloxime (118) 3-(4-(2,6-dichloro-4-(3,3-dichloro-2-propenyloxy) phenoxy)butyloxy)propionaldehyde O-tert-butyloxime (119) 3-(5-(2,6-dichloro-4-(3,3-dichloro-2-propenyloxy) phenoxy)pentyloxy)propionaldehyde O-tert-butyloxime (120) 3-(6-(2,6-dichloro-4-(3,3-dichloro-2-propenyloxy) phenoxy)hexyloxy)propionaldehyde O-tert-butyloxime (121) 3-(2-(2,6-diethyl-4-(3,3-dichloro-2-propenyloxy) phenoxy)ethoxy)propionaldehyde O-tert-butyloxime (122) 3-(3-(2,6-diethyl-4-(3,3-dichloro-2-propenyloxy) phenoxy)propyloxy)propionaldehyde O-tert-butyloxime (123) 3-(4-(2,6-diethyl-4-(3,3-dichloro-2-propenyloxy) phenoxy)butyloxy)propionaldehyde O-tert-butyloxime (124) 3-(5-(2,6-diethyl-4-(3,3-dichloro-2-propenyloxy) phenoxy)pentyloxy)propionaldehyde O-tert-butyloxime (125) 3-(6-(2,6-diethyl-4-(3,3-dichloro-2-propenyloxy) phenoxy)hexyloxy)propionaldehyde O-tert-butyloxime (126) 3-(2-(2-ethyl-6-methyl-4-(3,3-dichloro-2-propenyloxy)phenoxy)ethoxy)propionaldehyde O-tert-butyloxime (127) 3-(3-(2-ethyl-6-methyl-4-(3,3-dichloro-2-propenyloxy)phenoxy)propyloxy)propionaldehyde O-tert-butyloxime (128) 3-(4-(2-ethyl-6-methyl-4-(3,3-dichloro-2-propenyloxy)phenoxy)butyloxy)propionaldehyde O-tert-butyloxime (129) 3-(5-(2-ethyl-6-methyl-4-(3,3-dichloro-2-propenyloxy)phenoxy)pentyloxy)propionaldehyde O-tert-butyloxime (130) 3-(6-(2-ethyl-6-methyl-4-(3,3-dichloro-2-propenyloxy)phenoxy)hexyloxy)propionaldehyde O-tert-butyloxime (131) (2,6-dichloro-4-(3,3-dichloro-2-propenyloxy)phenoxy)acetaldehyde O-tert-butyloxime $n_D^{22.3}$ 1.5371

(132) (2,6-dichloro-4-(3,3-dichloro-2-propenyloxy)phenoxy)acetone O-tert-butyloxime (133) 3-(2,6-dichloro-4-(3,3-dichloro-2-propenyloxy)phenoxy)propionaldehyde O-tert-butyloxime, $n_D^{23.3}$ 1.5345

(134) 6-(2,6-dichloro-4-(3,3-dichloro-2-propenyloxy)phenoxy)hexanal O-tert-butyloxime, $n_D^{24.5}$ 1.5237

(135) (2,6-diethyl-4-(3,3-dichloro-2-propenyloxy)phenoxy)acetaldehyde O-tert-butyloxime (136) (2,6-diethyl-4-(3,3-dichloro-2-propenyloxy)phenoxy)acetone O-tert-butyloxime (137) 3-(2,6-diethyl-4-(3,3-dichloro-2-propenyloxy)phenoxy)propionaldehyde O-tert-butyloxime (138) 4-(2,6-diethyl-4-(3,3-dichloro-2-propenyloxy)phenoxy)butanal O-tert-butyloxime (139) 5-(2,6-diethyl-4-(3,3-dichloro-2-propenyloxy)phenoxy)pentanal O-tert-butyloxime (140) 6-(2,6-diethyl-4-(3,3-dichloro-2-propenyloxy)phenoxy)hexanal O-tert-butyloxime (141) (2-ethyl-6-methyl-4-(3,3-dichloro-2-propenyloxy)phenoxy)acetaldehyde O-tert-butyloxime (142) (2-ethyl-6-methyl-4-(3,3-dichloro-2-propenyloxy)phenoxy)acetone O-tert-butyloxime (143) 3-(2-ethyl-6-methyl-4-(3,3-dichloro-2-propenyloxy)phenoxy)propionaldehyde O-tert-butyloxime (144) 4-(2-ethyl-6-methyl-4-(3,3-dichloro-2-propenyloxy)phenoxy)butanal O-tert-butyloxime (145) 5-(2-ethyl-6-methyl-4-(3,3-dichloro-2-propenyloxy)phenoxy)pentanal O-tert-butyloxime (146) 6-(2-ethyl-6-methyl-4-(3,3-dichloro-2-propenyloxy)phenoxy)hexanal O-tert-butyloxime (147) 4-(2,6-diethyl-4-(3,3-dichloro-2-propenyloxy)phenoxy)butyloxyacetaldehyde oxime, $n_D^{24.5}$ 1.5278

(148) 4-(2,6-dichloro-4-(3,3-dichloro-2-propenyloxy)phenoxy)butyloxyacetaldehyde oxime, m.p., 62.8° C.

(149) 5-(2,6-dichloro-4-(3,3-dichloro-2-propenyloxy)phenoxy)pentyloxyacetaldehyde oxime, $n_D^{21.2}$ 1.5465

(150) 2-(2,6-dichloro-4-(3,3-dichloro-2-propenyloxy)phenoxy)acetophenone O-(3,3-dichloro-2-propenyl)oxime, $n_D^{23.4}$ 1.5929

(151) 2-(2,6-dichloro-4-(3,3-dichloro-2-propenyloxy)phenoxy)acetophenone O-tert-butyloxime, $n_D^{23.4}$ 1.5622

(152) 5-(2,6-dichloro-4-(3,3-dichloro-2-propenyloxy)phenoxy)pentanal oxime, $n_D^{23.4}$ 1.5600

(153) 5-(2,6-dichloro-4-(3,3-dichloro-2-propenyloxy)phenoxy)pentyloxyacetaldehyde O-isopropyloxime, $n_D^{24.0}$ 1.5242

(154) 5-(2,6-dichloro-4-(3,3-dichloro-2-propenyloxy)phenoxy)pentyloxycetaldehyde O-sec-butyloxime, $n_D^{24.0}$ 1.5211

(155) 5-(2,6-dichloro-4-(3,3-dichloro-2-propenyloxy)phenoxy)pentyloxyacetaldehyde O-isobutyloxime, $n_D^{25.2}$ 1.5206

(156) 5-(2,6-dichloro-4-(3,3-dichloro-2-propenyloxy)phenoxy)pentyloxyacetaldehyde O-neopentyloxime, $n_D^{25.2}$ 1.5106

(157) 5-(2,6-dichloro-4-(3,3-dichloro-2-propenyloxy)phenoxy)pentanal O-(4-trifluoromethylbenzyl)oxime, $n_D^{24.8}$ 1.5345

(158) 5-(2,6-dichloro-4-(3,3-dichloro-2-propenyloxy)phenoxy)pentyloxyacetaldehyde O-methyloxime, $n_D^{24.7}$ 1.5343

(159) 5-(2,6-dichloro-4-(3,3-dichloro-2-propenyloxy)phenoxy)pentyloxyacetaldehyde O-ethyloxime, $n_D^{24.7}$ 1.5291

(160) 5-(2,6-dichloro-4-(3,3-dichloro-2-propenyloxy)phenoxy)pentyloxyacetaldehyde O-benzyloxime, $n_D^{24.7}$ 1.5550

(161) 5-(2,6-dichloro-4-(3,3-dichloro-2-propenyloxy)phenoxy)pentyloxyacetaldehyde O-(2,2,2-trichloroethyl)oxime, $n_D^{24.4}$ 1.5423

(162) 5-(2,6-dichloro-4-(3,3-dichloro-2-propenyloxy)phenoxy)pentyloxyacetaldehyde O-phenyloxime, $n_D^{24.4}$ 1.5613

(163) 5-(2,6-dichloro-4-(3,3-dichloro-2-propenyloxy)phenoxy)pentyloxyacetaldehyde O-cyclohexyloxime, $n_D^{24.4}$ 1.5289

(164) 5-(2,6-dichloro-4-(3,3-dichloro-2-propenyloxy)phenoxy)pentyloxyacetaldehyde O-(2,2,2-tribromoethyl)oxime, $n_D^{25.3}$ 1.5671

(165) 5-(2,6-dichloro-4-(3,3-dichloro-2-propenyloxy)phenoxy)pentyloxyacetaldehyde O-(2,2,2-trifluoroethyl)oxime, $n_D^{25.3}$ 1.5058

(166) 4-(2,6-dichloro-4-(3,3-dichloro-2-propenyloxy)phenoxy)butyloxyacetaldehyde O-isopropyloxime, $n_D^{25.3}$ 1.5266

(167) 6-(2,6-dichloro-4-(3,3-dichloro-2-propenyloxy)phenoxy)hexyloxyacetaldehyde O-isopropyloxime, $n_D^{25.3}$ 1.5212

(168) 4-(2,6-dichloro-4-(3,3-dichloro-2-propenyloxy)phenoxy)butyloxyacetaldehyde O-(2,2,2-trichloroethyl)oxime, $n_D^{25.3}$ 1.5445 ( 169) 6-(2,6-dichloro-4-(3,3-dichloro-2-propenyloxy)phenoxy)hexyloxyacetaldehyde O-(2,2,2-trichloroethyl)oxime, $n_D^{25.3}$ 1.5372

(170) 5-(2,6-dichloro-4-(3,3-dichloro-2-propenyloxy)phenoxy)pentanal O-isopropyloxime, $n_D^{25.3}$ 1.5337

(171) 5-(2,6-dichloro-4-(3,3-dichloro-2-propenyloxy)phenoxy)pentanal O-(2,2,2-trichloroethyl)oxime, $n_D^{25.3}$ 1.5520

(172) 5-(2,6-dichloro-4-(3,3-dichloro-2-propenyloxy)phenoxy)pentanal O-phenyloxime, $n_D^{25.3}$ 1.5725

(173) 5-(2,6-dichloro-4-(3,3-dichloro-2-propenyloxy)phenoxy)pentyloxyacetone O-isopropyloxime, $n_D^{25.5}$ 1.5208

(174) 5-(2,6-dichloro-4-(3,3-dichloro-2-propenyloxy)phenoxy)pentyloxyacetone O-(2,2,2-trichloroethyl)oxime, $n_D^{25.5}$ 1.5378

(175) 5-(2,6-dichloro-4-(3,3-dichloro-2-propenyloxy)phenoxy)pentyloxyacetone O-benzyloxime, $n_D^{25.5}$ 1.5510

(176) 5-(2,6-dichloro-4-(3,3-dichloro-2-propenyloxy)phenoxy)pentyloxyacetone O-ethyloxime, $n_D^{25.5}$ 1.5262

(177) 5-(2,6-dichloro-4-(3,3-dichloro-2-propenyloxy)phenoxy)pentyloxyacetone O-acetyloxime, $n_D^{25.6}$ 1.5318

(178) 5-(2,6-dichloro-4-(3,3-dichloro-2-propenyloxy)phenoxy)pentyloxyacetone O-pivaloyloxime, $n_D^{25.6}$ 1.5195

(179) 5-(2,6-dichloro-4-(3,3-dichloro-2-propenyloxy)phenoxy)pentyloxyacetone O-(4-trifluoromethylbenzoyl)oxime, $n_D^{25.6}$ 1.5300

(180) 5-(2,6-dichloro-4-(3,3-dichloro-2-propenyloxy)phenoxy)pentyloxyacetone O-(N-tert-butylcarbamoyl)oxime, $n_D^{25.6}$ 1.5191

(181) 5-(2,6-dichloro-4-(3,3-dichloro-2-propenyloxy)phenoxy)pentyloxyacetone O-(N-phenylcarbamoyl)oxime, $n_D^{25.6}$ 1.5546

(182) 4-(2,6-dichloro-4-(3,3-dichloro-2-propenyloxy)phenoxy)butyloxyacetaldehyde O-(1,1,1,3,3,3-hexafluoro-2-propyl)oxime, $n_D^{24.5}$ 1.4829

(183) 5-(2,6-dichloro-4-(3,3-dichloro-2-propenyloxy)phenoxy)pentyloxyacetaldehyde O-(1,1,1,3,3,3-hexafluoro-2-propyl)oxime, $n_D^{24.5}$ 1.4821

(184) 5-(2,6-dichloro-4-(3,3-dichloro-2-propenyloxy)phenoxy)pentyloxyacetone O-(1,1,1,3,3,3-hexafluoro-2-propyl)oxime, $n_D^{24.5}$ 1.4807

(185) 5-(2,6-dichloro-4-(3,3-dichloro-2-propenyloxy)phenoxy)pentanal O-(1,1,1,3,3,3-hexafluoro-2-propyl)oxime, $n_D^{24.5}$ 1.4850

(186) (2,6-dichloro-4-(3,3-dichloro-2-propenyloxy)phenoxy)acetone O-(3-(5-trifluoromethyl-2-pyridyloxy)propyl)oxime, $n_D^{23.0}$ 1.5310

(187) 4-(2,6-dichloro-4-(3,3-dichloro-2-propenyloxy)phenoxy)butanal O-isopropyloxime (188) 6-(2,6-dichloro-4-(3,3-dichloro-2-propenyloxy)phenoxy)hexanal O-isopropyloxime (189) 4-(2,6-dichloro-4-(3,3-dichloro-2-propenyloxy)phenoxy)butanal O-(2,2,2-trichloroethyl)oxime (190) 6-(2,6-dichloro-4-(3,3-dichloro-2-propenyloxy)phenoxy)hexanal O-(2,2,2-trichloroethyl)oxime (191) 4-(2,6-dichloro-4-(3,3-dichloro-2-propenyloxy)phenoxy)butyloxyacetone O-isopropyloxime (192) 4-(2,6-dichloro-4-(3,3-dichloro-2-propenyloxy)phenoxy)butyloxyacetone O-(2,2,2-trichloroethyl)oxime (193) 5-(2,6-dichloro-4-(3,3-dichloro-2-propenyloxy)phenoxy)pentanal O-isobutyloxime (194) 5-(2,6-dichloro-4-(3,3-dichloro-2-propenyloxy)phenoxy)pentyloxyacetone O-isobutyloxime (195) 5-(2,6-dichloro-4-(3,3-dichloro-2-propenyloxy)phenoxy)pentanal O-sec-butyloxime (196) 5-(2,6-dichloro-4-(3,3-dichloro-2-propenyloxy)phenoxy)pentyloxyacetone O-sec-butyloxime (197) 5-(2,6-dichloro-4-(3,3-dichloro-2-propenyloxy)phenoxy)pentanal O-(2,2,2-tribromoethyl)oxime (198) 5-(2,6-dichloro-4-(3,3-dichloro-2-propenyloxy)phenoxy)pentyloxyacetone O-(2,2,2-tribromoethyl)oxime (199) 5-(2,6-dichloro-4-(3,3-dichloro-2-propenyloxy)phenoxy)pentanal O-(2,2,2-trifluoroethyl)oxime (200) 5-(2,6-dichloro-4-(3,3-dichloro-2-propenyloxy)phenoxy)pentyloxyacetone O-(2,2,2-trifluoroethyl)oxime (201) 4-(2,6-dichloro-4-(3,3-dichloro-2-propenyloxy)phenoxy)-2-butenyloxyacetone O-tert-butyloxime (202) 4-(2,6-dichloro-4-(3,3-dichloro-2-propenyloxy)phenoxy)-2-butynyloxyacetone O-tert-butyloxime (203) 2-(2-(2,6-dichloro-4-(3,3-dichloro-2-propenyloxy)phenoxy)ethoxy)ethoxyacetone O-tert-butyloxime, $n_D^{23.0}$ 1.5172

(204) 2-(N-(2-(2,6-dichloro-4-(3,3-dichloro-2-propenyloxy)phenoxy)ethyl)-N-methylamino)ethoxyacetone O-tert-butyloxime (205) 4-(2,6-dichloro-4-(3,3-dichloro-2-propenyloxy)phenoxy)cyclohexyloxyacetone O-tert-butyloxime (206) 7-(2,6-dichloro-4-(3,3-dichloro-2-propenyloxy)phenoxy)heptyloxyacetone O-tert-butyloxime (207) 1-(5-(2,6-dichloro-4-(3,3-dichloro-2-propenyloxy)phenoxy)pentyloxy)-2-butanone O-tert-butyloxime, $n_D^{23.4}$ 1.5140

(208) 1-(5-(2,6-dichloro-4-(3,3-dichloro-2-propenyloxy)phenoxy)pentyloxy)-3,3-dimethyl-2-butanone O-tert-butyloxime, $n_D^{23.4}$ 1.5102

(209) 2-(5-(2,6-dichloro-4-(3,3-dichloro-2-propenyloxy)phenoxy)pentyloxy)acetophenone O-tert-butyloxime, $n_D^{23.4}$ 1.5483

(210) 2-(5-(2,6-dichloro-4-(3,3-dichloro-2-propenyloxy)phenoxy)pentyloxy)cyclohexanone O-tert-butyloxime (211) 5-(2,6-dichloro-4-(3,3-dibromo-2-propenyloxy)phenoxy)pentyloxyacetone O-tert-butyloxime (212) 5-(2,6-dichloro-4-(3,3-dichloro-2-propenyloxy)phenoxy)pentyloxyacetone O-triphenylmethyloxime (213) 5-(2,6-dichloro-4-(3,3-dichloro-2-propenyloxy)phenoxy)pentyloxyacetone O-cyanomethyloxime (214) 5-(2,6-dichloro-4-(3,3-dichloro-2-propenyloxy)phenoxy)pentyloxyacetone O-(tert-butoxycarbonylmethyl)oxime (215) 5-(2,6-dichloro-4-(3,3-dichloro-2-propenyloxy)phenoxy)pentyloxyacetone O-(2,2-diethoxyethyl)oxime (216) 5-(2,6-dichloro-4-(3,3-dichloro-2-propenyloxy)phenoxy)pentyloxyacetone O-(p-toluenesulfonyl)oxime (217) 5-(2,6-dichloro-4-(3,3-dichloro-2-propenyloxy)phenoxy)pentyloxyacetone O-(N,N-diethylcarbamoyl)oxime (218) 5-(2,6-dichloro-4-(3,3-dichloro-2-propenyloxy)phenoxy)pentyloxyacetone O-(N-tert-butylthiocarbamoyl)oxime (219) 2-(2,6-dichloro-4-(3,3-dichloro-2-propenyloxy)phenoxy)ethoxyacetaldehyde oxime (220) 3-(2,6-dichloro-4-(3,3-dichloro-2-propenyloxy)phenoxy)propyloxyacetaldehyde oxime (221) 6-(2,6-dichloro-4-(3,3-dichloro-2-propenyloxy)phenoxy)hexyloxyacetaldehyde oxime (222) 2-(2,6-diethyl-4-(3,3-dichloro-2-propenyloxy)phenoxy)ethoxyacetaldehyde oxime (223) 3-(2,6-diethyl-4-(3,3-dichloro-2-propenyloxy)phenoxy)propyloxyacetaldehyde oxime (224) 5-(2,6-diethyl-4-(3,3-dichloro-2-propenyloxy)phenoxy)pentyloxyacetaldehyde oxime (225) 6-(2,6-diethyl-4-(3,3-dichloro-2-propenyloxy)phenoxy)hexyloxyacetaldehyde oxime (226) 2-(2-ethyl-6-methyl-4-(3,3-dichloro-2-propenyloxy)phenoxy)ethoxyacetaldehyde oxime (227) 3-(2-ethyl-6-methyl-4-(3,3-dichloro-2-propenyloxy)phenoxy)propyloxyacetaldehyde oxime
(228) 4-(2-ethyl-6-methyl-4-(3,3-dichloro-2-propenyloxy)phenoxy)butyloxyacetaldehyde oxime
(229) 5-(2-ethyl-6-methyl-4-(3,3-dichloro-2-propenyloxy)phenoxy)pentyloxyacetaldehyde oxime
(230) 6-(2-ethyl-6-methyl-4-(3,3-dichloro-2-propenyloxy)phenoxy)hexyloxyacetaldehyde oxime
(231) 2-(2,6-dichloro-4-(3,3-dichloro-2-propenyloxy)phenoxy)ethoxyacetone oxime
(232) 3-(2,6-dichloro-4-(3,3-dichloro-2-propenyloxy)phenoxy)propyloxyacetone oxime
(233) 4-(2,6-dichloro-4-(3,3-dichloro-2-propenyloxy)phenoxy)butyloxyacetone oxime
(234) 5-(2,6-dichloro-4-(3,3-dichloro-2-propenyloxy)phenoxy)pentyloxyacetone oxime, $n_D^{25.0}$ 1.5460
(235) 6-(2,6-dichloro-4-(3,3-dichloro-2-propenyloxy)phenoxy)hexyloxyacetone oxime
(236) 2-(2,6-diethyl-4-(3,3-dichloro-2-propenyloxy)phenoxy)ethoxyacetone oxime
(237) 3-(2,6-diethyl-4-(3,3-dichloro-2-propenyloxy)phenoxy)propyloxyacetone oxime
(238) 4-(2,6-diethyl-4-(3,3-dichloro-2-propenyloxy)phenoxy)butyloxyacetone oxime
(239) 5-(2,6-diethyl-4-(3,3-dichloro-2-propenyloxy)phenoxy)pentyloxyacetone oxime
(240) 6-(2,6-diethyl-4-(3,3-dichloro-2-propenyloxy)phenoxy)hexyloxyacetone oxime
(241) 2-(2-ethyl-6-methyl-4-(3,3-dichloro-2-propenyloxy)phenoxy)ethoxyacetone oxime
(242) 3-(2-ethyl-6-methyl-4-(3,3-dichloro-2-propenyloxy)phenoxy)propyloxyacetone oxime
(243) 4-(2-ethyl-6-methyl-4-(3,3-dichloro-2-propenyloxy)phenoxy)butyloxyacetone oxime
(244) 5-(2-ethyl-6-methyl-4-(3,3-dichloro-2-propenyloxy)phenoxy)pentyloxyacetone oxime
(245) 6-(2-ethyl-6-methyl-4-(3,3-dichloro-2-propenyloxy)phenoxy)hexyloxyacetone oxime
(246) 3-(2-(2,6-dichloro-4-(3,3-dichloro-2-propenyloxy)phenoxy)ethoxy)propionaldehyde oxime
(247) 3-(3-(2,6-dichloro-4-(3,3-dichloro-2-propenyloxy)phenoxy)propyloxy)propionaldehyde oxime
(248) 3-(4-(2,6-dichloro-4-(3,3-dichloro-2-propenyloxy)phenoxy)butyloxy)propionaldehyde oxime
(249) 3-(5-(2,6-dichloro-4-(3,3-dichloro-2-propenyloxy)phenoxy)pentyloxy)propionaldehyde oxime
(250) 3-(6-(2,6-dichloro-4-(3,3-dichloro-2-propenyloxy)phenoxy)hexyloxy)propionaldehydeoxime
(251) 3-(2-(2,6-diethyl-4-(3,3-dichloro-2-propenyloxy)phenoxy)ethoxy)propionaldehyde oxime
(252) 3-(3-(2,6-diethyl-4-(3,3-dichloro-2-propenyloxy)phenoxy)propyloxy)propionaldehyde oxime
(253) 3-(4-(2,6-diethyl-4-(3,3-dichloro-2-propenyloxy)phenoxy)butyloxy)propionaldehyde oxime
(254) 3-(5-(2,6-diethyl-4-(3,3-dichloro-2-propenyloxy)phenoxy)pentyloxy)propionaldehyde oxime
(255) 3-(6-(2,6-diethyl-4-(3,3-dichloro-2-propenyloxy)phenoxy)hexyloxy)propionaldehyde oxime
(256) 3-(2-(2-ethyl-6-methyl-4-(3,3-dichloro-2-propenyloxy)phenoxy)ethoxy)propionaldehyde oxime
(257) 3-(3-(2-ethyl-6-methyl-4-(3,3-dichloro-2-propenyloxy)phenoxy)propyloxy)propionaldehyde oxime
(258) 3-(4-(2-ethyl-6-methyl-4-(3,3-dichloro-2-propenyloxy)phenoxy)butyloxy)propionaldehyde oxime
(259) 3-(5-(2-ethyl-6-methyl-4-(3,3-dichloro-2-propenyloxy)phenoxy)pentyloxy)propionaldehyde oxime
(260) 3-(6-(2-ethyl-6-methyl-4-(3,3-dichloro-2-propenyloxy)phenoxy)hexyloxy)propionaldehyde oxime
(261) (2,6-dichloro-4-(3,3-dichloro-2-propenyloxy)phenoxy)acetaldehyde oxime
(262) (2,6-dichloro-4-(3,3-dichloro-2-propenyloxy)phenoxy)acetone oxime
(263) 3-(2,6-dichloro-4-(3,3-dichloro-2-propenyloxy)phenoxy)propionaldehyde oxime
(264) 4-(2,6-dichloro-4-(3,3-dichloro-2-propenyloxy)phenoxy)butanal oxime
(265) 6-(2,6-dichloro-4-(3,3-dichloro-2-propenyloxy)phenoxy)hexanal oxime
(266) (2,6-diethyl-4-(3,3-dichloro-2-propenyloxy)phenoxy)acetaldehyde oxime
(267) (2,6-diethyl-4-(3,3-dichloro-2-propenyloxy)phenoxy)acetone oxime
(268) 3-(2,6-diethyl-4-(3,3-dichloro-2-propenyloxy)phenoxy)propionaldehyde oxime
(269) 4-(2,6-diethyl-4-(3,3-dichloro-2-propenyloxy)phenoxy)butanal oxime
(270) 5-(2,6-diethyl-4-(3,3-dichloro-2-propenyloxy)phenoxy)pentanal oxime
(271) 6-(2,6-diethyl-4-(3,3-dichloro-2-propenyloxy)phenoxy)hexanal oxime
(272) (2-ethyl-6-methyl-4-(3,3-dichloro-2-propenyloxy)phenoxy)acetaldehyde oxime
(273) (2-ethyl-6-methyl-4-(3,3-dichloro-2-propenyloxy)phenoxy)acetone oxime
(274) 3-(2-ethyl-6-methyl-4-(3,3-dichloro-2-propenyloxy)phenoxy)propionaldehyde oxime
(275) 4-(2-ethyl-6-methyl-4-(3,3-dichloro-2-propenyloxy)phenoxy)butanal oxime
(276) 5-(2-ethyl-6-methyl-4-(3,3-dichloro-2-propenyloxy)phenoxy)pentanal oxime
(277) 6-(2-ethyl-6-methyl-4-(3,3-dichloro-2-propenyloxy)phenoxy)hexanal oxime
(278) 2-(2,6-dichloro-4-(3,3-dichloro-2-propenyloxy)phenoxy)acetophenone oxime
(279) 4-(2,6-dichloro-4-(3,3-dichloro-2-propenyloxy)phenoxymethyl)benzaldehyde O-(3,3-dichloro-2-propenyl)oxime, m.p., 76.2° C.
(280) 4-(2,6-dichloro-4-(3,3-dibromo-2-propenyloxy)phenoxymethyl)benzaldehyde O-(3,3-dichloro-2-propenyl)oxime, m.p., 88.2° C.
(281) 4-(2-(2,6-dichloro-4-(3,3-dichloro-2-propenyloxy)phenoxy)ethoxy)benzaldehyde O-(3,3-dichloro-2-propenyl)oxime, m.p., 88.0° C.
(282) 4-(2-(2,6-dichloro-4-(3,3-dichloro-2-propenyloxy)phenoxy)ethoxy)benzaldehyde O-(3,3-dibromo-2-propenyl)oxime, m.p., 90.8° C.
(283) 4-(3-(2,6-dichloro-4-(3,3-dichloro-2-propenyloxy)phenoxy)propyloxy)benzaldehyde O-(3,3-dichloro-2-propenyl)oxime, $n_D^{24.5}$ 1.5872
(284) 4-(3-(2,6-dichloro-4-(3,3-dichloro-2-propenyloxy)phenoxy)propyloxy)benzaldehyde O-(3,3-dibromo-2-propenyl)oxime, $n_D^{24.5}$ 1.5852

(285) 4-(4-(2,6-dichloro-4-(3,3-dichloro-2-propenyloxy)phenoxy)butyloxy)benzaldehyde O-(3,3-dichloro-2-propenyl)oxime, $n_D^{24.5}$ 1.5819

(286) 4-(4-(2,6-dichloro-4-(3,3-dichloro-2-propenyloxy)phenoxy)butyloxy)benzaldehyde O-(3,3-dibromo-2-propenyl)oxime, $n_D^{24.5}$ 1.5941

(287) 4-(2-(2,6-dichloro-4-(3,3-dichloro-2-propenyloxy)phenoxy)ethoxy)benzaldehyde O-ethyloxime, $n_D^{21.5}$ 1.5760

(288) 4-(3-(2,6-dichloro-4-(3,3-dichloro-2-propenyloxy)phenoxy)propyloxy)benzaldehyde O-ethyloxime, $n_D^{21.5}$ 1.5664

(289) 4-(4-(2,6-dichloro-4-(3,3-dichloro-2-propenyloxy)phenoxy)butyloxy)benzaldehyde O-ethyloxime, $n_D^{21.5}$ 1.5613

(290) 4-(2-(2,6-dichloro-4-(3,3-dichloro-2-propenyloxy)phenoxy)ethoxy)benzaldehyde O-tert-butyloxime, $n_D^{21.5}$ 1.5628

(291) 4-(3-(2,6-dichloro-4-(3,3-dichloro-2-propenyloxy)phenoxy)propyloxy)benzaldehyde O-tert-butyloxime, $n_D^{21.5}$ 1.5588

(292) 4-(4-(2,6-dichloro-4-(3,3-dichloro-2-propenyloxy)phenoxy)butyloxy)benzaldehyde O-tert-butyloxime, $n_D^{21.5}$ 1.5528

(293) 4'-(3-(2,6-dichloro-4-(3,3-dichloro-2-propenyloxy)phenoxy)propyloxy)acetophenone O-ethyloxime, $n_D^{24.5}$ 1.5948

(294) 4'-(3-(2,6-dichloro-4-(3,3-dichloro-2-propenyloxy)phenoxy)propyloxy)acetophenone O-tert-butyloxime, $n_D^{24.5}$ 1.5949

(295) 4'-(3-(2,6-dichloro-4-(3,3-dichloro-2-propenyloxy)phenoxy)propyloxy)acetophenone O-(3,3-dichloro-2-propenyl)oxime, $n_D^{24.5}$ 1.5950

(296) 4'-(3-(2,6-dichloro-4-(3,3-dichloro-2-propenyloxy)phenoxy)propyloxy)acetophenone O-(3,3-dibromo-2-propenyl)oxime, $n_D^{24.5}$ 1.5943

(297) 4'-(4-(2,6-dichloro-4-(3,3-dichloro-2-propenyloxy)phenoxy)butyloxy)acetophenone O-ethyloxime, m.p., 41.9° C.

(298) 4'-(4-(2,6-dichloro-4-(3,3-dichloro-2-propenyloxy)phenoxy)butyloxy)acetophenone O-tert-butyloxime, m.p., 56.4° C.

(299) 4'-(4-(2,6-dichloro-4-(3,3-dichloro-2-propenyloxy)phenoxy)butyloxy)acetophenone O-(3,3-dichloro-2-propenyl)oxime, $n_D^{24.5}$ 1.5785

(300) 4'-(4-(2,6-dichloro-4-(3,3-dichloro-2-propenyloxy)phenoxy)butyloxy)acetophenone O-(3,3-dibromo-2-propenyl)oxime, $n_D^{24.5}$ 1.5909

(301) 3-(3-(2,6-dichloro-4-(3,3-dichloro-2-propenyloxy)phenoxy)proyloxy)benzaldehyde O-methyloxime, $n_D^{24.5}$ 1.5802

(302) 3-(4-(2,6-dichloro-4-(3,3-dichloro-2-propenyloxy)phenoxy)butyloxy)benzaldehyde O-methyloxime $n_D^{24.5}$ 1.5756

(303) 3-(3-(2,6-dichloro-4-(3,3-dichloro-2-propenyloxy)phenoxy)propyloxy)benzaldehyde O-ethyloxime, m.p., 42.6° C.

(304) 3-(4-(2,6-dichloro-4-(3,3-dichloro-2-propenyloxy)phenoxy)butyloxy)benzaldehyde O-ethyloxime $n_D^{24.5}$ 1.5723

(305) 4-(3-(2,6-dichloro-4-(3,3-dichloro-2-propenyloxy)phenoxy)propyloxy)benzaldehyde O-methyloxime, $n_D^{24.5}$ 1.5871

(306) 4-(4-(2,6-dichloro-4-(3,3-dichloro-2-propenyloxy)phenoxy)butyloxy)benzaldehyde O-methyloxime, m.p., 63.5° C.

(307) 4'-(3-(2,6-dichloro-4-(3,3-dichloro-2-propenyloxy)phenoxy)propyloxy)acetophenone O-methyloxime, $n_D^{22.5}$ 1.5642

(308) 4'-(3-(2,6-dichloro-4-(3,3-dichloro-2-propenyoxy)phenoxy)propyloxy)acetophenone O-propyloxime, $n_D^{22.5}$ 1.5733

(309) 4'-(4-(2,6-dichloro-4-(3,3-dichloro-2-propenyloxy)phenoxy)butyloxy)acetophenone O-methyloxime, $n_D^{22.5}$ 1.5686

(310) 4'-(4-(2,6-dichloro-4-(3,3-dichloro-2-propenyloxy)phenoxy)butylaxy)acetophenone O-propyloxime, $n_D^{22.5}$ 1.5589

(311) 4-(2,6-dichloro-4-(3,3-dichloro-2-propenyloxy)phenoxymethyl)benzaldehyde O-methyloxime, m.p., 95.9° C.

(312) 4-(2,6-dichloro-4-(3,3-dichloro-2-propenyloxy)phenoxymethyl)benzaldehyde O-(2-propenyl)oxime, m.p., 75.6° C.

(313) 4-(2,6-dichloro-4-(3,3-dichloro-2-propenyloxy)phenoxymethyl)benzaldehyde O-benzyloxime, m.p., 70.3° C.

(314) 4-(2,6-dichloro-4-(3,3-dichloro-2-propenyloxy)phenoxymethl)benzaldehyde O-tert-butyloxime, $n_D^{24.5}$ 1.5713

(315) 4-(4-(2,6-dichloro-4-(3,3-dichloro-2-propenyloxy)phenoxy)butyloxy)benzaldehyde O-iso-propyloxime, $n_D^{24.5}$ 1.5643

(316) 4-(4-(2,6-dichloro-4-(3,3-dichloro-2-propenyloxy)phenoxy)butyloxy)benzaldehyde O-isobutyloxime, $n_D^{24.5}$ 1.5571

(317) 4'-(3-(2,6-dichloro-4-(3,3-dichloro-2-propenyloxy)phenoxy)propyloxy)benzophenone O-ethyloxime, $n_D^{24.5}$ 1.5943

(318) 4'-(3-(2,6-dichloro-4-(3,3-dichloro-2-propenyloxy)phenoxy)propyloxy)propiophenone O-ethyloxime, m.p., 42.4° C.

(319) 4'-(3-(2,6-dichloro-4-(3,3-dichloro-2-propenyloxy)phenoxy)propyloxy)valerophenone O-ethyloxime, $n_D^{24.5}$ 1.5535

(320) 4-(5-(2,6-dichloro-4-(3,3-dichloro-2-propenyloxy)phenoxy)pentyloxy)benzaldehyde O-ethyloxime, $n_D^{24.5}$ 1.5730

(321) 4'-(5-(2,6-dichloro-4-(3,3-dichloro-2-propenyloxy)phenoxy)pentyloxy)acetophenone O-ethyloxime, m.p., 56.1° C.

(322) 4'-(2-(2,6-dichloro-4-(3,3-dichloro-2-propenyloxy)phenoxy)ethyloxy)acetophenone O-ethyloxime, $n_D^{24.5}$ 1.5840

(323) 3-(2,6-dichloro-4-(3,3-dichloro-2-propenyloxy)phenoxymethyl)benzaldehyde O-(3,3-dichloro-2-propenyl)oxime, $n_D^{24.0}$ 1.6006

(324) 3-(2,6-dichloro-4-(3,3-dichloro-2-propenyloxy)phenoxymethyl)benzaldehyde O-benzyloxime, $n_D^{22.5}$ 1.6095

(325) 3-(2,6-dichloro-4-(3,3-dichloro-2-propenyloxy)phenoxymethyl)benzaldehyde O-tert-butyloxime, $n_D^{23.0}$ 1.5753

(326) 4-(2,6-dichloro-4-(3,3-dichloro-2-propenyloxy)phenoxymethyl)benzaldehyde O-ethyloxime, m.p., 84.8° C.

(327) 4-(2,6-dichloro-4-(3,3-dichloro-2-propenyloxy) phenoxymethyl)benzaldehyde O-propyloxime, m.p., 45.4° C.

(328) 4-(2,6-dichloro-4-(3,3-dichloro-2-propenyloxy) phenoxymethyl)benzaldehyde O-isopropyloxime, $n_D^{24.0}$ 1.5858

(329) 4-(2,6-dichloro-4-(3,3-dichloro-2-propenyloxy) phenoxymethyl)benzaldehyde O-sec-butyloxime, m.p., 59.6° C.

(330) 3-(2,6-dichloro-4-(3,3-dichloro-2-propenyloxy) phenoxymethyl)benzaldehyde O-allyl oxime, m.p., 63.9° C.

(331) 3-(2,6-dichloro-4-(3,3-dichloro-2-propenyloxy) phenoxymethyl)benzaldehyde O-sec-butyloxime, $n_D^{24.5}$ 1.5783

(332) 4'-(3-(2,6-dichloro-4-(3,3-dichloro-2-propenyloxy) phenoxy)propyloxy)propiophenone oxime, m.p., 140.0° C.

(333) 4-(5-(2,6-dichloro-4-(3,3-dichloro-2-propenyloxy) phenoxy)pentyloxy)benzaldehyde oxime, m.p., 90.1° C.

(334) 4'-(5-(2,6-dichloro-4-(3,3-dichloro-2-propenyloxy) phenoxy)pentyloxy)acetophenone oxime, m.p., 79.5° C.

(335) 3-(3-(2,6-dichloro-4-(3,3-dichloro-2-propenyloxy) phenoxy)propyloxy)benzaldehyde oxime, $n_D^{24.0}$ 1.5640

(336) 3'-(3-(2,6-dichloro-4-(3,3-dichloro-2-propenyloxy) phenoxy)propyloxy)valerophenone oxime, m.p., 87.0° C.

(337) 4'-(2-(2,6-dichloro-4-(3,3-dichloro-2-propenyloxy) phenoxy)ethoxy)acetophenone oxime, m.p., 121.0° C.

(338) 4-(3-(2,6-dichloro-4-(3,3-dichloro-2-propenyloxy) phenoxy)propyloxy)benzaldehyde O-propyloxime, $n_D^{24.5}$ 1.5703

(339) 4-(3-(2,6-dichloro-4-(3,3-dichloro-2-propenyloxy) phenoxy)propyloxy)benzaldehyde O-isopropyloxime, $n_D^{24.5}$ 1.5653

(340) 4-(3-(2,6-dichloro-4-(3,3-dichloro-2-propenyloxy) phenoxy)propyloxy)benzaldehyde O-sec-butyloxime, $n_D^{24.5}$ 1.5665

(341) 4-(3-(2,6-dichloro-4-(3,3-dichloro-2-propenyloxy) phenoxy)propyloxy)benzaldehyde O-iso-butyloxime, $n_D^{24.5}$ 1.5579

(342) 4-(3-(2,6-dichloro-4-(3,3-dichloro-2-propenyloxy) phenoxy)propyloxy)benzaldehyde O-allyloxime, $n_D^{24.5}$ 1.5990

(343) 4-(3-(2,6-dichloro-4-(3,3-dichloro-2-propenyloxy) phenoxy)propyloxy)benzaldehyde O-benzyloxime, $n_D^{24.5}$ 1.5886

(344) 4'-(2,6-dichloro-4-(3,3-dichloro-2-propenyloxy) phenoxymethyl)acetophenone O-(3,3-dichloro-2-propenyl)oxime, $n_D^{25.0}$ 1.5965

(345) 4'-(2,6-dichloro-4-(3,3-dichloro-2-propenyloxy) phenoxymethyl)acetophenone O-methyloxime, $n_D^{26.5}$ 1.5947

(346) 4'-(2,6-dichloro-4-(3,3-dichloro-2-propenyloxy) phenoxymethyl)acetophenone O-propyloxime, $n_D^{26.0}$ 1.5808

(347) 4'-(2,6-dichloro-4-(3,3-dichloro-2-propenyloxy) phenoxymethyl)acetophenone O-propyloxime, $n_D^{26.0}$ 1.5904

(348) 4'-(2,6-dichloro-4-(3,3-dichloro-2-propenyloxy) phenoxymethyl)acetophenone O-tert-butyloxime, $n_D^{25.5}$ 1.5717

(349) 4'-(2,6-dichloro-4-(3,3-dichloro-2-propenyloxy) phenoxymethyl)acetophenone O-ethyloxime, $n_D^{26.0}$ 1.5865

(350) 4'-(2,6-dichloro-4-(3,3-dichloro-2-propenyloxy) phenoxymethyl)acetophenone O-benzyloxime, $n_D^{26.5}$ 1.6655

(351) 4-(2-(2,6-dichloro-4-(3,3-dichloro-2-propenyloxy) phenoxy)ethyl)benzaldehyde O-methyloxime, $n_D^{24.5}$ 1.5921

(352) 4-(2-(2,6-dichloro-4-(3,3-dichloro-2-propenyloxy) phenoxy)ethyl)benzaldehyde O-ethyloxime, $n_D^{24.5}$ 1.5846

(353) 4-(2-(2,6-dichloro-4-(3,3-dichloro-2-propenyloxy) phenoxy)ethyl)benzaldehyde O-propyloxime, $n_D^{24.5}$ 1.5773

(354) 4-(2-(2,6-dichloro-4-(3,3-dichloro-2-propenyloxy) phenoxy)ethyl)benzaldehyde O-iso-propyloxime, $n_D^{24.5}$ 1.5762

(355) 4-(2-(2,6-dichloro-4-(3,3-dichloro-2-propenyloxy) phenoxy)ethyl)benzaldehyde O-sec-butyloxime, $n_D^{25.0}$ 1.5718

(356) 4-(2-(2,6-dichloro-4-(3,3-dichloro-2-propenyloxy) phenoxy)ethyl)benzaldehyde O-tert-butyloxime, $n_D^{26.0}$ 1.5669

(357) 4-(2-(2,6-dichloro-4-(3,3-dichloro-2-propenyloxy) phenoxy)ethyl)benzaldehyde O-allyl oxime, $n_D^{26.0}$ 1.5849

(358) 4-(2-(2,6-dichloro-4-(3,3-dichloro-2-propenyloxy) phenoxy)ethyl)benzaldehyde O-(3,3-dichloro-2-propenyl)oxime, $n_D^{26.5}$ 1.5932

(359) 4-(2-(2,6-dichloro-4-(3,3-dichloro-2-propenyloxy) phenoxy)ethyl)benzaldehyde O-benzyloxime, $n_D^{27.0}$ 1.5967

(360) 2-(4-(2,6-dichloro-4-(3,3-dichloro-2-propenyloxy) phenoxymethyl)phenoxy)acetaldehyde O-(3,3-dichloro-2-propenyl)oxime, m.p., 87.9° C.

(361) 4-(2-(2,6-dichloro-4-(3,3-dichloro-2-propenyloxy) phenoxy)ethyl)benzaldehyde O-(4-tert-butylbenzyl) oxime, $n_D^{26.0}$ 1.5818

(362) 4-(2-(2,6-dichloro-4-(3,3-dichloro-2-properiyloxy) phenoxy)ethyl)benzaldehyde O-cyclohexyloxime, $n_D^{26.0}$ 1.5685

(363) 4-(2-(2,6-dichloro-4-(3,3-dichloro-2-propenyloxy) phenoxy)ethyl)benzaldehyde O-(3-phenylpropyl) oxime, $n_D^{26.0}$ 1.5902

(364) 5-(1-(N-ethoxyimino)ethyl)-2-(3-(2,6-dichloro-4-(3,3-dichloro-2-propenyloxy)phenoxy)propyloxy) pyridine, $n_D^{24.5}$ 1.5701

(365) 4-(3-(2,6-dichloro-4-(3,3-dichloro-2-propenyloxy) phenoxy)propyl)benzaldehyde O-methyloxime, $n_D^{25.5}$ 1.5876

(366) 4-(3-(2,6-dichloro-4-(3,3-dichloro-2-propenyloxy) phenoxy)propyl)benzaldehyde O-ethyloxime, $n_D^{26.0}$ 1.5802

(367) 4-(3-(2,6-dichloro-4-(3,3-dichloro-2-propenyloxy) phenoxy)propyl)benzaldehyde O-propyloxime, $n_D^{25.5}$ 1.5763

(368) 4-(3-(2,6-dichloro-4-(3,3-dichloro-2-propenyloxy) phenoxy)propyl)benzaldehyde O-iso-propyloxime, $n_D^{25.5}$ 1.5734

(369) 4-(3-(2,6-dichloro-4-(3,3-dichloro-2-propenyloxy) phenoxy)propyl)benzaldehyde O-tert-butyloxime, $n_D^{25.5}$ 1.5673

(370) 4-(3-(2,6-dichloro-4-(3,3-dichloro-2-propenyloxy)phenoxy)propyl)benzaldehyde O-allyl oxime, $n_D^{25.5}$ 1.5844

(371) 4-(3-(2,6-dichloro-4-(3,3-dichloro-2-propenyloxy)phenoxy)propyl)benzaldehyde O-(3,3-dichloro-2-propenyl)oxime, $n_D^{25.0}$ 1.5920

(372) 4'-((2,6-dichloro-4-(3,3-dichloro-2-propenyloxy)phenoxy)methyl)acetophenone O-iso-propyloxime (373) 4'-((2,6-dichloro-4-(3,3-dichloro-2-propenyloxy)phenoxy)methyl)acetophenone O-butyloxime (374) 4'-((2,6-dichloro-4-(3,3-dichloro-2-propenyloxy)phenoxy)methyl)acetophenone O-iso-butyloxime (375) 4'-((2,6-dichloro-4-(3,3-dichloro-2-propenyloxy)phenoxy)methyl)acetophenone O-sec-butyloxime (376) 4-((2,6-dichloro-4-(3,3-dichloro-2-propenyloxy)phenoxy)methyl)benzaldehyde O-butyloxime (377) 3-((2,6-dichloro-4-(3,3-dichloro-2-propenyloxy)phenoxy)methyl)benzaldehyde O-methyloxime (378) 3-((2,6-dichloro-4-(3,3-dichloro-2-propenyloxy)phenoxy)methyl)benzaldehyde O-ethyloxime (379) 3-((2,6-dichloro-4-(3,3-dichloro-2-propenyloxy)phenoxy)methyl)benzaldehyde O-propyloxime (380) 3-((2,6-dichloro-4-(3,3-dichloro-2-propenyloxy)phenoxy)methyl)benzaldehyde O-iso-propyloxime (381) 3-((2,6-dichloro-4-(3,3-dichloro-2-propenyloxy)phenoxy)methyl)benzaldehyde O-iso-butyloxime (382) 4-(3-(2,6-dichloro-4-(3,3-dichloro-2-propenyloxy)phenoxy)propyl)benzaldehyde O-iso-butyloxime (383) 4-(3-(2,6-dichloro-4-(3,3-dichloro-2-propenyloxy)phenoxy)propyl)benzaldehyde O-sec-butyloxime (384) 4-(4-(2,6-dichloro-4-(3,3-dichloro-2-propenyloxy)phenoxy)butyl)benzaldehyde O-(3,3-dichloro-2-propenyl)oxime (385) 4-(4-(2,6-dichloro-4-(3,3-dichloro-2-propenyloxy)phenoxy)butyl)benzaldehyde O-methyloxime (386) 4-(4-(2,6-dichloro-4-(3,3-dichloro-2-propenyloxy)phenoxy)butyl)benzaldehyde O-ethyloxime (387) 4-(4-(2,6-dichloro-4-(3,3-dichloro-2-propenyloxy)phenoxy)butyl)benzaldehyde O-propyloxime (388) 4-(4-(2,6-dichloro-4-(3,3-dichloro-2-propenyloxy)phenoxy)butyl)benzaldehyde O-iso-propyloxime (389) 4-(4-(2,6-dichloro-4-(3,3-dichloro-2-propenyloxy)phenoxy)butyl)benzaldehyde O-butyloxime (390) 4-(4-(2,6-dichloro-4-(3,3-dichloro-2-propenyloxy)phenoxy)butyl)benzaldehyde O-iso-butyloxime (391) 4-(4-(2,6-dichloro-4-(3,3-dichloro-2-propenyloxy)phenoxy)butyl)benzaldehyde O-sec-butyloxime (392) 4-(4-(2,6-dichloro-4-(3,3-dichloro-2-propenyloxy)phenoxy)butyl)benzaldehyde O-tert-butyloxime (393) 4'-((2,6-dichloro-4-(3,3-dichloro-2-propenyloxy)phenoxy)methyl)-2,2,2-trifluoroacetophenone O-(3,3-dichloro-2-propenyl)oxime (394) 4'-((2,6-dichloro-4-(3,3-dichloro-2-propenyloxy)phenoxy)methyl)-2,2,2-trifluoroacetophenone O-methyloxime (395) 4'-((2,6-dichloro-4-(3,3-dichloro-2-propenyloxy)phenoxy)methyl)-2,2,2-trifluoroacetophenone O-ethyloxime (396) 4'-((2,6-dichloro-4-(3,3-dichloro-2-propenyloxy)phenoxy)methyl)-2,2,2-trifluoroacetophenone O-propyloxime (397) 4'-((2,6-dichloro-4-(3,3-dichloro-2-propenyloxy)phenoxy)methyl)-2,2,2-trifluoroacetophenone O-iso-propyloxime (398) 4'-((2,6-dichloro-4-(3,3-dichloro-2-propenyloxy)phenoxy)methyl)-2,2,2-trifluoroacetophenone O-butyloxime (399) 4'-((2,6-dichloro-4-(3,3-dichloro-2-propenyloxy)phenoxy)methyl)-2,2,2-trifluoroacetophenone O-iso-butyloxime (400) 4'-((2,6-dichloro-4-(3,3-dichloro-2-propenyloxy)phenoxy)methyl)-2,2,2-trifluoroacetophenone O-sec-butyloxime (401) 4'-((2,6-dichloro-4-(3,3-dichloro-2-propenyloxy)phenoxy)methyl)-2,2,2-trifluoroacetophenone O-tert-butyloxime (402) 4'-(2-(2,6-dichloro-4-(3,3-dichloro-2-propenyloxy)phenoxy)ethyl)-2,2,2-trifluoroacetophenone O-(3,3-dichloro-2-propenyl)oxime (403) 4'-(2-(2,6-dichloro-4-(3,3-dichloro-2-propenyloxy)phenoxy)ethyl)-2,2,2-trifluoroacetophenone O-methyloxime (404) 4'-(2-(2,6-dichloro-4-(3,3-dichloro-2-propenyloxy)phenoxy)ethyl)-2,2,2-trifluoroacetophenone O-ethyloxime (405) 4'-(2-(2,6-dichloro-4-(3,3-dichloro-2-propenyloxy)phenoxy)ethyl)-2,2,2-trifluoroacetophenone O-propyloxime (406) 4'-(2-(2,6-dichloro-4-(3,3-dichloro-2-propenyloxy)phenoxy)ethyl)-2,2,2-trifluoroacetophenone O-iso-propyloxime (407) 4'-(2-(2,6-dichloro-4-(3,3-dichloro-2-propenyloxy)phenoxy)ethyl)-2,2,2-trifluoroacetophenone O-butyloxime (408) 4'-(2-(2,6-dichloro-4-(3,3-dichloro-2-propenyloxy)phenoxy)ethyl)-2,2,2-trifluoroacetophenone O-iso-butyloxime (409) 4'-(2-(2,6-dichloro-4-(3,3-dichloro-2-propenyloxy)phenoxy)ethyl)-2,2,2-trifluoroacetophenone O-sec-butyloxime (410) 4'-(2-(2,6-dichloro-4-(3,3-dichloro-2-propenyloxy)phenoxy)ethyl)-2,2,2-trifluoroacetophenone O-tert-butyloxime (411) 4'-(3-(2,6-dichloro-4-(3,3-dichloro-2-propenyloxy)phenoxy)propyl)-2,2,2-trifluoroacetophenone O-(3,3-dichloro-2-propenyl)oxime (412) 4'-(3-(2,6-dichloro-4-(3,3-dichloro-2-propenyloxy)phenoxy)propyl)-2,2,2-trifluoroacetophenone O-methyloxime (413) 4'-(3-(2,6-dichloro-4-(3,3-dichloro-2-propenyloxy)phenoxy)propyl)-2,2,2-trifluoroacetophenone O-ethyloxime (414) 4'-(3-(2,6-dichloro-4-(3,3-dichloro-2-propenyloxy)phenoxy)propyl)-2,2,2-trifluoroacetophenone O-propyloxime (415) 4'-(3-(2,6-dichloro-4-(3,3-dichloro-2-propenyloxy)phenoxy)propyl)-2,2,2-trifluoroacetophenone O-iso-propyloxime (416) 4'-(3-(2,6-dichloro-4-(3,3-dichloro-2-propenyloxy)phenoxy)propyl)-2,2,2-trifluoroacetophenone O-butyloxime (417) 4'-(3-(2,6-dichloro-4-(3,3-dichloro-2-propenyloxy)phenoxy)propyl)-2,2,2-trifluoroacetophenone O-iso-butyloxime (418) 4'-(3-(2,6-dichloro-4-(3,3-dichloro-2-propenyloxy)phenoxy)propyl)-2,2,2-trifluoroacetophenone O-sec-butyloxime (419) 4'-(3-(2,6-dichloro-4-(3,3-dichloro-2-propenyloxy)phenoxy)propyl)-2,2,2-trifluoroacetophenone O-tert-butyloxime
(420) 4-(2-(2,6-dichloro-4-(3,3-dichloro-2-propenyloxy)phenoxy)ethoxy)benzaldehyde O-methyloxime
(421) 4-(2-(2,6-dichloro-4-(3,3-dichloro-2-propenyloxy)phenoxy)ethoxy)benzaldehyde O-propyloxime
(422) 4-(2-(2,6-dichloro-4-(3,3-dichloro-2-propenyloxy)phenoxy)ethoxy)benzaldehyde O-iso-propyloxime
(423) 4-(2-(2,6-dichloro-4-(3,3-dichloro-2-propenyloxy)phenoxy)ethoxy)benzaldehyde O-butyloxime
(424) 4-(2-(2,6-dichloro-4-(3,3-dichloro-2-propenyloxy)phenoxy)ethoxy)benzaldehyde O-iso-butyloxime
(425) 4-(2-(2,6-dichloro-4-(3,3-dichloro-2-propenyloxy)phenoxy)ethoxy)benzaldehyde O-sec-butyloxime
(426) 4-(3-(2,6-dichloro-4-(3,3-dichloro-2-propenyloxy)phenoxy)propyloxy)benzaldehyde O-butyloxime
(427) 4-(4-(2,6-dichloro-4-(3,3-dichloro-2-propenyloxy)phenoxy)butyloxy)benzaldehyde O-propyloxime
(428) 4-(4-(2,6-dichloro-4-(3,3-dichloro-3-propenyloxy)phenoxy)butyloxy)benzaldehyde O-sec-butyloxime
(429) 4-(4-(2,6-dichloro-4-(3,3-dichloro-4-propenyloxy)phenoxy)butyloxy)benzaldehyde O-butyloxime
(430) 4-(5-(2,6-dichloro-4-(3,3-dichloro-2-propenyloxy)phenoxy)pentyloxy)benzaldehyde O-methyloxime
(431) 4-(5-(2,6-dichloro-4-(3,3-dichloro-2-propenyloxy)phenoxy)pentyloxy)benzaldehyde O-propyloxime
(432) 4-(5-(2,6-dichloro-4-(3,3-dichloro-2-propenyloxy)phenoxy)pentyloxy)benzaldehyde O-iso-propyloxime
(433) 4-(5-(2,6-dichloro-4-(3,3-dichloro-2-propenyloxy)phenoxy)pentyloxy)benzaldehyde O-butyloxime
(434) 4-(5-(2,6-dichloro-4-(3,3-dichloro-2-propenyloxy)phenoxy)pentyloxy)benzaldehyde O-iso-butyloxime
(435) 4-(5-(2,6-dichloro-4-(3,3-dichloro-2-propenyloxy)phenoxy)pentyloxy)benzaldehyde O-sec-butyloxime
(436) 4-(5-(2,6-dichloro-4-(3,3-dichloro-2-propenyloxy)phenoxy)pentyloxy)benzaldehyde O-tert-butyloxime
(437) (2-(3-(2,6-dichloro-4-(3,3-dichloro-2-propenyloxy)phenoxy)propyloxy)-5-pyridyl)acetaldehyde O-methyloxime
(438) (2-(3-(2,6-dichloro-4-(3,3-dichloro-2-propenyloxy)phenoxy)propyloxy)-5-pyridyl)acetaldehyde O-ethyloxime
(439) (2-(3-(2,6-dichloro-4-(3,3-dichloro-2-propenyloxy)phenoxy)propyloxy)-5-pyridyl)acetaldehyde O-propyloxime
(440) (2-(3-(2,6-dichloro-4-(3,3-dichloro-2-propenyloxy)phenoxy)propyloxy)-5-pyridyl)acetaldehyde O-iso-propyloxime
(441) (2-(3-(2,6-dichloro-4-(3,3-dichloro-2-propenyloxy)phenoxy)propyloxy)-5-pyridyl)acetaldehyde O-butyloxime
(442) (2-(3-(2,6-dichloro-4-(3,3-dichloro-2-propenyloxy)phenoxy)propyloxy)-5-pyridyl)acetaldehyde O-iso-butyloxime
(443) (2-(3-(2,6-dichloro-4-(3,3-dichloro-2-propenyloxy)phenoxy)propyloxy)-5-pyridyl)acetaldehyde O-sec-butyloxime
(444) (2-(3-(2,6-dichloro-4-(3,3-dichloro-2-propenyloxy)phenoxy)propyloxy)-5-pyridyl)acetaldehyde O-tert-butyloxime
(445) (2-(3-(2,6-dichloro-4-(3,3-dichloro-2-propenyloxy)phenoxy)propyloxy)-5-pyridyl)acetaldehyde O-(3,3-dichloro-2-propenyl)oxime
(446) (2-(4-(2,6-dichloro-4-(3,3-dichloro-2-propenyloxy)phenoxy)butyloxy)-5-pyridyl)acetaldehyde O-methyloxime
(447) (2-(4-(2,6-dichloro-4-(3,3-dichloro-2-propenyloxy)phenoxy)butyloxy)-5-pyridyl)acetaldehyde O-ethyloxime
(448) (2-(4-(2,6-dichloro-4-(3,3-dichloro-2-propenyloxy)phenoxy)butyloxy)-5-pyridyl)acetaldehyde O-propyloxime
(449) (2-(4-(2,6-dichloro-4-(3,3-dichloro-2-propenyloxy)phenoxy)butyloxy)-5-pyridyl)acetaldehyde O-iso-propyloxime
(450) (2-(4-(2,6-dichloro-4-(3,3-dichloro-2-propenyloxy)phenoxy)butyloxy)-5-pyridyl)acetaldehyde O-butyloxime
(451) (2-(4-(2,6-dichloro-4-(3,3-dichloro-2-propenyloxy)phenoxy)butyloxy)-5-pyridyl)acetaldehyde O-iso-butyloxime
(452) (2-(4-(2,6-dichloro-4-(3,3-dichloro-2-propenyloxy)phenoxy)butyloxy)-5-pyridyl)acetaldehyde O-sec-butyloxime
(453) (2-(4-(2,6-dichloro-4-(3,3-dichloro-2-propenyloxy)phenoxy)butyloxy)-5-pyridyl)acetaldehyde O-tert-butyloxime
(454) (2-(4-(2,6-dichloro-4-(3,3-dichloro-2-propenyloxy)phenoxy)butyloxy)-5-pyridyl)acetaldehyde O-(3,3-dichloro-2-propenyl)oxime
(455) 2-(3-(2,6-dichloro-4-(3,3-dichloro-2-propenyloxy)phenoxy)propyloxy)-5-pyridyl phenyl ketone O-methyloxime
(456) 2-(3-(2,6-dichloro-4-(3,3-dichloro-2-propenyloxy)phenoxy)propyloxy)-5-pyridyl phenyl ketone O-ethyloxime
(457) 2-(3-(2,6-dichloro-4-(3,3-dichloro-2-propenyloxy)phenoxy)propyloxy)-5-pyridyl phenyl ketone O-propyloxime
(458) 2-(3-(2,6-dichloro-4-(3,3-dichloro-2-propenyloxy)phenoxy)propyloxy)-5-pyridyl phenyl ketone O-iso-propyloxime
(459) 2-(3-(2,6-dichloro-4-(3,3-dichloro-2-propenyloxy)phenoxy)propyloxy)-5-pyridyl phenyl ketone O-butyloxime
(460) 2-(3-(2,6-dichloro-4-(3,3-dichloro-2-propenyloxy)phenoxy)propyloxy)-5-pyridyl phenyl ketone O-iso-butyloxime
(461) 2-(3-(2,6-dichloro-4-(3,3-dichloro-2-propenyloxy)phenoxy)propyloxy)-5-pyridyl phenyl ketone O-sec-butyloxime
(462) 2-(3-(2,6-dichloro-4-(3,3-dichloro-2-propenyloxy)phenoxy)propyloxy)-5-pyridyl phenyl ketone O-tert-butyloxime
(463) 2-(3-(2,6-dichloro-4-(3,3-dichloro-2-propenyloxy)phenoxy)propyloxy)-5-pyridyl phenyl ketone O-(3,3-dichloro-2-propenyl)oxime
(464) 2-(4-(2,6-dichloro-4-(3,3-dichloro-2-propenyloxy)phenoxy)butyloxy)-5-pyridyl phenyl ketone O-methyloxime
(465) 2-(4-(2,6-dichloro-4-(3,3-dichloro-2-propenyloxy)phenoxy)butyloxy)-5-pyridyl phenyl ketone O-ethyloxime (466) 2-(4-(2,6-dichloro-4-(3,3-dichloro-2-propenyloxy)phenoxy)butyloxy)-5-pyridyl phenyl ketone O-propyloxime
(467) 2-(4-(2,6-dichloro-4-(3,3-dichloro-2-propenyloxy)phenoxy)butyloxy)-5-pyridyl phenyl ketone O-iso-propyloxime (468) 2-(4-(2,6-dichloro-4-(3,3-dichloro-2-propenyloxy) phenoxy)butyloxy)-5-pyridyl phenyl ketone O-butyloxime (469) 2-(4-(2,6-dichloro-4-(3,3-dichloro-2-propenyloxy) phenoxy)butyloxy)-5-pyridyl phenyl ketone O-iso-butyloxime (470) 2-(4-(2,6-dichloro-4-(3,3-dichloro-2-propenyloxy) phenoxy)butyloxy)-5-pyridyl phenyl ketone O-sec-butyloxime (471) 2-(4-(2,6-dichloro-4-(3,3-dichloro-2-propenyloxy) phenoxy)butyloxy)-5-pyridyl phenyl ketone O-tert-butyloxime (472) 2-(4-(2,6-dichloro-4-(3,3-dichloro-2-propenyloxy) phenoxy)butyloxy)-5-pyridyl phenyl ketone O-(3,3-dichloro-2-propenyl)oxime (473) 5-((2,6-dichloro-4-(3,3-dichloro-2-propenyloxy) phenoxy)methyl)-2-furfural O-methyloxime (474) 5-((2,6-dichloro-4-(3,3-dichloro-2-propenyloxy) phenoxy)methyl)-2-furfural O-ethyloxime (475) 5-((2,6-dichloro-4-(3,3-dichloro-2-propenyloxy) phenoxy)methyl)-2-furfural O-propyloxime (476) 5-((2,6-dichloro-4-(3,3-dichloro-2-propenyloxy) phenoxy)methyl)-2-furfural O-iso-propyloxime (477) 5-((2,6-dichloro-4-(3,3-dichloro-2-propenyloxy) phenoxy)methyl)-2-furfural O-butyloxime (478) 5-((2,6-dichloro-4-(3,3-dichloro-2-propenyloxy) phenoxy)methyl)-2-furfural O-iso-butyloxime (479) 5-((2,6-dichloro-4-(3,3-dichloro-2-propenyloxy) phenoxy)methyl)-2-furfural O-sec-butyloxime (480) 5-((2,6-dichloro-4-(3,3-dichloro-2-propenyloxy) phenoxy)methyl)-2-furfural O-tert-butyloxime (481) 5-((2,6-dichloro-4-(3,3-dichloro-2-propenyloxy) phenoxy)methyl)-2-furfural O-(3,3-dichloro-2-propenyl)oxime, m.p., 65.0° C.

(482) 5-((2,6-dichloro-4-(3,3-dichloro-2-propenyloxy) phenoxy)methyl)-2-thiophenecarboxaldehyde O-methyloxime (483) 5-((2,6-dichloro-4-(3,3-dichloro-2-propenyloxy) phenoxy)methyl)-2-thiophenecarboxaldehyde O-ethyloxime (484) 5-((2,6-dichloro-4-(3,3-dichloro-2-propenyloxy) phenoxy)methyl)-2-thiophenecarboxaldehyde O-propyloxime (485) 5-((2,6-dichloro-4-(3,3-dichloro-2-propenyloxy) phenoxy)methyl)-2-thiophenecarboxaldehyde O-iso-propyloxime (486) 5-((2,6-dichloro-4-(3,3-dichloro-2-propenyloxy) phenoxy)methyl)-2-thiophenecarboxaldehyde O-butyloxime (487) 5-((2,6-dichloro-4-(3,3-dichloro-2-propenyloxy) phenoxy)methyl)-2-thiophenecarboxaldehyde O-iso-butyloxime (488) 5-((2,6-dichloro-4-(3,3-dichloro-2-propenyloxy) phenoxy)methyl)-2-thiophenecarboxaldehyde O-sec-butyloxime (489) 5-((2,6-dichloro-4-(3,3-dichloro-2-propenyloxy) phenoxy)methyl)-2-thiophenecarboxaldehyde O-tert-butyloxime (490) 5-((2,6-dichloro-4-(3,3-dichloro-2-propenyloxy) phenoxy)methyl)-2-thiophenecarboxaldehyde O-(3,3-dichloro-2-propenyl)oxime (491) 5-((2,6-dichloro-4-(3,3-dichloro-2-propenyloxy) phenoxy)methyl)-2-pyrrolcarboxaldehyde O-methyloxime (492) 5-((2,6-dichloro-4-(3,3-dichloro-2-propenyloxy) phenoxy)methyl)-2-pyrrolcarboxaldehyde O-ethyloxime (493) 5-((2,6-dichloro-4-(3,3-dichloro-2-propenyloxy) phenoxy)methyl)-2-pyrrolcarboxaldehyde O-propyloxime (494) 5-((2,6-dichloro-4-(3,3-dichloro-2-propenyloxy) phenoxy)methyl)-2-pyrrolcarboxaldehyde O-iso-propyloxime (495) 5-((2,6-dichloro-4-(3,3-dichloro-2-propenyloxy) phenoxy)methyl)-2-pyrrolcarboxaldehyde O-butyloxime (496) 5-((2,6-dichloro-4-(3,3-dichloro-2-propenyloxy) phenoxy)methyl)-2-pyrrolcarboxaldehyde O-iso-butyloxime (497) 5-((2,6-dichloro-4-(3,3-dichloro-2-propenyloxy) phenoxy)methyl)-2-pyrrolcarboxaldehyde O-sec-butyloxime (498) 5-((2,6-dichloro-4-(3,3-dichloro-2-propenyloxy) phenoxy)methyl)-2-pyrrolcarboxaldehyde O-tert-butyloxime (499) 5-((2,6-dichloro-4-(3,3-dichloro-2-propenyloxy) phenoxy)methyl)-2-pyrrolcarboxaldehyde O-(3,3-dichloro-2-propenyl)oxime (500) 5-((2,6-dichloro-4-(3,3-dichloro-2-propenyloxy) phenoxy)methyl)-2-furfural O-(3,3-dibromo-2-propenyl)oxime (501) 4'-(2-(2,6-dichloro-4-(3,3-dichloro-2-propenyloxy) phenoxy)ethyl)acetophenone O-methyloxime, $n_D^{26.0}$ 1.5816

(502) 4'-(2-(2,6-dichloro-4-(3,3-dichloro-2-propenyloxy) phenoxy)ethyl)acetophenone O-ethyloxime, $n_D^{26.0}$ 1.5772

(503) 4'-(2-(2,6-dichloro-4-(3,3-dichloro-2-propenyloxy) phenoxy)ethyl)acetophenone O-propyloxime, $n_D^{28.0}$ 1.5732

(504) 4'-(2-(2,6-dichloro-4-(3,3-dichloro-2-propenyloxy) phenoxy)ethyl)acetophenone O-tert-butyloxime, $n_D^{27.5}$ 1.5559

(505) 4'-(2-(2,6-dichloro-4-(3,3-dichloro-2-propenyloxy) phenoxy)ethyl)acetophenone O-allyloxime, $n_D^{25.5}$ 1.5828

(506) 4'-(2-(2,6-dichloro-4-(3,3-dichloro-2-propenyloxy) phenoxy)ethyl)acetophenone O-(3,3-dichloro-2-propenyl)oxime, $n_D^{25.0}$ 1.5906

(507) 4-(4-(2,6-dichloro-4-(3,3-dichloro-2-propenyloxy) phenoxy)butyl)benzaldehyde O-methyloxime, $n_D^{26.5}$ 1.5802

(508) 4-(4-(2,6-dichloro-4-(3,3-dichloro-2-propenyloxy) phenoxy)butyl)benzaldehyde O-ethyloxime, $n_D^{26.5}$ 1.5744

(509) 4-(4-(2,6-dichloro-4-(3,3-dichloro-2-propenyloxy) phenoxy)butyl)benzaldehyde O-propyloxime, $n_D^{26.5}$ 1.5708

(510) 4-(4-(2,6-dichloro-4-(3,3-dichloro-2-propenyloxy) phenoxy)butyl)benzaldehyde O-tert-butyloxime, $n_D^{26.5}$ 1.5624

(511) 4-(4-(2,6-dichloro-4-(3,3-dichloro-2-propenyloxy) phenoxy)butyl)benzaldehyde O-allyloxime, $n_D^{26.5}$ 1.5794

(512) 4-(4-(2,6-dichloro-4-(3,3-dichloro-2-propenyloxy) phenoxy)butyl)benzaldehyde O-(3,3-dichloro-2-propenyl)oxime, $n_D^{26.5}$ 1.5856

(513) 3'-(3-(2,6-dichloro-4-(3,3-dichloro-2-propenyloxy) phenoxy)propyloxy)acetophenone O-methyloxime, $n_D^{25.5}$ 1.5786

(514) 3'-(3-(2,6-dichloro-4-(3,3-dichloro-2-propenyloxy) phenoxy)propyloxy)acetophenone O-ethyloxime, $n_D^{26.0}$ 1.5717

(515) 3'-(3-(2,6-dichloro-4-(3,3-dichloro-2-propenyloxy) phenoxy)propyloxy)acetophenone O-propyloxime, $n_D^{25.0}$ 1.5692

(516) 3'-(3-(2,6-dichloro-4-(3,3-dichloro-2-propenyloxy) phenoxy)propyloxy)acetophenone O-isopropyloxime, $n_D^{25.0}$ 1.5656

(517) 3'-(3-(2,6-dichloro-4-(3,3-dichloro-2-propenyloxy) phenoxy)propyloxy)acetophenone O-sec-butyloxime, $n_D^{25.0}$ 1.5606

(518) 3'-(3-(2,6-dichloro-4-(3,3-dichloro-2-propenyloxy) phenoxy)propyloxy)acetophenone O-tert-butyloxime, $n_D^{25.0}$ 1.5580

(519) 4-(3-(2,6-dichloro-4-(3,3-dichloro-2-propenyloxy) phenoxy)propyloxy)-2,2,2-trifluoroacetophenone oxime (520) 4'-(3-(2,6-dichloro-4-(3,3-dichloro-2-propenyloxy) phenoxy)propyloxy)-2,2,2-trifluoroacetophenone O-ethyloxime (521) 4'-(6-(2,6-dichloro-4-(3,3-dichloro-2-propenyloxy) phenoxy)hexyloxy)acetophenone O-ethyloxime (522) 4-(3-(2,6-dichloro-4-(3,3-dichloro-2-propenyloxy) phenoxy)propyloxy)acetophenone O-(1,1,1,3,3,3-hexafluoroisopropyl)oxime (523) benzaldehyde O-(3-(2,6-dichloro-4-(3,3-dichloro-2-propenyloxy)phenoxy)propyl)oxime, $n_D^{22.5}$ 1.5797

(524) 4-(trifluoromethyl)benzaldehyde O-(3-(2,6-dichloro-4-(3,3-dichloro-2-propenyloxy)phenoxy) propyl)oxime, $n_D^{22.5}$ 1.5462

(525) acetaldehyde O-(3-(2,6-dichloro-4-(3,3-dichloro-2-propenyloxy)phenoxy)propyl)oxime, $n_D^{22.5}$ 1.5437

(526) butanal O-(3-(2,6-dichloro-4-(3,3-dichloro-2-propenyloxy)phenoxy)propyl)oxime, $n_D^{22.5}$ 1.5361

(527) trimethylacetaldehyde O-(3-(2,6-dichloro-4-(3,3-dichloro-2-propenyloxy)phenoxy)propyl)oxime, $n_D^{22.5}$ 1.5262

(528) 4'-(trifluoromethyl)acetophenone O-(3-(2,6-dichloro-4-(3,3-dichloro-2-propenyloxy)phenoxy) propyl)oxime, $n_D^{21.0}$ 1.5433

(529) 4-(trifluoromethyl)benzaldehyde O-(4-(2,6-dichloro-4-(3,3-dichloro-2-propenyloxy)phenoxy) butyl)oxime, $n_D^{21.0}$ 1.5387

(530) trimethylacetaldehyde O-(4-(2,6-dichloro-4-(3,3-dichloro-2-propenyloxy)phenoxy)butyl)oxime, $n_D^{21.5}$ 1.5280

(531) 4'-(trifluoromethyl)acetophenone O-(4-(2,6-dichloro-4-(3,3-dichloro-2-propenyloxy)phenoxy) butyl)oxime, $n_D^{21.5}$ 1.5420

(532) acetaldehyde O-(4-(2,6-dichloro-4-(3,3-dichloro-2-propenyloxy)phenoxy)butyl)oxime, $n_D^{21.5}$ 1.5423

(533) benzaldehyde O-(4-(2,6-dichloro-4-(3,3-dichloro-2-propenyloxy)phenoxy)butyl)oxime, $n_D^{21.5}$ 1.5731

(534) butanal O-(4-(2,6-dichloro-4-(3,3-dichloro-2-propenyloxy)phenoxy)butyl)oxime, $n_D^{21.5}$ 1.5332

(535) 4-chlorobenzaldehyde O-(3-(2,6-dichloro-4-(3,3-dichloro-2-propenyloxy)phenoxy)propyl)oxime, $n_D^{21.5}$ 1.5850

(536) 4-chlorobenzaldehyde O-(4-(2,6-dichloro-4-(3,3-dichloro-2-propenyloxy)phenoxy)butyl)oxime, $n_D^{21.5}$ 1.5740

(537) 4-(trifluoromethyl)benzaldehyde O-(5-(2,6-dichloro-4-(3,3-dichloro-2-propenyloxy)phenoxy) pentyl)oxime, $n_D^{20.5}$ 1.5455

(538) 4'-(trifluoromethyl)acetophenone O-(5-(2,6-dichloro-4-(3,3-dichloro-2-propenyloxy)phenoxy) pentyl)oxime, $n_D^{20.5}$ 1.5421

(539) benzaldehyde O-(5-(2,6-dichloro-4-(3,3-dichloro-2-propenyloxy)phenoxy)pentyl)oxime, $n_D^{20.5}$ 1.5756

(540) 4-chlorobenzaldehyde O-(5-(2,6-dichloro-4-(3,3-dichloro-2-propenyloxy)phenoxy)pentyl)oxime, $n_D^{20.5}$ 1.5766

(541) acetaldehyde O-(5-(2,6-dichloro-4-(3,3-dichloro-2-propenyloxy)phenoxy)pentyl)oxime, $n_D^{22.5}$ 1.5391

(542) butanal O-(5-(2,6-dichloro-4-(3,3-dichloro-2-propenyloxy)phenoxy)pentyl)oxime, $n_D^{22.5}$ 1.5319

(543) hexanal O-(3-(2,6-dichloro-4-(3,3-dichloro-2-propenyloxy)phenoxy)propyl)oxime, $n_D^{22.5}$ 1.5313

(544) hexanal O-(4-(2,6-dichloro-4-(3,3-dichloro-2-propenyloxy)phenoxy)butyl)oxime, $n_D^{22.5}$ 1.5288

(545) trimethylacetaldehyde O-(5-(2,6-dichloro-4-(3,3-dichloro-2-propenyloxy)phenoxy)pentyl)oxime, $n_D^{23.0}$ 1.5178

(546) hexanal O-(5-(2,6-dichloro-4-(3,3-dichloro-2-propenyloxy)phenoxy)pentyl)oxime, $n_D^{23.0}$ 1.5250

(547) 4'-(trifluoromethyl)acetophenone O-(6-(2,6-dichloro-4-(3,3-dichloro-2-propenyloxy)phenoxy) hexyl)oxime, $n_D^{20.5}$ 1.5391

(548) 4-(trifluoromethyl)benzaldehyde O-(6-(2,6-dichloro-4-(3,3-dichloro-2-propenyloxy)phenoxy) hexyl)oxime, $n_D^{20.5}$ 1.5412

(549) 4'-(trifluoromethyl)acetophenone O-(2-(2,6-dichloro-4-(3,3-dichloro-2-propenyloxy)phenoxy) ethyl)oxime, $n_D^{23.5}$ 1.5468

(550) 4-(trifluoromethyl)benzaldehyde O-(2-(2,6-dichloro-4-(3,3-dichloro-2-propenyloxy)phenoxy) ethyl)oxime, m.p., 79.8° C.

(551) hexanal O-(6-(2,6-dichloro-4-(3,3-dichloro-2-propenyloxy)phenoxy)hexyl)oxime, $n_D^{21.0}$ 1.5238

(552) nonanal O-(5-(2,6-dichloro-4-(3,3-dichloro-2-propenyloxy)phenoxy)pentyl)oxime, $n_D^{22.0}$ 1.5189

(553) dodecylaldehyde O-(5-(2,6-dichloro-4-(3,3-dichloro-2-propenyloxy)phenoxy)pentyl)oxime, $n_D^{22.0}$ 1.5110

(554) nonanal O-(4-(2,6-dichloro-4-(3,3-dichloro-2-propenyloxy)phenoxy)butyl)oxime, $n_D^{22.0}$ 1.5166

(555) dodecylaldehyde O-(4-(2,6-dichloro-4-(3,3-dichloro-2-propenyloxy)phenoxy)butyl)oxime, $n_D^{22.0}$ 1.5100

(556) hexanal O-(2-(2,6-dichloro-4-(3,3-dichloro-2-propenyloxy)phenoxy)ethyl)oxime, $n_D^{21.5}$ 1.5351

(557) butanal O-(2-(2,6-dichloro-4-(3,3-dichloro-2-propenyloxy)phenoxy)ethyl)oxime, $n_D^{21.8}$ 1.5410

(558) butanal O-(6-(2,6-dichloro-4-(3,3-dichloro-2-propenyloxy)phenoxy)hexyl)oxime, $n_D^{23.0}$ 1.5295

(559) 3,3-dimethyl-2-butanone O-(5-(2,6-dichloro-4-(3,3-dichloro-2-propenyloxy)phenoxy)pentyl)oxime, $n_D^{24.5}$ 1.5233

(560) acetone O-(5-(2,6-dichloro-4-(3,3-dichloro-2-propenyloxy)phenoxy)pentyl)oxime, $n_D^{24.5}$ 1.5350

(561) 2-ethylbutanal O-(5-(2,6-dichloro-4-(3,3-dichloro-2-propenyloxy)phenoxy)pentyl)oxime, $n_D^{24.5}$ 1.5235

(562) 3,3-dimethyl-2-butanone O-(4-(2,6-dichloro-4-(3,3-dichloro-2-propenyloxy)phenoxy)butyl)oxime, $n_D^{22.0}$ 1.5277

(563) 4-methyl-2-pentanone O-(4-(2,6-dichloro-4-(3,3-dichloro-2-propenyloxy)phenoxy)butyl)oxime, $n_D^{24.5}$ 1.5265

(564) 4-methyl-2-pentanone O-(5-(2,6-dichloro-4-(3,3-dichloro-2-propenyloxy)phenoxy)pentyl)oxime, $n_D^{24.5}$ 1.5230

(565) n-butyloxyacetaldehyde O-(5-(2,6-dichloro-4-(3,3-dichloro-2-propenyloxy)phenoxy)pentyl)oxime, $n_D^{25.5}$ 1.5240

(566) cyclohexanone O-(5-(2,6-dichloro-4-(3,3-dichloro-2-propenyloxy)phenoxy)pentyl)oxime, $n_D^{25.5}$ 1.5440

(567) chloroacetaldehyde O-(5-(2,6-dichloro-4-(3,3-dichloro-2-propenyloxy)phenoxy)pentyl)oxime, $n_D^{25.0}$ 1.5451

(568) 6-chloro-3-pyridyl methyl ketone O-(4-(2,6-dichloro-4-(3,3-dichloro-2-propenyloxy)phenoxy)butyl)oxime, m.p., 79.5° C.

(569) 6-chloro-3-pyridyl methyl ketone O-(5-(2,6-dichloro-4-(3,3-dichloro-2-propenyloxy)phenoxy)pentyl)oxime, m.p., 67.7° C.

(570) cyclohexanone O-(4-(2,6-dichloro-4-(3,3-dichloro-2-propenyloxy)phenoxy)butyl)oxime, $n_D^{24.5}$ 1.5470

(571) tetrahydrothiopyran-4-one O-(4-(2,6-dichloro-4-(3,3-dichloro-2-propenyloxy)phenoxy)butyl)oxime, $n_D^{24.5}$ 1.5650

(572) tetrahydrothiopyran-4-one O-(5-(2,6-dichloro-4-(3,3-dichloro-2-propenyloxy)phenoxy)pentyl)oxime, $n_D^{25.0}$ 1.5612

(573) tetrahydro-4H-pyran-4-one O-(4-(2,6-dichloro-4-(3,3-dichloro-2-propenyloxy)phenoxy)butyl)oxime, $n_D^{25.0}$ 1.5459

(574) tetrahydro-4H-pyran-4-one O-(5-(2,6-dichloro-4-(3,3-dichloro-2-propenyloxy)phenoxy)pentyl)oxime, $n_D^{25.0}$ 1.5440

(575) tetrahydrothiopyran-4-one O-(6-(2,6-dichloro-4-(3,3-dichloro-2-propenyloxy)phenoxy)hexyl)oxime, $n_D^{25.0}$ 1.5541

(576) tetrahydro-4H-pyran-4-one O-(6-(2,6-dichloro-4-(3,3-dichloro-2-propenyloxy)phenoxy)hexyl)oxime, $n_D^{25.0}$ 1.5383

(577) 4-isopropylbenzaldehyde O-(4-(2,6-dichloro-4-(3,3-dichloro-2-propenyloxy)phenoxy)butyl)oxime, $n_D^{24.0}$ 1.5665

(578) 4-nitrobenzaldehyde O-(4-(2,6-dichloro-4-(3,3-dichloro-2-propenyloxy)phenoxy)butyl)oxime, m.p., 76.4° C.

(579) 4-isopropoxybenzaldehyde O-(4-(2,6-dichloro-4-(3,3-dichloro-2-propenyloxy)phenoxy)butyl)oxime, $n_D^{24.0}$ 1.5701

(580) 3-methyl-2-butanone O-(3-(2,6-dichloro-4-(3,3-dichloro-2-propenyloxy)phenoxy)propyl)oxime, $n_D^{25.0}$ 1.5330

(581) 3-methyl-2-butanone O-(4-(2,6-dichloro-4-(3,3-dichloro-2-propenyloxy)phenoxy)butyl)oxime, $n_D^{25.0}$ 1.5302

(582) 3-methyl-2-butanone O-(5-(2,6-dichloro-4-(3,3-dichloro-2-propenyloxy)phenoxy)pentyl)oxime, $n_D^{24.5}$ 1.5280

(583) 3-methyl-2-butanone O-(6-(2,6-dichloro-4-(3,3-dichloro-2-propenyloxy)phenoxy)hexyl)oxime, $n_D^{24.5}$ 1.5255

(584) 3-methyl-1-butanal O-(3-(2,6-dichloro-4-(3,3-dichloro-2-propenyloxy)phenoxy)propyl)oxime, $n_D^{24.5}$ 1.5296

(585) trimethylacetaldehyde O-(6-(2,6-dichloro-4-(3,3-dichloro-2-propenyloxy)phenoxy)hexyl)oxime, $n_D^{23.0}$ 1.5220

(586) 3,3-dimethyl-2-butanone O-(3-(2,6-dichloro-4-(3,3-dichloro-2-propenyloxy)phenoxy)propyl)oxime, $n_D^{23.0}$ 1.5281

(587) 3,3-dimethyl-2-butanone O-(6-(2,6-dichloro-4-(3,3-dichloro-2-propenyloxy)phenoxy)hexyl)oxime, $n_D^{23.0}$ 1.5230

(588) 4-methyl-2-pentanone O-(3-(2,6-dichloro-4-(3,3-dichloro-2-propenyloxy)phenoxy)propyl)oxime, $n_D^{23.0}$ 1.5295

(589) 4-methyl-2-pentanone O-(6-(2,6-dichloro-4-(3,3-dichloro-2-propenyloxy)phenoxy)hexyl)oxime, $n_D^{23.0}$ 1.5203

(590) 4,4-dimethyl-2-pentanone O-(3-(2,6-dichloro-4-(3,3-dichloro-2-propenyloxy)phenoxy)propyl)oxime, $n_D^{23.0}$ 1.5277

(591) 4,4-dimethyl-2-pentanone O-(4-(2,6-dichloro-4-(3,3-dichloro-2-propenyloxy)phenoxy)butyl)oxime, $n_D^{23.0}$ 1.5259

(592) 4,4-dimethyl-2-pentanone O-(5-(2,6-dichloro-4-(3,3-dichloro-2-propenyloxy)phenoxy)pentyl)oxime, $n_D^{23.0}$ 1.5205

(593) 4,4-dimethyl-2-pentanone O-(6-(2,6-dichloro-4-(3,3-dichloro-2-propenyloxy)phenoxy)hexyl)oxime, $n_D^{23.0}$ 1.5212

(594) 2-furaldehyde O-(4-(2,6-dichloro-4-(3,3-dichloro-2-propenyloxy)phenoxy)butyl)oxime, $n_D^{23.0}$ 1.5690

(595) 2-thiophenecarbaldehyde O-(4-(2,6-dichloro-4-(3,3-dichloro-2-propenyloxy)phenoxy)butyl)oxime, $n_D^{23.0}$ 1.5857

(596) 3-thiophenecarbaldehyde O-(4-(2,6-dichloro-4-(3,3-dichloro-2-propenyloxy)phenoxy)butyl)oxime, $n_D^{22.5}$ 1.5859

(597) 1-methyl-2-pyrrolecarbaldehyde O-(4-(2,6-dichloro-4-(3,3-dichloro-2-propenyloxy)phenoxy)butyl)oxime, $n_D^{22.5}$ 1.5802

(598) acetophenone O-(3-(2,6-dichloro-4-(3,3-dichloro-2-propenyloxy)phenoxy)propyl)oxime (599) acetophenone O-(4-(2,6-dichloro-4-(3,3-dichloro-2-propenyloxy)phenoxy)butyl)oxime (600) acetophenone O-(5-(2,6-dichloro-4-(3,3-dichloro-2-propenyloxy)phenoxy)pentyl)oxime (601) 4'-chloroacetophenone O-(3-(2,6-dichloro-4-(3,3-dichloro-2-propenyloxy)phenoxy)propyl)oxime (602) 4'-chloroacetophenone O-(4-(2,6-dichloro-4-(3,3-dichloro-2-propenyloxy)phenoxy)butyl)oxime (603) 4'-chloroacetophenone O-(5-(2,6-dichloro-4-(3,3-dichloro-2-propenyloxy)phenoxy)pentyl)oxime (604) benzaldehyde O-(3-(2,6-diethyl-4-(3,3-dichloro-2-propenyloxy)phenoxy)propyl)oxime (605) benzaldehyde O-(4-(2,6-diethyl-4-(3,3-dichloro-2-propenyloxy)phenoxy)butyl)oxime (606) benzaldehyde O-(5-(2,6-diethyl-4-(3,3-dichloro-2-propenyloxy)phenoxy)pentyl)oxime (607) 4-chlorobenzaldehyde O-(3-(2,6-diethyl-4-(3,3-dichloro-2-propenyloxy)phenoxy)propyl)oxime (608) 4-chlorobenzaldehyde O-(4-(2,6-diethyl-4-(3,3-dichloro-2-propenyloxy)phenoxy)butyl)oxime (609) 4-chlorobenzaldehyde O-(5-(2,6-diethyl-4-(3,3-dichloro-2-propenyloxy)phenoxy)pentyl)oxime (610) 4-(trifluoromethyl)benzaldehyde O-(3-(2,6-diethyl-4-(3,3-dichloro-2-propenyloxy)phenoxy)propyl)oxime (611) 4-(trifluoromethyl)benzaldehyde O-(4-(2,6-diethyl-4-(3,3-dichloro-2-propenyloxy)phenoxy)butyl)oxime
(612) 4-(trifluoromethyl)benzaldehyde O-(5-(2,6-diethyl-4-(3,3-dichloro-2-propenyloxy)phenoxy)pentyl)oxime
(613) acetophenone O-(3-(2,6-diethyl-4-(3,3-dichloro-2-propenyloxy)phenoxy)propyl)oxime
(614) acetophenone O-(4-(2,6-diethyl-4-(3,3-dichloro-2-propenyloxy)phenoxy)butyl)oxime
(615) acetophenone O-(5-(2,6-diethyl-4-(3,3-dichloro-2-propenyloxy)phenoxy)pentyl)oxime
(616) 4'-chloroacetophenone O-(3-(2,6-diethyl-4-(3,3-dichloro-2-propenyloxy)phenoxy)propyl)oxime
(617) 4'-chloroacetophenone O-(4-(2,6-diethyl-4-(3,3-dichloro-2-propenyloxy)phenoxy)butyl)oxime
(618) 4'-chloroacetophenone O-(5-(2,6-diethyl-4-(3,3-dichloro-2-propenyloxy)phenoxy)pentyl)oxime
(619) 4'-(trifluoromethyl)acetophenone O-(3-(2,6-diethyl-4-(3,3-dichloro-2-propenyloxy)phenoxy)propyl)oxime
(620) 4'-(trifluoromethyl)acetophenone O-(4-(2,6-diethyl-4-(3,3-dichloro-2-propenyloxy)phenoxy)butyl)oxime
(621) 4'-(trifluoromethyl)acetophenone O-(5-(2,6-diethyl-4-(3,3-dichloro-2-propenyloxy)phenoxy)pentyl)oxime
(622) hexanal O-(4-(2,6-diethyl-4-(3,3-dichloro-2-propenyloxy)phenoxy)butyl)oxime
(623) hexanal O-(5-(2,6-diethyl-4-(3,3-dichloro-2-propenyloxy)phenoxy)pentyl)oxime
(624) trimethylacetaldehyde O-(4-(2,6-diethyl-4-(3,3-dichloro-2-propenyloxy)phenoxy)butyl)oxime
(625) trimethylacetaldehyde O-(5-(2,6-diethyl-4-(3,3-dichloro-2-propenyloxy)phenoxy)pentyl)oxime
(626) 4-methyl-2-pentanone O-(4-(2,6-diethyl-4-(3,3-dichloro-2-propenyloxy)phenoxy)butyl)oxime
(627) 4-methyl-2-pentanone O-(5-(2,6-diethyl-4-(3,3-dichloro-2-propenyloxy)phenoxy)pentyl)oxime
(628) 3,3-dimethyl-2-butanone O-(4-(2,6-diethyl-4-(3,3-dichloro-2-propenyloxy)phenoxy)butyl)oxime
(629) 3,3-dimethyl-2-butanone O-(5-(2,6-diethyl-4-(3,3-dichloro-2-propenyloxy)phenoxy)pentyl)oxime
(630) 3-methyl-2-butanone O-(4-(2,6-diethyl-4-(3,3-dichloro-2-propenyloxy)phenoxy)butyl)oxime
(631) 3-methyl-2-butanone O-(5-(2,6-diethyl-4-(3,3-dichloro-2-propenyloxy)phenoxy)pentyl)oxime
(632) benzaldehyde O-(3-(2-ethyl-6-methyl-4-(3,3-dichloro-2-propenyloxy)phenoxy)propyl)oxime
(633) benzaldehyde O-(4-(2-ethyl-6-methyl-4-(3,3-dichloro-2-propenyloxy)phenoxy)butyl)oxime
(634) benzaldehyde O-(5-(2-ethyl-6-methyl-4-(3,3-dichloro-2-propenyloxy)phenoxy)pentyl)oxime
(635) 4-chlorobenzaldehyde O-(3-(2-ethyl-6-methyl-4-(3,3-dichloro-2-propenyloxy)phenoxy)propyl)oxime
(636) 4-chlorobenzaldehyde O-(4-(2-ethyl-6-methyl-4-(3,3-dichloro-2-propenyloxy)phenoxy)butyl)oxime
(637) 4-chlorobenzaldehyde O-(5-(2-ethyl-6-methyl-4-(3,3-dichloro-2-propenyloxy)phenoxy)pentyl)oxime
(638) 4-(trifluoromethyl)benzaldehyde O-(3-(2-ethyl-6-methyl-4-(3,3-dichloro-2-propenyloxy)phenoxy)propyl)oxime
(639) 4-(trifluoromethyl)benzaldehyde O-(4-(2-ethyl-6-methyl-4-(3,3-dichloro-2-propenyloxy)phenoxy)butyl)oxime
(640) 4-(trifluoromethyl)benzaldehyde O-(5-(2-ethyl-6-methyl-4-(3,3-dichloro-2-propenyloxy)phenoxy)pentyl)oxime
(641) acetophenone O-(3-(2-ethyl-6-methyl-4-(3,3-dichloro-2-propenyloxy)phenoxy)propyl)oxime
(642) acetophenone O-(4-(2-ethyl-6-methyl-4-(3,3-dichloro-2-propenyloxy)phenoxy)butyl)oxime
(643) acetophenone O-(5-(2-ethyl-6-methyl-4-(3,3-dichloro-2-propenyloxy)phenoxy)pentyl)oxime
(644) 4'-chloroacetophenone O-(3-(2-ethyl-6-methyl-4-(3,3-dichloro-2-propenyloxy)phenoxy)propyl)oxime
(645) 4'-chloroacetophenone O-(4-(2-ethyl-6-methyl-4-(3,3-dichloro-2-propenyloxy)phenoxy)butyl)oxime
(646) 4-chloroacetophenone O-(5-(2-ethyl-6-methyl-4-(3,3-dichloro-2-propenyloxy)phenoxy)pentyl)oxime
(647) 4'-(trifluoromethyl)acetophenone O-(3-(2-ethyl-6-methyl-4-(3,3-dichloro-2-propenyloxy)phenoxy)propyl)oxime
(648) 4'-(trifluoromethyl)acetophenone O-(4-(2-ethyl-6-methyl-4-(3,3-dichloro-2-propenyloxy)phenoxy)butyl)oxime
(649) 4'-(trifluoromethyl) acetophenone O-(5-(2-ethyl-6-methyl-4-(3,3-dichloro-2-propenyloxy)phenoxy)pentyl)oxime
(650) hexanal O-(4-(2-ethyl-6-methyl-4-(3,3-dichloro-2-propenyloxy)phenoxy)butyl)oxime
(651) hexanal O-(5-(2-ethyl-6-methyl-4-(3,3-dichloro-2-propenyloxy)phenoxy)pentyl)oxime
(652) trimethylacetaldehyde O-(4-(2-ethyl-6-methyl-4-(3,3-dichloro-2-propenyloxy)phenoxy)butyl)oxime
(653) trimethylacetaldehyde O-(5-(2-ethyl-6-methyl-4-(3,3-dichloro-2-propenyloxy)phenoxy)pentyl)oxime
(654) 4-methyl-2-pentanone O-(4-(2-ethyl-6-methyl-4-(3,3-dichloro-2-propenyloxy)phenoxy)butyl)oxime
(655) 4-methyl-2-pentanone O-(5-(2-ethyl-6-methyl-4-(3,3-dichloro-2-propenyloxy)phenoxy)pentyl)oxime
(656) 3,3-dimethyl-2-butanone O-(4-(2-ethyl-6-methyl-4-(3,3-dichloro-2-propenyloxy)phenoxy)butyl)oxime
(657) 3,3-dimethyl-2-butanone O-(5-(2-ethyl-6-methyl-4-(3,3-dichloro-2-propenyloxy)phenoxy)pentyl)oxime
(658) 3-methyl-2-butanone O-(4-(2-ethyl-6-methyl-4-(3,3-dichloro-2-propenyloxy)phenoxy)butyl)oxime
(659) 3-methyl-2-butanone O-(5-(2-ethyl-6-methyl-4-(3,3-dichloro-2-propenyloxy)phenoxy)pentyl)oxime
(660) benzaldehyde O-(3-(2-chloro-6-methyl-4-(3,3-dichloro-2-propenyloxy)phenoxy)propyl)oxime
(661) benzaldehyde O-(4-(2-chloro-6-methyl-4-(3,3-dichloro-2-propenyloxy)phenoxy)butyl)oxime
(662) benzaldehyde O-(5-(2-chloro-6-methyl-4-(3,3-dichloro-2-propenyloxy)phenoxy)pentyl)oxime
(663) 4-chlorobenzaldehyde O-(3-(2-chloro-6-methyl-4-(3,3-dichloro-2-propenyloxy)phenoxy)propyl)oxime
(664) 4-chlorobenzaldehyde O-(4-(2-chloro-6-methyl-4-(3,3-dichloro-2-propenyloxy)phenoxy)butyl)oxime
(665) 4-chlorobenzaldehyde O-(5-(2-chloro-6-methyl-4-(3,3-dichloro-2-propenyloxy)phenoxy)pentyl)oxime
(666) 4-(trifluoromethyl)benzaldehyde O-(3-(2-chloro-6-methyl-4-(3,3-dichloro-2-propenyloxy)phenoxy)propyl)oxime
(667) 4-(trifluoromethyl)benzaldehyde O-(4-(2-chloro-6-methyl-4-(3,3-dichloro-2-propenyloxy)phenoxy)butyl)oxime (668) 4-(trifluoromethyl)benzaldehyde O-(5-(2-chloro-6-methyl-4-(3,3-dichloro-2-propenyloxy)phenoxy)pentyl)oxime (669) acetophenone O-(3-(2-chloro-6-methyl-4-(3,3-dichloro-2-propenyloxy)phenoxy)propyl)oxime (670) acetophenone O-(4-(2-chloro-6-methyl-4-(3,3-dichloro-2-propenyloxy)phenoxy)butyl)oxime (671) acetophenone O-(5-(2-chloro-6-methyl-4-(3,3-dichloro-2-propenyloxy)phenoxy)pentyl)oxime (672) 4'-chloroacetophenone O-(3-(2-chloro-6-methyl-4-(3,3-dichloro-2-propenyloxy)phenoxy)propyl)oxime (673) 4'-chloroacetophenone O-(4-(2-chloro-6-methyl-4-(3,3-dichloro-2-propenyloxy)phenoxy)butyl)oxime (674) 4'-chloroacetophenone O-(5-(2-chloro-6-methyl-4-(3,3-dichloro-2-propenyloxy)phenoxy)pentyl)oxime (675) 4'-(trifluoromethyl)acetophenone O-(3-(2-chloro-6-methyl-4-(3,3-dichloro-2-propenyloxy)phenoxy)propyl)oxime (676) 4'-(trifluoromethyl)acetophenone O-(4-(2-chloro-6-methyl-4-(3,3-dichloro-2-propenyloxy)phenoxy)butyl)oxime (677) 4'-(trifluoromethyl)acetophenone O-(5-(2-chloro-6-methyl-4-(3,3-dichloro-2-propenyloxy)phenoxy)pentyl)oxime (678) hexanal O-(4-(2-chloro-6-methyl-4-(3,3-dichloro-2-propenyloxy)phenoxy)butyl)oxime (679) hexanal O-(5-(2-chloro-6-methyl-4-(3,3-dichloro-2-propenyloxy)phenoxy)pentyl)oxime (680) trimethylacetaldehyde O-(4-(2-chloro-6-methyl-4-(3,3-dichloro-2-propenyloxy)phenoxy)butyl)oxime (681) trimethylacetaldehyde O-(5-(2-chloro-6-methyl-4-(3,3-dichloro-2-propenyloxy)phenoxy)pentyl)oxime (682) 4-methyl-2-pentanone O-(4-(2-chloro-6-methyl-4-(3,3-dichloro-2-propenyloxy)phenoxy)butyl)oxime (683) 4-methyl-2-pentanone O-(5-(2-chloro-6-methyl-4-(3,3-dichloro-2-propenyloxy)phenoxy)pentyl)oxime (684) 3,3-dimethyl-2-butanone O-(4-(2-chloro-6-methyl-4-(3,3-dichloro-2-propenyloxy)phenoxy)butyl)oxime (685) 3,3-dimethyl-2-butanone O-(5-(2-chloro-6-methyl-4-(3,3-dichloro-2-propenyloxy)phenoxy)pentyl)oxime (686) 3-methyl-2-butanone O-(4-(2-chloro-6-methyl-4-(3,3-dichloro-2-propenyloxy)phenoxy)butyl)oxime (687) 3-methyl-2-butanone O-(5-(2-chloro-6-methyl-4-(3,3-dichloro-2-propenyloxy)phenoxy)pentyl)oxime (688) methyl 3-pyridyl ketone O-(4-(2,6-dichloro-4-(3,3-dichloro-2-propenyloxy)phenoxy)butyl)oxime, $n_D^{19.5}$ 1.5715

(689) methyl 2-pyridyl ketone O-(4-(2,6-dichloro-4-(3,3-dichloro-2-propenyloxy)phenoxy)butyl)oxime, $n_D^{19.5}$ 1.5717

(690) 4-(N,N-dimethylamino)benzaldehyde O-(4-(2,6-dichloro-4-(3,3-dichloro-2-propenyloxy)phenoxy)butyl)oxime, $n_D^{19.5}$ 1.5817

(691) 4-cyanobenzaldehyde O-(4-(2,6-dichloro-4-(3,3-dichloro-2-propenyloxy)phenoxy)butyl)oxime, m.p., 71.2° C.

(692) 4'-nitroacetophenone O-(4-(2,6-dichloro-4-(3,3-dichloro-2-propenyloxy)phenoxy)butyl)oxime, $n_D^{19.0}$ 1.5878

(693) 3'-nitroacetophenone O-(4-(2,6-dichloro-4-(3,3-dichloro-2-propenyloxy)phenoxy)butyl)oxime, $n_D^{19.0}$ 1.5719

(694) 2'-nitroacetophenone O-(4-(2,6-dichloro-4-(3,3-dichloro-2-propenyloxy)phenoxy)butyl)oxime, $n_D^{20.5}$ 1.5615

(695) methyl 4-pyridyl ketone O-(4-(2,6-dichloro-4-(3,3-dichloro-2-propenyloxy)phenoxy)butyl)oxime, $n_D^{20.5}$ 1.5586

The following is a production example for the intermediate compounds of formula (12).

Intermediate Production Example 1

Production of Intermediate Compound 2)

First, 10.0 g of 2,6-dichloro-4-(3,3-dichloro-2-propenyloxy)phenol, 14.0 g of 1,3-dibromopropane, and 50 ml of N,N-dimethylformamide were placed in a reaction vessel, to which 5.3 g of potassium carbonate was added. After stirring at room temperature for 12 hours, the reaction mixture was filtered. The filtrate was poured into diluted hydrochloric acid, and extracted with ethyl acetate. The ethyl acetate layer was washed twice with water, dried over anhydrous magnesium sulfate, and concentrated to give a crude product. This crude product was subjected to silica gel chromatography, which afforded 6.1 g (yield, 43%) of 1-(3-bromopropyloxy)-2,6-dichloro-4-(3,3-dichloro-2-propenyloxy)benzene.

Then, 10.0 g of 1-(3-bromopropyloxy)-2,6-dichloro-4-(3,3-dichloro-2-propenyloxy)benzene obtained in the same manner as described above, 4.0 g of N-hydroxyphthalimide, and 100 ml of N,N-dimethylformamide were placed in a reaction vessel, to which 3.4 g of potassium carbonate was added. After stirring at room temperature for 12 hours, the reaction mixture was poured into ice water, and extracted with ethyl acetate. The ethyl acetate layer was washed with water, dried over anhydrous magnesium sulfate, and concentrated to give a crude product. This crude product was washed with hexane, which afforded 9.4 g (yield, 78.3%) of N-(3-(2,6-dichloro-4-(3,3-dichloro- 2-propenyloxy)phenoxy)propyloxy)phthalimide, m.p., 97.3° C.

Then, 9.1 g of N-(3-(2,6-dichloro-4-(3,3-dichloro-2-propenyloxy)phenoxy)propyloxy)phthalimide was added to 150 ml of methanol, to which 1.9 g of hydrazine hydrate was added. The reaction mixture was stirred for 1 hour with heating under reflux, and returned to room temperature. To the reaction mixture was added 50 ml of water, from which the methanol was evaporated under reduced pressure. Further added were 15 ml of concentrated hydrochloric acid and 25 ml of water. The reaction mixture was stirred for 30 minutes with heating under reflux, returned to room temperature, and filtered. The crystals collected by filtration were added to 10% aqueous sodium hydrogencarbonate solution, and extracted with diethyl ether. The diethyl ether layer was washed with 10% aqueous sodium hydrogencarbonate solution and water. To this diethyl ether layer was added 3 ml of concentrated hydrochloric acid, and the mixture was concentrated and the dried, which afforded 6.8 g (yield, 92%) of O-(3-(2,6-dichloro-4-(3,3-dichloro-2-propenyloxy)phenoxy)propyl)hydroxylamine hydrochloride, m.p., 171.8° C.

Some specific examples of the intermediate compounds of formula (12) are shown below with their compound numbers and physical properties, if any.

1) O-(2-(2,6-dichloro-4-(3,3-dichloro-2-propenyloxy)phenoxy)ethyl)hydroxylamine hydrochloride, m.p., 172.2° C.

2) O-(3-(2,6-dichloro-4-(3,3-dichloro-2-propenyloxy)phenoxy)propyl)hydroxylamine hydrochloride, m.p., 171.8° C.

3) O-(4-(2,6-dichloro-4-(3,3-dichloro-2-propenyloxy)phenoxy)butyl)hydroxylamine hydrochloride, m.p., 105.3° C.
4) O-(5-(2,6-dichloro-4-(3,3-dichloro-2-propenyloxy)phenoxy)pentyl)hydroxylamine hydrochloride, m.p., 82.8° C.
5) O-(6-(2,6-dichloro-4-(3,3-dichloro-2-propenyloxy)phenoxy)hexyl)hydroxylamine hydrochloride, m.p., 94.0° C.
6) O-(3-(2,6-diethyl-4-(3,3-dichloro-2-propenyloxy)phenoxy)propyl)hydroxylamine hydrochloride
7) O-(4-(2,6-diethyl-4-(3,3-dichloro-2-propenyloxy)phenoxy)butyl)hydroxylamine hydrochloride
8) O-(5-(2,6-diethyl-4-(3,3-dichloro-2-propenyloxy)phenoxy)pentyl)hydroxylamine hydrochloride
9) O-(6-(2,6-diethyl-4-(3,3-dichloro-2-propenyloxy)phenoxy)hexyl)hydroxylamine hydrochloride
10) O-(3-(2-ethyl-6-methyl-4-(3,3-dichloro-2-propenyloxy)phenoxy)propyl)hydroxylamine hydrochloride
11) O-(4-(2-ethyl-6-methyl-4-(3,3-dichloro-2-propenyloxy)phenoxy)butyl)hydroxylamine hydrochloride
12) O-(5-(2-ethyl-6-methyl-4-(3,3-dichloro-2-propenyloxy)phenoxy)pentyl)hydroxylamine hydrochloride
13) O-(6-(2-ethyl-6-methyl-4-(3,3-dichloro-2-propenyloxy)phenoxy)hexyl)hydroxylamine hydrochloride
14) O-(3-(2-chloro-6-methyl-4-(3,3-dichloro-2-propenyloxy)phenoxy)propyl)hydroxylamine hydrochloride
15) O-(4-(2-chloro-6-methyl-4-(3,3-dichloro-2-propenyloxy)phenoxy)butyl)hydroxylamine hydrochloride
16) O-(5-(2-chloro-6-methyl-4-(3,3-dichloro-2-propenyloxy)phenoxy)pentyl)hydroxylamine hydrochloride
17) O-(6-(2-chloro-6-methyl-4-(3,3-dichloro-2-propenyloxy)phenoxy)hexyl)hydroxylamine hydrochloride The following are production examples for the carbonyl compounds of formula (22) including the intermediate compounds of formula (13) or (14) in the present invention.

Intermediate Production Example 2

Production of Intermediate Compound 18)

First, 2.06 g of terephthalaldehyde and 20 ml of ethanol were placed in a reaction vessel, to which 0.15 g of sodium borohydride was slowly added with stirring under ice cooling. After stirring at room temperature for 12 hours, the ethanol was evaporated. The residue was poured into diluted hydrochloric acid, and extracted with ethyl acetate. The ethyl acetate layer was washed twice with water, dried over anhydrous magnesium sulfate, and concentrated to give a crude product. This crude product was subjected to silica gel chromatography, which afforded 1.06 g (yield, 51%) of p-(hydroxymethyl)benzaldehyde.

To a mixture of 3.40 g of p-(hydroxymethyl)benzaldehyde obtained in the same manner as described above, 7.2 g of 2,6-dichloro-4-(3,3-dichloro-2-propenyloxy)phenol, 6.56 g of triphenylphosphine, and 50 ml of tetrahydrofuran was slowly added dropwise 5.05 g of diisopropyl azodicarboxylate with stirring under ice cooling. After stirring at room temperature for 12 hours, the reaction mixture was concentrated to give a residue. This residue was subjected to silica gel chromatography, which afforded 4.75 g (yield, 46%) of 4-((2,6-dichloro-4-(3,3-dichloro-2-propenyloxy)phenoxy)methyl)benzaldehyde, m.p., 93.9° C.

Intermediate Production Example 3

Production of Intermediate Compound 23)

First, 10.0 g of 2,6-dichloro-4-(3,3-dichloro-2-propenyloxy)phenol, 14.0 g of 1,3-dibromopropane, and 50 ml of N,N-dimethylformamide were placed in a reaction vessel, to which 5.3 g of potassium carbonate was added. After stirring at room temperature for 12 hours, the reaction mixture was filtered. The filtrate was poured into diluted hydrochloric acid, and extracted with ethyl acetate. The ethyl acetate layer was washed twice with water, dried over anhydrous magnesium sulfate, and concentrated to give a crude product. This crude product was subjected to silica gel chromatography, which afforded 6.1 g (yield, 43%) of 1-(3-bromopropyloxy)-2,6-dichloro-4-(3,3-dichloro-2-propenyloxy)benzene.

Then, 1.50 g of 1-(3-bromopropyloxy)-2,6-dichloro-4-(3,3-dichloro-2-propenyloxy)benzene obtained in the same manner as described above, 0.50 g of p-hydroxyacetophenone, and 30 ml of N,N-dimethylformamide were placed in a reaction vessel, to which 0.56 g of potassium carbonate was added. After stirring at room temperature for 24 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which afforded 1.51 g (yield, 89%) of 4'-(3-(2,6-dichloro-4-(3,3-dichloro-2-propenyloxy)phenoxy)propyloxy)acetophenone, m.p., 73.6° C.

Intermediate Production Example 4

Production of Intermediate Compound 35)

A mixture of 15.67 g of 4-bromophenetyl alcohol, 6.88 g of 3,4-dihydro-2H-pyran, a catalytic amount of p-toluenesulfonic acid monohydrate, and 100 ml of tetrahydrofuran was stirred. at room temperature for 24 hours. The reaction mixture was poured into water, and extracted twice with diethyl ether. The diethyl ether layers were combined, washed with saturated aqueous sodium hydrogencarbonate solution and saturated aqueous sodium chloride solution in this order, dried over anhydrous magnesium sulfate, and concentrated under reduced pressure, which afforded 21.5 g (yield, 97%) of 4-(2-(2-tetrahydropyranyloxy)ethyl)-1-bromobenzene, m.p., 93.9° C.

A mixture of 11.3 g of 4-(2-(2-tetrahydropyranyloxy)ethyl)-1-bromobenzene and 100 ml of tetrahydrofuran was cooled to −78° C., to which 25.9 ml of 1.56 M solution of n-butyl lithium in n-hexane was added dropwise over 15 minutes. After stirring at −78° C. for 1 hour, 4.2 ml of N,N-dimethylformamide was added dropwise at the same temperature over 15 minutes. After further stirring at −78° C. for 1 hour, 100 ml of saturated aqueous ammonium chloride solution was added, and the stirring was further continued until the reaction mixture came to room temperature. The reaction mixture was extracted twice with 200 ml of ethyl acetate, and the ethyl acetate layers were combined, washed three times with saturated aqueous ammonium chloride solution, and washed with saturated aqueous sodium chloride solution. The combined ethyl acetate layer was dried over anhydrous magnesium sulfate, and concentrated under reduced pressure to give a residue. This residue was subjected to silica gel chromatography, which afforded 7.20 g (yield, 78%) of 4-(2-(2-tetrahydropyranyloxy)ethyl) benzaldehyde, $n_D^{24.5}$ 1.5311.

A mixture of 6.50 g of 4-(2-(2-tetrahydropyranyloxy) ethyl)benzaldehyde, 130 ml of acetone, and 110 ml of 1M hydrochloric acid was stirred at room temperature for 24 hours. The reaction mixture was neutralized by the addition of saturated aqueous sodium hydrogencarbonate solution, and extracted twice with 200 ml of ethyl acetate. The ethyl acetate layers were combined, washed with saturated aqueous sodium chloride solution, dried over anhydrous magnesium sulfate, and concentrated under reduced pressure to give a residue. This residue was purified by silica gel chromatography, which 3.88 g (yield, 93%) of 4-(2-hydroxyethyl)benzaldehyde.

$^1$H-NMR (CDCl$_3$/TMS) δ (ppm): 1.42–1.88 (6H, m), 2.99 (2H, t), 3.42–3.49 (1H, m), 3.60–3.74 (2H, m), 3.94–4.04 (1H, m), 4.58–4.60 (1H, m), 7.38–7.43 (2H, m), 7.79–7.84 (2H, m), 9.98 (1H, s).

To a mixture of 3.88 g of 4-(2-hydroxyethyl) benzaldehyde, 6.7 g of 2,6-dichloro-4-(3,3-dichloro-2-propenyloxy)phenol, 100 ml of tetrahydrofuran, and 6.0 g of triphenylphosphine was added dropwise a solution of 4.7 g of diisopropyl azodicarboxylate dissolved in 20 ml of tetrahydrofuran at the ice temperature over 1 hour. After completion of the addition, the reaction mixture was stirred at room temperature for 24 hours, and concentrated under reduced pressure. The residue was subjected to silica gel chromatography, which afforded 6.63 g (yield, 69%) of 4-(2-(2,6-dichloro-4-(3,3-dichloro-2-propenyloxy)phenoxy) ethyl)benzaldehyde, m.p., 54.2° C.

Intermediate Production Example 5

Production of Intermediate Compound 37)

First, 11.1 g of 1-(3-bromopropyloxy)-2,6-dichloro-4-(3,3-dichloro-2-propenyloxy)benzene, 3.31 g of benzoic acid, and 50 ml of N,N-dimethylformamide were placed in a reaction vessel, to which 3.90 g of potassium carbonate was added. After stirring at room temperature for 24 hours, the reaction mixture was poured into water, and extracted twice with diethyl ether. The diethyl ether layers were combined, washed with water, dried over anhydrous magnesium sulfate, and concentrated to give a crude product. this crude product was subjected to silica gel chromatography, which afforded 11.6 g (yield, 95%) of 3,5-dichloro-4-(3-benzoyloxypropyloxy)-1-(3,3-dichloro-2-propenyloxy) benzene.

This 11.6 g of 3,5-dichloro-4-(3-benzoyloxypropyloxy)-1-(3,3-dichloro-2-propenyloxy)benzene, 15.2 g of 10% aqueous potassium hydroxide solution, and 300 ml of methanol were placed in a reaction vessel. After stirring at room temperature for 24 hours, the reaction mixture was concentrated. The concentrate was poured into water, and extracted twice with diethyl ether. The diethyl ether layers were combined, washed with water, dried over anhydrous magnesium sulfate, and concentrated to give a crude product. This crude product was subjected to silica gel chromatography, 7.41 g (yield, 83%) of 3-(2,6-dichloro-4-(3,3-dichloro-2-propenyloxy)phenoxy)-1-propyl alcohol.

Then, 2.00 g of 3-(2,6-dichloro-4-(3,3-dichloro-2-propenyloxy)phenoxy)-1-propyl alcohol obtained in the same manner as described above and 20 ml of tert-butyl methyl ether were placed in a reaction vessel, to which 0.24 g of sodium hydride (60% in oil) was slowly added with stirring under ice cooling. After 10 minutes, 0.9 g of 5-acetyl-2-chloropyridine (which had been produced in Reference Production Example 1 as described below) was added, and the mixture was stirred at room temperature for 1 hour and further stirred in an oil bath at 80° C. (internal temperature). After 5 hours, the reaction mixture was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which 0.62 g (yield, 23%) of 5-acetyl-2-(3-(2,6-dichloro-4-(3,3-dichloro-2-propenyloxy)phenoxy)propyloxy)pyridine, m.p., 90.5° C.

Intermediate Production Example 6

Production of Intermediate Compound 52)

To a mixture of 56.3 g of 1,4-butanediol and 400 ml of N,N-dimethylformamide was slowly added 11.0 g of 60% sodium hydride (in oil) with stirring under ice cooling. After stirring at room temperature for 12 hours, 49.3 g of bromoacetaldehyde diethylacetal was added dropwise, and the stirring was further continued at 60° C. for 8 hours. The reaction mixture was poured into ice water, and extracted twice with ethyl acetate. The ethyl acetate layers were combined, washed with water, dried over anhydrous magnesium sulfate, and concentrated to give a crude product. This crude product was subjected to silica gel chromatography, which afforded 21.6 g (yield, 41%) of 4-(2,2-diethoxyethoxy)butanol.

To a mixture of 2.30 g of 4-(2,2-diethoxyethoxy)butanol, 2.94 g of 2,6-dichloro-4-(3,3-dichloro-2-propenyloxy) phenol, 2.94 g of triphenylphosphine, and 30 ml of tetrahydrofuran was slowly added dropwise 2.48 g of diisopropylazodicarboxylate with stirring in a stream of nitrogen gas under ice cooling. After stirring at room temperature for 24 hours, the reaction mixture was concentrated to give a residue. This residue was subjected to silica gel chromatography, which afforded 4.48 g (yield, 73%) of 3,5-dichloro-1-(3,3-dichloro-2-propenyloxy)-4-(4-(2,2-diethoxyethoxy)butyloxy)benzene.

Then, 1.81 g of 3,5-dichloro-1-(3,3-dichloro-2-propenyloxy)-4-(4-(2,2-diethoxyethoxy)butyloxy)benzene was added to a mixture of 10 ml of acetic acid and 1 ml of concentrated hydrochloric acid with stirring under ice cooling, and the stirring was further continued for 15 minutes. The reaction mixture was poured into water, and extracted twice with diethyl ether. The diethyl ether layers were combined, washed with water, saturated aqueous sodium hydrogencarbonate solution, and saturated aqueous sodium chloride solution in this order, dried over anhydrous magnesium sulfate, and concentrated, which afforded 1.51 g (yield, 94%) of 4-(2,6-dichloro-4-(3,3-dichloro-2-propenyloxy)phenoxy)butyloxyacetaldehyde.

$^1$H-NMR (CDCl$_3$/TMS) δ (ppm): 1.92 (4H, m), 3.65 (2H, t), 3.99 (2H, t), 4.09 (2H, s), 4.58 (2H, d), 6.11 (1H, t), 6.84 (2H, s), 9.75 (1H, s).

Intermediate Production Example 7

Production of Intermediate Compound 57)

To a mixture of 16.0 g of 4-(2,2-diethoxyethoxy)butanol, 18.9 g of 2,6-diehtyl-4-benzoyloxyphenol (which had been produced according to the method as described in JP-A 8-337549/1996), 20.2 g of triphenylphosphine, and 200 ml of tetrahydrofuran was slowly added dropwise 17.0 g of diisopropyl azodicarboxylate with stirring under ice cooling in a stream of nitrogen gas. After stirring at room temperature for 6 hours, the reaction mixture was concentrated to give a residue. This residue was subjected to silica gel chromatography, which afforded 31.4 g (yield, 88%) of 3,5-diethyl-1-benzoyloxy-4-(4-(2,2-diethoxyethoxy) butyloxy)benzene, $n_D^{24.8}$ 1.5129.

To a solution of 31.0 g of 3,5-diethyl-1-benzoyloxy-4-(4-(2,2-diethoxyethoxy)butyloxy)benzene dissolved in 100 ml of methanol was added a solution of 5.1 g of potassium hydroxide dissolved in 25 g of water. After stirring at room temperature for 1 hour, the reaction mixture was acidified by the addition of diluted hydrochloric acid, and concentrated. The residue was poured into water, and extracted twice with ethyl acetate. The ethyl acetate layers were combined, washed with water, dried over anhydrous magnesium sulfate, and concentrated to give a crude product. This crude product was subjected to silica gel chromatography, which afforded 0.60 g (yield, 94%) of 3,5-diethyl-4-(4-(2,2-diethoxyethoxy)butyloxy)phenol, $n_D^{25.0}$ 1.4890.

Then, 19.9 g of 3,5-diethyl-4-(4-(2,2-diethoxyethoxy) butyloxy)phenol, 9.20 g of 1,1,3-trichloro-1-propene, 9.15 g of potassium carbonate, and 200 ml of N,N-dimethylformamide were placed in a reaction vessel. After stirring at room temperature for 24 hours, the reaction mixture was poured into water, and extracted twice with diethyl ether. The diethyl ether layers were combined, washed with water, dried over anhydrous magnesium, and concentrated to give a residue. This residue was subjected to silica gel chromatography, which afforded 25.4 g (yield, 91%) of 3,5-diethyl-1-(3,3-dichloro-2-propenyloxy)-4-(4-(2,2-diethoxyethoxy)butyloxy)benzene, $n_D^{26.0}$ 1.4991.

To a mixture of 9.27 g of 3,5-diethyl-1-(3,3-dichloro-2-propenyloxy)-4-(4-(2,2-diethoxyethoxy)butyloxy)benzene, 25 ml of acetic acid, and 5 ml of water was added 1 ml of concentrated hydrochloric acid at room temperature. After stirring at room temperature for 30 minutes, the reaction mixture was poured into water, and extracted twice with diethyl ether. The diethyl ether layers were combined, washed with water, aqueous sodium hydrogencarbonate solution, and aqueous sodium chloride solution in this order, dried over anhydrous magnesium sulfate, and concentrated, which afforded 7.62 g (yield, 98%) of 4-(2,6-diethyl-4-(3,3-dichloro-2-propenyloxy)phenoxy)butyloxyacetaldehyde.

$^1$H-NMR (CDCl$_3$/TMS) δ (ppm): 1.22 (6H, t), 1.88 (4H, m), 2.63 (4H, q), 3.63 (2H, t), 3.74 (2H, t), 4.09 (2H, s), 4.61 (2H, d), 6.14 (1H, t), 6.57 (2H, s), 9.75 (1H, s).

Intermediate Production Example 8

Production of Intermediate Compound 68)

First, 65.1 g of 1,5-pentanediol, 18.6 g of proparygyl chloride, 12.0 g of sodium hydroxide (powdery), 5.69 g of benzyltriethylammonium chloride, and 200 ml of tetrahydrofuran were placed in a reaction vessel, and reaction mixture was stirred for 4 hours with heating under reflux. The reaction mixture was filtered through Celite, and the filtrate was poured into water, and extracted twice with diethyl ether. The diethyl ether layers were combined, washed with water, dried over anhydrous magnesium sulfate, and concentrated to give a crude product. This crude product was subjected to silica gel chromatography, which afforded 12.4 g (yield, 35%) of 5-(2-propynyloxy)pentanol, $n_D^{263}$ 1.4533.

To a mixture of 2.35 g of 5-(2-propynyloxy)pentanol, 4.32 g of 2,6-dichloro-4-(3,3-dichloro-2-propenyloxy)phenol, 4.33 g of triphenylphosphine, and 30 ml of tetrahydrofuran was slowly added dropwise 3.64 g of diisopropyl azodicarboxylate with stirring under ice cooling in a stream of nitrogen gas. After stirring at room temperature for 24 hours, the reaction mixture was concentrated to give a residue. This residue was subjected to silica gel chromatography which afforded 5.17 g (yield, 84%) of 3,5-dichloro-1-(3,3-dichloro-2-propynyloxy)-4-(5-(2-propynyloxy)pentyloxy) benzene, $n_D^{25.5}$ 1.5400.

A mixture of 4.12 g of 3,5-dichloro-1-(3,3-dichloro-2-propenyloxy)-4-(5-(2-propenyloxy)pentyloxy)benzene, 0.36 g of mercury (II) sulfate, 5 ml of 1% aqueous sulfuric acid solution, and 50 ml of tetrahydrofuran was stirred at 60° C. for 1 hour. The reaction mixture was filtered through Celite, and the filtrate was poured into diluted hydrochloric acid, and extracted twice with diethyl ether. The diethyl ether layers were combined, washed with diluted hydrochloric acid and water in this order, dried over magnesium sulfate, and concentrated to give a crude product. This crude product was subjected to silica gel chromatography, which afforded 4.05 g (yield, 94%) of 5-(2,6-dichloro-4-(3,3-dichloro-2-propenyloxy)phenoxy)pentyloxyacetone, $n_D^{25.5}$ 1.5350.

Intermediate Production Example 9

Production of Intermediate Compound 99)

First, 16.3 g of 2,6-dichloro-4-(3,3-dichloro-2-propenyloxy)phenol, 20.7 g of potassium carbonate, 11.8 g of ethyl 5-bromovalerate, and 200 ml of N,N-dimethylformamide were placed in a reaction vessel. After stirring at room temperature for 24 hours, the reaction mixture was filtered. The filtrate was poured into diluted hydrochloric acid, and extracted twice with diethyl ether. The diethyl ether layers were combined, washed with water, dried over anhydrous magnesium sulfate, and concentrated to give a crude product. This crude product was subjected to silica gel chromatography, which 18.9 g (yield, 80%) of ethyl 5-(2,6-dichloro-4-(3,3-dichloro-2-propenyloxy) phenoxy)valerate, $n_D^{24.0}$ 1.5331.

To a mixture of 4.06 g of ethyl 5-(2,6-dichloro-4-(3,3-dichloro-2-propenyloxy)phenoxy)valerate and 50 ml of toluene was added dropwise 10.27 ml of 0.95 mol/liter diisobutyl aluminum hydride (hexane solution) over 30 minutes with stirring at −70° C. in a stream of nitrogen gas. After further stirring at −70° C. for 1 hour, 50 ml of saturated aqueous ammonium chloride solution was added. The reaction mixture was returned to room temperature, and poured into 50 ml of diluted hydrochloric acid, and extracted twice with toluene. The toluene layers were combined, washed with water, dried over anhydrous magnesium sulfate, and concentrated, which afforded 3.52 g (yield, 96%) of 5-(2,6-dichloro-4-(3,3-dichloro-2-propenyloxy)phenoxy)pentanal.

$^1$H-NMR (CDCl$_3$/TMS) δ (ppm): 1.80–2.11 (4H, brs), 2.58 (2H, t), 3.99 (2H, t), 4.62 (2H, d), 6.13 (1H, t), 6.85 (2H, d), 9.81 (1H, s).

Intermediate Production Example 10

Production of Intermediate Compound 96)

First, 8.64 g of 2,6-dichloro-4-(3,3-dichloro-2-propenyloxy)phenol, 4.98 g of potassium carbonate, 3.36 g of chloroacetone, and 50 ml of N,N-dimethylformamide were placed in a reaction vessel. After stirring at room temperature for 24 hours, the reaction mixture was filtered. The filtrate was poured into diluted hydrochloric acid, and extracted twice with diethyl ether. The diethyl ether layers were combined, washed with water, dried over anhydrous magnesium sulfate, and concentrated, which afforded 10.12 g (yield, 98%) of (2,6-dichloro-4-(3,3-dichloro-2-propenyloxy)phenoxy-acetone, m.p., 83.8° C.

Some specific examples of the carbonyl compounds of formula (22) including the intermediate compounds of formula (13) or (14) of the present invention are shown below with their compound numbers and their physical properties, if any.

18) 4-((2,6-dichloro-4-(3,3-dichloro-2-propenyloxy)phenoxy)methyl)benzaldehyde, m.p., 93.9° C.
19) 4-((2,6-dichloro-4-(3,3-dibromo-2-propenyloxy)phenoxy)methyl)benzaldehyde
20) 4-((2-(2,6-dichloro-4-(3,3-dichloro-2-propenyloxy)phenoxy)ethoxy)benzaldehyde, m.p., 81.3° C.
21) 4-(3-(2,6-dichloro-4-(3,3-dichloro-2-propenyloxy)phenoxy)propyloxy)benzaldehyde, m.p., 76.5° C.
22) 4-(4-(2,6-dichloro-4-(3,3-dichloro-2-propenyloxy)phenoxy)butyloxy)benzaldehyde, m.p., 54.9° C.
23) 4'-(3-(2,6-dichloro-4-(3,3-dichloro-2-propenyloxy)phenoxy)propyloxy)acetophenone, m.p., 73.6° C.
24) 4'-(4-(2,6-dichloro-4-(3,3-dichloro-2-propenyloxy)phenoxy)butyloxy)acetophenone, glassy
25) 3-(3-(2,6-dichloro-4-(3,3-dichloro-2-propenyloxy)phenoxy)propyloxy)benzaldehyde, $n_D^{24.5}$ 1.5809
26) 3-(4-(2,6-dichloro-4-(3,3-dichloro-2-propenyloxy)phenoxy)butyloxy)benzaldehyde, $n_D^{24.5}$ 1.5770
27) 4'-(3-(2,6-dichloro-4-(3,3-dichloro-2-propenyloxy)phenoxy)propyloxy)benzophenone, $n_D^{24.5}$ 1.5928
28) 4'-(3-(2,6-dichloro-4-(3,3-dichloro-2-propenyloxy)phenoxy)propyloxy)propiophenone, m.p., 39.8° C.
29) 4'-(3-(2,6-dichloro-4-(3,3-dichloro-2-propenyloxy)phenoxy)propyloxy)valerophenone, $n_D^{24.5}$ 1.5703
30) 4-(5-(2,6-dichloro-4-(3,3-dichloro-2-propenyloxy)phenoxy)pentyloxy)benzaldehyde, m.p., 41.4° C.
31) 4'-(5-(2,6-dichloro-4-(3,3-dichloro-2-propenyloxy)phenoxy)pentyloxy)acetophenone, m.p., 101.0° C.
32) 4'-(2-(2,6-dichloro-4-(3,3-dichloro-2-propenyloxy)phenoxy)ethyloxy)acetophenone, m.p., 100.1° C.
33) 3-((2,6-dichloro-4-(3,3-dichloro-2-propenyloxy)phenoxy)methyl)benzaldehyde
$^1$H-NMR (CDCl$_3$/TMS) δ (ppm): 4.61 (2H, d), 5.06 (2H, s), 6.13 (1H, t), 6.89 (2H, s), 7.58 (1H, t), 7.86 (1H, dt), 7.87 (1H, dt), 8.05 (1H, t), 10.06 (1H, s),
34) 4'-(2,6-dichloro-4-(3,3-dichloro-2-propenyloxy)phenoxymethyl)acetophenone, m.p., 88.6° C.
35) 4-(2-(2,6-dichloro-4-(3,3-dichloro-2-propenyloxy)phenoxy)ethyl)benzaldehyde, m.p., 54.2° C.
36) 4-((2,6-dichloro-4-(3,3-dichloro-2-propenyloxy)phenoxy)methyl)phenoxyacetaldehyde
37) 5-acetyl-2-(3-(2,6-dichloro-4-(3,3-dichloro-2-propenyloxy)phenoxy)propyloxy)pyridine, m.p., 90.5° C.
38) 4-(3-(2,6-dichloro-4-(3,3-dichloro-2-propenyloxy)phenoxy)propyl)benzaldehyde, m.p., 61.0° C.
39) 4-(4-(2,6-dichloro-4-(3,3-dichloro-2-propenyloxy)phenoxy)butyl)benzaldehyde
40) 4'-((2,6-dichloro-4-(3,3-dichloro-2-propenyloxy)phenoxy)methyl)-2,2,2-trifluoroacetophenone
41) 4-(2-(2,6-dichloro-4-(3,3-dichloro-2-propenyloxy)phenoxy)ethyl)-2,2,2-trifluoroacetophenone
42) 4'-(3-(2,6-dichloro-4-(3,3-dichloro-2-propenyloxy)phenoxy)propyl)-2,2,2-trifluoroacetophenone
43) (2-(3-(2,6-dichloro-4-(3,3-dichloro-2-propenyloxy)phenoxy)propyloxy)-5-pyridyl)acetaldehyde
44) (2-(4-(2,6-dichloro-4-(3,3-dichloro-2-propenyloxy)phenoxy)butyloxy)-5-pyridyl)acetaldehyde
45) 2-(3-(2,6-dichloro-4-(3,3-dichloro-2-propenyloxy)phenoxy)propyloxy)-5-pyridyl phenyl ketone
46) 2-(4-(2,6-dichloro-4-(3,3-dichloro-2-propenyloxy)phenoxy)butyloxy)-5-pyridyl phenyl ketone
47) 5-((2,6-dichloro-4-(3,3-dichloro-2-propenyloxy)phenoxy)methyl)-2-furfural
48) 5-((2,6-dichloro-4-(3,3-dichloro-2-propenyloxy)phenoxy)methyl)-2-thiophenecarboxaldehyde
49) 5-((2,6-dichloro-4-(3,3-dichloro-2-propenyloxy)phenoxy)methyl)-2-pyrrolcarboxaldehyde
50) 2-(2,6-dichloro-4-(3,3-dichloro-2-propenyloxy)phenoxy)ethoxyacetaldehyde
51) 3-(2,6-dichloro-4-(3,3-dichloro-2-propenyloxy)phenoxy)propyloxyacetaldehyde
$^1$H-NMR (CDCl$_3$/TMS) δ (ppm): 2.15 (2H, t), 3.83 (2H, t), 4.08 (2H, t), 4.12 (2H, s), 4.58 (2H, d), 6.11 (1H, t), 6.84 (2H, s), 9.74 (1H, s).
52) 4-(2,6-dichloro-4-(3,3-dichloro-2-propenyloxy)phenoxy)butyloxyacetaldehyde
$^1$H-NMR (CDCl$_3$/TMS) δ (ppm): 1.92 (4H, m), 3.65 (2H, t), 3.99 (2H, t), 4.09 (2H, s), 4.58 (2H, d), 6.11 (1H, t), 6.84 (2H, s), 9.75 (1H, s).
53) 5-(2,6-dichloro-4-(3,3-dichloro-2-propenyloxy)phenoxy)pentyloxyacetaldehyde
$^1$H-NMR (CDCl$_3$/TMS) δ (ppm): 1.59–1.77 (4H, brs), 1.86 (2H, brs), 3.58 (2H, t), 3.96 (2H, t), 4.07 (2H, s), 4.58 (2H, d), 6.11 (1H, t), 6.83 (2H, s), 9.74 (1H, s).
54) 6-(2,6-dichloro-4-(3,3-dichloro-2-propenyloxy)phenoxy)hexyloxyacetaldehyde
$^1$H-NMR (CDCl$_3$/TMS) δ (ppm): 1.4–1.9 (8H, m), 3.55 (2H, t), 3.95 (2H, t), 4.06 (2H, s), 4.58 (2H, d), 6.11 (1H, t), 6.83 (2H, s), 9.74 (1H, s).
55) 2-(2,6-diethyl-4-(3,3-dichloro-2-propenyloxy)phenoxy)ethoxycetaldehyde
56) 3-(2,6-diethyl-4-(3,3-dichloro-2-propenyloxy)phenoxy)propylxyacetaldehyde
57) 4-(2,6-diethyl-4-(3,3-dichloro-2-propenyloxy)phenoxy)butyloxyacetaldehyde
$^1$H-NMR (CDCl$_3$/TMS) δ (ppm): 1.22 (6H, t), 1.88 (4H, m), 2.63 (4H, q), 3.63 (2H, t), 3.74 (2H, t), 4.09 (2H, s), 4.61 (2H, d), 6.14 (1H, t), 6.57 (2H, s), 9.75 (1H, s).
58) 5-(2,6-diethyl-4-(3,3-dichloro-2-propenyloxy)phenoxy)pentyloxyacetaldehyde
$^1$H-NMR (CDCl$_3$/TMS) δ (ppm): 1.22 (6H, t), 1.60–1.82 (6H, brs), 2.63 (2H, q), 3.58 (2H, t), 3.71 (2H, t), 4.07 (2H, s), 4.61 (2H, d), 6.14 (1H, t), 6.57 (2H, s), 9.74 (1H, s).
59) 6-(2,6-diethyl-4-(3,3-dichloro-2-propenyloxyphenoxy)hexyloxyacetaldehyde
60) 2-(2-ethyl-6-methyl-4-(3,3-dichloro-2-propenyloxy)phenoxy)ethoxyacetaldehyde
61) 3-(2-ethyl-6-methyl-4-(3,3-dichloro-2-propenyloxy)phenoxy)propyloxyacetaldehyde
62) 4-(2-ethyl-6-methyl-4-(3,3-dichloro-2-propenyloxy)phenoxy)butyloxyacetaldehyde
63) 5-(2-ethyl-6-methyl-4-(3,3-dichloro-2-propenyloxy)phenoxy)pentyloxyacetaldehyde
64) 6-(2-ethyl-6-methyl-4-(3,3-dichloro-2-propenyloxy)phenoxy)hexyloxyacetaldehyde 65) 2-(2,6-dichloro-4-(3,3-dichloro-2-propenyloxy) phenoxy)ethoxyacetone
66) 3-(2,6-dichloro-4-(3,3-dichloro-2-propenyloxy) phenoxy)propyloxyacetone
67) 4-(2,6-dichloro-4-(3,3-dichloro-2-propenyloxy) phenoxy)butyloxyacetone
68) 5-(2,6-dichloro-4-(3,3-dichloro-2-propenyloxy) phenoxy)pentyloxyacetone, $n_D^{25.5}$ 1.5350
69) 6-(2,6-dichloro-4-(3,3-dichloro-2-propenyloxy) phenoxy)hexyloxyacetone
70) 2-(2,6-diethyl-4-(3,3-dichloro-2-propenyloxy) phenoxy)ethoxyacetone
71) 3-(2,6-diethyl-4-(3,3-dichloro-2-propenyloxy) phenoxy)propyloxyacetone
72) 4-(2,6-diethyl-4-(3,3-dichloro-2-propenyloxy) phenoxy)butyloxyacetone
73) 5-(2,6-diethyl-4-(3,3-dichloro-2-propenyloxy) phenoxy)pentyloxyacetone
74) 6-(2,6-diethyl-4-(3,3-dichloro-2-propenyloxy) phenoxy)hexyloxyacetone
75) 2-(2-ethyl-6-methyl-4-(3,3-dichloro-2-propenyloxy) phenoxy)ethoxyacetone
76) 3-(2-ethyl-6-methyl-4-(3,3-dichloro-2-propenyloxy) phenoxy)propyloxyacetone
77) 4-(2-ethyl-6-methyl-4-(3,3-dichloro-2-propenyloxy) phenoxy)butyloxyacetone
78) 5-(2-ethyl-6-methyl-4-(3,3-dichloro-2-propenyloxy) phenoxy)pentyloxyacetone
79) 6-(2-ethyl-6-methyl-4-(3,3-dichloro-2-propenyloxy) phenoxy)hexyloxyacetone
80) 3-(2-(2,6-dichloro-4-(3,3-dichloro-2-propenyloxy) phenoxy)thoxy)propionaldehyde
81) 3-(3-(2,6-dichloro-4-(3,3-dichloro-2-propenyloxy) phenoxy)proyloxy)propionaldehyde
82) 3-(4-(2,6-dichloro-4-(3,3-dichloro-2-propenyloxy) phenoxy)butyloxy)propionaldehyde
83) 3-(5-(2,6-dichloro-4-(3,3-dichloro-2-propenyloxy) phenoxy)pentyloxy)propionaldehyde
84) 3-(6-(2,6-dichloro-4-(3,3-dichloro-2-propenyloxy) phenoxy)hexyloxy)propionaldehyde
85) 3-(2-(2,6-diethyl-4-(3,3-dichloro-2-propenyloxy) phenoxy)ethoxy)propionaldehyde
86) 3-(3-(2,6-diethyl-4-(3,3-dichloro-2-propenyloxy) phenoxy)propyloxy)propionaldehyde
87) 3-(4-(2,6-diethyl-4-(3,3-dichloro-2-propenyloxy) phenoxy)butyloxy)propionaldehyde
88) 3-(5-(2,6-diethyl-4-(3,3-dichloro-2-propenyloxy) phenoxy)pentyloxy)propionaldehyde
89) 3-(6-(2,6-diethyl-4-(3,3-dichloro-2-propenyloxy) phenoxy)hexyloxy)propionaldehyde
90) 3-(2-(2-ethyl-6-methyl-4-(3,3-dichloro-2-propenyloxy)phenoxy)ethoxy)propionaldehyde
91) 3-(3-(2-ethyl-6-methyl-4-(3,3-dichloro-2-propenyloxy)phenoxy)propyloxy)propionaldehyde
92) 3-(4-(2-ethyl-6-methyl-4-(3,3-dichloro-2-propenyloxy)phenoxy)butyloxy)propionaldehyde
93) 3-(5-(2-ethyl-6-methyl-4-(3,3-dichloro-2-propenyloxy)phenoxy)pentyloxy)propionaldehyde
94) 3-(6-(2-ethyl-6-methyl-4-(3,3-dichloro-2-propenyloxy)phenoxy)hexyloxy)propionaldehyde
95) (2,6-dichloro-4-(3,3-dichloro-2-propenyloxy) phenoxy)acetaldehyde
96) (2,6-dichloro-4-(3,3-dichloro-2-propenyloxy) phenoxy)acetone, m.p., 83.8° C.
97) 3-(2,6-dichloro-4-(3,3-dichloro-2-propenyloxy) phenoxy)propionaldehyde
$^1$H-NMR (CDCl$_3$/TMS) δ (ppm): 2.91 (2H, dt), 4.33 (2H, t), 4.59 (2H, d), 6.11 (1H, t), 6.85 (2H, s), 9.97 (1H, d).
98) 4-(2,6-dichloro-4-(3,3-dichloro-2-propenyloxy) phenoxy)butanal
$^1$H-NMR (CDCl$_3$/TMS) δ (ppm): 2.14 (2H, tt), 2.80 (2H, t), 3.99 (2H, t), 4.58 (2H, d), 6.11 (1H, t), 6.83 (2H, s), 9.88 (1H, s).
99) 5-(2,6-dichloro-4-(3,3-dichloro-2-propenyloxy) phenoxy)pentanal
$^1$H-NMR (CDCl$_3$/TMS) δ (ppm): 1.80–2.11 (4H, brs), 2.58 (2H, t), 3.99 (2H, t), 4.62 (2H, d), 6.13 (1H, t), 6.85 (2H, d), 9.81 (1H, s).
100) 6-(2,6-dichloro-4-(3,3-dichloro-2-propenyloxy) phenoxy)hexanal
$^1$H-NMR (CDCl$_3$/TMS) δ (ppm): 1.50–1.95 (6H, brs), 2.48 (2H, t), 3.95 (2H, t), 4.58 (2H, d), 6.11 (1H, t), 6.83 (2H, s), 9.79 (1H, s).
101) (2,6-diethyl-4-(3,3-dichloro-2-propenyloxy) phenoxy)acetaldehyde
102) (2,6-diethyl-4-(3,3-dichloro-2-propenyloxy) phenoxy)acetone
103) 3-(2,6-diethyl-4-(3,3-dichloro-2-propenyloxy) phenoxy)propionaldehyde
104) 4-(2,6-diethyl-4-(3,3-dichloro-2-propenyloxy) phenoxy)butanal
105) 5-(2,6-diethyl-4-(3,3-dichloro-2-propenyloxy) phenoxy)pentanal
106) 6-(2,6-diethyl-4-(3,3-dichloro-2-propenyloxy) phenoxy)hexanal
107) (2-ethyl-6-methyl-4-(3,3-dichloro-2-propenyloxy) phenoxy)acetaldehyde
108) (2-ethyl-6-methyl-4-(3,3-dichloro-2-propenyloxy) phenoxy)acetone
109) 3-(2-ethyl-6-methyl-4-(3,3-dichloro-2-propenyloxy) phenoxy)propionaldehyde
110) 4-(2-ethyl-6-methyl-4-(3,3-dichloro-2-propenyloxy) phenoxy)butanal
111) 5-(2-ethyl-6-methyl-4-(3,3-dichloro-2-propenyloxy) phenoxy)pentanal
112) 6-(2-ethyl-6-methyl-4-(3,3-dichloro-2-propenyloxy) phenoxy)hexanal
113) 2-(2,6-dichloro-4-(3,3-dichloro-2-propenyloxy) phenoxy)acetophenone, m.p., 112.5° C.
114) 7-(2,6-dichloro-4-(3,3-dichloro-2-propenyloxy) phenoxy)heptyloxyacetone
115) 4-(2,6-dichloro-4-(3,3-dichloro-2-propenyloxy) phenoxy)-2-butenyloxyacetone
116) 2-(2-(2,6-dichloro-4-(3,3-dichloro-2-propenyloxy) phenoxy)ethoxy)ethoxyacetone
117) 2-(N-(2-(2,6-dichloro-4-(3,3-dichloro-2-propenyloxy)phenoxy)ethyl)-N-methylamino) ethoxyacetone
118) 4-(2,6-dichloro-4-(3,3-dichloro-2-propenyloxy) phenoxy)cyclohexyloxyacetone The following are production examples for the intermediate compounds of formula (15).

Intermediate Production Example 11

Production of Intermediate Compound 138)

First, 0.56 g of 2,6-dichloro-4-benzoyloxyphenol (which can be produced according to the method as described in JP-A 8-337549/1996), 0.30 g of potassium carbonate, 0.74 g of 5-(methanesulfonyloxy)pentyloxyacetone O-tert-butyloxime, and 10 ml of N,N-dimethylformamide are placed in a reaction vessel. After stirring at room temperature for 24 hours, the reaction mixture is poured into diluted hydrochloric acid, and extracted twice with diethyl ether. The diethyl ether layers are combined, washed with water, dried over anhydrous magnesium sulfate, and concentrated to give a crude product. This crude product is subjected to silica gel chromatography, which affords 5-(2,6-dichloro-4-(benzoyloxy)phenoxy)pentyloxyacetone O-tert-butyloxime.

To a solution of 0.99 g of 5-(2,6-dichloro-4-(benzoyloxy)phenoxy)pentyloxyacetone O-tert-butyloxime dissolved in 7.5 ml of methanol is added a solution of 0.15 g of potassium hydroxide dissolved in 1.5 ml of water. After stirring at room temperature for 1 hour, the reaction mixture is acidified by the addition of diluted hydrochloric acid, and concentrated. Water is added to the residue, and the mixture is extracted twice with ethyl acetate. The ethyl acetate layers are combined, washed with water, dried over anhydrous magnesium sulfate, and concentrated to give a crude product. This crude product is subjected to silica gel chromatography, which affords 5-(2,6-dichloro-4-hydroxyphenoxy)pentyloxyacetone O-tert-butyloxime.

Some specific examples of the intermediate compounds of formula (15) are shown below with their compound numbers and their physical properties, if any.

119) 4-(2,6-dichloro-4-hydroxyphenoxy)butanal O-isopropyloxime
120) 5-(2,6-dichloro-4-hydroxyphenoxy)pentanal O-isopropyloxime
121) 6-(2,6-dichloro-4-hydroxyphenoxy)hexanal O-isopropyloxime
122) 4-(2,6-dichloro-4-hydroxyphenoxy)butanal O-tert-butyloxime
123) 5-(2,6-dichloro-4-hydroxyphenoxy)pentanal O-tert-butyloxime
124) 6-(2,6-dichloro-4-hydroxyphenoxy)hexanal O-tert-butyloxime
125) 4-(2,6-dichloro-4-hydroxyphenoxy)butanal O-(2,2,2-trichloroethyl)oxime
126) 5-(2,6-dichloro-4-hydroxyphenoxy)pentanal O-(2,2,2-trichloroethyl)oxime
127) 6-(2,6-dichloro-4-hydroxyphenoxy)hexanal O-(2,2,2-trichloroethyl)oxime
128) 4-(2,6-dichloro-4-hydroxyphenoxy)butanal O-(3,3-dichloro-2-propenyl)oxime
129) 5-(2,6-dichloro-4-hydroxyphenoxy)pentanal O-(3,3-dichloro-2-propenyl)oxime
130) 6-(2,6-dichloro-4-hydroxyphenoxy)hexanal O-(3,3-dichloro-2-propenyl)oxime
131) 4-(2,6-dichloro-4-hydroxyphenoxy)butyloxyacetaldehyde O-isopropyloxime
132) 5-(2,6-dichloro-4-hydroxyphenoxy)pentyloxyacetaldehyde O-isopropyloxime
133) 4-(2,6-dichloro-4-hydroxyphenoxy)butyloxyacetone O-isopropyloxime
134) 5-(2,6-dichloro-4-hydroxyphenoxy)pentyloxyacetone O-isopropyloxime
135) 4-(2,6-dichloro-4-hydroxyphenoxy)butyloxyacetaldehyde O-tert-butyloxime
136) 5-(2,6-dichloro-4-hydroxyphenoxy)pentyloxyacetaldehyde O-tert-butyloxime
137) 4-(2,6-dichloro-4-hydroxyphenoxy)butyloxyacetone O-tert-butyloxime
138) 5-(2,6-dichloro-4-hydroxyphenoxy)pentyloxyacetone O-tert-butyloxime
139) 4-(2,6-dichloro-4-hydroxyphenoxy)butyloxyacetaldehyde O-(2,2,2-trichloroethyl)oxime
140) 5-(2,6-dichloro-4-hydroxyphenoxy)pentyloxyacetaldehyde O-(2,2,2-trichloroethyl)oxime
141) 4-(2,6-dichloro-4-hydroxyphenoxy)butyloxyacetone O-(2,2,2-trichloroethyl)oxime
142) 5-(2,6-dichloro-4-hydroxyphenoxy)pentyloxyacetone O-(2,2,2-trichloroethyl)oxime
143) 4-(2,6-dichloro-4-hydroxyphenoxy)butyloxyacetaldehyde O-(3,3-dichloro-2-propenyl)oxime
144) 5-(2,6-dichloro-4-hydroxyphenoxy)pentyloxyacetaldehyde O-(3,3-dichloro-2-propenyl)oxime
145) 4-(2,6-dichloro-4-hydroxyphenoxy)butyloxyacetone O-(3,3-dichloro-2-propenyl)oxime
146) 5-(2,6-dichloro-4-hydroxyphenoxy)pentyloxyacetone O-(3,3-dichloro-2-propenyl)oxime
147) 4-(2,6-dichloro-4-hydroxyphenoxymethyl)benzaldehyde O-sec-butyloxime
148) 4-(2,6-dichloro-4-hydroxyphenoxymethyl)benzaldehyde O-t-butyloxime
149) 4-(2-(2,6-dichloro-4-hydroxyphenoxy)ethyl)benzaldehyde O-sec-butyloxime
150) 4-(2-(2,6-dichloro-4-hydroxyphenoxy)ethyl)benzaldehyde O-allyloxime
151) 4-(2-(2,6-dichloro-4-hydroxyphenoxy)ethyl)benzaldehyde O-(3,3-dichloro-2-propenyl)oxime
152) 4-(3-(2,6-dichloro-4-hydroxyphenoxy) propyloxy)benzaldehyde O-n-propyloxime
153) 4-(3-(2,6-dichloro-4-hydroxyphenoxy)propyloxy)benzaldehyde O-isopropyloxime
154) 4-(3-(2,6-dichloro-4-hydroxyphenoxy)propyloxy)benzaldehyde O-sec-butyloxime
155) 4-(3-(2,6-dichloro-4-hydroxyphenoxy)propyloxy)benzaldehyde O-t-butyloxime
156) 4'-(3-(2,6-dichloro-4-hydroxyphenoxy)propyloxy)acetophenone O-ethyloxime
157) 4'-(3-(2,6-dichloro-4-hydroxyphenoxy)propyloxy)propiophenone O-ethyloxime
158) 4'-(4-(2,6-dichloro-4-hydroxyphenoxy)butyloxy)acetophenone O-ethyloxime
159) 4'-(4-(2,6-dichloro-4-hydroxyphenoxy)butyloxy)acetophenone O-n-propyloxime
160) 4-(4-(2,6-dichloro-4-hydroxyphenoxy)butyloxy)benzaldehyde O-isopropyloxime
161) 4'-(3-(2,6-dichloro-4-hydroxyphenoxy)propyloxy)-2,2,2-trifluoroacetophenone O-ethyloxime
162) 4-(trifluoromethyl)benzaldehyde O-(4-(2,6-dichloro-4-hydroxyphenoxy)butyl)oxime
163) 4'-(trifluoromethyl)acetophenone O-(4-(2,6-dichloro-4-hydroxyphenoxy)butyl)oxime
164) trimethylacetaldehyde O-(5-(2,6-dichloro-4-hydroxyphenoxy)pentyl)oxime
165) 3,3-dimethyl-2-butanone O-(5-(2,6-dichloro-4-hydroxyphenoxy)pentyl)oxime
166) 3,3-dimethyl-2-butanone O-(4-(2,6-dichloro-4-hydroxyphenoxy)butyl)oxime 167) 4-methyl-2-pentanone O-(4-(2,6-dichloro-4-hydroxyphenoxy)butyl)oxime 168) 4-methyl-2-pentanone O-(5-(2,6-dichloro-4-hydroxyphenoxy)pentyl)oxime 169) 3-methyl-2-butanone O-(5-(2,6-dichloro-4-hydroxyphenoxy)pentyl)oxime Reference Production Example 1 Production example for 5-acetyl-2-chloropyridine used in Intermediate Production Example 5.

First, 15.45 g of 6-chloronicotinic acid and 100 ml of diethyl ether were placed in a reaction vessel, to which 131 ml of methyl lithium (1.5 M ether solution) was slowly added dropwise with stirring under ice cooling (internal temperature, 0° C. to −5° C.). After completion of the addition, the reaction mixture was further stirred at room temperature for 24 hours, and concentrated. The residue was poured into diluted hydrochloric acid, and extracted twice with diethyl ether. The diethyl ether layers were combined, washed with water, dried over anhydrous magnesium sulfate, and concentrated. This crude product was subjected to silica gel chromatography, which 13.11 g (yield, 86%) of 5-acetyl-2-chloropyridine.

The following are production examples for the intermediate compounds of formula (21)

Reference Production Example 2

Production of O-(3,3-dichloro-2-propenyl) hydroxylamine Hydrochloride

To a mixture of 44 g of N-hydroxyphthalimide, 39 g of potassium carbonate, and 400 ml of N,N-dimethylformamide was added 41 g of 1,1,3-trichloro-1-propene at room temperature. After stirring at room temperature for 12 hours, the reaction mixture was poured into diluted hydrochloric acid to cause the deposition of crystals. These crystals were collected by filtration, washed with water and hexane in this order, and dried under reduced pressure, which afforded 66 g (yield, 90%) of N-(3,3-dichloro-2-propenyloxy)phthalimide.

To a mixture of 66 g of N-(3,3-dichloro-2-propenyloxy) phthalimide and 300 ml of chloroform was slowly added dropwise a mixture of 13 g of hydrazine hydrate and 17 ml of isopropyl alcohol at room temperature. After stirring 3 hours with heating under reflux, the reaction mixture was returned to room temperature, in which 100 ml of hexane was poured. The reaction mixture was filtered, and the filtrate was concentrated to give a residue, in which 100 ml of hexane was again poured. This hexane solution was again filtered, and hydrogen chloride gas was blown in the filtrate to cause the deposition of crystals. These crystals were collected by filtration, and dried under reduced pressure, which afforded 26 g (yield, 60%) of O-(3,3-dichloro-2-propenyl)hydroxylamine hydrochloride.

$^1$H-NMR (CDCl$_3$-CD$_3$OD/TMS) δ (ppm): 4.76 (2H, s), 6.17 (1H, t).

Reference Production Example 3

Production of O-(3-(5-trifluoromethyl-2-pyridyloxy) propyl)Hydroxylamine.

To a mixture of 12.6 g of 1,3-propanediol and 100 ml of N,N-dimethylformamide was added in portions 3.30 g of 60% sodium hydride (in oil) at room temperature over 30 minutes with stirring in a stream of nitrogen gas. After further stirring at room temperature for 1 hour, a solution of 10.0 g of 2-chloro-5-trifluoromethylpyridine in 20 ml of N,N-dimethylformamide was added dropwise over 40 minutes. After further stirring at room temperature overnight, 100 ml of about 2 N diluted hydrochloric acid was added over 15 minutes to complete the reaction. The reaction mixture was extracted twice with 500 ml of toluene in total. The toluene layers were combined, washed with diluted hydrochloric acid and saturated aqueous sodium hydrogencarbonate solution in this order, dried over anhydrous magnesium sulfate, and concentrated to give 9.70 g of oil. This oil was dissolved with heating in 300 ml of hexane, followed by recrystallization, which afforded 5.3 g (yield, 44%) of 2-(3-hydroxypropyloxy)-5-trifluoromethylpyridine, m.p., 46.6° C.

To a mixture of 20.0 g of 2-(3-hydroxypropyloxy)-5-trifluoromethylpyridine, 14.7 g of N-hydroxyphthalimide, 23.6 g of triphenylphosphine, and 200 ml of tetrahydrofuran was slowly added dropwise 20.0 g of diisopropyl azodicarboxylate with stirring under ice cooling in a stream of nitrogen gas. After stirring at room temperature for 24 hours, the reaction mixture was concentrated to give a residue. This residue was subjected to silica gel chromatography, which afforded 27.8 g (yield, 84%) of N-(3-(5-trifluoromethyl-2-pyridyloxy)propyloxy)phthalimide, m.p., 97.6° C.

To a mixture of 12.8 g of N-(3-(5-trifluoromethyl-2-pyridyloxy)propyloxy)phthalimide and 150 ml of chloroform was slowly added dropwise a mixture of 1.74 g of hydrazine hydrate and 1.5 ml of isopropyl alcohol at room temperature. After stirring for 3 hours with heating under reflux, the reaction mixture was returned to room temperature, in which 150 ml of hexane was poured. The reaction mixture was filtered through Celite, and the filtrate was concentrated to give a residue, in which 100 ml of hexane was again poured. This hexane solution was left stand in a refrigerator in 3 days. The deposited crystals were collected by filtration, and dried under reduced pressure, which afforded 7.0 g (yield, 85%) of O-(3-(5-trifluoromethyl-2-pyridyloxy)propyl)hydroxylamine, $n_D^{24.0}$ 1.4652.

Reference Production Example 4

O-(2,2,2-trichloroethyl)hydroxylamine Hydrochloride

To a mixture of 2.99 g of 2,2,2-trichloroethanol, 2.15 g of O-(2,4,6-trimethylbenzenesulfonyl)hydroxylamine (which had been produced according to the method as described in Synthesis, 1–17 (1977)), and 20 ml of diethyl ether was slowly added 0.68 g of sodium ethoxide with stirring under ice cooling. After stirring at room temperature for 5 hours, the deposited precipitate was removed by Celite filtration, and hexane was added to the filtrate. This hexane solution was bubbled with a blow of hydrogen chloride gas at room temperature to case the deposition of crystals. These crystals were collected by filtration, and dried under reduced pressure, which afforded 1.18 g (yield, 59%) of O-(2,2,2-trichloroethyl)hydroxylamine hydrochloride.

$^1$H-NMR (CDCl$_3$-CD$_3$OD/TMS) δ (ppm): 4.84 (2H, s).

The following are production examples for the intermediate compounds of formula (20).

Reference Production Example 7

Production of Compound 170)

First, 5.21 g of 1,5-pentanediol is placed in a reaction vessel, to which 0.22 g of 60% sodium hydride (in oil) is slowly added at room temperature with stirring in a stream of nitrogen gas. After stirring at room temperature until the evolution of hydrogen gas ceases, 0.75 g of chloroacetaldehyde O-tert-butyloxime is added at room temperature, and the reaction mixture is slowly warmed to 50° C. After further stirring at 50° C. for 3 hours, the reaction mixture is poured into water, and extracted twice with diethyl ether. The diethyl ether layers are combined, washed with water, diluted hydrochloric acid, and water in this order, dried over anhydrous magnesium sulfate, and concentrated to give a crude product. This crude product is subjected to silica gel chromatography, which affords 5-hydroxypentyloxyaldehyde O-tert-butyloxime.

Reference Production Example 8

Production of Intermediate Compound 171

First, 13.02 g of 1,5-pentanediol, 2.40 g of sodium hydroxide (powdery), 1.14 g of benzyltriethylammonium chloride, and 100 ml of tetrahydrofuran were placed in a reaction vessel, to which 8.18 g of chloroacetone O-tert-butyloxime was slowly added dropwise with stirring under heating under reflux. After further stirring for 8 hours, the reaction mixture was poured into diluted hydrochloric acid, and extracted twice with ethyl acetate. The ethyl acetate layers were combined, washed with diluted hydrochloric acid and water in this order, dried over anhydrous magnesium sulfate, and concentrated to give a crude product. This crude product was subjected to silica gel chromatography, which afforded 6.79 g (yield, 59%) of 5-hydroxypentyloxyacetone O-tert-butyloxime, $n_D^{20.0}$ 1.4493.

Some specific examples of the intermediate compounds of formula (20) are shown below with their compound numbers and their physical properties, if any.

170) 5-hydroxypentyloxyacetaldehyde O-tert-butyloxime
171) 5-hydroxypentyloxyacetone O-tert-butyloxime
172) 4-hydroxybutyloxyacetone O-tert-butyloxinme
173) 4-hydroxy-2-butenyloxyacetone O-tert-butyloxime
174) 4-hydroxy-2-butynyloxyacetone O-tert-butyloxime
175) 2-(2-hydroxyethoxy)ethoxyacetone O-tert-butyloxime, $n_D^{24.7}$ 1.4451
176) 2-(N-2-hydroxyethyl-N-methylamino)ethoxyacetone O-tert-butyloxime
177) 4-hydroxycyclohexyloxyacetone O-tert-butyloxime
178) 1-(5-hydroxypentyloxy)-2-butanone O-tert-butyloxime, $n_D^{21.4}$ 1.4479
179) 1-(5-hydroxypentyloxy)pinacolone O-tert-butyloxime, $n_D^{23.4}$ 1.4451
180) 2-(5-hydroxypentyloxy)acetophenone O-tert-butyloxime, $n_D^{23.4}$ 1.5090
181) 2-(5-hydroxypentyloxy)cyclohexanone O-tert-butyloxime The following are production examples for the intermediate compounds of formula (19). The intermediate compounds produced in Reference Production Example 10 or 12 can also be used as the starting material in Reference Production Example 7, and the intermediate compounds produced in Reference Production Example 11 or 13 can also be used as the starting material in Reference Production Example 8.

Reference Production Example 9

Production of Intermediate Compound 182)

To 2.94 g of 40% aqueous chloroacetaldehyde solution was added 2.94 g of O-(3,3-dichloro-2-propenyl) hydroxylamine hydrochloride with stirring at room temperature. After stirring at room temperature for 2 hours, the reaction mixture was extracted twice with diethyl ether. The diethyl ether layers were combined, washed with water, dried over anhydrous magnesium sulfate, and concentrated, which afforded 1.94 g (yield, 96%) of chloroacetaldehyde O-(3,3-dichloro-2-propenyl)oxime, $n_D^{23.2}$ 1.5038.

Reference Example 10

Production of Intermediate Compound 183)

To 9.81 g of 40% aqueous chloroacetaldehyde solution was added 3.77 g of O-tert-butylhydroxylamine hydrochloride with stirring at room temperature. After stirring at room temperature for 2 hours, the reaction mixture was extracted twice with diethyl ether. The diethyl ether layers were combined, washed with water, dried over anhydrous magnesium sulfate, and concentrated, which afforded 4.21 g (yield, 94%) of chloroacetaldehyde O-tert-butyloxime, $n_D^{23.2}$ 1.4418.

Reference Production Example 11

Production of Intermediate Compound 184)

A mixture of 1.51 g of O-tert-butylhydroxylamine hydrochloride, 0.93 g of chloroacetone, and 10 ml of diethyl ether is stirred at room temperature for 3 hours, poured into water, and extracted twice with diethyl ether. The diethyl ether layers are combined, washed with water, dried over anhydrous magnesium sulfate, and concentrated, which affords chloroacetone O-tert-butyloxime.

Reference Production Example 12

Production of Intermediate Compound 183)

To 3.92 g of 40% aqueous chloroacetoaldehyde solution is 2.08 g of hydroxylamine hydrochloride with stirring at room temperature. After stirring at room temperature for 24 hours, the reaction mixture is extracted twice with diethyl ether. The diethyl ether layers are combined, washed with water, dried over anhydrous magnesium sulfate, and concentrated, which affords 1.32 g (yield, 71%) of chloroacetoaldehyde oxime.

Then, 0.47 g of chloroacetoaldehyde oxime, 0.1 ml of concentrated sulflic acid, and 10 ml of diethyl ether are placed in a reaction vessel, into which isobutene gas is blown with stirring under ice cooling, and the stirring is further continued at room temperature. After completion of the reaction, the reaction mixture is slowly poured into saturated aqueous sodium hydrogencarbonate solution, and extracted twice with diethyl ether. The diethyl ether layers are combined, washed with 10% aqueous sodium hydroxide solution and water in this order, dried over anhydrous magnesium sulfate, and concentrated, which affords chloroacetoaldehyde O-tert-butyloxime.

Reference Production Example 13

Production of Intermediate Compound 184)

A mixture of 0.83 g of hydroxylamine hydrochloride, 0.93 g of chloroacetone, and 10 ml of diethyl ether is stirred at room temperature for 3 hours, poured into water, and extracted twice with diethyl ether. The diethyl ether layers are combined, washed with water, dried over anhydrous magnesium sulfate, and concentrated, which affords chloroacetone oxime.

Then, 0.54 g of chloroacetone oxime, 0.1 ml of concentrated sulfuric acid, and 10 ml of diethyl ether are placed in a reaction vessel, into which isobutene gas is blown with stirring under ice cooling, and the reaction mixture is further stirred at room temperature. After completion of the reaction, the reaction mixture is slowly poured into saturated aqueous sodium hydrogencarbonate solution, and extracted twice with diethyl ether. The diethyl ether layers are combined, washed with 10% aqueous sodium hydroxide solution and water in this order, dried over anhydrous magnesium hydroxide, and concentrated, which affords chloroacetone O-tert-butyloxyoxime.

Reference Production Example 14

Production of Intermediate Compound 189)

First, 0.22 g of 5-hydroxypentyloxyaldehyde O-tert-butyloxime, 0.12 g of triethylamine, and 10 ml of tetrahydrofuran are placed in a reaction vessel, to which 0.14 g of methanesulfonyl chloride is slowly added dropwise with stirring under ice cooling. After completion of the addition, the reaction mixture is further stirred at room temperature for 30 minutes, poured into diluted hydrochloric acid, and extracted twice with diethyl ether. The diethyl ether layers are combined, washed with water, dried over anhydrous magnesium sulfate, and concentrated, which affords 5-(methanesulfonyloxy)pentyloxyaldehyde O-tert-butyloxime.

Reference Production Example 15

Production of Intermediate Compound 190)

First, 0.23 g of 5-hydroxypentyloxyacetone O-tert-butyloxime, 0.12 g of triethylamine, and 10 ml of tetrahydrofuran are placed in a reaction vessel, to which 0.14 g of methanesulfonyl chloride is slowly added with stirring under ice cooling. After completion of the addition, the reaction mixture is further stirred at room temperature for 30 minutes, poured into diluted hydrochloric acid, and extracted twice with diethyl ether. The diethyl ether layers are combined, washed with water, dried over anhydrous magnesium sulfate, and concentrated, which affords 5-(methanesulfonyloxy)pentyloxyacetone O-tert-butyloxime.

Some specific examples of the intermediate compounds of formula (19) are shown below with their compound numbers and their physical properties, if any. Intermediate compounds 182) to 188) can also be sued as the starting materials for the production of intermediate compounds 170) to 181) of formula (19).

182) chloroacetaldehyde O-(3,3-dichloro-2-propenyl) oxime, $n_D^{23.2}$ 1.5038
183) chloroacetaldehyde O-tert-butyloxime, $n_D^{23.2}$ 1.4418
184) chloroacetone O-tert-butyloxime
185) 1-bromo-2-butanone O-tert-butyloxime
186) 1-bromopinacolone O-tert-butyloxime
187) 2-chloroacetophenone O-tert-butyloxime
188) 2-chlorocyclohexanone O-tert-butyloxime
189) 5-(methanesulfonyloxy)pentyloxyacetaldehyde O-tert-butyloxime
190) 5-(methanesulfonyloxy)pentyloxyacetone O-tert-butyloxime
191) 4-(methanesulfonyloxy)butyloxyacetone O-tert-butyloxime
192) 4-(methanesulfonyloxy)-2-butenyloxyacetone O-tert-butyloxime
193) 4-(methanesulfonyloxy)-2-butynyloxyacetone O-tert-butyloxime
194) 2-(2-(methanesulfonyloxy)ethoxy)ethoxyacetone O-tert-butyloxime
195) 2-(N-2-(methanesulfonyloxy)ethyl-N-methylamino) ethoxyacetone O-tert-butyloxime
196) 4-(methanesulfonyloxy)cyclohexyloxyacetone O-tert-butyloxime
197) 1-(5-(methanesulfonyloxy)pentyloxy)-2-butanone O-tert-butyloxime
198) 1-(5-(methanesulfonyloxy)pentyloxy)pinacolone O-tert-butyloxime
199) 2-(5-(methanesulfonyloxy)pentyloxy)acetophenone O-tert-butyloxime
200) 2-(5-(methanesulfonyloxy)pentyloxy) cyclohexanone O-tert-butyloxime The following are formulation examples in which "parts" are by weight and the present compounds are designated by their compound numbers as described above.

Formulation Example 1

Emulsifiable Concentrates

First, 10 parts of each of the present compounds (1) to (687) is dissolved in 35 parts of xylene and 35 parts of N,N-dimethylformamide, to which 14 parts of polyoxyethylene styrylphenyl ether and 6 parts of calcium dodecylbenzenesulfonate are added. The mixture is well stirred to give a 10% emulsifiable concentrate of each compound.

Formulation Example 2

Wettable Powders

First, 20 parts of each of the present compounds (1) to (687) is added to a mixture of 4 parts of sodium lauryl sulfate, 2 parts of calcium lignin sulfonate, 20 parts of synthetic hydrated silicon oxide fine powder, and 54 parts of diatomaceous earth. The mixture is stirred with a mixer to give a 20% wettable powder of each compound.

Formulation Example 3

Granules

To five parts of each of the present compounds (1) to (687) are added parts of synthetic hydrated silicon oxide fine powder, 5 parts of sodium dodecylbenzenesulfonate, 30 parts of bentonite, and 55 parts of clay, and the mixture is well stirred. A suitable amount of water is added to the mixture, which is further stirred, granulated with a granulator, and air-dried to give a 5% granule of each compound.

Formulation Example 4

Dusts

First, 1 part of each of the present compounds (1) to (687) is dissolved in a suitable amount of acetone, to which 5 parts of synthetic hydrated silicon oxide fine powder, 0.3 part of PAP, and 93.7 parts of clay are added, and the mixture is stirred with a mixer. The removal of acetone by evaporation gives a 1% dust of each compound.

Formulation Example 5

Flowables

First, 20 parts of each of the present compounds (1) to (687) is mixed with 1.5 parts of sorbitan trioleate and 28.5 parts of an aqueous solution containing 2 parts of polyvinyl alcohol. The mixture is pulverized into fine particles having a particle size of not more than 3 μm with a sand grinder, to which 40 parts of an aqueous solution containing 0.05 part of xanthan gum and 0.1 part of aluminum magnesium silicate is added and then 10 parts of propylene glycol is added. The mixture is stirred to give a 20% flowable of each compound.

Formulation Example 6

Oil Sprays

First, 0.1 part of each of the present compounds (1) to (687) is dissolved in 5 parts of xylene and 5 parts of trichloroethane. The solution is mixed with 89.9 parts of deodorized kerosine to give a 0.1% oil spray of each compound.

Formulation Example 7

Oil-based Aerosols

First, 0.1 part of each of the present compounds (1) to (687), 0.2 part of tetramethrin, 0.1 part of d-phenothrin, and 10 parts of trichloroethane are dissolved in 59.6 parts of deodorized kerosine, and the solution is put in an aerosol vessel. The vessel is equipped with a valve, through which 30 parts of a propellant (liquefied petroleum gas) is charged under increased pressure to give an oil-based aerosol of each compound.

Formulation Example 8

Water-based Aerosols

An aerosol vessel is filled with a mixture of 0.2 part of each of the present compounds (1) to (687), 0.2 part of d-allethrin, 0.2 part of d-phenothrin, 5 parts of xylene, 3.4 parts of deodorized kerosine, and 1 part of an emulsifier (ATMOS 300 available from Atlas Chemical Co.); and 50 parts of pure water. The vessel is equipped with a valve, through which 40 parts of a propellant (liquefied petroleum gas) are charged under increased pressure to give a water-based aerosol of each compound.

Formulation Example 9

Mosquito-coils

First, 0.3 g of each of the present compounds (1) to (687) is mixed with 0.3 g of d-allethrin, and the mixture is dissolved in 20 ml of acetone. The solution is uniformly mixed with 99.4 g of a carrier for mosquito-coils (prepared by mixing Tabu powder, pyrethrum marc powder and wood flour in the ratio of 4:3:3) under stirring. The mixture is well kneaded with 120 ml of water, molded, and dried to give a mosquito-coil of each compound.

Formulation Example 10

Electric Mosquito-mats

First, 0.4 g of each of the present compounds (1) to (687), 0.3 parts of d-allethrin, and 0.4 g of pipenyl butoxide are dissolved in acetone to have a total volume of 10 ml. Then, 0.5 ml of the solution is uniformly absorbed in a substrate for electric mosquito-mats having a size of 2.5 cm ×1.5 cm and a thickness of 0.3 cm (prepared by forming a fibrillated mixture of cotton linter and pulp into a sheet) to give an electric mosquito-mat of each compound.

Formulation Example 11

Heating Smoke Formulations

First, 100 mg of each of the present compounds (1) to (687) is dissolved in a suitable amount of acetone. The solution is absorbed in a porous ceramic plate having a size of 4.0 cm ×4.0 cm and a thickness of 1.2 cm to give a heating smoke formulation of each compound.

Formulation Example 12

Poison Baits

First, 10 mg of each of the present compounds (1) to (687) is dissolved in 0.5 ml of acetone, and the solution is uniformly mixed with 5 g of solid bait powder for animals (Breeding Solid Feed Powder CE-2 available from Japan Clea Co., Ltd.). The removal of acetone by air drying gives a 0.5% poison bait of each compound.

The following test examples are provided for demonstrating that the present compounds are useful as active ingredients of insecticidal/acaricidal agents. In these test examples, the present compounds are designated by their compound numbers as describe above and the compounds used for comparison are designated by their compound symbols as described below.

Compound (A): 4-(3-chloro-2-propenyloxy)phenoxyacetone O-ethyloxime (i.e., compound 9 as described in JP-A 61-72733, page 7)

Compound (B): 4-phenoxy-benzaldehyde O-(3-methylbutyl)oxime (i.e., compound 41 as described in JP-A 61-260054, page 4)

Test Example 1

Insecticidal Test Against *Spodoptera litura*

A 200-fold water dilution (500 ppm) of a test compound formulation obtained according to Formulation Example 1 or 2 was absorbed at a volume of 2 ml in an artificial diet (Insecta LF available from Nihon Nosan K.K.) having a weight of 13 g, which had been prepared in a polyethylene cup having a diameter of 11 cm. Five fourth-instar larvae of *Spodoptera litura* were set free in the cup. After 6 days, the survival of the larvae was examined to determine the mortality.

As a result, it was found that the present compounds (1)-(31), (33), (34), (47), (74)-(76), (90), (91), (103), (104), (131), (133), (134),(147)-(150), (152)-(186), (203), (279)-(393), (481), (523)-(556), (558)-(572), (574)-(597), and (688)-(695) exhibited a mortality of 80% or higher. In contrast, compounds (A) and (B) exhibited the mortality of 0%.

Test Example 2

Insecticidal Test Against *Plutella xylostella*

To a water dilution (50 ppm) of a test compound formulation obtained according to Formulation Example 1 was added a spreading agent (New RINOU available from Nihon Noyaku K.K.) at a dilution ratio of 3000-fold. The dilution was sprayed over potted cabbages at the four to five leaf stage at a volume of 25 ml per pot. After the treated plants were air dried, ten third-instar larvae of *Plutella xylostella* were set free on each pot. After 4 days, the mortality was determined.

As a result, it was found that the present compounds (1)-(22), (24)-(29), (33), (34), (47), (75), (76), (90), (91), (103), (104), (134), (153)-(161), (163)-(176), (180), (182)-(185), (279), (281), (283), (285), (287)-(299), (301)-(313), (315)-(321), (327), (332), (334), (336), (338)-(342), (351)-(360), (362)-(368), (370), (372)-(374), (376)-(382), (384)-(389), (391)-(393), (523), (524), (528)-(550), (558)-(566), (568)-(570), (573), (574), (576)-(579), (581)-(585), (589), (591)-(597), and (689)-(693) exhibited a mortality of 80% or higher. In contrast, compound (A) exhibited the mortality of 0%.

Test Example 3

Insecticidal Test Against *Heliothis virescens*

A water dilution (100 ppm) of a test compound formulation obtained according to Formulation Example 1 was added dropwise at a volume of 0.2 ml and uniformly spread over the surface of an artificial diet having a weight of 3 g, which had been prepared in a 30 ml plastic cup. After air drying, one second-instar larva of *Heliothis virescens* was set free in each cup. Ten larvae were used for each treatment. After 7 days, the mortality of the larvae was determined.

As a result, it was found that the present compounds (3), (5), (11), (14)-(17), (25)-(27), (33), (34), (47), (76), (90), (91), (104), (134), (153)-(156), (160), (161), (163)-(169), (171)-(175), (281)-(300), (305)-(310), (312)-(331), (338)-(343), (346), (347), (350)-(359), (523), (528)-(531), (533)-(540), (542)-(551), (559), and (561)-(564) exhibited a mortality of 80% or higher.

Test Example 4

Insecticidal Test Against *Helicoverpa armigera*

A cotton leaf fragment (diameter, 5 cm) was immersed for 10 seconds in a water dilution (100 ppm) of a test compound formulation obtained according to Formulation Example 1. This fragment was taken out from the dilution, air dried, and placed in a polyethylene cup having a diameter of 5.5 cm. One third-instar larva of Helicoverpa armigera was set free in each cup. Ten larvae were used for each treatment. After 5 days, the mortality of the larvae was determined.

As a result, it was found that the present compounds (2)-(6), (11), (14), (17), (24)-(26), (91), (104), (279), (283), (288), (291), (293), (303), (312), (318), (327), (329), (342), (355), (357), (358), (529), (531), (545), (562), (564), and (582) exhibited a mortality of 80% or more. In contrast, compound (A) exhibited the mortality of 0%.

Test Example 5

Insecticidal Test Against *Cydia pomonella*

A water dilution (100 ppm) of a test compound formulation obtained according to Formulation Example 1 was added dropwise at a volume of 0.2 ml and spread over the surface of an artificial diet having a weight of 3 g, which had been prepared in a 30 ml polyethylene cup. After air drying, placed in the cup was a piece of wax paper (about 2.5 cm square) having about 20 eggs which had been laid by *Cydia pomonella* and were just before hatching. Four pieces of such wax paper were used for each treatment. After 7 days, the mortality of the larvae was determined.

As a result, it was found that the present compounds (1)-(3), (6), (10), (11), (14)-(16), (25), (27), (33), (34), (47), (76), (90), (91), (153)-(156), (158)-(176), (279), (289)-(291), (293), (294), (297), (300), (306), (307), (309)-(315), (317)-(319), (323), (324), (326)-(331), (338)-(340), (352)-(359), (365), (378), (379), (381), (382), (481), (528)-(531), (533)-(540), (542)-(546), (549), (550), (558)-(566), (568)-(570), (572), (574), (575), (578), and (579) exhibited a mortality of 80% or higher.

Test Example 6

Acaricidal Test Against *Tetranychus urticae*

About twenty female adults of Tetranychus urticae were set free on brush bean (*Phaseolus vulgaris*) in the primary leaf stage, which had been potted in a plastic cup for 7 days after the seeding. After 6 days, a 200-fold water dilution (500 ppm) of a test compound formulation obtained according to Formulation Example 1 or 2 was sprayed at a volume of 15 ml over the plant. After 8 days, each compound was evaluated for acaricidal activity on the following criteria.

−: almost no damage and completely no surviving mites

±: slight damage and some few surviving mites

+: rather smaller damage and a rather fewer surviving mites than non-treatment case ++: same as non-treatment case As a result, it was found that the present compounds (6), (104), (173), (178), (306), (318), (327), (542), (582), (583), (589), (592), and (593) were evaluated at "−" or "±". In contrast, compounds (A) and (B) were evaluated at "+".

Test Example 7

Insecticidal Test Against *Musca domestica*

In the bottom of a polyethylene cup having a diameter of 5.5 cm was placed a piece of filter paper having the same size. A 200-fold water dilution (500 ppm) of a test compound formulation obtained according to Formulation Example 1 was added dropwise at a volume of 0.7 ml on the filter paper, and about 30 mg of sucrose as a diet was uniformly placed thereon. Ten female adults of houseflies (*Musca domestics*) were set free in the cup, and the cup was kept covered. After 1 day, the survival of the adults was determined to determine the mortality.

As a result, it was found that the present compounds (1), (4), (6), (7), (11)-(16), (18), (19), (22), (28), (29), (153), (155), (158), (159), (165)-(167), (170), (173), (175), (176), (180), (203), (287), (305), (307), (309), (318), (330), (332), (372)-(374), (376), (378), (481), (541), (542), (545), (551), (560), (565), (566), and (689) exhibited a mortality of 80% or higher. In contrast, compounds (A) and (B) used for comparison exhibited the mortality of 0%.

Industrial Applicability the present compounds have excellent insecticidal/acaricidal activity, so that they are satisfactorily effective for the control of noxious insects, mites and ticks.

What is claimed is:

1. An oxime compound of formula (1)

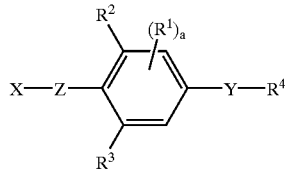

wherein:

$R^1$, $R^2$, and $R^3$ are independently halogen, $C_1$–$C_3$ alkyl, $C_1$–$C_3$ haloalkyl, $C_1$–$C_3$ alkoxy, $C_1$–$C_3$ haloalkoxy, nitro, or cyano;

$R^4$ is 3,3-dihalogeno-2-propenyl;
a is an integer of 0 to 2;
Y is oxygen;
z is oxygen;
X is $x^2$ of formula (2)

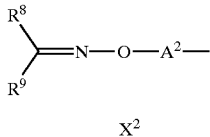

$x^2$ wherein:
$R^8$ and $R^9$ are independently hydrogen, $C_1-C_{11}$ alkyl, $C_1-C_6$ haloalkyl, $C_2-C_6$ alkenyl, $C_2-C_6$ haloalkenyl, $C_2-C_6$ alkynyl, $C_2-C_6$ haloalkynyl, $C_2-C_{10}$ alkoxyalkyl, $C_2-C_{10}$ alkylthioalkyl, or naphthyl,
or $C_3-C_7$ cycloalkyl optionally substituted with $C_1-C_4$ alkyl,
or $C_4-C_{10}$ cycloalkylalkyl optionally substituted with $C_1-C_4$ alkyl on the ring thereof,
or $C_5-C_6$ cycloalkenyl optionally substituted with $C_1-C_4$ alkyl,
or $C_6-C_8$ cycloalkenylalkyl optionally substituted with $C_1-C_4$ on the ring thereof,
or $T^2$-1 or $T^2$-2 of formula (4)

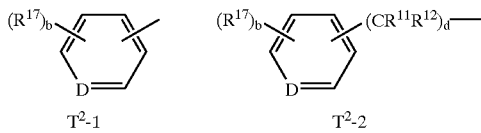

$T^2$-1      $T^2$-2 wherein:
$(R^{17})_b$'S are zero to five identical or different substituents selected from. halogen, $C_1-C_6$ alkyl, $C_1-C_3$ haloalkyl, $C_2-C_6$ alkenyl, $C_2-C_6$ haloalkenyl, $C_2-C_6$ alkynyl, $C_2-C_6$ haloalkynyl, $C_1-C_6$ alkoxy, $C_1-C_3$ haloalkoxy, $C_3-C_6$ alkenyloxy, $C_3-C_6$ haloalkenyloxy, $C_3-C_6$ alkynyloxy, $C_3-C_6$ haloalkynyloxy, $C_1-C_3$ alkylthio, $C_1-C_3$ haloalkylthio, $C_1-C_2$ alkylsulfinyl, $C_1-C_2$ alkylsulfonyl, $C_1-C_2$ haloalkylsulfinyl, $C_1-C_2$ haloalkylsulfonyl, $C_1-C_3$ hydroxylalkyl, $C_2-C_4$ alkoxyalkyl, $C_2-C_4$ alkylthioalkyl, dimethylamino, acetamido, acetyl, formyl, carboxyl, ($C_1-C_2$ alkyl)aminocarbonyl, [di($C_1-C_2$ alkyl)amino]carbonyl, ($C_1-C_6$ alkoxy)carbonyl, $C_3-C_6$ cycloalkyl, $C_5-C_6$ cycloalkenyl, $C_3-C_6$ cycloalkyloxy, $C_5-C_6$ cycloalkenyloxy, pentafluorosulfanyl ($F_5S$), cyano, or nitro,
or phenyl optionally substituted with halogen, $C_1-C_4$ alkyl, $C_1-C_3$ haloalkyl, $C_1-C_3$ alkoxy, or $C_1-C_3$ haloalkoxy,
or phenoxy optionally substituted with halogen, $C_1-C_4$ alkyl, $C_1-C_3$ haloalkyl, $C_1-C_3$ alkoxy, or $C_1-C_3$ haloalkoxy,
or benzyl optionally substituted with halogen, $C_1-C_4$ alkyl, $C_1-C_3$ haloalkyl, $C_1-C_3$ alkoxy, or $C_1-C_3$ haloalkoxy on the ring thereof,
or benzyloxy optionally substituted with halogen, $C_1-C_4$ alkyl, $C_1-C_3$ haloalkyl, $C_1-C_3$ alkoxy, or $C_1-C_3$ haloalkoxy on the ring thereof,
or when b is 2 to 5, two adjacent $R^{17}$'s are combined together at their ends to form trimethylene or tetramethylene;

D is —CH= or nitrogen;
$R^{11}$ and $R^{12}$ are independently hydrogen, $C_1-C_3$ alkyl or trifluoromethyl;
b is an integer of 0 to 5; and
d is an integer of 1 to 3;
or $R^8$ and $R^9$ are combined together at their ends to form a saturated or unsaturated 5- or 6-membered ring containing no hetero atoms in the ring;
$A^2$ is $A^2$-1, $A^2$-2, $A^2$-3, $A^2$-4, $A^2$-5, $A^2$-6, $A^2$-7, $A^2$-8, $A^2$-9, or $A^2$-10 of formula (9)
  $A^2$-1: $-(CR^{19}R^{20})_j-(CR^{23}=CR^{24})_h-(CR^{25}R^{26})_t-(CR^{27}=CR^{28})_p-(CR^{29}R^{30})_m-$
  $A^2$-2: $-(CR^{19}R_{20})_j-(CR^{23}=CR^{24})_h-(CR^{25}R^{26})_m-Q^1-(CR^{27}R^{28})_n-(CR^{29}=CR^{30})_p-(CR^{31}R^{32})_{f1}-$
  $A^2$-3: $-U^3-(CR^{19}R^{20})_t-(CR^{23}=CR^{24})_h-(CR^{25}R^{26})_u-(CR^{27}=CR^{28})_p-(CR^{29}R^{30})_j-$
  $A^2$-4: $-U^4-(CR^{19}R^{20})_j-(CR^{23}=CR^{24})_h-(CR^{25}R^{26})_t-(CR^{27}=CR^{28})_p-(CR^{29}R^{30})_m-$
  $A^2$-5: $-U^3-(CR^{19}R^{20})_t-(CR^{23}=CR^{24})_h-(CR^{25}R^{26})_j-Q^1-(CR^{27}R^{28})_m-(CR^{29}=CR^{30})_p-(CR^{31}R^{32})_n-$
  $A^2$-6: $-U_4-(CR^{19}R^{20})_j-(CR^{23}=CR^{24})_h-(CR^{25}R^{26})_m-Q^1-(CR^{27}R^{28})_n-(CR^{29}=CR^{30})_p-(CR^{31}R^{32})_{f1}-$
  $A^2$-7: $-U^3-(CR^{19}R^{20})_j-Q^1-(CR^{23}R^{24})_h-E-(CR^{25}R^{26})_p-$
  $A^2$-8: $-U^3-(CR^{19}R^{20})_t-Q^1-(CR^{23}R^{24})_j-C\equiv C-(CR^{25}R^{26})_m-$
  $A^2$-9: $-(CR^{19}R^{20})_h-E-(CR^{23}R^{24})_p-$
  $A^2$-10: $-(CR^{19}R^{20})_j-C\equiv C-(CR^{23}R^{24})_m-$
  wherein:
  $R^{19}$, $R^{20}$, $R^{23}$, $R^{24}$, $R^{25}$, $R^{26}$, $R^{27}$, $R^{28}$, $R^{29}$, $R^{30}$, $R^{31}$, and $R^{32}$ are independently hydrogen, $C_1-C_3$ alkyl or trifluoromethyl;
  h is an integer of 0 or 1;
  j is an integer of 1 to 3;
  m is an integer of 1 to 3;
  n is an integer of 1 to 3;
  p is an integer of 0 or 1;
  t is an integer of 0 to 3;
  u is an integer of 0 to 3;
  f1 is an integer of 1 to 3;
  $Q^1$ is oxygen, $S(O)_y$, or $NR^{33}$ wherein $R^{33}$ is hydrogen or $C_1-C_3$ alkyl, and y is an integer of 0 to 2;
  E is $C_5-C_6$ cycloalkylene;
$U^3$ is $U^3$-1, $U^3$-2, or $U^3$-3 of formula (10)

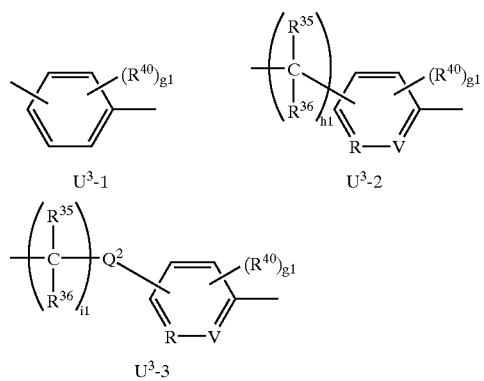

$U^3$-1      $U^3$-2

$U^3$-3 wherein:
$R^{35}$ and $R^{36}$ are independently hydrogen, $C_1-C_3$ alkyl, or trifluoromethyl;

($R^{40}$)$_{g1}$'s are zero to four identical or different substituents selected from halogen, $C_1$–$C_4$ alkyl, $C_1$–$C_3$ haloalkyl, $C_1$–$C_3$ alkoxy, or $C_1$–$C_3$ haloalkoxy;

R and V are —CH=;

g1 is an integer of 0 to 4;

h1 is an integer of 1 to 3;

i1 is an integer of 2 or 3; and $Q^2$ is oxygen, $S(O)_z$, or $NR^{34}$ wherein $R^{34}$ is hydrogen or $C_1$–$C_3$ alkyl, and z is an integer of 0 to 2;

$U^4$ is $U^4$-1, $U^4$-2, or $U^4$-3 of formula (11)

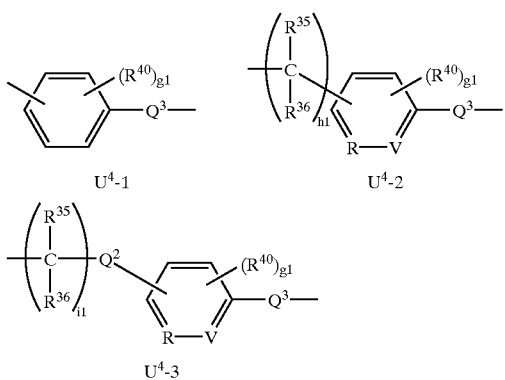

wherein:

$R^{35}$ and $R^{36}$ are independently hydrogen, $C_1$–$C_3$ alkyl, or trifluoromethyl;

($R^{40}$)$_{g1}$'s are zero to four identical or different substituents selected from halogen, $C_1$–$C_4$ alkyl, $C_1$–$C_3$ haloalkyl, $C_1$–$C_3$ alkoxy, or $C_1$–$C_3$ haloalkoxy;

R and V are -CH=;

g1 is an integer of 0 to 4;

h1 is an integer of 1 to 3;

i1 is an integer of 2 or 3;

$Q^2$ is oxygen, $S(O)_z$, or $NR^{34}$ wherein $R^{34}$ is hydrogen or $C_1$–$C_3$ alkyl, and z is an integer of 0 to 2; and $Q^3$ is oxygen, $S(O)_{e1}$, or $NR^{39}$ wherein $R^{39}$ is hydrogen or $C_1$–$C_3$ alkyl, and e1 is an integer of 0 to 2.

2. The oxime compound according to claim 1, wherein $R^8$ and $R^9$ are independently hydrogen, $C_1$–$C_{11}$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_{10}$ alkoxyalkyl, or $C_2$–$C_{10}$ alkylthioalkyl, or $C_3$–$C_7$ cycloalkyl optionally substituted with $C_1$–$C_4$ alkyl, or $C_4$–$C_{10}$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ alkyl on the ring thereof, or $T^2$-1 or $T^2$-2 of formula (4)

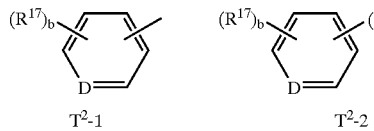

wherein $R^{17}$, D, $R^{11}$, $R^{12}$, b and d are as defined in claim 1, or $R^8$ and $R^9$ are combined together at their ends to form a saturated or unsaturated 5- or 6-membered ring containing no hetero atoms in the ring.

3. The oxime compound according to claim 2 wherein $A^2$ is $A^2$-1, $A^2$-2, $A^2$-3, $A^2$-4, $A^2$-5, or $A^2$-6.

4. The oxime compound according to claim 1, wherein a is 0.

5. The oxime compound according to claim 1, wherein $R^1$, $R^2$, and $R^3$ are independently halogen or $C_1$–$C_3$ alkyl.

6. The oxime compound according to claim 1, wherein $A^2$ is $A^2$-1.

7. The oxime compound according to claim 1, wherein $A^2$ is $A^2$-2.

8. The oxime compound according to claim 1, wherein $A^2$ is $A^2$-3.

9. The oxime compound according to claim 1, wherein $A^2$ is $A^2$-4.

10. The oxime compound according to claim 1, wherein $A^2$ is $A^2$-5.

11. The oxime compound according to claim 1, wherein $A^2$ is $A^2$-6.

12. The oxime compound according to claim 1, wherein $A^2$ is $A^2$-7 or $A^2$-9.

13. The oxime compound according to claim 1, wherein $A^2$ is $A^2$-8 or $A^2$-10.

14. The oxime compound according to claim 7, wherein $Q^1$ is oxygen.

15. The oxime compound according to claim 8, wherein $Q^2$ is oxygen.

16. The oxime compound according to claim 9, wherein $Q^2$ and $Q^3$ are both oxygen.

17. The oxime compound according to claim 10, wherein $Q^1$ is oxygen.

18. The oxime compound according to claim 11, wherein $Q^1$ is oxygen.

19. The oxime compound according to claim 12, wherein $Q^1$ and $Q^2$ are both oxygen.

20. The oxime compound according to claim 13, wherein $Q^1$ and $Q^2$ are both oxygen.

21. The oxime compound according to claim 17, wherein $Q^2$ is oxygen.

22. The oxime compound according to claim 18, wherein $Q^2$ and $Q^3$ are both oxygen.

23. The oxime compound according to claim 6, wherein h and p are both 0; and $R^{19}$, $R^{20}$, $R^{25}$, $R^{26}$, $R^{29}$, and $R^{30}$ are all hydrogen.

24. The oxime compound according to claim 14, wherein h and p are both 0; and $R^{19}$, $R^{20}$, $R^{25}$, $R^{26}$, $R^{27}$, $R^{28}$, $R_{31}$, and $R^{32}$ are all hydrogen.

25. The oxime compound according to claim 15, wherein h and p are both 0; and $R^{19}$, $R^{20}$, $R^{25}$, $R^{26}$, $R^{29}$, $R^{30}$, $R^{35}$, and $R^{36}$ are all hydrogen.

26. The oxime compound according to claim 16, wherein h and p are both 0; and $R^{19}$, $R^{20}$, $R^{25}$, $R^{26}$, $R^{29}$, $R^{30}$, $R^{35}$, and $R^{36}$ are all hydrogen.

27. The oxime compound according to claim 21, wherein h and p are both 0; $R^{19}$, $R^{20}$, $R^{25}$, $R^{26}$, $R^{27}$, $R^{28}$, $R^{31}$, $R^{32}$, $R^{35}$, and $R^{36}$ are all hydrogen.

28. The oxime compound according to claim 22, wherein h and p are both 0; and $R^{19}$, $R^{20}$, $R^{25}$, $R^{26}$, $R^{27}$, $R^{28}$, $R^{31}$, $R^{32}$, $R^{35}$, and $R^{36}$ are all hydrogen.

29. The oxime compound according to claim 19, wherein $R^{19}$, $R^{20}$, $R^{23}$, $R^{24}$, $R^{24}$, $R^{26}$, $R^{35}$, and $R^{36}$, and all hydrogen.

30. The oxime compound according to claim 20, wherein $R^{19}$, $R^{20}$, $R^{23}$, $R^{24}$, $R^{25}$, $R^{26}$, $R^{35}$, and $R^{36}$, and all hydrogen.

31. The oxime compound according to claim 1, wherein $R^8$ and $R^9$ are independently hydrogen, $C_1$–$C_{11}$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_{10}$ alkoxyalkyl, or $C_2$–$C_{10}$ alkylthioalkyl, or $C_3$–$C_7$ cycloalkyl optionally substituted with $C_1$–$C_4$ alkyl, or $C_4$–$C_{10}$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ alkyl on the ring thereof, or $R^8$ and $R^9$ are combined together at their ends to form a saturated or unsaturated 5- or 6-membered ring containing no hetero atoms in the ring.

32. The oxime compound according to claim 1, wherein $R^8$ and $R^9$ are independently hydrogen, $C_1$–$C_{11}$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_{10}$ alkoxyalkyl, or $C_2$–$C_{10}$ alkylthioalkyl, or $C_3$–$C_7$ cycloalkyl optionally substituted with $C_1$–$C_4$ alkyl, or $C_4$–$C_{10}$ cycloalkylalkyl optionally substituted with $C_1$–$C_4$ alkyl on the ring thereof, or $C_5$–$C_6$ cycloalkenyl optionally substituted with $C_1$–$C_4$ alkyl, or $C_6$–$C_8$ cycloalkenylalkyl optionally substituted with $C_1$–$C_4$ alkyl on the ring thereof.

33. The compound according to claim 1, which is 4'-(trifluoromethyl)acetophenone O-(4-(2,6-dichloro-4-(3,3-dichloro-2-propenyloxy)phenoxy)butyl)oxime.

34. The compound according to claim 1, which is trimethylacetaldehyde O-(5-(2,6-dichloro-4-(3,3-dichloro-2-propenyloxy)phenoxy)pentyl)oxime.

35. The compound according to claim 1, which is 3,3-dimethyl-2-butanone O-(5-(2,6-dichloro-4-(3,3-dichloro-2-propenyloxy)phenoxy)pentyl)-oxime.

36. The compound according to claim 1, which is 3,3-dimethyl-2-butanone O-(4-(2,6-dichloro-4-(3,3-dichloro-2-propenyloxy)phenoxy)butyl)-oxime.

37. The compound according to claim 1, which is 4-methyl-2-pentanone O-(4-(2,6-dichloro-4-(3,3-dichloro-2-propenyloxy)phenoxy)butyl)-oxime.

38. The compound according to claim 1, which is 4-methyl-2-pentanone O-(5-(2,6-dichloro-4-(3,3-dichloro-2-propenyloxy)phenoxy)pentyl)oxime.

39. The compound according to claim 1, which is 3-methy-2-butanone O-(5-(2,6-dichloro-4-(3,3-dichloro-2-propenyloxy)phenoxy)pentyl)oxime.

40. An insecticidal/acaricidal agent comprising as an active ingredient, an oxime compound according to claim 1.

41. A method for the extermination of insects, ticks or mites, comprising applying to the insects, ticks or mites, or to their habitats, an effective amount of an oxime compound according to claim 1.

42. The compound according to claim 1, which is 4-(trifluoromethyl)benzaldehyde O-(4-(2,6-dichloro-4-(3,3-dichloro-2-propenyloxy)phenoxy)butyl)oxime.

* * * * *

UNITED STATES PATENT AND TRADEMARK OFFICE
CERTIFICATE OF CORRECTION

PATENT NO. : 6,448,444 B2
DATED : September 10, 2002
INVENTOR(S) : Keiichi Izumi et al.

It is certified that error appears in the above-identified patent and that said Letters Patent is hereby corrected as shown below:

<u>Title page,</u>
Item [75], Inventors, please change the inventorship information from "Hiroshi Ikegami, Toyonaka; Keiichi Izumi, Narashino; Masaya Suzuki, Takarazuka; Noriyasu Sakamoto; Shigeru Saito, both of Toyonaka, all of (JP)."

to

-- Keiichi Izumi, Narashino; and Shigeru Saito, Toyonaka, both of (JP). --.

Signed and Sealed this

Seventeenth Day of June, 2003

JAMES E. ROGAN
*Director of the United States Patent and Trademark Office*